(12) United States Patent
Moore et al.

(10) Patent No.: US 11,645,531 B2
(45) Date of Patent: *May 9, 2023

(54) MIXED-REALITY SURGICAL SYSTEM WITH PHYSICAL MARKERS FOR REGISTRATION OF VIRTUAL MODELS

(71) Applicant: HOWMEDICA OSTEONICS CORP., Mahwah, NJ (US)

(72) Inventors: Jesse G. Moore, Germantown, TN (US); Sergii Poltaretskyi, Plougonvelin (FR); Jean Chaoui, Locmaria Plouzané (FR); Damien Cariou, Loperhet (FR)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/117,756

(22) Filed: Dec. 10, 2020

(65) Prior Publication Data
US 2021/0093414 A1 Apr. 1, 2021

Related U.S. Application Data

(63) Continuation of application No. PCT/US2019/036971, filed on Jun. 13, 2019.
(Continued)

(51) Int. Cl.
*A61B 34/00* (2016.01)
*A61B 34/10* (2016.01)
(Continued)

(52) U.S. Cl.
CPC ............ *A61B 34/25* (2016.02); *A61B 5/1114* (2013.01); *A61B 5/1121* (2013.01);
(Continued)

(58) Field of Classification Search
None
See application file for complete search history.

(56) References Cited

U.S. PATENT DOCUMENTS

| 5,682,886 A | 11/1997 | Delp et al. |
| 5,769,640 A | 6/1998 | Jacobus et al. |
| (Continued) |

FOREIGN PATENT DOCUMENTS

| EP | 1356413 A2 | 10/2003 |
| EP | 1395195 A1 | 3/2004 |
| (Continued) |

OTHER PUBLICATIONS

US 8,849,621 B2, 09/2014, Fitz et al. (withdrawn)
(Continued)

*Primary Examiner* — Jeffrey J Chow
(74) *Attorney, Agent, or Firm* — Shumaker & Sieffert, P.A.

(57) ABSTRACT

An example method includes obtaining, a virtual model of a portion of an anatomy of a patient obtained from a virtual surgical plan for an orthopedic joint repair surgical procedure to attach a prosthetic to the anatomy; identifying, based on data obtained by one or more sensors, positions of one or more physical markers positioned relative to the anatomy of the patient; and registering, based on the identified positions, the virtual model of the portion of the anatomy with a corresponding observed portion of the anatomy.

38 Claims, 131 Drawing Sheets

Related U.S. Application Data

(60) Provisional application No. 62/804,392, filed on Feb. 12, 2019, provisional application No. 62/804,402, filed on Feb. 12, 2019, provisional application No. 62/804,383, filed on Feb. 12, 2019, provisional application No. 62/778,797, filed on Dec. 12, 2018, provisional application No. 62/778,774, filed on Dec. 12, 2018, provisional application No. 62/778,791, filed on Dec. 12, 2018, provisional application No. 62/778,789, filed on Dec. 12, 2018, provisional application No. 62/778,778, filed on Dec. 12, 2018, provisional application No. 62/778,764, filed on Dec. 12, 2018, provisional application No. 62/778,788, filed on Dec. 12, 2018, provisional application No. 62/778,796, filed on Dec. 12, 2018, provisional application No. 62/778,772, filed on Dec. 12, 2018, provisional application No. 62/778,760, filed on Dec. 12, 2018, provisional application No. 62/778,782, filed on Dec. 12, 2018, provisional application No. 62/739,406, filed on Oct. 1, 2018, provisional application No. 62/687,014, filed on Jun. 19, 2018.

(51) Int. Cl.

| | |
|---|---|
| *A61B 90/00* | (2016.01) |
| *G02B 27/01* | (2006.01) |
| *G06F 3/0482* | (2013.01) |
| *G06T 11/00* | (2006.01) |
| *A61B 5/11* | (2006.01) |
| *A61B 5/00* | (2006.01) |
| *G06T 19/00* | (2011.01) |
| *G16H 30/40* | (2018.01) |
| *G16H 40/60* | (2018.01) |
| *H04N 13/332* | (2018.01) |
| *H04N 13/122* | (2018.01) |
| *A61B 17/16* | (2006.01) |
| *A61B 17/17* | (2006.01) |
| *G02B 27/00* | (2006.01) |
| *G16H 20/40* | (2018.01) |
| *G16H 50/50* | (2018.01) |
| *G16H 70/20* | (2018.01) |
| *G09B 9/00* | (2006.01) |
| *G09B 19/00* | (2006.01) |
| *G09B 23/28* | (2006.01) |
| *G06N 20/00* | (2019.01) |
| *G06F 3/01* | (2006.01) |
| *A61B 17/14* | (2006.01) |
| *G06T 7/55* | (2017.01) |
| *A61F 2/40* | (2006.01) |
| *A61B 90/92* | (2016.01) |
| *G16H 40/63* | (2018.01) |
| *G09B 5/06* | (2006.01) |
| *G16H 40/67* | (2018.01) |
| *G06T 19/20* | (2011.01) |
| *G16H 40/20* | (2018.01) |
| *G16H 30/20* | (2018.01) |
| *G06T 7/11* | (2017.01) |
| *G16H 50/30* | (2018.01) |
| *G06N 3/08* | (2023.01) |
| *G06T 7/00* | (2017.01) |
| *G16H 70/60* | (2018.01) |
| *G16H 50/70* | (2018.01) |
| *G06F 30/10* | (2020.01) |
| *G06K 9/62* | (2022.01) |
| *G16H 80/00* | (2018.01) |
| *G06F 3/04815* | (2022.01) |
| *G16H 50/20* | (2018.01) |
| *A61B 17/00* | (2006.01) |
| *A61F 2/46* | (2006.01) |
| *A61B 17/15* | (2006.01) |
| *G06F 3/0483* | (2013.01) |
| *A61B 34/20* | (2016.01) |
| *G06N 3/04* | (2023.01) |

(52) U.S. Cl.
CPC .......... *A61B 5/1127* (2013.01); *A61B 5/681* (2013.01); *A61B 17/142* (2016.11); *A61B 17/1604* (2013.01); *A61B 17/1626* (2013.01); *A61B 17/1659* (2013.01); *A61B 17/1684* (2013.01); *A61B 17/1703* (2013.01); *A61B 34/10* (2016.02); *A61B 34/76* (2016.02); *A61B 90/08* (2016.02); *A61B 90/36* (2016.02); *A61B 90/361* (2016.02); *A61B 90/37* (2016.02); *A61B 90/39* (2016.02); *A61B 90/92* (2016.02); *A61F 2/40* (2013.01); *A61F 2/4081* (2013.01); *G02B 27/0075* (2013.01); *G02B 27/017* (2013.01); *G02B 27/0172* (2013.01); *G06F 3/011* (2013.01); *G06F 3/0482* (2013.01); *G06F 3/04815* (2013.01); *G06F 30/10* (2020.01); *G06K 9/6261* (2013.01); *G06N 3/08* (2013.01); *G06N 20/00* (2019.01); *G06T 7/0012* (2013.01); *G06T 7/11* (2017.01); *G06T 7/55* (2017.01); *G06T 11/00* (2013.01); *G06T 19/006* (2013.01); *G06T 19/20* (2013.01); *G09B 5/06* (2013.01); *G09B 9/00* (2013.01); *G09B 19/003* (2013.01); *G09B 23/28* (2013.01); *G16H 20/40* (2018.01); *G16H 30/20* (2018.01); *G16H 30/40* (2018.01); *G16H 40/20* (2018.01); *G16H 40/60* (2018.01); *G16H 40/63* (2018.01); *G16H 40/67* (2018.01); *G16H 50/30* (2018.01); *G16H 50/50* (2018.01); *G16H 50/70* (2018.01); *G16H 70/20* (2018.01); *G16H 70/60* (2018.01); *G16H 80/00* (2018.01); *H04N 13/122* (2018.05); *H04N 13/332* (2018.05); *A61B 5/744* (2013.01); *A61B 17/151* (2013.01); *A61B 17/1775* (2016.11); *A61B 17/1778* (2016.11); *A61B 2017/00115* (2013.01); *A61B 2017/00119* (2013.01); *A61B 2034/102* (2016.02); *A61B 2034/104* (2016.02); *A61B 2034/105* (2016.02); *A61B 2034/107* (2016.02); *A61B 2034/108* (2016.02); *A61B 2034/2051* (2016.02); *A61B 2034/2055* (2016.02); *A61B 2034/2065* (2016.02); *A61B 2034/2068* (2016.02); *A61B 2034/252* (2016.02); *A61B 2034/254* (2016.02); *A61B 2090/062* (2016.02); *A61B 2090/0807* (2016.02); *A61B 2090/365* (2016.02); *A61B 2090/366* (2016.02); *A61B 2090/367* (2016.02); *A61B 2090/373* (2016.02); *A61B 2090/374* (2016.02); *A61B 2090/378* (2016.02); *A61B 2090/3762* (2016.02); *A61B 2090/397* (2016.02); *A61B 2090/3937* (2016.02); *A61B 2090/3945* (2016.02); *A61B 2505/05* (2013.01); *A61B 2562/0219* (2013.01); *A61F 2/4606* (2013.01); *A61F 2/4612* (2013.01); *A61F 2002/4011* (2013.01); *A61F 2002/4633* (2013.01); *A61F 2002/4658* (2013.01); *A61F 2002/4668* (2013.01); *G02B 2027/0141* (2013.01); *G02B 2027/0174* (2013.01); *G06F 3/0483* (2013.01); *G06N 3/04* (2013.01); *G06T 2200/24*

(2013.01); *G06T 2207/10016* (2013.01); *G06T 2207/20036* (2013.01); *G06T 2207/20081* (2013.01); *G06T 2207/20084* (2013.01); *G06T 2207/30008* (2013.01); *G06T 2207/30052* (2013.01); *G06T 2207/30204* (2013.01); *G06T 2210/41* (2013.01); *G06T 2219/2004* (2013.01); *G06V 2201/03* (2022.01); *G16H 50/20* (2018.01)

(56) References Cited

U.S. PATENT DOCUMENTS

| | | | |
|---|---|---|---|
| 5,824,085 A | 10/1998 | Sahay et al. | |
| 6,002,859 A | 12/1999 | DiGioia, III et al. | |
| 6,205,411 B1 | 3/2001 | DiGioia, III et al. | |
| 6,847,336 B1 | 1/2005 | Lemelson et al. | |
| 6,944,518 B2 | 9/2005 | Roose | |
| 7,388,972 B2 | 6/2008 | Kitson | |
| 7,468,075 B2 | 12/2008 | Lang et al. | |
| 7,493,153 B2 | 2/2009 | Ahmed et al. | |
| 7,534,263 B2 | 5/2009 | Burdulis, Jr. et al. | |
| 7,542,791 B2 | 6/2009 | Mire et al. | |
| 7,618,451 B2 | 11/2009 | Berez et al. | |
| 7,634,119 B2 | 12/2009 | Tsougarakis et al. | |
| 7,715,602 B2 | 5/2010 | Richard | |
| 7,717,956 B2 | 5/2010 | Lang | |
| 7,774,044 B2 | 8/2010 | Sauer et al. | |
| 7,799,077 B2 | 9/2010 | Lang et al. | |
| 7,857,821 B2 | 12/2010 | Couture et al. | |
| 7,885,701 B2 | 2/2011 | DiSilvestro et al. | |
| 7,981,158 B2 | 7/2011 | Fitz et al. | |
| 7,983,777 B2 | 7/2011 | Melton et al. | |
| 8,014,984 B2 | 9/2011 | Iannotti et al. | |
| 8,062,302 B2 | 11/2011 | Lang et al. | |
| 8,066,708 B2 | 11/2011 | Lang et al. | |
| 8,070,752 B2 | 12/2011 | Metzger et al. | |
| 8,077,950 B2 | 12/2011 | Tsougarakis et al. | |
| 8,078,440 B2 | 12/2011 | Otto et al. | |
| 8,083,745 B2 | 12/2011 | Lang et al. | |
| 8,092,465 B2 | 1/2012 | Metzger et al. | |
| 8,094,900 B2 | 1/2012 | Steines et al. | |
| 8,105,330 B2 | 1/2012 | Fitz et al. | |
| 8,147,496 B2 | 4/2012 | Couture et al. | |
| 8,160,326 B2 | 4/2012 | Zug et al. | |
| 8,172,775 B2 | 5/2012 | Warkentine et al. | |
| 8,175,683 B2 | 5/2012 | Roose | |
| 8,214,016 B2 | 7/2012 | Lavallee et al. | |
| 8,221,430 B2 | 7/2012 | Park et al. | |
| 8,234,097 B2 | 7/2012 | Steines et al. | |
| 8,241,296 B2 | 8/2012 | Wasielewski | |
| 8,282,646 B2 | 10/2012 | Schoenefeld et al. | |
| 8,337,501 B2 | 12/2012 | Fitz et al. | |
| 8,337,507 B2 | 12/2012 | Lang et al. | |
| 8,343,218 B2 | 1/2013 | Lang et al. | |
| 8,366,771 B2 | 2/2013 | Burdulis, Jr. et al. | |
| 8,380,471 B2 | 2/2013 | Iannotti et al. | |
| 8,457,790 B2 | 6/2013 | Blondel et al. | |
| 8,457,930 B2 | 6/2013 | Schroeder | |
| 8,460,304 B2 | 6/2013 | Fitz et al. | |
| 8,478,382 B2 * | 7/2013 | Burnside | A61B 5/06 600/424 |
| 8,480,679 B2 | 7/2013 | Park et al. | |
| 8,500,740 B2 | 8/2013 | Bojarski et al. | |
| 8,506,645 B2 | 8/2013 | Blaylock et al. | |
| 8,521,255 B2 | 8/2013 | DiSilvestro et al. | |
| 8,529,568 B2 | 8/2013 | Bojarski et al. | |
| 8,532,361 B2 | 9/2013 | Pavlovskaia et al. | |
| 8,532,807 B2 | 9/2013 | Metzger | |
| 8,545,509 B2 | 10/2013 | Park et al. | |
| 8,551,102 B2 | 10/2013 | Fitz et al. | |
| 8,551,103 B2 | 10/2013 | Fitz et al. | |
| 8,551,169 B2 | 10/2013 | Fitz et al. | |
| 8,551,178 B2 | 10/2013 | Sharkey et al. | |
| 8,556,906 B2 | 10/2013 | Fitz et al. | |
| 8,556,907 B2 | 10/2013 | Fitz et al. | |
| 8,556,971 B2 | 10/2013 | Lang | |
| 8,556,983 B2 | 10/2013 | Bojarski et al. | |
| 8,561,278 B2 | 10/2013 | Fitz et al. | |
| 8,562,611 B2 | 10/2013 | Fitz et al. | |
| 8,568,479 B2 | 10/2013 | Fitz et al. | |
| 8,574,303 B2 | 11/2013 | Sharkey et al. | |
| 8,585,708 B2 | 11/2013 | Fitz et al. | |
| 8,594,397 B2 | 11/2013 | Haimerl et al. | |
| 8,617,172 B2 | 12/2013 | Fitz et al. | |
| 8,617,242 B2 | 12/2013 | Philipp | |
| 8,623,026 B2 | 1/2014 | Wong et al. | |
| 8,634,617 B2 | 1/2014 | Tsougarakis et al. | |
| 8,638,998 B2 | 1/2014 | Steines et al. | |
| 8,657,827 B2 | 2/2014 | Fitz et al. | |
| 8,662,900 B2 | 3/2014 | Bell, III et al. | |
| 8,679,125 B2 | 3/2014 | Smith et al. | |
| 8,682,052 B2 | 3/2014 | Fitz et al. | |
| 8,690,945 B2 | 4/2014 | Fitz et al. | |
| 8,706,197 B2 | 4/2014 | Henning et al. | |
| 8,709,089 B2 | 4/2014 | Lang et al. | |
| 8,715,291 B2 | 5/2014 | Park et al. | |
| 8,731,885 B2 | 5/2014 | Iannotti et al. | |
| 8,735,773 B2 | 5/2014 | Lang | |
| 8,737,700 B2 | 5/2014 | Park et al. | |
| 8,777,875 B2 | 7/2014 | Park | |
| 8,794,977 B2 | 8/2014 | McGuan et al. | |
| 8,801,719 B2 | 8/2014 | Park et al. | |
| 8,814,877 B2 | 8/2014 | Wasielewski | |
| 8,861,818 B2 | 10/2014 | Ito et al. | |
| 8,876,830 B2 | 11/2014 | Hodorek et al. | |
| 8,882,779 B2 | 11/2014 | Park | |
| 8,884,618 B2 | 11/2014 | Mahfouz | |
| 8,888,782 B2 | 11/2014 | Smith et al. | |
| 8,903,530 B2 | 12/2014 | Metzger | |
| 8,906,107 B2 | 12/2014 | Bojarski et al. | |
| 8,908,937 B2 | 12/2014 | Beck | |
| 8,917,290 B2 | 12/2014 | Beck | |
| 8,932,361 B2 | 1/2015 | Tornier et al. | |
| 8,932,363 B2 | 1/2015 | Tsougarakis et al. | |
| 8,965,088 B2 | 2/2015 | Tsougarakis et al. | |
| 8,971,606 B2 | 3/2015 | Chaoui et al. | |
| 8,974,539 B2 | 3/2015 | Bojarski et al. | |
| 8,983,813 B2 | 3/2015 | Miles et al. | |
| 8,989,460 B2 | 3/2015 | Mahfouz | |
| 8,990,052 B2 | 3/2015 | Lavallee et al. | |
| 9,020,788 B2 | 4/2015 | Lang et al. | |
| 9,023,050 B2 | 5/2015 | Lang et al. | |
| 9,055,953 B2 | 6/2015 | Lang et al. | |
| 9,072,531 B2 | 7/2015 | Fitz et al. | |
| 9,084,617 B2 | 7/2015 | Lang et al. | |
| 9,097,890 B2 | 8/2015 | Miller et al. | |
| 9,107,679 B2 | 8/2015 | Lang et al. | |
| 9,107,680 B2 | 8/2015 | Fitz et al. | |
| 9,180,015 B2 | 11/2015 | Fitz et al. | |
| 9,186,161 B2 | 11/2015 | Lang et al. | |
| 9,208,263 B2 | 12/2015 | Pavlovskaia et al. | |
| 9,211,199 B2 | 12/2015 | Ratron | |
| 9,216,025 B2 | 12/2015 | Fitz et al. | |
| 9,220,516 B2 | 12/2015 | Lang et al. | |
| 9,220,517 B2 | 12/2015 | Lang et al. | |
| 9,220,572 B2 | 12/2015 | Meridew et al. | |
| 9,232,955 B2 | 1/2016 | Bonin, Jr. et al. | |
| 9,233,001 B2 | 1/2016 | Miles et al. | |
| 9,269,275 B2 | 2/2016 | Bell et al. | |
| 9,295,482 B2 | 3/2016 | Fitz et al. | |
| 9,301,812 B2 | 4/2016 | Kehres et al. | |
| 9,326,780 B2 | 5/2016 | Wong et al. | |
| 9,333,085 B2 | 5/2016 | Fitz et al. | |
| 9,345,551 B2 | 5/2016 | Mahfouz | |
| 9,351,743 B2 | 5/2016 | Kehres et al. | |
| 9,358,018 B2 | 6/2016 | Fitz et al. | |
| 9,358,114 B2 | 6/2016 | Hughes | |
| 9,402,726 B2 | 8/2016 | Linderman et al. | |
| 9,408,686 B1 | 8/2016 | Miller et al. | |
| 9,414,846 B2 | 8/2016 | Gillman et al. | |
| 9,433,471 B2 | 9/2016 | Zuhars | |
| 9,439,767 B2 | 9/2016 | Bojarski et al. | |
| 9,495,483 B2 | 11/2016 | Steines et al. | |
| 9,522,008 B2 | 12/2016 | Ferko et al. | |
| 9,532,730 B2 | 1/2017 | Wasielewski | |

(56) References Cited

U.S. PATENT DOCUMENTS

| | | |
|---|---|---|
| 9,538,962 B1 | 1/2017 | Hannaford et al. |
| 9,547,940 B1 | 1/2017 | Sun et al. |
| 9,554,910 B2 | 1/2017 | Vanasse et al. |
| 9,575,931 B2 | 2/2017 | Ratron |
| 9,579,106 B2 | 2/2017 | Lo et al. |
| 9,579,110 B2 | 2/2017 | Bojarski et al. |
| 9,603,711 B2 | 3/2017 | Bojarski et al. |
| 9,610,086 B2 | 4/2017 | Park et al. |
| 9,642,632 B2 | 5/2017 | Stemniski et al. |
| 9,645,785 B1 | 5/2017 | Hannaford et al. |
| 9,646,113 B2 | 5/2017 | Park et al. |
| 9,646,423 B1 | 5/2017 | Sun et al. |
| 9,649,117 B2 | 5/2017 | Stemniski et al. |
| 9,649,170 B2 | 5/2017 | Park et al. |
| 9,675,365 B2 | 6/2017 | Lancianese et al. |
| 9,675,461 B2 | 6/2017 | Mahfouz |
| 9,675,471 B2 | 6/2017 | Bojarski et al. |
| 9,681,925 B2 | 6/2017 | Azar et al. |
| 9,681,956 B2 | 6/2017 | Al Hares et al. |
| 9,684,768 B2 | 6/2017 | Lavallee et al. |
| 9,687,945 B2 | 6/2017 | Steines et al. |
| 9,700,420 B2 | 7/2017 | Fitz et al. |
| 9,715,563 B1 | 7/2017 | Schroeder |
| 9,775,680 B2 | 10/2017 | Bojarski et al. |
| 9,778,648 B2 | 10/2017 | Kumar et al. |
| 9,795,399 B2 | 10/2017 | Metzger et al. |
| 9,849,019 B2 | 12/2017 | Miller et al. |
| 9,855,146 B2 | 1/2018 | Schmieding |
| 9,861,387 B2 | 1/2018 | Metzger et al. |
| 9,861,446 B2 | 1/2018 | Lang |
| 9,895,230 B2 | 2/2018 | Mahfouz |
| 9,933,847 B1 | 4/2018 | Ross et al. |
| 9,943,370 B2 | 4/2018 | Asseln et al. |
| 9,956,047 B2 | 5/2018 | Borjarski et al. |
| 9,980,780 B2 | 5/2018 | Lang |
| 10,013,808 B2 | 7/2018 | Jones et al. |
| 10,016,243 B2 | 7/2018 | Esterberg |
| 10,052,170 B2 | 8/2018 | Saget et al. |
| 10,052,206 B2 | 8/2018 | Mahfouz |
| 10,064,686 B2 | 9/2018 | McKinnon et al. |
| 10,080,509 B2 | 9/2018 | Wasielewski |
| 10,154,239 B2 | 12/2018 | Casas |
| 10,159,530 B2 | 12/2018 | Lang |
| 10,194,131 B2 | 1/2019 | Casas |
| 10,194,990 B2 | 2/2019 | Amanatullah et al. |
| 10,511,822 B2 | 2/2019 | Casas |
| 10,258,427 B2 | 4/2019 | Saget et al. |
| 10,278,777 B1 | 5/2019 | Lang |
| 10,292,768 B2 | 5/2019 | Lang |
| 10,326,975 B2 | 6/2019 | Casas |
| 10,368,947 B2 | 8/2019 | Lang |
| 10,383,692 B1 | 8/2019 | Wang |
| 10,390,887 B2 | 8/2019 | Bischoff et al. |
| 10,390,890 B2 | 8/2019 | Jagga |
| 10,398,514 B2 | 9/2019 | Ryan et al. |
| 10,405,927 B1 | 9/2019 | Lang |
| 10,413,363 B2 | 9/2019 | Fahim et al. |
| 10,426,549 B2 | 10/2019 | Kehres et al. |
| 10,467,752 B2 | 11/2019 | Tanji |
| 10,478,255 B2 | 11/2019 | West et al. |
| 10,499,996 B2 | 12/2019 | de Almeida Barreto |
| 10,517,690 B2 | 12/2019 | Kosmecki et al. |
| 10,546,423 B2 | 1/2020 | Jones et al. |
| 10,548,667 B2 | 2/2020 | Flett et al. |
| 10,572,733 B2 | 2/2020 | Wells et al. |
| 10,580,217 B2 | 3/2020 | Jones et al. |
| 10,594,998 B1 | 3/2020 | Casas |
| 10,595,844 B2 | 3/2020 | Nawana et al. |
| 10,602,114 B2 | 3/2020 | Casas |
| 10,603,113 B2 | 3/2020 | Lang |
| 10,621,436 B2 | 4/2020 | Wells et al. |
| 10,646,283 B2 | 5/2020 | Johnson et al. |
| 10,646,285 B2 | 5/2020 | Siemionow et al. |
| 10,650,594 B2 | 5/2020 | Jones et al. |
| 10,679,417 B2 | 6/2020 | Wei et al. |
| 10,687,901 B2 * | 6/2020 | Thomas .................. G06T 19/20 |
| 10,716,643 B2 | 7/2020 | Justin et al. |
| 10,742,949 B2 | 8/2020 | Casas |
| 10,743,939 B1 | 8/2020 | Lang |
| 10,788,791 B2 | 9/2020 | Gellman et al. |
| 10,796,499 B2 | 10/2020 | de Almeida Barreto et al. |
| 10,799,296 B2 | 10/2020 | Lang |
| 10,810,799 B2 | 10/2020 | Tepper et al. |
| 10,820,948 B2 | 11/2020 | West et al. |
| 10,841,556 B2 | 11/2020 | Casas |
| 10,849,693 B2 | 12/2020 | Lang |
| 10,861,236 B2 | 12/2020 | Geri et al. |
| 10,869,727 B2 | 12/2020 | Yanof et al. |
| 10,881,462 B2 | 1/2021 | Heavener et al. |
| 10,895,906 B2 | 1/2021 | West et al. |
| 10,951,872 B2 | 3/2021 | Casas |
| 10,987,176 B2 | 4/2021 | Poltaretskyi et al. |
| 2002/0082498 A1 | 6/2002 | Wendt et al. |
| 2004/0002642 A1 | 1/2004 | Dekel et al. |
| 2004/0068187 A1 | 4/2004 | Krause et al. |
| 2004/0204644 A1 | 10/2004 | Tsougarakis et al. |
| 2004/0243148 A1 | 12/2004 | Wasielewski |
| 2004/0254454 A1 | 12/2004 | Kockro |
| 2006/0142657 A1 | 6/2006 | Quaid et al. |
| 2006/0142739 A1 | 6/2006 | DiSilestro et al. |
| 2007/0015999 A1 | 1/2007 | Heldreth et al. |
| 2007/0066917 A1 | 3/2007 | Hodorek et al. |
| 2007/0179626 A1 | 8/2007 | de la Barrera et al. |
| 2007/0198022 A1 | 8/2007 | Lang et al. |
| 2007/0233267 A1 | 10/2007 | Amirouche et al. |
| 2007/0239153 A1 | 10/2007 | Hodorek et al. |
| 2007/0249967 A1 | 10/2007 | Buly et al. |
| 2007/0288030 A1 | 12/2007 | Metzger et al. |
| 2008/0077158 A1 | 3/2008 | Haider et al. |
| 2008/0161815 A1 | 7/2008 | Schoenefeld et al. |
| 2008/0249395 A1 * | 10/2008 | Shachar .................. A61B 34/76 600/409 |
| 2008/0262812 A1 | 10/2008 | Arata et al. |
| 2008/0269596 A1 | 10/2008 | Revie et al. |
| 2008/0312659 A1 | 12/2008 | Metzger et al. |
| 2009/0076655 A1 | 3/2009 | Blondel et al. |
| 2009/0131548 A1 | 5/2009 | Muratoglu et al. |
| 2009/0138019 A1 | 5/2009 | Wasielewski |
| 2010/0054572 A1 | 3/2010 | Tsougarakis et al. |
| 2010/0274534 A1 | 10/2010 | Steines et al. |
| 2010/0277659 A1 | 11/2010 | Yang et al. |
| 2010/0311028 A1 | 12/2010 | Bell, III et al. |
| 2010/0312247 A1 * | 12/2010 | Tuma .................. A61B 17/175 606/89 |
| 2011/0010187 A1 | 1/2011 | Andersson et al. |
| 2011/0071802 A1 | 3/2011 | Bojarski et al. |
| 2011/0092978 A1 | 4/2011 | McCombs |
| 2011/0208256 A1 | 8/2011 | Zuhars |
| 2011/0257653 A1 | 10/2011 | Hughes et al. |
| 2011/0307016 A1 | 12/2011 | Reglos et al. |
| 2012/0065640 A1 | 3/2012 | Metzger et al. |
| 2012/0066892 A1 | 3/2012 | Lang et al. |
| 2012/0071893 A1 | 3/2012 | Smith et al. |
| 2012/0089191 A1 | 4/2012 | Altarac et al. |
| 2012/0122062 A1 | 5/2012 | Yang et al. |
| 2012/0141034 A1 | 6/2012 | Iannotti et al. |
| 2012/0157887 A1 | 6/2012 | Fanson et al. |
| 2012/0201440 A1 | 8/2012 | Steines et al. |
| 2012/0209392 A1 | 8/2012 | Angibaud et al. |
| 2012/0226481 A1 | 9/2012 | Carson |
| 2012/0265496 A1 | 10/2012 | Mahfouz |
| 2012/0271426 A1 | 10/2012 | Roche et al. |
| 2012/0276509 A1 | 11/2012 | Iannotti et al. |
| 2012/0277752 A1 | 11/2012 | Wasielewski |
| 2012/0290272 A1 | 11/2012 | Bryan |
| 2013/0012944 A1 | 1/2013 | McCombs |
| 2013/0023999 A1 | 1/2013 | Gregory |
| 2013/0114873 A1 | 5/2013 | Chaoui et al. |
| 2013/0185310 A1 | 7/2013 | De Guise et al. |
| 2013/0197529 A1 | 8/2013 | Metzger et al. |
| 2013/0197870 A1 | 8/2013 | Steines et al. |
| 2013/0211421 A1 | 8/2013 | Abovitz et al. |
| 2013/0230838 A1 | 9/2013 | Iannotti et al. |
| 2013/0267838 A1 | 10/2013 | Fronk et al. |

(56) References Cited

U.S. PATENT DOCUMENTS

| | | | |
|---|---|---|---|
| 2013/0336553 A1* | 12/2013 | Buisseret | G06T 7/13 382/128 |
| 2014/0022283 A1 | 1/2014 | Chan et al. | |
| 2014/0330112 A1 | 1/2014 | Wasielewski | |
| 2014/0347392 A1 | 1/2014 | Odessky et al. | |
| 2014/0081659 A1 | 3/2014 | Nawana et al. | |
| 2014/0115872 A1 | 5/2014 | Steines et al. | |
| 2014/0135857 A1 | 5/2014 | Zuhars | |
| 2014/0207139 A1 | 7/2014 | Smith et al. | |
| 2014/0221819 A1 | 8/2014 | Sarment | |
| 2014/0228860 A1 | 8/2014 | Steines et al. | |
| 2014/0244220 A1 | 8/2014 | McKinnon et al. | |
| 2014/0276872 A1 | 9/2014 | Song | |
| 2014/0324058 A1 | 10/2014 | Metzger et al. | |
| 2015/0016777 A1 | 1/2015 | Abovitz et al. | |
| 2015/0032070 A1 | 1/2015 | Colby | |
| 2015/0088293 A1 | 3/2015 | Metzger | |
| 2015/0123769 A1* | 5/2015 | Dalal | A61B 5/06 340/8.1 |
| 2015/0133820 A1 | 5/2015 | Zohar et al. | |
| 2015/0150688 A1 | 6/2015 | Vanasse et al. | |
| 2015/0248793 A1 | 9/2015 | Abovitz et al. | |
| 2015/0366628 A1 | 12/2015 | Ingmanson | |
| 2016/0015466 A1 | 1/2016 | Park et al. | |
| 2016/0015474 A1 | 1/2016 | Dekel | |
| 2016/0038243 A1 | 2/2016 | Miller et al. | |
| 2016/0074124 A1 | 3/2016 | Fitz et al. | |
| 2016/0100907 A1 | 4/2016 | Gomes | |
| 2016/0110517 A1 | 4/2016 | Taylor | |
| 2016/0119582 A1 | 4/2016 | Smurro | |
| 2016/0143699 A1* | 5/2016 | Tanji | A61B 34/20 600/431 |
| 2016/0157937 A1 | 6/2016 | Kehres et al. | |
| 2016/0166392 A1 | 6/2016 | Vanasse et al. | |
| 2016/0220105 A1 | 8/2016 | Duret | |
| 2016/0228132 A1 | 8/2016 | Kehres et al. | |
| 2016/0228193 A1 | 8/2016 | Moctezuma de la Barrera et al. | |
| 2016/0228195 A1 | 8/2016 | Park et al. | |
| 2016/0256222 A1 | 9/2016 | Walch | |
| 2016/0270854 A1 | 9/2016 | Chaoui | |
| 2016/0278867 A1 | 9/2016 | Dupuis et al. | |
| 2016/0287337 A1 | 10/2016 | Aram et al. | |
| 2016/0296285 A1 | 10/2016 | Chaoui et al. | |
| 2016/0324580 A1 | 11/2016 | Esterberg | |
| 2016/0324581 A1 | 11/2016 | Bojarsk et al. | |
| 2016/0324598 A1 | 11/2016 | Bothorel et al. | |
| 2016/0338778 A1 | 11/2016 | Zuhars | |
| 2017/0000615 A1 | 1/2017 | Mahfouz | |
| 2017/0035517 A1 | 2/2017 | Geri et al. | |
| 2017/0042619 A1 | 2/2017 | Brooks | |
| 2017/0042631 A1 | 2/2017 | Doo et al. | |
| 2017/0056183 A1 | 3/2017 | Steines et al. | |
| 2017/0071503 A1 | 3/2017 | Wasielewski | |
| 2017/0112627 A1 | 4/2017 | Ratron | |
| 2017/0128135 A1 | 5/2017 | McCarthy et al. | |
| 2017/0156890 A1 | 6/2017 | Bake et al. | |
| 2017/0258526 A1* | 9/2017 | Lang | A61B 34/74 |
| 2017/0273795 A1 | 9/2017 | Neichel et al. | |
| 2017/0286617 A1 | 10/2017 | Zimmer | |
| 2017/0296292 A1 | 10/2017 | Mahmood et al. | |
| 2017/0299864 A1 | 10/2017 | Vallius et al. | |
| 2017/0312032 A1 | 11/2017 | Amanatullah et al. | |
| 2017/0360512 A1 | 12/2017 | Couture et al. | |
| 2017/0367771 A1 | 12/2017 | Tako et al. | |
| 2017/0367834 A1 | 12/2017 | Fitz et al. | |
| 2018/0000547 A1 | 1/2018 | Kang et al. | |
| 2018/0008292 A1 | 1/2018 | Metzger et al. | |
| 2018/0008350 A1 | 1/2018 | Varadarajan et al. | |
| 2018/0046166 A1 | 2/2018 | Kumar et al. | |
| 2018/0049622 A1* | 2/2018 | Ryan | A61B 34/10 |
| 2018/0052277 A1 | 2/2018 | Schowengerdt et al. | |
| 2018/0071032 A1 | 3/2018 | de Almeida Barreto | |
| 2018/0078034 A1 | 3/2018 | Savall et al. | |
| 2018/0082480 A1 | 3/2018 | White et al. | |
| 2018/0089855 A1 | 3/2018 | Rodrigues et al. | |
| 2018/0103967 A1 | 4/2018 | Rouyer et al. | |
| 2018/0121728 A1 | 5/2018 | Wells et al. | |
| 2018/0140362 A1 | 5/2018 | Cali et al. | |
| 2018/0200002 A1* | 7/2018 | Kostrzewski | G02C 7/049 |
| 2018/0256256 A1 | 9/2018 | May et al. | |
| 2018/0280037 A1 | 10/2018 | Dassonville et al. | |
| 2018/0333207 A1 | 11/2018 | Moctezuma De la Barrera | |
| 2018/0344309 A1 | 12/2018 | Nawana et al. | |
| 2018/0344412 A1 | 12/2018 | Esterberg | |
| 2019/0035156 A1* | 1/2019 | Wei | G06T 17/00 |
| 2019/0053851 A1 | 2/2019 | Siemionow et al. | |
| 2019/0076198 A1 | 3/2019 | Berend et al. | |
| 2019/0142519 A1 | 5/2019 | Siemionow et al. | |
| 2019/0175285 A1 | 6/2019 | Siemionow et al. | |
| 2019/0183576 A1 | 6/2019 | Fahim et al. | |
| 2019/0192230 A1 | 6/2019 | Siemionow et al. | |
| 2019/0192232 A1 | 6/2019 | Altmann et al. | |
| 2019/0216452 A1 | 7/2019 | Nawana et al. | |
| 2019/0231432 A1 | 8/2019 | Amantullah | |
| 2019/0231433 A1 | 8/2019 | Amantullah | |
| 2019/0246088 A1 | 8/2019 | Casas | |
| 2019/0254753 A1 | 8/2019 | Johnson et al. | |
| 2019/0273916 A1 | 9/2019 | Benishti et al. | |
| 2019/0333480 A1 | 10/2019 | Lang | |
| 2019/0380792 A1 | 12/2019 | Poltaretskyi et al. | |
| 2020/0000527 A1 | 1/2020 | Cazal | |
| 2020/0008877 A1 | 1/2020 | Jo et al. | |
| 2020/0038112 A1 | 2/2020 | Amanatullah et al. | |
| 2020/0060765 A1 | 2/2020 | Fahim et al. | |
| 2020/0060767 A1 | 2/2020 | Lang | |
| 2020/0074748 A1 | 3/2020 | de Almeida Barreto et al. | |
| 2020/0078100 A1 | 3/2020 | Weinstein et al. | |
| 2020/0085511 A1 | 3/2020 | Oezbek et al. | |
| 2020/0093544 A1 | 3/2020 | Azizian | |
| 2020/0121413 A1 | 4/2020 | Kosmecki et al. | |
| 2020/0138518 A1 | 5/2020 | Lang | |
| 2020/0163723 A1 | 5/2020 | Wolf et al. | |
| 2020/0163739 A1 | 5/2020 | Messinger et al. | |
| 2020/0184729 A1 | 6/2020 | Jones et al. | |
| 2020/0188030 A1 | 6/2020 | Kopper et al. | |
| 2020/0197107 A1 | 6/2020 | Ryan et al. | |
| 2020/0219324 A1 | 7/2020 | Jones et al. | |
| 2020/0221060 A1 | 7/2020 | Casas | |
| 2020/0229869 A1 | 7/2020 | Dorman | |
| 2020/0229877 A1 | 7/2020 | Siemionow et al. | |
| 2020/0237256 A1 | 7/2020 | Farshad et al. | |
| 2020/0242845 A1 | 7/2020 | Jones et al. | |
| 2020/0246074 A1 | 8/2020 | Lang | |
| 2020/0246081 A1 | 8/2020 | Johnson | |
| 2020/0315734 A1 | 10/2020 | El Amm | |
| 2020/0330166 A1 | 10/2020 | Meglan et al. | |
| 2020/0352655 A1 | 11/2020 | Freese | |
| 2020/0360105 A1 | 11/2020 | Frey et al. | |
| 2020/0375666 A1 | 12/2020 | Murphy | |
| 2020/0388075 A1 | 12/2020 | Kazanzides et al. | |
| 2020/0409306 A1 | 12/2020 | Gelman et al. | |
| 2021/0022808 A1 | 1/2021 | Lang | |
| 2021/0022812 A1 | 1/2021 | Tako et al. | |
| 2021/0052348 A1 | 2/2021 | Schwagli et al. | |
| 2021/0059760 A1 | 3/2021 | Tseng et al. | |
| 2021/0059762 A1 | 3/2021 | Ng et al. | |
| 2021/0065451 A1 | 3/2021 | Tseng et al. | |
| 2021/0081035 A1 | 3/2021 | West et al. | |
| 2021/0085220 A1 | 3/2021 | Poltaretskyi et al. | |
| 2021/0090344 A1 | 3/2021 | Geri et al. | |
| 2021/0093329 A1 | 4/2021 | Poltaretskyi et al. | |
| 2021/0093385 A1 | 4/2021 | Morvan et al. | |
| 2021/0093386 A1 | 4/2021 | Poltaretskyi et al. | |
| 2021/0093387 A1 | 4/2021 | Poltaretskyi et al. | |
| 2021/0093388 A1 | 4/2021 | Poltaretskyi et al. | |
| 2021/0093389 A1 | 4/2021 | Poltaretskyi et al. | |
| 2021/0093390 A1 | 4/2021 | Poltaretskyi et al. | |
| 2021/0093391 A1 | 4/2021 | Poltaretskyi et al. | |
| 2021/0093392 A1 | 4/2021 | Poltaretskyi et al. | |
| 2021/0093395 A1 | 4/2021 | Chaoui et al. | |
| 2021/0093410 A1 | 4/2021 | Gaborit et al. | |
| 2021/0093413 A1 | 4/2021 | Poltaretskyi et al. | |
| 2021/0093415 A1 | 4/2021 | Moore et al. | |
| 2021/0097880 A1 | 4/2021 | Kuester et al. | |

(56) References Cited

U.S. PATENT DOCUMENTS

| | | | |
|---|---|---|---|
| 2021/0097886 A1 | 4/2021 | Kuester et al. | |
| 2021/0100620 A1 | 4/2021 | Chaoui et al. | |
| 2021/0104055 A1 | 4/2021 | Ni et al. | |
| 2021/0104325 A1 | 4/2021 | Chaoui et al. | |
| 2021/0106386 A1 | 4/2021 | Lang | |
| 2021/0121237 A1 | 4/2021 | Fanson et al. | |
| 2021/0134467 A1 | 5/2021 | Poltaretskyi et al. | |
| 2021/0346117 A1* | 11/2021 | Poltaretskyi | A61B 90/39 |
| 2021/0353383 A1* | 11/2021 | Kumar | G06K 9/4671 |

FOREIGN PATENT DOCUMENTS

| | | |
|---|---|---|
| EP | 1406203 A2 | 4/2004 |
| EP | 1676539 A1 | 5/2006 |
| EP | 1722705 A2 | 11/2006 |
| EP | 1743592 A1 | 1/2007 |
| EP | 1395194 B1 | 8/2007 |
| EP | 1872737 A2 | 1/2008 |
| EP | 1981409 A2 | 10/2008 |
| EP | 2119409 A1 | 11/2009 |
| EP | 2129317 A1 | 12/2009 |
| EP | 2175418 A2 | 4/2010 |
| EP | 2243445 A2 | 10/2010 |
| EP | 2319450 A1 | 5/2011 |
| EP | 2471483 A1 | 7/2012 |
| EP | 3097448 A1 | 11/2016 |
| EP | 3280344 A2 | 2/2018 |
| EP | 3355769 A1 | 8/2018 |
| EP | 3361979 A1 | 8/2018 |
| EP | 3420413 A1 | 1/2019 |
| EP | 3426179 A1 | 1/2019 |
| EP | 3443888 A1 | 2/2019 |
| EP | 3443923 A1 | 2/2019 |
| EP | 3443924 A1 | 2/2019 |
| EP | 3445048 A1 | 2/2019 |
| EP | 3498212 A1 | 6/2019 |
| EP | 3505133 A1 | 7/2019 |
| EP | 3512452 A1 | 7/2019 |
| EP | 3533409 A1 | 9/2019 |
| EP | 3566212 A1 | 11/2019 |
| EP | 3568070 A1 | 11/2019 |
| EP | 3592273 A1 | 1/2020 |
| EP | 3596658 A1 | 1/2020 |
| EP | 3609424 A1 | 2/2020 |
| EP | 3612126 A1 | 2/2020 |
| EP | 3612127 A1 | 2/2020 |
| EP | 3613055 A1 | 2/2020 |
| EP | 3618748 A1 | 3/2020 |
| EP | 3654867 A1 | 5/2020 |
| EP | 3658233 A1 | 6/2020 |
| EP | 3668426 A1 | 6/2020 |
| FR | 3062297 A1 | 8/2018 |
| WO | WO 2002029700 A2 | 4/2002 |
| WO | WO 2002100285 A1 | 12/2002 |
| WO | 2005/039430 A2 | 5/2005 |
| WO | WO 2005087125 A2 | 9/2005 |
| WO | WO 2007092841 A2 | 8/2007 |
| WO | WO 2007096741 A2 | 8/2007 |
| WO | WO 2007147235 A1 | 12/2007 |
| WO | WO 2008008893 A2 | 1/2008 |
| WO | WO 2008109751 A1 | 9/2008 |
| WO | WO 2015110859 A1 | 7/2015 |
| WO | WO 2016004993 A1 | 1/2016 |
| WO | WO 2016115423 A1 | 7/2016 |
| WO | WO 2016162789 A2 | 10/2016 |
| WO | WO 2017058710 A1 | 4/2017 |
| WO | WO 2017066373 A1 | 4/2017 |
| WO | WO 2017075122 A1 | 5/2017 |
| WO | WO 2017145155 A1 | 8/2017 |
| WO | WO 2017160651 A1 | 9/2017 |
| WO | 2017/221257 A1 | 12/2017 |
| WO | WO 2018052966 A1 | 3/2018 |
| WO | WO 2018057564 A1 | 3/2018 |
| WO | WO 2018060304 A1 | 4/2018 |
| WO | WO 2018129094 A1 | 7/2018 |
| WO | WO 2018132804 A1 | 7/2018 |
| WO | WO 2018148379 A1 | 8/2018 |
| WO | WO 2018164909 A1 | 9/2018 |
| WO | WO 2018165323 A1 | 9/2018 |
| WO | WO 2018169891 A1 | 9/2018 |
| WO | WO 2018170181 A1 | 9/2018 |
| WO | WO 2018189725 A1 | 10/2018 |
| WO | WO 2018195456 A1 | 10/2018 |
| WO | WO 2018195463 A1 | 10/2018 |
| WO | WO 2018195529 A1 | 10/2018 |
| WO | WO 2018200767 A1 | 11/2018 |
| WO | WO 2018203304 A1 | 11/2018 |
| WO | 2018/220050 A1 | 12/2018 |
| WO | WO 2019021236 A1 | 1/2019 |
| WO | WO 2019032143 A1 | 2/2019 |
| WO | WO 2019036524 A1 | 2/2019 |
| WO | WO 2019051080 A1 | 3/2019 |
| WO | WO 2019051464 A1 | 3/2019 |
| WO | WO 2019118215 A1 | 6/2019 |
| WO | WO 2019118216 A1 | 6/2019 |
| WO | WO 2019132781 A1 | 7/2019 |
| WO | WO 2019139931 A1 | 7/2019 |
| WO | WO 2019141704 A1 | 7/2019 |
| WO | WO 2019148154 A1 | 8/2019 |
| WO | WO 2019152269 A1 | 8/2019 |
| WO | WO 2019211741 A1 | 11/2019 |
| WO | WO 2019213777 A1 | 11/2019 |
| WO | WO 2019217795 A1 | 11/2019 |
| WO | WO 2019245848 A1 | 12/2019 |
| WO | WO 2019245849 A1 | 12/2019 |
| WO | WO 2019245851 A1 | 12/2019 |
| WO | WO 2019245852 A1 | 12/2019 |
| WO | WO 2019245853 A1 | 12/2019 |
| WO | WO 2019245854 A1 | 12/2019 |
| WO | WO 2019245856 A1 | 12/2019 |
| WO | WO 2019245857 A1 | 12/2019 |
| WO | WO 2019245860 A1 | 12/2019 |
| WO | WO 2019245861 A1 | 12/2019 |
| WO | WO 2019245862 A1 | 12/2019 |
| WO | WO 2019245864 A1 | 12/2019 |
| WO | WO 2019245865 A1 | 12/2019 |
| WO | WO 2019245866 A1 | 12/2019 |
| WO | WO 2019245867 A1 | 12/2019 |
| WO | WO 2019245868 A1 | 12/2019 |
| WO | WO 2019245869 A1 | 12/2019 |
| WO | WO 2019245870 A1 | 12/2019 |
| WO | WO 2020010034 A1 | 1/2020 |
| WO | WO 2020011688 A1 | 1/2020 |
| WO | WO 2020079098 A1 | 4/2020 |
| WO | WO 2020087141 A1 | 5/2020 |
| WO | WO 2020102665 A1 | 5/2020 |
| WO | WO 2020109903 A1 | 6/2020 |
| WO | WO 2020109904 A1 | 6/2020 |
| WO | WO 2020148292 A1 | 7/2020 |
| WO | WO 2020180917 A1 | 9/2020 |
| WO | WO 2020186194 A1 | 9/2020 |
| WO | WO 2020220208 A1 | 11/2020 |
| WO | WO 2020231655 A1 | 11/2020 |
| WO | WO 2020243483 A1 | 12/2020 |
| WO | WO 2020253280 A1 | 12/2020 |
| WO | WO 2021007418 A2 | 1/2021 |
| WO | WO 2021011760 A | 1/2021 |
| WO | WO 2021016429 A | 1/2021 |

OTHER PUBLICATIONS

US 9,451,972 B2, 09/2016, Lang et al. (withdrawn)
Office Action from U.S. Appl. No. 17/117,779, dated Sep. 30, 2021, 19 pp.
"Aurora—The Aurora Electromagnetic Tracking System," NDI, Nov. 2013, 8 pp.
"Blueprint 3d Planning Software + PSI," Wright Medical Group, retrieved from https://www.wright.com/blueprint-3d-planning-psi-system on Oct. 15, 2020, 9 pp.
"HoloLens 2," Microsoft HoloLens, retrieved from https://www.microsoft.com/en-us/hololens Oct. 15, 2020, 5 pp.
"In'Tech Medical launches Wayvio, a new intelligent solution to enhance the reliability of surgical instruments and streamline medi-

(56) References Cited

OTHER PUBLICATIONS cal device logistics," accessed from https://intech-medical.com/component/content/article/36-press-releases/58-in-tech-medical-launches-wayvio-a-new-intelligent-solution-to-enhance-the . . . on or about Nov. 12, 2018, 4 pp.
"Wayvio," Innovate How You Operate, accessed from http://www.wayvio.com/#features on or about Nov. 12, 2018, 5 pp.
"Work together from anywhere," Microsoft Dynamics 365 Remote Assist, downloaded from https://dynamics.microsoft.com/en-us/mixed-reality/remote-assist/ on Aug. 24, 2020, 8 pp.
Abdelhameed et al., "Neural network-based shoulder instability diagnosis modelling for robot-assisted rehabilitation systems," Systems Science & Control Engineering, ISSN: 2164-2583, Oct. 13, 2015, 11 pp.
Anogianakis et al., "Medical emergency aid through telematics: design, implementation guidelines and analysis of user requirements for the Mermaid project," Journal of Medical Informatics, vol. 52, Oct. 1998, 11 pp.
BIO-RSA, "Surgical Technique," Tornier, Jul. 2010, 20 pp.
Birkfellner et al., "Chapter 2—Tracking Devices," from Image-Guided Interventions, Springer Science, 2008, 23 pp. (Applicant points out, in accordance with MPEP 609.04(a), that the year of publication, 2008, is sufficiently earlier than the effective U.S. filing date, so that the particular month of publication is not in issue.).
Cho et al., "A Multi-ring Color Fiducial System and A Rule-Based Detection Method for Scalable Fiducial-tracking Augmented Reality," Proceedings of the International Conference of Virtual Reality Annual International Symposium, Feb. 1998, 15 pp.
Daftry et al., "Flexible and User-Centric Camera Calibration using Planar Fiducial Markers," British Machine Vision Conference, Sep. 9-13, 2013, 13 pp.
Daley, S., "The Cutting Edge: 10 Companies Bringing Virtual Reality & AR to the OR," Tech Jobs by Built In, Jun. 24, 2020, 13 pp.
Franz et al., "Electromagnetic Tracking in Medicine—A Review of Technology, Validation, and Applications," IEEE Transactions on Medical Imaging, vol. 33, No. 8, Aug. 2014, pp. 1702-1725.
Gackowski et al., "Development, Implementation, and Multicenter Clinical Validation of the TeleDICOM-Advanced, Interactive Teleconsultation System," Journal of Digital Imaging, vol. 24. No 3, Jun. 2011, pp. 541-551.
Giannotti et al., "Indices of risk assessment of fracture of the proximal humerus," Clinical Cases in Mineral and Bone Metabolism, published online May 2012, 3 pp.
Haramiishi et al., "CT and SPECT image fusion using external fiducial markers for detection of the sentinel lymph nodes in breast cancer," International Journal of Diagnostic Imaging, vol. 4, No. 2, accepted Mar. 28, 2017, 5 pp.
Inbone® II Total Ankle System—Surgical Technique, from Wright Medical Technology, Inc., Aug. 2015, 64 pp.
Infinity® Total Ankle System—Surgical Technique, from Wright Medical Technology, Inc., Aug. 2015, 76 pp.
Koulechov, "Leistungssteuerung chirurgischer Instrumente in der Kopf-Chirurgie," Technical University of Munich, In the German language only, Jan. 1, 2006. 152 pp. (Relevant sections figures 22, 24, 28; p. 40-p. 50).
Kruger, "Ein modulates Navigationssystem für die dentale Implantologie," Nov. 16, 2006, 142 pp. (English language unavailable; relevant section figure 27; p. 58, p. 83 See Int'l Search Report and Written Opinion for PCT/US2019/036992 for explanation of relevance.).
Maresceaux et al., "Bildfusion, virtuelie Realitat, Robotik und Navigation," English Abstract Only, Springer-Verlag, May 2002, 6 pp.
Mather et al., "Proximal humerus cortical bone thickness correlates with bone mineral density and can clinically rule out osteoporosis," Journal of Shoulder and Elbow Surgery, Jun. 2013. 7 pp.
Miller et al., "Augmented Reality and Telestrated Surgical Support for Point of Injury Combat Casualty Care: A Feasibility Study," International Conference on Augmented Cognition, Conference paper available online Jun. 3, 2018, 11 pp.
Nakao et al., "Augmented Endoscopic Images Overlaying Shape Changes in Bone Cutting Procedures," PLoS One, vol. 11, No. 9, Sep. 2016, 20 pp.
Poltaretskyi et al., "Prediction of the pre-morbid 3D anatomy of the proximal humerus based on the statistical shape modelling," The British Editorial Society of Bone & Joint Surgery, vol. 99-B, No. 7, Jul. 2017, 2 pp.
Prophecy Infinity Pre-Operative navigation Guides—Surgical Technique, by Wright Medical Technology, Inc., Oct. 2014, 80 pp.
Public Workshop—Medical Extended Reality: Toward Best Evaluation Practices For Virtual and Augmented Reality in Medicine, by United States of America Department of Health and Human Services Food and Drug Administration—Center for Devices and Radiological Health, Mar. 5, 2020, 188 pp.
Scalise et al., "Inter-rater reliability of an arthritic glenoid morphology classification system," Journal of Shoulder and Elbow Surgery; Jul./Aug. 2008, 3 pp.
Shukla et al., "Intraobserver and interobserver reliability of the modified Walch classification using radiographs and computed tomography," Journal of Shoulder and Elbow Surgery, vol. 28, Issue 4, Apr. 2019, available online Dec. 6, 2018, 6 pp.
Tan et al., "6D Object Pose Estimation with Depth Images: A Seamless Approach for Robotic Interaction and Augmented Reality," Sep. 5, 2017, 4 pp.
Tang et al., "Physio@Home: Exploring Visual Guidance and Feedback Techniques for Physiotherapy Exercises," Home Physiotherapy & Rehabilitation, Apr. 18, 2015, 10 pp.
Tingart et al., "The cortical thickness of the proximal humeral diaphysis predicts bone mineral density of the proximal humerus," The Journal of Bone & Joint Surgery, vol. 85-B, No. 4, May 2003, accepted after revision Sep. 24, 2002, 7 pp.
Traub et al., "Advanced Display and Visualization Concepts for Image Guided Surgery;" Journal of Display Technology, vol. 4, No. 4, Dec. 2008, 8 pp.
VanAmerongen, R., "How to run a demo with Microsoft Hololens and share your screen," from AMIS Technology Blog, AMIS, Data Driven Blog, dated Dec. 5, 2016, downloaded from https://technology.amis.nl/2016/12/05/demo-microsoft-hololens-and-share-your-screen/ on Oct. 21. 2020, 15 pp.
Wang et al., "Fiducial-Aided Robust Positioning of Optical Freeform Surfaces," Micromachines, accessed from www.mdpi.com/journal/micromachines, Jan. 30. 2018, 10 pp.
Wright "Aequalis Reversed II Shoulder System," Tornier, CAW-2145, May 12, 2016, 52 pp.
Wright Medical, "BluePrint Video-Wright Medical Announces the Acquisition of IMASCAP SAS", accessed from www.imascap.com/wp-content/uploads/2017/12/blueprintvid.mp4, Dec. 14, 2017, 9 pp.
Wright, "Aequalis Ascend Flex, Convertible Shoulder System," CAW-5396, Tornier, Mar. 2017, 88 pp.
Wright, "Aequalis Perform, Anatomic Glenoid System," CAW-5233, Tornier, Jul. 2017, 36 pp.
Wright, "BIO-RSA Bony Increased Offset—Reversed Shoulder Arthroplasty," Tornier, CAW-2150, Feb. 12, 2016, 20 pp.
Wright, "BluePrint, 3d Planning + PSI," User Manual V2.1. Tornier. CAW-8754, Nov. 2017, 18 pp.
Youtube, "06 IMASCAP," uploaded by Cesim Sante on Jun. 3, 2015, accessed from https://www.youtube.com/watch?v=ZT8Q5ZTF -Y, 1 pp.
Youtube, "Mixed Reality usage in orthopedic surgery," uploaded by Sergii Poltaretskyi on Feb. 20, 2019, accessed from https://www.youtube.com/watch?v=ewMIgku_cug&feature=youtu.be, 7 pp.
International Search Report find Written Opinion of International Application No. PCT/US2019/036973, dated Oct. 9, 2019, 16 pp.
International Preliminary Report on Patentability from International Application No. PCT/US2019/036973, dated Dec. 30, 2020, 9 pp.
International Search Report and Written Opinion of International Application No. PCT/USf2019/036980, dated Sep. 26, 2019, 16 pp.
International Preliminary Report on Patentability from International Application No. PCT/US2019/036980, dated Dec. 30, 2020, 10 pp.
International Search Report and Written Opinion of International Application No. PCT/US2019/036978, dated Oct. 1, 2019, 17 pp.

(56) References Cited

OTHER PUBLICATIONS

International Preliminary Report on Patentability from International Application No. PCT/US2019/036978, dated Dec. 30, 2020, 8 pp.
International Search Report and Written Opinion of International Application No. PCT/US2019/037004, dated Oct. 2, 2019, 18 pp.
International Preliminary Report on Patentability from International Application No. PCT/US2019/037004, dated Dec. 30, 2020, 9 pp.
International Search Report and Written Opinion of International Application No. PCT/US2019/036984, dated Oct. 2, 2019, 14 pp.
International Preliminary Report on Patentability from International Application No. PCT/US2019/036984, dated Dec. 30, 2020, 8 pp.
International Search Report and Written Opinion of International Application No. PCT/US2019/036996, Oct. 14, 2019, 14 pp.
International Preliminary Report on Patentability from International Application No. PCT/US2019/036996, dated Dec. 30, 2020, 9 pp.
International Search Report and Written Opinion of International Application No. PCT/US2019/036981, dated Jan. 21, 2020, 17 pp.
International Preliminary Report on Patentability from International Application No. PCT/US2019/036981, dated Dec. 30, 2020, 10 pp.
International Search Report find Written Opinion of International Application No. PCT/US2019/036986, dated Oct. 4, 2019, 18 pp.
International Preliminary Report on Patentability from International Application No. PCT/US2019/036986, dated Dec. 30, 2020, 11 pp.
International Search Report and Written Opinion of International Application No. PCT/US2019/036991, dated Oct. 4, 2019, 18 pp.
International Preliminary Report on Patentability from International Application No. PCT/US2019/036991, dated Dec. 30, 2020, 11 pp.
International Search Report and Written Opinion of International Application No. PCT/US2019/037008, dated Oct. 24, 2019, 20 pp.
International Preliminary Report on Patentability from International Application No. PCT/US2019/037008, dated Dec. 30, 2020, 11 pp.
Invitation to Restrict, or Pay Additional Fees from International Application No. PCT/US2019/036992, dated Sep. 20, 2019, 16 pp.
International Search Report and Written Opinion of International Application No. PCT/US2019/036992, dated Feb. 5, 2020, 24 pp.
International Preliminary Report on Patentability from International Application No. PCT/US2019/036992, dated Dec. 30, 2020, 14 pp.
International Search Report and Written Opinion of International Application No. PCT/US2019/036971, dated Sep. 26, 2019, 14 pp.
International Preliminary Report on Patentability from International Application No. PCT/US2019/036971, dated Dec. 30, 2020, 7 pp.
Invitation to Pay Additional Fees from International Application No. PCT/US2019/037003, dated Sep. 30, 2019, 12 pp.
International Search Report find Written Opinion of International Application No. PCT/US2019/037003, dated Dec. 18, 2019, 21 pp.
International Preliminary Report on Patentability from International Application No. PCT/US2019/037003, dated Dec. 30, 2020, 11 pp.
International Search Report and Written Opinion of International Application No. PCT/US2019/036993, dated Oct. 2, 2019, 14 pp.
International Preliminary Report on Patentability from International Application No. PCT/US2019/036993, dated Dec. 30, 2020, 8 pp.
International Search Report and Written Opinion of International Application No. PCT/US2019/036998, dated Oct. 2, 2019, 14 pp.
International Preliminary Report on Patentability from International Application No. PCT/US2019/036998, dated Dec. 30, 2020, 8 pp.
International Search Report and Written Opinion of International Application No. PCT/US2019/037007, dated Nov. 12, 2019, 12 pp.
International Preliminary Report on Patentability from International Application No. PCT/US2019/037007, dated Dec. 30, 2020, 8 pp.
International Search Report and Written Opinion of International Application No. PCT/US2019/037014, dated Oct. 7, 2019, 12 pp.
International Preliminary Report on Patentability from International Application No. PCT/US2019/037014, dated Dec. 30, 2020, 7 pp.
U.S. Appl. No. 17/221,320, filed Apr. 2, 2021, naming inventors Poltaretskyi et al.
U.S. Appl. No. 17/117,817, filed Dec. 10, 2020, naming inventors Poltaretskyi et al.
Response to Communication Pursuant to Rules 161(1) and 162 EPC dated Jan. 26, 2021, from counterpart European Application No. 19742097.9, filed Jul. 29, 2021, 18 pp.
Response to Office Action dated Sep. 30, 2021, from U.S. Appl. No. 17/117,779, filed Dec. 29, 2021, 12 pp.
"ArUco: a Minimal Library for Augmented Reality Applications Based on OpenCV," retrieved from https://www.uco.es/investiga/grupos/ava/node/26, on Nov. 5, 2019, 2 pp.
Boissonnat, "Shape Reconstruction from Planar Cross Sections," Computer Vision, Graphics, and Image Processing, vol. 44, Oct. 1988, 29 pp.
Marker et al., "Contour-Based Surface Reconstruction using Implicit Curve Fitting, and Distance Field Filtering and Interpolation," Volume Graphics, Jan. 2006, 9 pp.
Nguyen et al., "A New Segmentation Method for MRI Images of the Shoulder Joint," Fourth Canadian Conference on Computer and Robot Vision(CRV'07), May 28-30, 2007, 8 pp.
Notice of Allowance from U.S. Appl. No. 17/117,779, dated Jun. 2, 2022, 8 pp.
Final Office Action from U.S. Appl. No. 17/117,779, dated Mar. 11, 2022, 17 pp.
Response to Final Office Action dated Mar. 11, 2022, from U.S. Appl. No. 17/117,779, filed May 10, 2022, 10 pp.
Applicant-Initiated Interview Summary from U.S. Appl. No. 17/117,779, dated May 10, 2022, 2 pp.
Notice of Allowance from U.S. Appl. No. 17/117,779 dated Sep. 29, 2022, 9 pp.

* cited by examiner

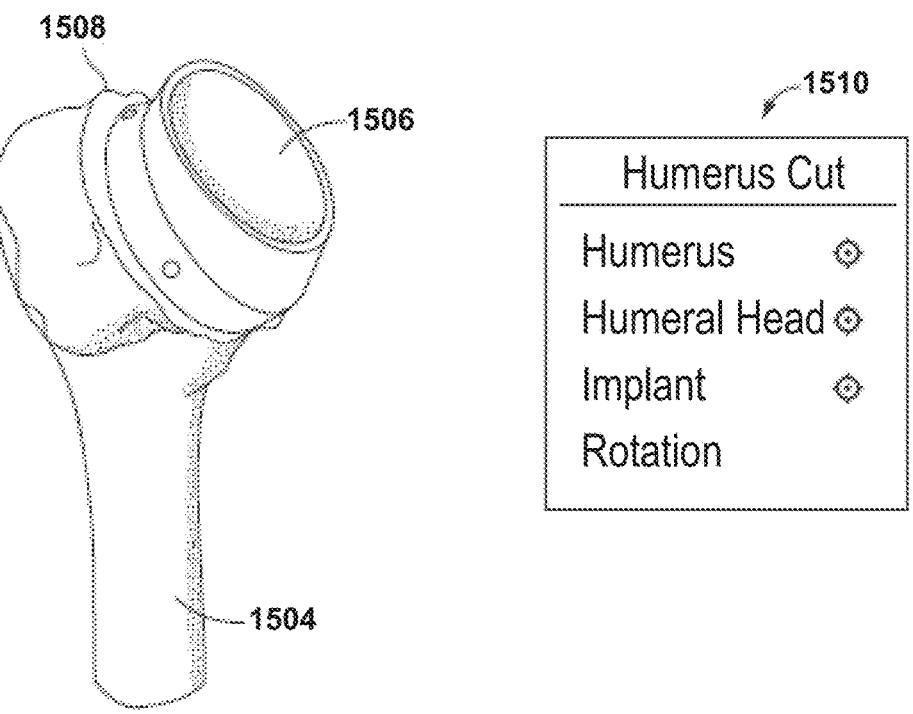
FIG. 15A
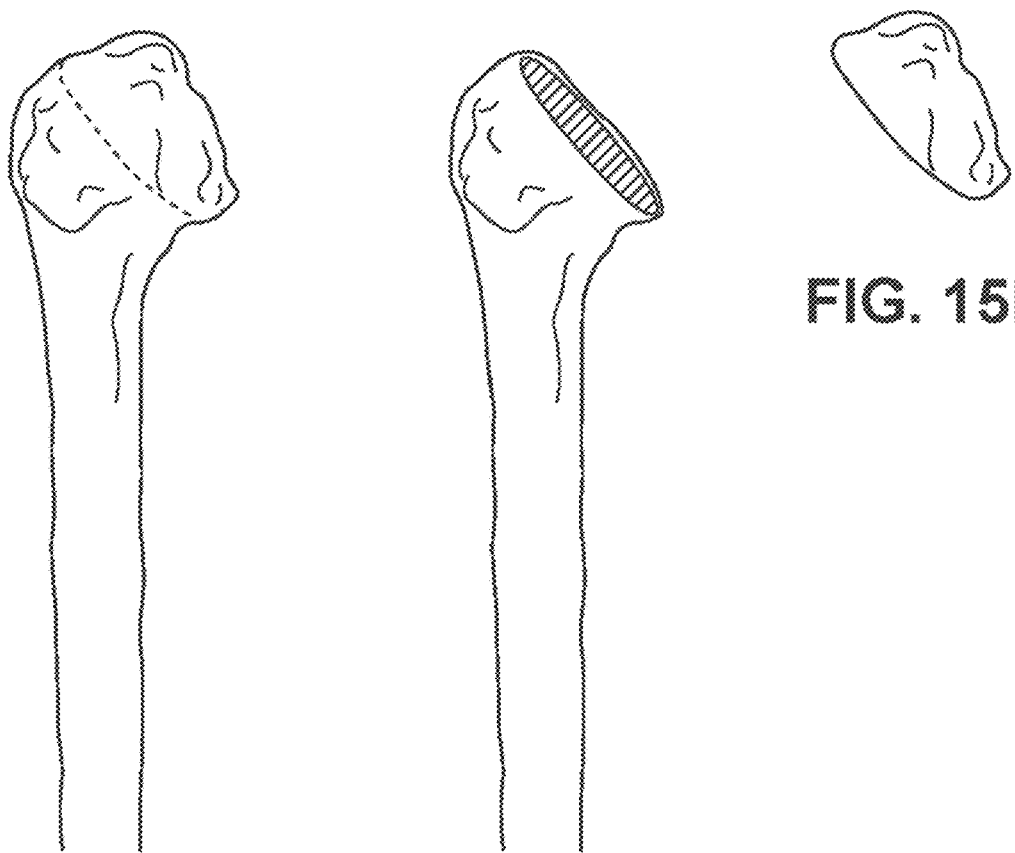
FIG. 15B    FIG. 15C
FIG. 15D

Control the position of the back side of the reamer. Use depth camera to fit a plane to the back side.

Add a plane marker (or other type of marker) to a reamer, in order to control the depth translation.

Plane as a marker. Detect points on the plane with depth camera and fit the plane to control the depth translation

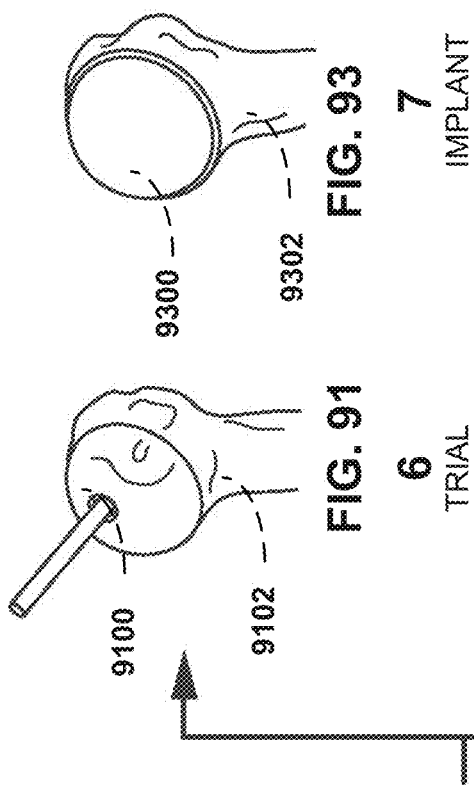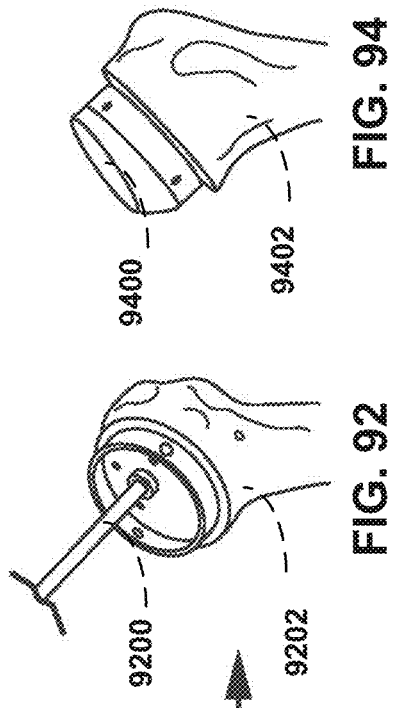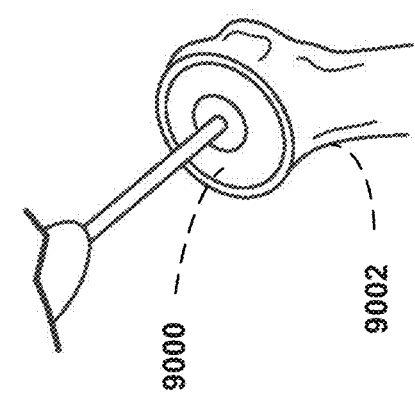
FIG. 90, FIG. 91, FIG. 92, FIG. 93, FIG. 94

MIXED-REALITY SURGICAL SYSTEM WITH PHYSICAL MARKERS FOR REGISTRATION OF VIRTUAL MODELS

This patent application is a continuation of International Application No. PCT/US2019/036971, filed Jun. 13, 2019, which claims the benefit of U.S. Provisional Patent Application No. 62/687,014, filed Jun. 19, 2018, U.S. Provisional Patent Application No. 62/739,406, filed Oct. 1, 2018, U.S. Provisional Patent Application No. 62/778,774, filed Dec. 12, 2018, U.S. Provisional Patent Application No. 62/778,789, filed Dec. 12, 2018, U.S. Provisional Patent Application No. 62/778,764, filed Dec. 12, 2018, U.S. Provisional Patent Application No. 62/778,797, filed Dec. 12, 2018, U.S. Provisional Patent Application No. 62/778,778, filed Dec. 12, 2018, U.S. Provisional Patent Application No. 62/778,788, filed Dec. 12, 2018, U.S. Provisional Patent Application No. 62/778,760, filed Dec. 12, 2018, U.S. Provisional Patent Application No. 62/778,772, filed Dec. 12, 2018, U.S. Provisional Patent Application No. 62/778,796, filed Dec. 12, 2018, U.S. Provisional Patent Application No. 62/778,782, filed Dec. 12, 2018, U.S. Provisional Patent Application No. 62/778,791, filed Dec. 12, 2018, U.S. Provisional Patent Application 62/804,383, filed Feb. 12, 2019, U.S. Provisional Patent Application 62/804,392, filed Feb. 12, 2019, and U.S. Provisional Patent Application 62/804,402, filed Feb. 12, 2019.

BACKGROUND

Surgical joint repair procedures involve repair and/or replacement of a damaged or diseased joint. Many times, a surgical joint repair procedure, such as joint arthroplasty as an example, involves replacing the damaged joint with a prosthetic that is implanted into the patient's bone. Proper selection of a prosthetic that is appropriately sized and shaped and proper positioning of that prosthetic to ensure an optimal surgical outcome can be challenging. To assist with positioning, the surgical procedure often involves the use of surgical instruments to control the shaping of the surface of the damaged bone and cutting or drilling of bone to accept the prosthetic.

Today, virtual visualization tools are available to surgeons that use three-dimensional modeling of bone shapes to facilitate preoperative planning for joint repairs and replacements. These tools can assist surgeons with the design and/or selection of surgical guides and implants that closely match the patient's anatomy and can improve surgical outcomes by customizing a surgical plan for each patient.

SUMMARY

This disclosure describes a variety of techniques for providing preoperative planning, medical implant design and manufacture, intraoperative guidance, postoperative analysis, and/or training and education for surgical joint repair procedures. The techniques may be used independently or in various combinations to support particular phases or settings for surgical joint repair procedures or provide a multi-faceted ecosystem to support surgical joint repair procedures. In various examples, the disclosure describes techniques for preoperative surgical planning, intra-operative surgical planning, intra-operative surgical guidance, intra-operative surgical tracking and post-operative analysis using mixed reality (MR)-based visualization. In some examples, the disclosure also describes surgical items and/or methods for performing surgical joint repair procedures. In some examples, this disclosure also describes techniques and visualization devices configured to provide education about an orthopedic surgical procedure using mixed reality.

The details of various examples of the disclosure are set forth in the accompanying drawings and the description below. Various features, objects, and advantages will be apparent from the description, drawings, and claims.

BRIEF DESCRIPTION OF THE DRAWINGS

FIG. 15A is an example of a humerus cut page of the user interface of FIG. 10, according to an example of this disclosure.

FIGS. 15B-15D are examples of hiding virtual objects in the humerus cut page of FIG. 15A, according to an example of this disclosure.

FIG. 90 is a view of an example protect procedure in a shoulder arthroplasty procedure.

FIG. 91 and FIG. 92 are views of an example trial procedure in a shoulder arthroplasty procedure.

FIG. 93 and FIG. 94 are views of an example implant procedure in a shoulder arthroplasty procedure.

FIG. 131 is a conceptual block diagram of an educational system for orthopedic surgical education to be used by a teacher and a plurality of students where one or more of the students are located remotely relative to the teacher.

FIGS. 132 and 133 are conceptual block diagrams of other educational systems that use MR and/or VR for orthopedic surgical education.

FIG. 134 is a conceptual block diagram of an educational system that uses MR and/or VR for orthopedic surgical education where the teacher and the students are able to manipulate different virtual models that include virtual information.

FIG. 135 is a conceptual block diagram of an educational system that use MR and/or VR for orthopedic surgical education where the teacher is able to assign manipulation rights to a virtual model to allow students to manipulate the virtual model.

FIGS. 136-139 are flow diagrams illustrating educational techniques that can be performed with the aid of MR and/or VR.

FIG. 140 is a conceptual block diagram of an educational system that use MR and/or VR for orthopedic surgical education where a user is able to launch a manipulatable copy of a virtual model.

FIG. 141 is a conceptual block diagram of an educational system that use MR and/or VR for orthopedic surgical education where students and teachers are able to view and compare several different virtual models.

FIG. 142 is a conceptual block diagram of an educational system that use MR and/or VR for orthopedic surgical education where a teacher has a virtual control menu for controlling MR/VR educational content.

FIG. 143 is a conceptual block diagram of an educational system that use MR and/or VR for orthopedic surgical education where a teacher and students have virtual control elements for controlling MR/VR educational content.

FIG. 144 is a flow diagram illustrating educational techniques that can be performed with the aid of MR and/or VR.

FIG. 145 is a conceptual block diagram of an educational system that includes features to help educate a remote user on specific details of an ongoing surgical procedure.

FIGS. 146 and 147 are flow diagrams illustrating interoperative educational techniques that to help educate a remote user on specific details of an ongoing surgical procedure.

Figure 148:
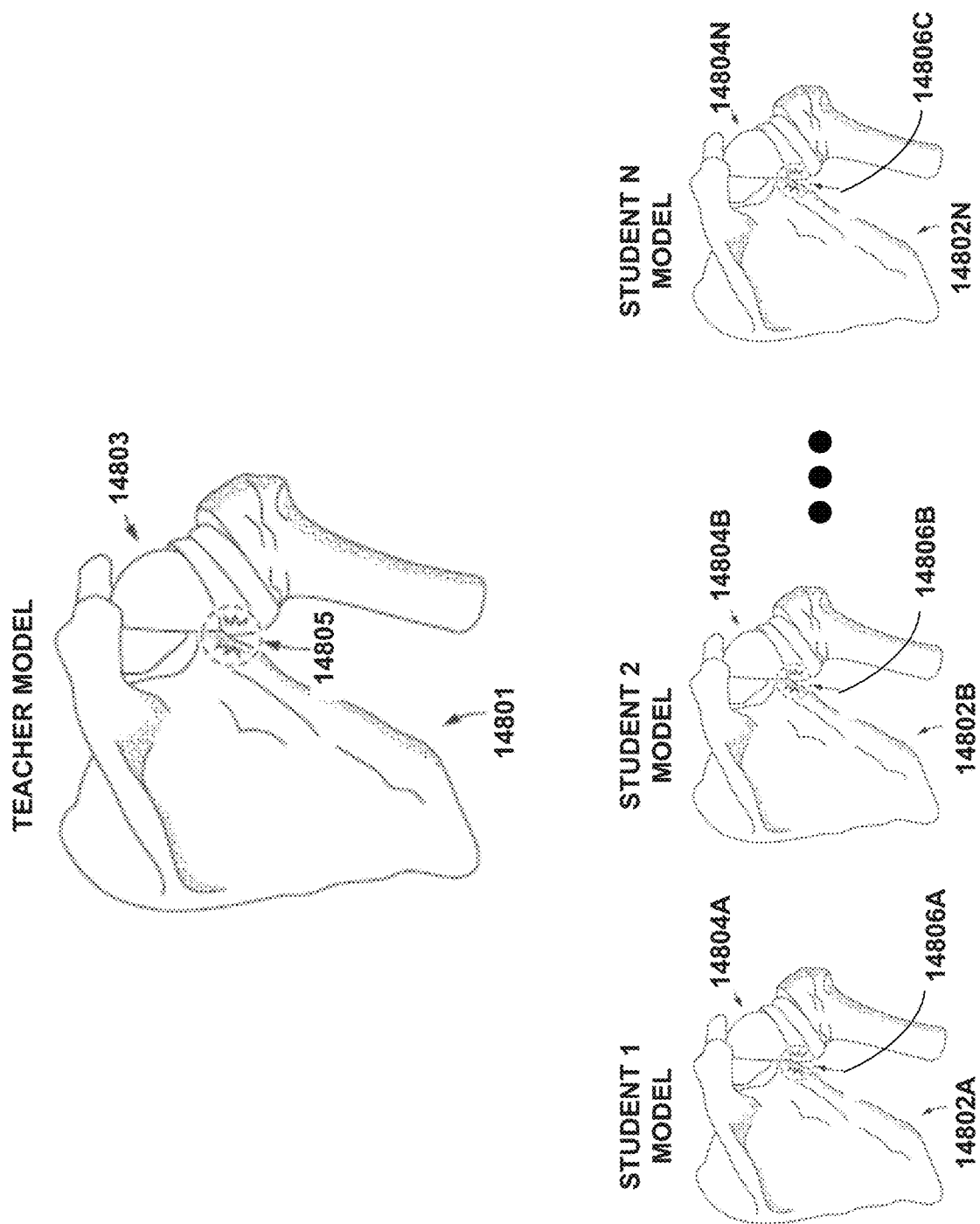

FIG. 148 is one conceptual example showing a virtual teacher model of an example virtual shoulder and multiple student models that have similar virtual content to the teacher model.

Figure 149:
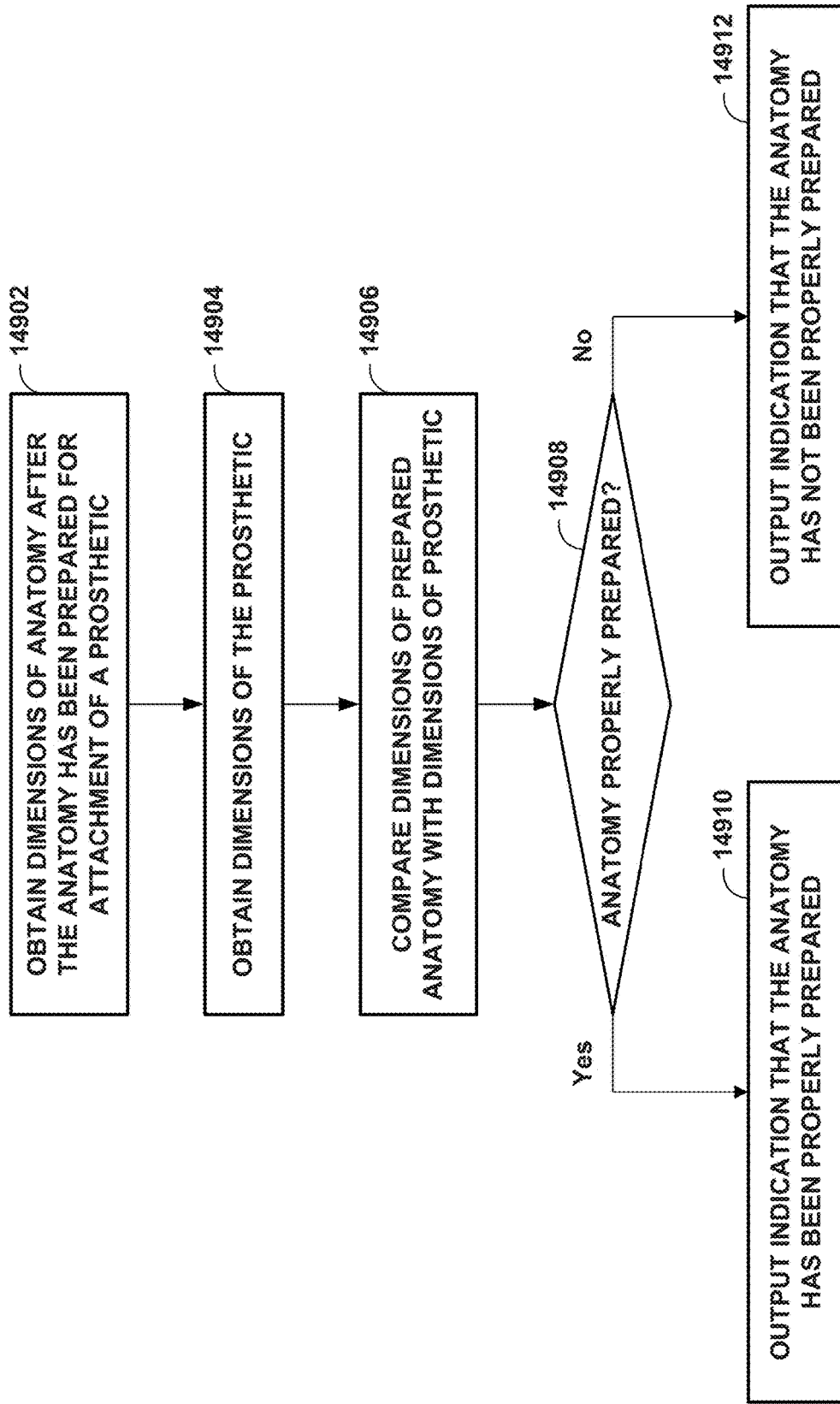

FIG. 149 is a flow diagram illustrating example techniques for MR aided validation of anatomy preparation, in accordance with one or more techniques of this disclosure.

Figure 150:
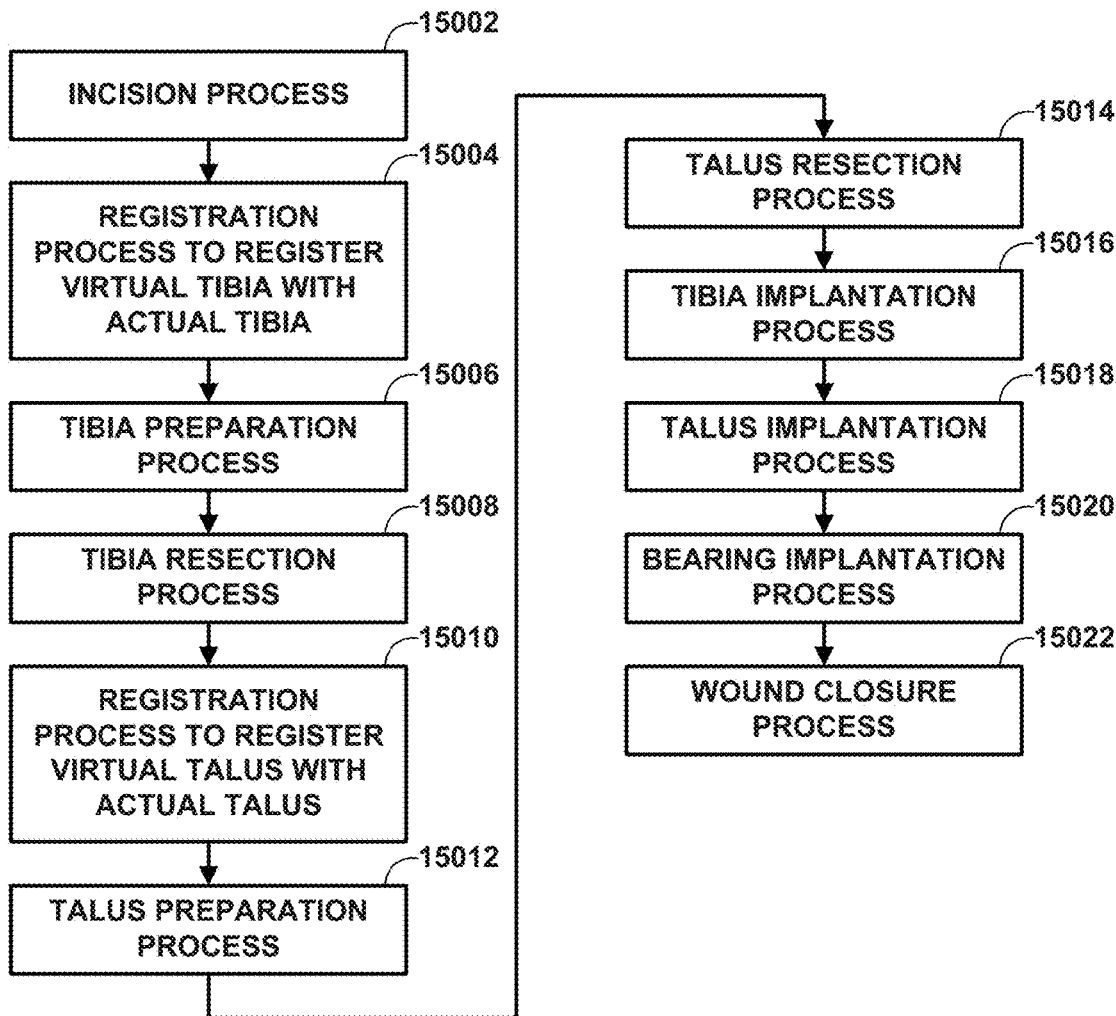

FIG. 150 is a flowchart illustrating example stages of an ankle joint repair surgery.

Figure 151A:
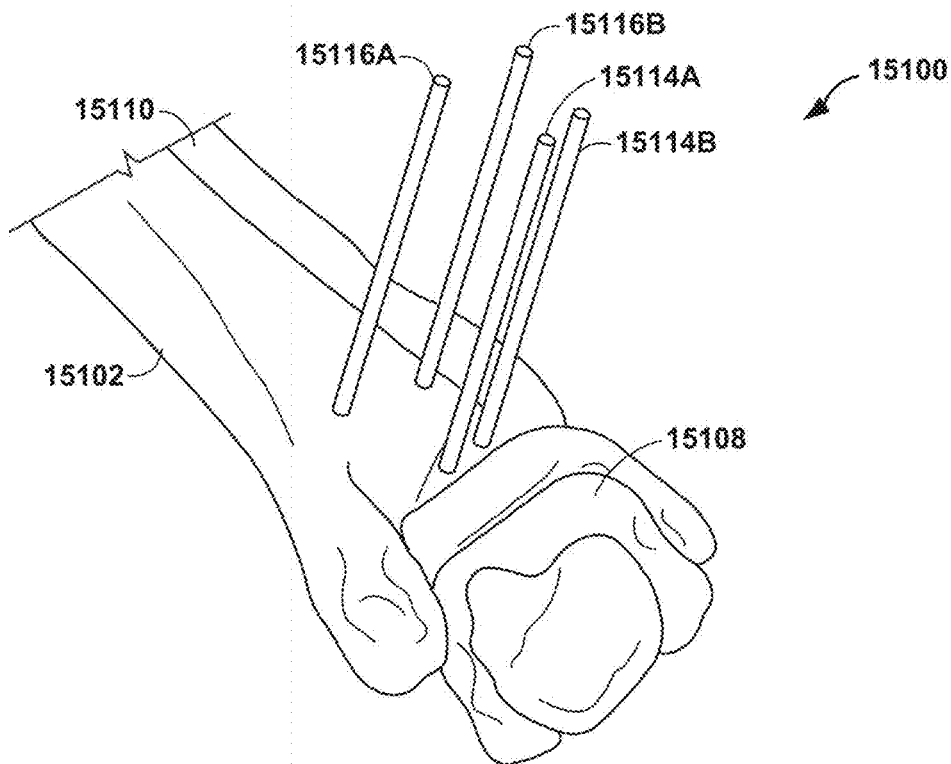
Figure 151B:
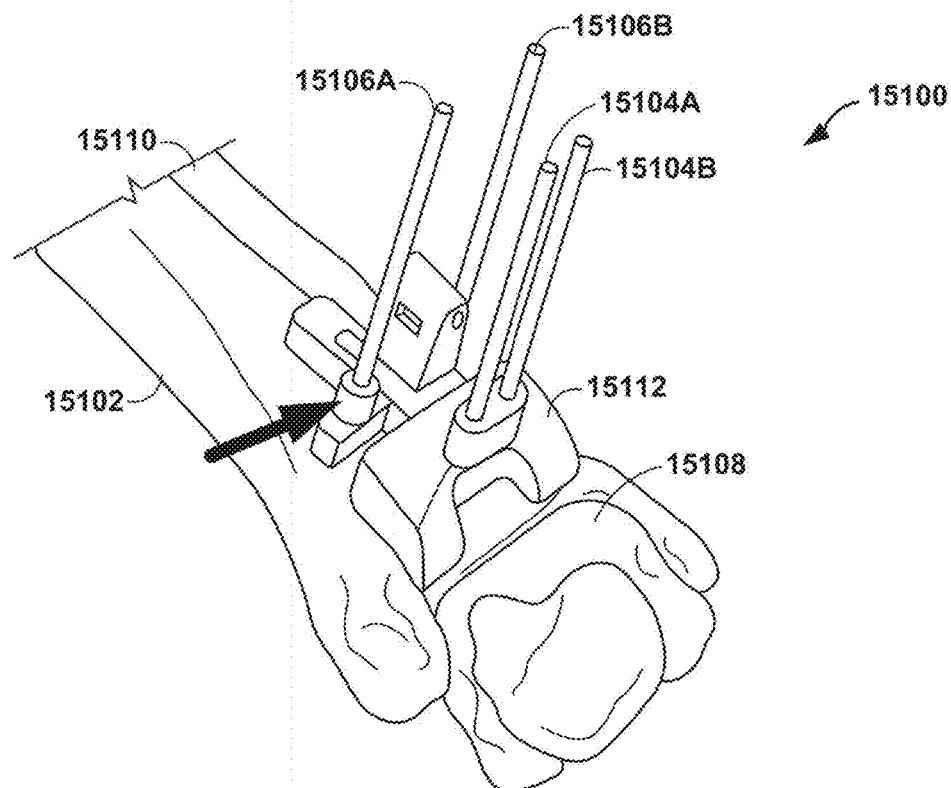

FIGS. 151A and 151B are conceptual diagrams illustrating example attachment of guide pins to a tibia.

Figure 152:
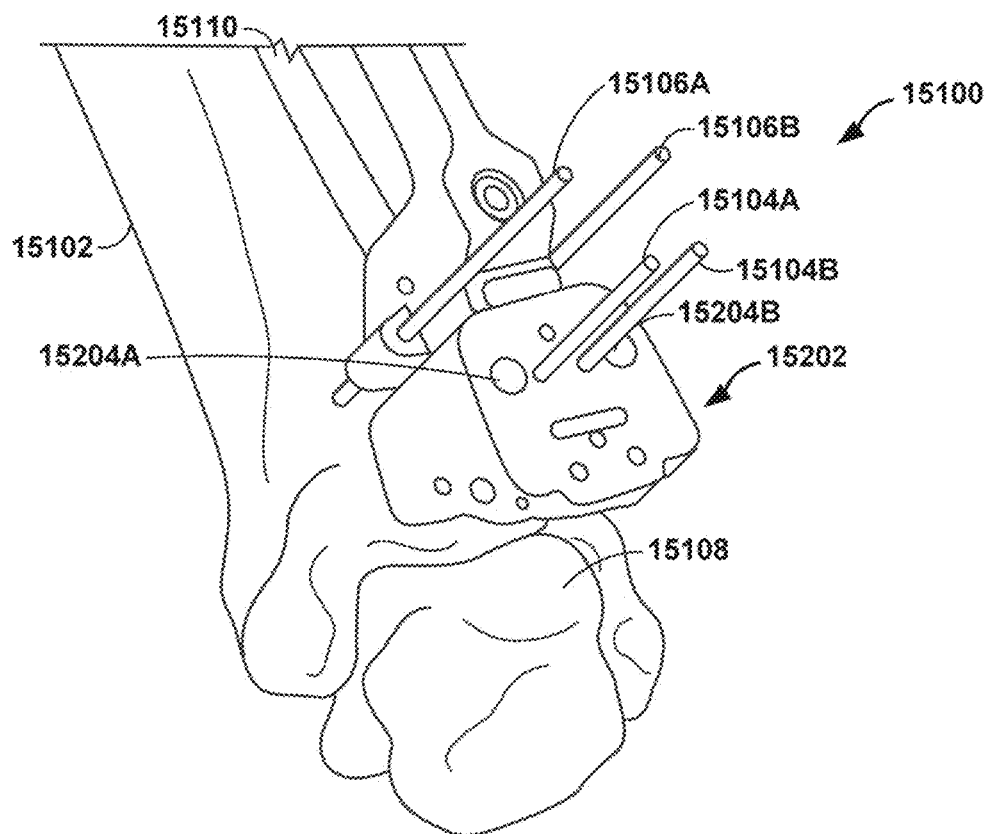

FIG. 152 is a conceptual diagram illustrating example drilling of holes in a tibia.

Figure 153:
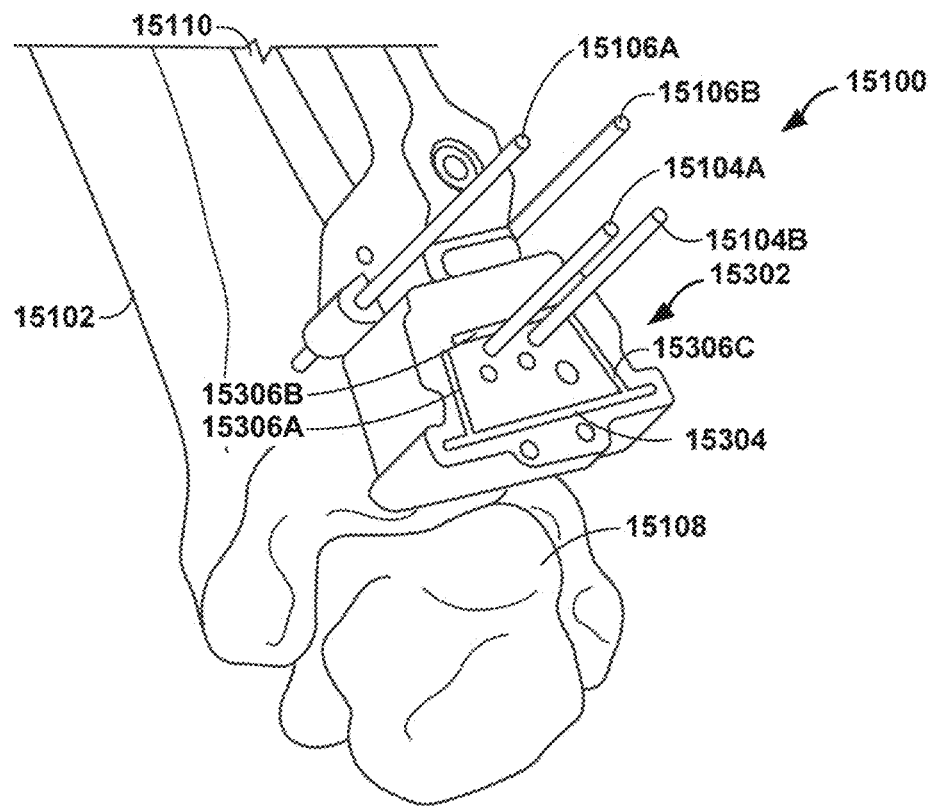

FIG. 153 is a conceptual diagram illustrating example resection of a tibia.

Figure 154A:
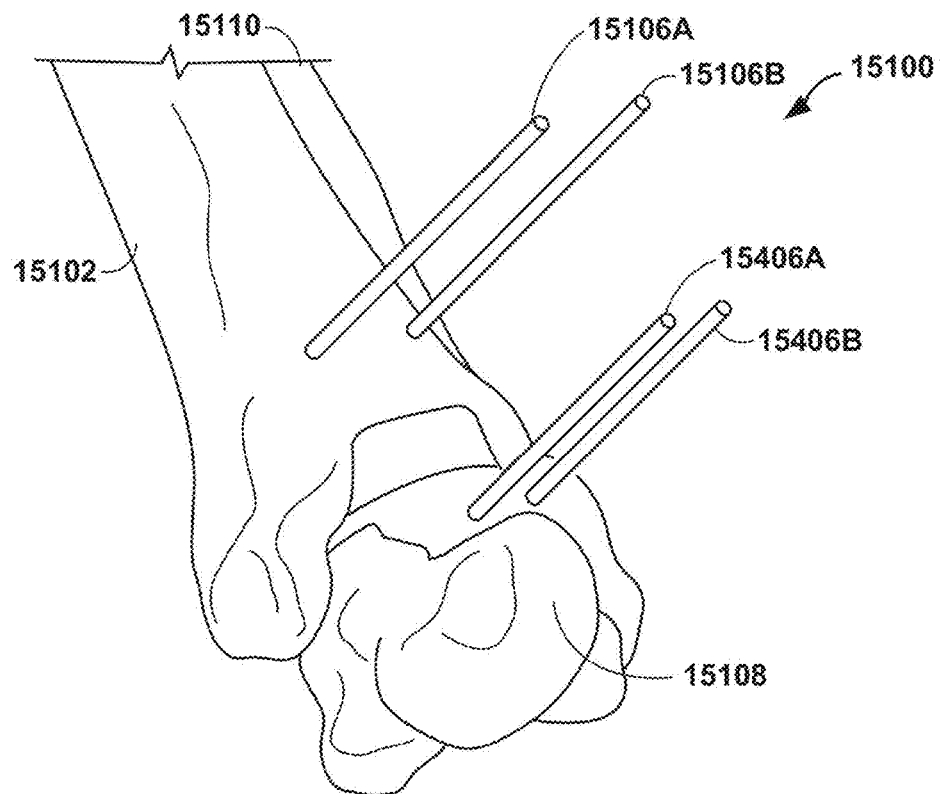
Figure 154B:
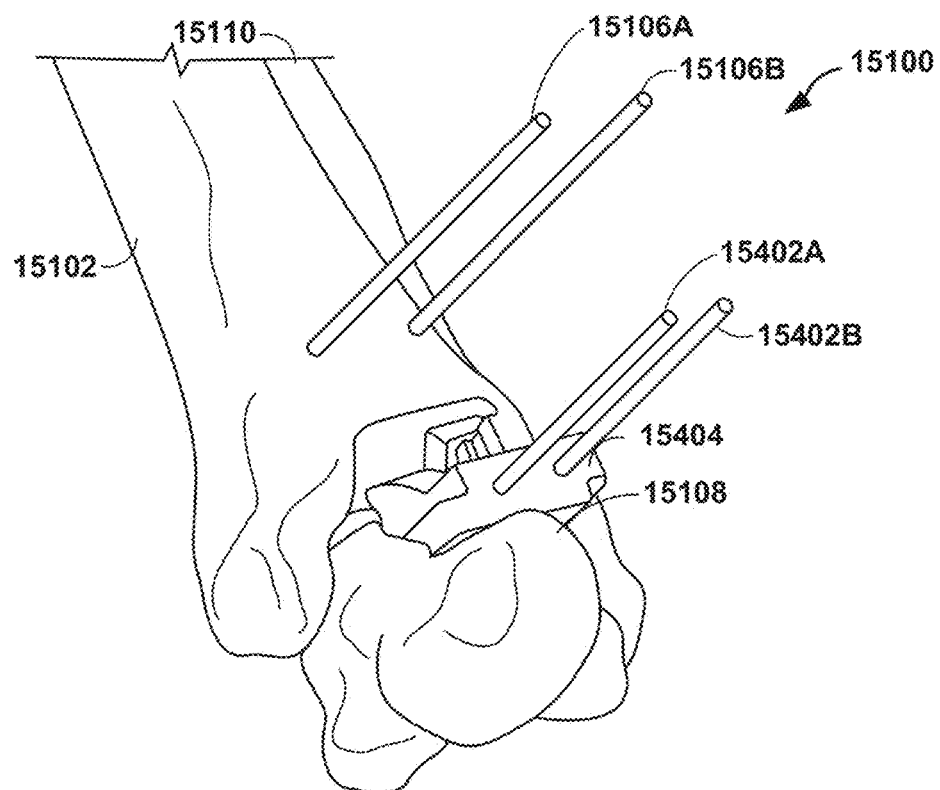

FIGS. 154A and 154B are conceptual diagrams illustrating example guide pins installed in a talus during a talus preparation process.

Figure 155:
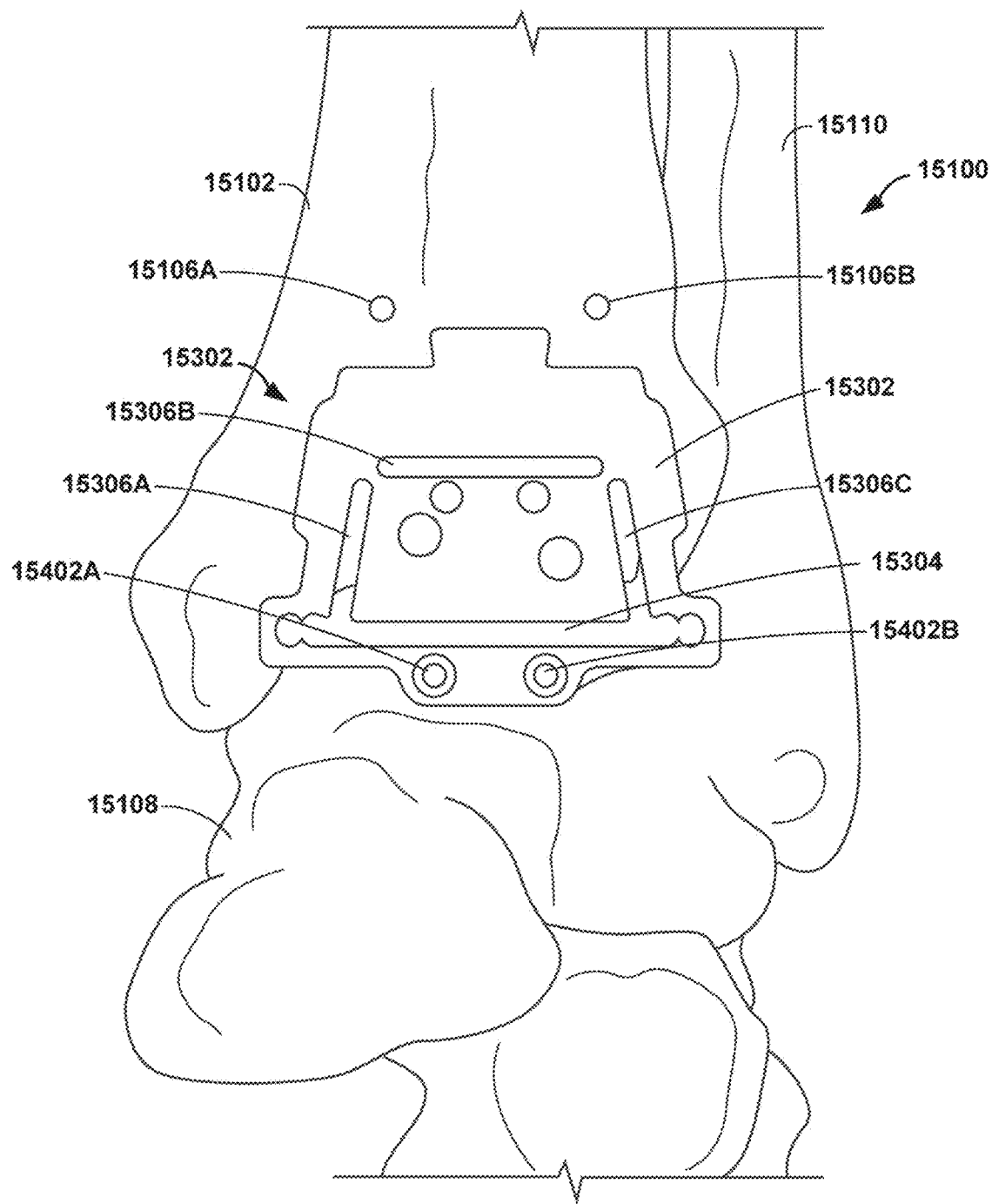

FIG. 155 is a conceptual diagram illustrating example resection of a talus.

Figure 156:
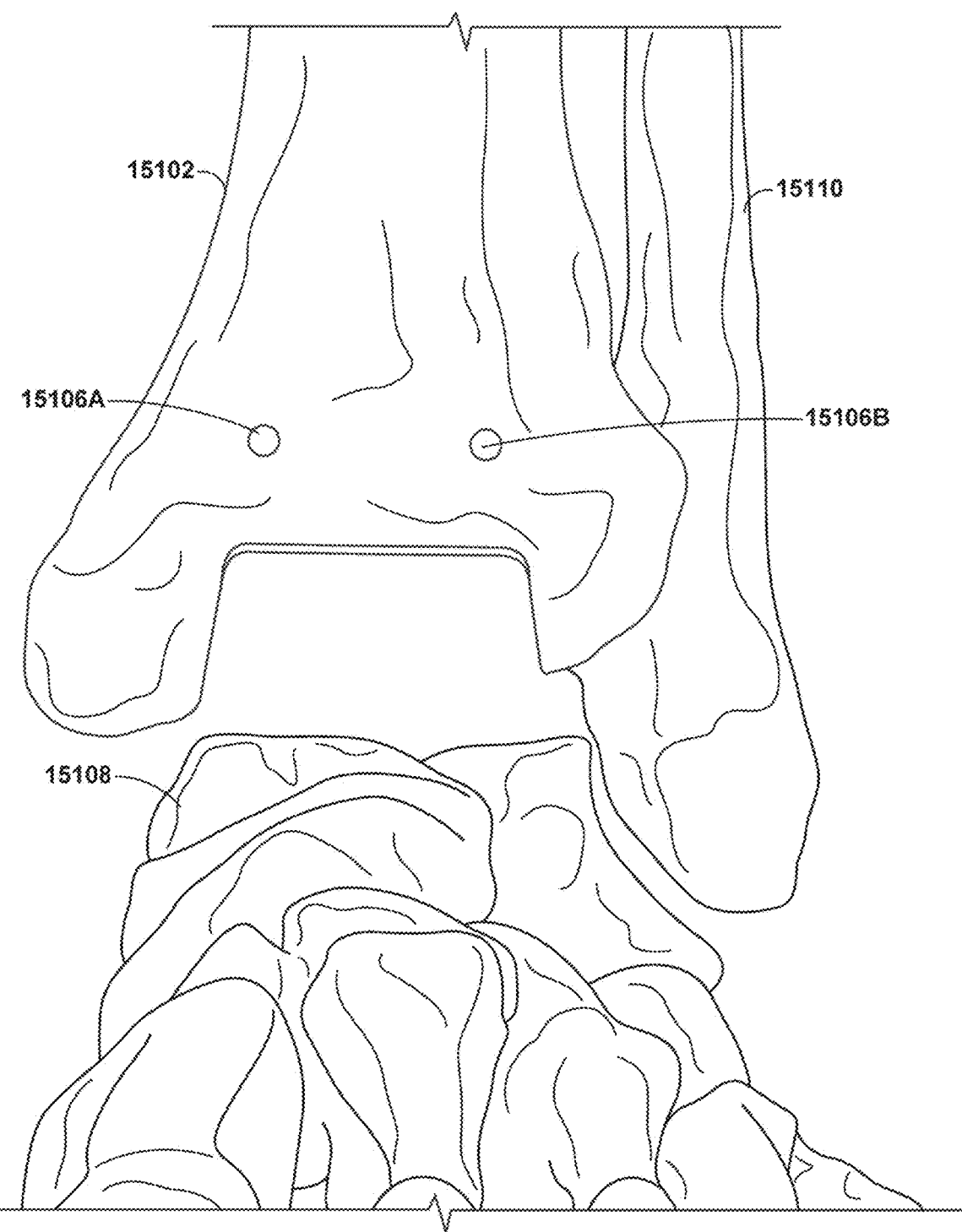

FIG. 156 is a conceptual diagram of an example ankle after performance of a tibial resection and a talar resection.

Figure 157A:
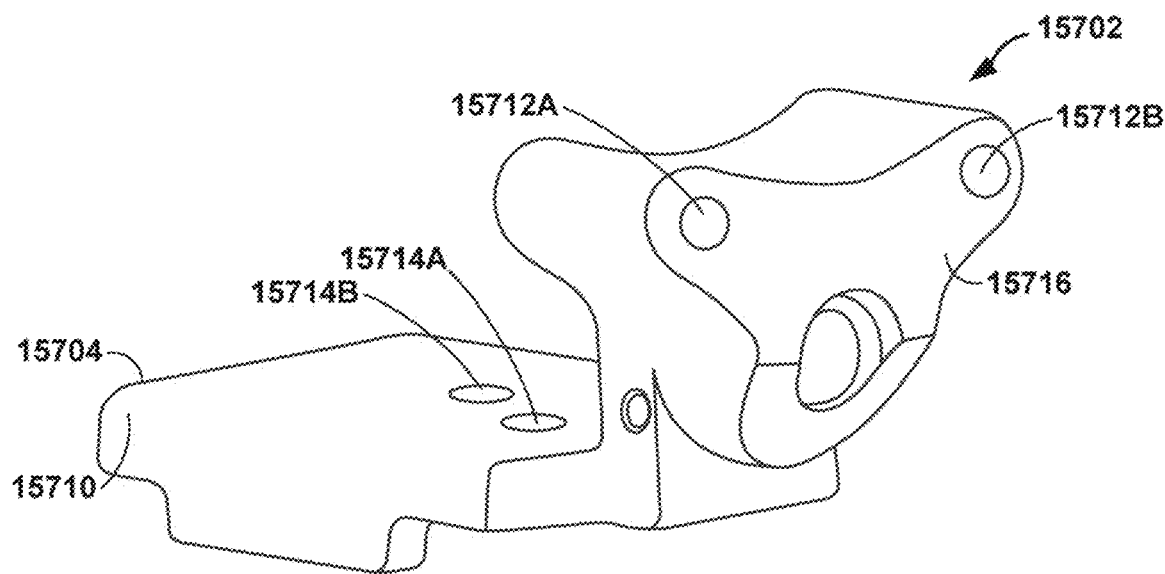
Figure 157B:
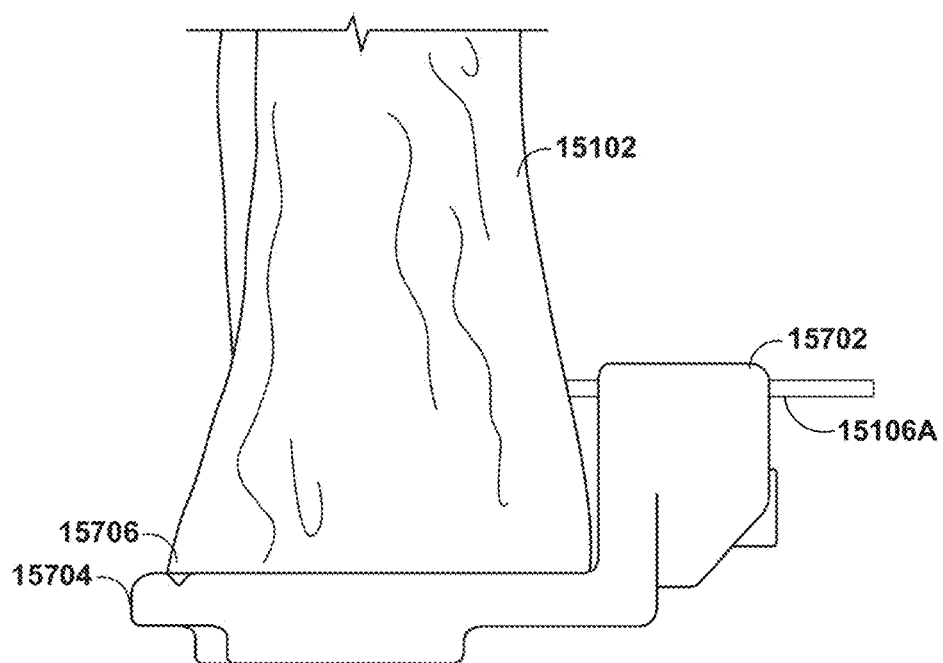
Figure 157C:
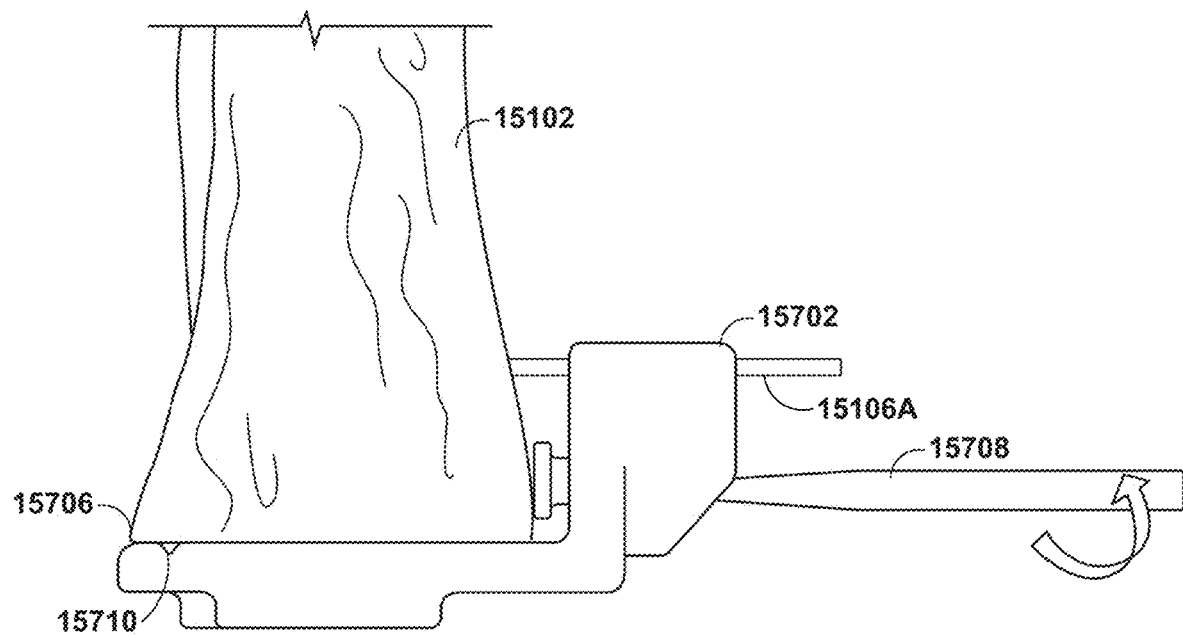

FIGS. 157A-157C are conceptual diagrams illustrating an example of tibial tray trialing.

Figure 158:
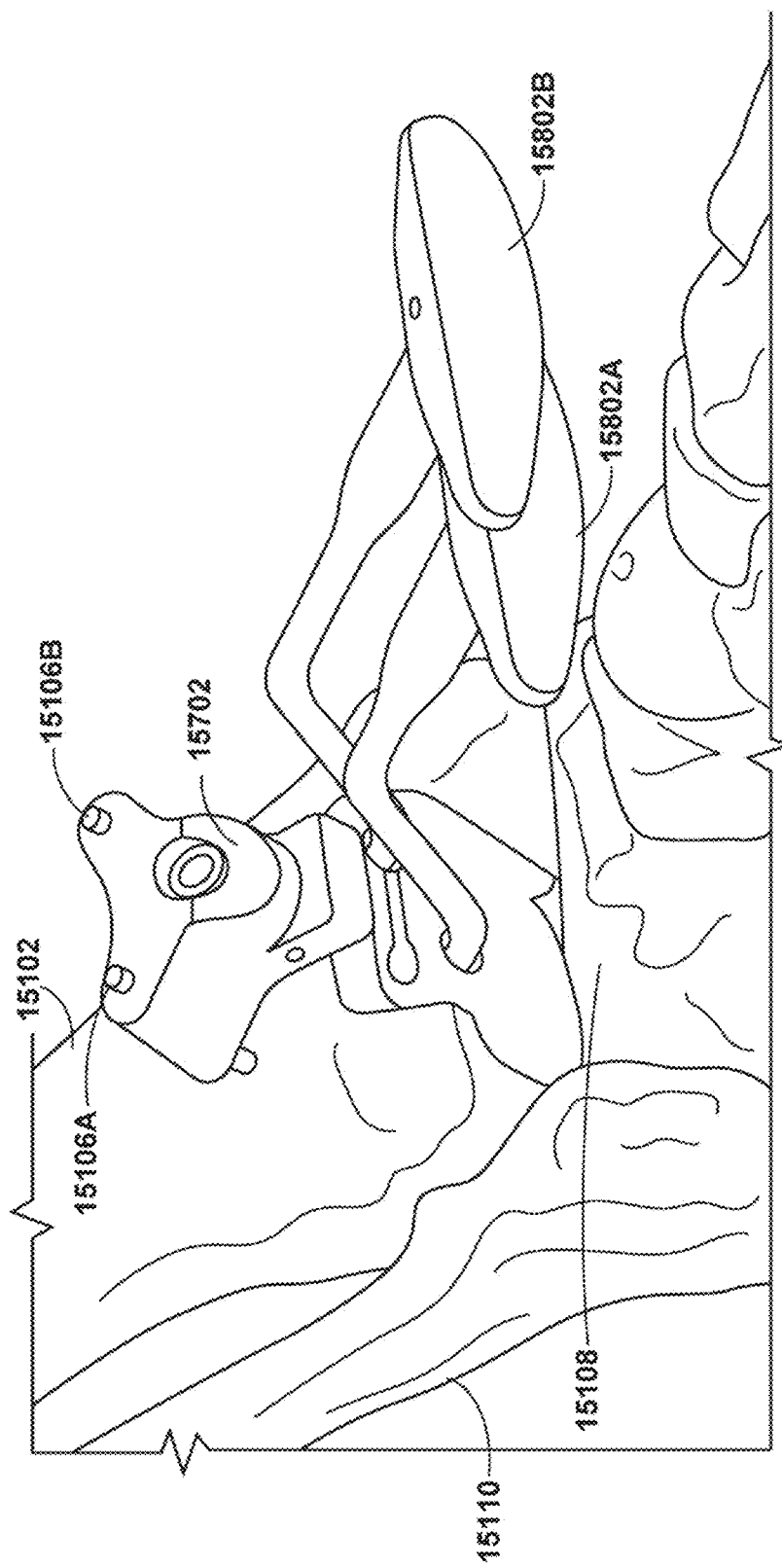

FIG. 158 is a conceptual diagram illustrating an example creation of tibial implant anchorage.

Figure 159A:
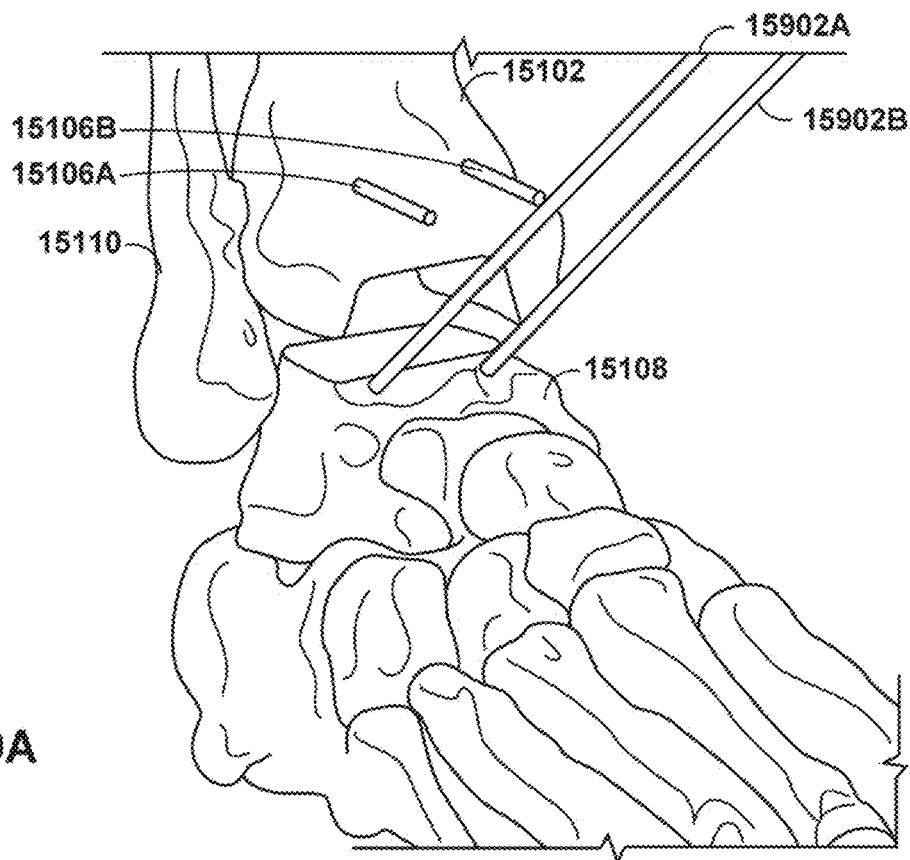
Figure 159B:
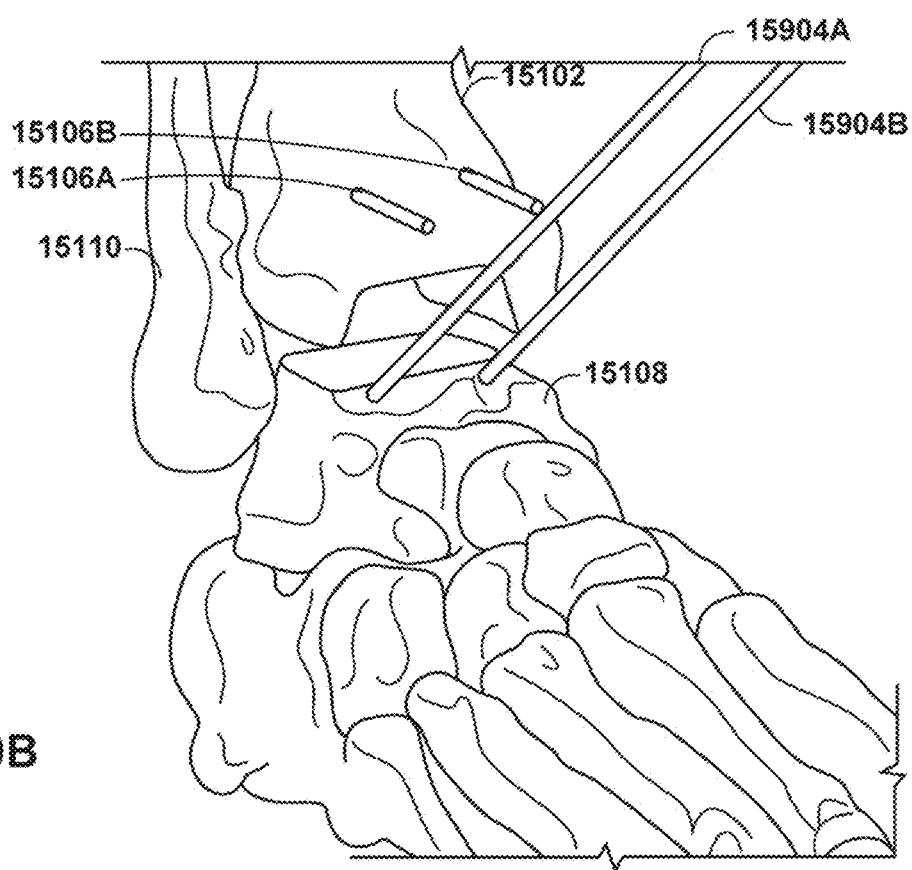

FIGS. 159A and 159B are conceptual diagrams illustrating an example attachment of guide pins to a talus.

Figure 160:
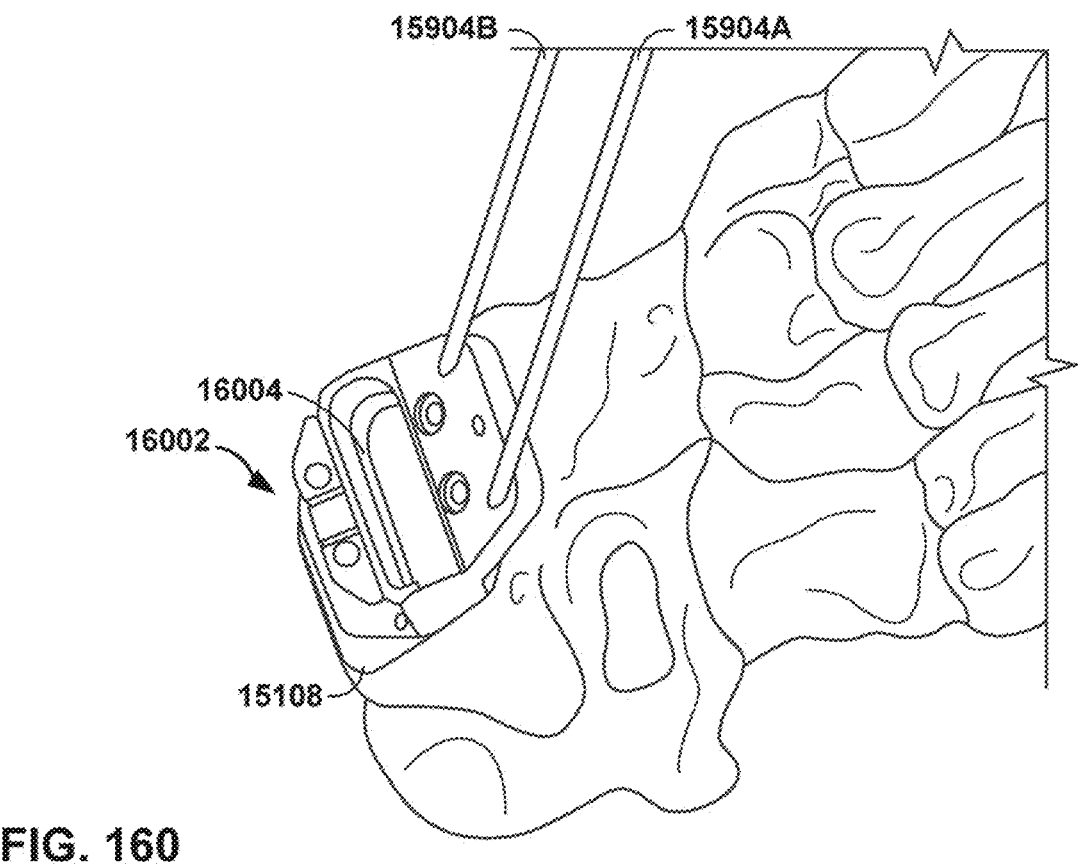

FIG. 160 is a conceptual diagram of an example talar resection guide on a talus.

Figure 161:
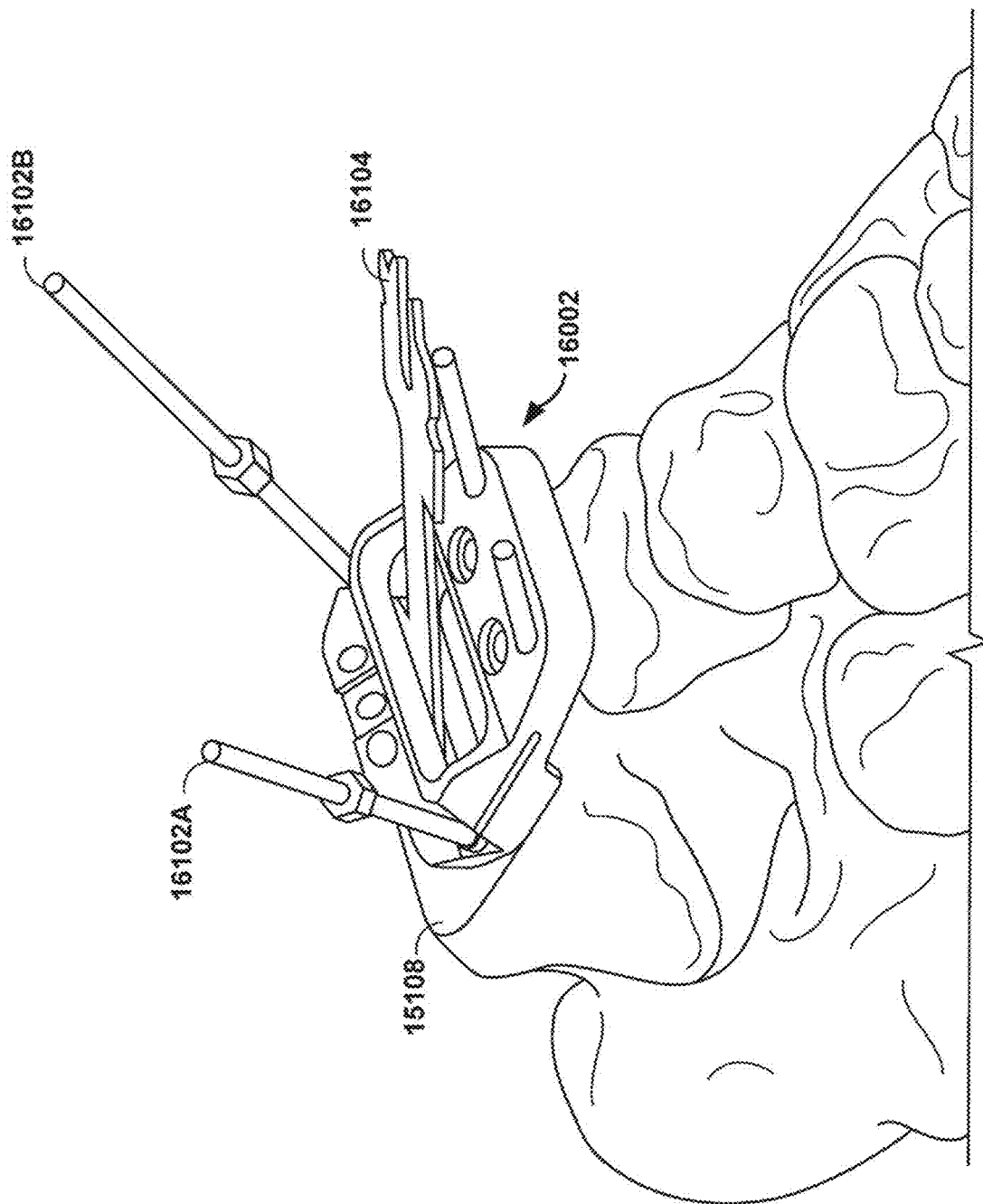

FIG. 161 is a conceptual diagram of an example posterior talar chamfer resection.

Figure 162:
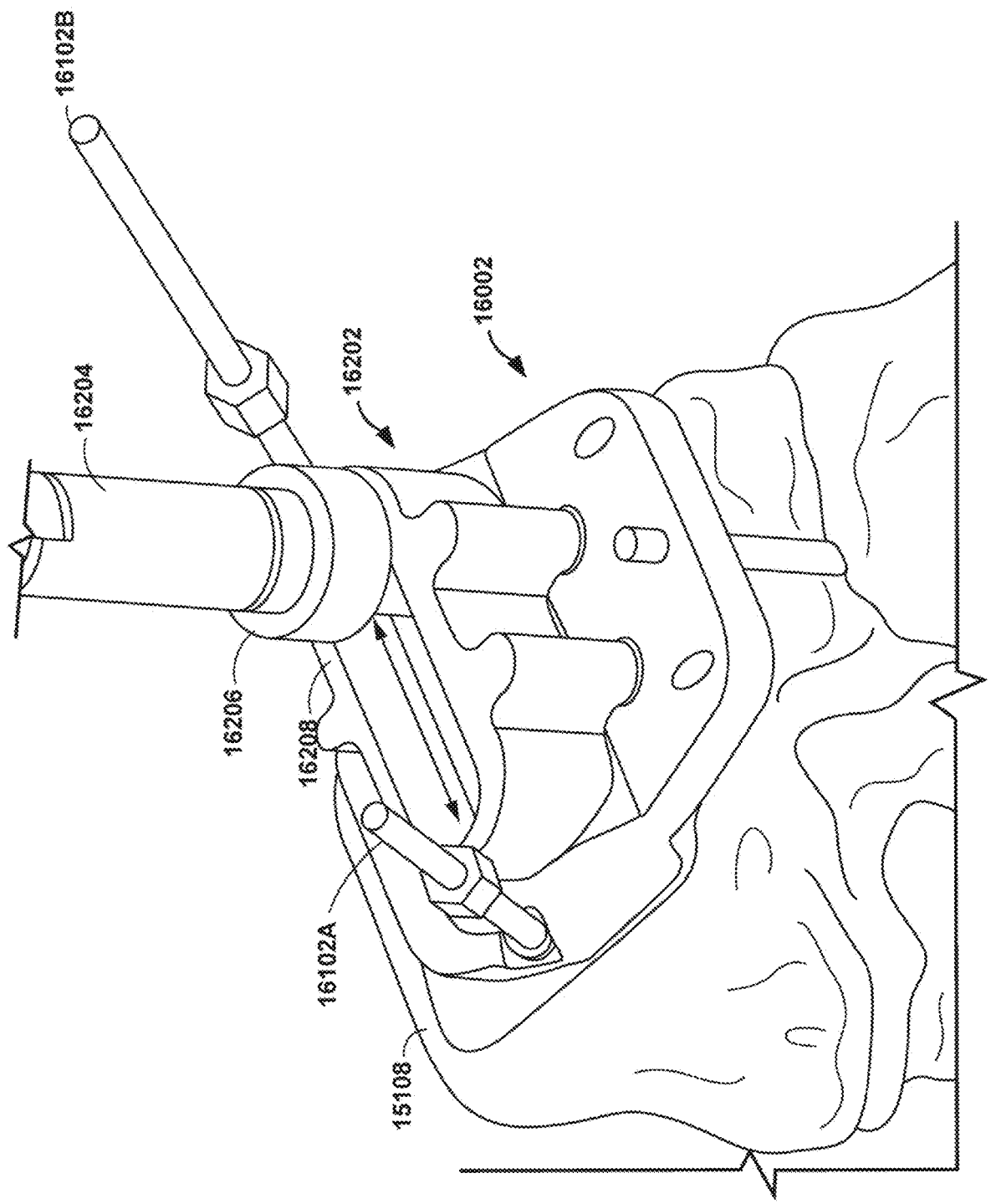
Figure 163:
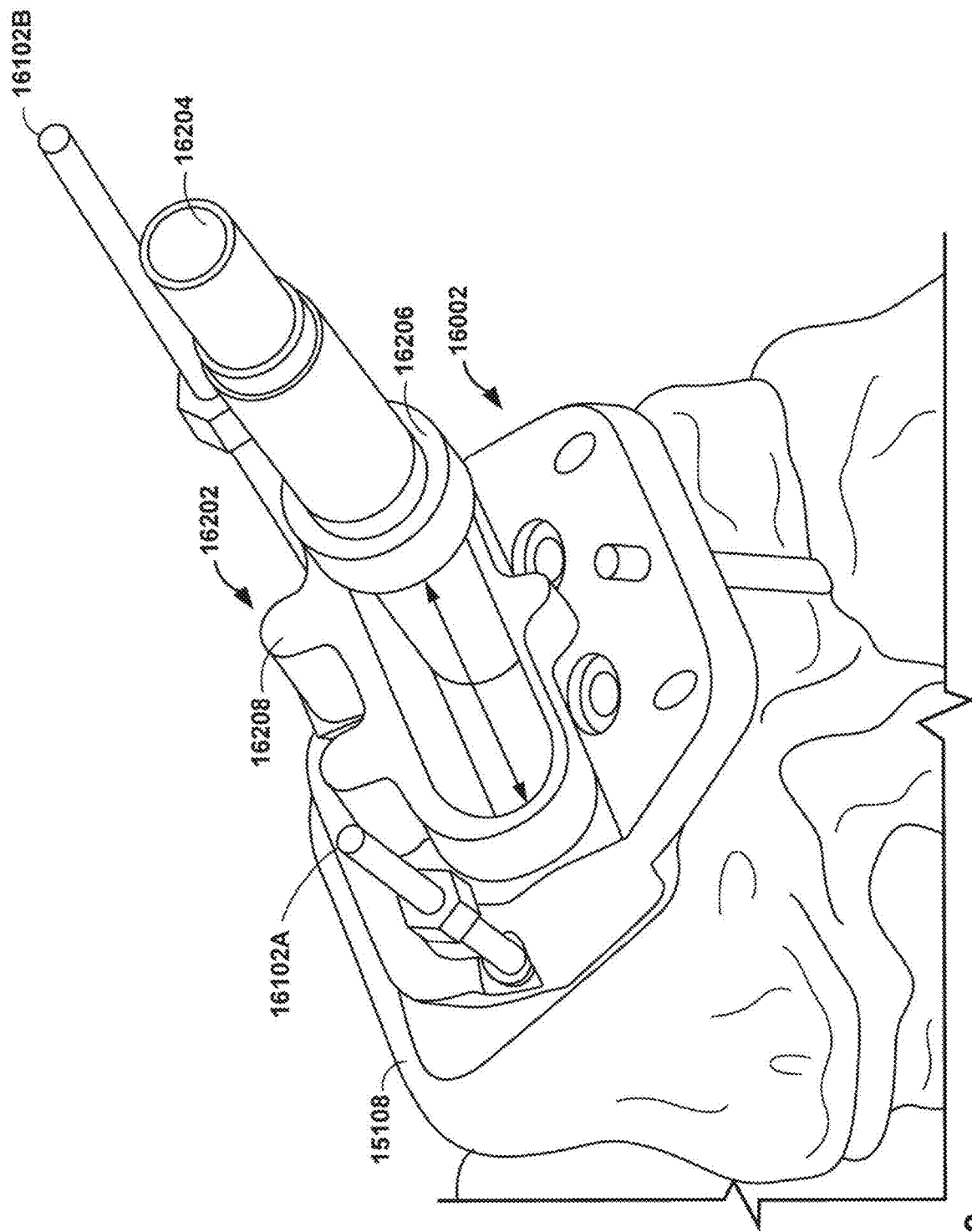

FIGS. 162 and 163 are conceptual diagrams of example anterior talar chamfer resections.

Figure 164:
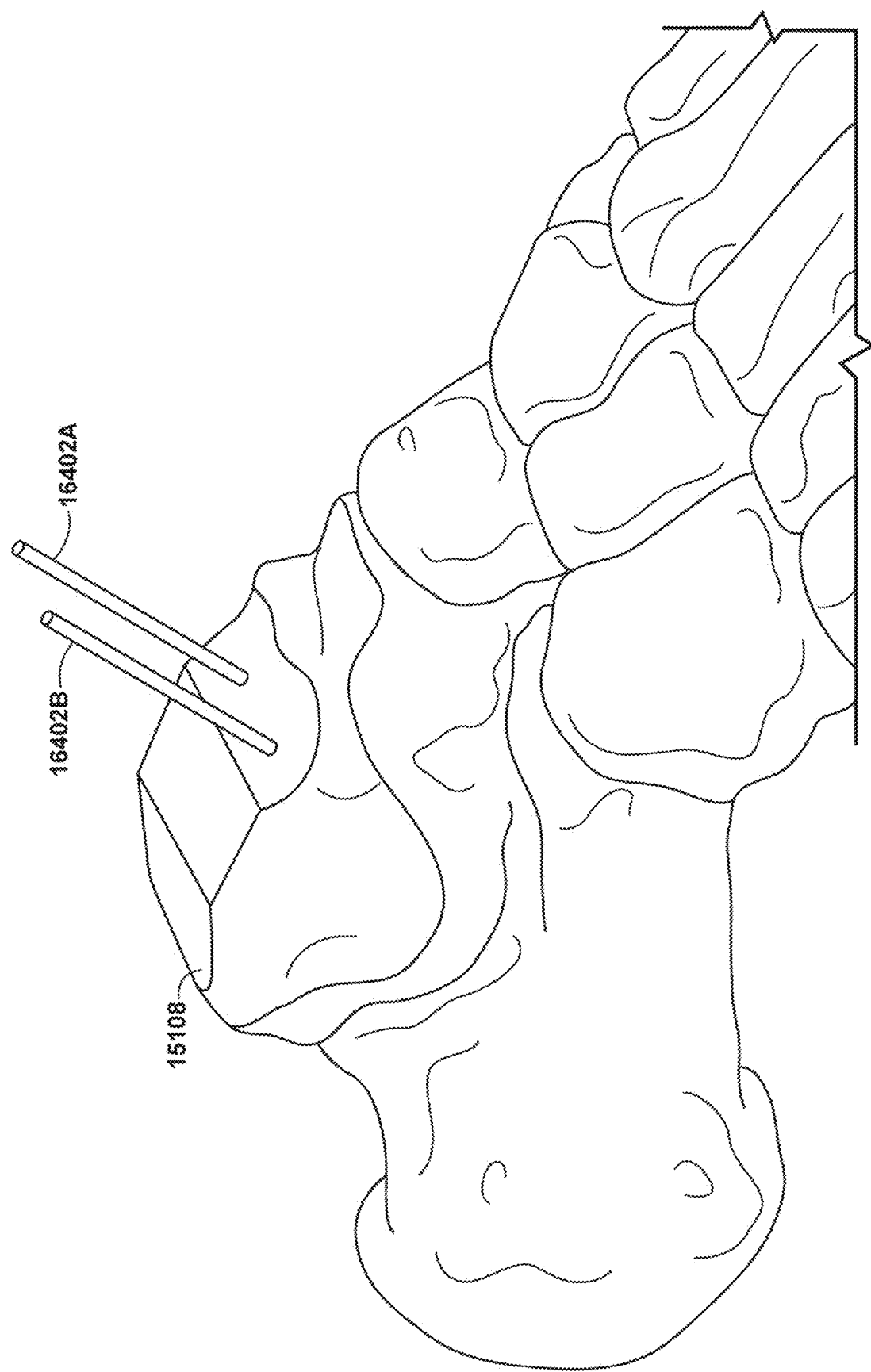
Figure 165:
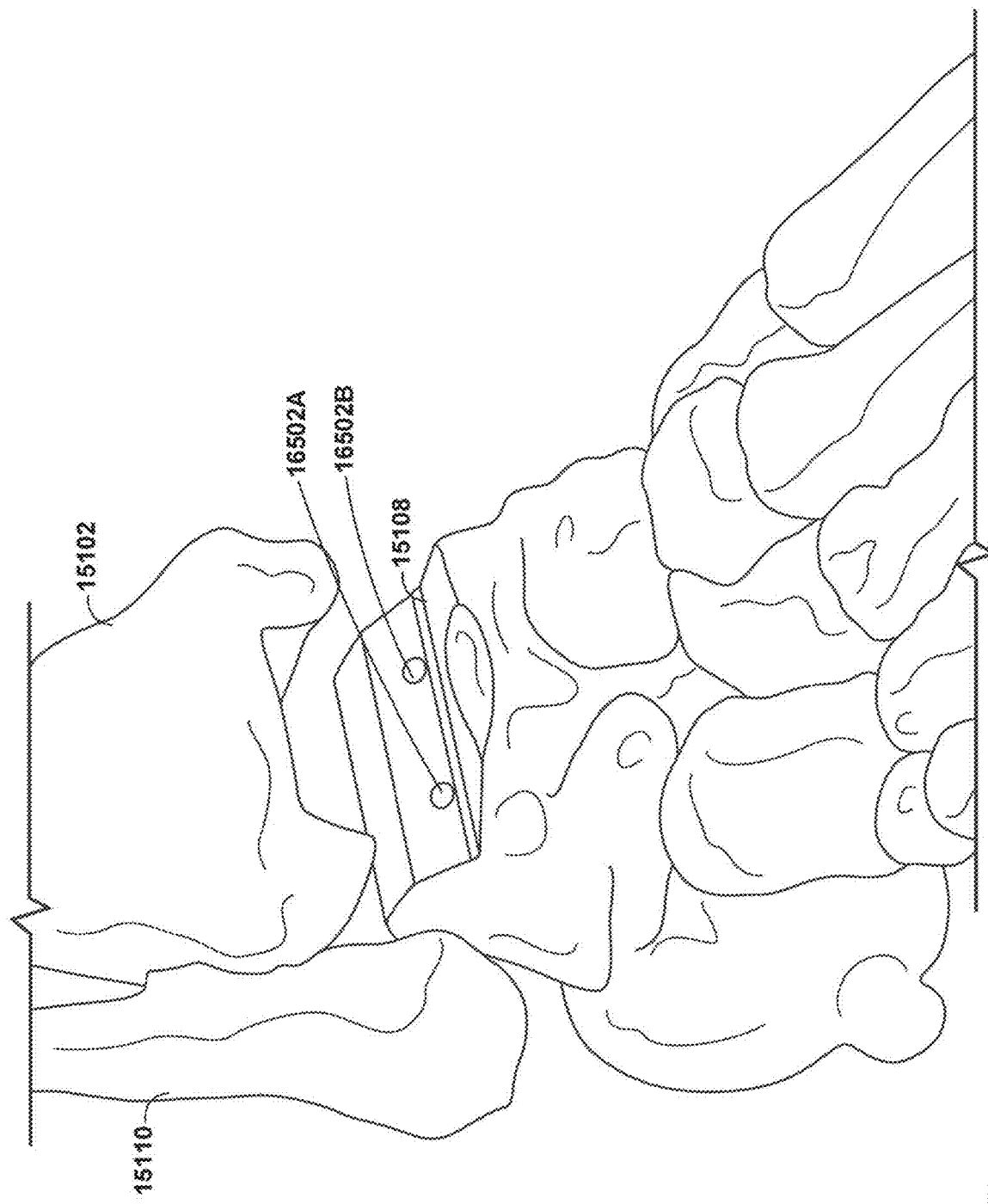

FIGS. 164 and 165 are conceptual diagrams illustrating an example creation of talar implant anchorage.

Figure 166:
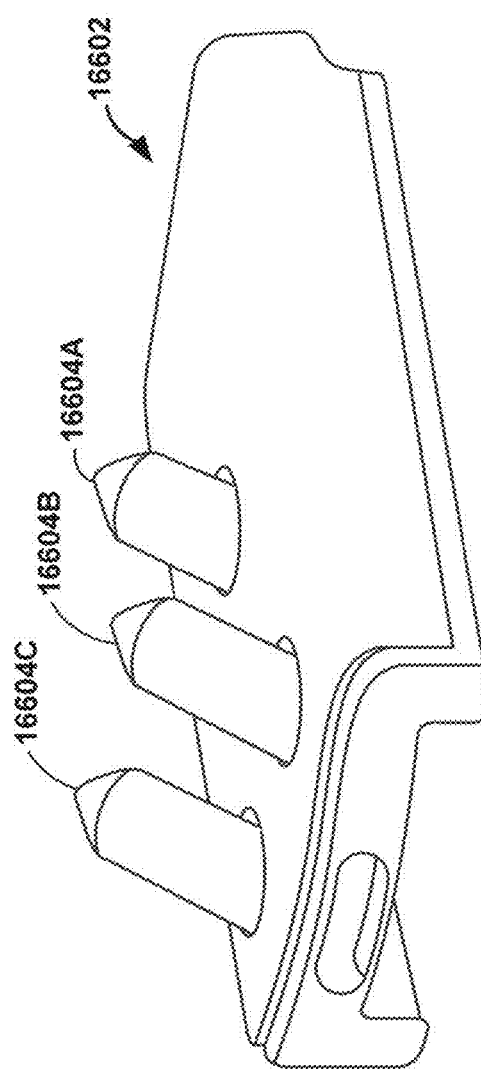

FIG. 166 is a conceptual diagram illustrating an example tibial implant.

Figure 167:
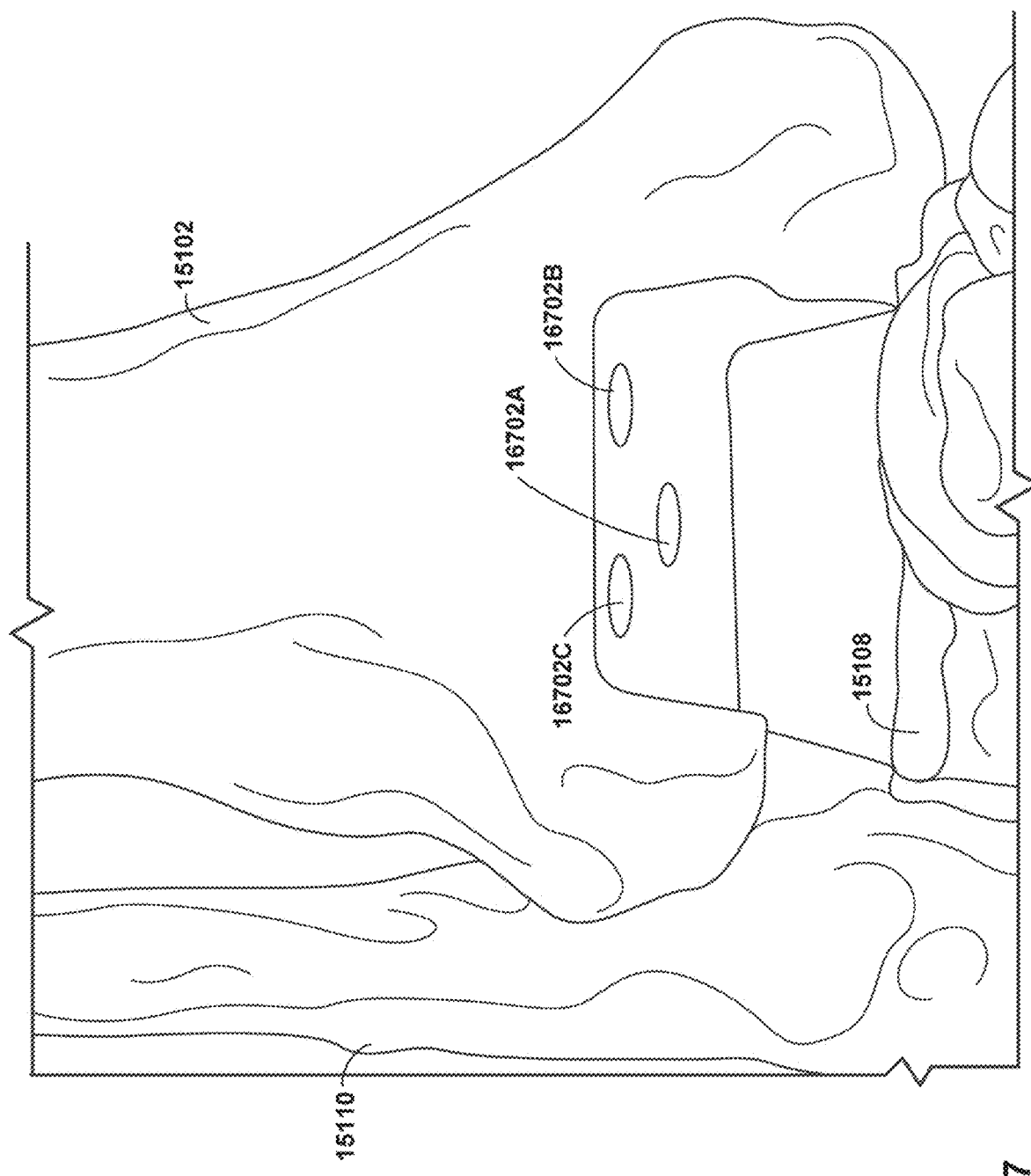

FIG. 167 is a conceptual diagram illustrating an example of a prepared tibia.

Figure 168:
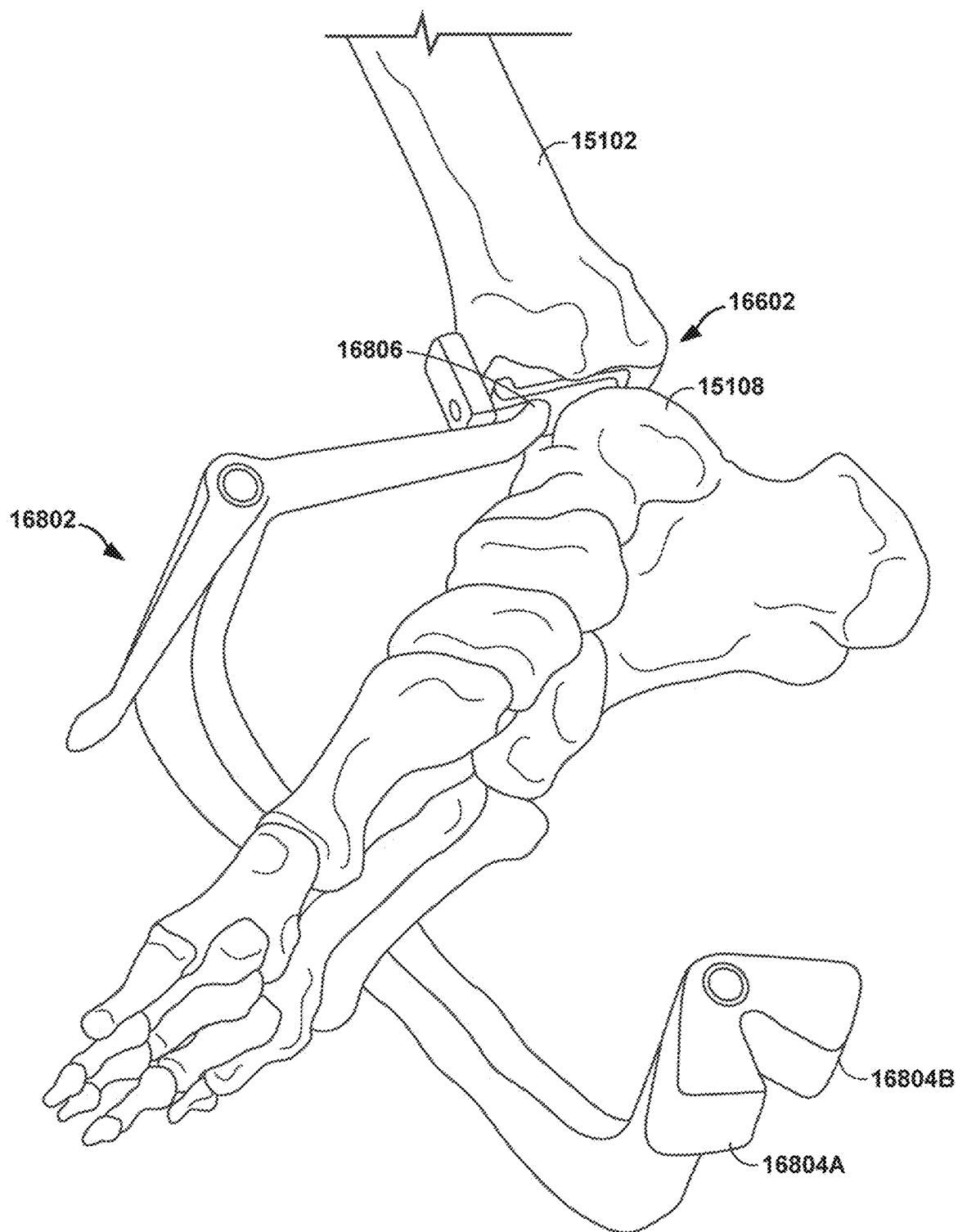

FIG. 168 is a conceptual diagram illustrating example impaction of a tibial implant into a tibia.

Figure 169:
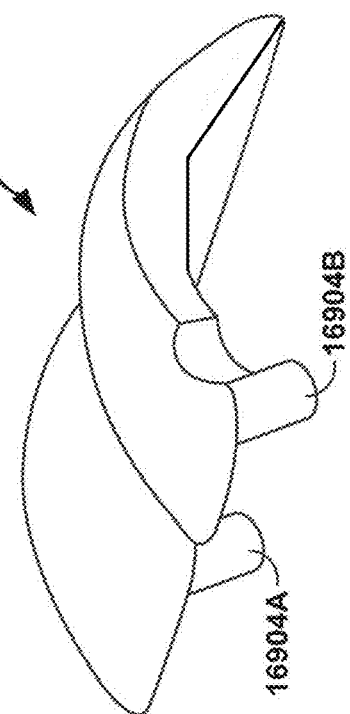

FIG. 169 is a conceptual diagram illustrating an example talar implant.

Figure 170:
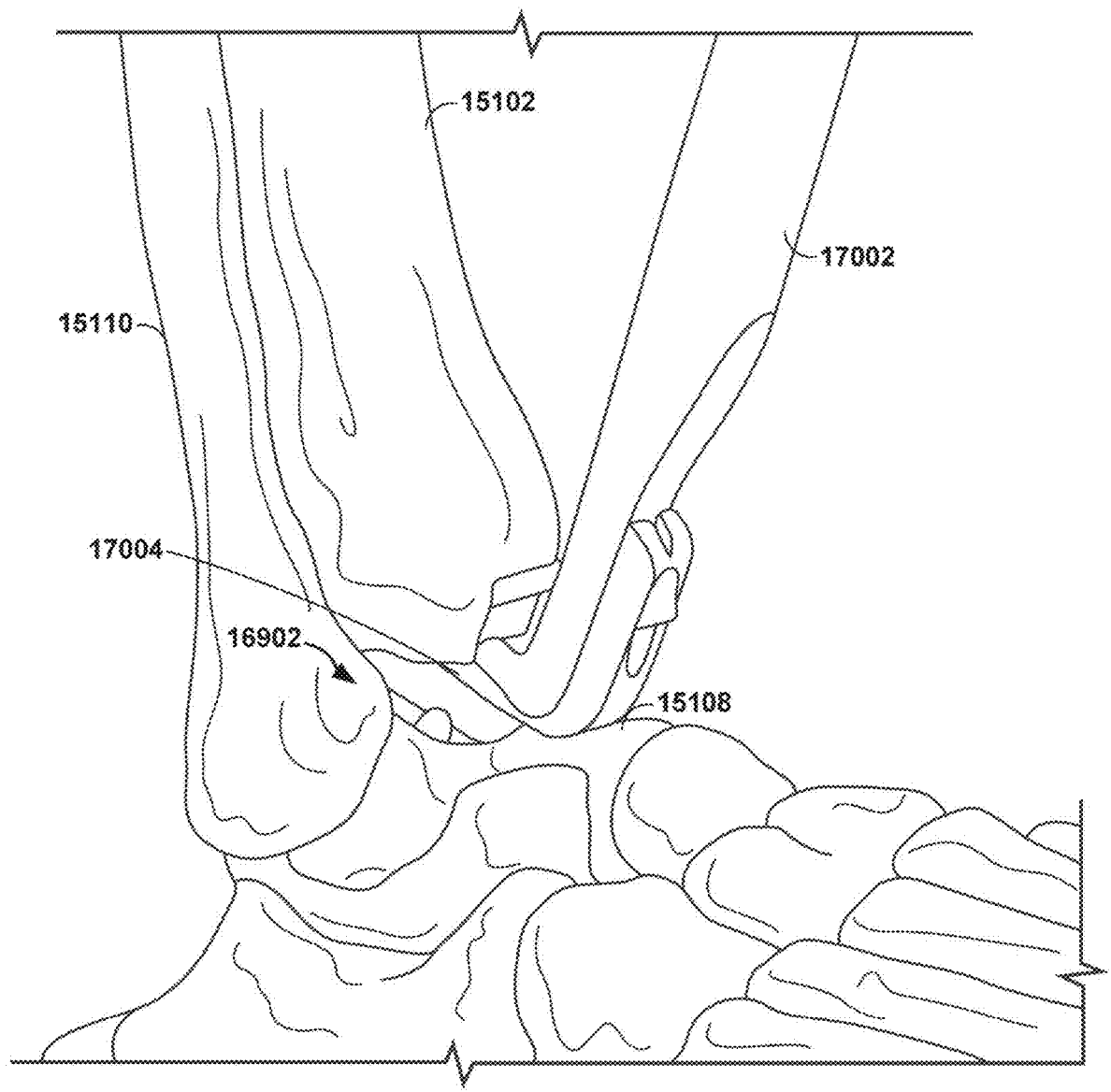

FIG. 170 is a conceptual diagram illustrating example impaction of a talar implant into a talus.

Figure 171:
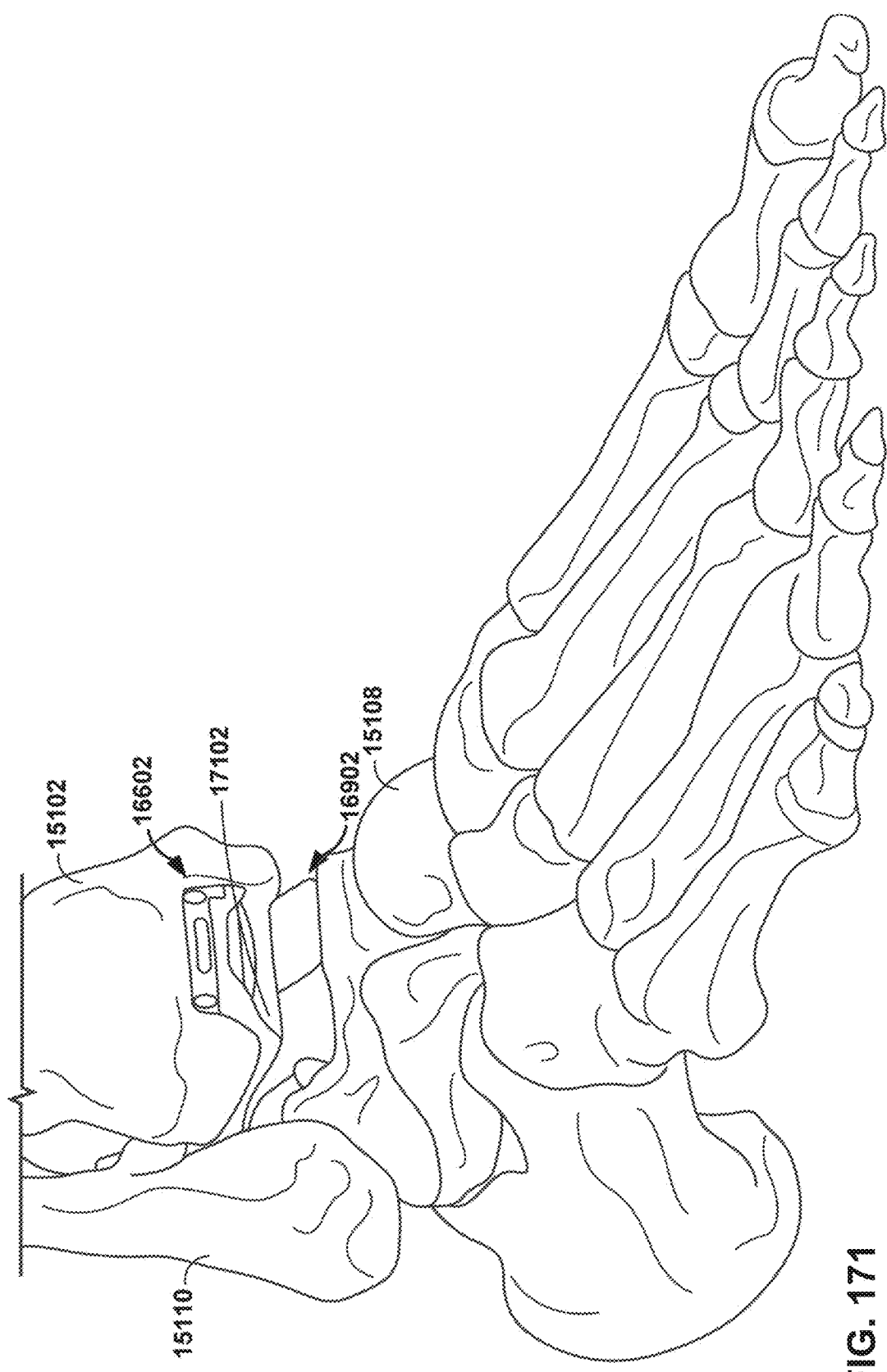

FIG. 171 is a conceptual diagram illustrating an example bearing implanted between a tibial implant and a talar implant.

Figure 172:
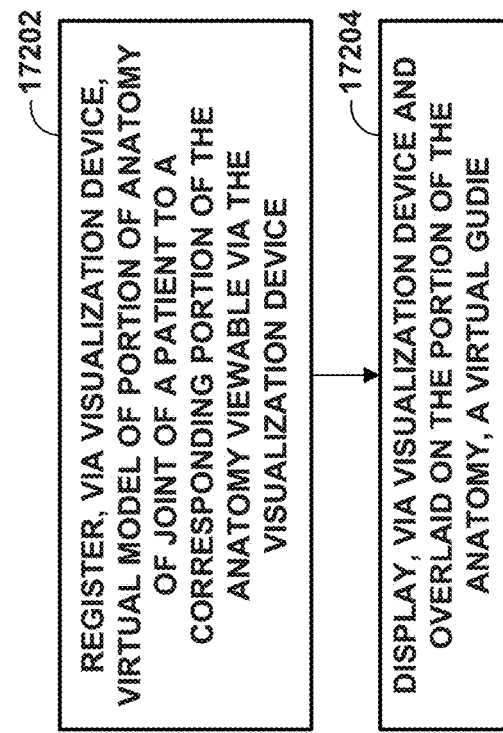

FIG. 172 is a flow diagram illustrating an example technique for MR aided surgery, in accordance with one or more techniques of this disclosure.

DETAILED DESCRIPTION

Certain examples of this disclosure are described with reference to the accompanying drawings, wherein like reference numerals denote like elements. It should be understood, however, that the accompanying drawings illustrate only the various implementations described herein and are not meant to limit the scope of various technologies described herein. The drawings show and describe various examples of this disclosure.

In the following description, numerous details are set forth to provide an understanding of the present invention. However, it will be understood by those skilled in the art that the present invention may be practiced without these details and that numerous variations or modifications from the described examples may be possible.

Orthopedic surgery can involve implanting one or more prosthetic devices to repair or replace a patient's damaged or diseased joint. Today, virtual surgical planning tools are available that use image data of the diseased or damaged joint to generate an accurate three-dimensional bone model that can be viewed and manipulated preoperatively by the surgeon. These tools can enhance surgical outcomes by allowing the surgeon to simulate the surgery, select or design an implant that more closely matches the contours of the patient's actual bone, and select or design surgical instruments and guide tools that are adapted specifically for repairing the bone of a particular patient. Use of these planning tools typically results in generation of a preoperative surgical plan, complete with an implant and surgical instruments that are selected or manufactured for the individual patient. Oftentimes, once in the actual operating environment, the surgeon may desire to verify the preoperative surgical plan intraoperatively relative to the patient's actual bone. This verification may result in a determination that an adjustment to the preoperative surgical plan is needed, such as a different implant, a different positioning or orientation of the implant, and/or a different surgical guide for carrying out the surgical plan. In addition, a surgeon may want to view details of the preoperative surgical plan relative to the patient's real bone during the actual procedure in order to more efficiently and accurately position and orient the implant components. For example, the surgeon may want to obtain intra-operative visualization that provides guidance for positioning and orientation of implant components, guidance for preparation of bone or tissue to receive the implant components, guidance for reviewing the details of a procedure or procedural step, and/or guidance for selection of tools or implants and tracking of surgical procedure workflow.

Accordingly, this disclosure describes systems and methods for using a mixed reality (MR) visualization system to assist with creation, implementation, verification, and/or modification of a surgical plan before and during a surgical procedure. Because MR, or in some instances VR, may be used to interact with the surgical plan, this disclosure may also refer to the surgical plan as a "virtual" surgical plan. Visualization tools other than or in addition to mixed reality visualization systems may be used in accordance with techniques of this disclosure. A surgical plan, e.g., as generated by the BLUEPRINT™ system or another surgical planning platform, may include information defining a variety of features of a surgical procedure, such as features of particular surgical procedure steps to be performed on a patient by a surgeon according to the surgical plan including, for example, bone or tissue preparation steps and/or steps for selection, modification and/or placement of implant components. Such information may include, in various examples, dimensions, shapes, angles, surface contours, and/or orientations of implant components to be selected or modified by surgeons, dimensions, shapes, angles, surface contours and/or orientations to be defined in bone or tissue by the surgeon in bone or tissue preparation steps, and/or positions, axes, planes, angle and/or entry points defining placement of implant components by the surgeon relative to patient bone or tissue. Information such as dimensions, shapes, angles, surface contours, and/or orientations of anatomical features of the patient may be derived from imaging (e.g., x-ray, CT, MRI, ultrasound or other images), direct observation, or other techniques.

In this disclosure, the term "mixed reality" (MR) refers to the presentation of virtual objects such that a user sees images that include both real, physical objects and virtual objects. Virtual objects may include text, 2-dimensional surfaces, 3-dimensional models, or other user-perceptible elements that are not actually present in the physical, real-world environment in which they are presented as coexisting. In addition, virtual objects described in various examples of this disclosure may include graphics, images, animations or videos, e.g., presented as 3D virtual objects or 2D virtual objects. Virtual objects may also be referred to as virtual elements. Such elements may or may not be analogs of real-world objects. In some examples, in mixed reality, a camera may capture images of the real world and modify the images to present virtual objects in the context of the real world. In such examples, the modified images may be displayed on a screen, which may be head-mounted, handheld, or otherwise viewable by a user. This type of mixed reality is increasingly common on smartphones, such as where a user can point a smartphone's camera at a sign written in a foreign language and see in the smartphone's screen a translation in the user's own language of the sign superimposed on the sign along with the rest of the scene captured by the camera. In some examples, in mixed reality, see-through (e.g., transparent) holographic lenses, which may be referred to as waveguides, may permit the user to view real-world objects, i.e., actual objects in a real-world environment, such as real anatomy, through the holographic lenses and also concurrently view virtual objects.

The Microsoft HOLOLENS™ headset, available from Microsoft Corporation of Redmond, Wash., is an example of a MR device that includes see-through holographic lenses, sometimes referred to as waveguides, that permit a user to view real-world objects through the lens and concurrently view projected 3D holographic objects. The Microsoft HOLOLENS™ headset, or similar waveguide-based visualization devices, are examples of an MR visualization device that may be used in accordance with some examples of this disclosure. Some holographic lenses may present holographic objects with some degree of transparency through see-through holographic lenses so that the user views real-world objects and virtual, holographic objects. In some examples, some holographic lenses may, at times, completely prevent the user from viewing real-world objects and instead may allow the user to view entirely virtual environments. The term mixed reality may also encompass scenarios where one or more users are able to perceive one or more virtual objects generated by holographic projection. In other words, "mixed reality" may encompass the case where a holographic projector generates holograms of elements that appear to a user to be present in the user's actual physical environment.

In some examples, in mixed reality, the positions of some or all presented virtual objects are related to positions of physical objects in the real world. For example, a virtual object may be tethered to a table in the real world, such that the user can see the virtual object when the user looks in the direction of the table but does not see the virtual object when the table is not in the user's field of view. In some examples, in mixed reality, the positions of some or all presented virtual objects are unrelated to positions of physical objects in the real world. For instance, a virtual item may always appear in the top right of the user's field of vision, regardless of where the user is looking.

Augmented reality (AR) is similar to MR in the presentation of both real-world and virtual elements, but AR generally refers to presentations that are mostly real, with a few virtual additions to "augment" the real-world presentation. For purposes of this disclosure, MR is considered to include AR. For example, in AR, parts of the user's physical environment that are in shadow can be selectively brightened without brightening other areas of the user's physical environment. This example is also an instance of MR in that the selectively-brightened areas may be considered virtual objects superimposed on the parts of the user's physical environment that are in shadow.

Furthermore, in this disclosure, the term "virtual reality" (VR) refers to an immersive artificial environment that a user experiences through sensory stimuli (such as sights and sounds) provided by a computer. Thus, in virtual reality, the user may not see any physical objects as they exist in the real world. Video games set in imaginary worlds are a common example of VR. The term "VR" also encompasses scenarios where the user is presented with a fully artificial environment in which some virtual object's locations are based on the locations of corresponding physical objects as they relate to the user. Walk-through VR attractions are examples of this type of VR.

The term "extended reality" (XR) is a term that encompasses a spectrum of user experiences that includes virtual reality, mixed reality, augmented reality, and other user experiences that involve the presentation of at least some perceptible elements as existing in the user's environment that are not present in the user's real-world environment. Thus, the term "extended reality" may be considered a genus for MR and VR. XR visualizations may be presented in any of the techniques for presenting mixed reality discussed elsewhere in this disclosure or presented using techniques for presenting VR, such as VR goggles.

These mixed reality systems and methods can be part of an intelligent surgical planning system that includes multiple subsystems that can be used to enhance surgical outcomes. In addition to the preoperative and intraoperative applications discussed above, an intelligent surgical planning system can include postoperative tools to assist with patient recovery and which can provide information that can be used to assist with and plan future surgical revisions or surgical cases for other patients.

Accordingly, systems and methods are also described herein that can be incorporated into an intelligent surgical planning system, such as artificial intelligence systems to assist with planning, implants with embedded sensors (e.g., smart implants) to provide postoperative feedback for use by the healthcare provider and the artificial intelligence system, and mobile applications to monitor and provide information to the patient and the healthcare provider in real-time or near real-time.

Visualization tools are available that utilize patient image data to generate three-dimensional models of bone contours to facilitate preoperative planning for joint repairs and replacements. These tools allow surgeons to design and/or select surgical guides and implant components that closely match the patient's anatomy. These tools can improve surgical outcomes by customizing a surgical plan for each patient. An example of such a visualization tool for shoulder repairs is the BLUEPRINT™ system available from Wright Medical Technology, Inc. The BLUEPRINT™ system provides the surgeon with two-dimensional planar views of the bone repair region as well as a three-dimensional virtual model of the repair region. The surgeon can use the BLUEPRINT™ system to select, design or modify appropriate implant components, determine how best to position and orient the implant components and how to shape the surface of the bone to receive the components, and design, select or modify surgical guide tool(s) or instruments to carry out the surgical plan. The information generated by the BLUEPRINT™ system is compiled in a preoperative surgical plan for the patient that is stored in a database at an appropriate location (e.g., on a server in a wide area network, a local area network, or a global network) where it can be accessed by the surgeon or other care provider, including before and during the actual surgery.

Figure 1:
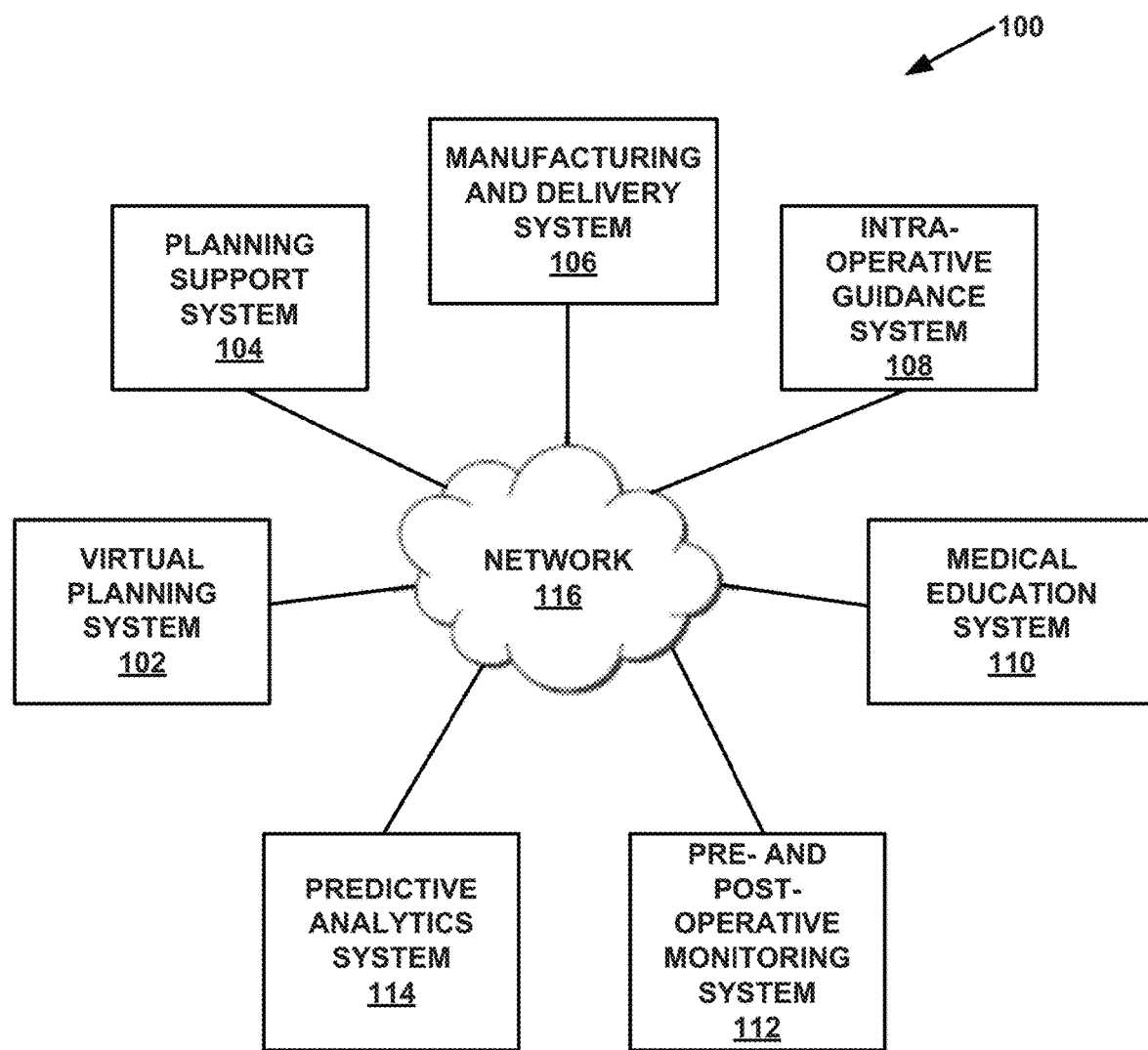
FIG. 1 is a block diagram of an orthopedic surgical system according to an example of this disclosure.

FIG. 1 is a block diagram of an orthopedic surgical system 100 according to an example of this disclosure. Orthopedic surgical system 100 includes a set of subsystems. In the example of FIG. 1, the subsystems include a virtual planning system 102, a planning support system 104, a manufacturing and delivery system 106, an intraoperative guidance system 108, a medical education system 110, a monitoring system 112, a predictive analytics system 114, and a communications network 116. In other examples, orthopedic surgical system 100 may include more, fewer, or different subsystems. For example, orthopedic surgical system 100 may omit medical education system 110, monitoring system 112, predictive analytics system 114, and/or other subsystems. In some examples, orthopedic surgical system 100 may be used for surgical tracking, in which case orthopedic surgical system 100 may be referred to as a surgical tracking system. In other cases, orthopedic surgical system 100 may be generally referred to as a medical device system.

Users of orthopedic surgical system 100 may use virtual planning system 102 to plan orthopedic surgeries. Users of orthopedic surgical system 100 may use planning support system 104 to review surgical plans generated using orthopedic surgical system 100. Manufacturing and delivery system 106 may assist with the manufacture and delivery of items needed to perform orthopedic surgeries. Intraoperative guidance system 108 provides guidance to assist users of orthopedic surgical system 100 in performing orthopedic surgeries. Medical education system 110 may assist with the education of users, such as healthcare professionals, patients, and other types of individuals. Pre- and postoperative monitoring system 112 may assist with monitoring patients before and after the patients undergo surgery. Predictive analytics system 114 may assist healthcare professionals with various types of predictions. For example, predictive analytics system 114 may apply artificial intelligence techniques to determine a classification of a condition of an orthopedic joint, e.g., a diagnosis, determine which type of surgery to perform on a patient and/or which type of implant to be used in the procedure, determine types of items that may be needed during the surgery, and so on.

The subsystems of orthopedic surgical system 100 (i.e., virtual planning system 102, planning support system 104, manufacturing and delivery system 106, intraoperative guidance system 108, medical education system 110, pre- and postoperative monitoring system 112, and predictive analytics system 114) may include various systems. The systems in the subsystems of orthopedic surgical system 100 may include various types of computing systems, computing devices, including server computers, personal computers, tablet computers, smartphones, display devices, Internet of Things (IoT) devices, visualization devices (e.g., mixed reality (MR) visualization devices, virtual reality (VR) visualization devices, holographic projectors, or other devices for presenting extended reality (XR) visualizations), surgical tools, and so on. A holographic projector, in some examples, may project a hologram for general viewing by multiple users or a single user without a headset, rather than viewing only by a user wearing a headset. For example, virtual planning system 102 may include a MR visualization device and one or more server devices, planning support system 104 may include one or more personal computers and one or more server devices, and so on. A computing system is a set of one or more computing systems configured to operate as a system. In some examples, one or more devices may be shared between two or more of the subsystems of orthopedic surgical system 100. For instance, in the previous examples, virtual planning system 102 and planning support system 104 may include the same server devices.

In the example of FIG. 1, the devices included in the subsystems of orthopedic surgical system 100 may communicate using communications network 116. Communications network 116 may include various types of communication networks including one or more wide-area networks, such as the Internet, local area networks, and so on. In some examples, communications network 116 may include wired and/or wireless communication links.

Figure 2:
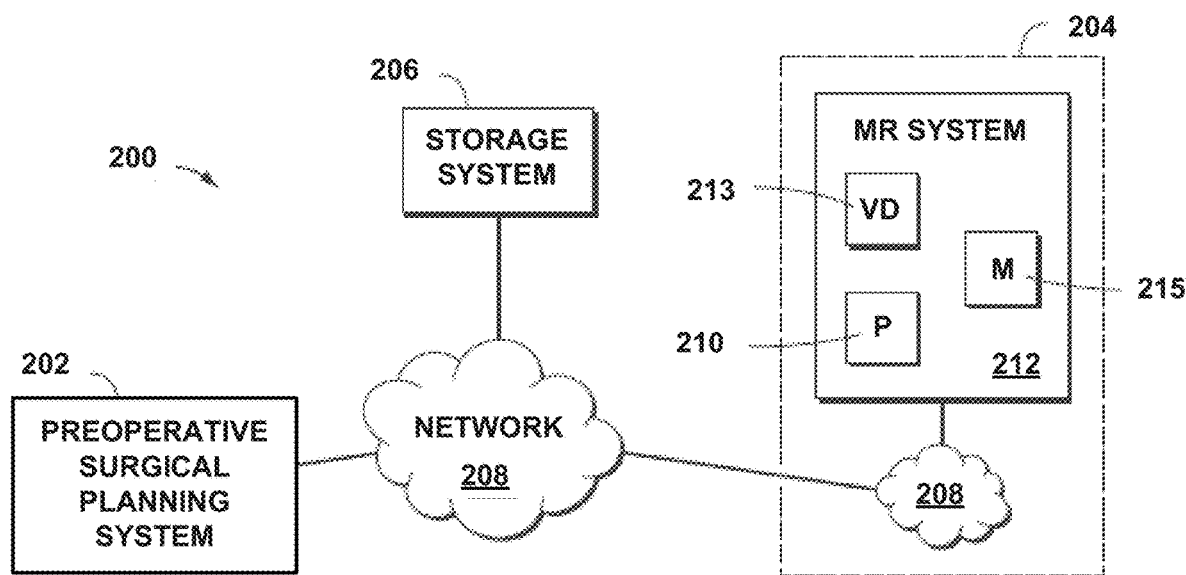
FIG. 2 is a block diagram of an orthopedic surgical system that includes a mixed reality (MR) system, according to an example of this disclosure.

Many variations of orthopedic surgical system 100 are possible in accordance with techniques of this disclosure. Such variations may include more or fewer subsystems than the version of orthopedic surgical system 100 shown in FIG. 1. For example, FIG. 2 is a block diagram of an orthopedic surgical system 200 that includes one or more mixed reality (MR) systems, according to an example of this disclosure. Orthopedic surgical system 200 may be used for creating, verifying, updating, modifying and/or implementing a surgical plan. In some examples, the surgical plan can be created preoperatively, such as by using a virtual surgical planning system (e.g., the BLUEPRINT™ system), and then verified, modified, updated, and viewed intraoperatively, e.g., using MR visualization of the surgical plan. In other examples, orthopedic surgical system 200 can be used to create the surgical plan immediately prior to surgery or intraoperatively, as needed. In some examples, orthopedic surgical system 200 may be used for surgical tracking, in which case orthopedic surgical system 200 may be referred to as a surgical tracking system. In other cases, orthopedic surgical system 200 may be generally referred to as a medical device system.

In the example of FIG. 2, orthopedic surgical system 200 includes a preoperative surgical planning system 202, a healthcare facility 204 (e.g., a surgical center or hospital), a storage system 206, and a network 208 that allows a user at healthcare facility 204 to access stored patient information, such as medical history, image data corresponding to the damaged joint or bone and various parameters corresponding to a surgical plan that has been created preoperatively (as examples). Preoperative surgical planning system 202 may be equivalent to virtual planning system 102 of FIG. 1 and, in some examples, may generally correspond to a virtual planning system similar or identical to the BLUEPRINT™ system.

In the example of FIG. 2, healthcare facility 204 includes a mixed reality (MR) system 212. In some examples of this disclosure, MR system 212 includes one or more processing device(s) (P) 210 to provide functionalities that will be described in further detail below. Processing device(s) 210 may also be referred to as processor(s). In addition, one or more users of MR system 212 (e.g., a surgeon, nurse, or other care provider) can use processing device(s) (P) 210 to generate a request for a particular surgical plan or other patient information that is transmitted to storage system 206 via network 208. In response, storage system 206 returns the requested patient information to MR system 212. In some examples, the users can use other processing device(s) to request and receive information, such as one or more processing devices that are part of MR system 212, but not part of any visualization device, or one or more processing devices that are part of a visualization device (e.g., visualization device 213) of MR system 212, or a combination of one or more processing devices that are part of MR system 212, but not part of any visualization device, and one or more processing devices that are part of a visualization device (e.g., visualization device 213) that is part of MR system 212.

In some examples, multiple users can simultaneously use MR system 212. For example, MR system 212 can be used in a spectator mode in which multiple users each use their own visualization devices so that the users can view the same information at the same time and from the same point of view. In some examples, MR system 212 may be used in a mode in which multiple users each use their own visualization devices so that the users can view the same information from different points of view.

In some examples, processing device(s) 210 can provide a user interface to display data and receive input from users at healthcare facility 204. Processing device(s) 210 may be configured to control visualization device 213 to present a user interface. Furthermore, processing device(s) 210 may be configured to control visualization device 213 to present virtual images, such as 3D virtual models, 2D images, and so on. Processing device(s) 210 can include a variety of different processing or computing devices, such as servers, desktop computers, laptop computers, tablets, mobile phones and other electronic computing devices, or processors within such devices. In some examples, one or more of processing device(s) 210 can be located remote from healthcare facility 204. In some examples, processing device(s) 210 reside within visualization device 213. In some examples, at least one of processing device(s) 210 is external to visualization device 213. In some examples, one or more processing device(s) 210 reside within visualization device 213 and one or more of processing device(s) 210 are external to visualization device 213.

In the example of FIG. 2, MR system 212 also includes one or more memory or storage device(s) (M) 215 for storing data and instructions of software that can be executed by processing device(s) 210. The instructions of software can correspond to the functionality of MR system 212 described herein. In some examples, the functionalities of a virtual surgical planning application, such as the BLUE-PRINT™ system, can also be stored and executed by processing device(s) 210 in conjunction with memory storage device(s) (M) 215. For instance, memory or storage system 215 may be configured to store data corresponding to at least a portion of a virtual surgical plan. In some examples, storage system 206 may be configured to store data corresponding to at least a portion of a virtual surgical plan. In some examples, memory or storage device(s) (M) 215 reside within visualization device 213. In some examples, memory or storage device(s) (M) 215 are external to visualization device 213. In some examples, memory or storage device(s) (M) 215 include a combination of one or more memory or storage devices within visualization device 213 and one or more memory or storage devices external to the visualization device.

Network 208 may be equivalent to network 116. Network 208 can include one or more wide area networks, local area networks, and/or global networks (e.g., the Internet) that connect preoperative surgical planning system 202 and MR system 212 to storage system 206. Storage system 206 can include one or more databases that can contain patient information, medical information, patient image data, and parameters that define the surgical plans. For example, medical images of the patient's diseased or damaged bone typically are generated preoperatively in preparation for an orthopedic surgical procedure. The medical images can include images of the relevant bone(s) taken along the sagittal plane and the coronal plane of the patient's body. The medical images can include X-ray images, magnetic resonance imaging (MRI) images, computerized tomography (CT) images, ultrasound images, and/or any other type of 2D or 3D image that provides information about the relevant surgical area. Storage system 206 also can include data identifying the implant components selected for a particular patient (e.g., type, size, etc.), surgical guides selected for a particular patient, and details of the surgical procedure, such as entry points, cutting planes, drilling axes, reaming depths, etc. Storage system 206 can be a cloud-based storage system (as shown) or can be located at healthcare facility 204 or at the location of preoperative surgical planning system 202 or can be part of MR system 212 or visualization device (VD) 213, as examples.

MR system 212 can be used by a surgeon before (e.g., preoperatively) or during the surgical procedure (e.g., intraoperatively) to create, review, verify, update, modify and/or implement a surgical plan. In some examples, MR system 212 may also be used after the surgical procedure (e.g., postoperatively) to review the results of the surgical procedure, assess whether revisions are required, or perform other postoperative tasks. To that end, MR system 212 may include a visualization device 213 that may be worn by the surgeon and (as will be explained in further detail below) is operable to display a variety of types of information, including a 3D virtual image of the patient's diseased, damaged, or postsurgical joint and details of the surgical plan, such as a 3D virtual image of the prosthetic implant components selected for the surgical plan, 3D virtual images of entry points for positioning the prosthetic components, alignment axes and cutting planes for aligning cutting or reaming tools to shape the bone surfaces, or drilling tools to define one or more holes in the bone surfaces, in the surgical procedure to properly orient and position the prosthetic components, surgical guides and instruments and their placement on the damaged joint, and any other information that may be useful to the surgeon to implement the surgical plan. MR system 212 can generate images of this information that are perceptible to the user of the visualization device 213 before and/or during the surgical procedure.

In some examples, MR system 212 includes multiple visualization devices (e.g., multiple instances of visualization device 213) so that multiple users can simultaneously see the same images and share the same 3D scene. In some such examples, one of the visualization devices can be designated as the master device and the other visualization devices can be designated as observers or spectators. Any observer device can be re-designated as the master device at any time, as may be desired by the users of MR system 212.

In this way, FIG. 2 illustrates a surgical planning system that includes a preoperative surgical planning system 202 to generate a virtual surgical plan customized to repair an anatomy of interest of a particular patient. For example, the virtual surgical plan may include a plan for an orthopedic joint repair surgical procedure (e.g., to attach a prosthetic to anatomy of a patient), such as one of a standard total shoulder arthroplasty or a reverse shoulder arthroplasty. In this example, details of the virtual surgical plan may include details relating to at least one of preparation of anatomy for attachment of a prosthetic or attachment of the prosthetic to the anatomy. For instance, details of the virtual surgical plan may include details relating to at least one of preparation of a glenoid bone, preparation of a humeral bone, attachment of a prosthetic to the glenoid bone, or attachment of a prosthetic to the humeral bone. In some examples, the orthopedic joint repair surgical procedure is one of a stemless standard total shoulder arthroplasty, a stemmed standard total shoulder arthroplasty, a stemless reverse shoulder arthroplasty, a stemmed reverse shoulder arthroplasty, an augmented glenoid standard total shoulder arthroplasty, and an augmented glenoid reverse shoulder arthroplasty.

The virtual surgical plan may include a 3D virtual model corresponding to the anatomy of interest of the particular patient and a 3D model of a prosthetic component matched to the particular patient to repair the anatomy of interest or selected to repair the anatomy of interest. Furthermore, in the example of FIG. 2, the surgical planning system includes a storage system 206 to store data corresponding to the virtual surgical plan. The surgical planning system of FIG. 2 also includes MR system 212, which may comprise visualization device 213. In some examples, visualization device 213 is wearable by a user. In some examples, visualization device 213 is held by a user, or rests on a surface in a place accessible to the user. MR system 212 may be configured to present a user interface via visualization device 213. The user interface may present details of the virtual surgical plan for a particular patient. For instance, the details of the virtual surgical plan may include a 3D virtual model of an anatomy of interest of the particular patient. The user interface is visually perceptible to the user when the user is using visualization device 213. For instance, in one example, a screen of visualization device 213 may display real-world images and the user interface on a screen. In some examples, visualization device 213 may project virtual, holographic images onto see-through holographic lenses and also permit a user to see real-world objects of a real-world environment through the lenses. In other words, visualization device 213 may comprise one or more see-through holographic lenses and one or more display devices that present imagery to the user via the holographic lenses to present the user interface to the user.

In some examples, visualization device 213 is configured such that the user can manipulate the user interface (which is visually perceptible to the user when the user is wearing or otherwise using visualization device 213) to request and view details of the virtual surgical plan for the particular patient, including a 3D virtual model of the anatomy of interest (e.g., a 3D virtual bone model of the anatomy of interest, such as a glenoid bone or a humeral bone) and/or a 3D model of the prosthetic component selected to repair an anatomy of interest. In some such examples, visualization device 213 is configured such that the user can manipulate the user interface so that the user can view the virtual surgical plan intraoperatively, including (at least in some examples) the 3D virtual model of the anatomy of interest (e.g., a 3D virtual bone model of the anatomy of interest). In some examples, MR system 212 can be operated in an augmented surgery mode in which the user can manipulate the user interface intraoperatively so that the user can visually perceive details of the virtual surgical plan projected in a real environment, e.g., on a real anatomy of interest of the particular patient. In this disclosure, the terms real and real world may be used in a similar manner. For example, MR system 212 may present one or more virtual objects that provide guidance for preparation of a bone surface and placement of a prosthetic implant on the bone surface. Visualization device 213 may present one or more virtual objects in a manner in which the virtual objects appear to be overlaid on an actual, real anatomical object of the patient, within a real-world environment, e.g., by displaying the virtual object(s) with actual, real-world patient anatomy viewed by the user through holographic lenses. For example, the virtual objects may be 3D virtual objects that appear to reside within the real-world environment with the actual, real anatomical object.

Figure 3:
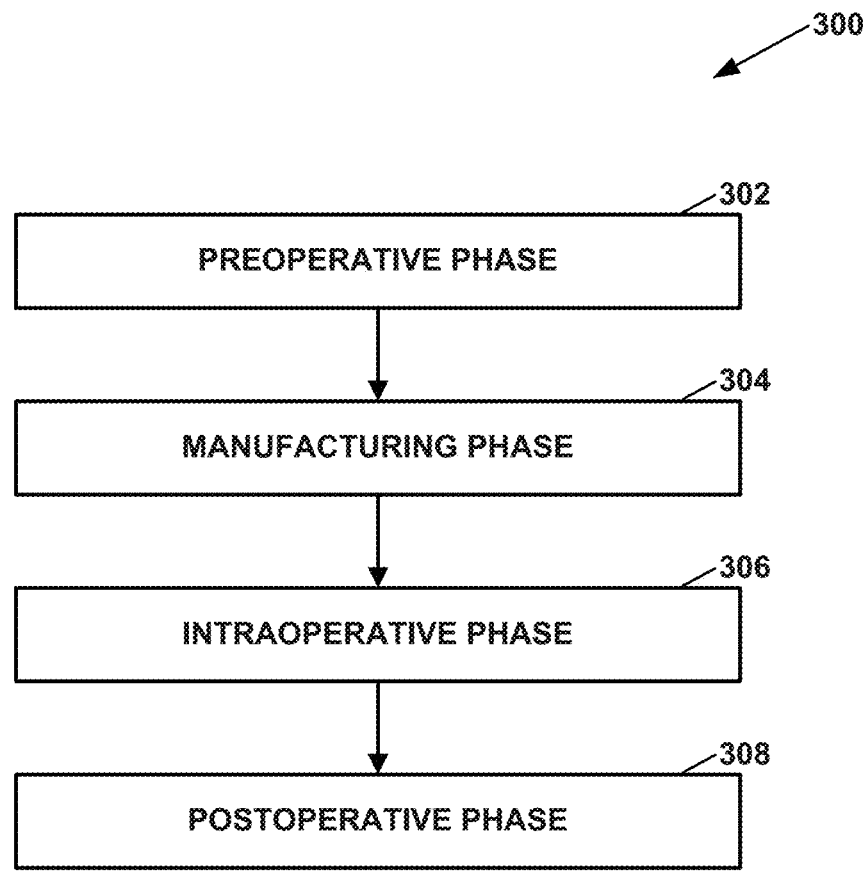
FIG. 3 is a flowchart illustrating example phases of a surgical lifecycle.

FIG. 3 is a flowchart illustrating example phases of a surgical lifecycle 300. In the example of FIG. 3, surgical lifecycle 300 begins with a preoperative phase (302). During the preoperative phase, a surgical plan is developed. The preoperative phase is followed by a manufacturing and delivery phase (304). During the manufacturing and delivery phase, patient-specific items, such as parts and equipment, needed for executing the surgical plan are manufactured and delivered to a surgical site. In some examples, it is unnecessary to manufacture patient-specific items in order to execute the surgical plan. An intraoperative phase follows the manufacturing and delivery phase (306). The surgical plan is executed during the intraoperative phase. In other words, one or more persons perform the surgery on the patient during the intraoperative phase. The intraoperative phase is followed by the postoperative phase (308). The postoperative phase includes activities occurring after the surgical plan is complete. For example, the patient may be monitored during the postoperative phase for complications.

As described in this disclosure, orthopedic surgical system 100 (FIG. 1) may be used in one or more of preoperative phase 302, the manufacturing and delivery phase 304, the intraoperative phase 306, and the postoperative phase 308. For example, virtual planning system 102 and planning support system 104 may be used in preoperative phase 302. Manufacturing and delivery system 106 may be used in the manufacturing and delivery phase 304. Intraoperative guidance system 108 may be used in intraoperative phase 306. Some of the systems of FIG. 1 may be used in multiple phases of FIG. 3. For example, medical education system 110 may be used in one or more of preoperative phase 302, intraoperative phase 306, and postoperative phase 308; pre- and postoperative monitoring system 112 may be used in preoperative phase 302 and postoperative phase 308. Predictive analytics system 114 may be used in preoperative phase 302 and postoperative phase 308.

Figure 4:
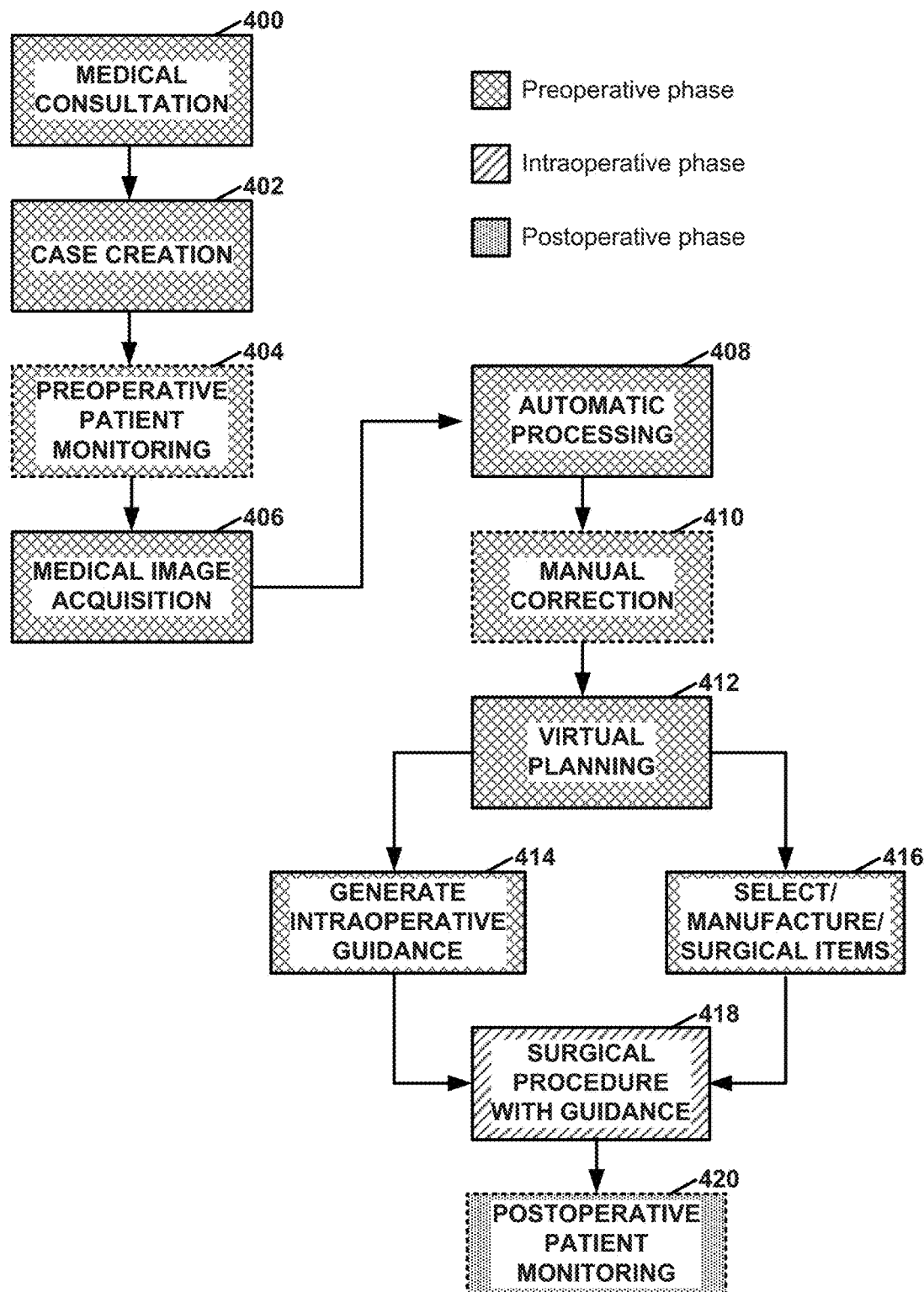
FIG. 4 is a flowchart illustrating preoperative, intraoperative and postoperative workflows in support of an orthopedic surgical procedure.

Various workflows may exist within the surgical process of FIG. 3. For example, different workflows within the surgical process of FIG. 3 may be appropriate for different types of surgeries. FIG. 4 is a flowchart illustrating preoperative, intraoperative and postoperative workflows in support of an orthopedic surgical procedure. In the example of FIG. 4, the surgical process begins with a medical consultation (400). During the medical consultation (400), a healthcare professional evaluates a medical condition of a patient. For instance, the healthcare professional may consult the patient with respect to the patient's symptoms. During the medical consultation (400), the healthcare professional may also discuss various treatment options with the patient. For instance, the healthcare professional may describe one or more different surgeries to address the patient's symptoms.

Furthermore, the example of FIG. 4 includes a case creation step (402). In other examples, the case creation step occurs before the medical consultation step. During the case creation step, the medical professional or other user establishes an electronic case file for the patient. The electronic case file for the patient may include information related to the patient, such as data regarding the patient's symptoms, patient range of motion observations, data regarding a surgical plan for the patient, medical images of the patients, notes regarding the patient, billing information regarding the patient, and so on.

The example of FIG. 4 includes a preoperative patient monitoring phase (404). During the preoperative patient monitoring phase, the patient's symptoms may be monitored. For example, the patient may be suffering from pain associated with arthritis in the patient's shoulder. In this example, the patient's symptoms may not yet rise to the level of requiring an arthroplasty to replace the patient's shoulder. However, arthritis typically worsens over time. Accordingly, the patient's symptoms may be monitored to determine whether the time has come to perform a surgery on the patient's shoulder. Observations from the preoperative patient monitoring phase may be stored in the electronic case file for the patient. In some examples, predictive analytics system 114 may be used to predict when the patient may need surgery, to predict a course of treatment to delay or avoid surgery or make other predictions with respect to the patient's health.

Additionally, in the example of FIG. 4, a medical image acquisition step occurs during the preoperative phase (406). During the image acquisition step, medical images of the patient are generated. The medical images may be generated in a variety of ways. For instance, the images may be generated using a Computed Tomography (CT) process, a Magnetic Resonance Imaging (MRI) process, an ultrasound process, or another imaging process. The medical images generated during the image acquisition step include images of an anatomy of interest of the patient. For instance, if the patient's symptoms involve the patient's shoulder, medical images of the patient's shoulder may be generated. The medical images may be added to the patient's electronic case file. Healthcare professionals may be able to use the medical images in one or more of the preoperative, intraoperative, and postoperative phases.

Furthermore, in the example of FIG. 4, an automatic processing step may occur (408). During the automatic processing step, virtual planning system 102 (FIG. 1) may automatically develop a preliminary surgical plan for the patient. In some examples of this disclosure, virtual planning system 102 may use machine learning techniques to develop the preliminary surgical plan based on information in the patient's virtual case file.

The example of FIG. 4 also includes a manual correction step (410). During the manual correction step, one or more human users may check and correct the determinations made during the automatic processing step. In some examples of this disclosure, one or more users may use mixed reality or virtual reality visualization devices during the manual correction step. In some examples, changes made during the manual correction step may be used as training data to refine the machine learning techniques applied by virtual planning system 102 during the automatic processing step.

A virtual planning step (412) may follow the manual correction step in FIG. 4. During the virtual planning step, a healthcare professional may develop a surgical plan for the patient. In some examples of this disclosure, one or more users may use mixed reality or virtual reality visualization devices during development of the surgical plan for the patient.

Furthermore, in the example of FIG. 4, intraoperative guidance may be generated (414). The intraoperative guidance may include guidance to a surgeon on how to execute the surgical plan. In some examples of this disclosure, virtual planning system 102 may generate at least part of the intraoperative guidance. In some examples, the surgeon or other user may contribute to the intraoperative guidance.

Additionally, in the example of FIG. 4, a step of selecting and manufacturing surgical items is performed (416). During the step of selecting and manufacturing surgical items, manufacturing and delivery system 106 (FIG. 1) may manufacture surgical items for use during the surgery described by the surgical plan. For example, the surgical items may include surgical implants, surgical tools, and other items required to perform the surgery described by the surgical plan.

In the example of FIG. 4, a surgical procedure may be performed with guidance from intraoperative system 108 (FIG. 1) (418). For example, a surgeon may perform the surgery while wearing a head-mounted MR visualization device of intraoperative system 108 that presents guidance information to the surgeon. The guidance information may help guide the surgeon through the surgery, providing guidance for various steps in a surgical workflow, including sequence of steps, details of individual steps, and tool or implant selection, implant placement and position, and bone surface preparation for various steps in the surgical procedure workflow.

Postoperative patient monitoring may occur after completion of the surgical procedure (420). During the postoperative patient monitoring step, healthcare outcomes of the patient may be monitored. Healthcare outcomes may include relief from symptoms, ranges of motion, complications, performance of implanted surgical items, and so on. Pre- and postoperative monitoring system 112 (FIG. 1) may assist in the postoperative patient monitoring step.

The medical consultation, case creation, preoperative patient monitoring, image acquisition, automatic processing, manual correction, and virtual planning steps of FIG. 4 are part of preoperative phase 302 of FIG. 3. The surgical procedures with guidance steps of FIG. 4 is part of intraoperative phase 306 of FIG. 3. The postoperative patient monitoring step of FIG. 4 is part of postoperative phase 308 of FIG. 3.

As mentioned above, one or more of the subsystems of orthopedic surgical system 100 may include one or more mixed reality (MR) systems, such as MR system 212 (FIG. 2). Each MR system may include a visualization device. For instance, in the example of FIG. 2, MR system 212 includes visualization device 213. In some examples, in addition to including a visualization device, an MR system may include external computing resources that support the operations of the visualization device. For instance, the visualization device of an MR system may be communicatively coupled to a computing device (e.g., a personal computer, backpack computer, smartphone, etc.) that provides the external computing resources. Alternatively, adequate computing resources may be provided on or within visualization device 213 to perform necessary functions of the visualization device.

Figure 5:
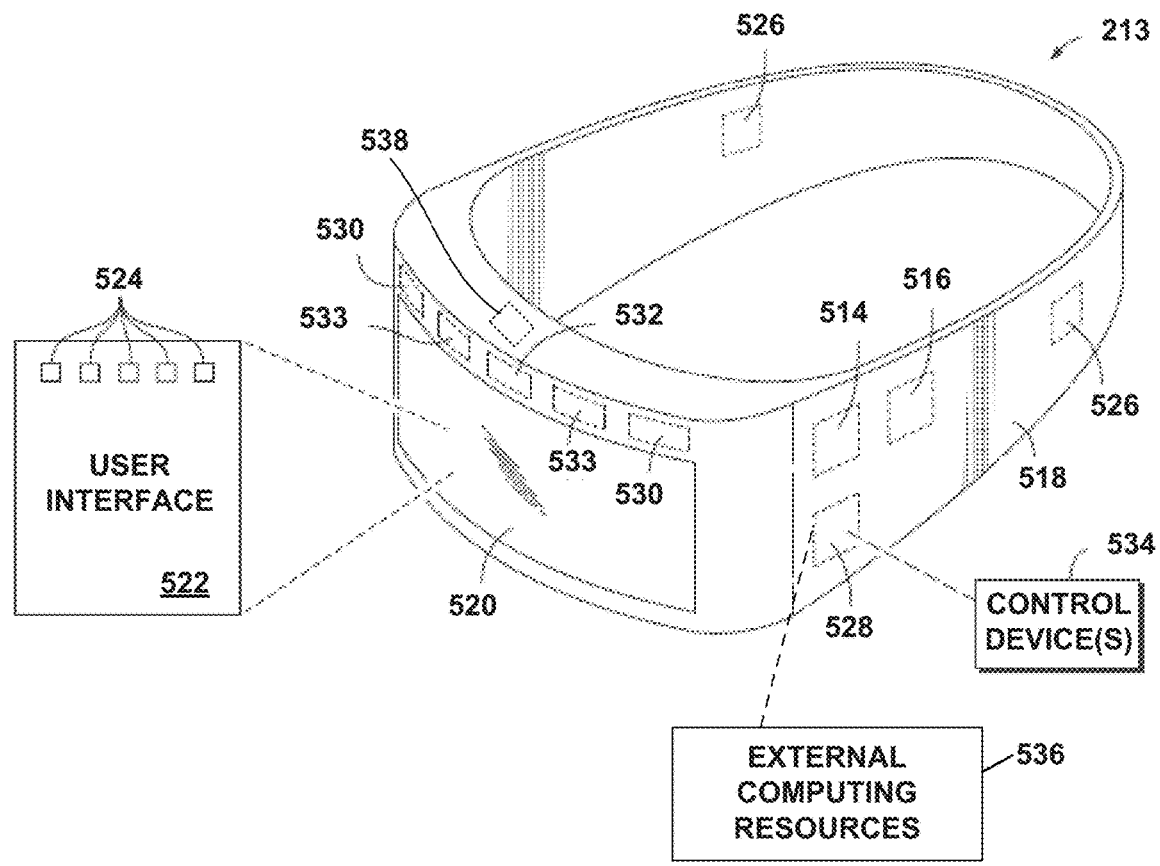
FIG. 5 is a schematic representation of a visualization device for use in a mixed reality (MR) system, according to an example of this disclosure.

FIG. 5 is a schematic representation of visualization device 213 for use in an MR system, such as MR system 212 of FIG. 2, according to an example of this disclosure. As shown in the example of FIG. 5, visualization device 213 can include a variety of electronic components found in a computing system, including one or more processor(s) 514 (e.g., microprocessors or other types of processing units) and memory 516 that may be mounted on or within a frame 518. Furthermore, in the example of FIG. 5, visualization device 213 may include a transparent screen 520 that is positioned at eye level when visualization device 213 is worn by a user. In some examples, screen 520 can include one or more liquid crystal displays (LCDs) or other types of display screens on which images are perceptible to a surgeon who is wearing or otherwise using visualization device 213 via screen 520. Other display examples include organic light emitting diode (OLED) displays. In some examples, visualization device 213 can operate to project 3D images onto the user's retinas using techniques known in the art.

In some examples, screen 520 may include see-through holographic lenses. sometimes referred to as waveguides, that permit a user to see real-world objects through (e.g., beyond) the lenses and also see holographic imagery projected into the lenses and onto the user's retinas by displays, such as liquid crystal on silicon (LCoS) display devices, which are sometimes referred to as light engines or projectors, operating as an example of a holographic projection system 538 within visualization device 213. In other words, visualization device 213 may include one or more see-through holographic lenses to present virtual images to a user. Hence, in some examples, visualization device 213 can operate to project 3D images onto the user's retinas via screen 520, e.g., formed by holographic lenses. In this manner, visualization device 213 may be configured to present a 3D virtual image to a user within a real-world view observed through screen 520, e.g., such that the virtual image appears to form part of the real-world environment. In some examples, visualization device 213 may be a Microsoft HOLOLENS™ headset, available from Microsoft Corporation, of Redmond, Wash., USA, or a similar device, such as, for example, a similar MR visualization device that includes waveguides. The HOLOLENS™ device can be used to present 3D virtual objects via holographic lenses, or waveguides, while permitting a user to view actual objects in a real-world scene, i.e., in a real-world environment, through the holographic lenses.

Although the example of FIG. 5 illustrates visualization device 213 as a head-wearable device, visualization device 213 may have other forms and form factors. For instance, in some examples, visualization device 213 may be a handheld smartphone or tablet.

Visualization device 213 can also generate a user interface (UI) 522 that is visible to the user, e.g., as holographic imagery projected into see-through holographic lenses as described above. For example, UI 522 can include a variety of selectable widgets 524 that allow the user to interact with a mixed reality (MR) system, such as MR system 212 of FIG. 2. Imagery presented by visualization device 213 may include, for example, one or more 3D virtual objects. Details of an example of UI 522 are described elsewhere in this disclosure. Visualization device 213 also can include a speaker or other sensory devices 526 that may be positioned adjacent the user's ears. Sensory devices 526 can convey audible information or other perceptible information (e.g., vibrations) to assist the user of visualization device 213.

Visualization device 213 can also include a transceiver 528 to connect visualization device 213 to a processing device 510 and/or to network 208 and/or to a computing cloud, such as via a wired communication protocol or a wireless protocol, e.g., Wi-Fi, Bluetooth, etc. Visualization device 213 also includes a variety of sensors to collect sensor data, such as one or more optical camera(s) 530 (or other optical sensors) and one or more depth camera(s) 532 (or other depth sensors), mounted to, on or within frame 518. In some examples, the optical sensor(s) 530 are operable to scan the geometry of the physical environment in which a user of MR system 212 is located (e.g., an operating room) and collect two-dimensional (2D) optical image data (either monochrome or color). Depth sensor(s) 532 are operable to provide 3D image data, such as by employing time of flight, stereo or other known or future-developed techniques for determining depth and thereby generating image data in three dimensions. Other sensors can include motion sensors 533 (e.g., Inertial Mass Unit (IMU) sensors, accelerometers, etc.) to assist with tracking movement.

MR system 212 processes the sensor data so that geometric, environmental, textural, or other types of landmarks (e.g., corners, edges or other lines, walls, floors, objects) in the user's environment or "scene" can be defined and movements within the scene can be detected. As an example, the various types of sensor data can be combined or fused so that the user of visualization device 213 can perceive 3D images that can be positioned, or fixed and/or moved within the scene. When a 3D image is fixed in the scene, the user can walk around the 3D image, view the 3D image from different perspectives, and manipulate the 3D image within the scene using hand gestures, voice commands, gaze line (or direction) and/or other control inputs. As another example, the sensor data can be processed so that the user can position a 3D virtual object (e.g., a bone model) on an observed physical object in the scene (e.g., a surface, the patient's real bone, etc.) and/or orient the 3D virtual object with other virtual images displayed in the scene. In some examples, the sensor data can be processed so that the user can position and fix a virtual representation of the surgical plan (or other widget, image or information) onto a surface, such as a wall of the operating room. Yet further, in some examples, the sensor data can be used to recognize surgical instruments and the position and/or location of those instruments.

Visualization device 213 may include one or more processors 514 and memory 516, e.g., within frame 518 of the visualization device. In some examples, one or more external computing resources 536 process and store information, such as sensor data, instead of or in addition to in-frame processor(s) 514 and memory 516. In this way, data processing and storage may be performed by one or more processors 514 and memory 516 within visualization device 213 and/or some of the processing and storage requirements may be offloaded from visualization device 213. Hence, in some examples, one or more processors that control the operation of visualization device 213 may be within visualization device 213, e.g., as processor(s) 514. Alternatively, in some examples, at least one of the processors that controls the operation of visualization device 213 may be external to visualization device 213, e.g., as processor(s) 210. Likewise, operation of visualization device 213 may, in some examples, be controlled in part by a combination one or more processors 514 within the visualization device and one or more processors 210 external to visualization device 213.

For instance, in some examples, when visualization device 213 is in the context of FIG. 2, processing of the sensor data can be performed by processing device(s) 210 in conjunction with memory or storage device(s) (M) 215. In some examples, processor(s) 514 and memory 516 mounted to frame 518 may provide sufficient computing resources to process the sensor data collected by cameras 530, 532 and motion sensors 533. In some examples, the sensor data can be processed using a Simultaneous Localization and Mapping (SLAM) algorithm, or other known or future-developed algorithms for processing and mapping 2D and 3D image data and tracking the position of visualization device 213 in the 3D scene. In some examples, image tracking may be performed using sensor processing and tracking functionality provided by the Microsoft HOLOLENS™ system, e.g., by one or more sensors and processors 514 within a visualization device 213 substantially conforming to the Microsoft HOLOLENS™ device or a similar mixed reality (MR) visualization device.

In some examples, MR system 212 can also include user-operated control device(s) 534 that allow the user to operate MR system 212, use MR system 212 in spectator mode (either as master or observer), interact with UI 522 and/or otherwise provide commands or requests to processing device(s) 210 or other systems connected to network 208. As examples, control device(s) 534 can include a microphone, a touch pad, a control panel, a motion sensor or other types of control input devices with which the user can interact.

Figure 6:
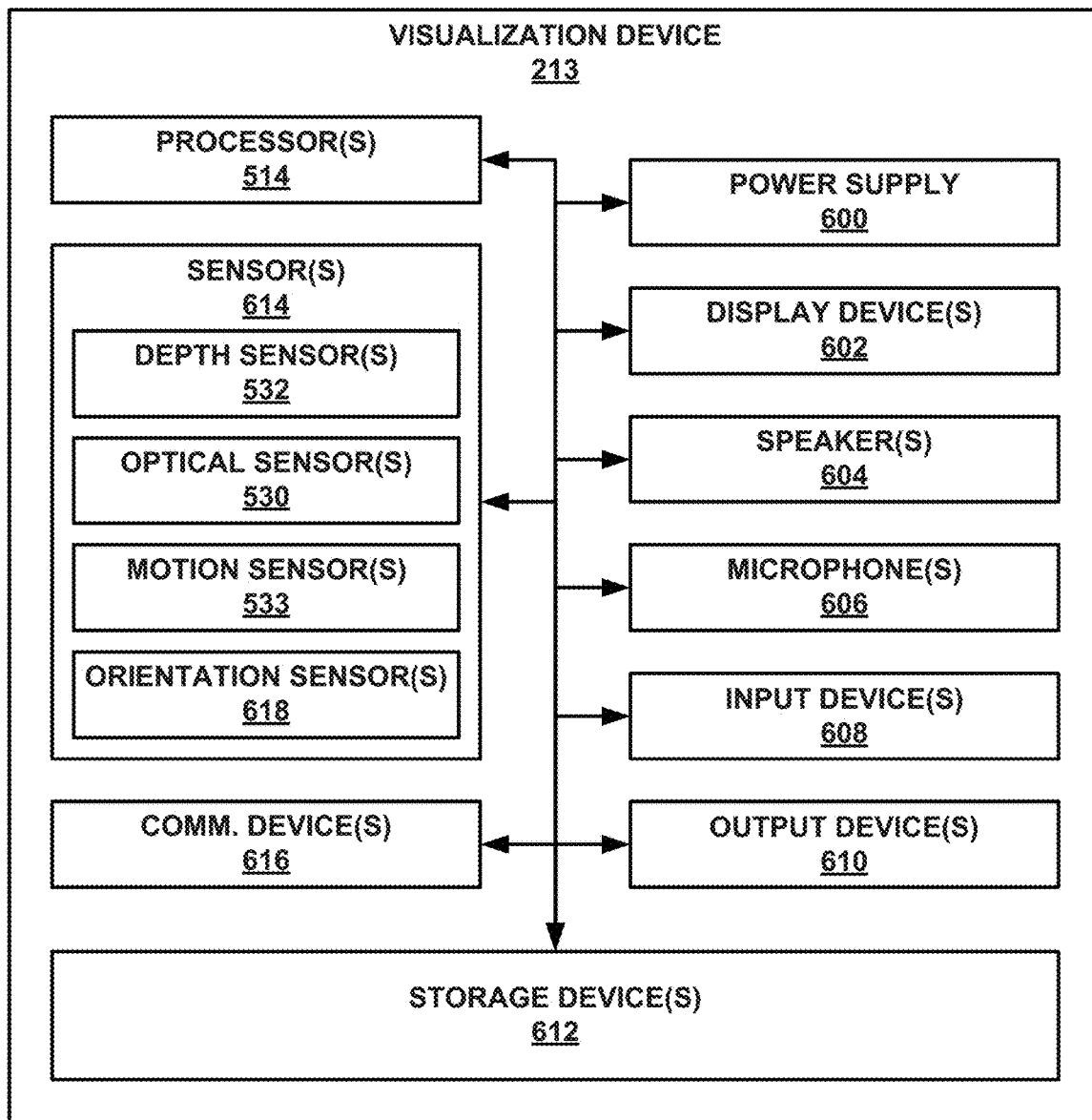
FIG. 6 is a block diagram illustrating example components of a visualization device for use in a mixed reality (MR) system, according to an example of this disclosure.

FIG. 6 is a block diagram illustrating example components of visualization device 213 for use in a MR system. In the example of FIG. 6, visualization device 213 includes processors 514, a power supply 600, display device(s) 602, speakers 604, microphone(s) 606, input device(s) 608, output device(s) 610, storage device(s) 612, sensor(s) 614, and communication devices 616. In the example of FIG. 6, sensor(s) 616 may include depth sensor(s) 532, optical sensor(s) 530, motion sensor(s) 533, and orientation sensor(s) 618. Optical sensor(s) 530 may include cameras, such as Red-Green-Blue (RGB) video cameras, infrared cameras, or other types of sensors that form images from light. Display device(s) 602 may display imagery to present a user interface to the user.

Speakers 604, in some examples, may form part of sensory devices 526 shown in FIG. 5. In some examples, display devices 602 may include screen 520 shown in FIG. 5. For example, as discussed with reference to FIG. 5, display device(s) 602 may include see-through holographic lenses, in combination with projectors, that permit a user to see real-world objects, in a real-world environment, through the lenses, and also see virtual 3D holographic imagery projected into the lenses and onto the user's retinas, e.g., by a holographic projection system. In this example, virtual 3D holographic objects may appear to be placed within the real-world environment. In some examples, display devices 602 include one or more display screens, such as LCD display screens, OLED display screens, and so on. The user interface may present virtual images of details of the virtual surgical plan for a particular patient.

In some examples, a user may interact with and control visualization device 213 in a variety of ways. For example, microphones 606, and associated speech recognition processing circuitry or software, may recognize voice commands spoken by the user and, in response, perform any of a variety of operations, such as selection, activation, or deactivation of various functions associated with surgical planning, intra-operative guidance, or the like. As another example, one or more cameras or other optical sensors 530 of sensors 614 may detect and interpret gestures to perform operations as described above. As a further example, sensors 614 may sense gaze direction and perform various operations as described elsewhere in this disclosure. In some examples, input devices 608 may receive manual input from a user, e.g., via a handheld controller including one or more buttons, a keypad, a touchscreen, joystick, trackball, and/or other manual input media, and perform, in response to the manual user input, various operations as described above.

As discussed above, surgical lifecycle 300 may include a preoperative phase 302 (FIG. 3). One or more users may use orthopedic surgical system 100 in preoperative phase 302. For instance, orthopedic surgical system 100 may include virtual planning system 102 to help the one or more users generate a virtual surgical plan that may be customized to an anatomy of interest of a particular patient. As described herein, the virtual surgical plan may include a 3-dimensional virtual model that corresponds to the anatomy of interest of the particular patient and a 3-dimensional model of one or more prosthetic components matched to the particular patient to repair the anatomy of interest or selected to repair the anatomy of interest. The virtual surgical plan also may include a 3-dimensional virtual model of guidance information to guide a surgeon in performing the surgical procedure, e.g., in preparing bone surfaces or tissue and placing implantable prosthetic hardware relative to such bone surfaces or tissue.

Figure 7:
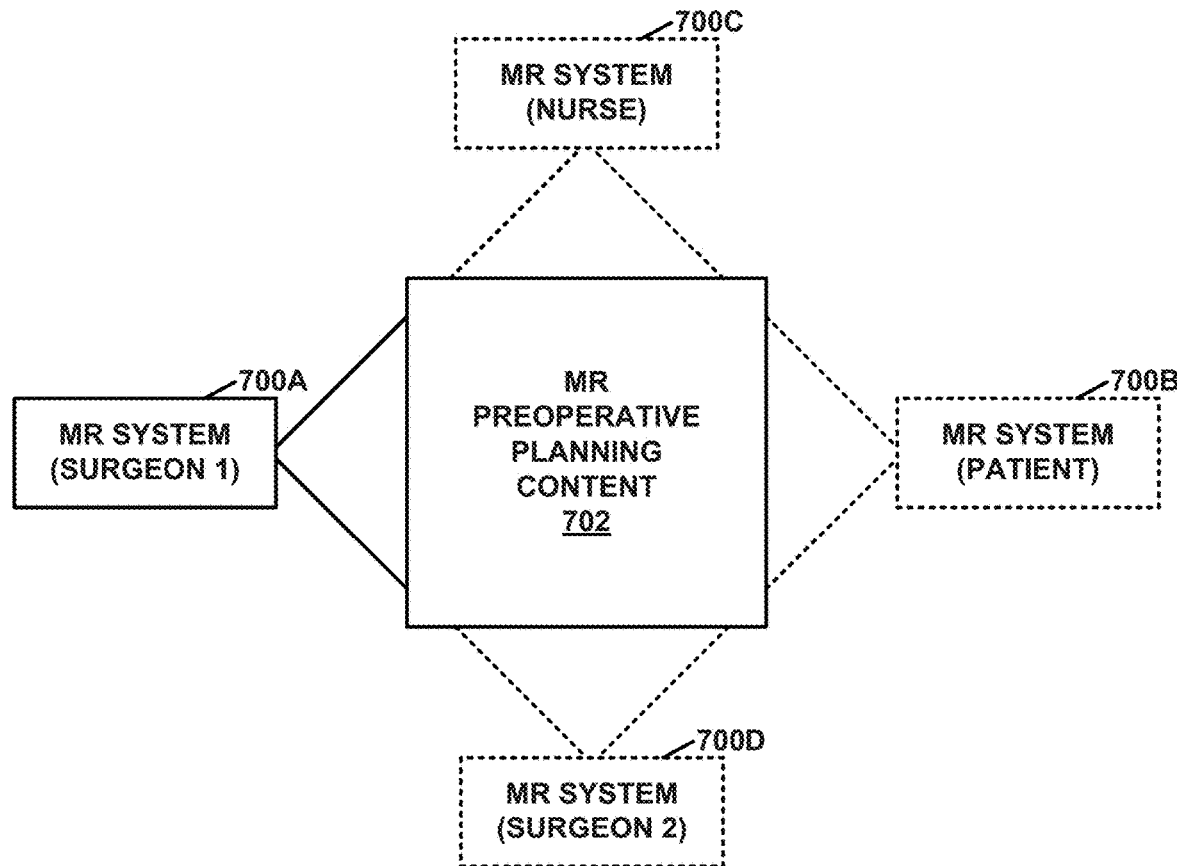
FIG. 7 is a conceptual diagram illustrating an example setting in which a set of users use mixed reality (MR) systems of an orthopedic surgical system during a preoperative phase.

FIG. 7 is a conceptual diagram illustrating an example setting in which a set of users use MR systems of orthopedic surgical system 100 during preoperative phase 302. In the example of FIG. 7, a surgeon may use (e.g., wear) a visualization device (e.g., visualization device 213) of a first MR system 700A (e.g., MR system 212). The visualization device of MR system 700A may present MR preoperative planning content 702 to the surgeon during preoperative phase 302. As described in detail elsewhere in this disclosure, MR preoperative planning content 702 may help the surgeon plan for a surgery.

Furthermore, in the example of FIG. 7, one or more other users may use visualization devices of MR systems of orthopedic surgical system 100 to view MR preoperative planning content 702. For example, a patient may use a visualization device of a second MR system 700B during preoperative phase 302. The visualization device of MR system 700B may present MR preoperative planning content 702 to the patient. For instance, as described in detail elsewhere in this disclosure, MR preoperative planning content 702 may include virtual 3D model information to be presented using MR to help the patient understand one or more of the patient's current condition and the surgery to be performed on the patient.

In the example of FIG. 7, a nurse or other healthcare professional may use a visualization device of a third MR system 700C during preoperative phase 302. The visualization device of MR system 700C may present MR preoperative planning content 702 to the nurse or other healthcare professional. For instance, in one example, MR preoperative planning content 702 may help the nurse understand a surgery before the surgery happens.

Furthermore, in the example of FIG. 7, a second surgeon may use a visualization device of a fourth MR system 700D. The visualization device of MR system 700D may present MR preoperative planning content 702 to the second surgeon. This may allow the surgeons to collaborate to develop and review a surgical plan for the patient. For instance, surgeons may view and manipulate the same preoperative planning content 702 at the same or different times. MR systems 700A, 700B, 700C, and 700D may collectively be referred to herein as "MR systems 700."

Thus, as described in the examples above, two or more of the individuals described above (e.g., the first surgeon, the patient, the nurse, and the second surgeon) can view the same or different MR preoperative planning content 702 at the same time. In examples where two or more of the individuals are viewing the same MR preoperative planning content 702 at the same time, the two or more individuals may concurrently view the same MR preoperative guidance content 702 from the same or different perspectives. Moreover, in some examples, two or more of the individuals described above can view the same or different MR preoperative planning content 702 at different times. Preoperative planning content 702 may include an information model of a surgical plan, virtual 3D model information representing patient anatomy, such as bone and/or tissue, alone, or in combination with virtual 3D model information representing surgical procedure steps and/or implant placement and positioning. Examples of preoperative planning content 702 may include a surgical plan for a shoulder arthroplasty, virtual 3D model information representing scapula and/or glenoid bone, or representing humeral bone, with virtual 3D model information of instruments to be applied to the bone or implants to be positioned on or in the bone. In some examples, multiple users may be able to change and manipulate preoperative planning content 702.

Figure 8:
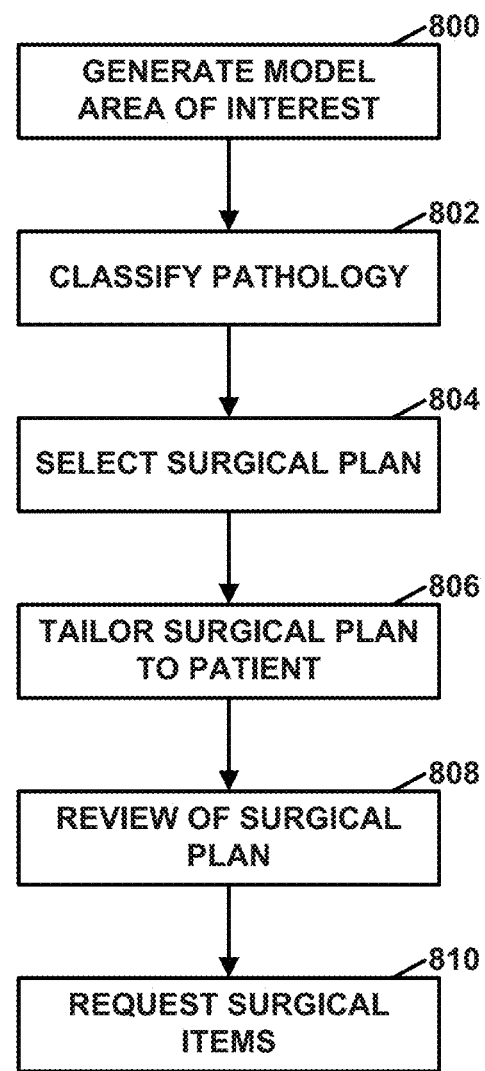
FIG. 8 is a flowchart illustrating example steps in the preoperative phase of the surgical lifecycle.

FIG. 8 is a flowchart illustrating example steps in preoperative phase 302 of surgical lifecycle 300. In other examples, preoperative phase 302 may include more, fewer, or different steps. Moreover, in other examples, one or more of the steps of FIG. 8 may be performed in different orders. In some examples, one or more of the steps may be performed automatically within a surgical planning system such as virtual planning system 102 (FIG. 1) or 202 (FIG. 2).

In the example of FIG. 8, a model of the area of interest is generated (800). For example, a scan (e.g., a CT scan, MRI scan, or other type of scan) of the area of interest may be performed. For example, if the area of interest is the patient's shoulder, a scan of the patient's shoulder may be performed. Furthermore, a pathology in the area of interest may be classified (802). In some examples, the pathology of the area of interest may be classified based on the scan of the area of interest. For example, if the area of interest is the user's shoulder, a surgeon may determine what is wrong with the patient's shoulder based on the scan of the patient's shoulder and provide a shoulder classification indicating the classification or diagnosis, e.g., such as primary glenoid humeral osteoarthritis (PGHOA), rotator cuff tear arthropathy (RCTA) instability, massive rotator cuff tear (MRCT), rheumatoid arthritis, post-traumatic arthritis, and osteoarthritis.

Additionally, a surgical plan may be selected based on the pathology (804). The surgical plan is a plan to address the pathology. For instance, in the example where the area of interest is the patient's shoulder, the surgical plan may be selected from an anatomical shoulder arthroplasty, a reverse shoulder arthroplasty, a post-trauma shoulder arthroplasty, or a revision to a previous shoulder arthroplasty. The surgical plan may then be tailored to patient (806). For instance, tailoring the surgical plan may involve selecting and/or sizing surgical items needed to perform the selected surgical plan. Additionally, the surgical plan may be tailored to the patient in order to address issues specific to the patient, such as the presence of osteophytes. As described in detail elsewhere in this disclosure, one or more users may use mixed reality systems of orthopedic surgical system 100 to tailor the surgical plan to the patient.

The surgical plan may then be reviewed (808). For instance, a consulting surgeon may review the surgical plan before the surgical plan is executed. As described in detail elsewhere in this disclosure, one or more users may use mixed reality (MR) systems of orthopedic surgical system 100 to review the surgical plan. In some examples, a surgeon may modify the surgical plan using an MR system by interacting with a UI and displayed elements, e.g., to select a different procedure, change the sizing, shape or positioning of implants, or change the angle, depth or amount of cutting or reaming of the bone surface to accommodate an implant.

Additionally, in the example of FIG. 8, surgical items needed to execute the surgical plan may be requested (810).

As described in the following sections of this disclosure, orthopedic surgical system 100 may assist various users in performing one or more of the preoperative steps of FIG. 8.

Figure 9:
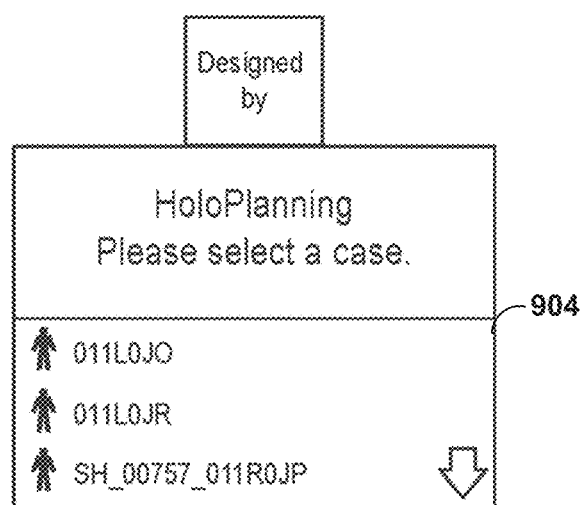
FIG. 9 illustrates an example welcome page for selecting a surgical case, according to an example of this disclosure.

FIG. 9 illustrates an example welcome page for selecting a surgical case, according to an example of this disclosure. The Welcome page, which may be presented by MR visualization device 213 to a user, displays a menu 904 that allows the user to scroll through and select a specific patient's surgical plan that is stored on and retrieved from storage system 206 in system 200 (FIG. 2) or in memory or storage device 215 of MR visualization device 213 (FIG. 2).

Figure 10:
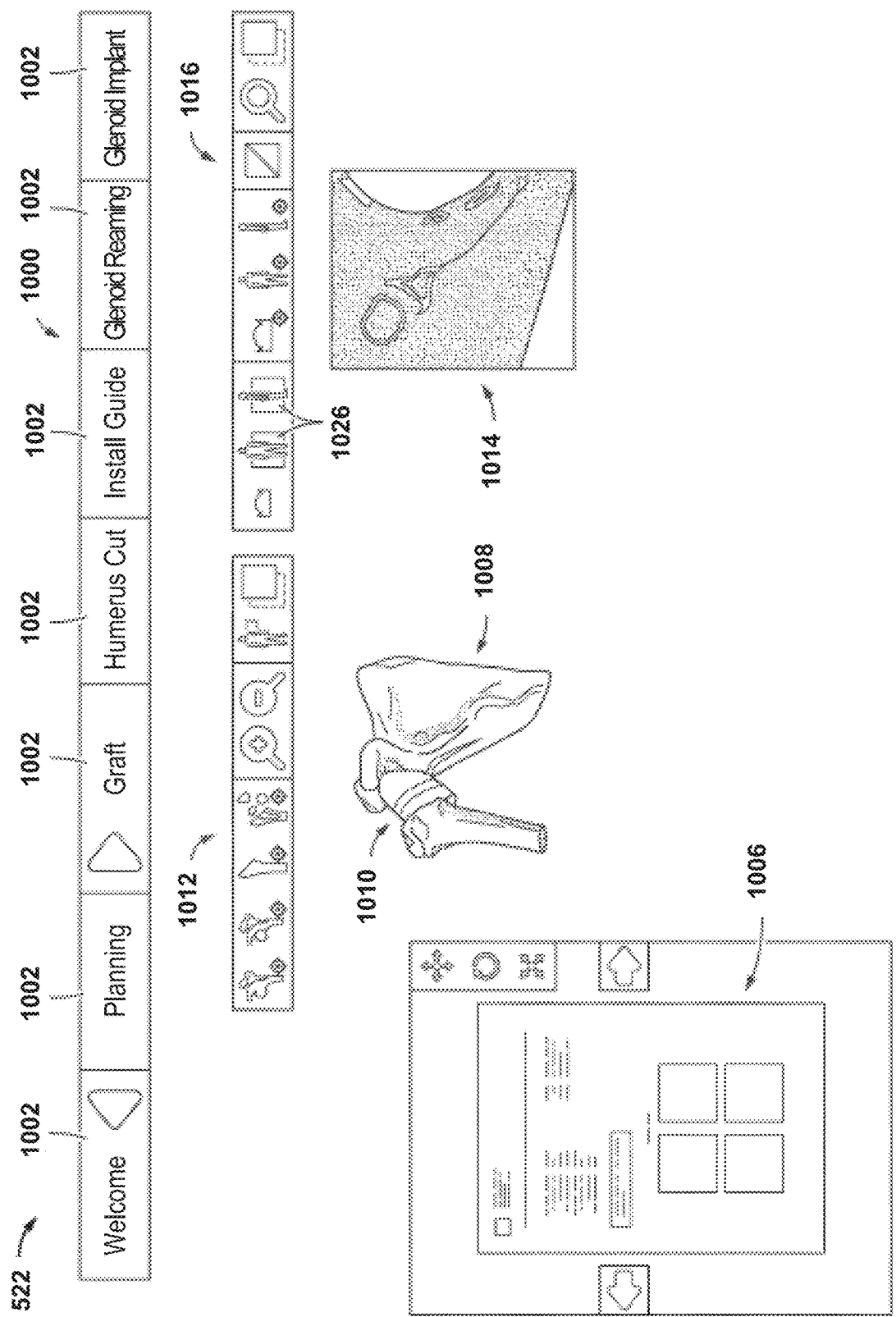
FIG. 10 illustrates an example of a page of a user interface of a mixed reality (MR) system, according to an example of this disclosure.

FIG. 10 illustrates an example of a page of a user interface of a mixed reality system, according to an example of this disclosure, e.g. as produced for a particular patient's surgical plan selected from the welcome page of FIG. 9. Using visualization device 213, a user can perceive and interact with UI 522. In the example shown in FIG. 10, UI 522 includes a workflow bar 1000 with selectable buttons 1002 that represent a surgical workflow, spanning various surgical procedure steps for operations on the humerus and glenoid in a shoulder arthroplasty procedure. Selection of a button 1002 can lead to display of various selectable widgets with which the user can interact, such as by using hand gestures, voice commands, gaze direction, connected lens and/or other control inputs. Selection of widgets can launch various modes of operation of MR system 212, display information or images generated by MR system 212, allow the user to further control and/or manipulate the information and images, lead to further selectable menus or widgets, etc.

The user can also organize or customize UI 522 by manipulating, moving and orienting any of the displayed widgets according to the user's preferences, such as by visualization device 213 or other device detecting gaze direction, hand gestures and/or voice commands. Further, the location of widgets that are displayed to the user can be fixed relative to the scene. Thus, as the user's gaze (i.e., eye direction) moves to view other features of the user interface 522, other virtual images, and/or real objects physically present in the scene (e.g., the patient, an instrument set, etc.), the widgets may remain stationary and do not interfere with the user's view of the other features and objects. As yet another example, the user can control the opacity or transparency of the widgets or any other displayed images or information. The user also can navigate in any direction between the buttons 1002 on the workflow bar 1000 and can select any button 1002 at any time during use of MR system 212. Selection and manipulation of widgets, information, images or other displayed features can be implemented based on visualization device 213 or other device detecting user gaze direction, hand motions, voice commands or any combinations thereof.

In the example of FIG. 10, UI 522 is configured for use in shoulder repair procedures and includes, as examples, buttons 1002 on workflow bar 1000 that correspond to a "Welcome" page, a "Planning" page, a "Graft" page, a "Humerus Cut" page, an "Install Guide" page, a "Glenoid Reaming" page, and a "Glenoid Implant" page. The presentation of the "Install Guide" page may be optional as, in some examples, glenoid reaming may be accomplished using virtual guidance and without the application of a glenoid guide.

As shown FIG. 10, the "Planning" page in this example of UI 522 displays various information and images corresponding to the selected surgical plan, including an image 1006 of a surgical plan file (e.g., a pdf file or other appropriate media format) that corresponds to the selected plan (including preoperative and postoperative information); a 3D virtual bone model 1008 and a 3D virtual implant model 1010 along with a 3D image navigation bar 1012 for manipulating the 3D virtual models 1008, 1010 (which may be referred to as 3D images); a viewer 1014 and a viewer navigation bar 1016 for viewing a multi-planar view associated with the selected surgical plan. MR system 212 may present the "Planning" page as a virtual MR object to the user during preoperative phase 302 (FIG. 3). For instance, MR system 212 may present the "Planning" page to the user to help the user classify a pathology, select a surgical plan, tailor the surgical plan to the patient, revise the surgical plan, and review the surgical plan, as described in steps 802, 804, 806, and 808 of FIG. 8.

The surgical plan image 1006 may be a compilation of preoperative (and, optionally, postoperative) patient information and the surgical plan for the patient that are stored in a database in storage system 206. In some examples, surgical plan image 1006 can correspond to a multi-page document through which the user can browse. For example, further images of pages can display patient information, information regarding the anatomy of interest, postoperative measurements, and various 2D images of the anatomy of interest. Yet further page images can include, as examples, planning information associated with an implant selected for the patient, such as anatomy measurements and implant size, type and dimensions; planar images of the anatomy of interest; images of a 3D model showing the positioning and orientation of a surgical guide selected for the patient to assist with execution of the surgical plan; etc.

It should be understood that the surgical plan image 1006 can be displayed in any suitable format and arrangement and that other implementations of the systems and techniques described herein can include different information depending upon the needs of the application in which the plan image 1006 is used.

Referring again FIG. 10, the Planning page of UI 522 also may provide images of the 3D virtual bone model 1008 and the 3D model of the implant components 1010 along with navigation bar 1012 for manipulating 3D virtual models 1008, 1010. For example, selection or de-selection of the icons on navigation bar 1012 allow the user to selectively view different portions of 3D virtual bone model 1008 with or without the various implant components 1010. For example, the scapula of virtual bone model 1008 and the glenoid implant of implant model 1010 have been de-selected, leaving only the humerus bone and the humeral implant components visible. Other icons can allow the user to zoom in or out, and the user also can rotate and re-orient 3D virtual models 1008, 1010, e.g., using gaze detection, hand gestures and/or voice commands.

Figure 12:
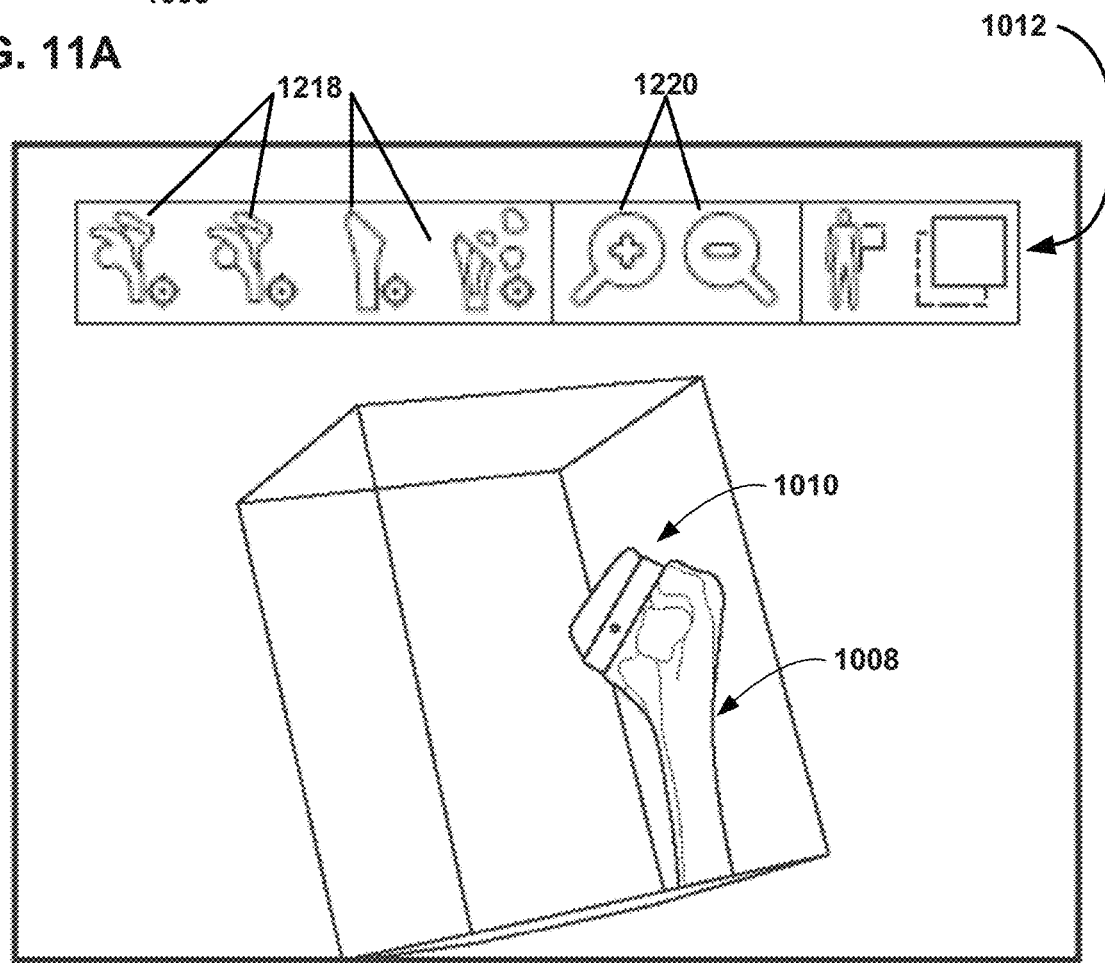
FIG. 12 illustrates effects of de-selection of icons in the navigation bar of FIG. 10.

The Planning page of UI 522 also provides images of 3D virtual bone model 1008 and the 3D model of the implant components 1010 along with navigation bar 1012 for manipulating 3D virtual models 1008, 1010. For example, as shown in FIG. 12, selection or de-selection of icons 1218 (FIG. 12) on the navigation bar 1012 allow the user to selectively view different portions of the 3D virtual bone model 1008 with or without the various implant components 1010. In this example, the scapula of virtual bone model 1008 and the glenoid implant of the implant model 1010 have been de-selected, leaving only the humerus bone and the humeral implant components visible. Icons 1220 (FIG. 12) allow the user to zoom in or out, and the user also can rotate and re-orient the 3D virtual models 1008, 1010 using gaze detection, hand gestures and/or voice commands.

Figure 11A:
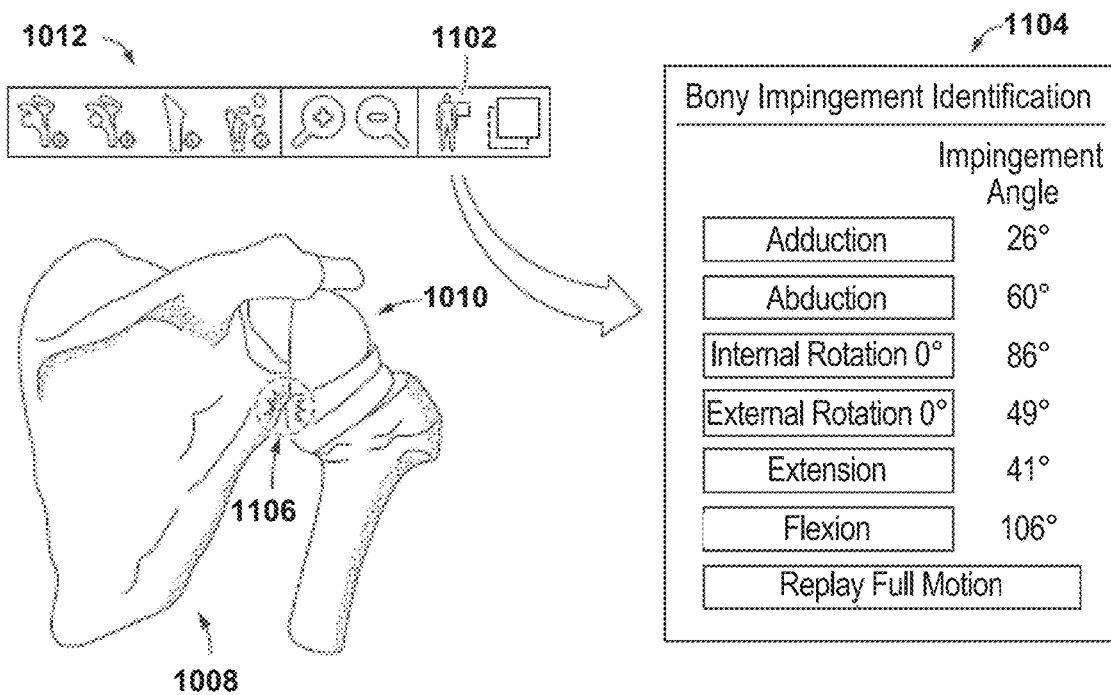
FIG. 11A is an example of information that can be displayed on a page of the user interface of FIG. 10.

In the example of FIG. 11A, selection of range-of-motion icon 1102 on navigation bar 1012 of the "Planning" page launches a range-of-motion mode in which the user can test or confirm the selection, placement and/or positioning of the implant components 1010 by simulating various different motions of the anatomy with the prosthetic implant implanted according to the preoperative surgical plan for the patient. In this example, by using gaze direction, hand motions detected by motion sensors or other control devices and/or voice commands, the user can select anatomical motions, such as adduction, abduction, internal/external rotation, elevation, flexion, and extension or any other joint movement simulation such as movements corresponding to daily functional tasks. In the example of FIG. 11A, a range-of-motion menu 1104 includes selectable elements corresponding to different types of motions.

In response to receiving an indication of user input to select one of the movement (i.e., "Adduction," "Abduction," "Internal Rotation 0 degrees," "External Rotation 0 degrees," "Extension," and "Flexion"), MR system 212 may present an MR animation of 3D virtual model 1008 exhibiting the selected movement type. For example, if the user selected abduction, MR system 212 may present an animation of the humerus of 3D virtual model 1008 rotating vertically relative to the scapula of 3D virtual model 1008. Furthermore, in the example of FIG. 11A, range-of-motion menu 1104 includes a "Replay Full Motion" element 1125. In response to receiving an indication of user input to select element 1125, MR system 212 may present an animation of the humerus of 3D virtual model 1008 moving in each of the movement types listed in range-of-motion menu 1104.

Range-of-motion menu 1104 also lists an impingement angle for each of the types of motion. In the example of FIG. 11A, the impingement angle for a type of motion is an angle at which a bony impingement occurs when performing the type of motion. A bony impingement occurs when a bone contacts another bone or when a moving implanted surgical component (e.g., a cup member connected to the humerus, a talar implant, a tibial implant, etc.) contacts a bone. Bony impingements may be painful and may cause wear on the bone. Because bony impingements represent contact between two hard surfaces, bony impingements also represent the theoretical limits to ranges of motion. In the example of FIG. 11A, the impingement angles represent angles determined for a given virtual surgical plan, including implant components, along with component size, position and angle, specified by the virtual surgical plan.

Visualization of the simulated ranges of motion using MR system 212 can help the surgeon confirm the surgical plan or may lead the surgeon to update or modify the preoperative surgical plan. For example, in FIG. 11A, the user has selected the adduction button on a range-of-motion menu 1104. A collision 1106 between a scapula and a humerus-mounted cup component during the adduction simulation is highlighted (e.g., in red) in the MR visualization by visualization device 213. In another example, a collision between a talus bone and a tibial implant, or between a talar implant and a tibia, may be highlighted in an MR visualization by visualization device 213. To further aid the user, MR system 212 may rotate the 3D models, walk around the 3D models, hide or show parts of the 3D models, or perform other actions to observe the 3D models.

If a bony impingement (i.e., a collision) occurs at an angle within the normal range of motion for a patient, this may indicate to the surgeon that a change in certain parameters of the surgical plan (e.g., size, type, position or orientation of implant components) may be needed. However, if such a collision occurs at an angle outside the normal range of motion for the patient, there may be no need for the surgeon to change the parameters of the surgical plan. Rather, other tissues of the patient may stop the motion before a collision occurs. For instance, in the example of FIG. 11A, the patient's side or tendons attached to the humerus may prevent collision 1106 from actually occurring. However, the normal range of motion for abduction is 180° while menu 1104 indicates that a bony impingement would occur at an angle of 60°. Thus, with the current parameters of the surgical plan shown in FIG. 11A, the patient would not even be able to raise their arm to a horizontal position. This disclosure may use the term "premature collision" to refer to a bony impingement that occurs within a normal range of motion.

Showing collisions, such as collision 1106, as part of an MR presentation of animation of a range of motion may help the surgeon understand how to change certain parameters of the surgical plan. For example, a bony impingement between the humerus and either the acromion or coracoid process may limit the patient's range of motion during abduction. Thus, in this example, the surgeon may be able to determine that the ball component should be offset rearward by seeing that a premature bony collision occurs between the patient's humerus and acromion during abduction but no collision occurs between the patient's humerus and coracoid process during abduction. However, if there is a premature bony collision between the humerus and both the acromion and coracoid process, the surgeon may determine that a differently sized ball component or wedge is required. Enabling the surgeon to see, rotate, walk around, or otherwise interact with the 3D virtual bone model and 3D virtual implant model may help the surgeon make this determination.

Figure 11B:
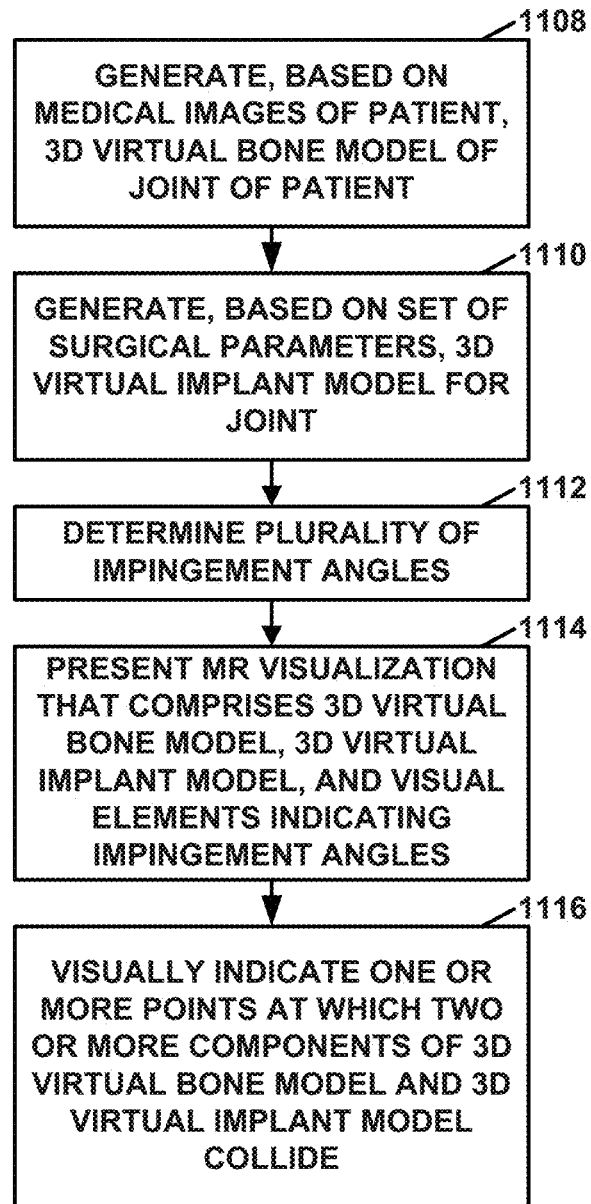
FIG. 11B is a flowchart illustrating an example operation to assist in surgical parameter selection, in accordance with a technique of this disclosure.

FIG. 11B is a flowchart illustrating an example operation to assist in surgical parameter selection, in accordance with a technique of this disclosure. Thus, in accordance with a technique of this disclosure, a computing system, such as MR system 212 or preoperative surgical planning system 202 (FIG. 2) may generate, based on medical images of a patient, a 3-dimensional (3D) virtual model of a joint of the patient (1108). The joint may be various types of joints, such as the shoulder joint, ankle, knee, elbow, or wrist.

Additionally, the computing system may also generate, based on a set of surgical parameters, a 3D virtual implant model for the joint (1110). In an example where the joint is a shoulder joint, the 3D virtual implant model may include a ball component, a cup component, and a humeral stem component, as shown in FIG. 11A. Virtual implant models for other joints or other surgeries on the shoulder joint may include different components. The set of surgical parameters may indicate sizes, shapes, positions, or other aspects of components of one or more components of an implant for the joint. Generating the 3D virtual implant model may comprise selecting and arranging virtual objects that correspond to components of the implant that have the sizes indicated by the set of surgical parameters.

Additionally, the computing system may determine a plurality of impingement angles based on the 3D virtual bone model and the 3D virtual implant model (1112). Each respective impingement angle of the plurality of impingement angles corresponds to a different motion type in a plurality of motion types of the joint. For each respective impingement angle of the plurality of impingement angles, the respective impingement angle indicates an angle at which a bony impingement occurs during the motion type corresponding to the respective impingement angle. In some examples, the computing system may determine the impingement angles by moving components of the 3D virtual bone model and 3D virtual implant model and detecting where collisions between virtual objects in the 3D virtual bone model and 3D virtual implant model occur. In examples where the joint is a shoulder joint, the motion types may include adduction, abduction, internal rotation, external rotation, extension, and flexion. In examples where the joint is an ankle joint, the motion types may include plantarflexion and dorsiflexion.

A MR visualization device, such as visualization device 213 (FIG. 2), may present a MR visualization that includes the 3D virtual bone model, the 3D virtual implant model, and visual elements indicating a plurality of impingement angles (1114). FIG. 11A shows an example of such an MR visualization. The MR visualization device may present the MR visualization at various times during a surgical lifecycle. For instance, the MR visualization device may present the MR visualization during preoperative phase 302 (FIG. 3), intraoperative phase 306, or postoperative phase 308. Hence, a surgeon or other user may view the range of MR motion visualization when planning a surgery, e.g., as a virtual model, during the course of a surgery, e.g., alone as a virtual model or in conjunction with viewing of actual patient anatomy and presentation of virtual, intra-operative guidance elements, or after completion of a surgery, e.g., as a virtual model.

Furthermore, the MR visualization device may visually indicate in the MR visualization one or more points at which two or more components of the 3D virtual bone model and 3D virtual implant model collide (1116), e.g., producing an impingement 1106. In some examples, the MR visualization device may indicate the points of collision by presenting, in the MR visualization, one or more impingement identifiers in areas of the one or more points. The impingement identifiers may include glowing areas, arrows, highlighted areas, colors, flashing elements, geometric shapes, outlines, or other types of indicators may be used to visually indicate the points of collision.

In some examples, the MR visualization device may present an animation of the 3D virtual bone model and 3D virtual implant model moving according to a motion type of the plurality of motion types. In some examples, the MR visualization device may present an animation of the 3D virtual bone model and 3D virtual implant model moving according to each motion type of a plurality of motion types. In either example, the MR visualization device may present the animation in response to receiving an indication of user input, such as a hand gesture selecting an element corresponding to the motion type in menu 1104 or voice command. For instance, with respect to FIG. 11A, the MR visualization device may present an animation of the humerus moving according to an abduction/adduction motion type relative to the scapula in response to receiving an indication of user input to select the adduction element of menu 1104, the abduction element of menu 1104, or the "Replay Full Motion" element of menu 1104. In examples where the MR visualization device presents the animation, the MR visualization device may visually indicate, during the animation, one or more points at which two or more components of the 3D virtual bone model and 3D virtual implant model collide. Furthermore, in some examples, the MR visualization device may generate an audible or tactile notification during the animation when the two or more components of the 3D virtual bone model and 3D virtual implant model collide. For instance, a speaker of MR visualization device may output the audible notification (e.g., as a beeping or clicking sound) when the animation shows a frame in which a collision occurs. A vibration unit of MR visualization device may generate tactile notification is a vibration when the animation shows a frame in which a collision occurs.

As discussed elsewhere in this disclosure, a user may use the information in the MR visualization regarding the impingement angles and collision points to determine whether to make adjustments to the surgical parameters.

Returning to the example of FIG. 10, the Planning page presented by visualization device 213 also includes multiplanar image viewer 1014 (e.g., a DICOM viewer) and navigation bar 1016 that allow the user to view patient image data and to switch between displayed slices and orientations. For example, the user can select 2D Planes icons 1026 on navigation bar 1016 so that the user can view the 2D sagittal and coronal planes of the patient's body in multi-planar image viewer 1014.

Workflow bar 1000 in FIG. 10 includes further pages that correspond to steps in the surgical workflow for a particular orthopedic procedure (here, a shoulder repair procedure). In the example of FIG. 10, workflow bar 1000 includes elements labeled "Graft," "Humerus Cut," "Install Guide," "Glenoid Reaming," and "Glenoid Implant" that correspond to workflow pages for steps in the surgical workflow for a shoulder repair procedure. In general, these workflow pages include information that can be useful for a health care professional during planning of or during performance of the surgical procedure, and the information presented upon selection of these pages is selected and organized in a manner that is intended to minimize disturbances or distractions to the surgeon during a procedure. Thus, the amount of displayed information is optimized and the utility of the displayed information is maximized. These workflow pages may be used as part of intraoperative phase 306 (FIG. 3) to guide a surgeon, nurse or other medical technician through the steps in a surgical procedure. In some examples, these workflow pages may be used as part of preoperative phase 302 (FIG. 3) to enable a user to visualize 3-dimensional models of objects involved in various steps of a surgical workflow.

In the example shown, each workflow page that can be selected by the user (e.g., a surgeon) can include an Augment Surgery widget, such as Augment Surgery widget 1300 (shown in FIG. 13), that, when selected, launches an operational mode of MR system 212 in which a user using (e.g., wearing) visualization device 213 (FIG. 2) can see the details (e.g., virtual images of details) of the surgical plan projected and matched onto the patient bone and use the plan intraoperatively to assist with the surgical procedure. In general, the Augment Surgery mode allows the surgeon to register the virtual 3D model of the patient's anatomy of interest (e.g., glenoid) with the observed real anatomy so that the surgeon can use the virtual surgical planning to assist with implementation of the real surgical procedure, as will be explained in further detail below. There may be different Augment Surgery widgets for each of the steps of the surgery that the surgeon uses during actual surgery. The Augment Surgery widgets for different steps may include different text, control, icons, graphics, etc.

Figure 14:
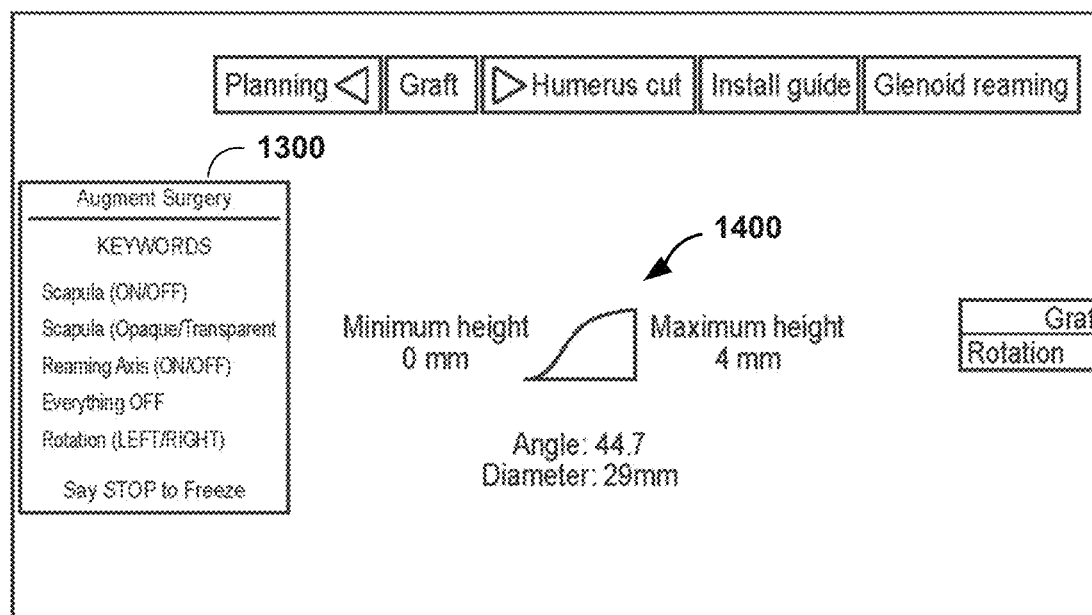
FIG. 14 is a conceptual diagram illustrating an example of information displayed in a workflow page of the user interface of FIG. 10.

In this example of a shoulder repair procedure, and with reference FIG. 10, the workflow pages of UI 522 that can be used by the surgeon include "Graft", "Humerus Cut", "Install Guide", "Glenoid Reaming", and "Glenoid Implant". The "Graft" step and "Install Guide" steps may be optional. For example, it may not be necessary to take a graft in every procedure and the use of a glenoid reaming guide may not be necessary if MR reaming axis guidance is presented to the user by visualization device 213. A user may view the workflow pages during the preoperative phase 302, during the intraoperative phase 306, or at other times. It may be helpful to a surgeon to view the workflow pages during the preoperative phase 302 in order to tailor a surgical plan for the patient, to review the steps of a surgical plan, or perform other tasks. It may be helpful to a surgeon to view the workflow pages in the intraoperative phase 306 to refresh the surgeon on the anatomy of the patient involved in the corresponding surgical steps, to obtain information on how to perform certain actions during the corresponding surgical steps, to take inventory of surgical instruments, implants or other surgical items needed in the surgical steps, and so on. As mentioned, each of the workflow pages generally corresponds to a step in the workflow for the particular surgical procedure. Thus, for example, the Graft page allows the user to visualize a bone graft 1402 (FIG. 14) matched for a particular patient and provides the user with sufficient information for selecting, designing and/or modifying the shape and dimensions of bone graft 1402, if desired. As an example, bone graft 1402 may be a bone graft taken from the humerus or another bone.

As another example, with reference to FIG. 15A, the Humerus Cut page presents the user with a 3D model 1504 of the humerus and a 3D model of the humeral implant components 1506, and a cutting plane 1508 on the humeral head, e.g., for application of a cutting tool such as a rotary or reciprocating saw to remove a portion of the humeral head. In response to selection of other items on menu 1510 on this page, visualization device 213 can remove the 3D model of the humeral implant components 1506 from the presented imagery and provide images of the humeral head before and after cutting, as examples.

FIGS. 15B-15D are examples of hiding virtual objects in humerus cut page of FIG. 15A, according to an example of this disclosure. As noted above, menu 1510 of FIG. 15A enables a user to selectively add or remove 3D models of components of the patient's humerus and implant components 1506. For instance, in the examples of FIGS. 15B-15D, the user has removed the 3D models of the implant components 1506. In FIG. 15B, the user has chosen to view the humerus and humeral head. In FIG. 15C, the user has chosen to view the humerus and not the humeral head. In FIG. 15D, the user has chosen to view the humeral head and not the humerus. In this example, the presentation of the humerus without the humeral head may be selected to show a humeral cutting plane for removal of the portion of the humeral head according to the virtual surgical plan, e.g., to permit placement of an implant component such as a humeral ball or plate component on the humerus in the course of the surgical procedure.

As another example (not shown), an Osteophytes item can be presented for selection on the menu page by visualization device 213. When selected, an osteophytes assessment feature is activated in which osteophytes can be identified, projected, highlighted or hidden on the patient bone in the MR visualization presented to the user by visualization device 213.

Figure 16:
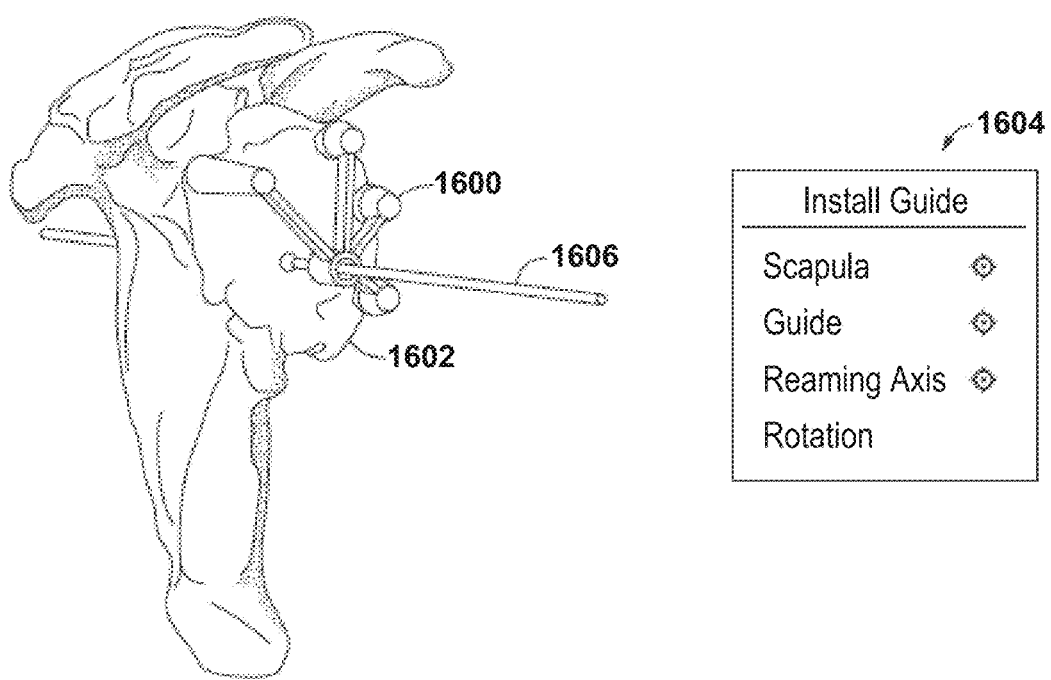
FIG. 16 is an example of an install guide page of the user interface of FIG. 10, according to an example of this disclosure.

With reference to FIG. 16, the Install Guide page allows the user to visualize a physical position of a patient-specific or patient-matched guide 1600, e.g., for guidance of a drill to place a reaming guide pin in the glenoid bone, on the patient's glenoid 1602 in order to assist with the efficient and correct placement of the guide 1600 during the actual surgical procedure. Selection of items on menu 1604 can remove features from the 3D images or add other parameters of the surgical plan, such as a reaming axis 1606, e.g., by voice commands, gaze direction and/or hand gesture selection. Placement of guide 1600 may be unnecessary for procedures in which visualization device 213 presents a virtual reaming axis or other virtual guidance, instead of a physical guide, to guide a drill for placement of a reaming guide pin in the glenoid bone. The virtual guidance or other virtual objects presented by visualization device 213 may include, for example, one or more 3D virtual objects. In some examples, the virtual guidance may include 2D virtual objects. In some examples, the virtual guidance may include a combination of 3D and 2D virtual objects.

Figure 17:
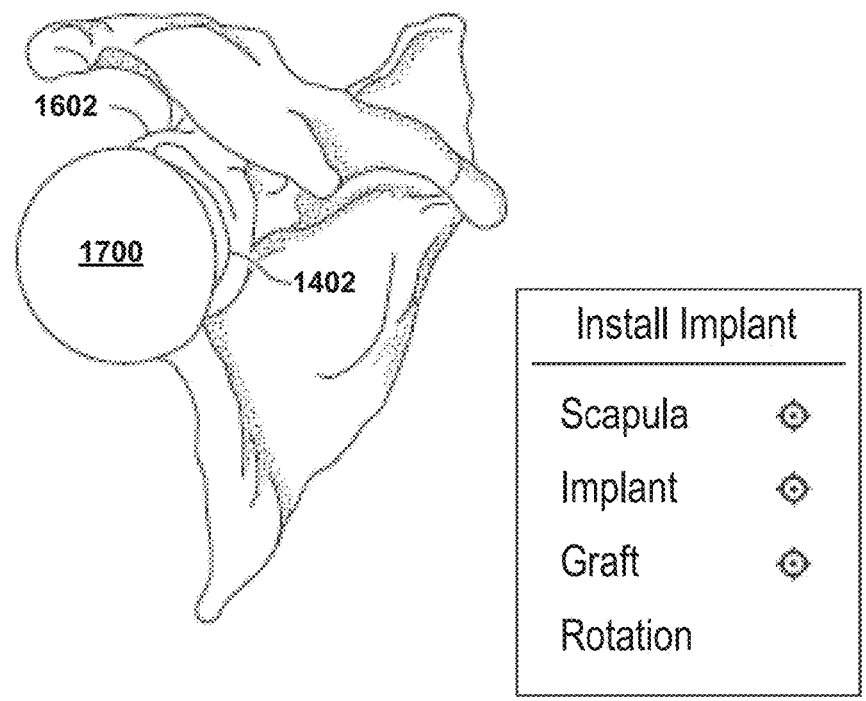
FIG. 17 is an example of an install implant page of the user interface of FIG. 10, according to an example of this disclosure.

With reference to FIG. 17, the Glenoid Implant page allows the user to visualize the orientation and placement of a glenoid implant 1700 and bone graft 1402 on glenoid 1602.

It should be understood that the workflow pages illustrated and described herein are examples and that UI 522 can include fewer, more, or different pages. For example, in applications of MR system 212 for procedures involving other patient anatomies, such as the ankle, foot, knee, hip or elbow, UI 522 can include pages corresponding to the particular steps specific to the surgical workflow for those procedures.

The images displayed on UI 522 of MR system 212 can be viewed outside or within the surgical operating environment and, in spectator mode, can be viewed by multiple users outside and within the operating environment at the same time. In some circumstances, such as in the operating environment, the surgeon may find it useful to use a control device 534 to direct visualization device 213 such that certain information should be locked into position on a wall or other surface of the operating room, as an example, so that the information does not impede the surgeon's view during the procedure. For example, relevant surgical steps of the surgical plan can be selectively displayed and used by the surgeon or other care providers to guide the surgical procedure.

In various some examples, the display of surgical steps can be automatically controlled so that only the relevant steps are displayed at the appropriate times during the surgical procedure.

As discussed above, surgical lifecycle 300 may include an intraoperative phase 306 during which a surgical operation is performed. One or more users may use orthopedic surgical system 100 in intraoperative phase 306.

Figure 18:
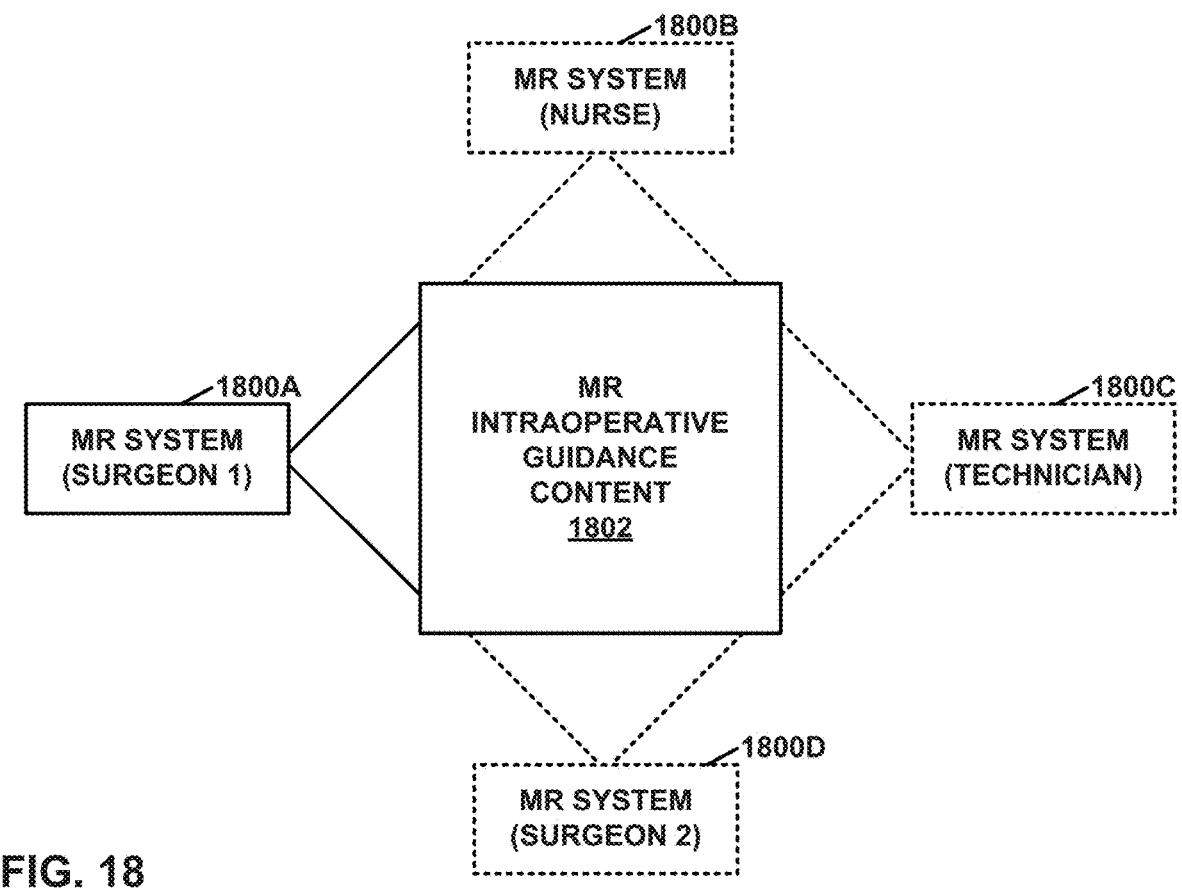
FIG. 18 is a conceptual diagram illustrating an example setting in which a set of users use MR systems of an orthopedic surgical system during an intraoperative phase.

FIG. 18 is a conceptual diagram illustrating an example setting in which a set of one or more users use MR systems of orthopedic surgical system 100 during intraoperative phase 306. In the example of FIG. 18, a surgeon may wear a visualization device (e.g., visualization device 213) of a first MR system 1800A (e.g., MR system 212). The visualization device of MR system 1800A may present MR intraoperative guidance content 1802 to the surgeon during intraoperative phase 306. As described in detail elsewhere in this disclosure, MR intraoperative guidance content 1802 may help the surgeon perform for a surgical operation.

Additionally, in the example of FIG. 18, one or more other users may use visualization devices of MR systems of orthopedic surgical system 100 to view MR intraoperative guidance content 1802. For example, a nurse may use a visualization device of an MR system 1800B of orthopedic surgical system 100. Furthermore, in the example of FIG. 18, a technician may use a visualization device of an MR system 1800C of orthopedic surgical system 100. In the example of FIG. 18, a second surgeon may use a visualization device of an MR system 1800D of orthopedic surgical system 100. MR systems 1800A, 1800B, 1800C, and 1800D may be referred to herein collectively as "MR systems 1800." In some examples, a television or other display device may present the view of the surgeon, which may include virtual objects, to one or more other individuals, such as a nurse, surgeon, or technician.

Two or more of the individuals described above (e.g., the first surgeon, the nurse, the technician, the second surgeon) may view the same or different MR intraoperative guidance content 1802 at the same time. In examples where two or more of the individuals are viewing the same MR intraoperative guidance content 1802 at the same time, the two or more individuals may concurrently view the same MR intraoperative guidance content 1802 from the same or different perspectives.

One or more users may use orthopedic surgical system 100 in an intraoperative setting. For example, the users may manipulate a user interface presented by MR systems 1800 so that the users can view a virtual surgical plan intraoperatively. For instance, in this example, the users may view a 3D virtual model of an anatomy of interest (e.g., a 3-dimensional virtual bone model of an anatomy of interest).

Figure 19:
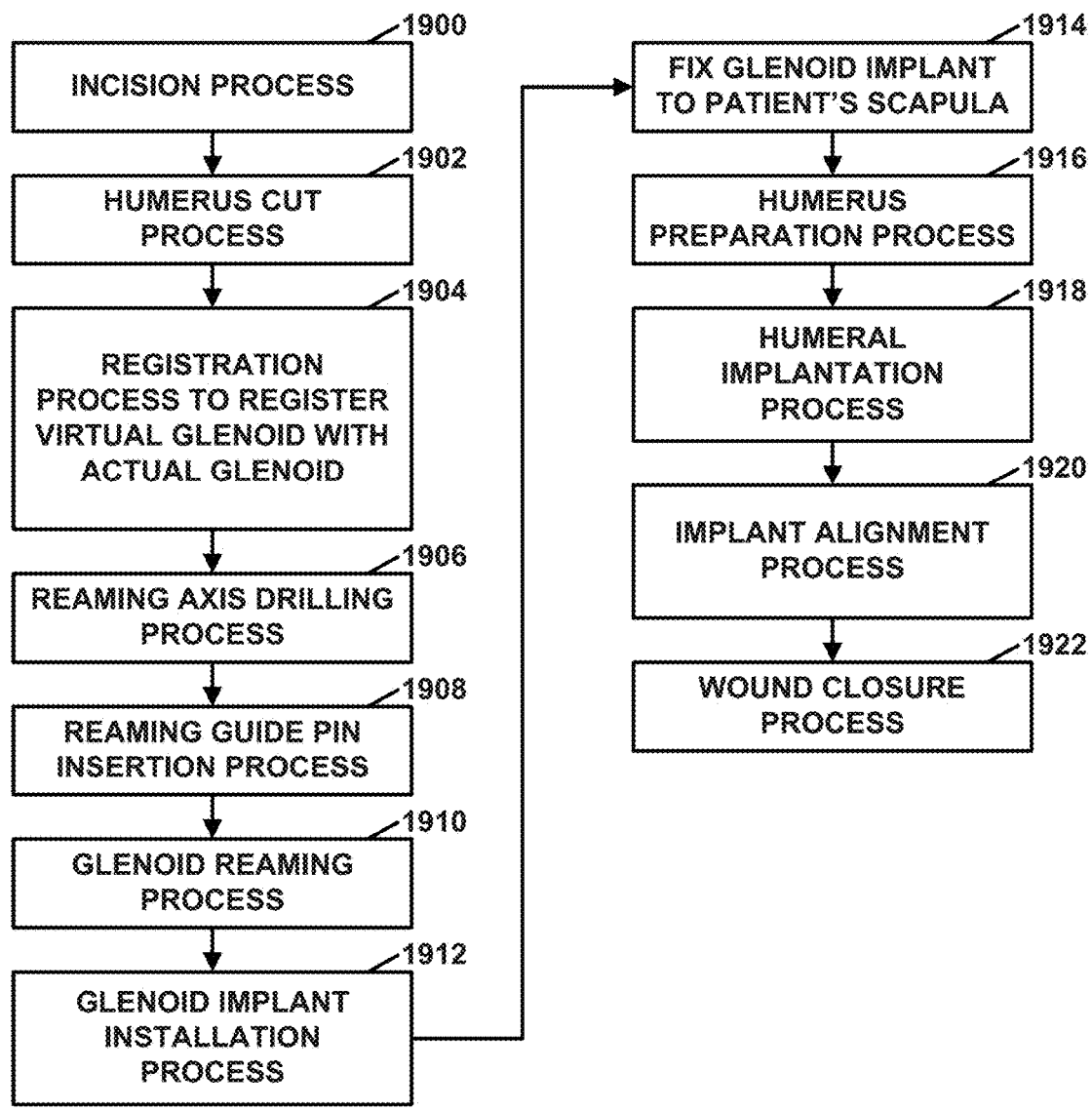
FIG. 19 is a flowchart illustrating example stages of a shoulder joint repair surgery.

In some examples, one or more users, including at least one surgeon, may use orthopedic surgical system 100 in an intraoperative setting to perform shoulder surgery. FIG. 19 is a flowchart illustrating example stages of a shoulder joint repair surgery. As discussed above, FIG. 19 describes an example surgical process for a shoulder surgery. The surgeon may wear or otherwise use visualization device 213 during each step of the surgical process of FIG. 10. In other examples, a shoulder surgery may include more, fewer, or different steps. For example, a shoulder surgery may include step for adding a bone graft, adding cement, and/or other steps. In some examples, visualization device 213 may present virtual guidance to guide the surgeon, nurse, or other users, through the steps in the surgical workflow.

In the example of FIG. 19, a surgeon performs an incision process (1900). During the incision process, the surgeon makes a series of incisions to expose a patient's shoulder joint. In some examples, an MR system (e.g., MR system 212, MR system 1800A, etc.) may help the surgeon perform the incision process, e.g., by displaying virtual guidance imagery illustrating how to where to make the incision.

Furthermore, in the example of FIG. 19, the surgeon may perform a humerus cut process (1902). During the humerus cut process, the surgeon may remove a portion of the humeral head of the patient's humerus. Removing the portion of the humeral head may allow the surgeon to access the patient's glenoid. Additionally, removing the portion of the humeral head may allow the surgeon to subsequently replace the portion of the humeral head with a humeral implant compatible with a glenoid implant that the surgeon plans to implant in the patient's glenoid.

As discussed above, the humerus preparation process may enable the surgeon to access the patient's glenoid. In the example of FIG. 19, after performing the humerus preparation process, the surgeon may perform a registration process that registers a virtual glenoid object with the patient's actual glenoid bone (1904) in the field of view presented to the surgeon by visualization device 213.

Figure 20A:
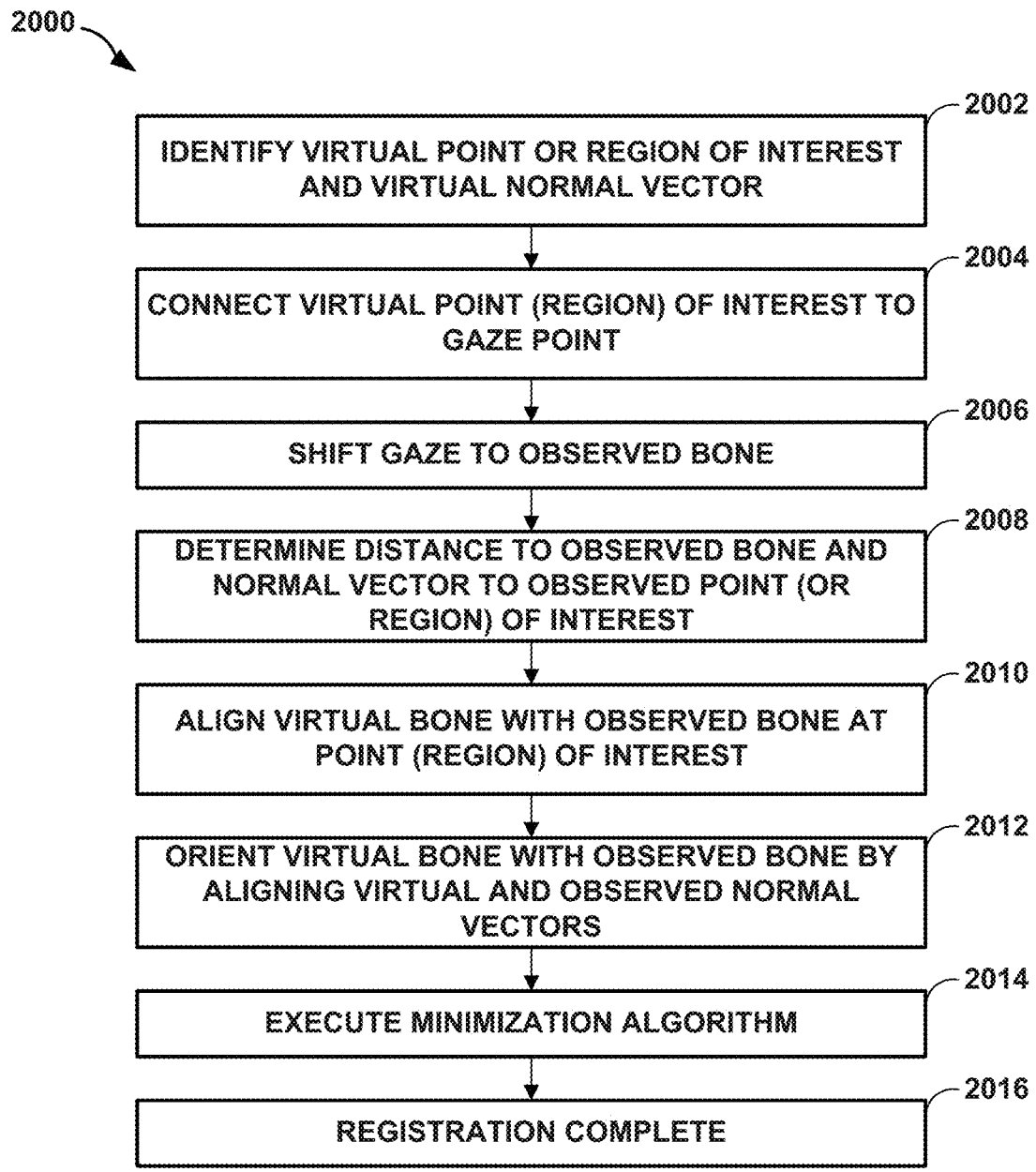
FIGS. 20A and 20B illustrate example techniques for registering a 3-dimensional virtual bone model with an observed real bone structure of a patient during joint repair surgery.
Figure 20B:
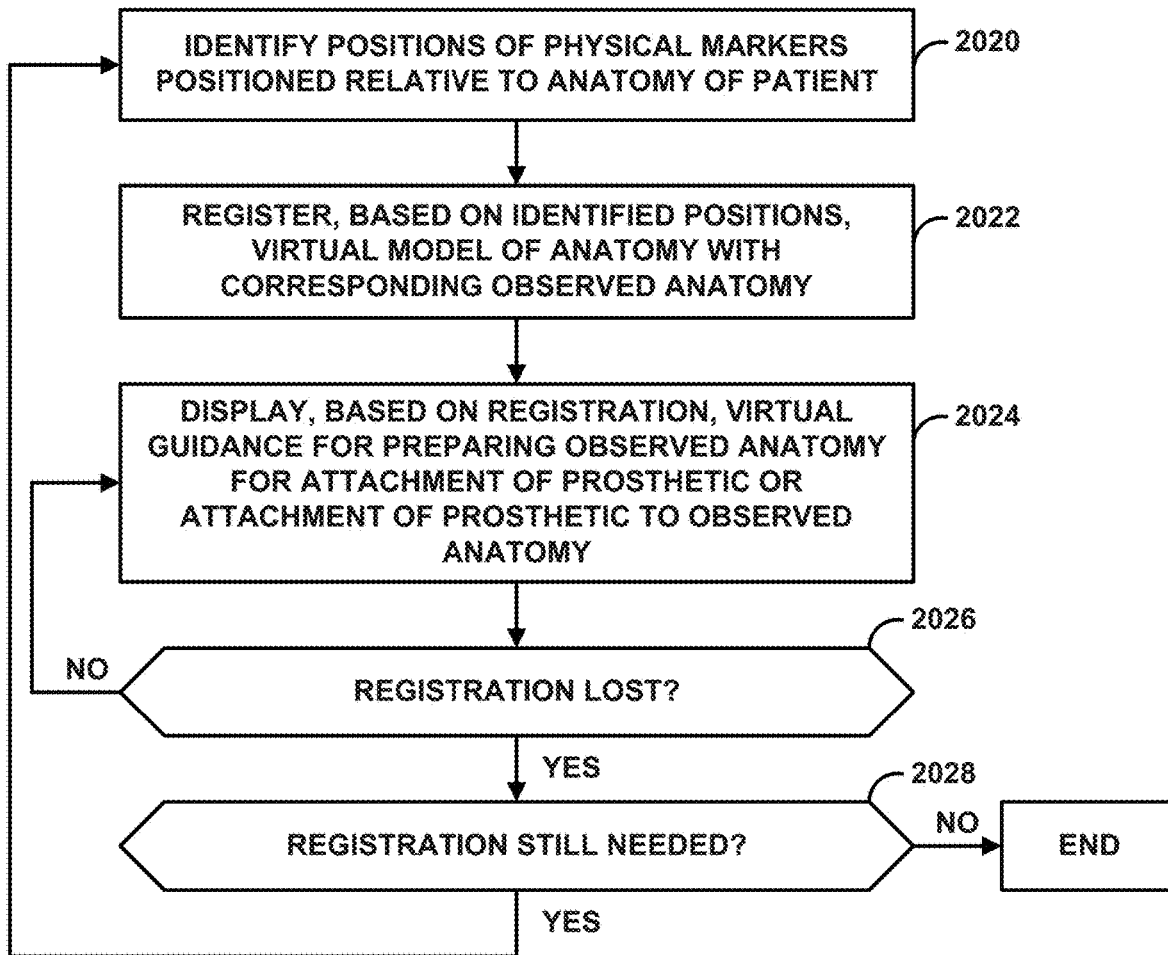

FIG. 20A illustrates an example of a technique 2000 for registering a 3D virtual bone model 1008 with a real observed bone structure 2200 of a patient. In other words, FIG. 20A is an example of a process flow, e.g., performed by visualization device 213, for registering a virtual bone model with an observed bone that is implemented in a mixed reality system, such as the mixed reality system 212 of FIG. 2. FIG. 20B, described below, illustrates another technique 2018 for registering 3D virtual bone model 1008 bone structure 2200, using physical registration markers.

With further reference to FIG. 20A, 3D virtual bone model 1008 may be a model of all or part of one or more bones. The process flow of FIG. 20A may be performed as part of the registration process of step 1904 of FIG. 19. The registration process may be carried out in two steps: initialization and optimization (e.g., minimization). During initialization, the user of MR system 212 uses the visualization device 213 in conjunction with information derived from the preoperative virtual planning system 102, the orientation of the user's head (which provides an indication of the direction of the user's eyes (referred to as "gaze" or "gaze line"), rotation of the user's head in multiple directions, sensor data collected by the sensors 530, 532 and/or 533 (or other acquisitions sensors), and/or voice commands and/or hand gestures to visually achieve an approximate alignment of the 3D virtual bone model 1008 with observed bone structure 2200. More particularly, at block 2002, a point or region of interest on the surface of the virtual bone model 1008 and a virtual normal vector to the point (or region) of interest on the surface of the region are identified during the preoperative planning using the virtual planning system 102.

At block 2004, MR system 212 connects the identified point (or region) of interest to the user's gaze point (e.g., a central point in the field of view of visualization device 213).

Thus, when the head of the user of visualization device 213 is then moved or rotated, the virtual bone model 1008 also moves and rotates in space.

In the example of a shoulder arthroplasty procedure, the point of interest on the surface of virtual bone model 1008 can be an approximate center of the virtual glenoid that can be determined by using a virtual planning system 102, such as the BLUEPRINT™ planning system. In some examples, the approximate center of the virtual glenoid can be determined using a barycenter find algorithm, with the assistance of machine learning algorithms or artificial intelligence systems, or using another type of algorithm. For other types of bone repair/replacement procedures, other points or regions of the bone can be identified and then connected to the user's gaze line or gaze point.

The ability to move and rotate virtual bone model 1008 in space about the user's gaze point alone generally is not sufficient to orient virtual bone model 1008 with the observed bone. Thus, as part of the initialization procedure, MR system 212 also determines the distance between visualization device 213 and a point (or points) on the surface of the observed bone in the field of view of visualization device 213 and the orientation of that surface using sensor data collected from the depth, optical, and motion sensors 530, 532, 533 (block 2008). For example, a glenoid is a relatively simple surface because, locally, it can be approximated by a plane. Thus, the orientation of the glenoid surface can be approximated by determining a vector that is normal (i.e., perpendicular) to a point (e.g., a central point) on the surface. This normal vector is referred to herein as the "observed normal vector." It should be understood, however, that other bones may have more complex surfaces, such as the humerus or knee. For these more complex cases, other surface descriptors may be used to determine orientation.

Regardless of the particular bone, distance information can be derived by MR system 212 from depth camera(s) 532. This distance information can be used to derive the geometric shape of the surface of an observed bone. That is, because depth camera(s) 532 provide distance data corresponding to any point in a field of view of depth camera(s) 532, the distance to the user's gaze point on the observed bone can be determined. With this information, the user can then move 3D virtual bone model 1008 in space and approximately align it with the observed bone at a point or region of interest using the gaze point (block 2010 in FIG. 20A). That is, when the user shifts gaze to observed bone structure 2200 (block 2006 in FIG. 20A), virtual bone model 1008 (which is connected to the user's gaze line) moves with the user's gaze. The user can then align 3D virtual bone model 1008 with observed bone structure 2200 by moving the user's head (and thus the gaze line), using hand gestures, using voice commands, and/or using a virtual interface to adjust the position of virtual bone model 1008. For instance, once 3D virtual bone model 1008 is approximately aligned with observed bone structure 2200, the user may provide a voice command (e.g., "set") that causes MR system 212 to capture the initial alignment. The orientation ("yaw" and "pitch") of the 3D model can be adjusted by rotating the user's head, using hand gestures, using voice commands, and/or using a virtual interface which rotate 3D virtual bone model 1008 about the user's gaze line so that an initial (or approximate) alignment of the virtual and observed objects can be achieved (block 2012 in FIG. 20A). In this manner, virtual bone model 1008 is oriented with the observed bone by aligning the virtual and observed normal vectors. Additional adjustments of the initial alignment can be performed as needed. For instance, after providing the voice command, the user may provide additional user input to adjust an orientation or a position of virtual bone model 1008 relative to observed bone structure 2200. This initial alignment process is performed intraoperatively (or in real time) so that the surgeon can approximately align the virtual and observed bones. In some examples, such as where the surgeon determines that the initial alignment is inadequate, the surgeon may provide user input (e.g., a voice command, such as "reset") that causes MR system 212 to release the initial alignment such that point 2106 is again locked to the user's gaze line.

At block 2014 of FIG. 20A, when the user detects (e.g., sees) that an initial alignment of 3D virtual bone model 1008 with observed bone structure 2200 has been achieved (at least approximately), the user can provide an audible or other perceptible indication to inform MR system 212 that a fine registration process (i.e., execution of an optimization (e.g., minimization) algorithm) can be started. For instance, the user may provide a voice command (e.g., "match") that causes MR system 212 to execute a minimization algorithm to perform the fine registration process. The optimization process can employ any suitable optimization algorithm (e.g., a minimization algorithm such as an Iterative Closest Point or genetic algorithm) to perfect alignment of virtual bone model 1008 with observed bone structure 2200. At block 2016 of FIG. 20A, upon completion of execution of the optimization algorithm, the registration procedure is complete.

Figure 21:
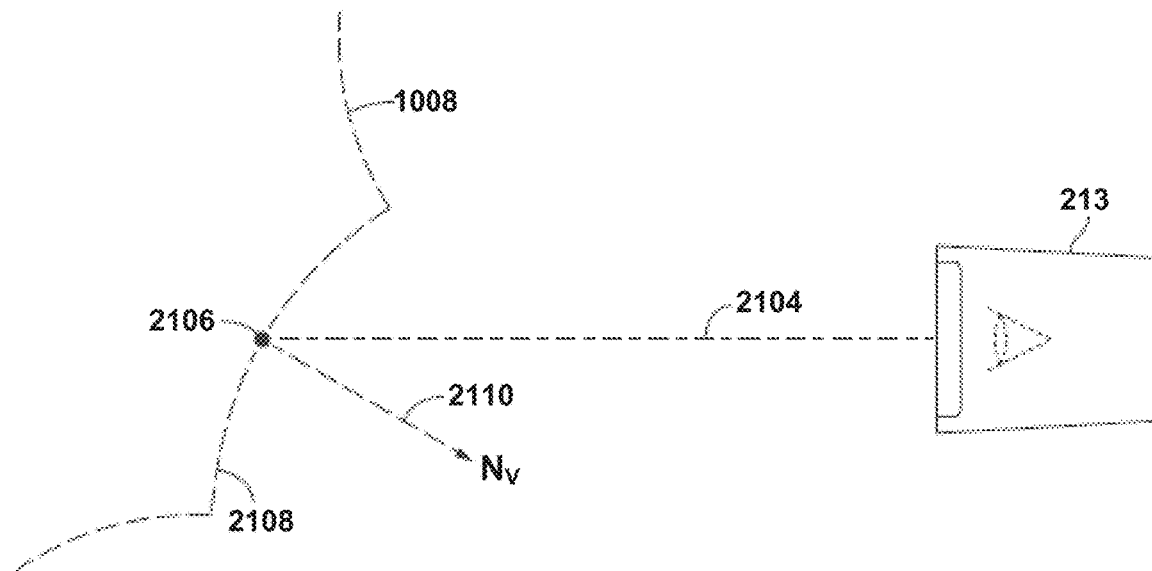
FIG. 21 is a conceptual diagram illustrating steps of an example registration process for a shoulder arthroplasty procedure.
Figure 22:
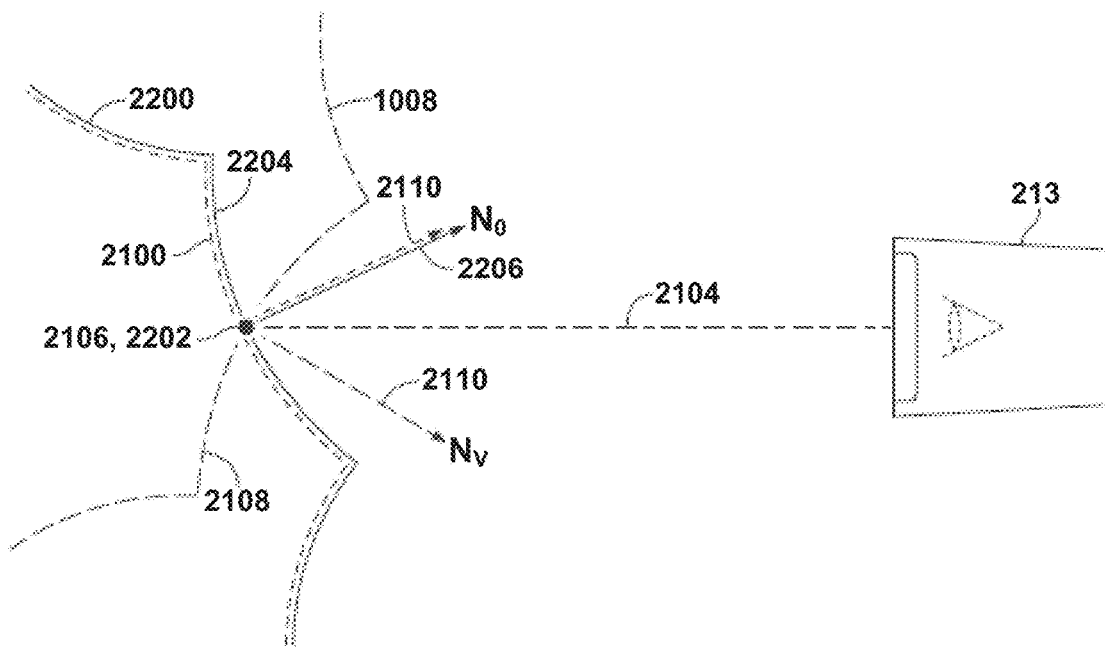
FIG. 22 is a conceptual diagram illustrating additional steps of the example registration process of the shoulder arthroplasty procedure of FIG. 21.

FIG. 21 is a conceptual diagram illustrating steps of an example registration process for a shoulder arthroplasty procedure. FIG. 22 is a conceptual diagram illustrating additional steps of the example registration process of the shoulder arthroplasty procedure of FIG. 21. In FIG. 21, a gaze line 2104 of a user of visualization device 213 is connected with the previously identified point of interest (or gaze point) 2106 on a surface 2108 of 3D virtual bone model 1008 (a glenoid). FIG. 21 also shows a virtual normal vector (Nv) 2110 to point 2106 on surface 2108. In FIG. 22, the user of visualization device 213 shifts gaze line 2104 to a region of interest 2202 on surface 2204 of observed bone structure 2200. Because gaze line 2104 is connected to the center point 2106 of virtual bone model 1008, shifting gaze line 2104 aligns virtual center point 2106 of virtual bone model 1008 with the observed region of interest 2202. However, as shown in FIG. 22, simply shifting the gaze aligns the center points/regions 2106, 2202, but may not properly orient the virtual bone model 1008 (shown in dashed lines) with observed bone structure 2200. Once an observed normal vector (NO) 2206 is determined as discussed above, visualization device 213 can adjust the orientation (pitch and yaw) of virtual bone model 1008 until the proper orientation is achieved (shown in dotted lines) and virtual normal vector (VN) 2110 is aligned with observed normal vector 2206. The user may rotate virtual bone model 1008 around the aligned axes passing through the glenoid for proper alignment of virtual bone model 1008 with the corresponding real bone.

Figures 23, 24:
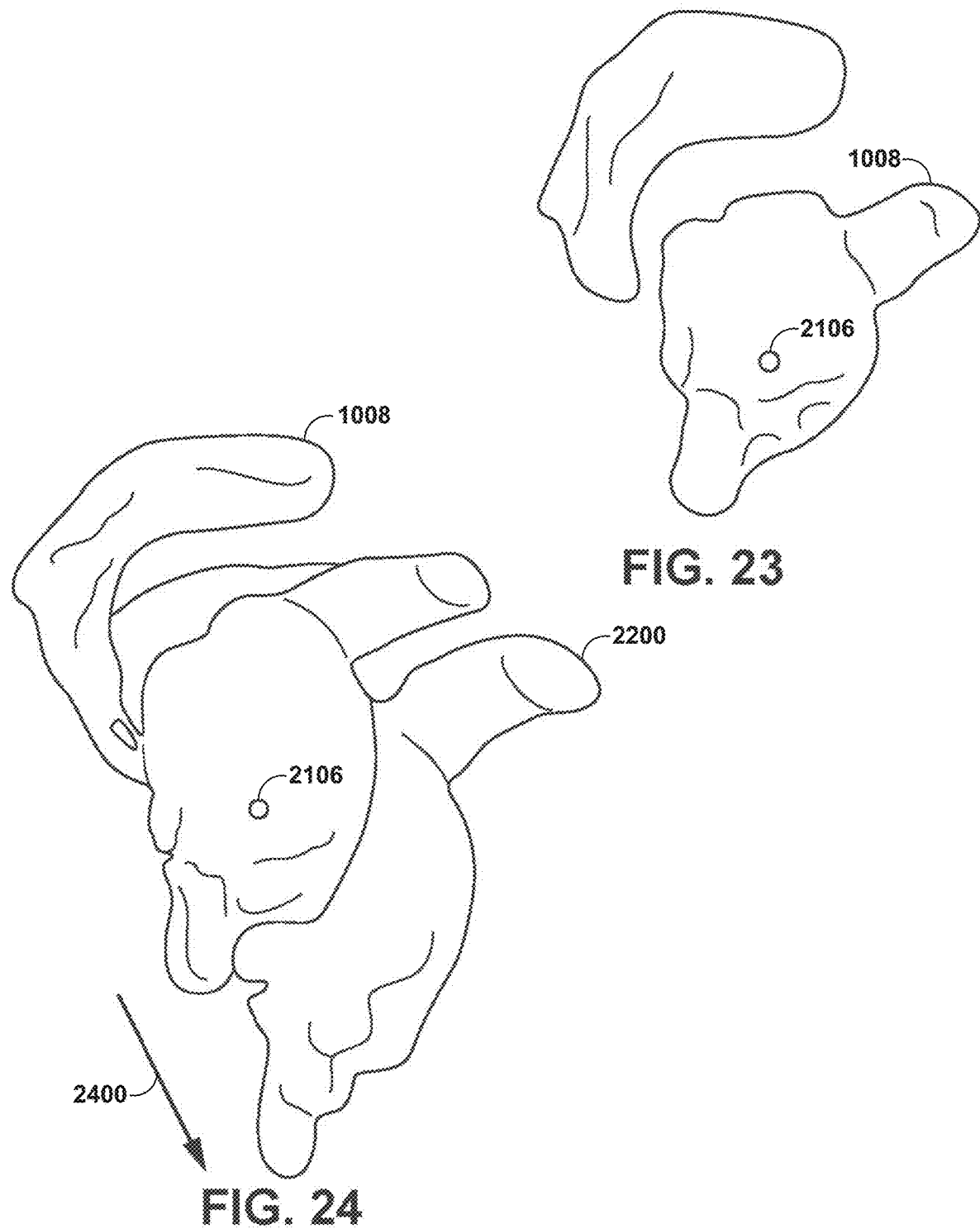
FIG. 23 and FIG. 24 are conceptual diagrams further illustrating an example registration process for a shoulder arthroplasty procedure.

FIG. 23 and FIG. 24 are conceptual diagrams illustrating an example registration process for a shoulder arthroplasty procedure. Similar to the registration process shown in FIG. 21, FIG. 23 illustrates the viewpoint of a user of visualization device 213. As shown in FIG. 23, point of interest 2106 is shown on virtual bone model 1008. As discussed above, as the gaze of the user is connected to point 2106, the user may move virtual bone model 1008 by shifting their gaze, in which case visualization device 213 detects the gaze shift and moves the virtual bone model in a corresponding manner. As shown in FIG. 24, to align virtual bone model 1008 with observed bone structure 2200, the user may shift their gaze in the direction indicated by arrow 2400.

For some surgical bone repair procedures, such as shoulder arthroplasties, alignment and orientation of the virtual and observed bone using only the user's gaze can be challenging. These challenges arise due to many factors, including that the bone (e.g., glenoid) is located quite deep under the skin so that even after the surgical incision is made, it can be difficult to position the visualization device 213 close to the bone; shadows may obscure the bone; the entire bone surface of interest may not be visible; and it can be difficult for the user to maintain a steady and stable gaze which can result in instability in the positioning of the virtual bone. In some examples, to address these challenges, the registration procedure can be facilitated through the use of virtual landmark(s) placed at specific location(s) on the bone (e.g., the center of the glenoid for a shoulder arthroplasty procedure). In such examples, the location at which the virtual landmark is placed and the surface normal at that location can be used to automatically determine the initialization transformation (or registration transformation) for the virtual and observed bones. If desired, the alignment achieved between the virtual and observed bone using the virtual landmark can be further adjusted by the user using voice commands, hand gestures, virtual interface buttons, and/or by positioning additional virtual markers at various locations on the bone surface.

Figure 25:
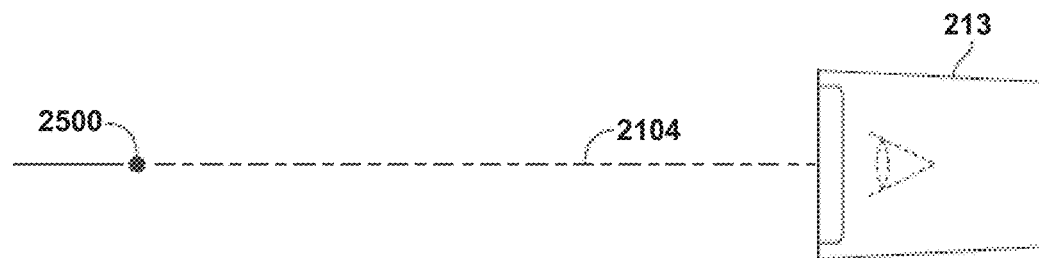
FIG. 25 is a conceptual diagram illustrating an example registration procedure using a virtual marker.
Figure 26:
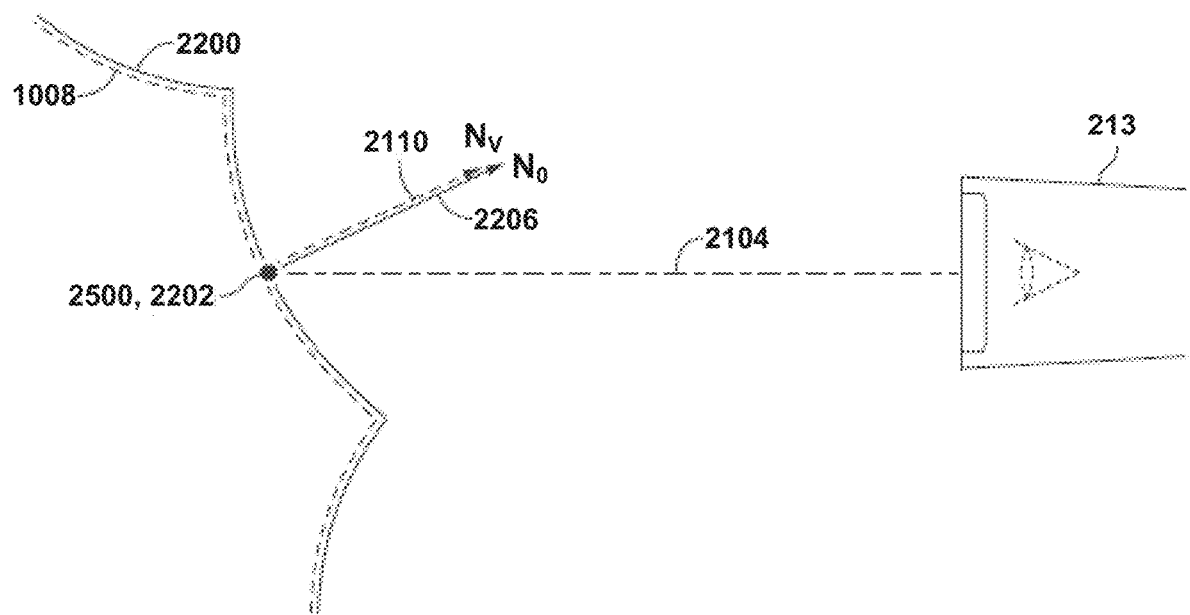
FIG. 26 is a conceptual diagram illustrating additional steps of the example registration procedure of FIG. 25 using a virtual marker.

FIG. 25 illustrates an example registration procedure using a virtual marker 2500. FIG. 26 is a conceptual diagram illustrating additional steps of the example registration procedure of FIG. 20A using a virtual marker. In the example of FIG. 25 and FIG. 26, the user of visualization device 213 shifts a gaze line 2104 to set virtual marker 2500 at a center region 2202 (e.g., center point) of observed bone structure 2200. With the help of the virtually positioned marker 2500, the virtual normal vector 2110 and the observed normal vector 2206, the initialization transformation between virtual bone model 1008 and observed bone structure 2200 can be determined. Then, the optimization algorithm (or registration algorithm) is executed, as described above, in order to obtain an optimal registration between virtual bone model 1008 and observed bone structure 2200.

In some examples, the initialization procedure can be implemented based on a region of interest on the bone surface instead of a point of interest. In such examples, the image data collected by the depth and/or optical camera(s) 530, 532 (FIG. 5) of visualization device 213 can be processed to detect surface descriptors that will facilitate identification of the position and orientation of the observed bone and to determine an initialization transformation between the virtual and observed bones.

As discussed above, in some examples, the initialization may be aided by the user (e.g., aided by the user shifting gaze line 2104 to set virtual marker 2500 at a center region 2202 of observed bone structure 2200). In some examples, MR system 212 may perform the entire registration process (e.g., including any initialization steps) with minimal or no aid from the user. For instance, MR system 212 may process the image data collected by the depth and/or optical camera (s) 530, 532 (FIG. 5) to automatically identify a location of the anatomy of interest (e.g., observed bone structure 2200). As such, MR system 212 may register a virtual model of a portion of anatomy to a corresponding observed portion of anatomy in response to the user looking at the portion of anatomy (e.g., the surgeon, while wearing visualization device 213, may merely look at the portion of anatomy). MR system 212 may automatically identify the location using any suitable technique. For example, MR system 212 may use a machine learned model (i.e., use machine learning, such as a random forest algorithm) to process the image data and identify the location of the anatomy of interest.

In more general terms, the registration methods described with reference to FIG. 20A and FIG. 20B can be viewed as determining a first local reference coordinate system with respect to the 3D virtual model and determining a second local reference coordinate system with respect to the observed real anatomy. In some examples, MR system 212 also can use the optical image data collected from optical cameras 530 and/or depth cameras 532 and/or motion sensors 533 (or any other acquisition sensor) to determine a global reference coordinate system with respect to the environment (e.g., operating room) in which the user is located. In other examples, the global reference coordinate system can be defined in other manners. In some examples, depth cameras 532 are externally coupled to visualization device 213, which may be a mixed reality headset, such as the Microsoft HOLOLENS headset or a similar MR visualization device. For instance, depth cameras 532 may be removable from visualization device 213. In some examples, depth cameras 532 are part of visualization device 213, which again may be a mixed reality headset. For instance, depth cameras 532 may be contained within an outer housing of visualization device 213.

The registration process may result in generation of a transformation matrix that then allows for translation along the x, y, and z axes of the 3D virtual bone model and rotation about the x, y and z axes in order to achieve and maintain alignment between the virtual and observed bones.

Figure 30A:
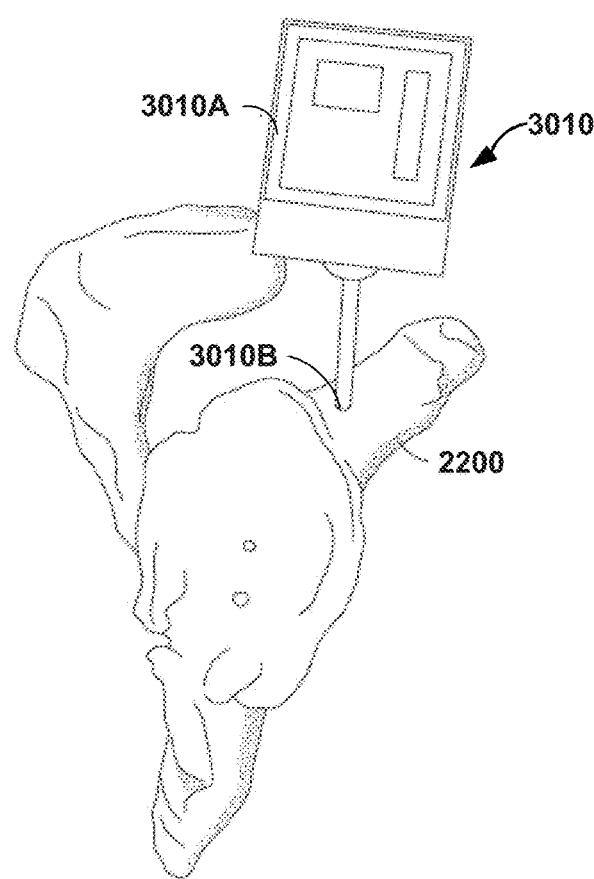
FIGS. 30A-30E illustrate examples of physical markers that can be employed in the mixed reality (MR) system of FIG. 1, according to an example of this disclosure.
Figure 30B:
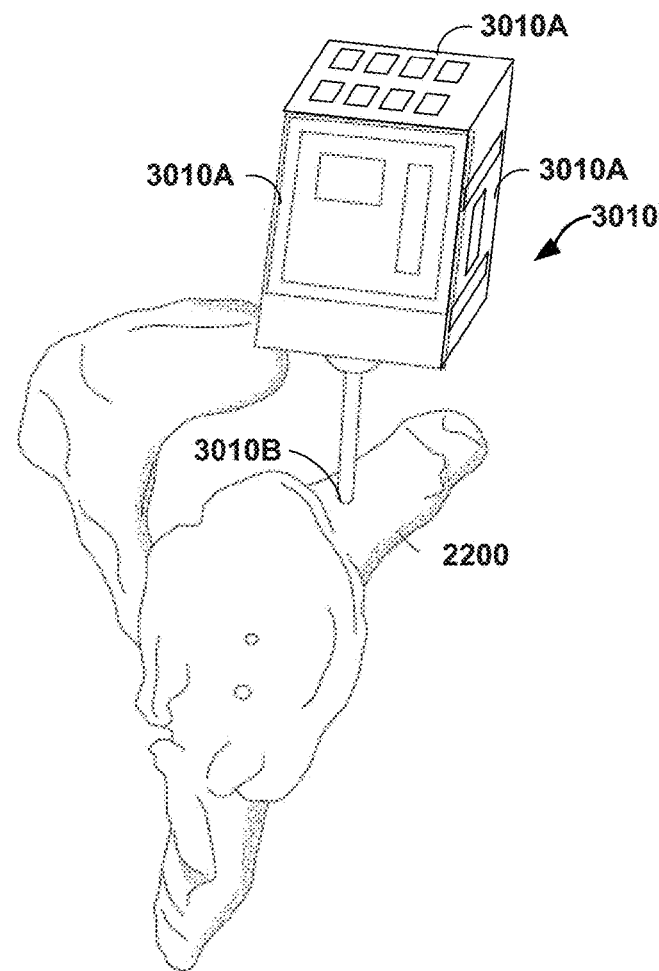

In some examples, one or more of the virtual markers can be replaced and/or supplemented with one or more physical markers, such as optical markers or electromagnetic markers, as examples. FIGS. 30A-30E illustrate examples of physical markers positioned around the real observed bone structure 2200. In general, the one or more physical markers may be positioned at various positions on or around the object being registered (e.g., real observed bone structure 2200 or a tool). As shown in the examples of FIG. 30A and FIG. 30B, a fixed optical marker 3010 may be used in a shoulder arthroplasty procedure to define the location of the acromion of the scapula on the real observed bone structure 2200. In the example of FIG. 30A, fixed optical marker 3010 may include a planar fiducial marker 3010A on a single face of the optical marker. In the example of FIG. 30B, fixed optical marker 3010 may include planar fiducial markers 3010A on multiple faces of the optical marker. Where a physical marker includes fiducial markers of multiple faces, the fiducial markers may be the same on every face or different faces may include different fiducial markers. As shown in FIGS. 30A and 30B, the fiducial marker may be positioned on a portion of the physical marker that is proximal to a tip 3010B of the marker 3010. In some examples, MR system 212 may obtain a distance between a feature of the fiducial marker (e.g., a centroid or center point) and the tip of the physical marker. As one example, the distance may be predetermined and stored in a memory of MR system 212. As another example, MR system 212 may determine the distance based on optical characteristic of the fiducial marker (i.e., the distance may be encoded in the fiducial marker).

Figure 30C:
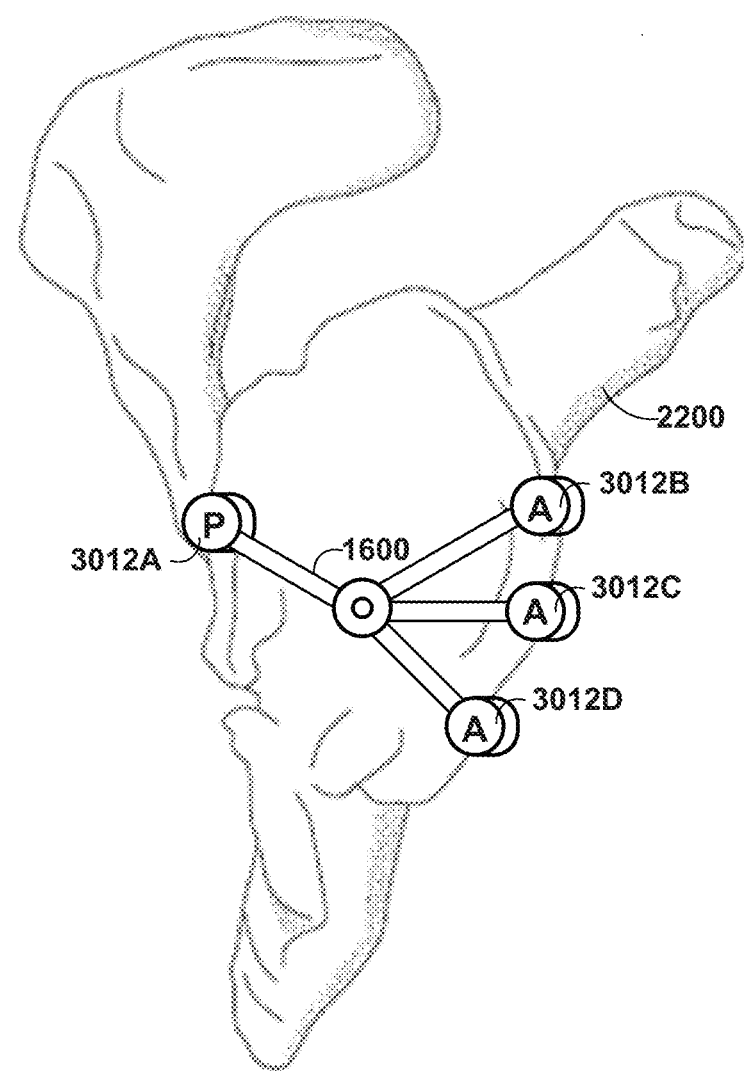

As shown in the example of FIG. 30C, physical markers 3012A-3012D (collectively, "physical markers 3012") can be positioned at various positions around the real observed bone structure 2200. In some examples, the various positions of the physical markers may correspond to positions (e.g., attachment points) of patient matched guide 1600 of FIG. 16. Knowledge of the acromion location and the location of the center of the glenoid (which may be set virtually) may allow MR system 212 to automatically initialize/register the virtual bone without the need for the user to employ head movements and rotations.

In general, the physical markers may be placed anywhere. For instance, the physical markers can be attached to the patient (e.g., non-sterile field), surgically exposed anatomy (sterile field), instruments, anywhere in surgical field of view, or any other suitable location.

The physical markers can be any type of marker that enables identification of a particular location relative to the real observed object (e.g., bone structure 2200). Examples of physical markers include, but are not necessarily limited to, passive physical markers and active physical markers. Passive physical markers may have physical parameters that aid in their identification by MR system 212. For instance, physical markers may have a certain shape (e.g., spherical markers that may be attached to the real observed bone structure 2200), and/or optical characteristics (e.g., reflective materials, colors (e.g., colors, such a green, that are more visible in a surgical environment), bar codes (including one-dimensional or two-dimensional bars, such as QR codes), or the like) that aid in their identification by MR system 212. The passive physical markers can be three-dimensional or two-dimensional. Passive physical markers may be considered passive in that their presence/position is passively detected by MR system 212. The passive physical markers may be flat or flexible two-dimensional stickers having planar fiducial markers that can be adhesively mounted to bone, tools or other structures, e.g., via an adhesive back layer exposed upon removal of a release layer. Alternatively, passive physical markers may be fixed to bone, e.g., with surgical adhesive, screws, nails, clamps and/or other fixation mechanisms.

Figure 30D:
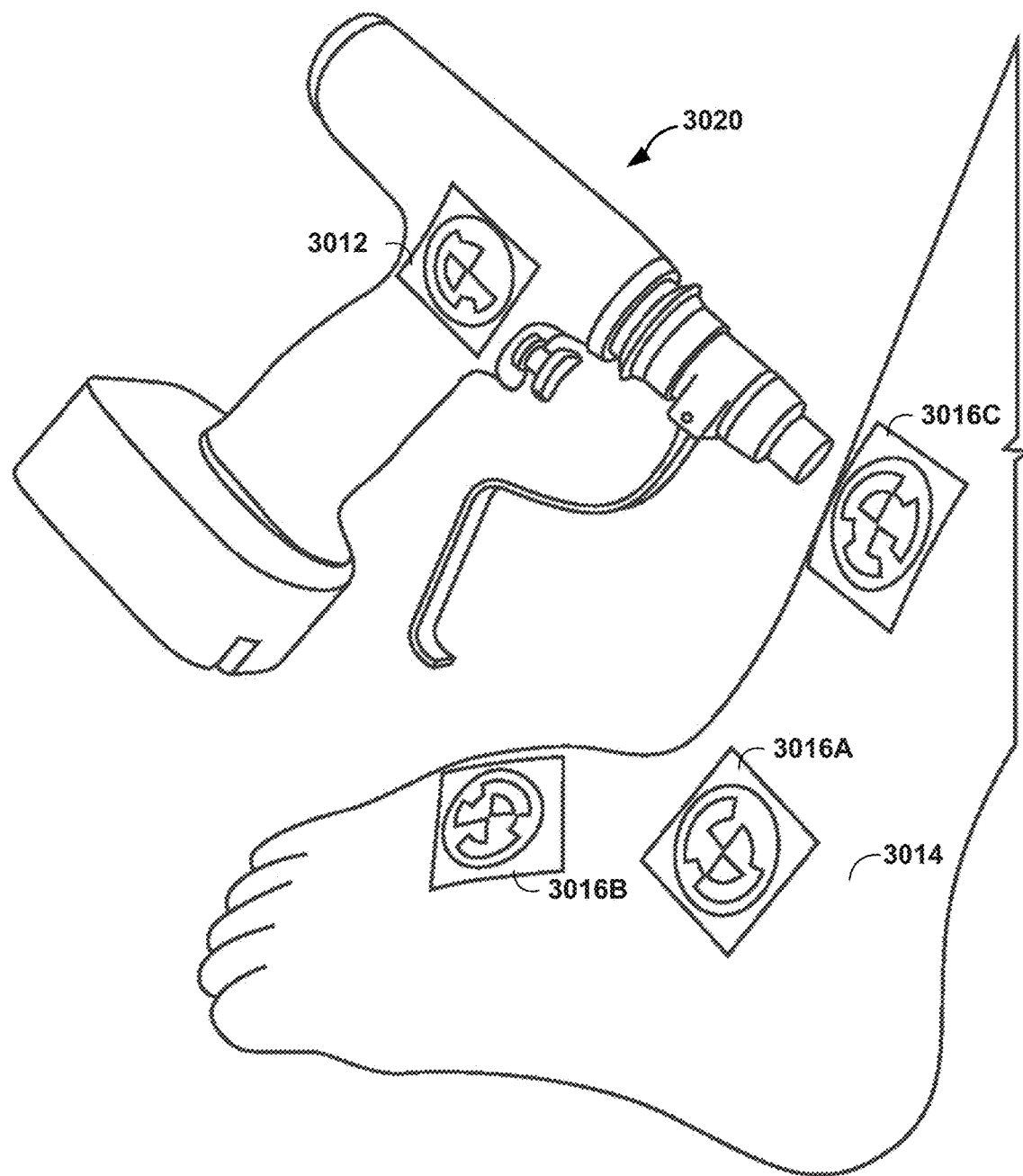

As shown in the example of FIG. 30D, stickers 3016A-3016C that include planar fiducial markers are shown as being attached to, or around, observed ankle 3014. Additionally, sticker 3018 that includes a planar fiducial marker is shown as being attached to drill 3020.

Active physical markers may perform one or more actions that aid in their identification by MR system 212. For instance, active physical markers may output signals (e.g., electromagnetic signals) that aid in their identification by MR system 212. Examples of active physical markers include, but are not limited to, sensors or transmitters for the trakSTAR™ and/or driveBAY™ systems available from Northern Digital Inc.

Electromagnetic tracking (i.e., tracking using electromagnetic physical markers, referred to as "EM tracking") may be accomplished by positioning sensors within a magnetic field of known geometry, which may be created by a field generator (FG). The sensors may measure magnetic flux or magnetic fields. A tracking device may control the FG and receive measurements from the sensors. Based on the received measurements, the tracking device may determine the locations/positions of the sensors. A more detailed description on EM tracking may be found in Alfred M. Franz et. al, "Electromagnetic Tracking in Medicine—A Review of Technology, Validation, and Applications," IEEE TRANSACTIONS ON MEDICAL IMAGING, VOL. 33, NO. 8, August 2014.

Figure 30E:
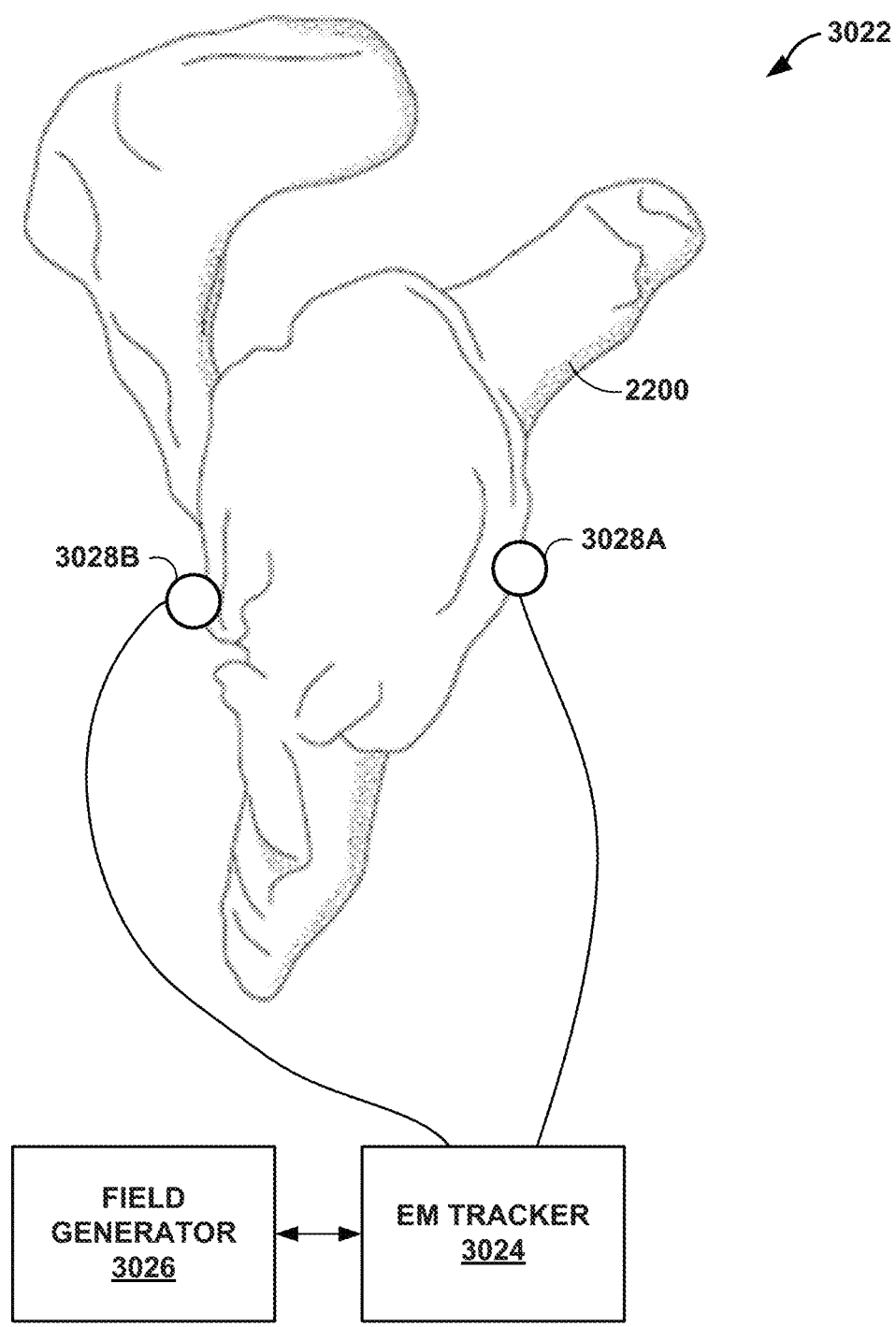

FIG. 30E illustrates an example of electromagnetic physical markers positioned around the real observed bone structure 2200. As illustrated in FIG. 30E, electromagnetic (EM) tracking system 3022 (which may be included within MR system 204 of FIG. 2) includes electromagnetic (EM) tracker 3024, field generator 3004, and one or more EM physical markers 3028A and 3028B (collectively "EM physical markers 3028"). EM physical markers 3006 may be positioned near and/or attached to the object to be tracked (e.g., observed bone structure 2200, an instrument, or the like) using the techniques described above. For instance, EM physical markers 3006 may be attached using surgical adhesive, screws, nails, clamps and/or other fixation mechanisms.

Field generator 3004 may be configured to output/generate a magnetic field with a known geometry. Examples of field generator 3004 include, but are not necessarily limited to, permanent magnets or by electromagnetism. In the electromagnetism case, the structure of the magnetic reference field may be governed by the law of Biot-Savart. The geometry of the emitting coil assembly and the type of current sent through the coils determines the shape and the geometric properties of the aforementioned field.

EM tracker 3024 may be configured to control the operation of field generator 3004. For instance, EM tracker 3024 may control parameters of the EM field generated by field generator 3004 by adjusting the current flowing through coils of field generator 3004. EM tracker 3024 may receive signals from EM physical markers 3006. For instance, EM tracker may receive measurements of magnetic flux and/or magnetic fields from EM physical markers 3006. EM tracker 3024 may determine the positions/orientations/locations of EM physical markers 3006 based on the received measurements.

EM tracker 3024 and field generator 3004 may each be standalone components, may be integrated into a single component, or may be included within another component. For instance, EM tracker 3024 may be included within MR system 212 of FIG. 2. EM tracker 3024 may output the determined positions/orientations/locations of EM physical markers 3006 to one or more other components of MR system 204 (e.g., processing devices 210).

EM tracking system 3022 may be utilized to perform registration with or without the use of other markers. As one example, EM tracking system 3022 may be utilized to register a virtual model of a bone to a corresponding observed bone without the use of other physical markers or virtual markers. As another example, EM tracking system 3022 may be utilized to register a virtual model of a bone to a corresponding observed bone in conjunction with other physical markers and/or virtual markers.

FIG. 20B illustrates an example of a technique 2018 for registering a 3D virtual bone model 1008 with a real observed bone structure 2200 of a patient using physical markers (e.g., any combination of passive and active physical markers). In other words, FIG. 20B is an example of a process flow, e.g., performed by visualization device 213, for registering a virtual bone model with an observed bone that is implemented in a mixed reality system, such as the mixed reality system 212 of FIG. 2. 3D virtual bone model 1008 may be a model of all or part of one or more bones. The process flow of FIG. 20B may be performed as part of the registration process of step 1904 of FIG. 19. As described below, the registration process of FIG. 20B may be used in addition to, or in place of, the registration process of FIG. 20A.

In operation, the practitioner may place one or more physical markers at specific positions. In some examples, MR system 212 may output instructions as to where the practitioner should place the physical markers. The prescribed locations may correspond to specific locations on a virtual model that corresponds to the observed bone structure 2200. For instance, in one example, visualization device 213 may display instructions for the practitioner to attach the physical markers (e.g., with surgical adhesive, screws, nails, clamps and/or other fixation mechanisms) at locations corresponding to positions of patient matched guide 1600 of FIG. 16 (e.g., regardless of whether patient matched guide 1600 is available for use). In other words, the practitioner may attach the physical makers at the locations where the patient matched guide 1600 would attach, even if patient matched guide 1600 is not present. In other examples, the prescribed locations may be indicated by text, graphical or audible information to cause the surgeon to select corresponding locations on the physical bone or tool(s) for attachment or other placement of the markers. For instance, MR system 212 may output graphic information to guide the surgeon in attaching tip 3010B of optical marker 3010 of FIG. 30A to the acromion of the scapula.

MR system 212 may utilize data from one or more sensors (e.g., one or more of sensors 614 of visualization device 213 of FIG. 6) to identify the location of the physical markers (2020). For instance, MR system 212 may use data generated by any combination of depth sensors 532 and/or optical sensors 530 to identify a specific position (e.g., coordinates) of each of the physical markers. As one specific example, MR system 212 may utilize optical data generated by optical sensors 530 to identify a centroid of optical marker 3010A of FIG. 30A. MR system 212 may then utilize depth data generated by depth sensors 532 and/or optical data generated by optical sensors 530 to determine a position and/or orientation of the identified centroid. MR system 212 may determine a distance between the centroid and an attachment point of the physical marker. For instance, MR system 212 may determine a distance between a centroid of fiducial marker 3010A and tip 3010B of optical marker 3010 of FIG. 30A. Based on the determined distance (i.e., between the centroid and the attachment point) and the determined position/orientation of the centroid, MR system 212 may determine a position/orientation of the attachment point.

MR system 212 may register the virtual model with the observed anatomy based on the identified positions (2022) of the physical markers. For instance, where the physical markers are placed on the observed bone structure 2200 at locations that correspond to specific location(s) on the virtual model that corresponds to the observed bone structure 2200, MR system 212 may generate a transformation matrix between the virtual model and the observed bone structure 212. This transformation matrix may be similar to the transformation matrix discussed above in that it allows for translation along the x, y, and z axes of the virtual model and rotation about the x, y and z axes in order to achieve and maintain alignment between the virtual and observed bones. In some examples, after registration is complete, MR system 212 utilize the results of the registration to perform simultaneous localization and mapping (SLAM) to maintain alignment of the virtual model to the corresponding observed object.

As discussed in further detail below, MR system 212 may display, based on the registration, virtual guidance for preparing the observed anatomy for attachment of a prosthetic or virtual guidance for attaching the prosthetic to the observed anatomy (2024). For instance, MR system 212 may provide virtual guidance as described below with reference to any combination of FIGS. 34-71.

As discussed above, the physical markers may be used in addition to, or in place of, the virtual markers (e.g., virtual marker 2500). In other words, MR system 212 may perform registration of a virtual model of a bone to corresponding observed bone using any combination of physical and virtual markers. In some examples, using physical markers (either alone or with virtual markers) may enable MR system 212 to reduce the amount of time required to perform registration and/or may result in more accurate registration.

In some examples, MR system 212 may use one of virtual markers or physical markers as a primary registration marker and use the other as a secondary, or supplemental, registration marker. As one example, MR system 212 may begin a registration process by attempting to perform registration using the primary registration marker. In such examples, if MR system 212 is not able to adequately complete registration (e.g., cannot generate a mapping, such as a transformation matrix, between the virtual and observed anatomy) using only the primary registration marker, MR system 212 may attempt to perform registration using only the secondary registration marker or a combination of the primary registration marker and the secondary registration marker. In one specific example, if MR system 212 is not able to adequately complete registration using only virtual marker(s), MR system 212 may attempt to perform registration using only physical marker(s) or a combination of virtual registration marker(s) and physical registration marker(s).

In situations where MR system 212 is not able to adequately complete registration using only the primary registration marker, MR system 212 may output a request for the practitioner to perform one or more actions to enable registration using the secondary registration marker. As one example, where the secondary registration marker is a physical marker, MR system 212 may output a request for the practitioner to position a physical marker at a particular location relative to the observed anatomy. As another example, where the secondary registration marker is a virtual marker, MR system 212 may output a request and corresponding graphical user interface (e.g., 3D virtual bone model 1008) for the practitioner to perform the initial alignment procedure described above with reference to FIG. 20A.

In some examples, the practitioner may remove the physical markers (e.g., after registration is complete). For instance, after MR system 212 has completed the registration process using the physical markers, MR system 212 may output an indication that the physical markers may be removed. In example where the physical markers are removed, MR system 212 may maintain the registration of the virtual bone model to the observed bone using virtual markers or any other suitable tracking technique.

In some examples, the practitioner may not remove the physical markers until a later point in the surgery. For instance, the practitioner may not remove the physical markers until registration of the virtual model to the observed bone is no longer required (e.g., after all virtual guidance that uses the registration has been displayed and corresponding surgical steps have been completed).

In some examples, MR system 212 may be able to maintain the registration between a virtual bone model and observed bone (e.g., glenoid, humerus, or other bone structure) throughout the procedure. However, in some cases, MR system 212 may lose, or otherwise be unable to maintain, the registration between the virtual bone model and observed bone. For instance, MR system 212 may lose track of one of more of the markers (e.g., virtual, physical, or both). This loss may be the result of any number of factors including, but not limited to, body fluids (e.g., blood)

occluding the markers, the markers becoming dislodged (e.g., a physical marker being knocked out of position), and the like. As such, MR system 212 may periodically determine whether registration has been lost (2026).

In some examples, MR system 212 may determine that registration has been lost where a confidence distance between a virtual point and a corresponding physical point exceeds a threshold confidence distance (e.g., a clinical value). MR system 212 may periodically determine the confidence distance as a value that represents the accuracy of the current registration. For instance, MR system 212 may determine that a distance between a virtual point and a corresponding physical point is less than 3 mm.

In some examples, MR system 212 may output a representation of the confidence distance. As one example, MR system 212 may cause visualization device 213 to display a numerical value of the confidence distance. As another example, MR system 212 may cause visualization device 213 to display a graphical representation of the confidence distance relative to the threshold confidence distance (e.g., display a green circle if the confidence distance is less than half of the threshold confidence distance, display a yellow circle if the confidence distance is between half of the threshold confidence distance and the threshold confidence distance, and display a red circle if the confidence distance greater than the threshold confidence distance).

In some examples, MR system 212 may utilize the same threshold confidence distance throughout a surgical procedure. For instance, MR system 212 may utilize a particular threshold confidence distance for all humeral and scapula work steps (e.g., described below with reference to FIGS. 34-71). In some examples, MR system 212 may utilize different threshold confidence distances for various parts a surgical procedure. For instance, MR system 212 may utilize a first threshold confidence distance for a first set of work steps and use a second threshold confidence distance (that is different than the first threshold confidence distance) for a first set of work steps for a second set of work steps.

Where registration has not been lost ("No" branch of 2026), MR system 212 may continue to display virtual guidance (2024). However, where MR system 212 loses registration ("Yes" branch of 2026), MR system 212 may perform one or more actions to re-register the virtual bone model to the observed bone. As one example, MR system 212 may automatically attempt to perform the registration process without further action from the practitioner. For instance, where physical markers have not been removed. MR system 212 may perform the registration process using the physical markers. Alternatively, where the physical markers have been removed (or were never placed), MR system 212 may output a request for the practitioner to place the physical markers. As such, MR system 212 may be considered to periodically register the virtual model with the observed bone.

In some examples, as opposed to automatically attempting re-registration where registration is lost, MR system 212 may selectively perform re-registration based on whether registration is still needed (2028). In some examples, MR system 212 may determine that registration is still needed if additional virtual guidance will be displayed. Where MR system 212 determines that registration is no longer needed ("No" branch of 2028), MR system 212 may end the registration procedure.

As described above, MR system 212 may utilize any combination of virtual and physical markers to enable registration of virtual models to corresponding observed structures. MR system 212 may use any of the markers to perform an initial registration and, where needed, MR system 212 may use any of the markers to perform a re-registration. The markers used for the initial registration may be the same as or may be different than the markers used for any re-registrations.

In some examples, to enhance the accuracy and quality of registration, during the initialization stage of the registration process, MR system 212 can compute and display spatial constraints for user head pose and orientation. These constraints can be computed in real time and depend on the position of the user, and/or the orientation, and/or the distance to the observed bone, and/or the depth camera characteristics. For example, MR system 212 may prompt the user to move closer to the observed bone, to adjust the head position so that the user's gaze line is perpendicular to the surface of interest of the observed bone, or to make any other adjustments that can be useful to enhance the registration process and which may depend on the particular surgical application and/or the attributes of the particular anatomy of interest and/or the characteristics of the optical and depth sensors that are employed in MR system 212.

In some examples, depth camera(s) 532 detect distance by using a structured light approach or time of flight of an optical signal having a suitable wavelength. In general, the wavelength of the optical signal is selected so that penetration of the surface of the observed anatomy by the optical signal transmitted by depth camera(s) 532 is minimized. It should be understood, however, that other known or future developed techniques for detecting distance also can be employed.

As discussed below, the registration techniques described herein may be performed for any pair of virtual model and observed object. As one example, an MR system may utilize the registration techniques to register a virtual model of a bone to an observed bone. For instance, an MR system may utilize the registration techniques to register a virtual model of a glenoid/humerus/ankle to a corresponding observed glenoid/humerus/ankle. As another example, an MR system may utilize the registration techniques to register a virtual model of an implant to an observed implant. An MR system may utilize the registration techniques to register a virtual model of a tool to an observed tool. For instance, an MR system may utilize the registration techniques to register a virtual model of a drill to a corresponding observed drill.

In some examples, an MR system may perform the registration techniques once for a particular pair of a virtual model and an observed object (e.g., within a particular surgical procedure). For instance, an MR system may register a virtual model of a glenoid with an observed glenoid and utilize the registration to provide virtual guidance for multiple steps of a surgical procedure. In some examples, an MR system may perform the registration techniques multiple times for a particular pair of a virtual model and an observed object (e.g., within a particular surgical procedure). For instance, an MR system may first register a virtual model of a glenoid with an observed glenoid and utilize the registration to provide virtual guidance for one or more steps of a surgical procedure. Then, for example, after material has been removed from the glenoid (e.g., via reaming), the MR system may register another virtual model of the glenoid (that accounts for the removed material) with an observed glenoid and use the subsequent registration to provide virtual guidance for one or more other steps of the surgical procedure.

Figure 27:
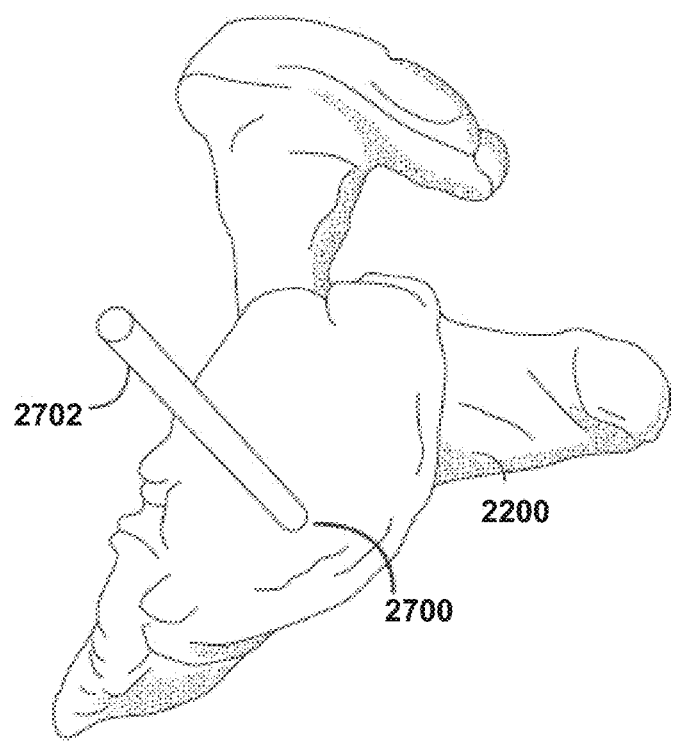
FIG. 27 illustrates an image perceptible to a user when in an augment surgery mode of a mixed reality (MR) system, according to an example of this disclosure.

Once registration is complete the surgical plan can be executed using the Augment Surgery mode of MR system 212. For example, FIG. 27 illustrates an image perceptible to a user when in the augment surgery mode of a mixed reality system, according to an example of this disclosure. As shown in the example of FIG. 27, the surgeon can visualize a virtually planned entry point 2700 and drilling axis 2702 on observed bone structure 2200 and use those virtual images to assist with positions and alignment of surgical tools. Drilling axis 2702 may also be referred to as a reaming axis, and provides a virtual guide for drilling a hole in the glenoid for placement of a guide pin that will guide a reaming process. In some cases, drilling and placing the guide pin comprises a one-step process of drilling the guide pin into place (e.g., the guide pin may be "self-tapping").

Figure 28:
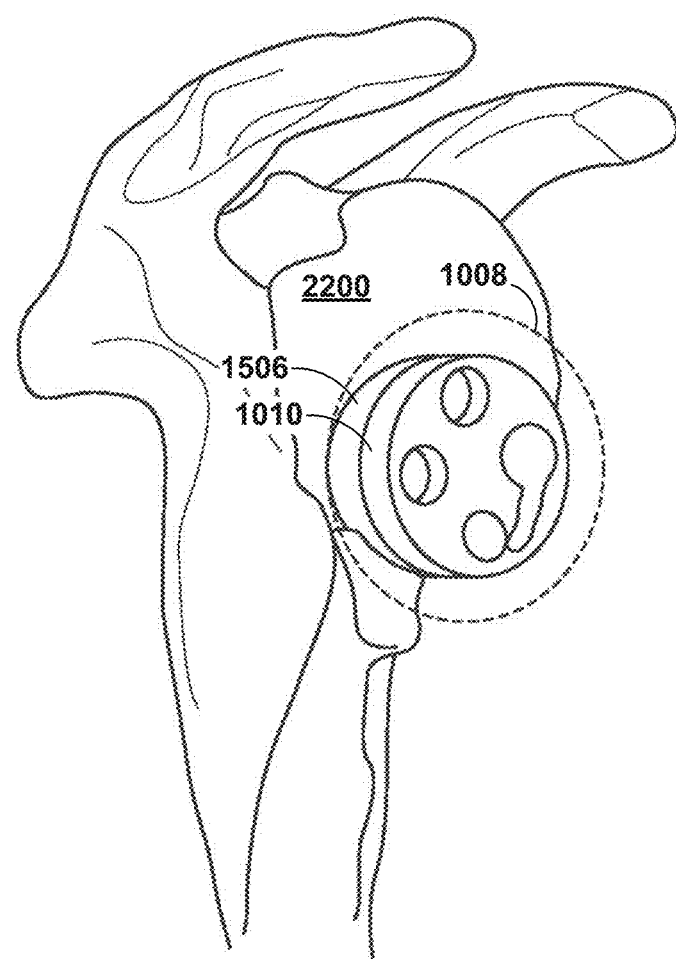
FIG. 28 illustrates an example of virtual images that a surgeon can see of implant components in an augment surgery mode of a mixed reality (MR) system.
Figure 29:
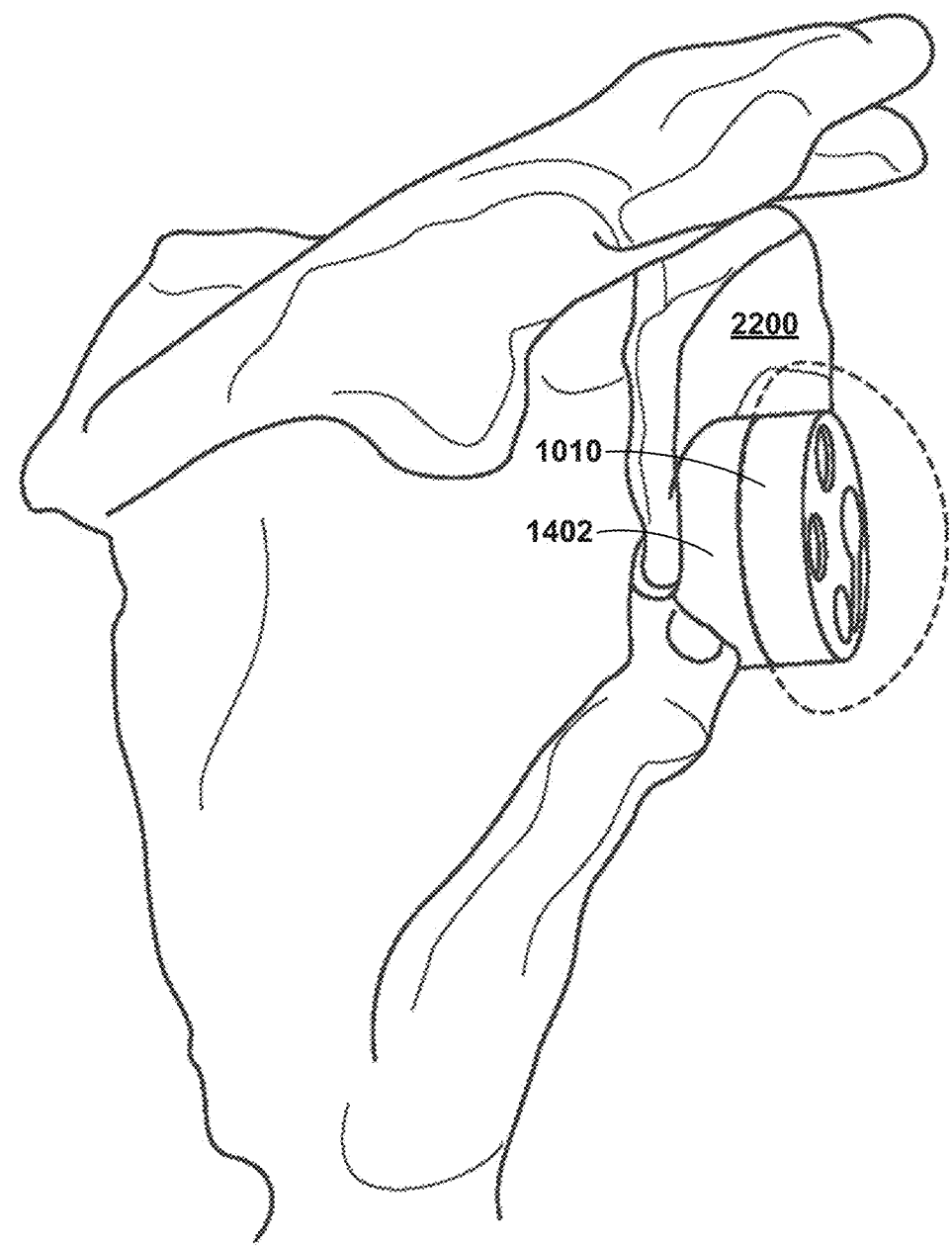
FIG. 29 illustrates an example of virtual images that a surgeon can see of implant components in an augment surgery mode of a mixed reality (MR) system.

FIG. 28 illustrates an example of virtual images that a surgeon can see of implant components via visualization device 213. Similarly, FIG. 29 illustrates an example of virtual images that a surgeon can see of implant components. In the examples of FIG. 28 and FIG. 29, the surgeon also can see virtual images of the implant components (e.g., the virtual bone model 1008), including the graft 1402, superimposed on observed bone structure 2200. Also, the surgeon can see the osteophytes and which part of the bone represents osteophytes.

The registration process may be used in conjunction with the virtual planning processes and/or intra-operative guidance described elsewhere in this disclosure. Thus, in one example, a virtual surgical plan is generated or otherwise obtained to repair an anatomy of interest of a particular patient (e.g., the shoulder joint of the particular patient). In instances where the virtual surgical plan is obtained, another computing system may generate the virtual surgical plan and an MR system (e.g., MR system 212) or other computing system obtains at least a portion of the virtual surgical plan from a computer readable medium, such as a communication medium or a non-transitory storage medium. In this example, the virtual surgical plan may include a 3D virtual model of the anatomy of interest generated based on pre-operative image data and a prosthetic component selected for the particular patient to repair the anatomy of interest. Furthermore, in this example, a user may use a MR system (e.g., MR system 212) to implement the virtual surgical plan. In this example, as part of using the MR system, the user may request the virtual surgical plan for the particular patient.

Additionally, the user may view virtual images of the surgical plan projected within a real environment. For example, MR system 212 may present 3D virtual objects such that the objects appear to reside within a real environment, e.g., with real anatomy of a patient, as described in various examples of this disclosure. In other words, MR system 212 may output, for viewing by a user, virtual images of the virtual surgical plan projected within a real environment, where the virtual images of the virtual surgical plan including the 3D virtual model of the anatomy of interest. In this example, the virtual images of the surgical plan may include one or more of the 3D virtual model of the anatomy of interest, a 3D model of the prosthetic component selected to repair the anatomy of interest, and virtual images of a surgical workflow to repair the anatomy of interest. The virtual images of the surgical workflow may include text, graphics, or animations indicating one or more steps to perform as part of performing the surgery to repair the anatomy of interest. Furthermore, in this example, the user may register the 3D virtual model with a real anatomy of interest of the particular patient. The user may then implement the virtually generated surgical plan to repair the real anatomy of interest based on the registration. In other words, in the augmented surgery mode, the user can use the visualization device to align the 3D virtual model of the anatomy of interest with the real anatomy of interest.

In such examples, the MR system implements a registration process whereby the 3D virtual model is aligned (e.g., optimally aligned) with the real anatomy of interest. In this example, the user may register the 3D virtual model with the real anatomy of interest without using virtual or physical markers. In other words, the 3D virtual model may be aligned (e.g., optimally aligned) with the real anatomy of interest without the use of virtual or physical markers. The MR system may use the registration to track movement of the real anatomy of interest during implementation of the virtual surgical plan on the real anatomy of interest. In some examples, the MR system may track the movement of the real anatomy of interest without the use of tracking markers.

In some examples, as part of registering the 3D virtual model with the real anatomy of interest, the 3D virtual model can be aligned (e.g., by the user) with the real anatomy of interest and generate a transformation matrix between the 3D virtual model and the real anatomy of interest based on the alignment. The transformation matrix provides a coordinate system for translating the virtually generated surgical plan to the real anatomy of interest. For instance, the registration process may allow the user to view 3D virtual models of anatomical features associated with steps of the virtual surgical plan projected on corresponding real anatomical features of interest during the surgery on the patient. The steps of the virtual surgical plan projected on the real anatomy of interest include identification of an entry point for positioning a prosthetic implant to repair the real anatomical feature of interest. In some examples, the alignment of the 3D virtual model with the real anatomy of interest may generate a transformation matrix that may allow the user to view steps of the virtual surgical plan (e.g., identification of an entry point for positioning a prosthetic implant to repair the real anatomy of interest) projected on the real anatomy of interest.

In some examples, the registration process (e.g., the transformation matrix generated using the registration process) may allow the user to implement the virtual surgical plan on the real anatomy of interest without use of tracking markers. In some examples, aligning the 3D virtual model with the real anatomy of interest including positioning a point of interest on a surface of the 3D virtual model at a location of a corresponding point of interest on a surface of the real anatomy of interest and adjusting an orientation of the 3D virtual model so that a virtual surface normal at the point of interest is aligned with a real surface normal at the corresponding point of interest. In some such examples, the point of interest is a center point of a glenoid.

With continued reference to FIG. 19, after performing the registration process, the surgeon may perform a reaming axis drilling process (1906). During the reaming axis drilling process, the surgeon may drill a reaming axis guide pin hole in the patient's glenoid to receive a reaming guide pin. In some examples, at a later stage of the shoulder surgery, the surgeon may insert a reaming axis pin into the reaming axis guide pin hole. In some examples, the reaming axis pin may itself be the drill bit that is used to drill the reaming axis guide pin hole (e.g., the reaming axis pin may be self-tapping). Thus, in such examples, it may be unnecessary to perform a separate step of inserting the reaming axis pin. In some examples, an MR system (e.g., MR system 212, MR system 1800A, etc.) may present a virtual reaming axis to help the surgeon perform the drilling in alignment with the reaming axis and thereby place the reaming guide pin in the correct location and with the correct orientation.

The surgeon may perform the reaming axis drilling process in one of various ways. For example, the surgeon may perform a guide-based process to drill the reaming axis pin hole. In the case, a physical guide is placed on the glenoid to guide drilling of the reaming axis pin hole. In other examples, the surgeon may perform a guide-free process, e.g., with presentation of a virtual reaming axis that guides the surgeon to drill the reaming axis pin hole with proper alignment. An MR system (e.g., MR system 212, MR system 1800A, etc.) may help the surgeon perform either of these processes to drill the reaming axis pin hole.

Furthermore, in the surgical process of FIG. 19, the surgeon may perform a reaming axis pin insertion process (1908). During the reaming axis pin insertion process, the surgeon inserts a reaming axis pin into the reaming axis pin hole drilled into the patient's scapula. In some examples, an MR system (e.g., MR system 212, MR system 1800A, etc.) may present virtual guidance information to help the surgeon perform the reaming axis pin insertion process.

After performing the reaming axis insertion process, the surgeon may perform a glenoid reaming process (1910). During the glenoid reaming process, the surgeon reams the patient's glenoid. Reaming the patient's glenoid may result in an appropriate surface for installation of a glenoid implant. In some examples, to ream the patient's glenoid, the surgeon may affix a reaming bit to a surgical drill. The reaming bit defines an axial cavity along an axis of rotation of the reaming bit. The axial cavity has an inner diameter corresponding to an outer diameter of the reaming axis pin. After affixing the reaming bit to the surgical drill, the surgeon may position the reaming bit so that the reaming axis pin is in the axial cavity of the reaming bit. Thus, during the glenoid reaming process, the reaming bit may spin around the reaming axis pin. In this way, the reaming axis pin may prevent the reaming bit from wandering during the glenoid reaming process. In some examples, multiple tools may be used to ream the patient's glenoid. An MR system (e.g., MR system 212, MR system 1800A, etc.) may present virtual guidance to help the surgeon or other users to perform the glenoid reaming process. For example, the MR system may help a user, such as the surgeon, select a reaming bit to use in the glenoid reaming process. In some examples, the MR system present virtual guidance to help the surgeon control the depth to which the surgeon reams the user's glenoid. In some examples, the glenoid reaming process includes a paleo reaming step and a neo reaming step to ream different parts of the patient's glenoid.

Additionally, in the surgical process of FIG. 19, the surgeon may perform a glenoid implant installation process (1912). During the glenoid implant installation process, the surgeon installs a glenoid implant in the patient's glenoid. In some instances, when the surgeon is performing an anatomical shoulder arthroplasty, the glenoid implant has a concave surface that acts as a replacement for the user's natural glenoid. In other instances, when the surgeon is performing a reverse shoulder arthroplasty, the glenoid implant has a convex surface that acts as a replacement for the user's natural humeral head. In this reverse shoulder arthroplasty, the surgeon may install a humeral implant that has a concave surface that slides over the convex surface of the glenoid implant. As in the other steps of the shoulder surgery of FIG. 19, an MR system (e.g., MR system 212, MR system 1800A, etc.) may present virtual guidance to help the surgeon perform the glenoid installation process.

In some examples, the glenoid implantation process includes a process to fix the glenoid implant to the patient's scapula (1914). In some examples, the process to fix the glenoid implant to the patient's scapula includes drilling one or more anchor holes or one or more screw holes into the patient's scapula and positioning an anchor such as one or more pegs or a keel of the implant in the anchor hole(s) and/or inserting screws through the glenoid implant and the screw holes, possibly with the use of cement or other adhesive. An MR system (e.g., MR system 212, MR system 1800A, etc.) may present virtual guidance to help the surgeon with the process of fixing the glenoid implant the glenoid bone, e.g., including virtual guidance indicating anchor or screw holes to be drilled or otherwise formed in the glenoid, and the placement of anchors or screws in the holes.

Furthermore, in the example of FIG. 19, the surgeon may perform a humerus preparation process (1916). During the humerus preparation process, the surgeon prepares the humerus for the installation of a humerus implant. In instances where the surgeon is performing an anatomical shoulder arthroplasty, the humerus implant may have a convex surface that acts as a replacement for the patient's natural humeral head. The convex surface of the humerus implant slides within the concave surface of the glenoid implant. In instances where the surgeon is performing a reverse shoulder arthroplasty, the humerus implant may have a concave surface and the glenoid implant has a corresponding convex surface. As described elsewhere in this disclosure, an MR system (e.g., MR system 212, MR system 1800A, etc.) may present virtual guidance information to help the surgeon perform the humerus preparation process.

Furthermore, in the example surgical process of FIG. 19, the surgeon may perform a humerus implant installation process (1918). During the humerus implant installation process, the surgeon installs a humerus implant on the patient's humerus. As described elsewhere in this disclosure, an MR system (e.g., MR system 212, MR system 1800A, etc.) may present virtual guidance to help the surgeon perform the humerus preparation process.

After performing the humerus implant installation process, the surgeon may perform an implant alignment process that aligns the installed glenoid implant and the installed humerus implant (1920). For example, in instances where the surgeon is performing an anatomical shoulder arthroplasty, the surgeon may nest the convex surface of the humerus implant into the concave surface of the glenoid implant. In instances where the surgeon is performing a reverse shoulder arthroplasty, the surgeon may nest the convex surface of the glenoid implant into the concave surface of the humerus implant. Subsequently, the surgeon may perform a wound closure process (1922). During the wound closure process, the surgeon may reconnect tissues severed during the incision process in order to close the wound in the patient's shoulder.

As mentioned elsewhere in this disclosure, a user interface of MR system 212 may include workflow bar 1000. Workflow bar 1000 include icons corresponding to workflow pages. In some examples, each workflow page that can be selected by the user (e.g., a surgeon) can include an Augment Surgery widget 1300 (such as that shown in FIG. 13), that, when selected, launches an operational mode of MR system 212 in which a user wearing or otherwise using visualization device 213 can see the details (e.g., virtual images of details) of the surgical plan projected and matched onto the patient bone and use the plan intraoperatively to assist with the surgical procedure. In general, the Augment Surgery mode allows the surgeon to register the virtual 3D model of the patient's anatomy of interest (e.g., glenoid) with the observed real anatomy so that the surgeon can use the virtual surgical planning to assist with implementation of the real surgical procedure, as will be explained in further detail below.

Figure 13:
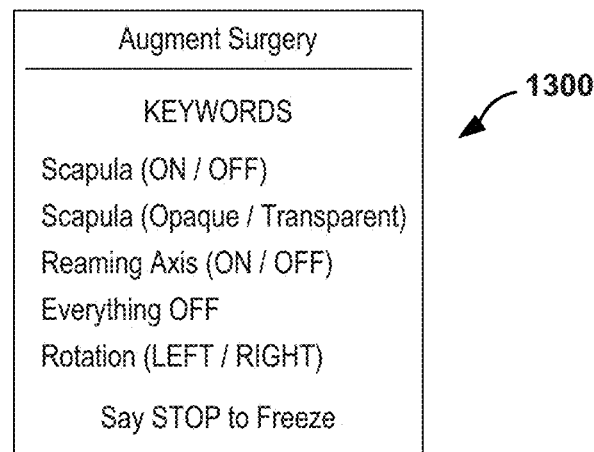
FIG. 13 is an example of an Augment Surgery mode widget that is displayed on various pages of the user interface of FIG. 10, according to an example of this disclosure.

An example of Augment Surgery widget 1300 is shown in FIG. 13. Selection of the widget 1300 initiates an augmented surgery mode of operation of MR system 212. Upon initiation of the augmented surgery mode, 3D virtual bone model 1008 of the patient's relevant bone structure is registered with the observed bone structure (i.e., the patient's real bone) so that details of a virtually planned procedure can be visualized and superimposed on the observed bone. For example, for a shoulder arthroplasty procedure, these details can include entry points, drilling axes, osteophytes and cutting surfaces/planes, as examples. As shown in FIG. 13, Augment Surgery widget 1300 may permit a user to select, e.g., with voice command keywords, whether the scapula is shown or not (Scapula ON/OFF) and, if shown, whether the scapula is shown as opaque or transparent (Scapula Opaque/Transparent). In addition, the user may select, e.g., with voice command keywords, whether a glenoid reaming axis is shown or not (Reaming Axis ON/OFF), whether everything is not shown (Everything Off), whether to rotate the displayed virtual objects to the left or to the right (Rotation Left/Right), and whether to STOP the rotation (Say STOP to Freeze).

As noted above, Augment Surgery widget 1300 may permit a user to select whether the scapula is shown as opaque or transparent (Scapula Opaque/Transparent). In some examples, the user may use a voice command, hand gesture, or other type of command to select whether to show the scapula as opaque or transparent. When the user selects the element for controlling whether the scapula is opaque or transparent, visualization device 213 may increase or decrease the opacity of the model of the scapula. In some examples, visualization device 213 may continue changing the opacity of the model until visualization device 213 receives an indication of user input, such as a voice command, to stop changing the opacity. Changing the opacity of the model of the scapula, especially the glenoid portion of the scapula may help the user to better see the model of the scapula under different lighting conditions.

For a shoulder arthroplasty application, the registration process may start by virtualization device 213 presenting the user with 3D virtual bone model 1008 of the patient's scapula and glenoid that was generated from preoperative images of the patient's anatomy, e.g., by surgical planning system 102. The user can then manipulate 3D virtual bone model 1008 in a manner that aligns and orients 3D virtual bone model 1008 with the patient's real scapula and glenoid that the user is observing in the operating environment. As such, in some examples, the MR system may receive user input to aid in the initialization and/or registration. However, discussed above, in some examples, the MR system may perform the initialization and/or registration process automatically (e.g., without receiving user input to position the 3D bone model). For other types of arthroplasty procedures, such as for the knee, hip, foot, ankle or elbow, different relevant bone structures can be displayed as virtual 3D images and aligned and oriented in a similar manner with the patient's actual, real anatomy.

Regardless of the particular type of joint or anatomical structure involved, selection of the augment surgery mode initiates a procedure where 3D virtual bone model 1008 is registered with an observed bone structure. In general, the registration procedure can be considered as a classical optimization problem (e.g., either minimization or maximization). For a shoulder arthroplasty procedure, known inputs to the optimization (e.g., minimization) analysis are the 3D geometry of the observed patient's bone (derived from sensor data from the visualization device 213, including depth data from the depth camera(s) 532) and the geometry of the 3D virtual bone derived during the virtual surgical planning state (such as by using the BLUEPRINT™ system). Other inputs include details of the surgical plan (also derived during the virtual surgical planning stage, such as by using the BLUEPRINT™ system), such as the position and orientation of entry points, cutting planes, reaming axes and/or drilling axes, as well as reaming or drilling depths for shaping the bone structure, the type, size and shape of the prosthetic components, and the position and orientation at which the prosthetic components will be placed or, in the case of a fracture, the manner in which the bone structure will be rebuilt.

Upon selection of a particular patient from the welcome page of UI 522 of MR system 212 (FIG. 5), the surgical planning parameters associated with that patient are connected with the patient's 3D virtual bone model 1008, e.g., by one or more processors of visualization device 213. In the Augment Surgery mode, registration of 3D virtual bone model 1008 (with the connected preplanning parameters) with the observed bone by visualization device 213 allows the surgeon to visualize virtual representations of the surgical planning parameters on the patient.

The optimization (e.g., minimization) analysis that is implemented to achieve registration of the 3D virtual bone model 1008 with the real bone generally is performed in two stages: an initialization stage and an optimization (e.g., minimization) stage. During the initialization stage, the user approximately aligns the 3D virtual bone model 1008 with the patient's real bone, such as by using gaze direction, hand gestures and/or voice commands to position and orient, or otherwise adjust, the alignment of the virtual bone with the observed real bone. The initialization stage will be described in further detail below. During the optimization (e.g., minimization) stage, which also will be described in detail below, an optimization (e.g., minimization) algorithm is executed that uses information from the optical camera(s) 530 and/or depth camera(s) 532 and/or any other acquisition sensor (e.g., motion sensors 533) to further improve the alignment of the 3D model with the observed anatomy of interest. In some examples, the optimization (e.g., minimization) algorithm can be a minimization algorithm, including any known or future-developed minimization algorithm, such as an Iterative Closest Point algorithm or a genetic algorithm as examples.

In this way, in one example, a mixed reality surgical planning method includes generating a virtual surgical plan to repair an anatomy of interest of a particular patient. The virtual surgical plan including a 3D virtual model of the anatomy of interest is generated based on preoperative image data and a prosthetic component selected for the particular patient to repair the anatomy of interest. Furthermore, in this example, a MR visualization system may be used to implement the virtual surgical plan. In this example, using the MR system may comprise requesting the virtual surgical plan for the particular patient. Using the MR system also comprises viewing virtual images of the surgical plan projected within a real environment. For example, visualization device 213 may be configured to present one or more 3D virtual images of details of the surgical plan that are projected within a real environment, e.g., such that the virtual image(s) appear to form part of the real environment. The virtual images of the surgical plan may include the 3D virtual model of the anatomy of interest, a 3D model of the prosthetic component, and virtual images of a surgical workflow to repair the anatomy of interest. Using the MR system may also include registering the 3D virtual model with a real anatomy of interest of the particular patient. Additionally, in this example, using the MR system may include implementing the virtually generated surgical plan to repair the real anatomy of interest based on the registration.

Furthermore, in some examples, the method comprises registering the 3D virtual model with the real anatomy of interest without using virtual or physical markers. The method may also comprise using the registration to track movement of the real anatomy of interest during implementation of the virtual surgical plan on the real anatomy of interest. The movement of the real anatomy of interest may be tracked without the use of tracking markers. In some instances, registering the 3D virtual model with the real anatomy of interest may comprise aligning the 3D virtual model with the real anatomy of interest and generating a transformation matrix between the 3D virtual model and the real anatomy of interest based on the alignment. The transformation matrix provides a coordinate system for translating the virtually generated surgical plan to the real anatomy of interest. In some examples, aligning may comprise virtually positioning a point of interest on a surface of the 3D virtual model within a corresponding region of interest on a surface of the real anatomy of interest; and adjusting an orientation of the 3D virtual model so that a virtual surface shape associated with the point of interest is aligned with a real surface shape associated with the corresponding region of interest. In some examples, aligning may further comprise rotating the 3D virtual model about a gaze line of the user. The region of interest may be an anatomical landmark of the anatomy of interest. The anatomy of interest may be a shoulder joint. In some examples, the anatomical landmark is a center region of a glenoid.

In some examples, after a registration process is complete, a tracking process can be initiated that continuously and automatically verifies the registration between 3D virtual bone model 1008 and observed bone structure 2200 during the Augment Surgery mode. During a surgery, many events can occur (e.g., patient movement, instrument movement, loss of tracking, etc.) that may disturb the registration between the 3D anatomical model and the corresponding observed patient anatomy or that may impede the ability of MR system 212 to maintain registration between the model and the observed anatomy. Therefore, by implementing a tracking feature, MR system 212 can continuously or periodically verify the registration and adjust the registration parameters as needed. If MR system 212 detects an inappropriate registration (such as patient movement that exceeds a threshold amount), the user may be asked to re-initiate the registration process.

In some examples, tracking can be implemented using one or more optical markers, such as the marker 3010 shown in FIG. 30, that is fixed to a particular location on the anatomy. MR system 212 monitors the optical marker(s) in order to track the position and orientation of the relevant anatomy in 3D space. If movement of the marker is detected, MR system 212 can calculate the amount of movement and then translate the registration parameters accordingly so as to maintain the alignment between the 3D model and the observed anatomy without repeating the registration process.

In other examples, tracking is markerless. For example, rather than using optical markers, MR system 212 implements markerless tracking based on the geometry of the observed anatomy of interest. In some examples, the markerless tracking may rely on the location of anatomical landmarks of the bone that provide well-defined anchor points for the tracking algorithm. In situations or applications in which well-defined landmarks are not available, a tracking algorithm can be implemented that uses the geometry of the visible bone shape or other anatomy. In such situations, image data from optical camera(s) 530 and/or depth cameras(s) 532 and/or motion sensors 533 (e.g., IMU sensors) can be used to derive information about the geometry and movement of the visible anatomy. An example of a tracking algorithm that can be used for markerless tracking is described in David J. Tan, et al., "6D Object Pose Estimation with Depth Images: A Seamless Approach for Robotic Interaction and Augmented Reality," arXiv: 1709.01459v1 [cs,CV] (Sep. 5, 2017), although any suitable tracking algorithm can be used. In some examples, the markerless tracking mode of MR system 212 can include a learning stage in which the tracking algorithm learns the geometry of the visible anatomy before tracking is initiated. The learning stage can enhance the performance of tracking so that tracking can be performed in real time with limited processing power.

Figure 31:
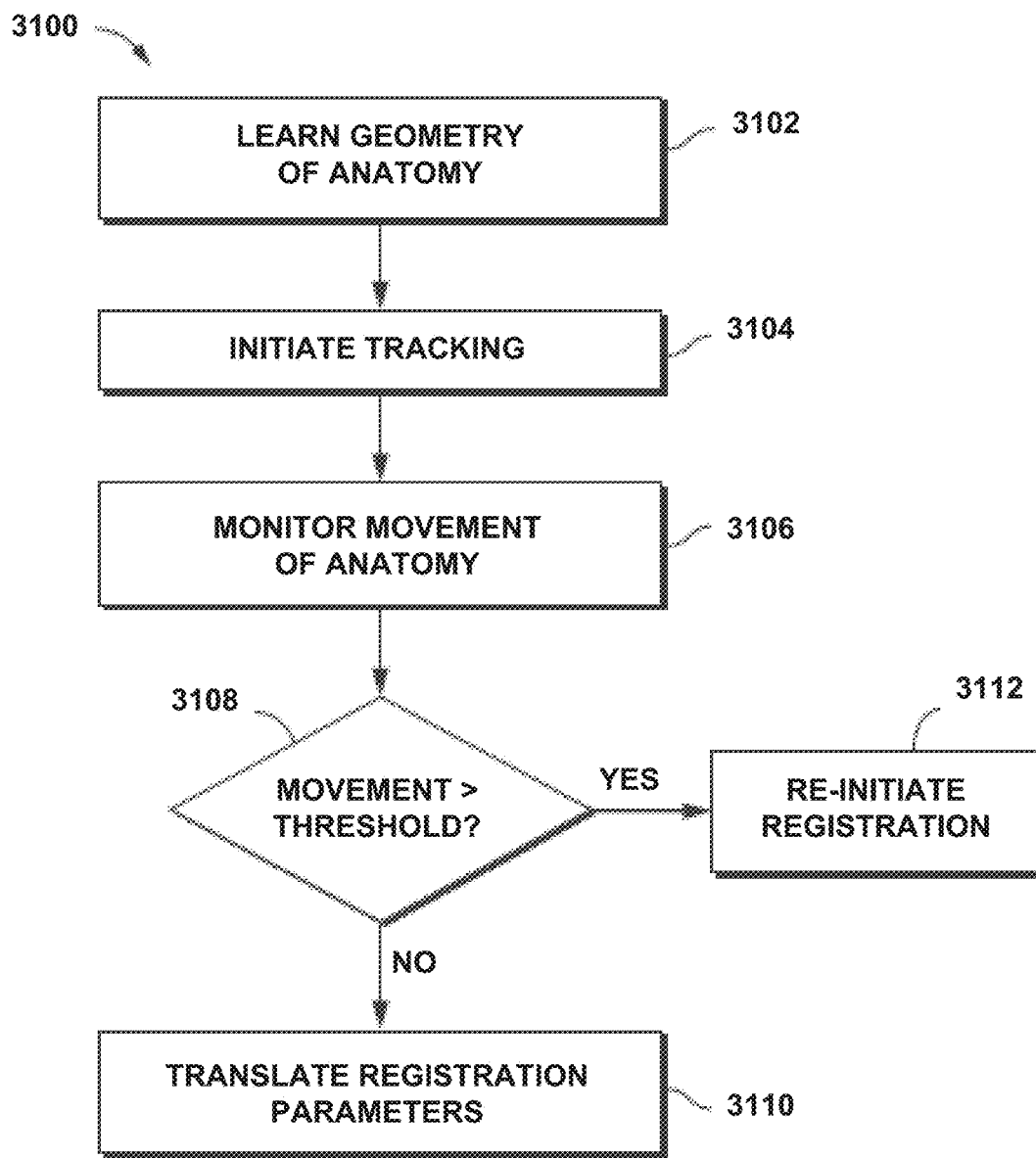
FIG. 31 is an example of a process flow for tracking in the augment surgery mode of the mixed reality (MR) system, according to an example of this disclosure.

FIG. 31 illustrates an example of a process flow 3100 for tracking in an augment surgery mode of MR system 212, according to an example of this disclosure. The process of FIG. 31 may be performed by visualization device 213 of MR system 212. At block 3102, a learning process is performed during which the tracking algorithm learns the geometry of the anatomy of interest based on a virtual bone model. In some examples, the learning is performed offline (i.e., before the surgery). At block 3104, tracking is initiated during the Augment Surgery Mode. At block 3106, movement of the anatomy of interest is continuously (or periodically) monitored. At block 3108, if detected movement exceeds a threshold amount, the user may be prompted to re-initiate the registration process of FIG. 20A or FIG. 20B (block 3112). As discussed above, in some examples, MR system 212 may automatically re-initiate and/or perform the registration process if detected movement exceeds the threshold amount. Otherwise, the amount of movement is used to translate the registration parameters, as needed (block 3110).

In some examples, marker and markerless tracking can both be implemented. For example, optical markers can be used as a back-up to the markerless tracking algorithm or as a verification of the tracking algorithm. Further, the choice of implementing marker and/or markerless tracking can be left to the discretion of the user or may depend on the particular surgical procedure and the specific anatomical features that are visible.

In some examples, to guide a surgeon in accordance with the surgical plan, surgical instruments or tools (marker (e.g., visible, infrared, etc.) or markerless (e.g., tool geometry)) can be tracked to ensure that instrument pose and orientation are correct using any of the same tracking techniques described above. To guide the surgeon's use of the surgical instruments, MR system 212 can display visible indicators or provide other perceptible indications (e.g., vibrations, audible beeps, etc.) that prompt the surgeon to move the instrument in certain directions. For example, MR system 212 can generate circles visible to the surgeon that, when concentric, indicate that the tool is aligned according to the surgical plan.

On occasion, during a surgery, the surgeon may determine that there is a need to modify the preoperative surgical plan. MR system 212 allows for intraoperative modifications to the surgical plan that then can be executed in the Augmented Surgery Mode. For instance, in some examples, the user can manipulate the user interface so that the user can view the virtual surgical plan intraoperatively, including at least the 3D virtual bone anatomy of interest. In such examples, the user can manipulate the user interface so that the user can modify the virtual surgical plan intraoperatively. As an example, selection of the Planning page on the workflow bar 1000 of the UI 522 shown in FIG. 10, which allows the surgeon to view and manipulate 3D virtual bone model 1008 of the patient's anatomy and the prosthetic implant components 1010. Using UI 522, the surgeon can rotate and translate the implant components 1010 and change their type and size if desired. If changes are made, the virtual surgical plan is automatically updated with the new parameters, which can then be connected with 3D virtual bone model 1008 when in the Augment Surgery mode. If registration has previously been completed with the prior version of the virtual surgical plan, the planning parameters can be updated. If the modifications to the virtual surgical plan require the surgeon to repeat the registration process, MR system 212 can prompt the surgeon to do so.

As discussed elsewhere in this disclosure, orthopedic surgical procedures may involve performing various work on a patient's anatomy. Some examples of work that may be performed include, but are not necessarily limited to, cutting, drilling, reaming, screwing, adhering, and impacting. In general, it may be desirable for a practitioner (e.g., surgeon, physician's assistant, nurse, etc.) to perform the work as accurately as possible. For instance, if a surgical plan for implanting a prosthetic in a particular patient specifies that a portion of the patient's anatomy is to be reamed at a particular diameter to a particular depth, it may desirable for the surgeon to ream the portion of the patient's anatomy to as close as possible to the particular diameter and to the particular depth (e.g., to increase the likelihood that the prosthetic will fit and function as planned and thereby promote a good health outcome for the patient).

Figure 32C:
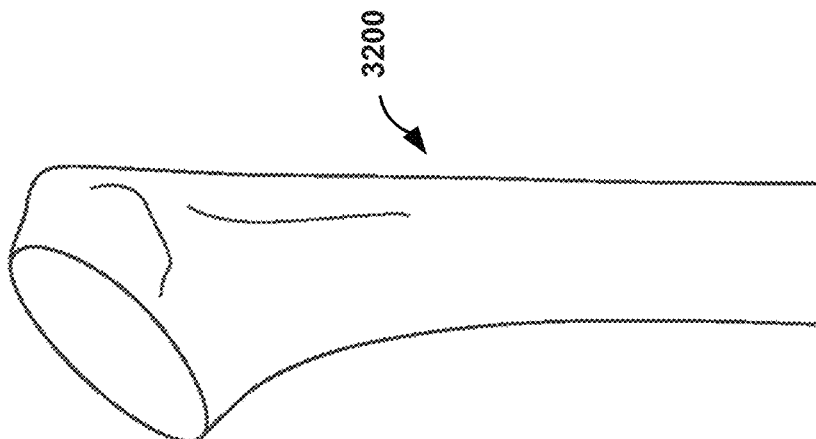
FIGS. 32A-32C illustrate steps a surgeon may perform to resect a humeral head of a humerus in a shoulder arthroplasty procedure.
Figure 32B:
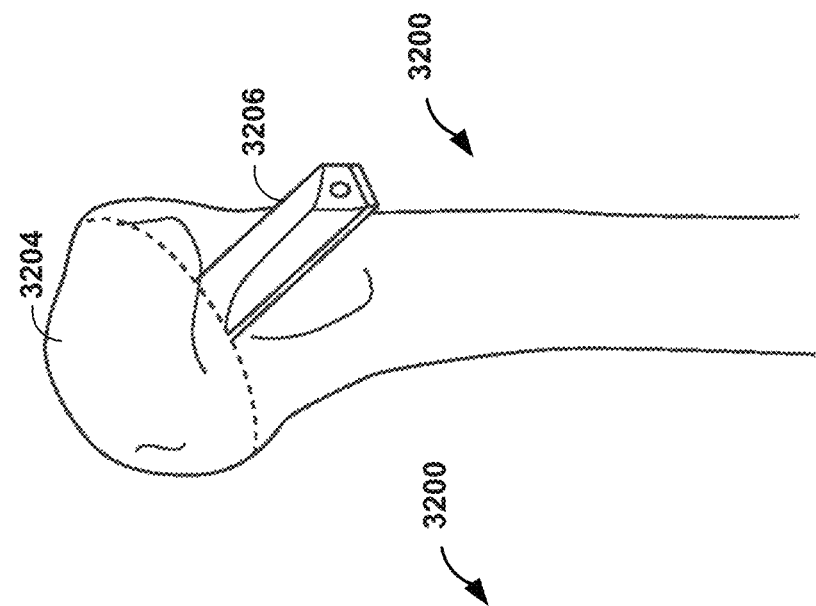
Figure 32A:
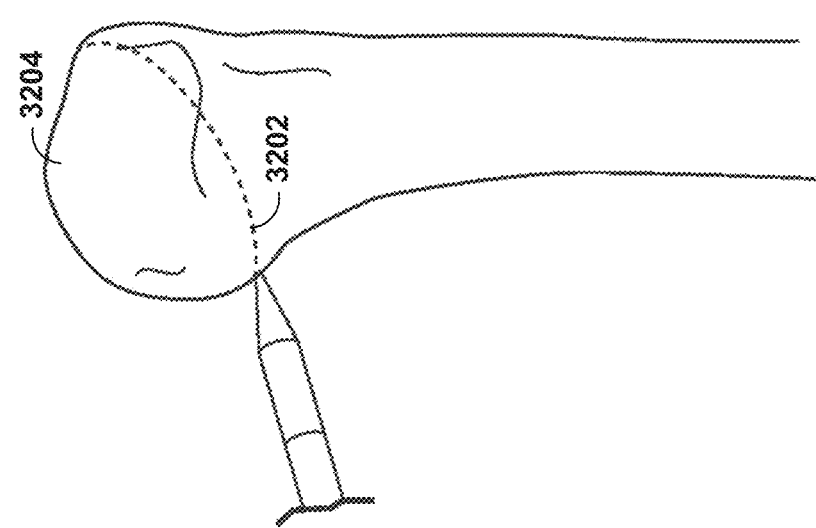

In some examples, a surgeon may perform one of more work operations by "free hand" (i.e., by applying or otherwise using a tool without mechanical or visual guides/aids for the tool). For instance, as shown in FIGS. 32A-32C, in the course of a shoulder arthroplasty procedure, a surgeon may perform a surgical step of resection of humeral head 3204 of humerus 3200 by visually estimating (e.g., "eyeballing") and marking anatomical neck 3202 of humerus 3200. The surgeon may then perform the resection of humeral head 3204 by guiding cutting tool 3206 (e.g., a blade of an oscillating saw) along the marked anatomical neck 3202 with the surgeon's free hand, i.e., without mechanical or visual guidance. However, performing surgical steps involving these types of work operations entirely by free hand may introduce unwanted error, possibly undermining the results of the orthopedic surgical procedure.

Figure 33:
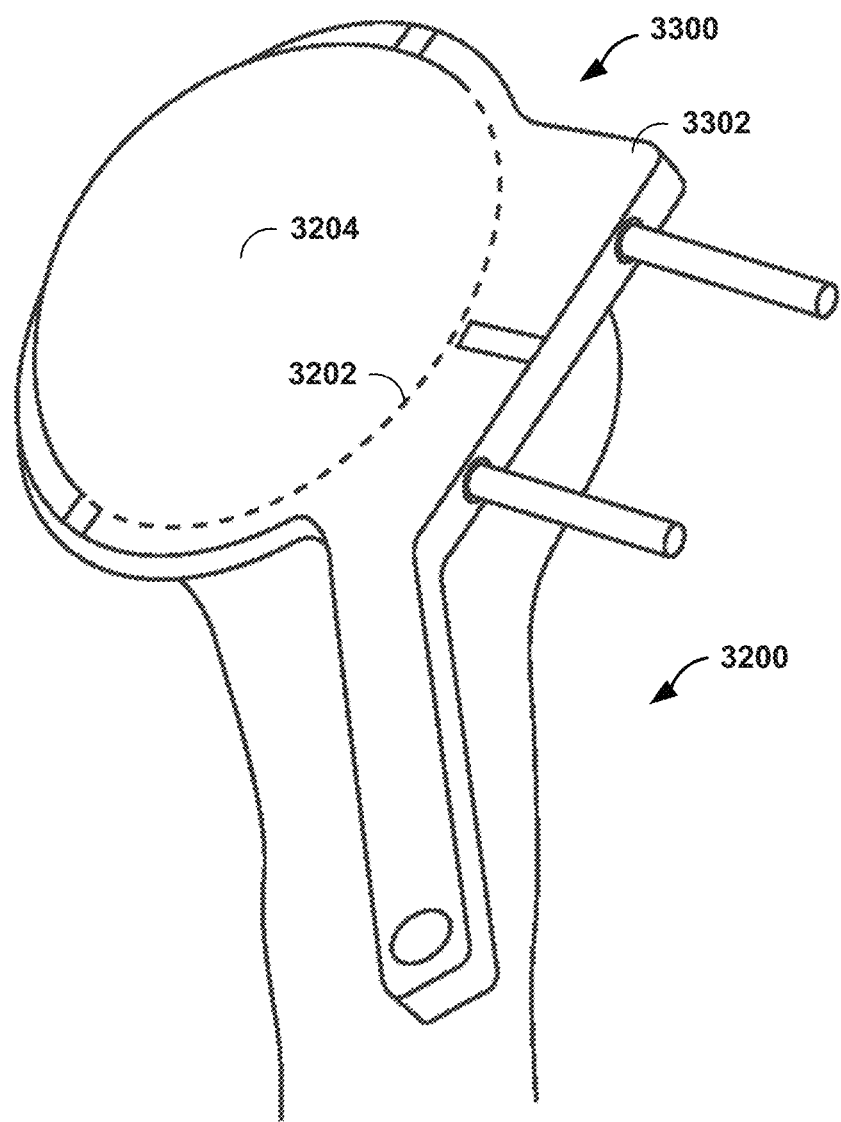
FIG. 33 illustrates a mechanical guide for resection of the humeral head in a shoulder arthroplasty procedure.

In some examples, in the course of an orthopedic surgical procedure, a surgeon may perform one of more work operations, which also may be referred to as surgical steps, with the assistance of a mechanical guide. For instance, as shown in FIG. 33, a surgeon may attach mechanical guide 3300 on humerus 3200 prior to performing a resection of humeral head 3204 (e.g., as part of performing the humerus cut process of step 1902 of FIG. 19). The surgeon may adjust one or more components of mechanical guide 3300 such that top surface 3302 of mechanical guide 3300 is co-planar with anatomic neck 3202 of humerus 3200 (for purposes of illustration, anatomic neck 3202 is illustrated as a broken line). After attaching mechanical guide 3300 to humeral head 3204 and adjusting the mechanical guide, the surgeon may perform the resection of humeral head 3204 by guiding a cutting tool (e.g., a blade of an oscillating saw) along top surface 3302. However, utilizing a mechanical guide may be undesirable. As one example, attachment and/or adjustment of a mechanical guide introduces additional time into a surgical procedure. As another example, the mechanical guide is an additional tool that may result in additional cost for the mechanical guide and/or additional time for sterilizing and tracking the mechanical guide (e.g., during the procedure and during the pre-closing inventory).

In accordance with one or more techniques of this disclosure, a visualization system, such as MR visualization system 212, may be configured to display virtual guidance including one or more virtual guides for performing work on a portion of a patient's anatomy. For instance, the visualization system may display a virtual cutting plane overlaid on an anatomic neck of the patient's humerus. In some examples, a user such as a surgeon may view real-world objects in a real-world scene. The real-world scene may be in a real-world environment such as a surgical operating room. In this disclosure, the terms real and real-world may be used in a similar manner. The real-world objects viewed by the user in the real-world scene may include the patient's actual, real anatomy, such as an actual glenoid or humerus, exposed during surgery. The user may view the real-world objects via a see-through (e.g., transparent) screen, such as see-through holographic lenses, of a head-mounted MR visualization device, such as visualization device 213, and also see virtual guidance such as virtual MR objects that appear to be projected on the screen or within the real-world scene, such that the MR guidance object(s) appear to be part of the real-world scene, e.g., with the virtual objects appearing to the user to be integrated with the actual, real-world scene. For example, the virtual cutting plane/line may be projected on the screen of a MR visualization device, such as visualization device 213, such that the cutting plane is overlaid on, and appears to be placed within, an actual, observed view of the patient's actual humerus viewed by the surgeon through the transparent screen, e.g., through see-through holographic lenses. Hence, in this example, the virtual cutting plane/line may be a virtual 3D object that appears to be part of the real-world environment, along with actual, real-world objects.

A screen through which the surgeon views the actual, real anatomy and also observes the virtual objects, such as virtual anatomy and/or virtual surgical guidance, may include one or more see-through holographic lenses. The holographic lenses, sometimes referred to as "waveguides," may permit the user to view real-world objects through the lenses and display projected holographic objects for viewing by the user. As discussed above, an example of a suitable head-mounted MR device for visualization device 213 is the Microsoft HOLOLENS™ headset, available from Microsoft Corporation, of Redmond, Wash., USA. The HOLOLENS™ headset includes see-through, holographic lenses, also referred to as waveguides, in which projected images are presented to a user. The HOLOLENS™ headset also includes an internal computer, cameras and sensors, and a projection system to project the holographic content via the holographic lenses for viewing by the user. In general, the Microsoft HOLOLENS™ headset or a similar MR visualization device may include, as mentioned above, LCoS display devices that project images into holographic lenses, also referred to as waveguides, e.g., via optical components that couple light from the display devices to optical waveguides. The waveguides may permit a user to view a real-world scene through the waveguides while also viewing a 3D virtual image presented to the user via the waveguides. In some examples, the waveguides may be diffraction waveguides.

The presentation virtual guidance such as of a virtual cutting plane may enable a surgeon to accurately resect the humeral head without the need for a mechanical guide, e.g., by guiding a saw along the virtual cutting plane displayed via the visualization system while the surgeon views the actual humeral head. In this way, a visualization system, such as MR system 212 with visualization device 213, may enable surgeons to perform accurate work (e.g., with the accuracy of mechanical guides but without the disadvantages of using mechanical guides). This "guideless" surgery may, in some examples, provide reduced cost and complexity.

The visualization system (e.g., MR system 212/visualization device 213) may be configured to display different types of virtual guides. Examples of virtual guides include, but are not limited to, a virtual point, a virtual axis, a virtual angle, a virtual path, a virtual plane, and a virtual surface or contour. As discussed above, the visualization system (e.g., MR system 212/visualization device 213) may enable a user to directly view the patient's anatomy via a lens by which the virtual guides are displayed, e.g., projected. The virtual guides may guide or assist various aspects of the surgery. For instance, a virtual guide may guide at least one of preparation of anatomy for attachment of the prosthetic or attachment of the prosthetic to the anatomy.

The visualization system may obtain parameters for the virtual guides from a virtual surgical plan, such as the virtual surgical plan described herein. Example parameters for the virtual guides include, but are not necessarily limited to: guide location, guide orientation, guide type, guide color, etc.

The visualization system may display a virtual guide in a manner in which the virtual guide appears to be overlaid on an actual, real anatomical object of the patient, within a real-world environment, e.g., by displaying the virtual guide(s) with actual, real-world patient anatomy (e.g., at least a portion of the patient's anatomy) viewed by the user through holographic lenses. For example, the virtual guides may be 3D virtual objects that appear to reside within the real-world environment with the actual, real anatomical object.

The techniques of this disclosure are described below with respect to a shoulder arthroplasty surgical procedure. Examples of shoulder arthroplasties include, but are not limited to, reversed arthroplasty, augmented reverse arthroplasty, standard total shoulder arthroplasty, augmented total shoulder arthroplasty, and hemiarthroplasty. However, the techniques are not so limited, and the visualization system may be used to provide virtual guidance information, including virtual guides in any type of surgical procedure. Other example procedures in which a visualization system, such as MR system 212, may be used to provide virtual guides include, but are not limited to, other types of orthopedic surgeries; any type of procedure with the suffix "plasty," "stomy," "ectomy," "clasia," or "centesis,"; orthopedic surgeries for other joints, such as elbow, wrist, finger, hip, knee, ankle or toe, or any other orthopedic surgical procedure in which precision guidance is desirable.

A typical shoulder arthroplasty includes various work on a patient's scapula and performing various work on the patient's humerus. The work on the scapula may generally be described as preparing the scapula (e.g., the glenoid cavity of the scapula) for attachment of a prosthesis and attaching the prosthesis to the prepared scapula. Similarly, the work on the humerus may generally be described as preparing the humerus for attachment of a prosthesis and attaching the prosthesis to the prepared humerus. As described herein, the visualization system may provide guidance for any or all work performed in such an arthroplasty procedure.

As discussed above, a MR system (e.g., MR system 212, MR system 1800A of FIG. 18, etc.) may receive a virtual surgical plan for attaching a prosthetic to a patient and/or preparing bones, soft tissue or other anatomy of the patient to receive the prosthetic. The virtual surgical plan may specify various work to be performed and various parameters for the work to be performed. As one example, the virtual surgical plan may specify a location on the patient's glenoid for performing reaming and a depth for the reaming. As another example, the virtual surgical plan may specify a surface for resecting the patient's humeral head. As another example, the virtual surgical plan may specify locations and/or orientations of one or more anchorage locations (e.g., screws, stems, pegs, keels, etc.).

Figure 50:
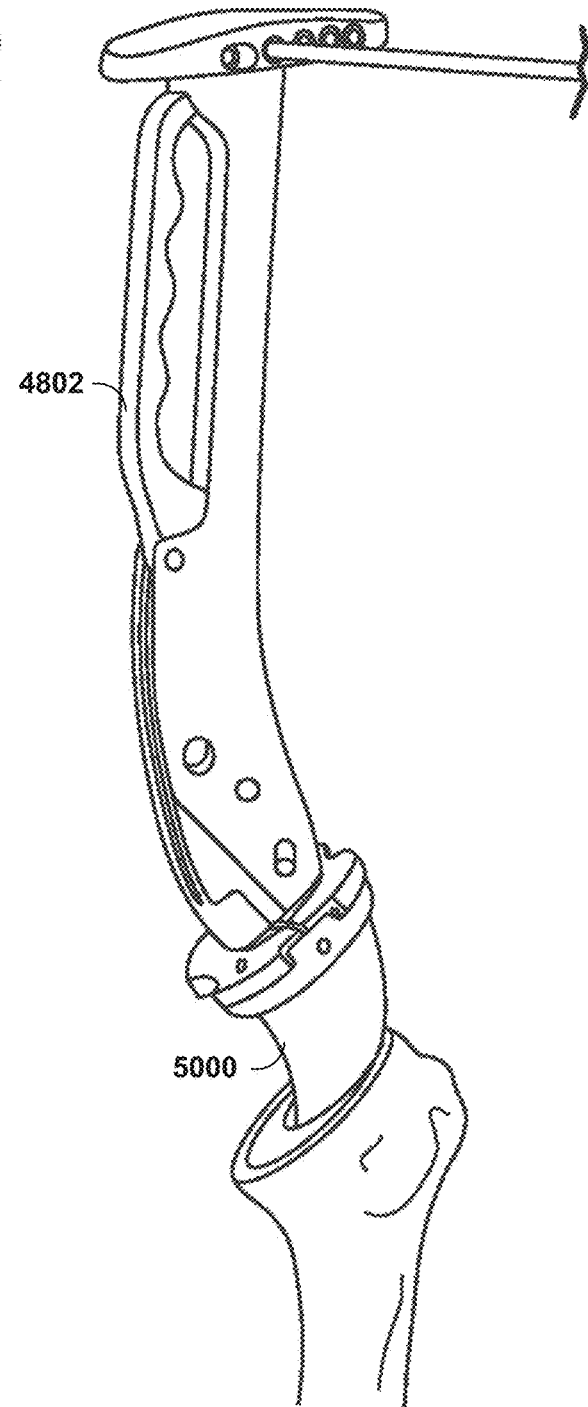
FIG. 50 is a conceptual diagram illustrating an MR system providing virtual guidance for attaching an implant to a humerus in a shoulder arthroplasty procedure, in accordance with one or more techniques of this disclosure.

In some examples, MR system 212 may provide virtual guidance to assist a surgeon in performing work on a patient's humerus. As shown in FIGS. 34-41, MR system 212 may provide virtual guidance to assist a surgeon in preparing and removing a bone graft from a head of the patient's humerus. As shown in FIGS. 42A-49, MR system 212 may provide virtual guidance to assist a surgeon in humeral preparation, such as cutting to remove all or a portion of the humeral head. FIG. 50 is a conceptual diagram illustrating MR system 212 providing virtual guidance for attaching an implant to a humerus, in accordance with one or more techniques of this disclosure. A tool may be used to attach the implant to humerus 3200. For instance, the surgeon may utilize handle 4802 to insert prosthesis 5000 into the prepared humerus 3200. In some examples, one or more adhesives (e.g., glue, cement, etc.) may be applied to prosthesis 5000 and/or humerus 3200 prior to insertion. As shown in FIG. 50, MR system 212 may provide virtual guidance to assist a surgeon in humeral implant positioning, such as preparation of the humerus to receive an implant and positioning of the implant within the humerus.

Figure 63:
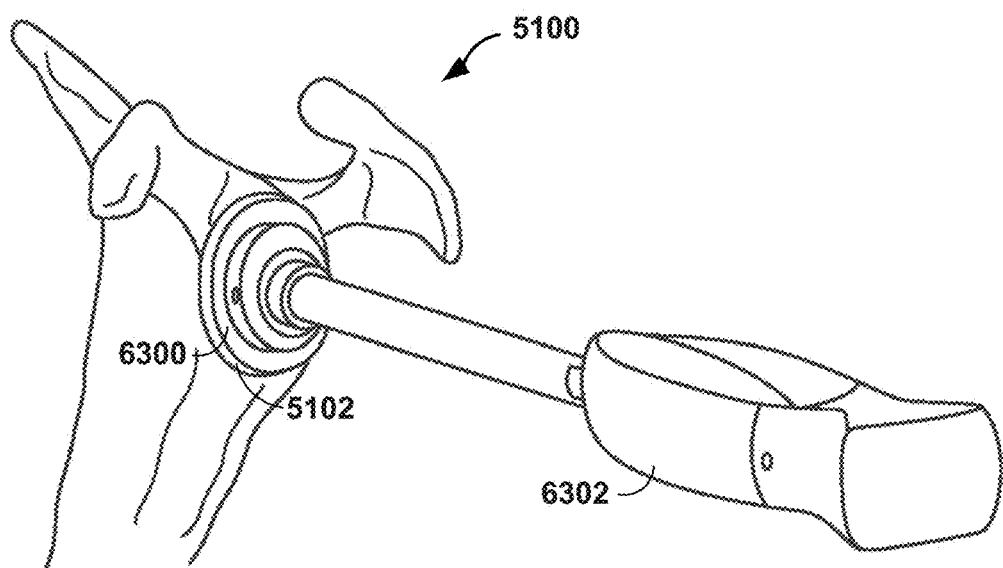
FIG. 63 is a conceptual diagram illustrating an MR system providing virtual guidance for attaching an implant to a glenoid in a shoulder arthroplasty procedure, in accordance with one or more techniques of this disclosure.
Figure 64:
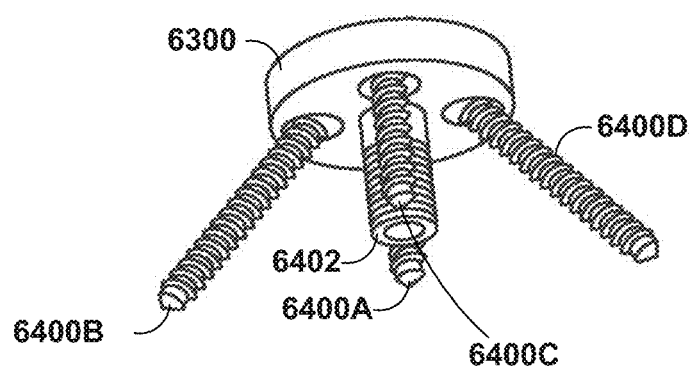
FIGS. 64 and 65 illustrate screws and a central stem that may be used to attach a prosthesis to a glenoid in a shoulder arthroplasty procedure.
Figure 65:
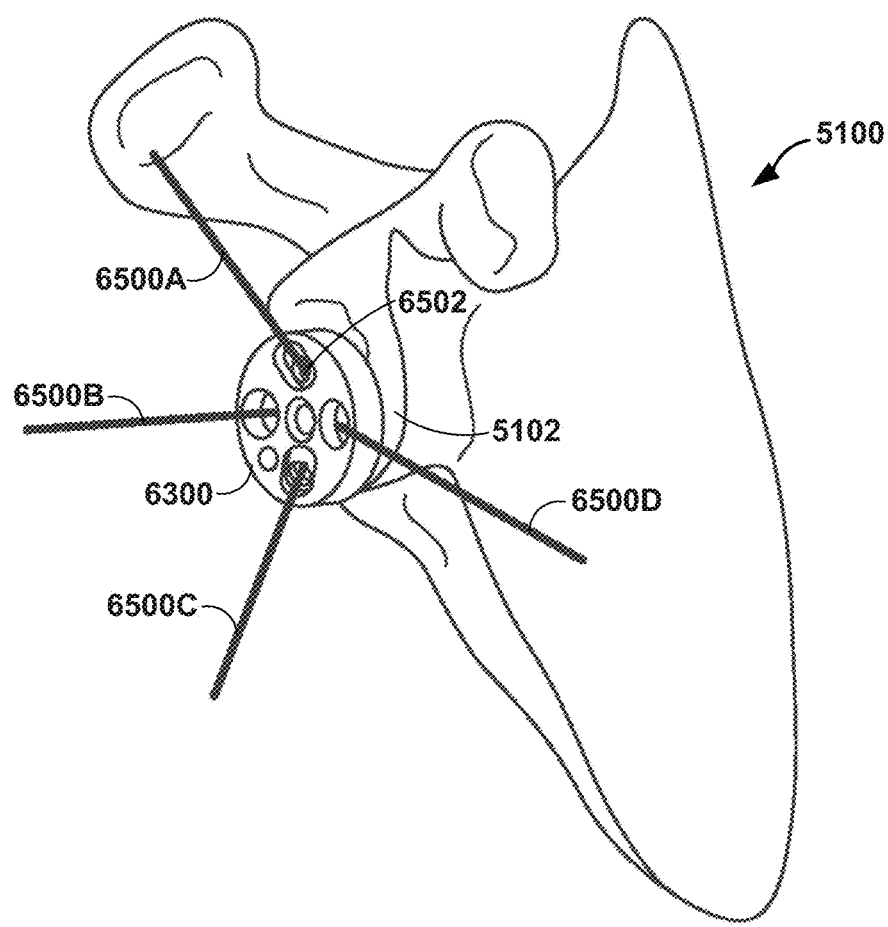

In some examples, MR system 212 may provide virtual guidance to assist a surgeon in performing work on a patient's scapula. As shown in FIGS. 51-62, the MR system may provide virtual guidance to assist a surgeon in scapula preparation (e.g., as part of performing the reaming axis drilling process of step 1906 of FIG. 19, as part of performing the reaming axis guide pin insertion process of step 1908 of FIG. 19, and/or as part of performing the glenoid remaining process of step 1910 of FIG. 19). As shown in FIGS. 63-65, the MR system may provide virtual guidance to assist a surgeon in scapula implant positioning (e.g., as part of performing the glenoid implant installation process of step 1912 of FIG. 19).

Many different techniques may be used to prepare a humerus for prosthesis attachment and to perform actual prosthesis attachment. Regardless of the technique used, MR system 212 may provide virtual guidance to assist in one or both of the preparation and attachment. As such, while the following techniques are examples in which MR system 212 provides virtual guidance, MR system 212 may provide virtual guidance for other techniques.

In an example technique, the work steps include resection of a humeral head, creating a pilot hole, sounding, punching, compacting, surface preparation, with respect to the humerus, and attaching an implant to the humerus. Additionally, in some techniques, the work steps may include bone graft work steps, such as installation of a guide in a humeral head, reaming of the graft, drilling the graft, cutting the graft, and removing the graft, e.g., for placement with an implant for augmentation of the implant relative to a bone surface such as the glenoid.

A surgeon may perform one or more steps to expose a patient's humerus. For instance, the surgeon may make one or more incisions to expose the upper portion of the humerus including the humeral head. The surgeon may position one or more retractors to maintain the exposure. In some examples, MR system 212 may provide guidance to assist in the exposure of the humerus, e.g., by making incisions, and/or placement of retractors.

Figure 34:
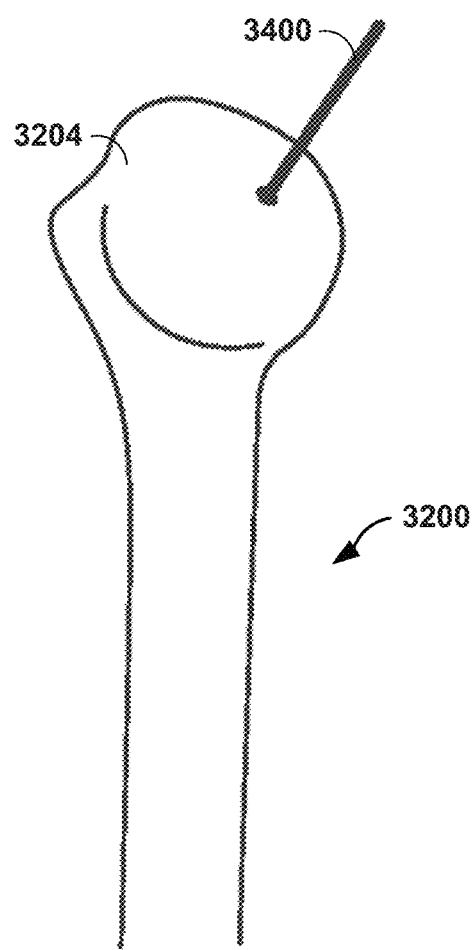
FIGS. 34 and 35 are conceptual diagrams illustrating an MR system providing virtual guidance for installation of a mechanical guide in a humeral head in a shoulder arthroplasty procedure, in accordance with one or more techniques of this disclosure.
Figure 35:
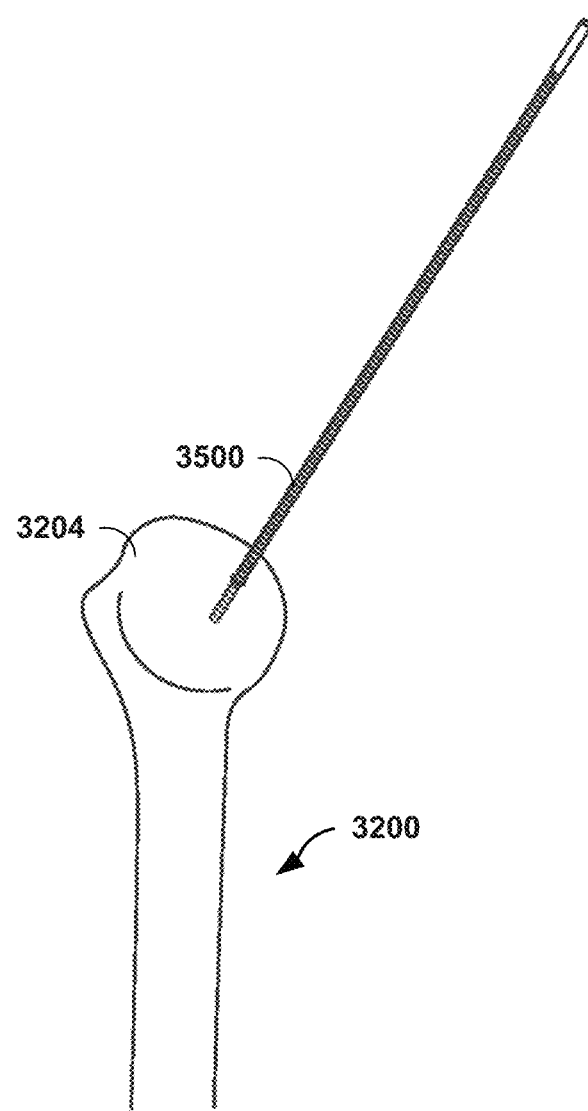

FIGS. 34 and 35 are conceptual diagrams illustrating an MR system providing virtual guidance for installation of a mechanical guide in a humeral head, in accordance with one or more techniques of this disclosure. It is noted that, for purposes of illustration, the surrounding tissue and some bone is omitted from FIGS. 34 and 35, and other figures. As shown in FIG. 34, MR system 212 may display virtual axis 3400 on humeral head 3204 of humerus 3200. FIG. 34 and subsequent figures illustrate what the surgeon, or other user, would see when viewing via visualization device 213. In particular, when viewing via visualization device 213, the surgeon would see a portion of humerus 3200 and virtual axis 3400 (and/or other virtual guidance) overlaid on the portion of humerus 3200.

To display virtual axis 3400, MR system 212 may determine a location on a virtual model of humerus 3200 at which a guide is to be installed. MR system 212 may obtain the location from a virtual surgical plan (e.g., the virtual surgical plan described above as generated by virtual planning system 202). The location obtained by MR system 212 may specify one or both of coordinates of a point on the virtual model and a vector. The point may be the position at which the guide is to be installed and the vector may indicate the angle/slope at which the guide is to be installed. As such, MR system 212 may display a virtual drilling axis having parameters obtained from the virtual surgical plan, the virtual drilling axis configured to guide drilling of one or more holes in the glenoid (e.g., for attachment of a guide pin to the scapula).

As discussed above, the virtual model of humerus 3200 may be registered with humerus 3200 such that coordinates on the virtual model approximately correspond to coordinates on humerus 3200. As such, by displaying virtual axis 3400 at the determined location on the virtual model, MR system 212 may display virtual axis 3400 at the planned position on humerus 3200.

The surgeon may attach a physical guide using the displayed virtual guidance. For instance, where the guide is a guide pin with a self-tapping threaded distal tip, the surgeon may align the guide pin with the displayed virtual axis 3400 and utilize a drill or other instrument to install the guide pin. In some examples, MR system 212 may display depth guidance information to enable the surgeon to install the guide pin to a planned depth. Examples of depth guidance information are discussed in further detail herein with reference to FIGS. 66-68.

FIG. 35 is a conceptual diagram illustrating guide 3500 as installed in humeral head 3204. Guide 3500 may take the form of an elongated pin to be mounted in a hole formed in the humeral head. As shown in FIGS. 34 and 35, by displaying virtual axis 3400, a surgeon may install guide 3500 at the planned position on humeral head 3204. In this way, MR system 212 may enable the installation of a guide without the need for an additional mechanical guide.

As discussed above, MR system 212 may provide virtual guidance, such as virtual markers, to assist the surgeon in the installation of the guide pin. For instance, in the example of FIG. 34, MR system 212 may display virtual axis 3400 to assist the surgeon in the installation of the guide pin. Other examples of virtual markers that MR system 212 may display include, but are not limited to axes, points, circles, rings, polygons, X shapes, crosses, or any other shape or combination of shapes. MR system 212 may display the virtual markers as static or with various animations or other effects.

Figure 36A:
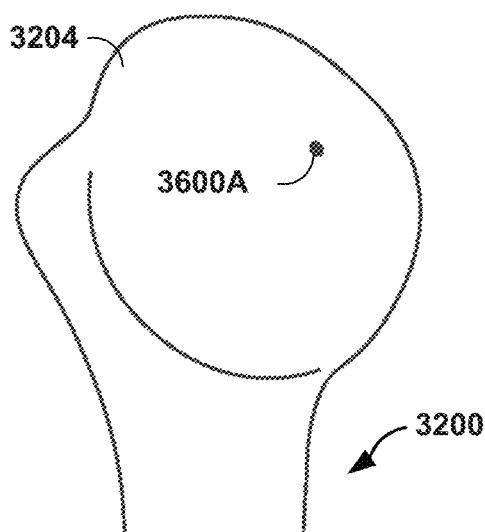
FIGS. 36A-36D illustrate examples of virtual markers that an MR system may display.
Figure 36B:
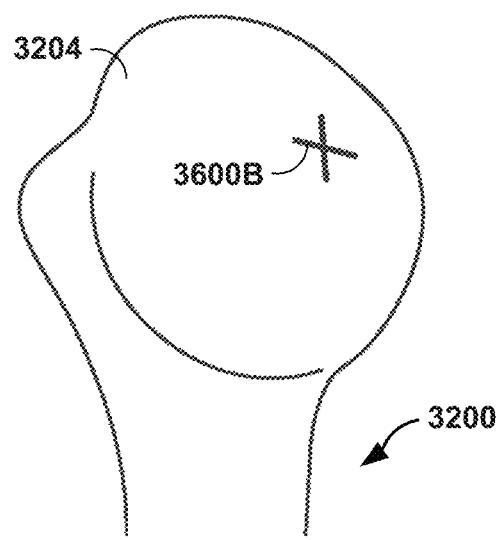
Figure 36C:
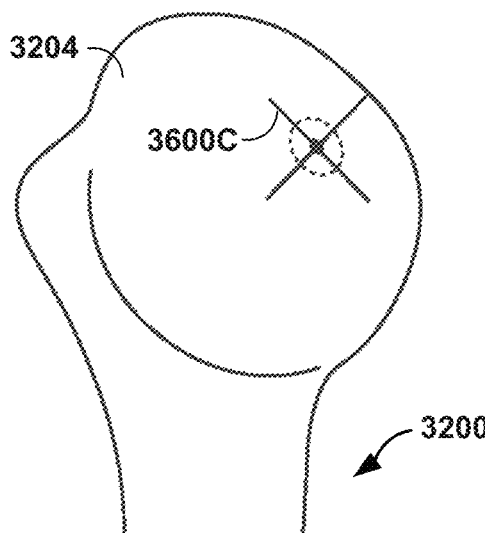
Figure 36D:
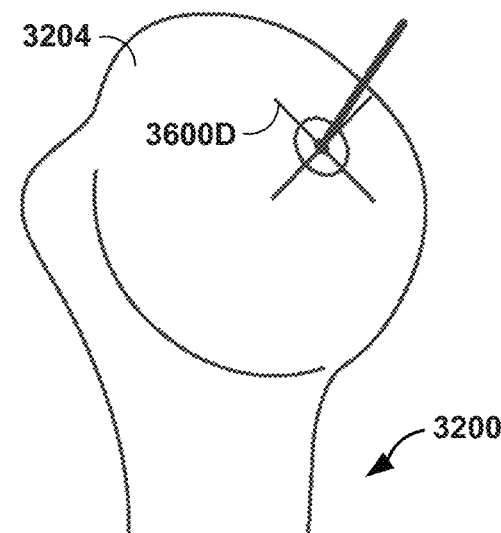

FIGS. 36A-36D illustrate examples of virtual markers that MR system 212 may display. FIG. 36A illustrates an example in which MR system 212 displays virtual marker 3600A as a point. FIG. 36B illustrates an example in which MR system 212 displays virtual marker 3600B as a cross/X shape. FIG. 36C illustrates an example in which MR system 212 displays virtual marker 3600C as a reticle. FIG. 36D illustrates an example in which MR system 212 displays virtual marker 3600D as combination of a reticle and an axis.

As discussed above, in some examples, MR system 212 may display the virtual markers with various animations or other effects. As one example, MR system 212 may display a virtual marker as a reticle having a rotating ring. As another example, MR system 212 may display a virtual marker as a flashing cross/X shape.

MR system 212 may display the virtual markers with particular colors. For instance, in some examples, MR system 212 may preferably display the virtual markers in a color other than red, such as green, blue, yellow, etc. Displaying the virtual markers in a color or colors other than red may provide one or more benefits. For instance, as blood appears red and blood may be present on or around the anatomy of interest, a red colored virtual marker may not be visible.

The use of the various types of virtual markers described above is not limited to installation of the guide pin. For instance, MR system 212 may display any of the virtual markers described above to assist the surgeon in performing any work. As one example, MR system 212 may display any of the virtual markers described above to assist the surgeon in performing any work on humerus 3200. As another example, MR system 212 may display any of the virtual markers described above to assist the surgeon in performing any work on scapula 5100.

Figure 37:
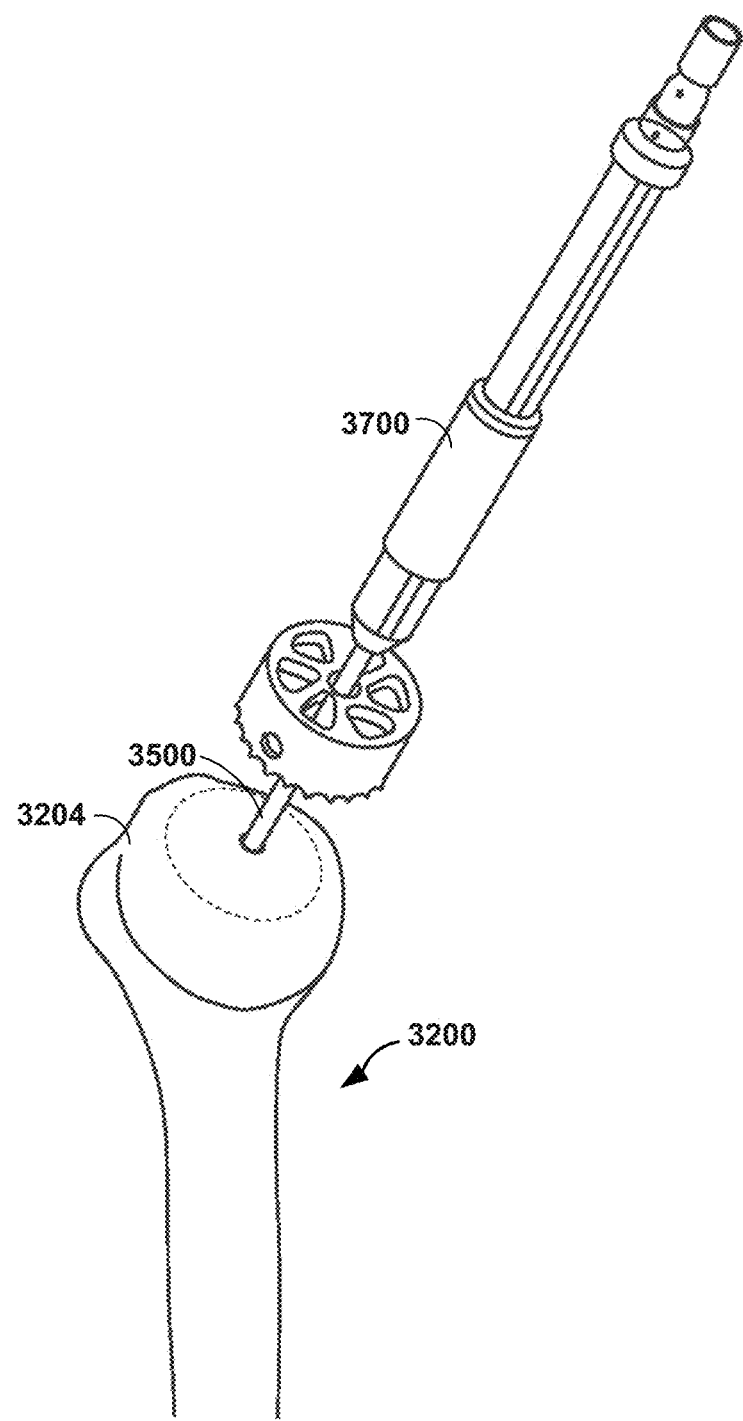
FIGS. 37 and 38 are conceptual diagrams illustrating an MR system providing virtual guidance for reaming of a graft in a humeral head in a shoulder arthroplasty procedure, in accordance with one or more techniques of this disclosure.
Figure 38:
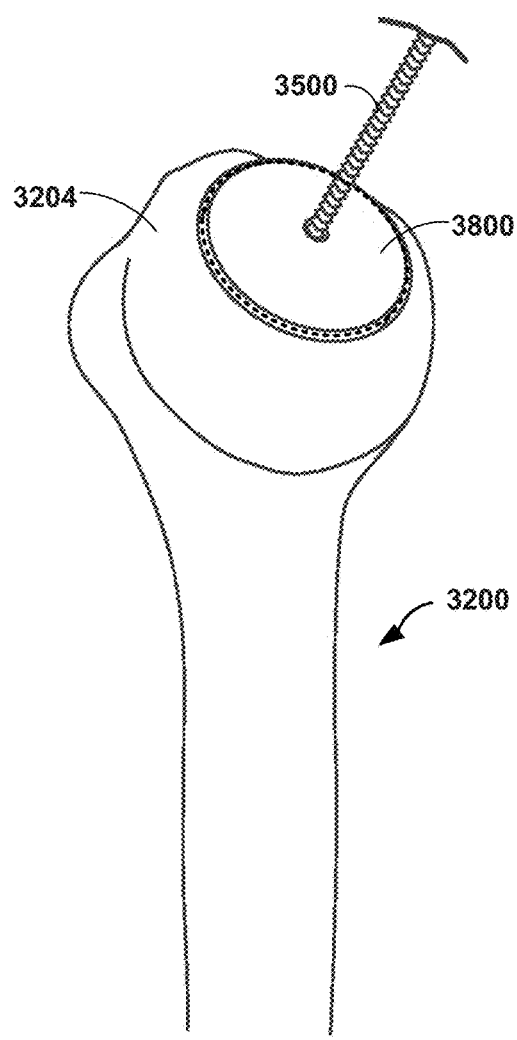

FIGS. 37 and 38 are conceptual diagrams illustrating an MR system providing virtual guidance for reaming of a graft in a humeral head, in accordance with one or more techniques of this disclosure. As shown in FIGS. 37 and 38, graft reaming tool 3700 may be used to ream the surface of humeral head 3204 and cut outline 3800 (shown in FIG. 38).

The surgeon may connect graft reaming tool 3700 to a drill or other instrument and MR system 212 may display virtual guidance to assist in reaming the surface of humeral head 3204 and cutting outline 3800. For instance, MR system 212 may display depth guidance to enable the surgeon to ream the surface of humeral head 3204 and cut outline 3800 to a target depth (e.g., depth guidance similar to the depth guidance discussed below with reference to FIGS. 66-68). As another example, MR system 212 may provide targeting guidance. For instance, MR system 212 may display one or both of a virtual marker that identifies a center point or prescribed axis of the reaming (e.g., as discussed above with reference to FIGS. 36A-36D) and/or an indication of whether graft reaming tool 3700 is aligned with the prescribed axis. As shown in FIG. 38, the surgeon may remove graft reaming tool 3700 from guide 3500 after performing the reaming.

In this example, graft reaming tool 3700 may be a cannulated reaming tool configured to be positioned and/or guided by a guide pin, such as guide 3500. In other examples, graft reaming tool 3700 may not be cannulated and may be guided without the assistance of a physical guide pin. For instance, MR system 212 may provide virtual guidance (e.g., depth guidance and/or targeting guidance such as a displayed virtual marker) to enable a surgeon to ream a graft from humeral head 3204 without the use of guide 3500. As such, MR system 212 may display a virtual reaming axis having parameters (e.g., position, size, and/or orientation relative to the virtual model of the scapula) obtained from the virtual surgical plan. The displayed virtual reaming axis may be configured to guide reaming of the humeral head and/or a graft from the humeral head.

Figure 40:
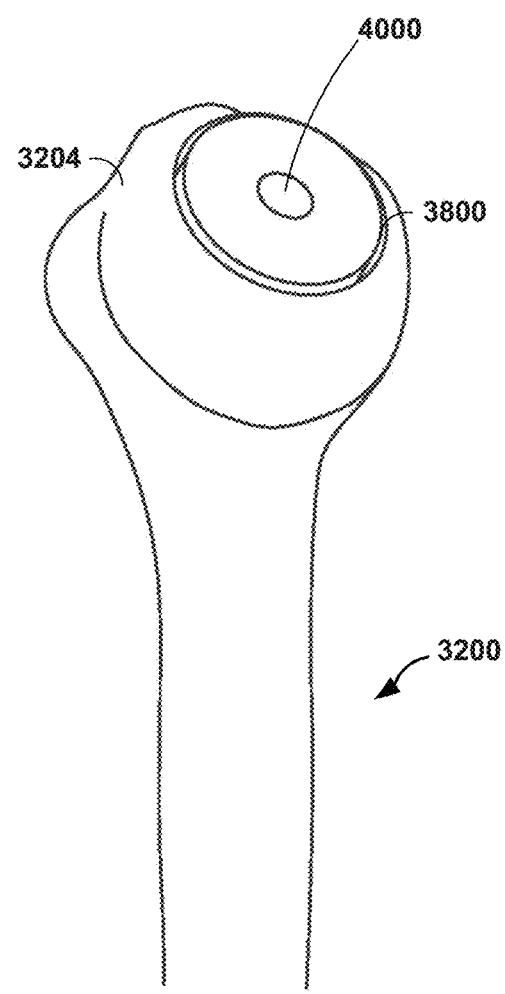
FIGS. 39 and 40 are conceptual diagrams illustrating an MR system providing virtual guidance for drilling a graft in a humeral head in a shoulder arthroplasty procedure, in accordance with one or more techniques of this disclosure.
Figure 39:
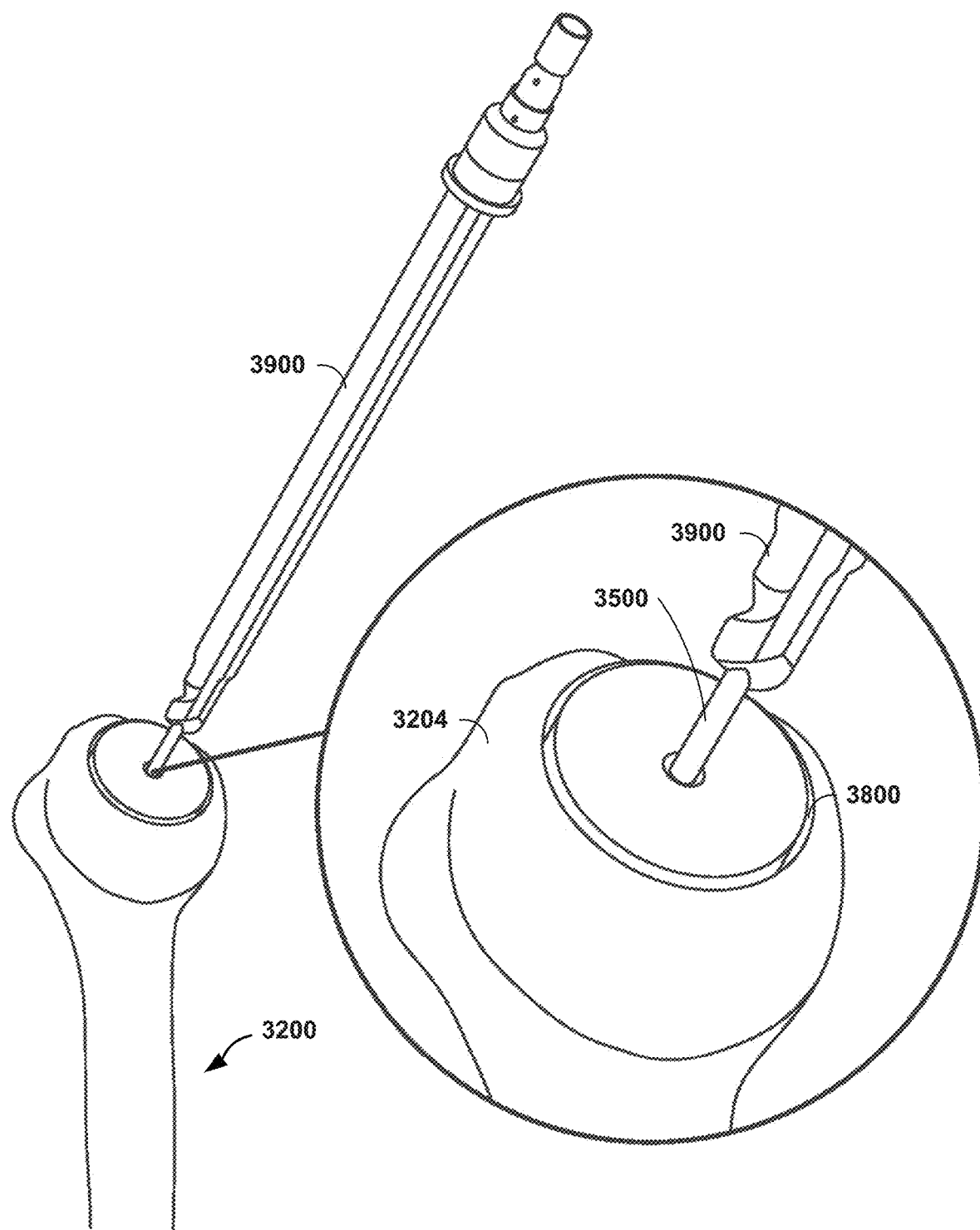

FIGS. 39 and 40 are conceptual diagrams illustrating an MR system, such as MR system 212, providing virtual guidance for drilling a graft in a humeral head, in accordance with one or more techniques of this disclosure. As shown in FIGS. 39 and 40, drill bit 3900 may be used to drill central hole 4000 in humeral head 3204.

The surgeon may connect drill bit 3900 to a drill or other instrument and MR system 212 may display virtual guidance to assist in the creation of central hole 4000. For instance, MR system 212 may display depth guidance to enable the surgeon to drill central hole 4000 to a target depth (e.g., depth guidance similar to the depth guidance discussed below with reference to FIGS. 66-68). As another example, MR system 212 may provide targeting guidance. For instance, MR system 212 may display one or both of a virtual marker that identifies a center point or prescribed axis of the drilling (e.g., as discussed above with reference to FIGS. 36A-36D) and/or an indication of whether drill bit 3900 is on a prescribed axis.

In this example, drill bit 3900 may be a cannulated reaming tool configured to be positioned and/or guided by a guide pin, such as guide 3500. In other examples, drill bit 3900 may not be cannulated and may be guided without the assistant of a physical guide pin. For instance, MR system 212 may provide virtual guidance (e.g., depth guidance and/or targeting guidance such as a virtual marker) to enable a surgeon to drill central hole 4000 without the use of guide 3500.

Figure 41:
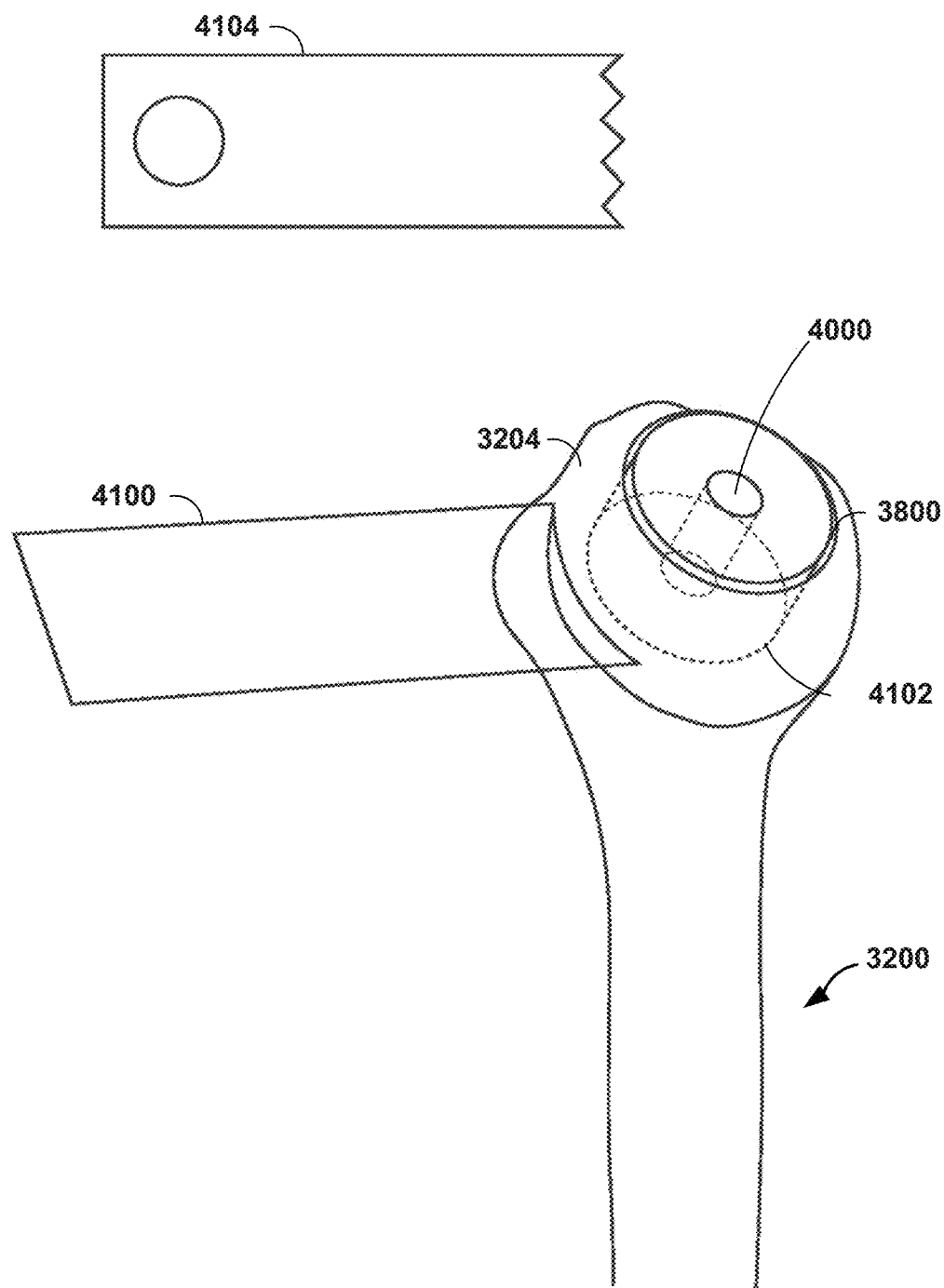
FIG. 41 is a conceptual diagram illustrating an MR system providing virtual guidance for cutting of a graft in a humeral head in a shoulder arthroplasty procedure, in accordance with one or more techniques of this disclosure.

FIG. 41 is a conceptual diagram illustrating an MR system providing virtual guidance for cutting of a graft in a humeral head, in accordance with one or more techniques of this disclosure. As shown in FIG. 41, the reaming and drilling work steps discussed above may result in graft 4102 having a toroid shape with the bottom surface still attached to humerus 3200. The surgeon may use a tool, such as oscillating saw 4104, to cut graft 4102 from humerus 3200.

MR system 212 may display virtual guidance to assist in the cutting process. As one example, MR system 212 may provide targeting guidance. For instance, MR system 212 may display a virtual marker such as virtual cutting surface 4100 (e.g., a virtual cutting plane or any of the virtual markers discussed above with reference to FIGS. 36A-36D) that indicates where the surgeon should cut using the tool and/or an indication of whether the tool (e.g., oscillating saw 4104) is aligned with the virtual cutting surface. MR system 212 may obtain the position and orientation of the virtual cutting plane from the virtual surgical plan. As such, MR system 212 may display a virtual cutting plane having parameters (e.g., position, size, and/or orientation relative to the virtual model of the humeral head) obtained from a virtual surgical plan that guides cutting of a graft from a humeral head. As shown in FIG. 41, MR system 212 may display virtual cutting surface 4100 on a plane parallel to, or the same as, the bottom of graft 4102. As another example, MR system 212 may display a virtual model of graft 4102. For instance, MR system 212 may display an outline of graft 4102. As another example, MR system 212 may provide depth guidance (e.g., depth guidance similar to the depth guidance discussed below with reference to FIGS. 66-68). For instance, MR system 212 may display depth guidance to enable the surgeon to cut to a target depth.

The surgeon may utilize the graft for any purpose. For instance, the surgeon may utilize the graft to fill empty space between a prosthesis an a glenoid of the patient and/or provide/increase an offset when attaching a prosthesis to a glenoid of the patient.

In order to prepare the humerus for implantation of the prosthesis, the surgeon may resect, cut, or otherwise remove the humeral head. Several MR assisted techniques for humeral head resection are contemplated, including techniques involving cutting the humeral head with removal of a graft and cutting the humeral head without removal of a graft. In a first example technique, MR system 212 may display a virtual cutting surface, such as a virtual cutting plane, that guides the surgeon in resecting the humeral head, e.g., without taking a graft. In this case, there may be no need for a mechanical guide, making the procedure less complex and possibly less costly, while still maintaining accuracy. Further details of the first example technique are discussed below with reference to FIGS. 42A-42C. In a second example technique, MR system 212 may display a virtual axis that guides the surgeon in installing a physical guide, i.e., mechanical guide, on the humerus, which then guides the surgeon in resecting the humeral head. Further details of the second example technique are discussed below with reference to FIG. 43.

Figure 42C:
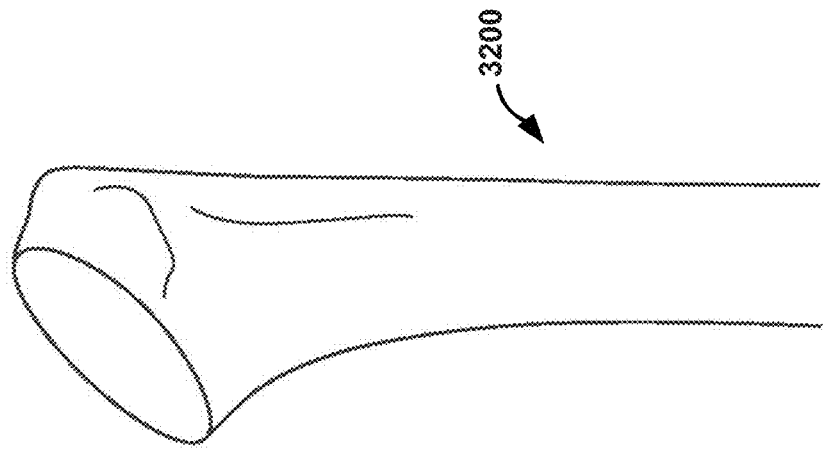
FIGS. 42A-42C are conceptual diagrams illustrating an MR system providing virtual guidance for resection of a humeral head in a shoulder arthroplasty procedure, in accordance with one or more techniques of this disclosure.
Figure 42B:
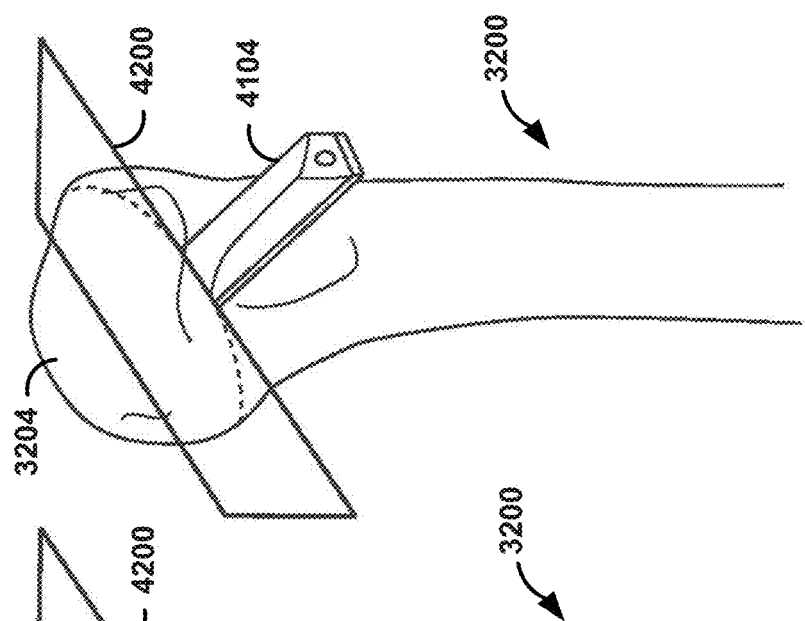
Figure 42A:
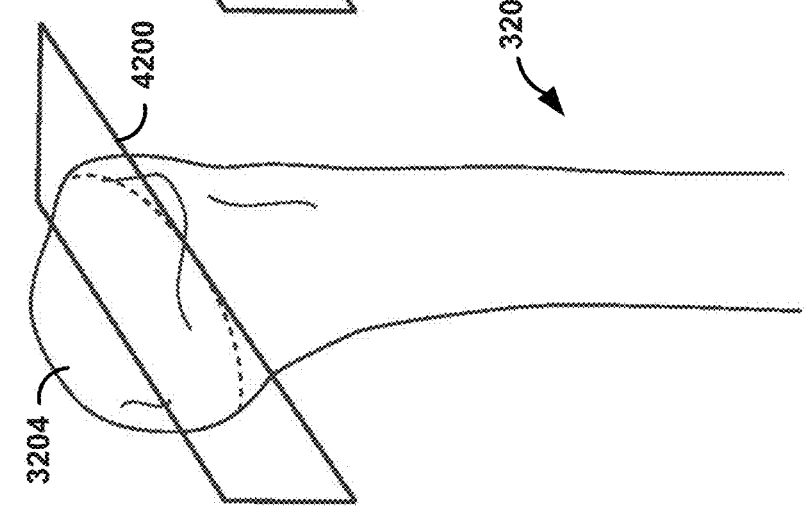

FIGS. 42A-42C are conceptual diagrams illustrating an MR system providing virtual guidance for resection of a humeral head, in accordance with one or more techniques of this disclosure. As shown in FIGS. 42A and 42B, MR system 212 may display virtual cutting plane 4200 at a planned position on humerus 3200. To display virtual cutting plane 4200, MR system 212 may determine a location on a virtual model of humerus 3200 at which humeral head 3204 is to be resected. MR system 212 may obtain the location from a virtual surgical plan (e.g., the virtual surgical plan described above). As such, MR system 212 may display a virtual cutting surface (e.g., cutting plane) having parameters (e.g., position, size, and/or orientation relative to the virtual model of the humerus) obtained from the virtual surgical plan that guides resection of a portion of a head of the humerus.

As discussed above, a virtual model of humerus 3200 may be registered with humerus 3200 such that coordinates on the virtual model approximately correspond to coordinates on humerus 3200. As such, by displaying virtual cutting plane 4200 at the determined location on the virtual model, MR system 212 may display virtual cutting plane 4200 at the planned position on humerus 3200.

The surgeon may resect humeral head 3204 using the displayed virtual guidance. For instance, the surgeon may utilize oscillating saw 4104 to resect humeral head 3204 by cutting along virtual cutting plane 4200. In some examples, MR system 212 may display targeting guidance to indicate whether the tool (e.g., oscillating saw 4104) is on the prescribed plane.

Figure 43:
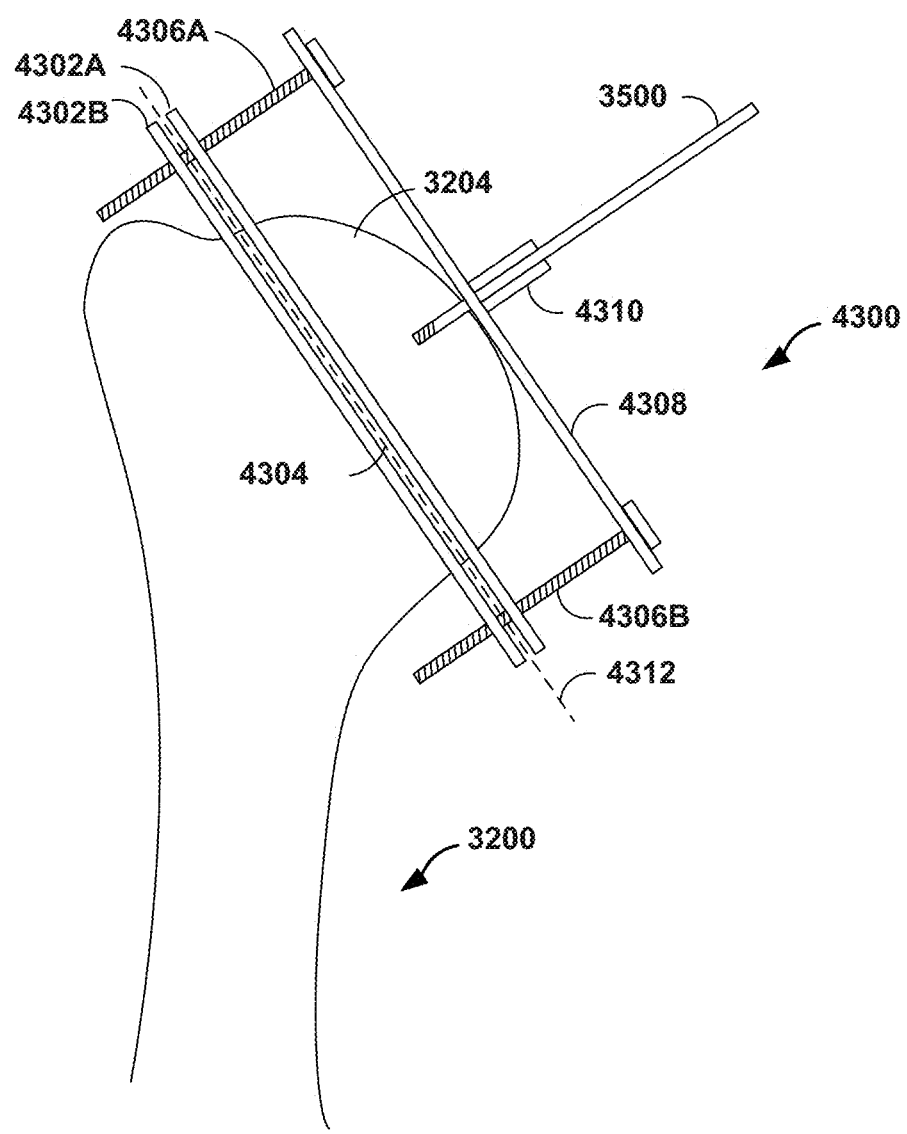
FIG. 43 is a conceptual diagram illustrating a physical guide for humeral head resection that is positioned using virtual guidance in a shoulder arthroplasty procedure, in accordance with one or more techniques of this disclosure.

FIG. 43 is a conceptual diagram illustrating a physical guide for humeral head resection that is positioned using virtual guidance, in accordance with one or more techniques of this disclosure. As discussed above, in the second example technique, MR system 212 may display a virtual axis that guides the surgeon in installing a physical guide, which guides the surgeon in resecting the humeral head. For instance, MR system 212 may display a virtual marker, such as a virtual axis, using techniques similar to those discussed above with reference to FIGS. 34 and 35. The surgeon may use the virtual axis to guide installation of physical guide 3500 (e.g., a guide pin). As such, MR system 212 may display a virtual drilling axis having parameters (e.g., position, size, and/or orientation relative to the virtual model of the humerus) obtained from the virtual surgical plan that guides attachment of a guide pin to the humerus. As discussed above, the guide pin may be configured to guide attachment of a resection guide to the humerus.

The surgeon may use guide 3500 to assist in the installation of resection guide 4300 (e.g., the guide pin may be configured to guide attachment of a resection guide to the humerus). In general, resection guide 4300 may be a physical assembly configured to physically guide a tool (e.g., an oscillating saw) for resecting a humeral head. In the example of FIG. 43, resection guide 4300 includes plates 4302A and 4302B (collectively, "plates 4302"), upper plate 4308, adjustment screws 4306A and 4306B (collectively, "adjustment screws 4306"), and guide receiver 4310.

Guide receiver 4310 may be sized to accept guide 3500 such that resection guide 4300 may be passed over guide 3500. Plates 4302 define slot 4304, which may be sized to receive and guide a physically guide a tool (e.g., an oscillating saw) between plates 4302 and across cutting plane 4312. Upper plate 4308 may be configured to rest against a top of humeral head 3204 (either native or after work has been performed to remove a graft). Adjustment screws 4306 may be collectively or independently adjusted to position plates 4302, and thus cutting plane 4312, relative to upper plate 4308.

MR system 212 may provide virtual guidance to assist in the positioning of resection guide 4300. As one example, MR system 212 may display a virtual cutting plane at the desired location of cutting plane 4312. The surgeon may adjust adjustment screws 4306 until slot 4304 is alighted with the virtual cutting plane. In some examples, MR system 212 may provide guidance as to which of adjustment screws 4306 is to be tightened or loosened. Once resection guide 4300 is properly configured (e.g., slot 4304 is alighted with the virtual cutting plane), the surgeon may operate a tool to resect humeral head 3204.

Figure 44:
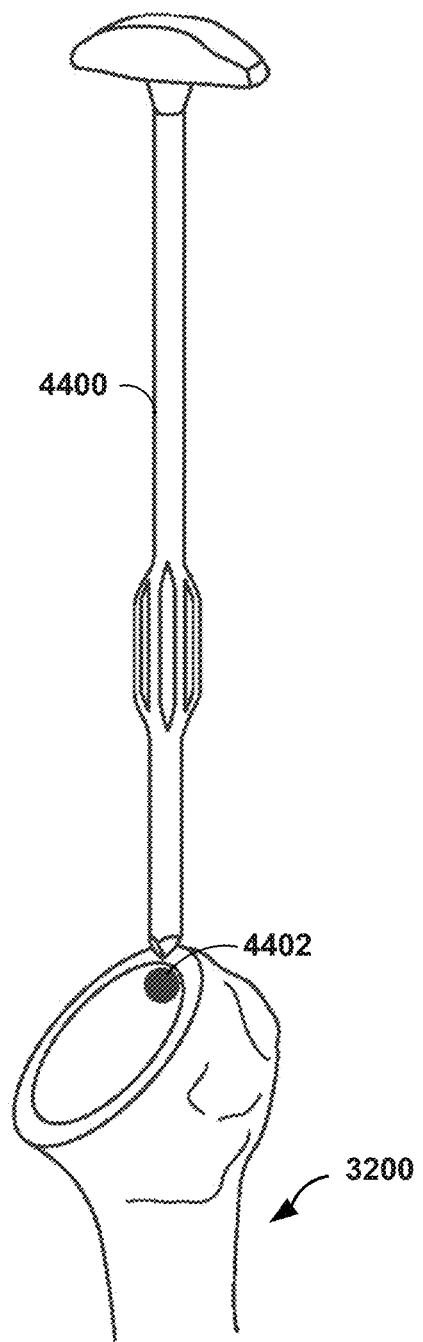
FIGS. 44 and 45 are conceptual diagrams illustrating an MR system providing virtual guidance for creating a pilot hole in a humerus in a shoulder arthroplasty procedure, in accordance with one or more techniques of this disclosure.
Figure 45:
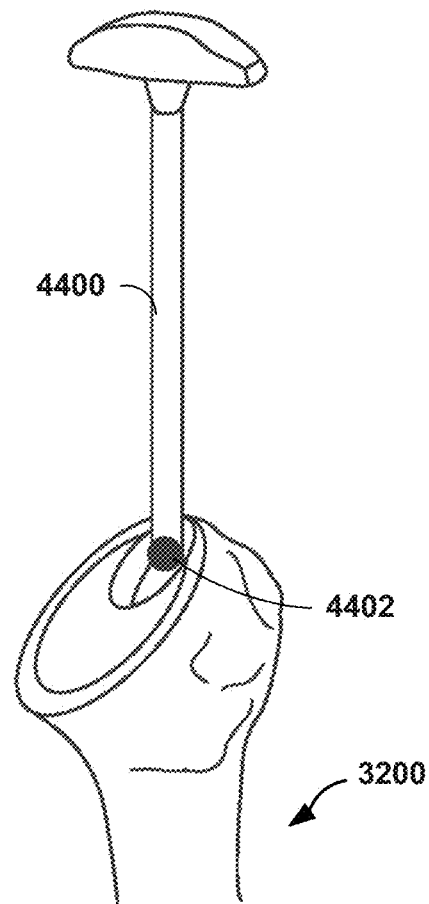

FIGS. 44 and 45 are conceptual diagrams illustrating an MR system providing virtual guidance for creating a pilot hole in a humerus, in accordance with one or more techniques of this disclosure. As shown in FIGS. 44 and 45, starter awl 4400 may be used to create a pilot hole in-line with a humeral canal at a hinge point of the resection.

MR system 212 may provide virtual guidance to assist in the creation of the pilot hole. As one example, MR system 212 may display targeting guidance, such as a virtual marker (e.g., virtual point 4402) that represents the location at which the surgeon should create the pilot hole. For instance, MR system 212 may display a virtual axis having parameters (e.g., position, size, and/or orientation relative to the virtual model of the humerus) obtained from the virtual surgical plan that guides creation of a pilot hole in the humerus after a head of the humerus has been resected. As another example MR system 212 may display depth guidance, e.g., the depth guidance discussed below with reference to FIGS. 66-68, to assist the surgeon in creating the pilot hole to a prescribed depth.

Figure 46:
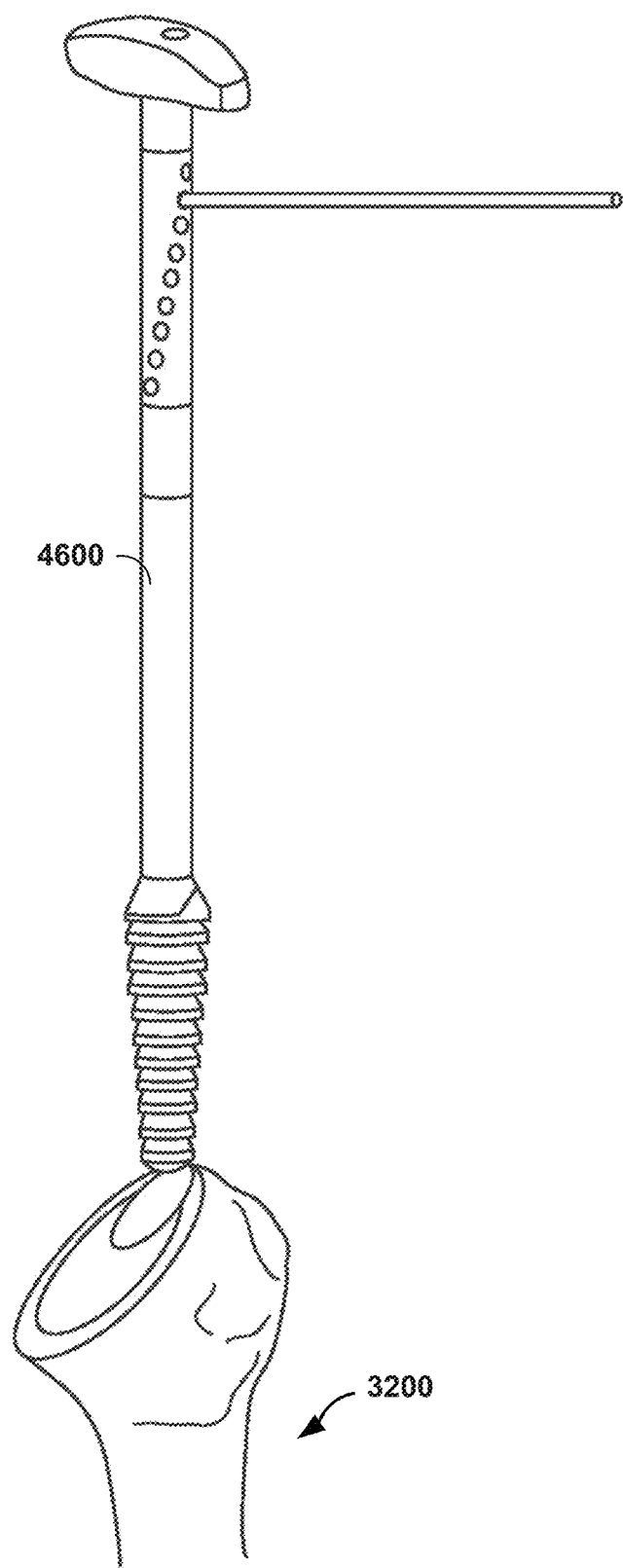
FIG. 46 is a conceptual diagram illustrating an MR system providing virtual guidance for sounding a humerus in a shoulder arthroplasty procedure, in accordance with one or more techniques of this disclosure.

FIG. 46 is a conceptual diagram illustrating an MR system providing virtual guidance for sounding a humerus, in accordance with one or more techniques of this disclosure. As shown in FIG. 46, sounder 4600 may be used to determine an upper size limit of a distal portion of humerus 3200. In some examples, as discussed herein, multiple sounders of different sizes may be used to the upper size limit.

MR system 212 may provide virtual guidance to assist in the sounding. As one example, MR system 212 may display virtual targeting guidance for sounder 4600. For instance, MR system 212 may display a virtual marker (e.g., as discussed above with reference to FIGS. 36A-36D) that indicates where sounder 4600 should be inserted.

Figure 47:
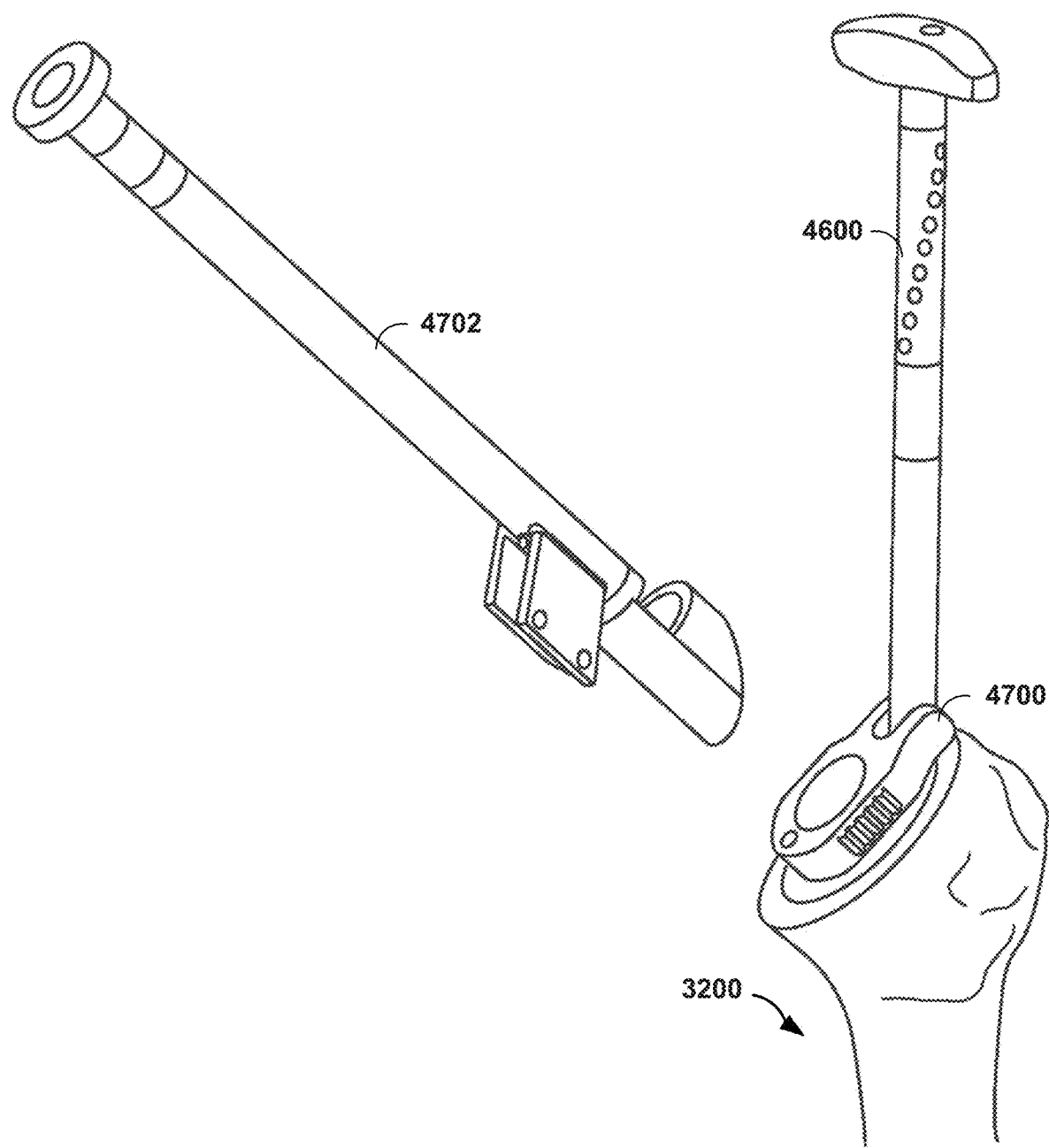
FIG. 47 is a conceptual diagram illustrating an MR system providing virtual guidance for punching a humerus in a shoulder arthroplasty procedure, in accordance with one or more techniques of this disclosure.

FIG. 47 is a conceptual diagram illustrating an MR system providing virtual guidance for punching a humerus, in accordance with one or more techniques of this disclosure. As shown in FIG. 47, the surgeon may attach punch template 4700 to sounder 4600 (or the final sounder determined during the sounding step). The surgeon may then place punch 4702 into template 4700 until punch 4702 bottoms out on template 4700. The surgeon may then remove the scored bone by pulling sounder 4600, template 4700, and punch 4702 out of humerus 3200.

MR system 212 may provide virtual guidance to assist in the punching. As one example, MR system 212 may display an indication of whether punch 4702 is properly positioned in template 4700. For instance, where punch 4702 is properly positioned in template 4700, MR system 212 may display a virtual marker that indicates proper position (e.g., a checkmark). Similarly, where punch 4702 is not properly positioned in template 4700, MR system 212 may display a virtual marker that indicates improper position (e.g., an X).

Figure 48:
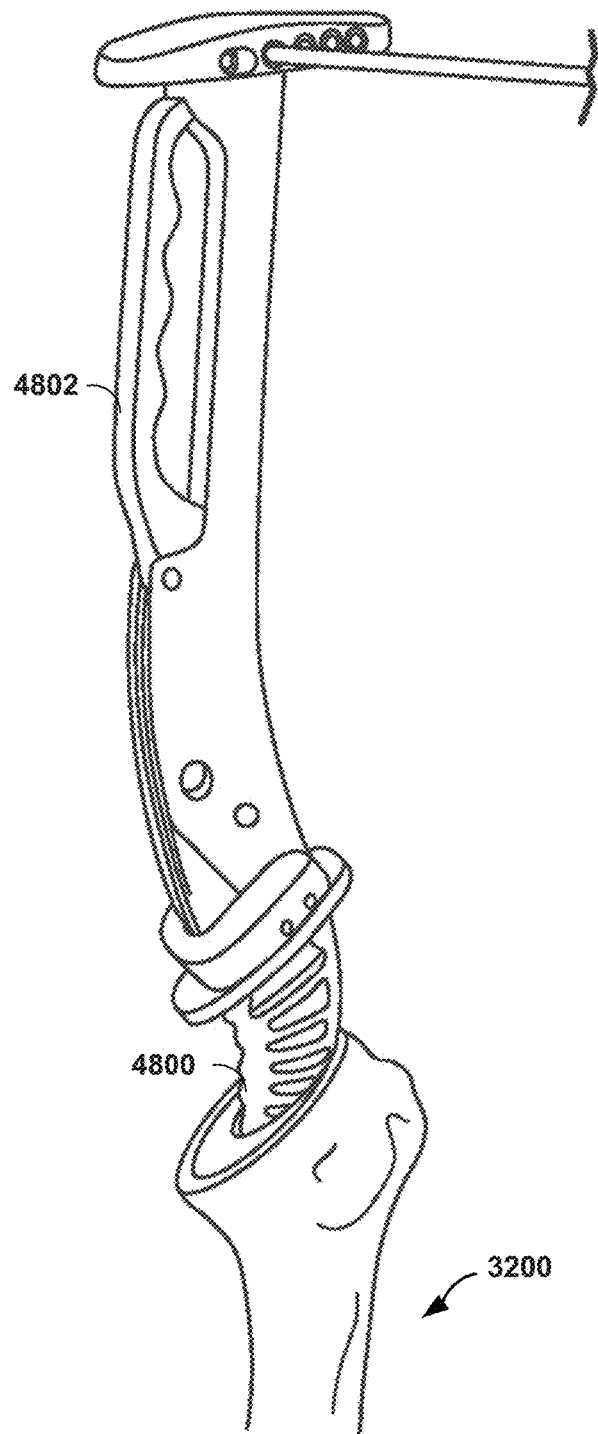
FIG. 48 is a conceptual diagram illustrating an MR system providing virtual guidance for compacting a humerus in a shoulder arthroplasty procedure, in accordance with one or more techniques of this disclosure.

FIG. 48 is a conceptual diagram illustrating an MR system providing virtual guidance for compacting a humerus, in accordance with one or more techniques of this disclosure. As shown in FIG. 48, compactor 4800 may be attached to handle 4802 and inserted into humerus 3200. In some examples, multiple compactors may be used. For instance, the surgeon may begin with a compactor three sizes below a size of the final sounder and compact sequentially until satisfactory fixation is achieved. Satisfactory fixation can be assessed by a slight torque motion of handle 4802. Compactor 4800 should not move within the humerus during this test if satisfactory fixation has been achieved.

MR system 212 may provide virtual guidance to assist in the compacting. As one example, MR system 212 may display indication of whether satisfactory fixation has been achieved. For instance, where MR system 212 determines that satisfactory fixation has been achieved, MR system 212 may display a virtual marker that indicates satisfactory fixation (e.g., a checkmark). Similarly, where MR system 212 determines that satisfactory fixation has not been achieved, MR system 212 may display a virtual marker that indicates unsatisfactory fixation (e.g., an X).

The surgeon may disconnect compactor 4800 (e.g., the final compactor) from handle 4802. The surgeon may then perform one or more surface preparation steps.

Figure 49:
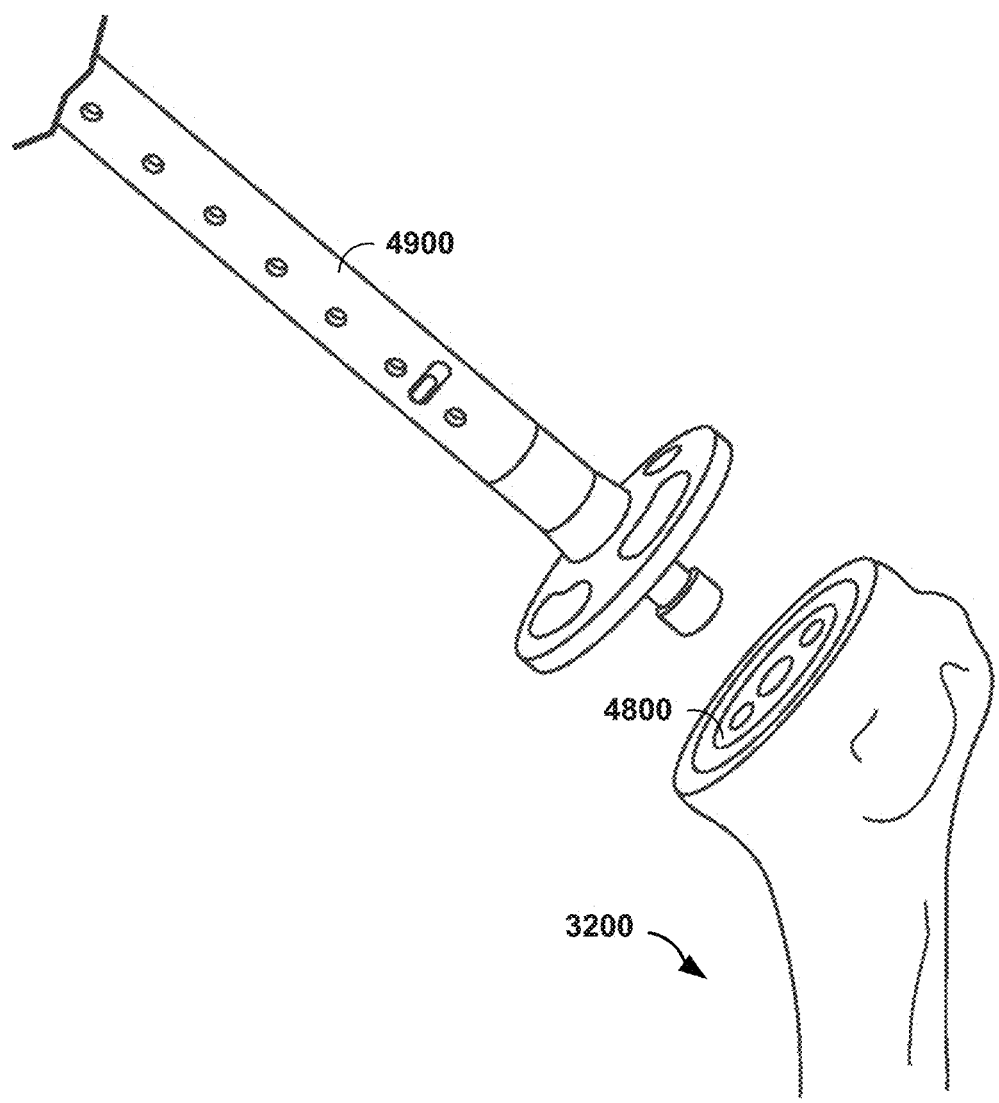
FIG. 49 is a conceptual diagram illustrating an MR system providing virtual guidance for preparing a surface of a humerus in a shoulder arthroplasty procedure, in accordance with one or more techniques of this disclosure.

FIG. 49 is a conceptual diagram illustrating an MR system providing virtual guidance for preparing a surface of a humerus, in accordance with one or more techniques of this disclosure. As shown in FIG. 49, the surgeon may use surface planner 4900 to prepare a surface of humerus 3200 (e.g., to ensure a flat resection true to the prosthesis).

MR system 212 may provide virtual guidance to assist in the surface preparation. For instance, MR system 212 may provide targeting guidance (e.g., similar to the targeting guidance discussed below with reference to FIGS. 66-68) to aid the surgeon in keeping surface planner 4900 on a planned/prescribed axis.

Many different techniques may be used to prepare a scapula for prosthesis attachment and to perform actual prosthesis attachment. Regardless of the technique used, MR system 212 may provide virtual guidance to assist in one or both of the preparation and attachment. As such, while the following techniques are examples in which MR system 212 provides virtual guidance, MR system 212 may provide virtual guidance for other techniques.

In an example technique, the surgical procedure steps include installation of a guide in a glenoid of the scapula, reaming the glenoid, creating a central hole in the glenoid, creating additional anchorage positions in the glenoid, and attaching an implant to the prepared glenoid. As a guide pin is used, the example technique may be considered a cannulated technique. However, the techniques are similarly applicable to non-cannulated techniques.

A surgeon may perform one or more steps to expose a patient's glenoid. For instance, with the patient's arm abducted and internally rotated, the surgeon may make one or more incisions to expose the glenoid. The surgeon may position one or more retractors to maintain the exposure. In some examples, MR system 212 may provide guidance to assist in the exposure and/or placement of retractors.

Figure 51:
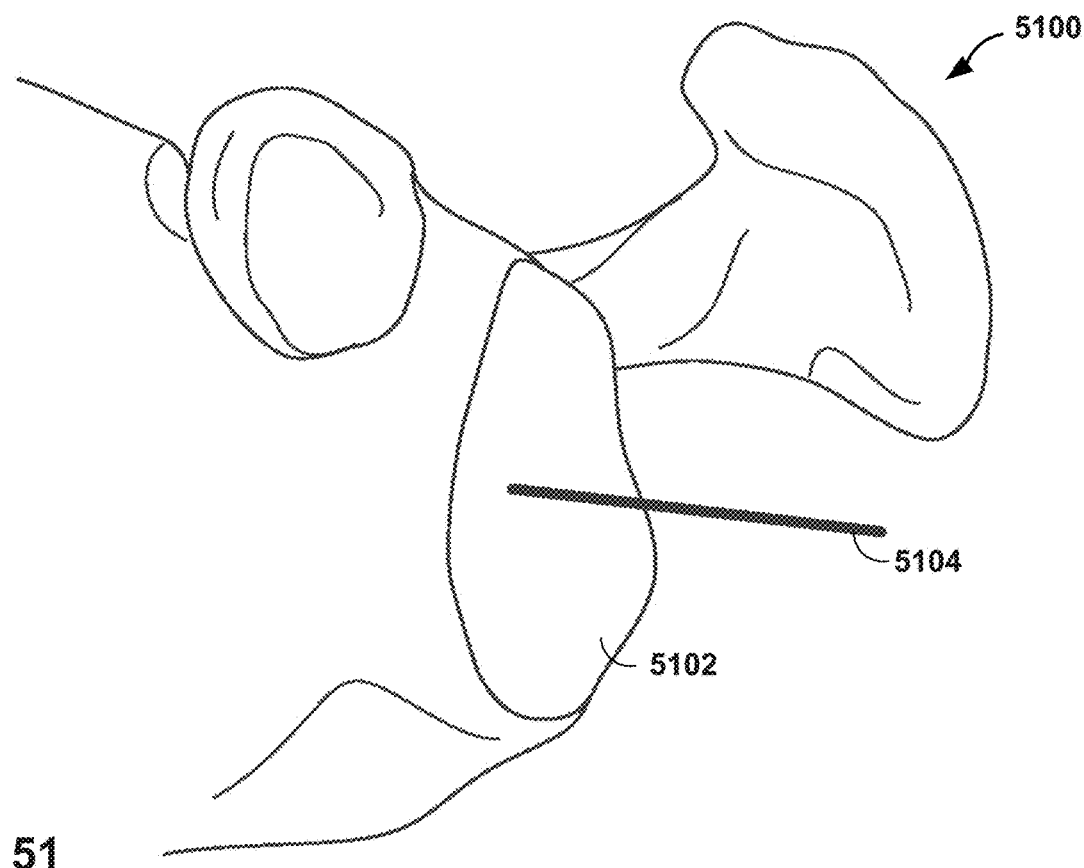
FIG. 51 is a conceptual diagram illustrating an MR system providing virtual guidance to the user for installation of a guide in a glenoid of a scapula in a shoulder arthroplasty procedure, in accordance with one or more techniques of this disclosure.

FIG. 51 is a conceptual diagram illustrating an MR system providing virtual guidance to a user for installation of a guide in a glenoid of a scapula, in accordance with one or more techniques of this disclosure. As shown in FIG. 51, MR system 212 may display virtual guidance, e.g., in the form of virtual axis 5104, on glenoid 5102 of scapula 5100. To display virtual axis 5104, MR system 212 may determine a location on a virtual model of glenoid 5102 at which a guide is to be installed. MR system 212 may obtain the location from a virtual surgical plan (e.g., the virtual surgical plan described above). The location obtained by MR system 212 may specify one or both of coordinates of a point on the virtual model and a vector. The point may be the position at which the guide is to be installed and the vector may indicate the angle/slope at which the guide is to be installed. As such, MR system 212 may display a virtual reaming axis having parameters (e.g., position, size, and/or orientation relative to the virtual model of the scapula) obtained from the virtual surgical plan. The displayed virtual reaming axis may be configured to guide reaming of the glenoid.

As discussed above, the virtual model of glenoid 5102 may be registered with glenoid 5102 such that coordinates on the virtual model approximately correspond to coordinates on glenoid 5102. As such, by displaying virtual axis 5104 at the determined location on the virtual model, MR system 212 may display virtual axis 5104 at the planned position on glenoid 5102.

As also discussed above, the virtual model of glenoid 5102 may be selectively displayed after registration. For instance, after the virtual model of glenoid 5102 is registered with glenoid 5102, MR system 212 may cease displaying of the virtual model. Alternatively, MR system 212 may continue to display the virtual model overlaid on glenoid 5102 after registration. The display of the virtual model may be selective in that the surgeon may activate or deactivate display of the virtual model.

MR system 212 may display the virtual model and/or virtual guides with varying opacity (e.g., transparency). The opacity may be adjusted automatically, manually, or both. As one example, the surgeon may provide user input to MR system 212 to manually adjust the opacity of the virtual model and/or virtual guides. As another example, MR system 212 may automatically adjust the opacity based on an amount of light in the viewing field (e.g., amount of light where the surgeon is looking). For instance, MR system 212 may adjust the opacity (e.g., increase the transparency) of the virtual model and/or virtual guides to positively correlate with the amount of light in the viewing field (e.g., brighter light results in increased opacity/decreased transparency and dimmer light results in decreased opacity/increased transparency).

The surgeon may attach a physical guide using the displayed virtual guidance. As one example, where the guide is a guide pin with a self-tapping threaded distal tip, the surgeon may align the guide pin with the displayed virtual axis 5104 and utilize a drill or other instrument to install the guide pin. As another example, where the guide is a guide pin without a self-tapping tip, the surgeon may align a drill bit of a drill with the displayed virtual axis 5104 and operate the drill to form a hole to receive the guide pin and then install the guide pin in the hole. In some examples, MR system 212 may display depth guidance information to enable the surgeon to install the guide pin to a planned depth. Examples of depth guidance information are discussed in further detail herein with reference to FIG. 66.

Figure 52:
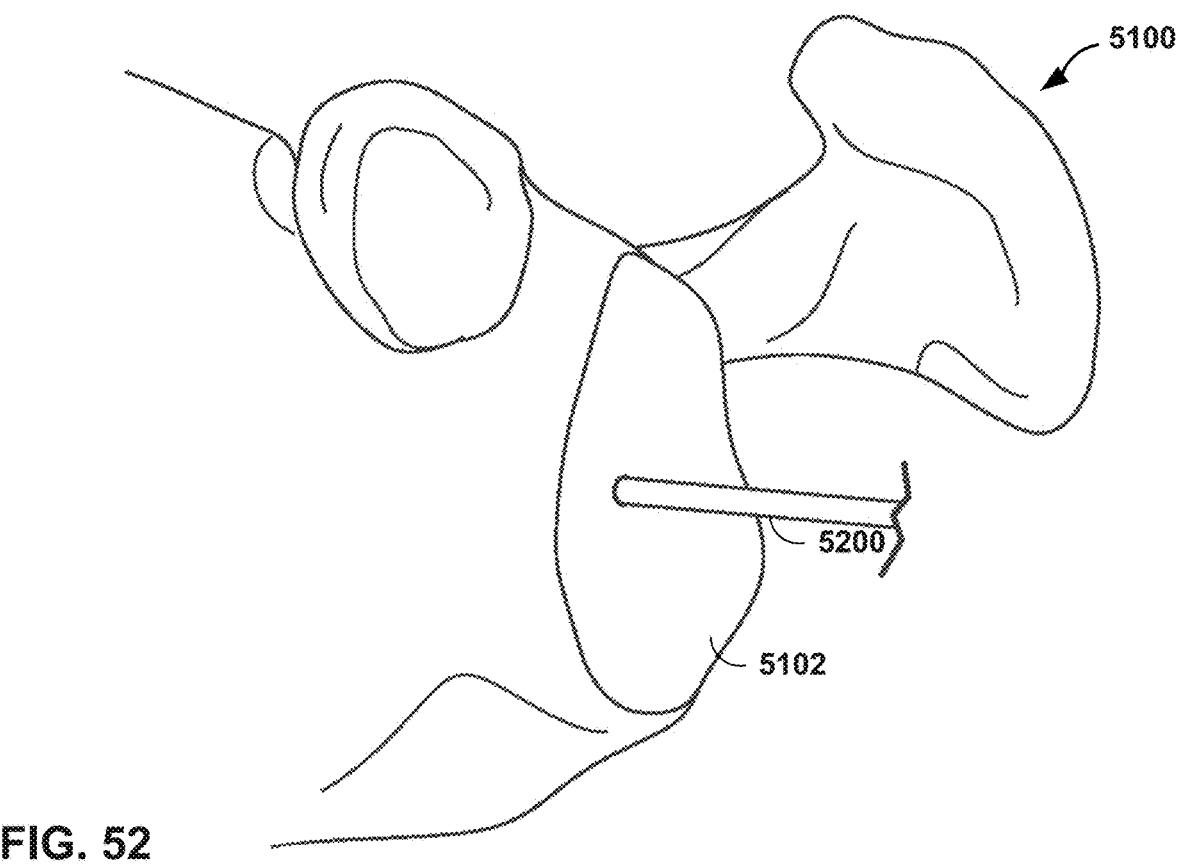
FIG. 52 is a conceptual diagram illustrating an example guide as installed in a glenoid in a shoulder arthroplasty procedure.

FIG. 52 is a conceptual diagram illustrating guide 5200, i.e., a guide pin in this example, as installed in glenoid 5102. As shown in FIGS. 51 and 52, by displaying virtual axis 5104, a surgeon may drill in alignment with the virtual axis, which may be referred to as a reaming axis, and thereby form a hole for installation of guide 5200 at the planned position on glenoid 5102. In this way, MR system 212 may enable the installation of a guide without the need for an additional mechanical guide.

Figure 53:
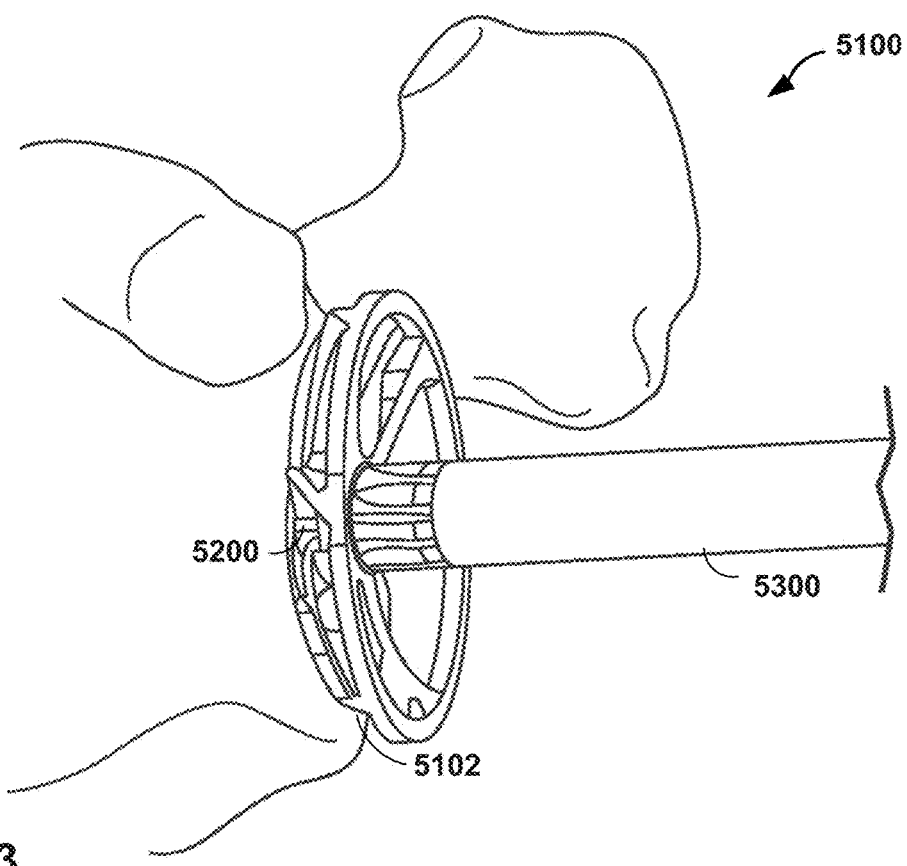
FIG. 53 is a conceptual diagram illustrating an MR system providing virtual guidance for reaming a glenoid in a shoulder arthroplasty procedure, in accordance with one or more techniques of this disclosure.

FIG. 53 is a conceptual diagram illustrating an MR system providing virtual guidance for reaming a glenoid, in accordance with one or more techniques of this disclosure. As shown in FIG. 53, reaming tool 5300 may be used to ream the surface of glenoid 5102. In this example, reaming tool 5300 may be a cannulated reaming tool configured to be positioned and/or guided by a guide pin, such as guide 5200. For example, the shaft of cannulated reaming tool may receive guide 5200 such that the tool shaft is mounted substantially concentrically with the pin. In other examples, reaming tool 5300 may not be cannulated and may be guided without the assistance of a physical guide pin.

The surgeon may attach reaming tool 5300 to guide 5200 (e.g., insert proximal tip of guide 5200 into reaming tool 5300), and attach a drill or other instrument to rotate reaming tool 5300. To perform the reaming, the surgeon may rotate reaming tool 5300 to advance reaming tool 5300 down guide 5200 until reaming is complete.

MR system 212 may display virtual guidance to assist in the reaming process. As one example MR system 212 may provide depth guidance. For instance, MR system 212 may display depth guidance to enable the surgeon to ream to a target depth. As another example, MR system 212 may provide targeting guidance. For instance, MR system 212 may display an indication of whether reaming tool 5300 is aligned with a virtual reaming axis.

While described herein as a single reaming step, the surgery may include multiple reaming steps. The various reaming steps may use the same axis/guide pin or may use different axes/guide pins. In examples where different reaming steps use different axes, MR system 212 may provide virtual guidance for reaming using the different axes.

Figure 54:
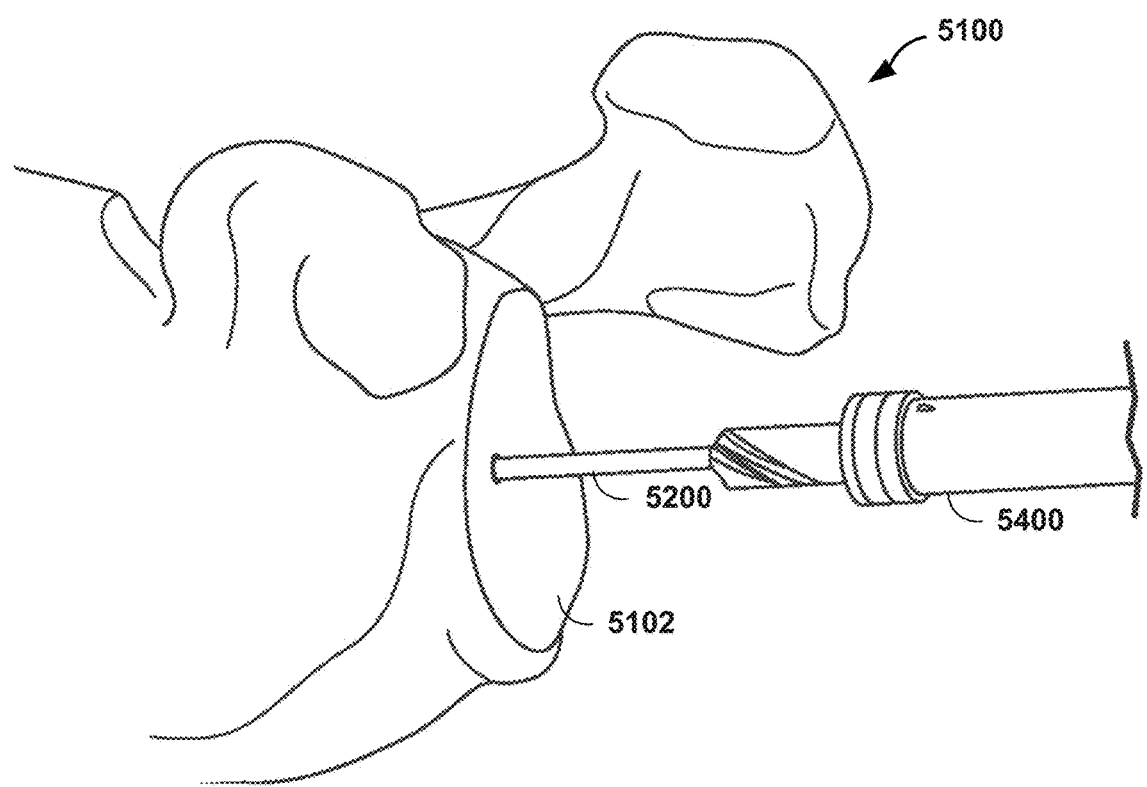
FIGS. 54 and 55 are conceptual diagrams illustrating an MR system providing virtual guidance for creating a central hole in a glenoid (e.g., post-reaming) in a shoulder arthroplasty procedure, in accordance with one or more techniques of this disclosure.
Figure 55:
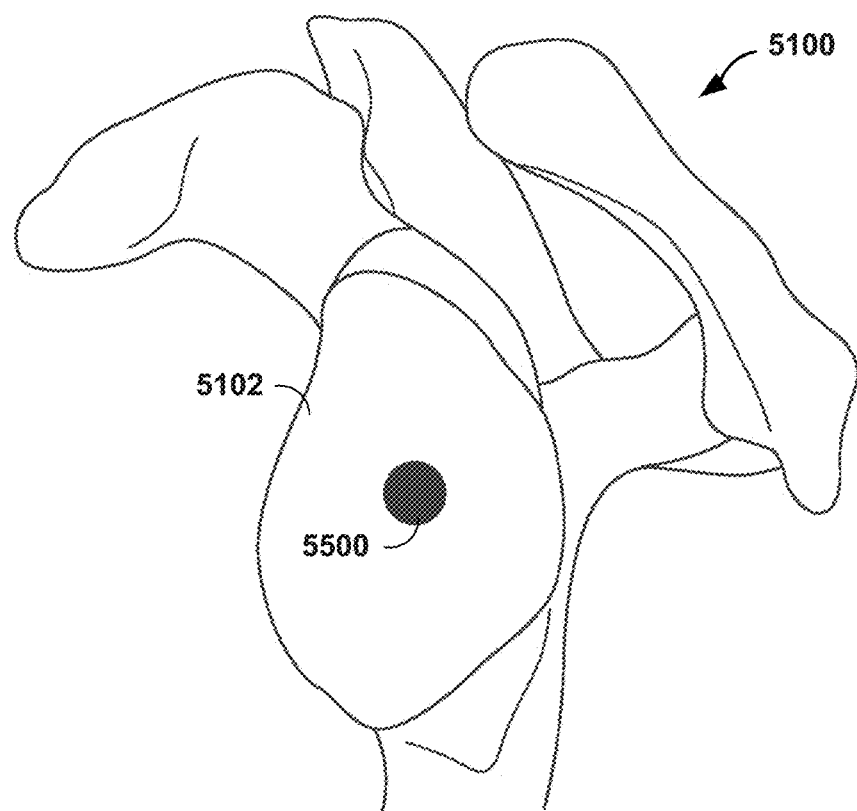

FIGS. 54 and 55 are conceptual diagrams illustrating an MR system providing virtual guidance for creating a central hole in a glenoid (e.g., post-reaming), in accordance with one or more techniques of this disclosure. As shown in FIGS. 54 and 55, drill bit 5400 may be used to drill central hole 5500 in glenoid 5102. In this example, drill bit 5400 may be a cannulated drill bit configured to be positioned and/or guided by a guide pin, such as guide 5200. In other examples, drill bit 5400 may not be cannulated and may be guided without the assistance of a physical guide pin. For instance, MR system 212 may provide virtual guidance (e.g., any combination of virtual markers, depth guidance, and/or targeting guidance discussed below with reference to FIGS. 66-68) to enable a surgeon to drill glenoid 5102 without the use of guide 5200. As discussed in further detail below, central hole 5500 may facilitate the attachment of a prosthesis to glenoid 5102, e.g., via one or more anchors.

MR system 212 may display virtual guidance to assist in the creation of central hole 5500. For instance, MR system 212 may display depth guidance to enable the surgeon to drill central hole 5500 to a target depth. As another example, MR system 212 may provide targeting guidance (e.g., any combination of virtual markers and/or targeting guidance discussed below with reference to FIGS. 66-68). For instance, MR system 212 may display an indication of whether drill bit tool 5400 is on a prescribed axis selected to form the central hole 5500 at a proper position at with a proper orientation.

In addition to a central hole (e.g., central hole 5500), it may be desirable for the surgeon to create additional anchorage positions in the glenoid. This additional anchorage positions may improve the fixation between the prosthesis and the glenoid. For instance, the additional anchorage positions may provide anti-rotation support between the prosthesis and the glenoid. Several different styles of anchorage may be used, depending on the type of prosthesis to be installed. Some examples of anchorage include, but are not necessarily limited to, keel and pegged anchors. However, the virtual guidance techniques discussed herein may be applicable to any type of anchorage. Example MR guidance for keel type anchorage is discussed below with reference to FIGS. 56-59. Example MR guidance for pegged type anchorage is discussed below with reference to FIGS. 60-62. In each case, the anchorage may help in placing a glenoid implant, such as a glenoid base plate for anatomic arthroplasty or a glenoid base plate and glenosphere for reverse arthroplasty, onto the glenoid and fixing it in place.

Figure 56:
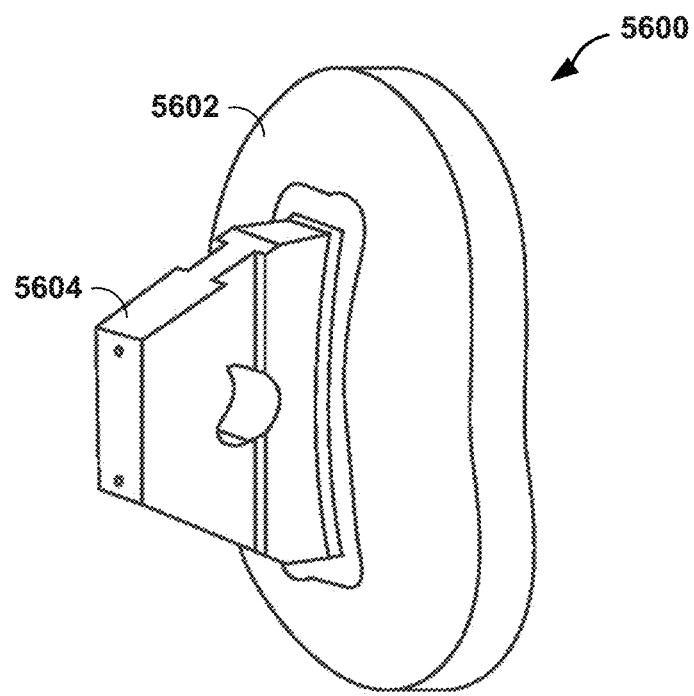
FIG. 56 is a conceptual diagram illustrating a glenoid prosthesis with keel type anchorage.

FIG. 56 is a conceptual diagram illustrating a glenoid prosthesis with keel type anchorage. As shown in FIG. 56, glenoid prosthesis 5600 includes rear surface 5602 configured to engage a prepared surface of glenoid 5102 (e.g., a reamed surface), and a keel anchor 5604 configured to be inserted in a keel slot created in glenoid 5102 (e.g., keel slot 5902 of FIG. 59).

Figure 59:
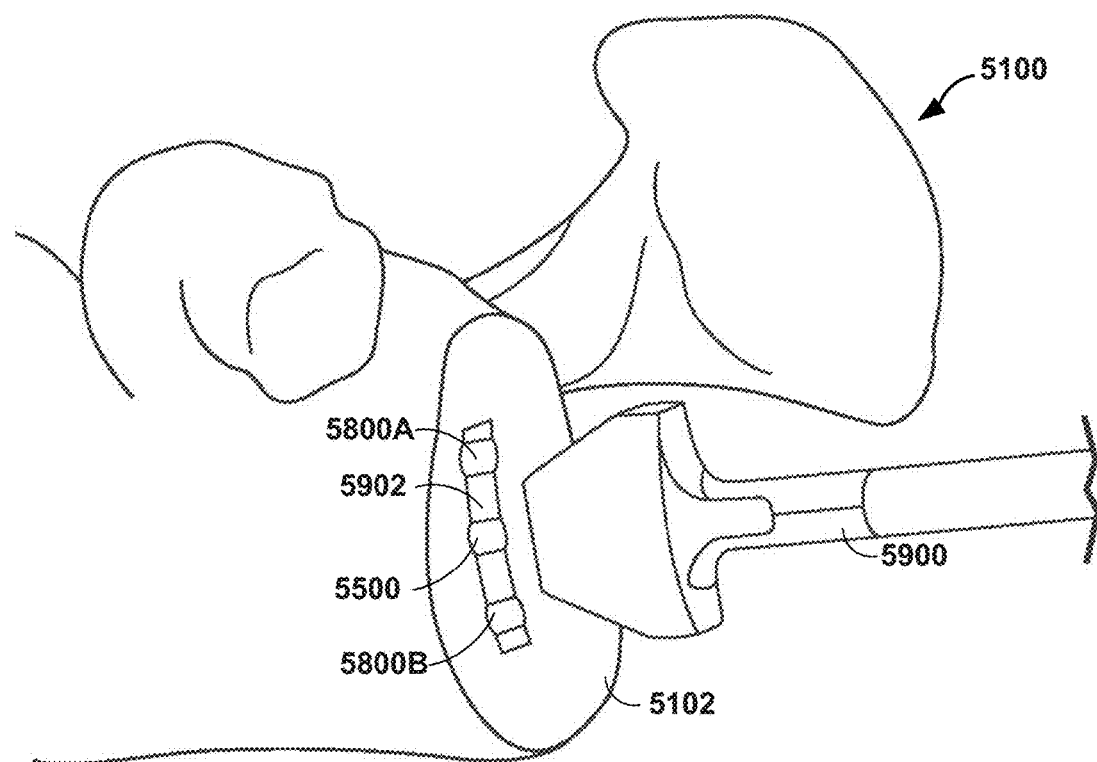
FIGS. 57-59 are conceptual diagrams illustrating an MR system providing virtual guidance for creating keel type anchorage positions in a glenoid in a shoulder arthroplasty procedure, in accordance with one or more techniques of this disclosure.
Figure 57:
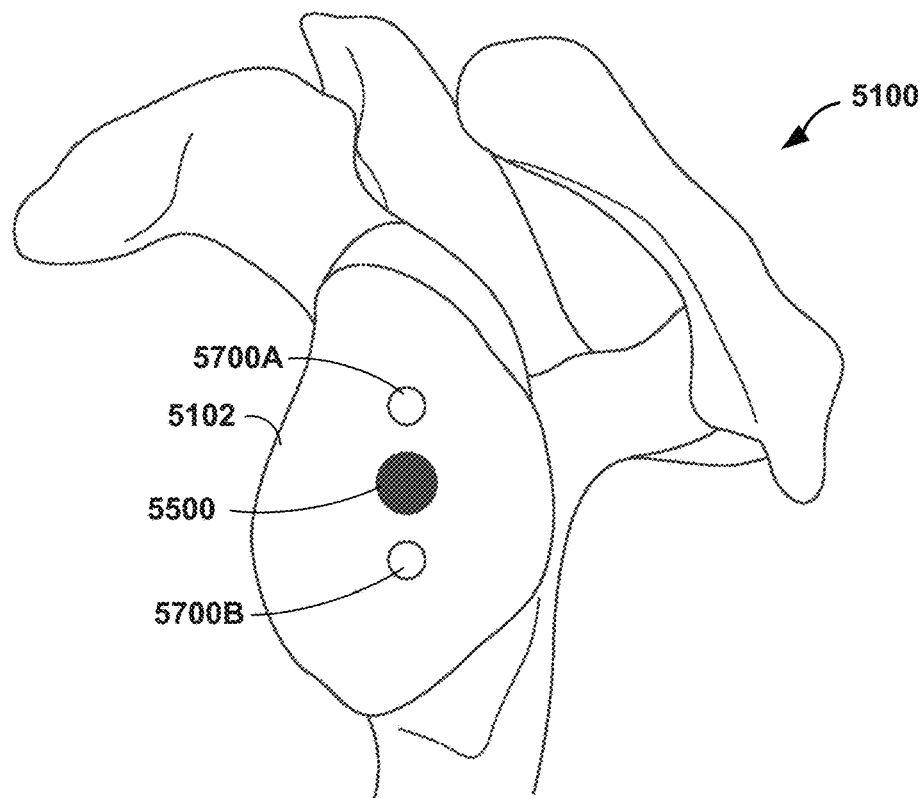
Figure 58:
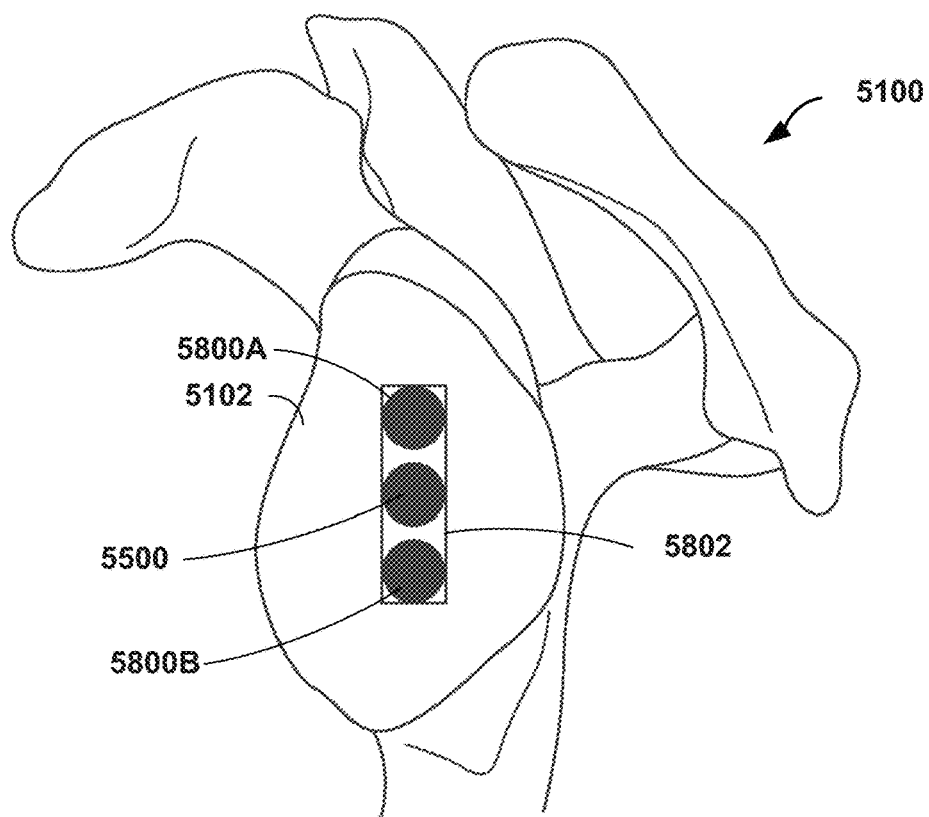

FIGS. 57-59 are conceptual diagrams illustrating an MR system providing virtual guidance for creating keel type anchorage positions in a glenoid, in accordance with one or more techniques of this disclosure. As shown in FIG. 57, MR system 212 may provide virtual guidance for drilling additional holes in glenoid 5102. MR system 212 may provide the virtual guidance for drilling the additional holes in any of a variety of manners. As one example, MR system 212 may display virtual guidance such as virtual markers having specified shapes (e.g., axes, arrows, points, circles, X shapes, crosses, targets, etc.), sizes and/or colors, at the locations the additional holes are to be drilled. For instance, in the example of FIG. 57, MR system 212 may display virtual markers 5700A and 5700B at the locations the additional holes are to be drilled. As another example, MR system 212 may display virtual axes at the locations the additional holes are to be drilled to aid the surgeon in properly aligning a drill bit to make the holes in the glenoid bone. For instance, MR system 212 may display (e.g., at the locations the additional holes are to be drilled) a plurality of virtual drilling axes having respective parameters obtained from the virtual surgical plan, each respective virtual drilling axis of the plurality of virtual drilling axes configured to guide drilling of a respective hole in the glenoid MR system 212 may determine the locations of the additional holes based on the virtual surgical plan. For instance, similar to virtual axis 5104 of FIG. 51, MR system 212 may obtain, from the virtual surgical plan, the location(s) of the additional holes to be drilled on the virtual model of glenoid 5102. As such, by displaying virtual markers 5700A and 5700B at the determined locations on the virtual model, MR system 212 may display virtual markers 5700A and 5700B at the planned positions on glenoid 5102. As discussed above, the virtual surgical plan may be patient specific in that the plan may be specifically developed for a particular patient. As such, the planned positioned on glenoid 5102 at which MR system 212 displays virtual markers 5700A and 5700B may be considered patient-specific planned positions. Therefore, the locations of the planned positions will vary from patient to patient according to individual patient-specific surgical plans.

The surgeon may utilize a drill bit and a drill to create the additional hole(s) at the location(s) indicated by MR system 212. For instance, as shown in FIG. 58, the surgeon may drill hole 5800A at the location of virtual marker 5700A and drill hole 5800B at the location of virtual marker 5700B. The surgeon may use the same drill bit for each hole or may use different drill bits for different holes.

MR system 212 may provide virtual guidance for the drilling in addition to or in place of the virtual markers, such as those described above, which indicate the locations the additional holes are to be drilled. As one example, MR system 212 may provide targeting guidance to indicate whether the drill is on a target axis. In this case, as an addition or alternative to the virtual markers, MR system 212 may display guide axes that extend outward from the locations of each of the respective holes to be drilled. As another example, MR system 212 may display a mask with holes in the mask that correspond to the locations at which the holes are to be drilled. As another example, MR system 212 may display depth guidance to enable the surgeon to drill holes 5800A and 5800B to target depths (e.g., depth guidance discussed below with reference to FIGS. 66-68).

MR system 212 may provide virtual guidance for working the holes into a keel slot that may accept keel anchor 5604 of glenoid prosthesis 5600. As an example, MR system 212 may display virtual outline 5802 around holes 5800A, 5500, and 5800B. For instance, MR system 212 may display virtual outline 5802 as approximately corresponding to a final outline of the desired keel slot to be created.

The surgeon may utilize a tool to work holes 5800A, 5500, and 5800B into keel slot 5902. As shown in FIG. 59, the surgeon may utilize keel punch 5900 to work holes 5800A, 5500, and 5800B into keel slot 5902. For instance, the surgeon may impact keel punch 5900 into the area indicated by virtual outline 5802. In this case, virtual outline 5802 defines a shape and dimension of the desired keel slot 5902, permitting the surgeon to work the holes into a form that visually matches or approximates the displayed virtual outline of the keel slot.

MR system 212 may provide additional or alternative virtual guidance for creating keel slot 5902. As one example, MR system 212 may display depth guidance to enable the surgeon to impact keel punch 5900 to a target depth (e.g., depth guidance similar to the depth guidance discussed below with reference to FIGS. 66-68). As another example, MR system 212 may provide targeting guidance to indicate whether keel punch 5900 is on a target axis (e.g., targeting guidance similar to the targeting guidance discussed below with reference to FIGS. 66-68). As another example, MR system 212 may display a mask with a cutout for virtual outline 5802.

Figure 60:
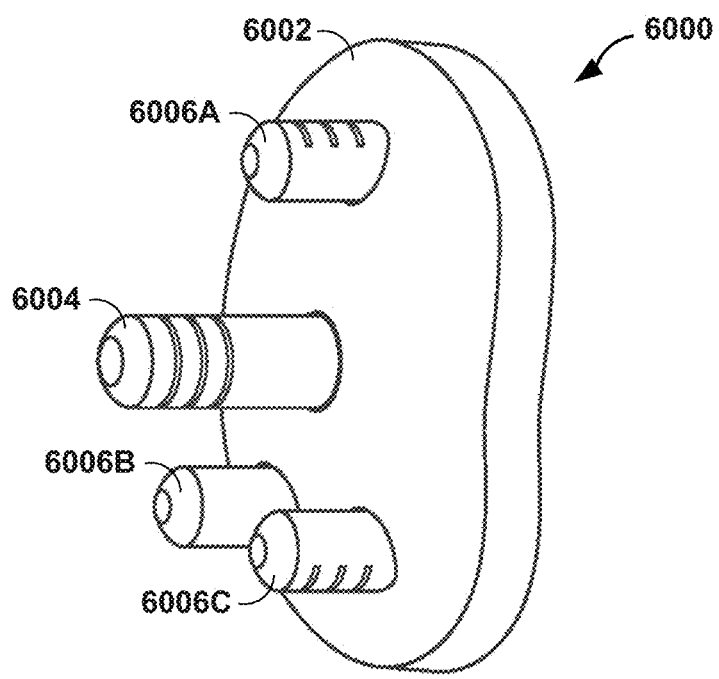
FIG. 60 is a conceptual diagram illustrating a glenoid prosthesis with pegged type anchorage.

FIG. 60 is a conceptual diagram illustrating a glenoid prosthesis with pegged type anchorage. As shown in FIG. 60, glenoid prosthesis 6000 includes rear surface 6002 configured to engage a prepared surface of glenoid 5102 (e.g., a reamed surface), a central peg anchor 6004 configured to be inserted in a central hole created in glenoid 5102, and one or more peg anchors 6006A-6006C (collectively, "peg anchors 6006") respectively configured to be inserted in additional holes created in glenoid 5102.

Figure 61:
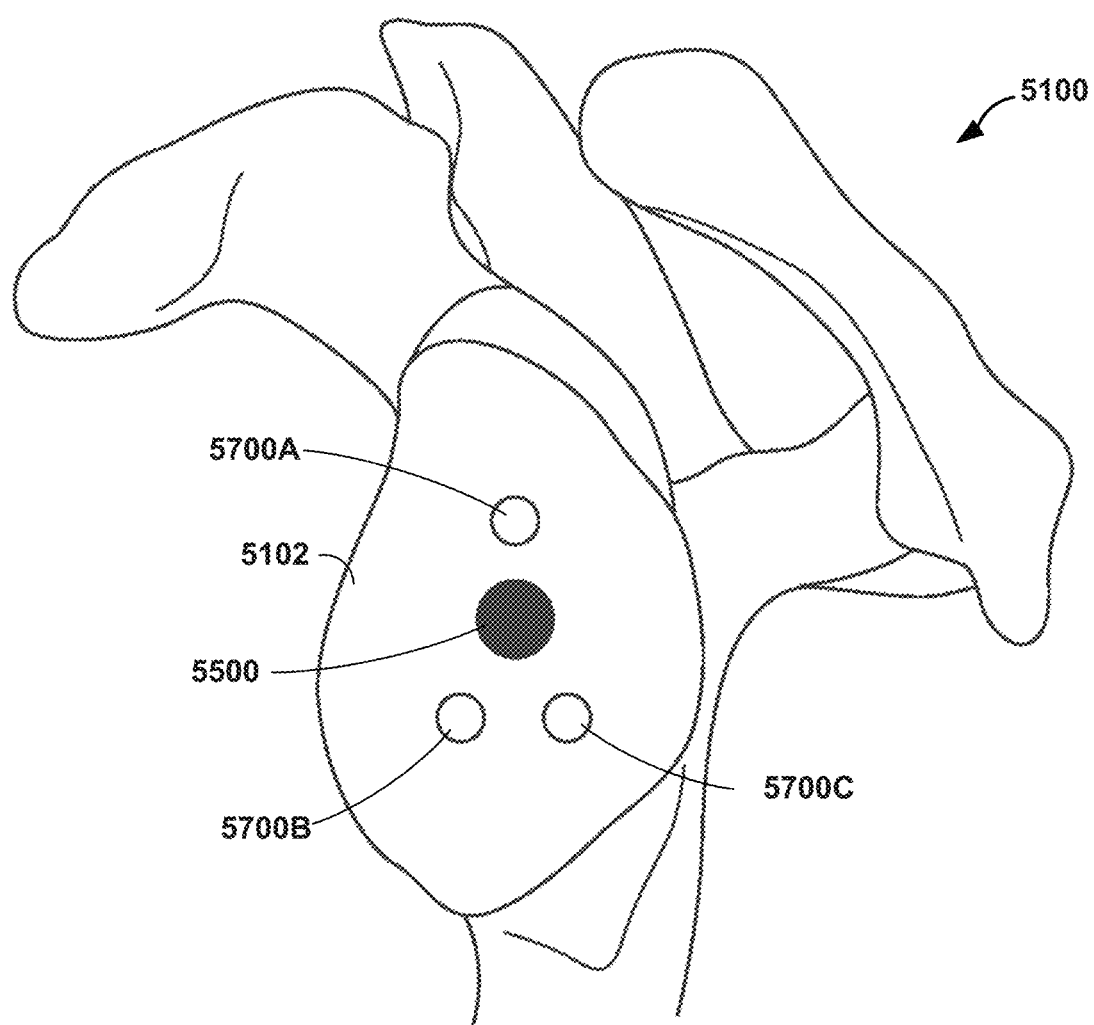
FIGS. 61 and 62 are conceptual diagrams illustrating an MR system providing virtual guidance for creating pegged type anchorage positions in a glenoid in a shoulder arthroplasty procedure, in accordance with one or more techniques of this disclosure.
Figure 62:
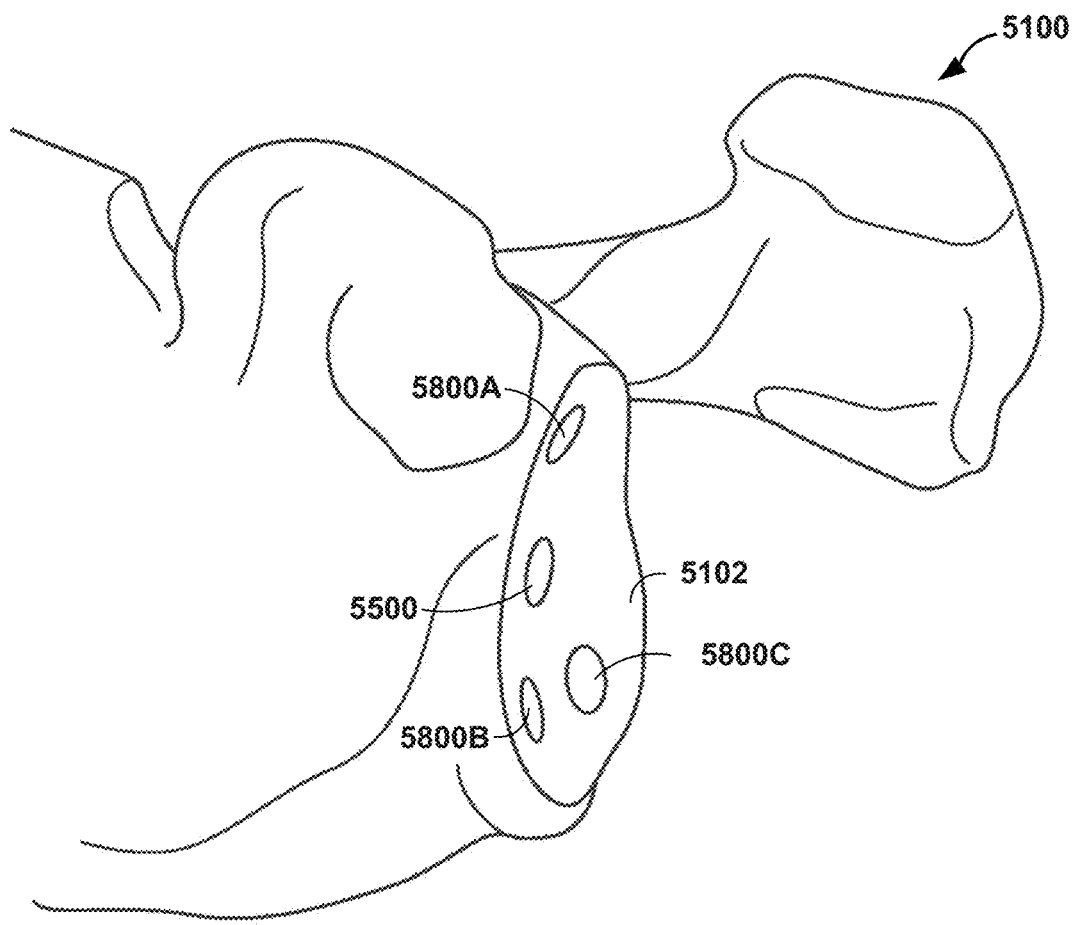

FIGS. 61 and 62 are conceptual diagrams illustrating an MR system providing virtual guidance for creating pegged type anchorage positions in a glenoid, in accordance with one or more techniques of this disclosure. As shown in FIG. 61, MR system 212 may provide virtual guidance for drilling additional holes in glenoid 5102. MR system 212 may provide the virtual guidance for drilling the additional holes in any of a variety of manners. As one example, MR system 212 may display virtual markers (e.g., axes, points, circles, X shapes, etc.) at the locations the additional holes are to be drilled. For instance, in the example of FIG. 61, MR system 212 may display virtual markers 5700A-5700C at the locations the additional holes are to be drilled. As another example, MR system 212 may display virtual axes extending from the locations at which the additional holes are to be drilled. As another example, MR system 212 may display a mask (effectively an inverse of the virtual markers) that indicates where the holes are to be drilled.

MR system 212 may determine the locations of the additional holes based on the virtual surgical plan. For instance, similar to virtual axis 5104 of FIG. 51, MR system 212 may obtain, from the virtual surgical plan, which may be patient-specific, the location(s) of the additional holes to be drilled on the virtual model of glenoid 5102. As such, by displaying virtual markers 5700A-5700C at the determined locations on the virtual model, MR system 212 may display virtual markers 5700A-5700C at the planned positions on glenoid 5102.

The surgeon may utilize a drill bit (or multiple drill bits) and a drill to create the additional hole(s) at the location(s) indicated by MR system 212. For instance, as shown in FIG. 62, the surgeon may drill hole 5800A at the location of virtual marker 5700A, drill hole 5800B at the location of virtual marker 5700B, and drill hole 5800C at the location of virtual marker 5700C.

MR system 212 may provide virtual guidance for the drilling in addition to or in place of the virtual markers that indicate the locations the additional holes are to be drilled. As one example, MR system 212 may provide targeting guidance to indicate whether the drill is on a target axis. As another example, MR system 212 may display depth guidance to enable the surgeon to drill holes 5800A-5800C to target depths.

It is noted that different implants may have different profiles, such as augmented profiles. Additionally, as discussed herein, some implants may be implanted with additional materials harvested from the patient, such as bone grafts. In some of such examples, MR system 212 may provide virtual guidance for placement of the additional materials. For instance, MR system 212 may provide virtual guidance for attaching a bone graft to an implant and guidance for attaching the graft/implant assembly to the patient.

In some examples, regardless of the anchorage type being used, the surgeon may utilize a trial component to determine whether glenoid 5102 has been properly prepared. The trial component may have a rear surface and anchors sized and positioned identical to the rear surface and anchors of the prosthesis to be implanted.

FIG. 149 is a flow diagram illustrating example techniques for MR aided validation of anatomy preparation, in accordance with one or more techniques of this disclosure. As discussed above, in some examples, a trial component may be used to determine whether a portion of a patient's anatomy has been properly prepared. For instance, a trial component with surfaces matching the surfaces of a prosthetic to be implanted may be placed in/around/against/etc. prepared anatomy. If the surfaces of the trial component match up with the surfaces of the prepared anatomy, the surgeon may determine that the anatomy has been properly prepared. However, in some examples, it may be desirable to determine whether anatomy has been properly prepared without requiring the use of a trial component.

In accordance with one or more techniques of this disclosure, MR system 212 may perform a virtual trialing to determine whether glenoid 5102 has been properly prepared. For instance, MR system 212 may obtain one or more dimensions of a glenoid of the scapula after the glenoid has been prepared for attachment of the prosthetic (14902). As one example, one or more sensors of MR system 212 (e.g., one or more depth cameras and/or one or more RGB cameras) may capture data of the prepared glenoid 5102. MR system 212 may determine, based on the captured data, one or more dimensions of the prepared glenoid 5102.

MR system 212 may obtain dimensions of a prosthetic to be implanted (14904). For instance, MR system 212 may obtain the dimensions of the prosthetic from a virtual surgical plan, a database of prosthetic dimensions, or any other suitable source.

MR system 212 may compare the determined dimensions to the obtained dimensions of the prosthetic to be implanted (14906) to determine whether the anatomy has been properly prepared (14908). For instance, MR system 212 may determine that the anatomy has been properly prepared where a difference between the determined dimensions and the dimensions of the prosthetic to be implanted is less than a threshold. Similarly, MR system 212 may determine that the anatomy has not been properly prepared where a difference between the determined dimensions and the dimensions of the prosthetic to be implanted is greater than the threshold. As one example, if a difference between the determined dimensions and the dimensions of the prosthetic to be implanted is less than a threshold, MR system 212 may determine that glenoid 5102 has been properly prepared (e.g., to receive the prosthetic). Similarly, if the difference between the determined dimensions and the dimensions of the prosthetic to be implanted is greater than the threshold, MR system 212 may determine that glenoid 5102 has not been properly prepared.

MR system 212 may output an indication of whether glenoid 5102 has been properly prepared to receive the implant, otherwise referred to as a prosthetic (14910/14912). As one example, MR system 212 may output a graphical indication that glenoid 5102 has been properly prepared to receive the prosthetic. As another example, MR system 212 may output a haptic or audible indication (e.g., via sensory devices 526) that glenoid 5102 has been properly prepared to receive the prosthetic. In situations where MR system 212 determines that glenoid 5102 has not been properly prepared, MR system 212 may provide virtual guidance for additional work to be performed by the surgeon in order to properly prepare glenoid 5102.

The above-described MR aided validation techniques may be used for any type of anatomy, e.g., in any of a variety of joint repair surgical procedures. As one example, as described above, the MR aided validation techniques may be used to determine whether a glenoid has been properly prepared. As another example, the MR aided validation techniques may be used to determine whether a humerus has been properly prepared. As another example, the MR aided validation techniques may be used to determine whether a tibia has been properly prepared. As another example, the MR aided validation techniques may be used to determine whether a talus has been properly prepared. As another example, the MR aided validation techniques may be used to determine whether a femur has been properly prepared.

FIG. 63 is a conceptual diagram illustrating an MR system providing virtual guidance for attaching an implant to a glenoid, in accordance with one or more techniques of this disclosure. A tool may be used to attach the implant (e.g., a pegged implant, a keeled implant, or any other type of implant) to glenoid 5102. For instance, the surgeon may utilize impactor 6302 to insert prosthesis 6300 into the prepared glenoid 5102. In some examples, one or more adhesives (e.g., glue, cement, etc.) may be applied to prosthesis 6300 and/or glenoid 5102 prior to impaction.

In some examples, one or more fasteners may be used to attach a prosthesis to glenoid 5102. For instance, as shown in FIGS. 64 and 65, screws 6400A-6400D (collectively, "screws 6400") and central stem 6402 may be used to attach prosthesis 6300 to glenoid 5102. These fasteners may be used in addition to, or in place of, any anchorages included in the prosthesis (e.g., pegs, keels, etc.).

MR system 212 may provide virtual guidance to facilitate the installation of the additional fasteners. For instance, as shown in FIG. 65, MR system 212 may display virtual axes 6500A-6500D (collectively, "virtual axes 6500"), which may be referred to as "virtual screw axes," to guide the surgeon in the installation of screws 6400 (e.g., into glenoid 5102). In examples where screws 6400 are "self-tapping", MR system 212 may display virtual guidance (e.g., virtual axes) to guide insertion of screws 6400. For instance, MR system 212 may display a virtual screw axis having parameters (e.g., position, size, and/or orientation relative to the virtual model of the scapula) obtained from the virtual surgical plan that guides insertion of a screw into the glenoid. In examples where screws 6400 are not "self-tapping", MR system 212 may display virtual guidance (e.g., virtual axes) to guide drilling of pilot holes for screws 6400. For instance, MR system 212 may display a virtual drilling axis having parameters (e.g., position, size, and/or orientation relative to the virtual model of the scapula) obtained from the virtual surgical plan that guides drilling of one or more holes (e.g., one or more pilot holes, and/or one or more clearance holes) in the glenoid (e.g., for a screw of screws 6400).

To display the virtual guides for installation of the fasteners, MR system 212 may register a virtual model of the prosthesis to the actual observed prosthesis. For instance, MR system 212 may obtain a virtual model of prosthesis 6300 from the virtual surgical plan and perform the registration in a manner similar to the registration process described above with reference to FIGS. 17-20.

MR system 212 may obtain locations for each of the fasteners to be installed. For instance, MR system 212 may obtain, from the virtual surgical plan, coordinates on the virtual model of the prosthesis and vector for each of the fasteners. In some examples, MR system 212 may determine that the coordinates for each fastener are the centroid of a corresponding hole in the prosthesis. For instance, MR system 212 may determine that the coordinates for screw 6400A are the centroid of hole 6502.

The surgeon may install the fasteners using the displayed virtual guidance. For instance, the surgeon may use a screwdriver or other instrument to install screws 6400.

MR system 212 may display virtual guidance to assist in the fastener attachment. As one example MR system 212 may provide depth guidance. For instance, MR system 212 may display depth guidance to enable the surgeon to install each of screws 6400 to a target depth. As another example, MR system 212 may provide targeting guidance. For instance, MR system 212 may display an indication of whether each of screws 6400 is being installed on a prescribed axis. As another example, MR system 212 may provide guidance on an order in which to tighten screws 6400. For instance, MR system 212 may display a virtual marker on a particular screw of screws 6400 that is to be tightened.

As discussed above, MR system 212 may provide a wide variety of virtual guidance. Example of virtual guidance that may be provided by MR system 212 include, but are not limited to, targeting guidance and depth guidance. MR system 212 may provide targeting guidance to assist a surgeon in performing work (e.g., drilling a hole, reaming, installing a screw, etc.) along a particular axis. MR system 212 may provide depth guidance to assist a surgeon in performing work (e.g., drilling a hole, reaming, installing a screw, etc.) to a desired depth.

Figure 66:
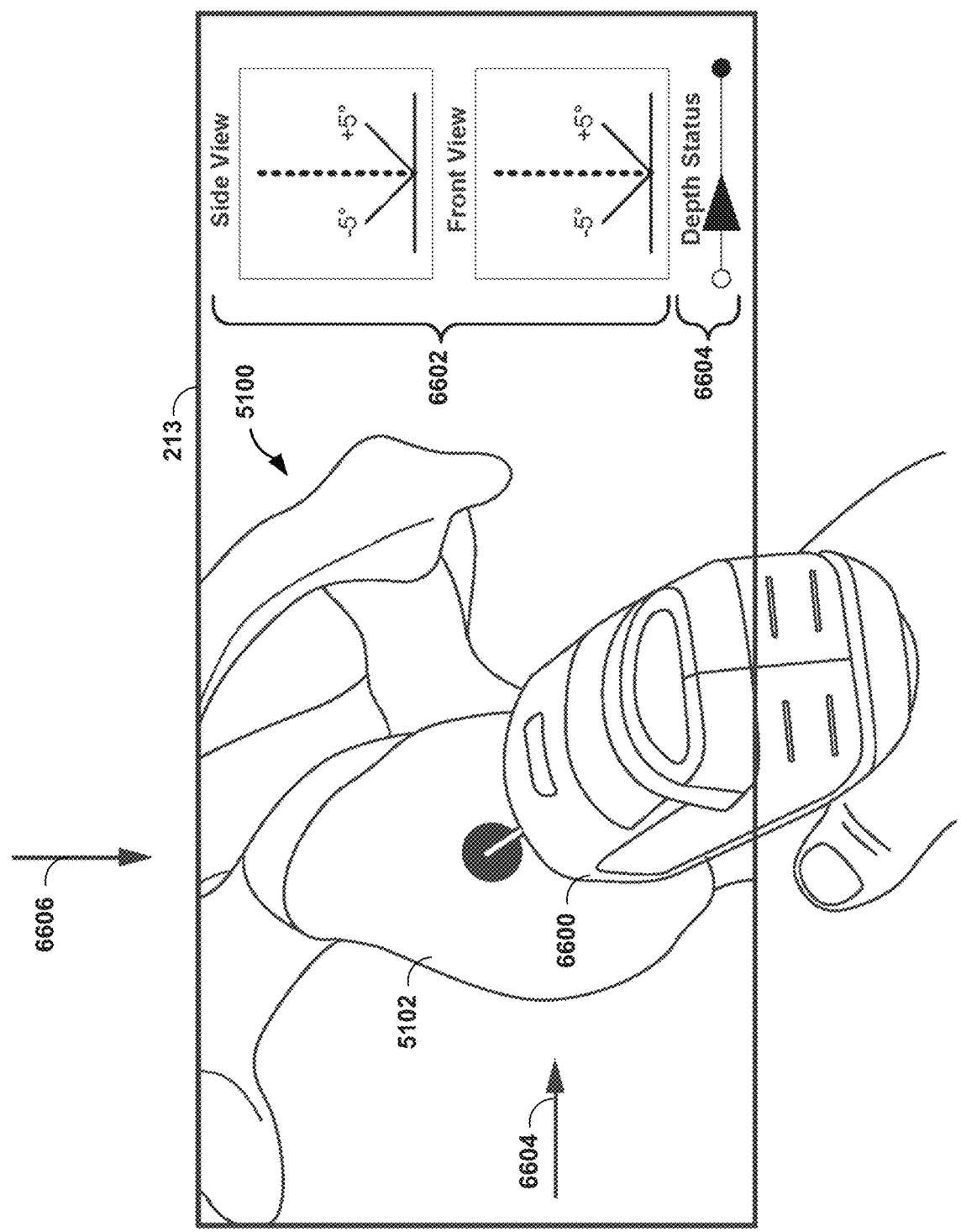
FIG. 66 is a conceptual diagram of virtual guidance that may be provided by an MR system in a shoulder arthroplasty procedure, in accordance with one or more techniques of this disclosure.

FIG. 66 is a conceptual diagram of virtual guidance that may be provided by an MR system, in accordance with one or more techniques of this disclosure. As shown in FIG. 66, a surgeon may view a portion of scapula 5100 through visualization device 213.

As discussed above, in some examples, the surgeon may utilize one or more tools to perform work on portion of a patient's anatomy (e.g., scapula 5100, humerus 3200, etc.). For instance, the surgeon may utilize a drill, such as drill 6600, to install guide 5200, operate reaming tool 5300, operate drill bit 5400, and/or install screws 6400. However, as shown in FIG. 66, drill 6600 may obstruct at least some of the portion of scapula 5100 on which the surgeon is performing the work.

In accordance with one or more techniques of this disclosure, MR system 212 may utilize visualization device 213 to provide a surgeon with graphical targeting guidance 6602 and graphical depth guidance 6604 for work the surgeon is performing on the portion of scapula 5100 (or humerus 3200). For instance, to display graphical targeting guidance 6602, MR system 212 may determine a current orientation of the tool being used (e.g., drill 6600 or a bit/instrument attached thereto) and a target orientation (e.g., a target vector obtained via a virtual surgical plan). MR system 212 may determine the current orientation of the tool being used using any number of techniques. As one example, MR system 212 may determine the current orientation of the tool being used based on orientation data received from one or more sensors (e.g., accelerometers, gyroscopes, etc.) attached to the tool. As another example, MR system 212 may determine the current orientation of the tool being used based on data captured by one or more sensors of visualization device 213 (e.g., optical cameras 530, depth cameras 532, etc.).

In some examples, MR system 212 may display graphical targeting guidance 6602 as a graphical representation of one or more viewpoints (in addition to the viewpoint of the surgeon). The graphical representations may be referred to as synthesized views. For example, as shown in FIG. 66, MR system 212 may display a graphical representation of a side view from the viewpoint indicated by arrow 6606 and a graphical representation of a top view from the viewpoint indicated by arrow 6606. The side view may be a left side view or a right-side view. Similarly, the top view may be a bottom view. In some examples, the display of top/bottom/left/right views may be selectable by the surgeon. Additionally or alternatively, MR system 212 may automatically select which views to display (e.g., select default views) based on whether the surgical procedure is being performed on a left or right side of the patient.

In FIG. 66 the graphical representations of the additional viewpoints show a relative angular difference between a current orientation of the tool being used (e.g., drill 6600 or a bit/instrument attached thereto) and a target orientation (e.g., a target vector). Other graphical representations that may be displayed by MR system 212 include, but are not limited to, reticles, numerical values (e.g., a numerical value of the relative angular difference), symbolic representations (e.g., checkmarks/Xes, colored shading, etc.), or any other graphical representation of a relationship between a current orientation of the tool being used and a target vector extending to a target position on the bone (e.g., a glenoid of a scapula, a humerus, or any other bone). It is understood that MR system 212 may display the additional viewpoints in addition to or in place of other virtual guidance. For instance, MR system 212 may simultaneously display the additional view points and a virtual axis/cutting surface.

For instance, to display graphical depth guidance 6604, MR system 212 may determine a current depth of the tool being used (e.g., drill 6600 or a bit/instrument attached thereto) and a target depth (e.g., a target depth obtained via a virtual surgical plan). MR system 212 may determine the current depth of the tool being used using any number of techniques. As one example, MR system 212 may determine the current depth of the tool being used based on orientation data received from one or more sensors (e.g., accelerometers, gyroscopes, etc.) attached to the tool. As another example, MR system 212 may determine the current depth of the tool being used based on data captured by one or more sensors of visualization device 213 (e.g., optical cameras 530, depth cameras 532, etc.). As another example, MR system 212 may determine the current depth of the tool as described herein with reference to FIGS. 73-79.

MR system 212 may display graphical depth guidance 6604 as a graphical representation of a relationship between the current depth and the target depth. In FIG. 66 the graphical representation of the relationship between the current depth and the target depth is shown as an arrow that advances from a starting depth (illustrated as a white circle in this example) and the target depth (illustrated as a black circle in this example). Other graphical representations that may be displayed by MR system 212 include, but are not limited to, numerical values (e.g., a numerical value of the remaining depth; a numerical value of the current depth and a numerical value of the target depth; etc.), symbolic representations (e.g., a checkmark when the target depth has been achieved, colored shading, etc.), or any other graphical representation of a relationship between the current depth and the target depth.

As discussed herein, visualization device 213 of MR system 212 may display the virtual guidance on a lens through-which the surgeon is viewing the patient's anatomy. As such, in some examples, the virtual guidance may be regarded as mixed reality (MR) guidance.

MR system 212 may output guidance in other forms in addition to or in place of the graphical guidance (targeting and/or depth). For instance, MR system 212 may output audio and/or haptic guidance for one or both of targeting and depth. As one example, MR system 212 may output haptic depth guidance by causing one or both of a tool currently being used and/or visualization device 213 to vibrate when the target depth is reached. As another example, MR system 212 may output haptic targeting guidance by causing one or both of a tool currently being used and/or visualization device 213 to vibrate when the orientation of the tool drifts more than a threshold amount from the target orientation.

As another example, MR system 212 may output audio depth guidance by causing visualization device 213 to output an audible representation of a difference between the current depth and the target depth. For instance, visualization device 213 may output a tone that increases in volume as the target depth is approached and changes frequency when the target depth is reached. As another example, MR system 212 may output audio targeting guidance by causing visualization device 213 to output audio to indicate when the orientation of the tool drifts more than a threshold amount from the target orientation.

For instance, visualization device 213 may output a tone in a left ear of the surgeon in response to determining that the tool is drifting left of the target orientation and a tone in a right ear of the surgeon in response to determining that the tool is drifting right of the target orientation. Similarly, visualization device 213 may output a tone perceived by the surgeon as being above the surgeon in response to determining that the tool is drifting up from of the target orientation and a tone perceived by the surgeon as being below the surgeon in response to determining that the tool is drifting down from the target orientation In some examples, visualization device 213 (e.g., via one or more of sensory devices 526) may output the audio targeting guidance using three-dimensional audio. For instance, visualization device 213 may output a tone to be perceived as being in front of/to the left of/to the right of/behind/above/below the surgeon in response to determining that the tool is drifting in a corresponding direction.

While illustrated as being from certain view angles and orientations, it is noted that the virtual guidance described herein may be displayed from any view angle or orientation. For instance, the relative position of a virtual guide (e.g., axis, point, surface, etc.) to an observed anatomical object may be maintained even as a user of visualization device 213 moves their head and/or moves around the patient's anatomy.

As discussed above, MR system 212 may register virtual models of a patient's anatomy with corresponding observed anatomy. As one example, MR system 212 may register a virtual model of a patient's glenoid with the patient's actual glenoid as observed by one or more sensors of visualization device 213. As another example, MR system 212 may register a virtual model of a patient's humerus with the patient's actual humerus as observed by one or more sensors of visualization device 213.

In some examples, an initial registration may be sufficient to support MR system 212 providing virtual guidance for all work steps performed on a particular piece of anatomy. For instance, an initial registration of the virtual model of a patient's glenoid with the patient's actual glenoid as observed by one or more sensors of visualization device 213 may be sufficient to enable MR system 212 to provide virtual guidance for all work steps performed on the glenoid (e.g., installation of a guide pin, reaming, creating anchorage points, etc.).

However, in some examples, MR system 212 may perform additional registrations. For instance, after performing a particular work step on a piece of anatomy, MR system 212 may re-register a virtual model of the piece of anatomy that takes into account the work step performed (e.g., an additional virtual model that incorporates planned work). As one example, after a surgeon reams a patient's glenoid, MR system 212 may obtain a subsequent virtual model of the glenoid that includes the planned reaming and register the subsequent virtual model to the observed reamed glenoid in a manner similar to the registration process described above with reference to FIGS. 17-20.

In some examples, MR system 212 may be configured to provide instructions for how the surgeon is to perform steps of the workflow. For instance, in response to user input (e.g., voice commands, gestures, etc.), MR system 212 may display an animation, video, or text to describe how a particular step or steps are to be performed. The instructions may be general or may be patient specific.

As discussed above, MR system 212 may provide virtual guidance for performing work on a patient. For instance, visualization device 213 may display virtual guidance to a surgeon using visualization device 213. Additionally, as discussed herein, other individuals may use visualization devices. MR system 212 may provide virtual guidance to multiple individuals using respective visualization devices. The virtual guidance may be same for all individuals or may different. For instance, MR system 212 may provide different virtual guidance to different individuals that is tailored to the individuals' roles in the operating room.

For purposes of illustration several figures show more of the patient's anatomy than would actually be visible during surgery (e.g., as portions would be obscured by tissue). For instance, FIG. 34 illustrates more of humerus 3200 than would actually be visible during surgery and FIG. 51 illustrates more of scapula 5100 than would actually be visible during surgery.

As discussed above, in some examples, MR system 212 may display a virtual model of a portion of a patient's anatomy overlaid on an observed portion of the patient's anatomy. For instance, during a registration procedure, visualization device 213 may display a 3D virtual model of a patient's glenoid overlaid on the patient's actual glenoid. The 3D virtual model may appear, for example, to be within a real-world environment with the actual glenoid. In some examples, MR system 212 may only display the virtual model during the registration process. In other examples, MR system 212 may display the virtual model during other portions of the surgical procedure. For instance, MR system 212 may display a virtual model of a portion of a patient's anatomy overlaid on an actual portion of the patient's anatomy while the surgeon performs work (e.g., cutting, drilling, reaming, prosthesis attachment, trialing, etc.) on the actual portion of the patient's anatomy.

In some examples, MR system 212 may display the virtual model such that the virtual model obscures a corresponding portion of the patient's anatomy. In some examples, MR system 212 may display the virtual model such that the virtual model does not completely obscure a corresponding portion of the patient's anatomy (e.g., display at least some of the virtual model overlaid on the corresponding portion of the patient's anatomy). As one example, MR system 212 may display the virtual model such that a region of interest on the actual portion of the patient's anatomy (e.g., a location on the patient's anatomy at which work is to be performed) is not obscured (at least not totally obscured) by the virtual model. For instance, MR system 212 may display the virtual model such that a location on the anatomy indicated by a virtual guide (e.g., corresponding to the region of interest on the actual portion of the patient's anatomy) is not completely obscured by the displayed virtual model. For example, MR system 212 may display a virtual model of a glenoid with a "hole" or missing region surrounding the area at which the guide pin is to be installed. The "hole" or missing region may be referred to as a virtual hole in the virtual model. As another example, MR system 212 may display an outline of the virtual model.

Figure 69:
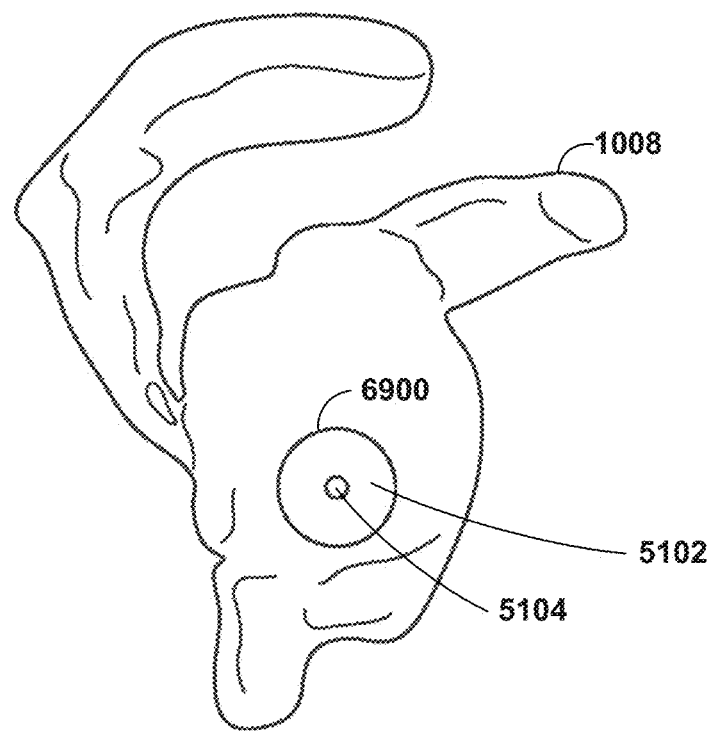
FIG. 69 is a conceptual diagram illustrating an example virtual model with a missing region surrounding an area of interest.
Figure 70:
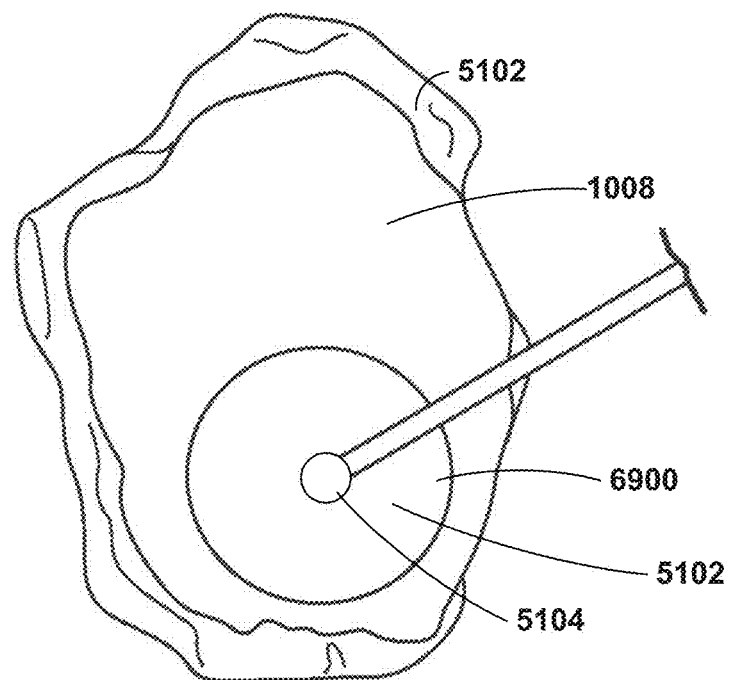
FIG. 70 is a conceptual diagram illustrating an example virtual model with a missing region surrounding an area of interest.

FIGS. 69 and 70 are conceptual diagrams illustrating example virtual models with missing regions surrounding areas of interest. Similar to FIG. 51, FIGS. 69 and 70 are other examples of virtual guidance to assist a surgeon in installing a guide pin. As shown in FIGS. 69 and 70, MR system 212 may display virtual bone model 1008 as including virtual hole 6900 surrounding a region that includes a virtual guide such as virtual axis 5104 (i.e., a region corresponding to a location on the anatomy indicated by a virtual guide). As can be seen, while at least some of virtual bone model 1008 is still displayed, a portion of glenoid 5102 is unobscured by virtual bone model 1008 due to the inclusion of virtual hole 6900.

In some examples, the virtual hole may have a hard boundary. In some examples, MR system 212 may display the virtual model as fading (e.g., in opacity) as the location on the anatomy indicated by the virtual guide is approached. For instance, MR system 212 may display a perimeter of the virtual model with a particular opacity and reduce the opacity (e.g., fade the virtual model out) in the direction of the location on the anatomy.

Figure 71:
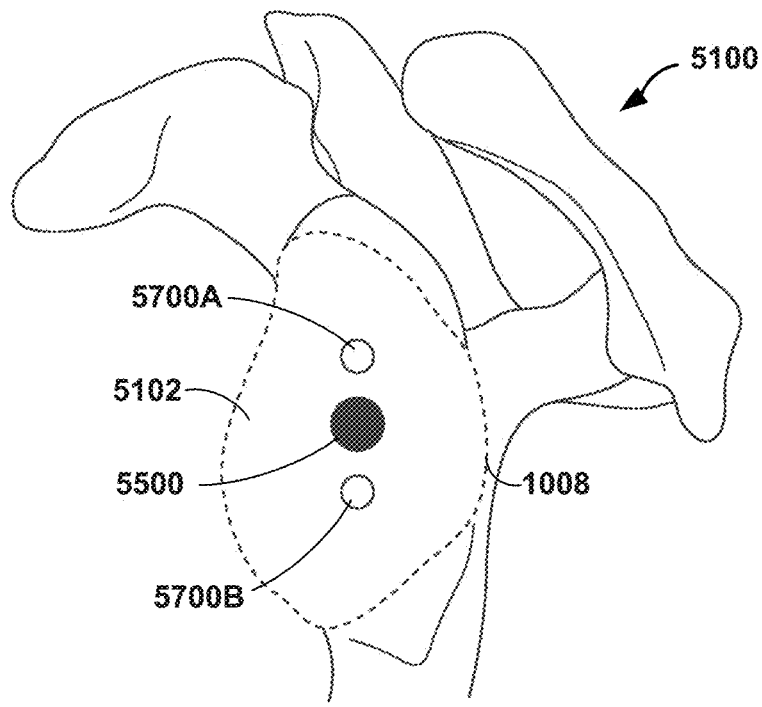
FIG. 71 is a conceptual diagram illustrating an example virtual model with a missing region surrounding an area of interest.

FIG. 71 is a conceptual diagram illustrating an example virtual model with a missing region surrounding an area of interest. Similar to FIG. 57, FIG. 71 is another example of virtual guidance to assist a surgeon creating anchorage points. As shown in FIG. 71, MR system 212 may display virtual bone model 1008 as a perimeter around glenoid 5102. As can be seen, while at least some of virtual bone model 1008 is still displayed, a portion of glenoid 5102 is unobscured by virtual bone model 1008.

Presenting a virtual hole in the virtual model may provide the surgeon with a better view of an actual, real anatomical surface, such as a bone surface, promoting visibility of the surface as the surgeon performs operations to prepare the surface to receive a prosthetic implant or operations for placement of the prosthetic implant on the surface. Maintaining at least some display of the virtual model while work is being performed may provide one or more advantages. For instance, if at least a portion of the virtual model (e.g., a perimeter, an outline, a virtual model with a hole, etc.) is displayed while work is being performed with the assistance of virtual guidance, the surgeon can be confident that MR system 212 is displaying the virtual guidance at the proper location(s). In particular, as the surgeon would be able to see that the displayed portion of the virtual model is properly aligned with the observed anatomy and the virtual guidance is displayed based on the position of the virtual model, the surgeon would be confident that MR system 212 is displaying the virtual guidance at the proper location(s).

As discussed above, in some examples, the surgeon may utilize one or more tools to perform work on portion of a patient's anatomy (e.g., scapula 5100, humerus 3200, etc.). For instance, the surgeon may utilize a drill, such as drill 6600, to install guide 5200, operate reaming tool 5300, operate drill bit 5400, and/or install screws 6400. Such tools may be powered and controllable, e.g., by a manual button, trigger, or switch. As also discussed above, in some examples, MR system 212 may provide virtual guidance to assist in the performance of the work. For instance, MR system 212 may provide targeting guidance, depth guidance, and the like.

In accordance with one or more techniques of this disclosure, a MR system may be configured to positively control operation of one or more tools used to perform work. For instance, MR system 212 may selectively adjust operation of a drill, such as drill 6600, based on whether the drill is accurately positioned on a virtual axis. Adjustment of operation may include powering the tool on, powering the tool off, enabling the tool to be manually powered on by the surgeon, disabling the tool from being manually powered on by the surgeon, and/or controlling a speed, torque or force of the tool, such as a rotational speed, torque or force. In this way, MR system 212 may achieve closed-loop control over one or more tools. In some examples, closed-loop control may be a function of the monitored positioning of the tool or a portion of the tool relative to prescribed axes, positions, angles or the like, which, in some examples, also may be illustrated visually to the surgeon by display of virtual guidance.

Figure 72:
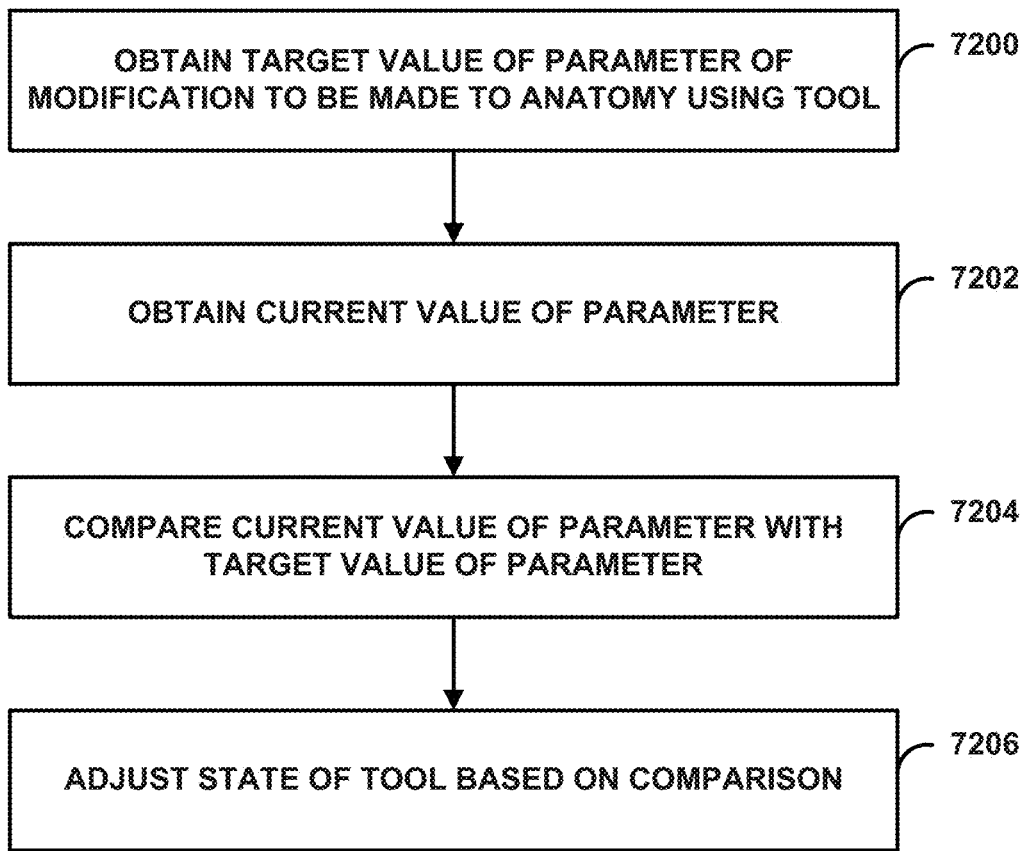
FIG. 72 is a flow diagram illustrating example techniques for closed loop tool control in surgical procedures, in accordance with one or more techniques of this disclosure.

FIG. 72 is a flow diagram illustrating example techniques for closed loop tool control in surgical procedures, in accordance with one or more techniques of this disclosure. In operation, MR system 212 may obtain, from a virtual surgical plan, a target value of a parameter of a modification to be made to a portion of a patient's anatomy with a tool (7200). Examples of parameters include, locations at which holes are to be drilled, depths (e.g., drilling depths, reaming depths, etc.), locations of cutting surfaces, etc. As one specific example, MR system 212 may obtain a location on a glenoid at which a guide pin is to be installed (e.g., the location on glenoid 5102 at which MR system 212 is described as displaying virtual axis 5104 in FIG. 51). As another specific example, MR system 212 may determine a depth to ream a glenoid.

MR system 212 may obtain a current value of the parameter (7202). As one example, MR system 212 may determine a current location/depth of the tool being used based on orientation data received from one or more sensors (e.g., accelerometers, gyroscopes, etc.) attached to the tool. For instance, MR system 212 may determine a current orientation of the tool based on data measured by an accelerometer attached to the tool. As another example, MR system 212 may determine the current location/depth of the tool being used based on data captured by one or more sensors of visualization device 213 (e.g., optical cameras 530, depth cameras 532, etc.). For instance, MR system 212 may register a virtual model of the tool to the observed tool. As another example, MR system 212 may determine the current location/depth of the tool as described herein with reference to FIGS. 73-79.

MR system 212 may compare the current value of the parameter and the target value of the parameter (7204). As one example, MR system 212 may determine a difference between a current orientation/axis of the tool and a target axis. In some examples, the target axis may be illustrated by a virtual guidance axis displayed by MR system 212 for viewing by the surgeon, e.g., to aid the surgeon in aligning the tool (e.g., such as a drill bit reaming shaft) with an axis prescribed by the surgical plan. Similarly, other virtual guidance such as virtual placement markers, angle indications or depth indications and/or other virtual guidance may be displayed as virtual guidance during detection and modification of a parameter of the tool. In other examples, the parameter or parameters of the tool may be controlled, e.g., by MR system 212, and the parameter monitored without displaying a virtual guidance axis, virtual placement markers, virtual angle indications, virtual depth indications, and/or other virtual guidance. For instance, MR system 212 may determine that the current orientation/axis of the tool is 5 degrees off from a target axis (e.g., MR system 212 may determine a difference between the current orientation of the tool (as determined based on data measured by an accelerometer attached to the tool) and a prescribed axis is 5 degrees). As another example, MR system 212 may determine a difference between a current depth of the tool and a target depth. For instance, where the current depth is 3 mm, e.g., from an initial drilling surface plane, and the target depth is 7 mm, MR system 212 may determine that the current depth is 4 mm short of the target depth.

MR system 212 may automatically and selectively adjust a state of the tool based on the comparison (7206). As one example, MR system 212 may gate operation of the tool based on the comparison. For instance, MR system 212 may allow operation of the tool where the difference between the target value and the current value is less than a threshold. For example, MR system 212 may activate the tool or enable power to permit a surgeon to manually activate the tool. Similarly, MR system 212 may prevent operation of the tool where the difference between the target value and the current value is greater than a threshold. For example, MR system 212 may deactivate the tool or disable power so that the surgeon is not permitted to manually activate the tool. As another example, MR system 212 may throttle speed, torque, force or another operating parameter or otherwise limit operation of the tool based on the comparison. For instance, MR system 212 may allow operation of the tool at full power where the difference between the target value and the current value is less than a threshold. Similarly, MR system 212 may reduce the operating power (e.g., rotational speed, torque output, etc.) of the tool where the difference between the target value and the current value is greater than a threshold. For instance, MR system 212 may reduce the operating power by some function of the difference between the target value and the current value.

While MR system 212 is described as automatically and selectively adjusting the state of the tool, actual activation/deactivation of the tool may be manually performed by the surgeon. For instance, where MR system 212 is allowing operation of the tool, the tool may not actually activate until the surgeon pulls a trigger or actuates a button or other control input of the tool, e.g., a trigger or button of a drill motor of the tool. Additionally, in some examples, MR system 212 and/or the tool may include an override that enables the surgeon to activate the tool regardless of whether MR system 212 is currently allowing operation of the tool.

MR system 212 and the tool may communicate via any suitable manner. Both wired and wireless communication links are contemplated. For instance, MR system 212 and the tool may communicate over a Bluetooth link, a Wi-Fi link (e.g., according to any of the IEEE 802.11 standards), a wired serial connection (e.g., RS-232 or USB), 3G, 4G or 5G, or any other suitable communication link.

MR system 212 may enforce the positive control over the tool via the communication link or any other technique. As one example, MR system 212 may output, via the communication link, data to the tool indicating whether operation of the tool is being gated or throttled. As another example, MR system 212 may control a power supply of the tool such that MR system 212 may prevent the tool from receiving power (or adjust the amount of power received) when operation of the tool is being gated or throttled. For instance, the tool may be powered via a "smart plug" and MR system 212 may control activation of the smart plug when operation of the tool is being gated or throttled. In addition, the activated, deactivated or otherwise adjusted status of the tool may be communicated to the surgeon, e.g., audibly or visually via augmented reality (AR) or MR content displayed by MR system 212.

The tool may be any type of tool usable by a surgeon. Examples of tools include, but are not limited to, drills, saws, lasers, and any other type of tool used during surgery. Such tools may be manually driven by the surgeon or powered by a motor, such as a rotating or reciprocating motor or a vibrating motor, such as a piezoelectric generator. The tool may be considered to be manually guidable in that the position/orientation/location of the tool is controlled by the surgeon by moving and/or rotating the tool. As such, in some examples, the tool may be considered to be a hand-held tool, such as a hand-held drill, e.g., having a drill motor and a chuck or other interface to receive a shaft carrying a working bit, such as a drill bit, reaming element, or other working element.

The positive control of the tool may be used in conjunction with any other techniques of this disclosure. For instance, MR system 212 may both provide virtual graphical guidance and positive tool control as described above. As one specific example, MR system 212 may provide the virtual graphical guidance discussed above with reference to FIG. 66 at the same time MR system 212 is performing closed-loop tool control.

Figure 67:
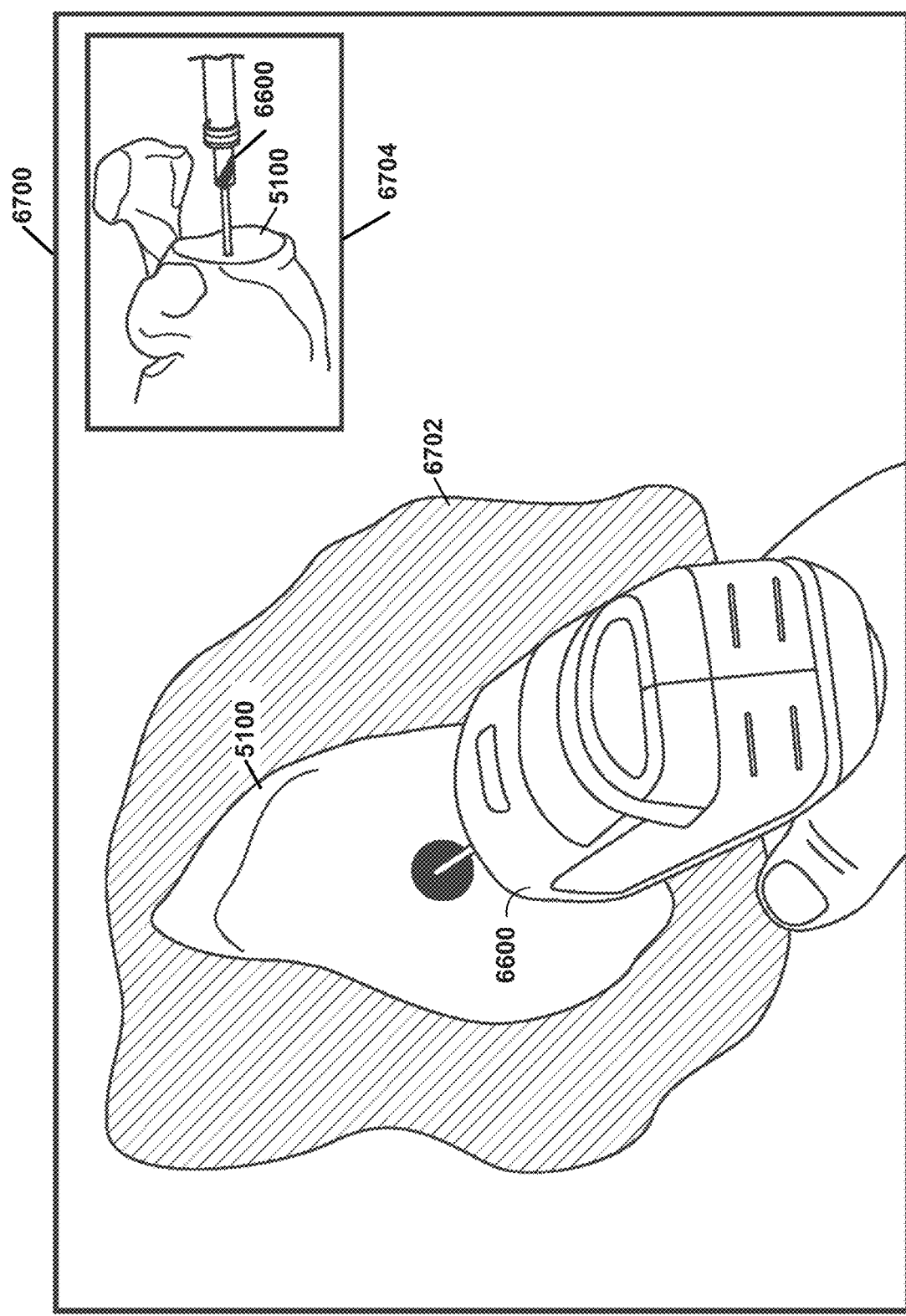
FIG. 67 is a conceptual diagram of an example view that may be provided by an MR system in a shoulder arthroplasty procedure and that provides a secondary view window, in accordance with one or more techniques of this disclosure.

FIG. 67 is a conceptual diagram of an example view 6700 that may be provided by an MR system and that provides a secondary view window, in accordance with one or more techniques of this disclosure. The example of FIG. 67 shows what a surgeon may see while using an MR visualization device (e.g., visualization device 213) during an orthopedic shoulder surgery. Particularly, in the example of FIG. 67, the surgeon may view an exposed portion of scapula 5100 and an area of tissue 6702 that surrounds the exposed portion of scapula 5100.

As discussed above with respect to FIG. 66, the surgeon may use one or more tools to perform work on portion of a patient's anatomy (e.g., scapula 5100, humerus 3200, etc.). For instance, the surgeon may use a drill, such as drill 6600, to install guide 5200, operate reaming tool 5300, operate drill bit 5400, and/or install screws 6400. However, as shown in FIG. 67, drill 6600 may obstruct at least some of the portion of scapula 5100 on which the surgeon is performing the work. Furthermore, it may be challenging for the surgeon to assess how deeply a tool, such as a bit of drill 6600, has penetrated a tissue or a bone. This may be especially challenging when the surgeon is looking down the length of a drill, such as drill 6600.

Hence, in accordance with one or more techniques of this disclosure, visualization device 213 of MR system 212 may generate a MR visualization that includes a secondary view window 6704, which may be a sub-window overlaid or otherwise composed with any contents, such as other virtual guidance, of a main window. Secondary view window 6704, along with other virtual guidance (e.g., virtual markers, depth guidance, etc.) may appear along with physical, real-world objects in the surgeon's field of view. Thus, in the example of FIG. 67, the surgeon may see secondary view window 6704 along with the exposed portion of scapula 5100, tissue 6702, and drill 6600, as well as any virtual guidance such as a virtual axis or virtual entry point. In some examples, the surgeon or other user may resize or reposition secondary view window 6704.

Secondary view window 6704 contains images representing a different perspective on a surgical site. For instance, in the example of FIG. 67, the surgical site is a patient's glenoid and the surgeon is drilling a hole in the exposed glenoid portion of the patient's scapula 5100. Furthermore, in the example of FIG. 67, the surgeon's perspective is substantially down an axis of drill 6600. Relative to the patient, the surgeon's perspective in FIG. 67 is in a frontal axis of the patient. Accordingly, in the example of FIG. 67, secondary view window 6704 contains images representing the glenoid portion of the patient's scapula from a perspective other than down the axis of drill 6600. That is, in the example of FIG. 67, the images in secondary view window 6704 are not in any frontal axis of the patient. Rather, in the example of FIG. 67, the images presented in secondary view window 6704 are from a perspective 90° rotated from the perspective of the surgeon. For instance, relative to the patient, the images presented in secondary view window 6704 may be in a sagittal axis.

The surgeon may use secondary view window 6704 to check the depth to which the tool has penetrated. For instance, in the example of FIG. 67, the surgeon may use secondary view window 6704 to determine how far a bit of drill 6600 has penetrated scapula 5100.

The images presented in secondary view window 6704 may be generated in various ways. For instance, in one example, the images presented in secondary view window 6704 may be captured by a video camera. In some such examples, the video camera may be worn or held by a person other than the surgeon, such as a nurse. For instance, the video camera may be mounted on a visualization device worn by a nurse (e.g., a visualization device of MR system 1800B (FIG. 18). In some examples, the video camera may be mounted on a fixed wall, mechanical arm, robot, or other physical object.

In other examples, the images presented in secondary view window 6704 may comprise or consist of virtual objects. For instance, the images presented in secondary view window 6704 may include a virtual 3-dimensional model of the patient's anatomy. Additionally, the images presented in secondary view window 6704 may include a virtual 3-dimensional model of a tool being used by the surgeon. Thus, in the example of FIG. 67, secondary view window 6704 may include a virtual 3-dimensional model of the patient's scapula 5100 and a virtual 3-dimensional model of drill 6600. The virtual 3-dimensional model of the patient's anatomy may be the same as that used during preoperative planning of the surgery. In addition, in some examples, secondary view window 6704 may include virtual guidance such as a virtual reaming or drilling axis, a virtual cutting plan, a virtual entry point or the like.

In examples where the images presented in secondary view window 6704 comprise or consist of virtual objects, the patient's anatomy may be registered with a corresponding virtual model of the patient's anatomy, as described elsewhere in this disclosure. For instance, the patient's glenoid may be registered to a virtual model of the patient's glenoid. Thus, a computing system (e.g., MR system 212 (FIG. 2) may be able to determine the position and orientation of the patient's anatomy in a 3-dimensional space. Furthermore, the computing system may receive information from one or more sensors (e.g., cameras, motion sensors, etc.) that enable the computing system to determine a location of a tool (e.g., drill 6600) in the same 3-dimensional space. One or more markers on the tool may assist the computing system in identifying the location of the tool. Accordingly, the computing system may determine the position of the tool relative the patient's anatomy. The computing system may generate the images of secondary view window 6704 based on the relative positions of the patient's anatomy and the tool. Thus, in the example of FIG. 67, the computing system may generate a MR visualization in secondary view window 6704 that shows the relative positions of the virtual 3-dimensional models of the patient's scapula 5100 and a bit of drill 6600.

Presenting virtual 3-dimensional models of the patient's anatomy and a tool used by the surgeon may address a certain set of challenges. For instance, in examples where a nurse holds or wears a camera that feeds images into secondary view window 6704, the nurse's natural movements may create camera shake that may be distracting to the surgeon. To compensate for camera shake, a computing system may need to apply image stabilization, which may be computationally expensive, potentially resulting in battery drain, and may result in a reduced field of view. Furthermore, virtual 3-dimensional models in secondary view window 6704 do not suffer from camera shake in this way, which may conserve computation resources otherwise expended on image stabilizing, as well as potentially increased field of view and reduced surgeon distraction.

Another potential advantage of using virtual 3-dimensional models may be that unneeded background information may be omitted from secondary view window 6704. For instance, in the example of FIG. 67, tissue 6702 may be omitted from the images presented in secondary view window 6704. Omitting unneeded background information may further reduce visual distraction for the surgeon. Furthermore, the surgeon may be able to rotate or otherwise change the perspective of the virtual 3-dimensional models shown in secondary view window 6704 to angles that may be impractical for a human nurse to obtain with a handheld or head-worn camera. Accordingly, fixed position video cameras or mechanical-arm mounted cameras may need to be used to achieve the perspective that the surgeon may want. The use of virtual 3-dimensional models may eliminate the need for expending hospital resources on such cameras and mounting systems.

Figure 68:
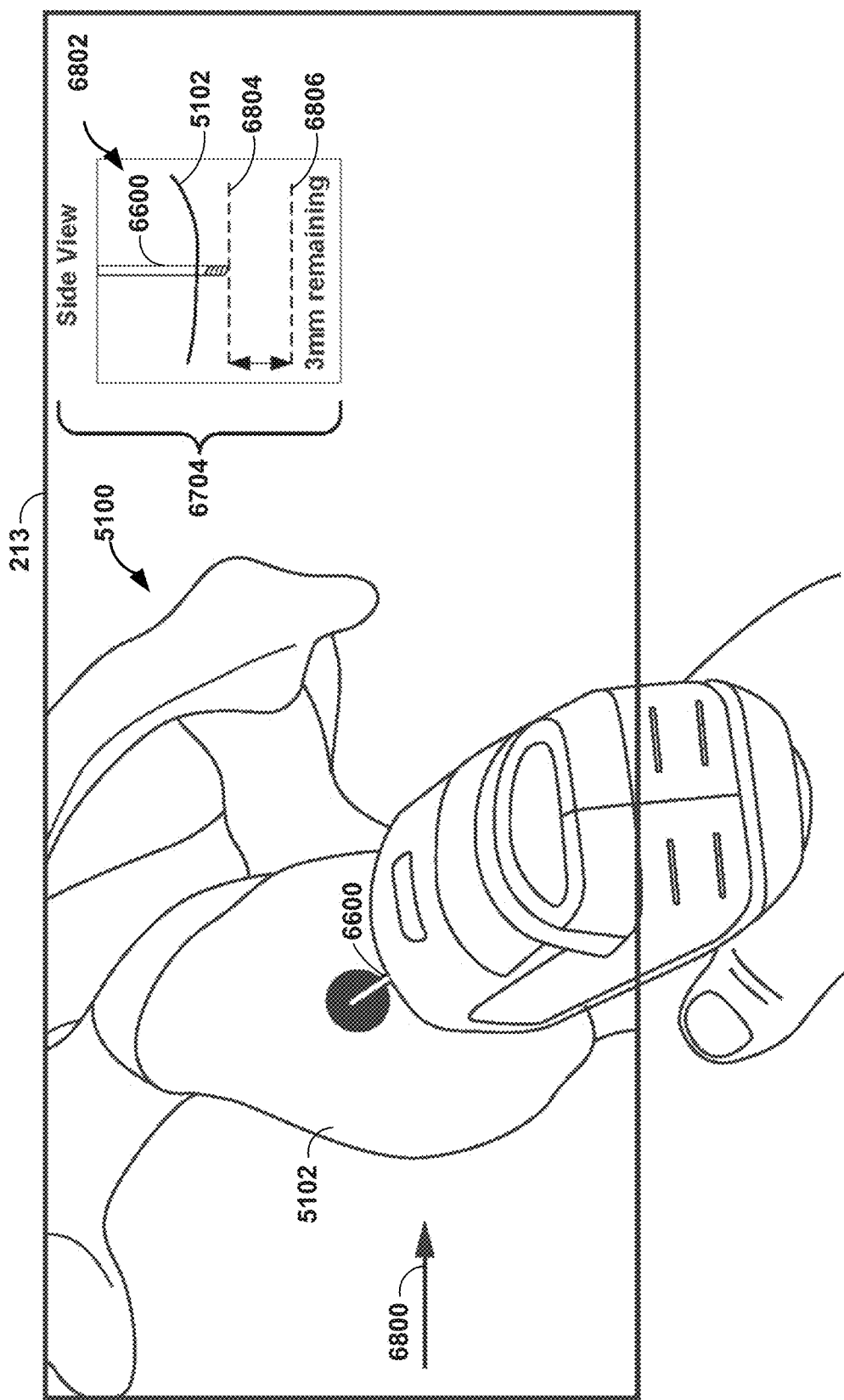
FIG. 68 is a conceptual diagram in which an MR system displays graphical depth guidance that includes an illustration that depicts a location of a drill relative to a scapula in a shoulder arthroplasty procedure.

In some examples, MR system 212 may display graphical depth guidance by displaying an illustration of a location of a portion of the anatomy and a location of a tool relative to the portion of the anatomy. For example, as illustrated in FIG. 68, MR system 212 may display a secondary view window 6704 that includes image 6802, which depicts a location of drill 6600 relative to scapula 5100. As shown in FIG. 68, image 6802 may further depict current depth 6804 and target depth 6806. As discussed above, the depth guidance may include a numerical value of a difference between current depth 6804 and target depth 6806 (i.e., "3 mm remaining").

MR system 212 may render the illustration of the location of the portion of the anatomy and the location of the tool relative to the portion of the anatomy may from any view (e.g., top view, left side view, right side view, above view, below view, etc.). In the example of FIG. 68, MR system 212 renders the image from the side view indicated by arrow 6800.

As described elsewhere in this disclosure, a computing system (e.g., virtual planning system 102) may generate an information model of a surgery. The information model of the surgery describes a surgical workflow that comprises a series of steps that a surgeon would perform in order to complete a surgery. For example, the surgical workflow may comprise the series of steps shown in the example of FIG. 19. Furthermore, as described elsewhere in this disclosure, a computing system (e.g., intraoperative guidance system 108 (FIG. 1), computing systems 11706 (FIG. 117), etc.) may mark steps of the surgical workflow as complete as the surgeon progresses through the surgical workflow.

In accordance with a technique of this disclosure, MR system 212 may automatically display secondary view window 6704 at appropriate steps of the surgical workflow and hide secondary view window 6704 at other steps of the surgical workflow. For example, MR system 212 may show secondary view window 6704 during steps of the surgical workflow in which the surgeon uses a drill and hide secondary view window 6704 otherwise. Furthermore, in some examples, default perspectives of secondary view window 6704 when showing virtual 3-dimensional models may be tied to steps in the surgical workflow. For instance, in one example, secondary view window 6704 may have a default perspective along a frontal axis of the patient in one step of the surgical workflow and may have a default perspective along a longitudinal axis of the patient in another step of the surgical workflow. The default perspective may be a perspective of secondary view window 6704 presented before a user modifies the perspective of secondary view window 6704.

Another aspect of this disclosure is directed to a mixed reality (MR)-based technique for tracking and presenting depth of a tooling bit in a medical procedure. The techniques may be particularly useful for orthopedic medical procedures, such as shoulder surgeries, ankle surgeries, knee surgeries, hip surgeries, or any joint repair surgical procedure or augmentation. Although the techniques may be useful in a wide variety of orthopedic procedures, they may be especially useful in both anatomical and reverse-anatomical shoulder reconstruction surgeries. Indeed, the techniques may be helpful for reversed arthroplasty, augmented reverse arthroplasty, standard total shoulder arthroplasty, augmented total shoulder arthroplasty, hemispherical should surgery, or other types of shoulder surgery. Even more specifically, the techniques may be especially useful in mixed reality (MR)-based techniques for glenoid reaming, e.g., reaming of glenoid bone to condition a bone surface to receive an implant, in an anatomical shoulder reconstruction surgery.

In general, the tooling bit that is being tracked for depth-tracking may comprise any type of medical tool, including a drill bit, a reaming element, a grinding element, or any element that is configured to rotate on a rotating shaft.

The techniques may be used for drilling, reaming or grinding to a desired depth, e.g., relative to a fixed or known location, such as a starting point of the tooling bit at the start of the drilling, reaming or grinding process. In some examples, the starting point is defined by a virtual plane, which may be selected by the user to initialize the drilling, reaming or grinding process. After defining the starting point, downward movement of the depth aid element along the axis can be used to track downward depth of the tooling bit.

For anatomical shoulder reconstruction surgeries, for example, the techniques and tools described herein may be well-suited for tracking depth of a reaming tool when performing reaming on a glenoid bone of a patient. In some examples, mixed reality (MR) devices (e.g., mixed reality headset), such as visualization device 213 of MR system 212, may be used to implement one or more depth cameras according to this disclosure. An MR device such as visualization device 213 may be an example of an MR system 212. For instance, an MR device may be an MR system that is enclosed within a housing. The MR device, equipped with one or more depth cameras, may be configured to detect and track a depth of point of a tooling bit relative to a target depth. In some examples, the MR device is able to track displacement relative to a starting point, which may be determined by a registration process. For example, after drilling and inserting a guide pin, and upon placing a reaming element at a reaming location of the guide pin, a registration process may be performed on a depth tracking element, and thereafter, depth tracking of the depth tracking element may be used as a proxy for depth tracking of the reaming element.

Depth tracking of the tooling bit may be based upon depth tracking of another element that is positioned a fixed and known distance from the tooling bit along a rotational axis associated with the tooling bit. In some examples, the techniques use mixed reality to track the depth of something that moves co-axially with the tooling bit. For example, the techniques may use a depth aid element located at a fixed and known location relative to the tooling bit. Or alternatively, rather than adding a depth aid element, the techniques may track a medical drill housing, or another element of the medical device. In yet another example, the techniques may track a backside of the tooling bit, which may be the back side of a reaming element.

Mixed reality may be used for the tracking, and a registration process may be performed to register a virtual element to the medical device. For example, the virtual element may be registered to a depth aid element of the device, or possibly to a medical device housing of a surgical drill, or possibly to the backside of the tooling bit. The virtual element may correspond to a shape of a portion of the device or a shape of a depth aid element, or in some cases, the virtual element may simply comprise depth plane that is orthogonal to an axis of the tooling bit and positioned a fixed and known distance from the tooling bit. This disclosure contemplates depth tracking with depth cameras. In some cases, the depth cameras are part of a mixed reality system such as MR system 212, but in other cases, the depth cameras may operate outside of a mixed reality environment.

Figure 73:
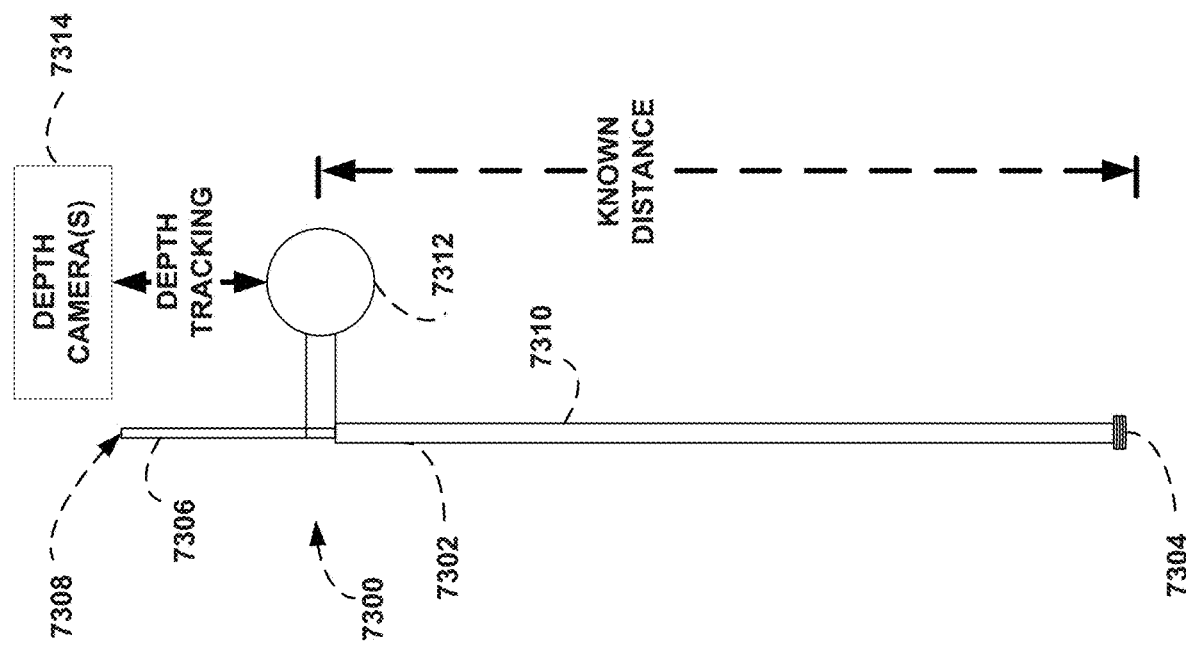
FIG. 73 is a conceptual side view of a portion of a medical device and depth cameras consistent with an example of this disclosure.

FIG. 73 is a conceptual side view of a portion of a medical device 7300 and depth cameras 7314 consistent with an example of this disclosure. In some examples, drill 6600 (FIG. 66, FIG. 67) is an instance of medical device 7300. Medical device 7300 comprises a rotatable shaft 7302 and a tooling bit 7304 located on a distal end of rotatable shaft 7302. In this example, tooling bit 7304 may comprise a drilling element, e.g., designed for drilling into bone of a patient, or a reaming element, e.g., designed for reaming bone of a patient. The opposing proximal end 7308 of rotating shaft 7302 may be coupled to a medical drill that rotates shaft 7302 during the medical procedure. The medical drill may comprise a powered drill that is manually controlled by user actuation of a trigger or other user input or automatically controlled by a controller, e.g., in response to control signals such as control signals generated responsive to detected depth of the tooling bit. The medical drill may include a surgical motor that is coupled to shaft 7302 to rotate the shaft.

As shown in FIG. 73, medical device 7300 includes a depth aid element 7312 positioned at a fixed location relative to an axis of rotatable shaft 7302. Since depth aid element 7312 is positioned at a fixed location relative to tooling bit 7304 along an axis of rotatable shaft 7302, depth aid element 7312 moves co-linearly with tooling bit 7304 along the axis. In other words, depth aid element 7312 is positioned a known, fixed distance from tooling bit 7304 along rotatable shaft 7302. Therefore, tracking of the location of depth aid element 7312 along the axis can be used as a proxy for tracking of the location of tooling bit 7304. Accordingly, upon placing tooling bit 7304 at a desired tooling location of the patent, a system can track the location of depth aid element 7312 to monitor drilling depth of tooling bit 7304.

Depth cameras 7314 are configured to capture one or more images of the depth aid element 7312. For example, depth cameras 7314 may use multiple images from multiple cameras that are positioned at fixed and known locations relative to one another, and parallax calculations can be performed to determine the depth of depth aid element 7312. Prior to such depth tracking, a registration process may be performed so that depth cameras 7314 are properly registered to depth aid element 7312. Additional details on the depth aid registration process are described in greater detail below. In any case, the depth of depth aid element 7312 can be determined and used as a proxy for determining depth of tooling bit 7304. One or more processors (not shown in FIG. 73) can be configured to determine the depth of tooling bit 7304 along the rotatable axis, based on analysis of the images captured by depth cameras 7314, e.g., by performing the parallax calculations described above or other depth determination processing.

As one example, in order to position depth aid element 7312 at a known, fixed distance from tooling bit 7304, rotatable shaft 7302 may be configured to include a first portion 7306 that has a different diameter than a second portion 7310. The different diameters of first portion 7306 and second portion 7310 can create a mechanical stop for securing the position of depth aid element 7312. For example, depth aid element 7312 may include a hole that is sized similar to (and slightly larger than) a diameter of first portion 7306 and smaller than second portion 7310. In this way, depth aid element 7312 can be positioned properly such that it remains a known, fixed distance from tooling bit 7304 along rotatable shaft 7302. In other examples, however, a wide variety of other structures or techniques may be used to ensure that depth aid element 7312 is secured a known, fixed distance from tooling bit 7304 along rotatable shaft 7302. In some examples, a ring of ball bearings may be positioned at the physical point of interaction between depth aid element 7312 and second portion 7310 so as to reduce or substantially eliminate friction between depth aid element 7312 and second portion 7310. In some cases, depth aid element 7312 may be rotationally fixed, and in other cases, depth aid element 7312 may rotate along with rotating shaft 7302.

In order to facilitate good depth tracking of depth aid element 7312 by depth cameras 7314, depth aid element 7312 may be designed to include one or more spherically shaped elements (i.e., one or more spherical elements) or/and one or more cylindrically shaped elements (i.e., one or more cylindrical elements). Some or all of depth aid element 7312 may comprise a spherical or cylindrical element, or in some cases, multiple spheres and/or cylindrical elements may be included on depth aid element 7312. Substantially oversized spherical elements and/or cylindrical elements may facilitate better depth tracking than other shapes, although other shapes and sizes may be used. The spherical and/or cylindrical elements may be partially spherical, partially cylindrical, fully cylindrical, fully specially. Other examples of shapes that may be desirable for depth aid element may include cone shapes. The conical, spherical and/or cylindrical shapes may extend in a direction parallel to rotatable shaft 7302.

Also, it may be desirable for depth aid element 7312 to be relatively large in order to ensure that it can provide good depth tracking capabilities. For example, it may be advantageous to ensure that depth aid element 7312 is an oversized element to help with depth tracking, and e.g., it should usually be larger than other components of medical device 7300, such as the diameter of rotatable shaft 7302 and the diameter of tooling bit 7304. Additional details and desirable shapes of depth aid element 7312 are described in greater detail below.

In other examples, in order to facilitate good depth tracking of depth aid element 7312 by depth cameras 7314, depth aid element 7312 may be designed to include a planar surface that defines a plane that is perpendicular to an axis that is parallel to rotatable shaft 7302. In some examples, a planar surface may define a good feature for depth tracking, and in some examples, a planar surface may work better than spheres or cylinders. In some examples, depth aid element 7312 may include one or more planar surfaces in one or more planes that are perpendicular to an axis that is parallel to rotatable shaft 7302. In some examples, depth aid element 7312 may include one or more planar surfaces in combination with one or more cylindrical shapes and/or one or more spherical shapes. As a non-limiting example, the depth plane or depth aid elements may be sized in a range of approximately 15-30 mm.

Figure 74:
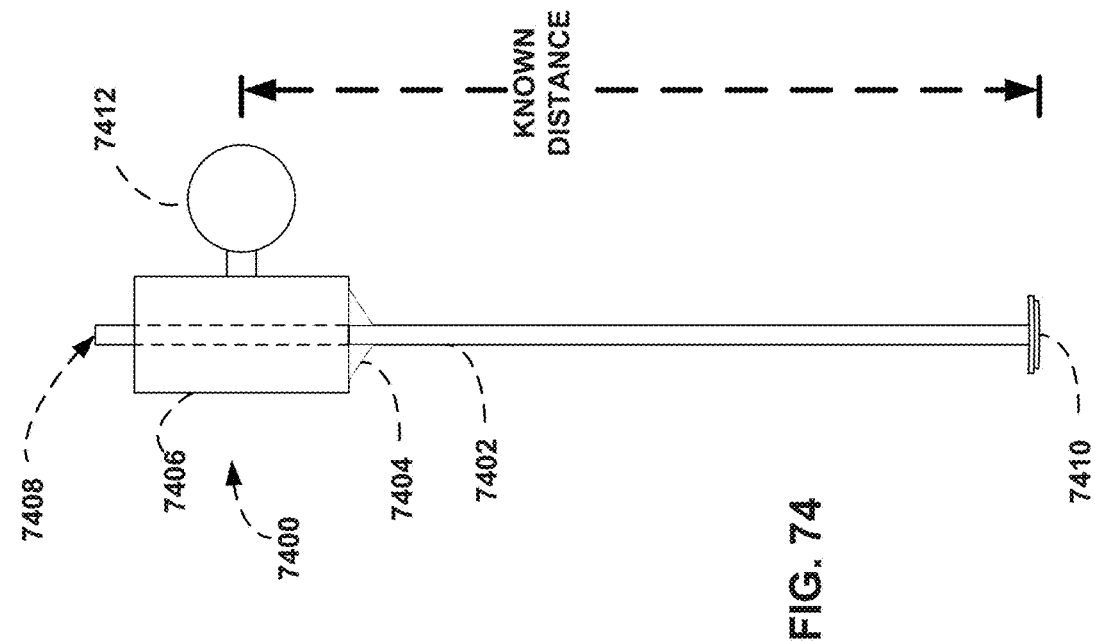
FIG. 74 is a conceptual side view of a portion of a medical device consistent with this disclosure.

FIG. 74 is a conceptual side view of a portion of a medical device 7400 consistent with an example of this disclosure. Medical device 7400 comprises a rotatable shaft 7402 and a tooling bit 7410 located on a distal end of rotatable shaft 7402. In this example, tooling bit 7410 may comprise a reaming element, e.g., designed for reaming a glenoid bone of a patient to remove bone and prepare the glenoid surface for an anatomical shoulder reconstruction surgery. The opposing proximal end 7408 of rotating shaft 7402 may be coupled to a medical reaming tool that rotates shaft 7402 during the procedure.

As shown in FIG. 74, medical device 7400 includes a depth aid element 7412 positioned at a fixed location relative to an axis of rotatable shaft 7402. Like in FIG. 73, in FIG. 74, since depth aid element 7412 is positioned at a fixed location relative to tooling bit 7410 along an axis of rotatable shaft 7402, depth aid element 7412 moves co-linearly with tooling bit 7410 along the axis. In other words, depth aid element 7412 is positioned at a known, fixed distance from tooling bit 7410 along rotatable shaft 7402. Therefore, tracking of the location of depth aid element 7412 along the axis can be used as a proxy for tracking of the location of tooling bit 7410. Accordingly, upon placing tooling bit 7410 at a desired tooling location of the patent, e.g., at a location of a patient's glenoid bone for purposes of glenoid reaming, a system can track the location of depth aid element 7412 to monitor reaming depth of tooling bit 7410. In some cases, a guide pin may be installed on the patient's glenoid bone to orient and guide the reaming process (e.g., in reaming guide pin insertion process of action 1910 of FIG. 19). The reaming depth, for example, may correspond to the depth into the bone where bone is removed from the glenoid.

Depth cameras are not shown in FIG. 74, but like FIG. 73, such depth cameras may be used to capture one or more images of the depth aid element 7412 as described above with regard to FIG. 73. One or more processors (not shown in FIG. 73) can be configured to determine the depth of tooling bit 7410 along the rotatable axis, based on analysis of the images captured by depth cameras. The processors, for example, may be processors of an MR device, such as microprocessor 515 of visualization device 213 of MR system 212 described herein. Alternatively, processing could be performed remotely by a local or remote computer or a so-called "cloud computer" connected to the depth cameras by a network.

In the example of FIG. 74, in order to position depth aid element 7412 a known, fixed distance from tooling bit 7410, rotatable shaft 7402 may be configured to include a stopper 7404 having a larger diameter than the rest of rotatable shaft 7402. Stopper 7404 creates a mechanical stop for securing the position of depth aid element 7412 along rotatable shaft 7402. For example, depth aid element 7412 may include a mechanical connection portion 7406 that includes a hole that is sized similar (and slightly larger than) a diameter of rotatable shaft 7402. Stopper 7404 holds depth aid element 7412 in place with the aid of gravity or with the additional aid of a locking mechanism (not shown). In this way, depth aid element 7412 can be positioned properly such that it remains a known, fixed distance from tooling bit 7410 along rotatable shaft 7402.

Rotatable shaft 7402 may be free to rotate within the hole defined through depth aid element 7412 such that depth aid element 7412 stays rotationally fixed and does not rotate when rotatable shaft 7402 rotates. Or in some cases, depth aid element 7412 may rotate with the rotation of shaft 7402. However, rotation of depth aid element 7412 may not be desirable, so additional mechanical elements or stops (not shown) may also be used to ensure that depth aid element 7412 is not allowed to rotate when shaft 7402 rotates. In some examples, a ring of ball bearings or other types of friction-reducing elements may be positioned at the physical point of interaction between depth aid element 7412 and stopper 7404 so as to reduce or substantially eliminate friction between depth aid element 7412 and stopper 7404 especially when rotatable shaft 7402 is rotating.

Figure 75:
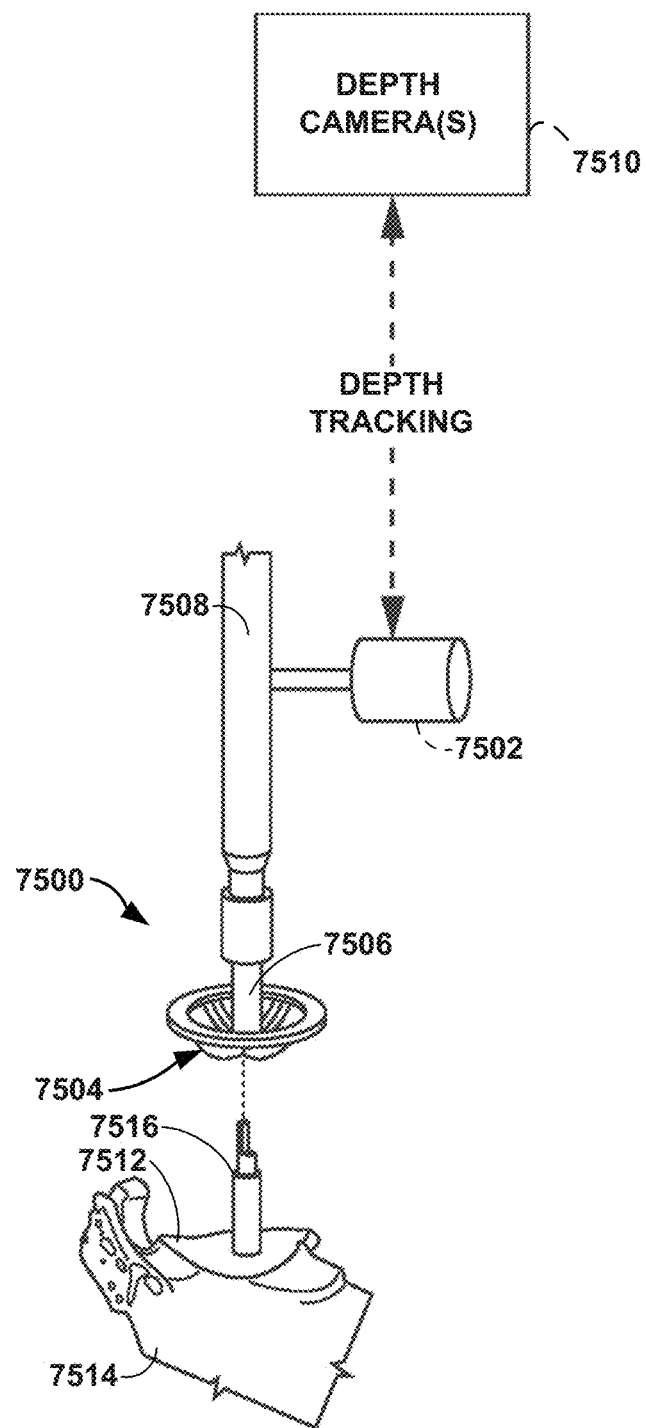
FIG. 75 is a conceptual perspective view of a mixed reality (MR) system and example reaming tool that includes a depth aid element consistent with an example of this disclosure.

FIG. 75 is a conceptual perspective view of a mixed reality (MR) system and example reaming tool 7500 that includes a depth aid element 7502 consistent with an example of this disclosure. Reaming tool 7500 may comprise a reaming bit 7504 that rotates about an axis defined by rotatable shaft 7506. Shaft 7506 may rotate within sleeve 7508. Depth aid element 7502 may be secured to sleeve 7508 so that it is fixed at a known distance from a reaming surface of reaming bit 7504. Sleeve 7508 may be connected to the housing of a surgical drill, and thus, sleeve 7508 may be considered part of such surgical drill housing. By securing depth aid element 7502 to sleeve 7508, depth aid element can remain rotationally fixed when shaft 7506 rotates. At the same time, depth aid element 7502 will remain a fixed distance from reaming surface of reaming bit 7504 during the reaming process.

Depth cameras 7510 are configured to capture one or more images of the depth aid element 7502. For example, similar to the example described above, depth cameras 7510 may use multiple images from multiple cameras that are positioned at fixed and known locations relative to one another, and parallax calculations can be performed to determine the depth of depth aid element 7502. In this way, the depth of depth aid element 7502 can be determined and used as a proxy for determining depth of a reaming surface of reaming bit 7504. One or more processors (not shown in FIG. 75) can be configured to perform the parallax calculations to determine the depth of the reaming surface of reaming bit 7504 along the rotatable axis defined by shaft 7506, based on analysis of the images captured by depth cameras 7510. The processors, for example, may be processors of an MR device, such as microprocessor 515 of visualization device 213 described herein. In this way, depth-based tracking of reaming bit 7504 can be facilitated when reaming a surface 7512 of a glenoid bone 7514 of a patient. In some examples were visualization device 213 is used for depth tracking, audible, tactile or visual feedback, for example, may be indicative of depth.

Optionally, the procedure may also make use of a mechanical jig 7516, which may be a guide pin that is secured to the patient's glenoid 7514. Mechanical jig 7516 may be inserted with the aid of a surgical drill, and it may provide a mechanical mechanism for guiding the reaming process and possibly controlling reaming depth of reaming bit 7504. In some examples, depth aid element 7502 may be used in combination with a jig-based approach to glenoid reaming (as shown in FIG. 75). In other examples, however, depth aid element 7502 may facilitate the elimination of jig 7516 in favor of depth control based only on depth detection, rather than mechanical limitation. In other words, the use of depth aid element 7502 may facilitate the glenoid reaming procedure and depth control without the need for a mechanical jig 7516.

Figure 76:
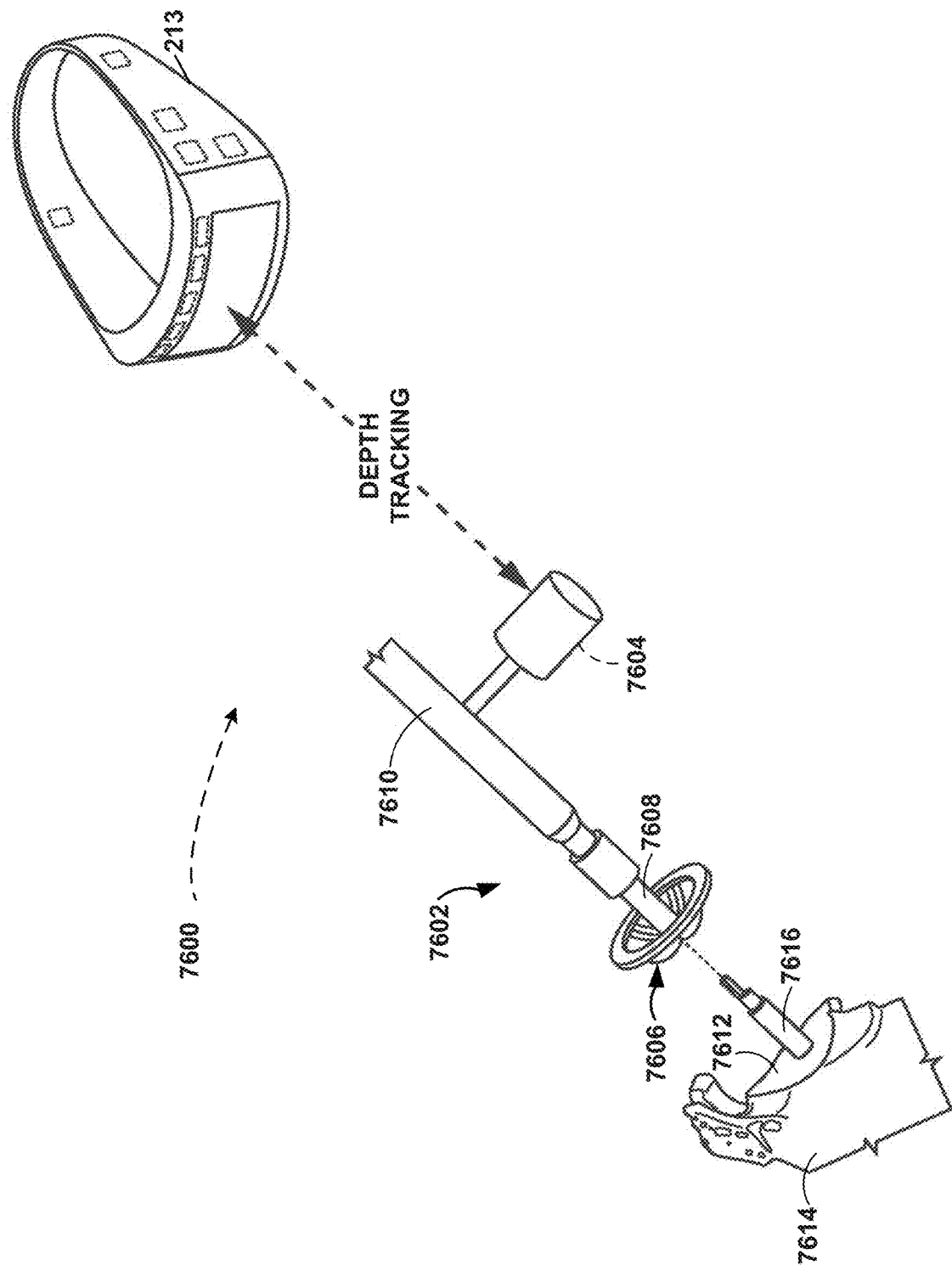
FIG. 76 is a conceptual perspective view of a mixed reality system that makes use of an example reaming tool that includes a depth aid element consistent with an example of this disclosure.

FIG. 76 is a conceptual perspective view of a mixed reality system 1051 that makes use of an example reaming tool 7602 that includes a depth aid element 7604 consistent with an example of this disclosure. Reaming tool 7602 may comprise a reaming bit 7606 that rotates about an axis defined by rotatable shaft 7608. Shaft 7608 may rotate within sleeve 7610. Depth tracking element 7604 may be secured to sleeve 7610 so that it is fixed at a known distance from a reaming surface of reaming bit 7606. Sleeve 7610 may be connected to the housing of a surgical drill, and thus, sleeve 7610 may be considered part of such surgical drill housing. By securing depth aid element 7604 to sleeve 7610, depth aid element can remain rotationally fixed when shaft 7608 rotates. At the same time, depth aid element 7604 will remain a fixed distance from reaming surface of reaming bit 7606 during the reaming process.

The example shown in FIG. 76 may utilize a visualization device 213, which may comprise a mixed reality (MR) device such as a mixed reality headset or goggles worn by a surgeon or other user, that include additional depth cameras. In some examples, the depth cameras may be included as an internal part of visualization device 213 and in other examples, depth cameras may be external to the visualization device so as to provide better depth tracking capabilities.

According to this disclosure, depth cameras 532 (FIG. 5) of visualization device 213 or other depth sensors are configured to capture one or more images of the depth aid element 7604. For example, similar to the other examples described herein, depth cameras 532 may use multiple images from multiple cameras that are positioned at fixed and known locations relative to one another, and parallax calculations can be performed to determine the depth of depth aid element 7604. In this way, the depth of depth aid element 7604 can be determined and used as a proxy for determining depth of a reaming surface of reaming bit 7606. Microprocessor 515 (FIG. 5) of visualization device 213 may be configured to determine the depth of the reaming surface of reaming bit 7606 along the rotatable axis defined by shaft 7608, based on analysis of the images captured by depth cameras 532. The images captured by depth cameras 532 may contain depth information. In particular, microprocessor 515 may perform parallax calculations based on analysis of the images captured by depth cameras 532 in order to determine depth of depth aid element 7604. In this way, depth-based tracking of reaming bit 7606 (by virtue of tracking depth aid element 7604) can be facilitated in a mixed reality environment when performing a reaming procedure on a surface 7612 of a patient's glenoid 7614. In some examples were visualization device 213 is used for depth tracking, audible, tactile or visual feedback, for example, may be indicative of depth. For example, visualization device 213 may provide or issue alerts to a user, and such alerts may be indicative of depth. The alerts may be graphical, color-based, color changing, symbols, shape or size-changing symbols, textual, visual, audible, tactile, or other types of alerts.

In still other examples, a medical device system may be configured to automatically control the medical device to limit rotation of a rotatable shaft based on the depth of the tooling bit along the axis relative to a desired depth of the tooling bit for the medical procedure. For example, drilling, reaming or tooling by the medical device may be automatically disabled once the system detects that depth of the tooling bit has reached a desired depth. In some examples, the medical device system may be configured to control the medical device or other medical devices using the closed loop control techniques described with respect to FIG. 72 and elsewhere in this disclosure.

As noted, the procedure may also make use of a mechanical jig 7616 secured to the patient's glenoid 7614. Mechanical jig 7616 may comprise a guide pin, and it may provide a mechanical mechanism for guiding the reaming bit 7616, and optionally for controlling or limiting reaming depth of reaming bit 7616. In some examples, depth aid element 7604 may be used in combination with a jig-based approach to glenoid reaming (as shown in FIG. 76). In other examples, however, depth aid element 7604 may facilitate the elimination of jig 7616 altogether, in mixed reality system 7600. In other words, the use of depth aid element 7604 and a mixed reality visualization device 213 with depth cameras 532 may facilitate the glenoid reaming procedure and depth control without the need for a mechanical jig 7616.

Figure 77:
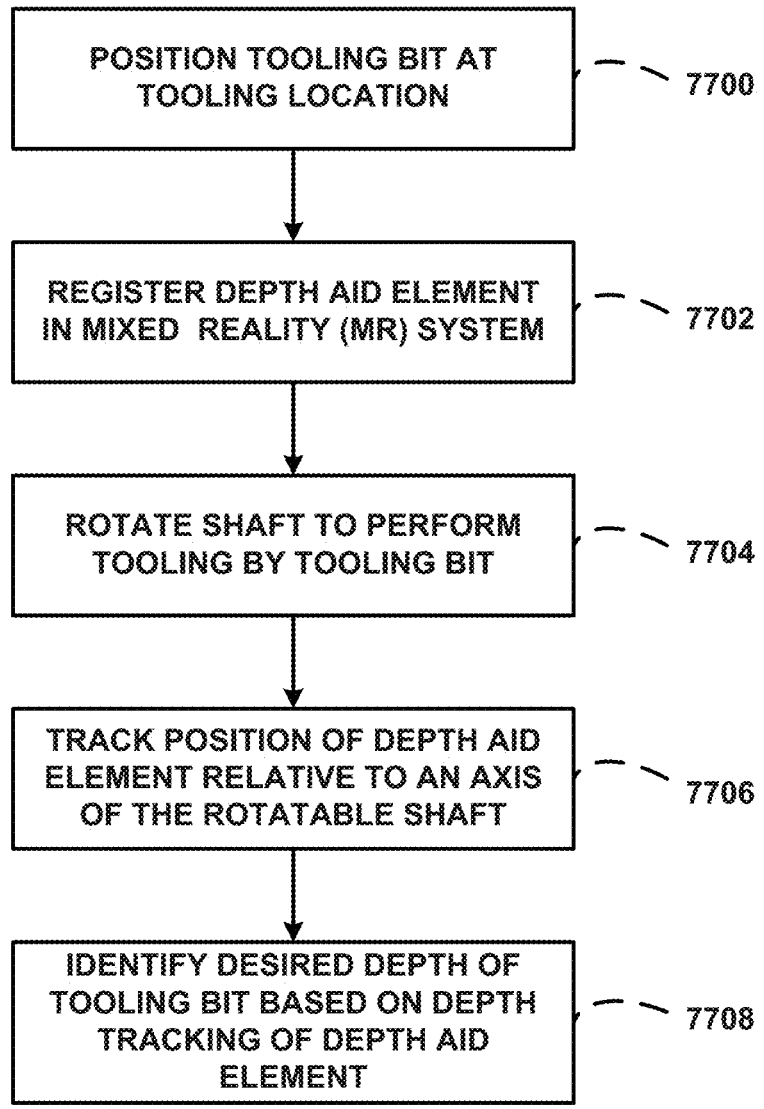
FIG. 77 is a flow diagram illustrating an example process consistent with an example of this disclosure.

FIG. 77 is a flow diagram illustrating an example process consistent with an example of this disclosure. FIG. 77 will be described from the perspective of the system shown in FIG. 73, although the same principles may apply to other systems described herein. As shown in FIG. 77, a surgeon may position tooling bit 7304 at a tooling location within a patient (7700). As noted, tooling bit 7304 may comprise a drilling element, a reaming element, or any of a wide variety of tooling elements designed to rotate about an axis. Indeed, the technique of FIG. 77 may be particularly well suited for a reaming procedure performed on a patient's glenoid bone with the aid of a mixed reality system.

In some cases, a mechanical jig (e.g., a guide pin) may be inserted into a patient's glenoid to define positioning of the tooling bit 7304. In any case, once tooling bit 7304 is placed at the desired location (7700), e.g., a starting location, the depth of depth aid element 7312 along an axis of rotatable shaft 7302 can be registered by depth cameras 7314 (7702). The registration process may simply be a process of identifying a starting location of depth aid element 7312, or in some examples, the registration process may include a process of registering a virtual element to depth aid element 7312. After defining the starting location of tooling bit 7304 at a tooling location, that starting location can also be set or defined for depth aid element 7312 via a registration process performed by a visualization device 213 such as that described herein. Then, after the registration process, visualization device 213 can track the depth of depth aid element 7312 as a proxy for defining the depth of tooling bit 7304.

Registration process (1104) may be a process of identifying three or more points so as to define a depth plane associated with depth aid element 7312. For example, a user using visualization device 213 may select three or more points in space to define a plane, and then initiate a point matching algorithm by visualization device 213 to define the plane as a virtual plane. In some examples, the user may select the points in various ways, such as one or more of hand gestures, a virtual interface, gaze selection, voice commands, or other input techniques.

After visualization device 213 performs the point matching algorithm to define the plane, visualization device 213 may be able to track that plane by tracking the three or more identified points with depth cameras.

Figure 80:
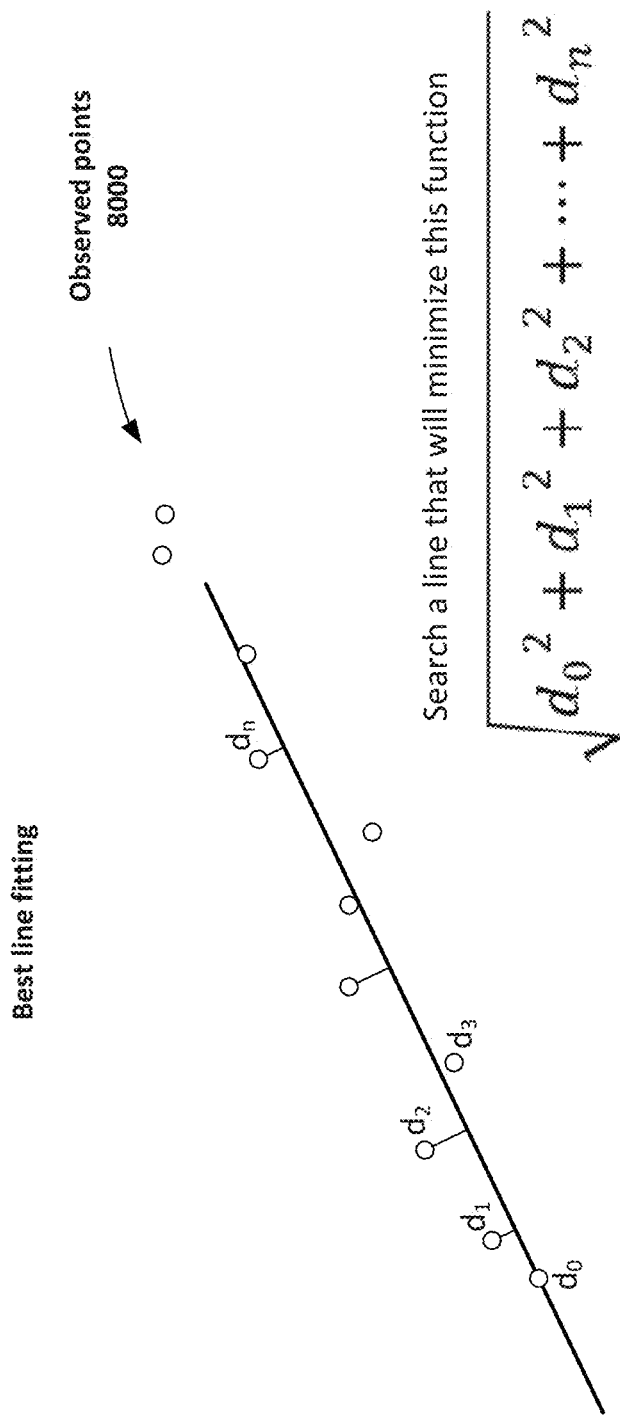
FIGS. 80, 81, and 82 are additional illustrations showing one example registration process registering a location of a depth aid element.
Figure 81:
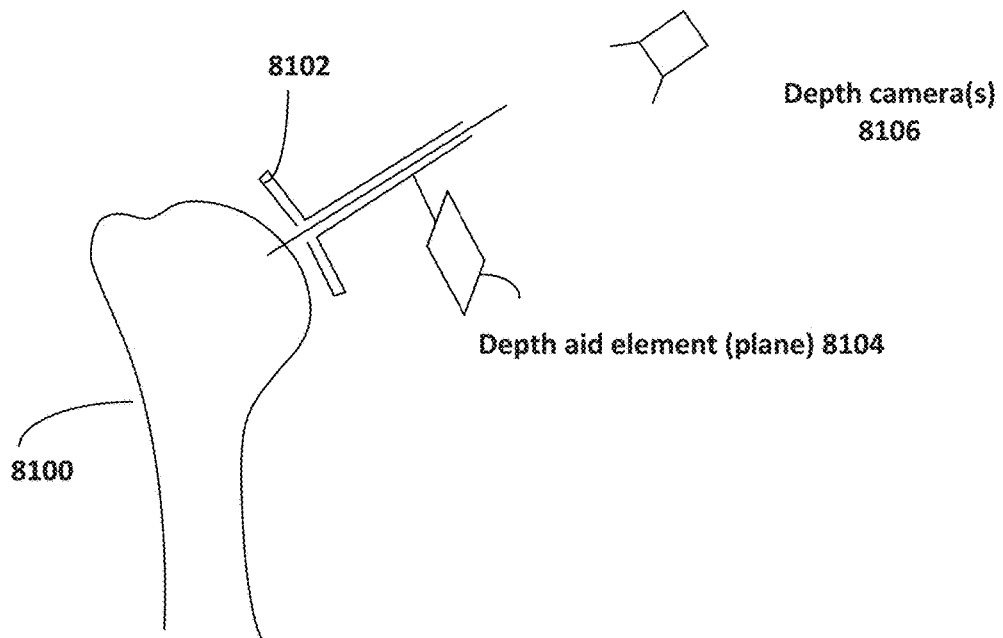
Figure 82:
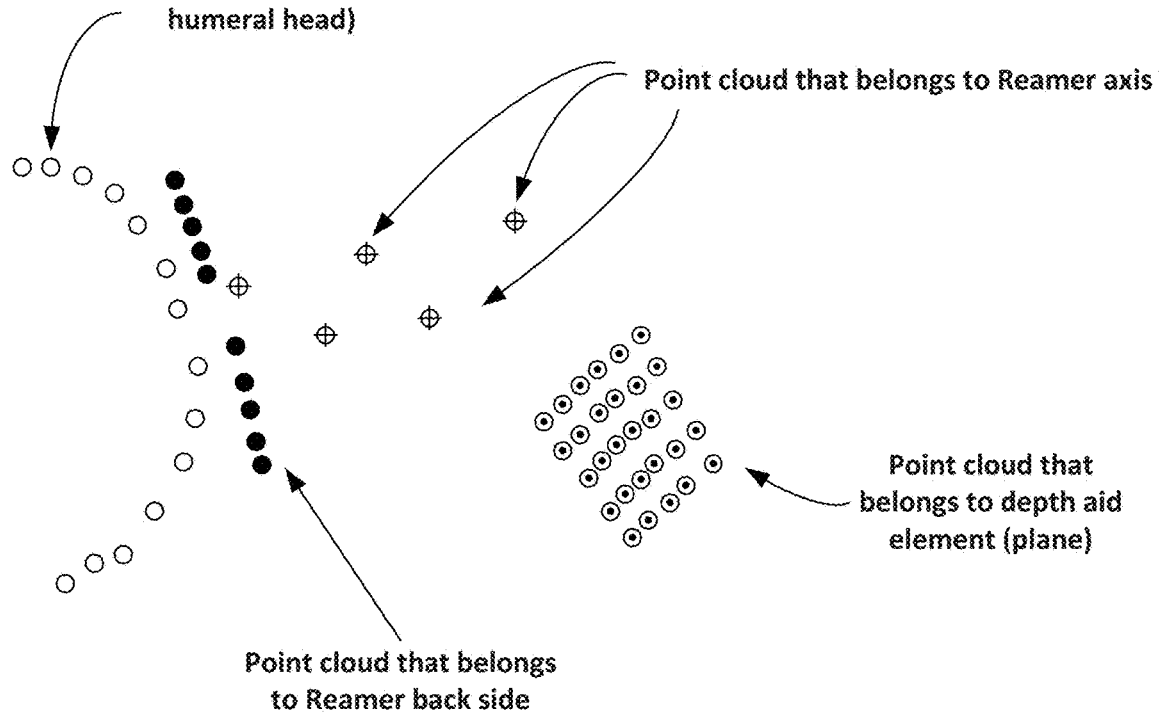

FIGS. 80, 81, and 82 are additional illustrations showing one example registration process registering a location of a depth aid element. In particular, FIG. 80 is an example illustration of "best line fitting" whereby observed points 8000 along a line can define the line according to a best fit. Upon identifying observed points 8000, which may be represented by $d_0, d_1, d_2 \ldots d_n$, visualization device 213 may search a line that will minimize the function $\sqrt{d_0^2+d_1^2+d_2^2+\ldots d_n^2}$. To define a depth plane, in an analogous manner to the best line fitting, upon identifying three or more observed points to define a plane, visualization device 213 may search a plane that will minimize a planar function.

FIG. 81 shows a scene (schematically) of a humerus 8100 with an installed reamer 8102 and depth aid element as a plane 8104. Exemplary depth camera(s) 8106 are also shown, which in some examples, may be part of or integrated with visualization device 213. Depth camera(s) 8106 measure a distance to every pixel in its field of view, and in this way, depth camera(s) 8106 can obtain a point cloud that represents the geometry of an observed scene.

Depth camera(s) 8106 can generate, as output to visualization device 213, a point cloud (and no classification may be done at this stage). Once visualization device 213 has this point cloud, visualization device 213 can apply an algorithm that will classify the points in the point cloud. As an illustrative example, FIG. 82 illustrates various point clouds that can be observed by depth camera(s) 8106 and defined by visualization device 213. The illustrated point clouds shown in FIG. 82 include a point cloud observed with a depth camera, which may be points that belong to an observed humeral head). The illustrated point clouds shown in FIG. 82 may also include a point cloud that belongs to a reamer axis, a point cloud that belongs to a reamer back side, and a point cloud that belongs to the depth aid element (plane).

Visualization device 213 may be configured to refine the classifications and determine only the points that belong to the depth aid element (plane). Once visualization device 213 determines these points, that belong to the depth aid element (plane), visualization device 213 can fit a plane to these points (e.g., according to a best fit plane function or equation). Again, FIG. 80 is an example illustration of "best line fitting" whereby observed points 8000 along a line can define the line according to a best fit. A best fit plane can be defined in a similar way. Once visualization device 213 determines the best fit plane for the first time, visualization device 213 can perform a simple tracking algorithm that will determine the best fit plane at each frame that comes from the depth camera(s).

In another possible example of depth aid registration, the registration process for registering a starting location of depth aid element 7312 may be similar registration process for registering a virtual image of a patient's glenoid bone to the actual glenoid bone of the patient, as described elsewhere in this disclosure. According to FIG. 77, in this example, depth cameras 7314 of FIG. 73 may be part of a mixed reality system that performs the registration process of depth aid element 7312. In some examples, depth tracking of depth aid element 7312 occurs relative to a starting location identified by registering depth aid element 7312, while in other cases, depth tracking may be performed to monitor actual depth of depth aid element 7312 relative to the depth cameras, which may not always require registration of depth aid element 7312. Moreover, although described primarily in the context of shoulder surgery and reaming of a patient's glenoid bone, the depth tracking techniques of this disclosure may also be used for other surgical procedures, such as for one or more steps of an ankle surgery.

In some examples, the registration process may set and adjust a virtual element via "SET" and "ADJUST" techniques similar to those described elsewhere in this disclosure. Using a visualization device 213 a user may initiate a "SET" to present a virtual element, which may be a virtual version of the depth aid element that defines a depth plane, a virtual version of a backside of a reaming bit that defines a depth plane, a virtual version of a medical device housing or surgical drill that defines a depth plane, a virtual version of another portion of a medical drill that defines a depth plane, or possibly just a depth plane that is perpendicular to an axis of the tooling bit. The user may implement an "ADJUST" technique to adjust the position of the virtual element, e.g., using gesture-based controls in the mixed reality system. Once placed and adjusted to a desired location, the process may then implement a matching algorithm to "MATCH" the virtual element to a corresponding real-world element. In this way, a virtual element useful for depth tracking can be registered to a real-world element, such as a depth aid element 7312.

Regardless of how the registration is performed, once the depth of depth aid element 7312 is registered (7702) with the tooling bit positioned in a location for tooling, the surgeon may then activate the medical device attached at proximal end 7308 of rotatable shaft 7302 so as to cause rotation of shaft 7302 and thereby perform tooling by tooling bit 7304 (7704). The surgeon may exert pressure down the axis of rotatable shaft 7302 to cause drilling or reaming by tooling bit 7304. Again, the system may be especially useful for reaming of a patient's glenoid bone during an anatomical shoulder reconstruction surgery, in which case the tooling bit 7304 would be a reaming element rather than a drill bit. Although some aspects of this disclosure have focused on reaming depth, it may also be helpful to monitor depth when drilling the hole to receive a guide pin, e.g., depth tracking of the drilling depth for placing the reaming pin. A guide pin could then be placed in the hole and the reaming tool may be used with the guide pin. Other instances of drilling depth tracking may be also be desirable, e.g., for drilling holes to receive mounting pegs of the glenoid plate, or for drilling, reaming or other tooling of the talus and/or tibia in ankle surgery.

In any case, while performing the tooling by tooling process (7704), depth cameras 7314 can be used to track the position of depth aid element 7312 relative to an axis of rotatable shaft 7302 (7706). In this way, the reaming depth (or drilling depth) of tooling bit 7304 can be tracked and monitored by tracking the position of depth aid element 7312.

In some examples, the process may also identify a desired depth of tooling bit 7304 based on depth tracking of depth aid element 7312 (7708). For example, referring to FIG. 76, depth tracking by depth cameras 532 of visualization device 213 may be performed with the aid of user interface 522, which may present mixed reality information to a user indicative of depth of a tooling bit (such as reaming element 7606) during the medical procedure. In some examples, user interface 522 may present an indication of current actual depth of reaming element 7606. In some examples, user interface 522 may present an indication of a desired depth of reaming element 7606, which may be determined by a preoperative plan. The desired depth may be shown relative to the actual current depth, and in some examples, user interface 522 may present an indication of the remaining depth needed to achieve the desired depth. Audible, tactile or visual feedback, for example, may be indicative of depth.

Other mechanisms for medical device tool control (such as described elsewhere in this disclosure) may also be used to help a surgeon achieve a desired depth and help avoid over drilling or over reaming. For example, audible or visual cues may be presented to the surgeon via visualization device 213 based on the depth tracking of depth aid element 7604. Smart control of the medical device may also be implemented based on the depth tracking of depth aid element 7604. In some example, the medical reaming device may be disabled if reaming depth is determined to meet or exceed the desired depth defined by the preoperative plan. These or other cues or controls may be used based on the tracking of depth aid element 7604 in order to improve the medical procedure.

Figure 78:
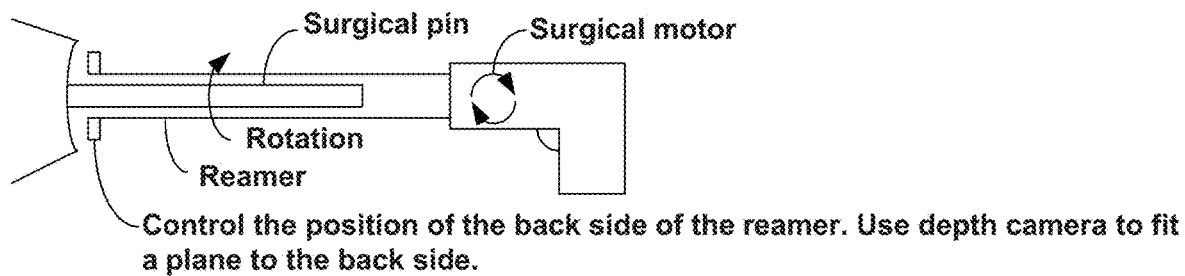
FIG. 78 is a side view of anther depth tracking example, which may eliminate the need for a specially-designed depth aid element.

FIG. 78 is a side view of anther depth tracking example, which may eliminate the need for a specially-designed depth aid element. In this example, a visualization device such as visualization device 213 (not shown in FIG. 78) may monitor depth of a back surface (i.e., a non-reaming surface) of a reaming element. The system may be designed to track (and possibly control) the position of the back side of the reaming element. In this example, a depth plane may be registered to the back side of the reaming element, e.g., via a registration process similar to that described herein for registering a depth aid element or for registering a 3D model to a patient's glenoid bone. In this example, the registration process may involve registering a virtual element to the reaming element (e.g., by registering a virtual plane or a virtual version of the reaming element to the backside of the actual reaming element)

By registering a depth plane to a back side of the reaming element, as shown in FIG. 78, depth tracking of the reaming element may then be achieved. The use of a depth aid element as described herein, however, may be desirable relative to tracking the back side of the reaming element because blood or other substances may inhibit the ability to accurately track the back side of the reaming element when reaming is being performed on a patient.

Referring again to FIG. 78, in still other examples, depth tracking may be performed with respect to a surgical motor (or the medical device that includes the surgical motor), and the depth of the surgical motor (or medical device) could be used as a proxy for depth of the reaming element. Like the depth aid elements described herein the surgical motor illustrated in FIG. 78 may be located a fixed and known distance from a distal end of the reaming element. Thus, upon registering and tracking depth of the surgical motor (which may involve registering a virtual element of the surgical motor to the real surgical motor), tracking can be achieved on the reaming element in a similar manner to the depth tracking described herein with respect to the depth aid element. In this example, a depth plane may be registered to the surgical motor, via a registration process as described above. By registering a depth plane to a surgical motor, depth tracking of the reaming element may then be achieved. The example shown in FIG. 76, where depth aid element 7604 is secured to a sleeve 7610 may be considered an example where depth aid element 7604 is attached to the housing of the surgical tool. Sleeve 7610, for example, may form part of the housing of a surgical drill, in some examples.

Figure 79:
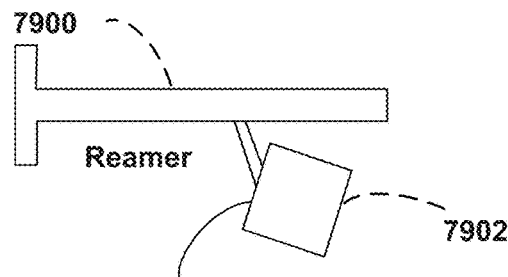
FIG. 79 is another side view showing an example of a depth aid element attached at a fixed location relative to a reamer.

FIG. 79 is another side view showing an example of a depth aid element 7902 attached at a fixed location relative to a reamer 7900. The example of FIG. 79 may be consistent with other examples that use an attached depth aid element. According to this example, a visualization device such as visualization device 213 (not shown in FIG. 79) may be used to add a plane marker (or other type of virtual marker element) to a reamer 7900 in order to track and control depth of the distal end of the reamer. The virtual element may comprise a virtual plane that is registered to the depth aid element 7902. Using visualization device 213, the system can detect points on the plane with depth cameras and fit the plane to a physical depth aid element 7902 that is attached to the reamer 7900. In this example, a depth plane may be registered to depth aid element 7902, via a registration process similar to that described above and also described elsewhere in this disclosure, e.g., for registering a 3D model to a patient's glenoid bone. By registering a depth plane to depth aid element 7902, depth tracking of reamer 7900 can be achieved.

In some examples, the disclosure is directed to a number of automation-based assistance features and techniques related to surgical, intra-operative workflow guidance, some of which may be designed to aid a nurse (or other medical assistant, technician, or surgeon) in an orthopedic surgical procedure, such as an orthopedic joint repair surgical procedure, such as a shoulder repair surgery. It may be difficult for an operating room nurse to know all of the details of a surgical procedure, such as the next surgical step or which next instrument is needed for the next surgical step, especially if the nurse does not help with the surgical procedure on a regular basis. For example, the nurse may assist with a range of surgical procedures having different requirements and details for surgical steps and instruments, implants or other surgical items used in those steps. The techniques and devices of this disclosure may help to automate the process to aid the nurse and help reduce errors in the surgery.

In some examples, the techniques leverage surgical items that are designed with advanced features, such as sensors, accelerometers, and/or light sources. One or more processing devices, such as a processing device associated with MR system 212 or another computing system, may track the surgical items during the surgical procedure and monitor their use. Moreover, the one or more processing devices may help control the advanced features of the surgical items in assisting the nurse with surgical item selection as the procedure is performed. For example, a set of surgical items may be illuminated by light sources (e.g., light emitting diodes) that reside within such surgical items, in order to inform the nurse that such tools are needed for the surgical procedure. Moreover, the lighting may be synchronized with the procedure, such that surgical items are illuminated when such surgical items are needed, e.g., at particular points during the course of the orthopedic surgical procedure. In some examples, a light source of a selected surgical item may be illuminated based on a specified use of the surgical item defined in a surgical plan associated with the surgical procedure.

In other cases, surgical items are identified to the nurse by illumination or by virtual elements presented via mixed reality on visualization devices such as visualization device 213 of MR system 212. Examples of virtual elements presented via MR to identify surgical items may include highlighting of the identified surgical items using regions of semitransparent color, virtual circles surrounding identified surgical items, virtual arrows pointing to identified surgical items, virtual outlines around identified surgical items, virtual objects that block the view of other non-identified surgical items, increasing opacity over other non-identified surgical items, and so on. In some examples, one or more surgical items of the surgical procedure may be connected to a controller (e.g., a device that controls lights on the surgical items or a mixed reality system). Such connectivity may not be required in examples where MR is used to identify surgical items. After a surgical item is used, the next instrument that is needed for the procedure may be highlighted, lit, identified by one or more virtual elements presented in MR, or otherwise identified to the nurse in an automated way. The automated identification of surgical items may be synchronized with the steps in the workflow of the surgical procedure, such that surgical items are identified when such surgical items are needed, e.g., at particular points during the course of the orthopedic surgical procedure. In this way, techniques and devices of this disclosure may help to automate the process to aid the nurse and help reduce errors in the surgery.

In some cases, a set of surgical items may be illuminated (e.g., using MR visualizations, using lights on surgical items, using lights in a tray, or using another method or combination of methods) during a surgical procedure to aid the nurse with surgical item selection, and specific types of illumination may be used for different surgical items in the set. For example, previously-used surgical items, currently used surgical items, and subsequently needed surgical items of the procedure may be illuminated with different colors or coloring effects, or different lights or spatial or temporal lighting patterns. By integrating light sources directly into surgical items, the lighting accuracy can be better ensured relative to other techniques that use backlighting or lighting in trays or tables, in which case the lighting may be incorrect if the surgical item is moved. Moreover, item tracking can also help to ensure that item identification is accurate and well documented during the surgical procedure. Automated documentation of surgical items during their use in a surgical procedure can eliminate the need for surgeons or nurses to physically track and focus on such documentation, allowing the surgeons or nurses to focus on other aspects of the procedure.

Indeed, item tracking may also be used to help document and log the surgical procedure, as well as provide a safety check to ensure that the correct surgical item is being used, e.g., relative to a preoperative plan, which may be a patient-specific surgical plan having one or more features that are specifically prescribed for a particular patient. Object-based mixed reality (MR) detection of surgical items may help with surgical item verification. In some examples, surgical item use may also be monitored or verified with item tracking that monitors accelerometer data of accelerometers in the surgical items. In some cases, item tracking may be used in combination with other item tracking or other item registration techniques, such as bar code or other optical code scanning, RFID reading or other automation, e.g., using optical code scanners, RFID readers or other machine automation tools. In some cases, optical code reading, RFID reading, or other machine automation may be incorporated into a visualization device, like visualization device 213 in order to allow such automation in an MR environment without the need for additional bar code readers or RFID readers. In this way, surgical procedure documentation may be improved by tracking and verifying that the correct surgical items are used at the proper states of the procedure. In order to facilitate optical code scanning of surgical items by visualization device 213, some or all of the surgical items may include optically scannable codes, such as one-dimensional bar codes or two-dimensional bar codes, which may be printed on the surgical items or affixed to the surgical items. Visualization device 213 may detect a particular surgical item and record its use in a medical procedure based on detecting the optically scannable code. Likewise, boxes of surgical items or trays may include optically scannable bar codes that may be scanned by visualization device 213. In some examples, instead of or in addition to the use of optical codes, visualization device 213 may use computer image recognition and/or optical character recognition to identify surgical items.

In some examples, some or all of the techniques of this disclosure may be implemented with the aid of mixed reality (MR) visualization. For example, rather than using lights that are integrated into surgical items themselves, virtual information may be presented by a visualization device at a position on or adjacent to the real-world surgical items viewable by a user via the visualization device, such as a mixed reality headset worn by the nurse during the operating procedure. An example of such a MR headset is visualization device 213 of MR system 212, e.g., as shown in FIGS. 2 and 5. Moreover, the use of MR may enable the identification of surgical items into which it may be impractical to integrate lights, such as implantable devices, wound closure products, and other types of surgical items. This may eliminate the need for lighting within surgical items themselves, although lighting within certain surgical items may still be desirable even when MR is used. In other words, in some examples, the MR implementations may be used in place of physical lighting in surgical items, although in other examples, mixed reality implementations may be used in combination with physical lighting in the surgical items. Moreover, mixed reality may be used in combination with other advanced features in the surgical items, such as lights, sensors, accelerometers or other tracking features.

In some examples, a user may view a real-world scene including the environment of an operating room, the patient's actual anatomy, i.e., real anatomy, such as actual bone or soft tissue anatomy (e.g., glenoid or humerus bone in a shoulder arthroplasty) that is exposed during surgery. The user may view this scene through a transparent screen, e.g., through see-through, transparent holographic lenses, of a head-mounted MR device, such as visualization device 213 described in this disclosure, and the user may also see a virtual MR object or objects projected on or in the screen, such that the MR object(s) appear to be part of the real-world scene, e.g., with the virtual objects appearing to the user to be in overlay or otherwise integrated within the actual, real-world scene. For example, as discussed above, virtual information may be presented or overlaid or presented adjacent to a particular real-world surgical item, in order to identify the status of the surgical item in the surgical procedure, e.g., as a surgical item to be used in a current step of surgical procedure, a previously-used surgical item, or a surgical item to be used in the next step or a future step of the surgical procedure. The virtual information may be projected as holographic imagery on the screen of an MR visualization device, such as visualization device 213, e.g., via holographic lenses, that a holographic image is overlaid on a real-world surgical item visible through the screen.

In addition to aiding a nurse with surgical item selection, the techniques and features described herein may also improve surgical item tracking and documentation of the surgical procedure. As previously discussed, surgical items may include tools, implantable devices, trays of other surgical items, or other physical objects that may be used during a surgery. Moreover, the system may be communicatively coupled to an inventory of surgical items that are available. In this case, if a surgeon needs a surgical item that is not present or if the surgeon needs to change one or more steps of the procedure relative to a preoperative plan, features described herein may allow the nurse to check hospital inventory to see if other surgical items are immediately available for use in the procedure. If so, the nurse may direct another assistant to fetch the necessary surgical item from inventory, while avoiding the need to send the assistant for a manual check on surgical item availability. This can save important time during a procedure and help to avoid unnecessary down time.

In some examples, the techniques of this disclosure may facilitate more accurate documentation of a surgical procedure and more accurate documentation of the surgical items used during that procedure. With the use of a visualization device and mixed reality, a nurse may be able to automatically document surgical item use. Object identification and object tracking of surgical items may be performed by a computing system of the visualization device to help track surgical item selection and surgical item use. For example, when a surgeon takes a first surgical item for use, the system may detect that the surgical item is in the hand of the surgeon, e.g., based on sensor data from the surgical item, image-based object detection, or scanned indicia on the surgical item. Such object tracking (e.g., visual shape detection of surgical item or visual detection of indicia on the surgical item, or by using sensor data from the surgical item) may be used in place of or in combination with other automation, such as optical code scanning, RFID reading, or other item tracking automation. In some examples, object-detection based item tracking may be used as a verification and further documentation of item use, e.g., in addition to optical code scanning, RFID reading, or other item tracking automation. Again, in some cases, optical code scanning, RFID reading, or other item tracking automation features may be integrated into an MR device, such as visualization device 213. Visualization device 213 may document surgical item use and save this documentation for record keeping and postoperative analysis. Referring again to FIG. 6, for example, visualization device 213 may record tracking information associated with surgical item use into storage device(s) 612 for documentation and later retrieval. For example, upon detecting a surgical item or any specific use of a surgical item by visualization device 213, a time stamp of such detection and the type of detection (RFID scan, bar code scan, object detection of the surgical item or other automated surgical item detection), the detected surgical item and the time stamp associated with that detection can be stored in storage device(s) 612 for documentation of the surgical procedure and later retrieval. Also, in some examples, one or more surgical items may communicate with visualization device 213, e.g., via communication device(s) 616 and a corresponding communication device or module in the surgical items, so as to convey sensor information, accelerometer data, lighting (as well as time stamps associated with any such information or data) to visualization device 213 for documentation of the surgical item use during the surgical procedure and for later retrieval. In this way, accurate documentation of the surgical procedure may be achieved and the procedure itself may be improved. Advanced features in the surgical item, such as sensors and accelerometers may be used to aid item tracking so as to verify and document when surgical items are used in the procedure by monitoring accelerometer data.

Figure 83:
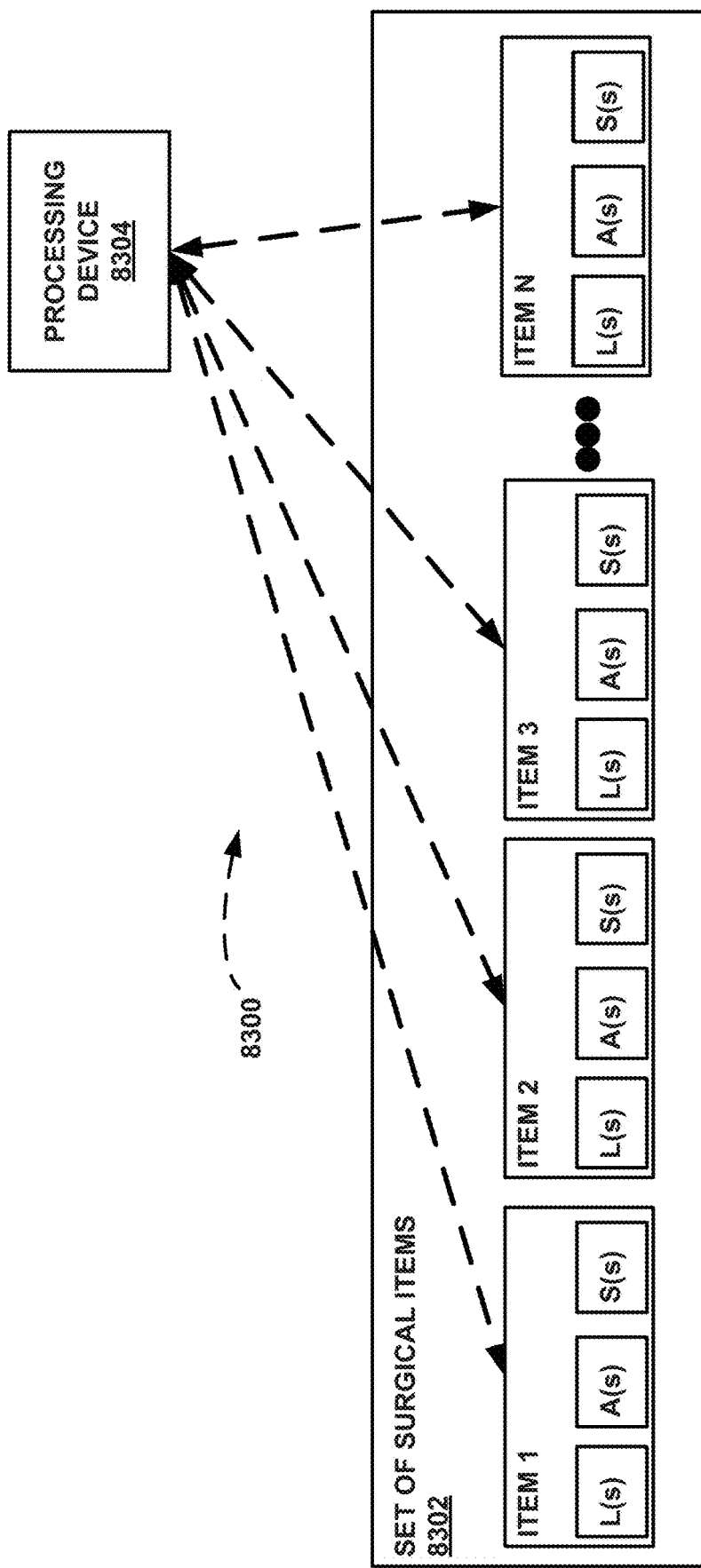
FIG. 83 is a block diagram illustrating a system comprising a set of surgical items and a processing device in accordance with an example of this disclosure.

FIG. 83 is a block diagram illustrating a system 8300 comprising a set of surgical items 8302 and a processing device 8304 in accordance with an example of this disclosure. Surgical items 8302 may be tracked using item tracking techniques of this disclosure. In this example, each of surgical items 8302 includes one or more light sources shown as "L(s)." The light sources L(s) may comprise light emitting diodes (LEDs), although other types of semiconductor light elements or other types of light sources may also be used for light sources L(s). Semiconductor lighting such as LEDs may be desirable because of factors such as low energy use, high efficiency, long life, and high intensity. Moreover, lighting effects such as different colors, intensities or pulsing or flickering effects may be easy to control and achieve with LEDs, which may comprise multi-color LEDs capable of illuminating lights of different colors. In some examples, colors may be selected for use in identifying surgical items for a given environment. For the surgery room, for example, it may be desirable to avoid the color red and the color green may be very visible for item identification. The LEDs may have associated LED controllers configured to drive the LEDs.

Light sources L(s) may be mounted on or within each of the surgical items within the set of surgical items 8302. Each surgical item may include a battery, an antenna and communication circuity, e.g., within each of the surgical item in order to power the light, and provide for communication capabilities with processing device 8304, which may control the lights. The lights may be disposed within a cavity or compartment of a housing of a surgical item. The lights may be part of a light module that includes communication circuity, an antenna and battery. The lights may be positioned or located for effective lighting of the respective surgical items during the surgical procedure, e.g., on a top side, bottom side, or any desirable location. In some examples, a lighting module may be disposably or permanently affixed on the surgical item. The lights or lighting modules may be designed to withstand sterilization. Acoustic or vibratory feedback modules (e.g., to "buzz" the surgical item with tactile feedback or to "beep" the surgical items with audio feedback) may also be used in addition to or instead of lights. If desired, a surgical item may also include an on/off switch to enable the selectable lighting when the surgical item is in use, and to disable the lighting, when the surgical item is not in use.

Figure 104:
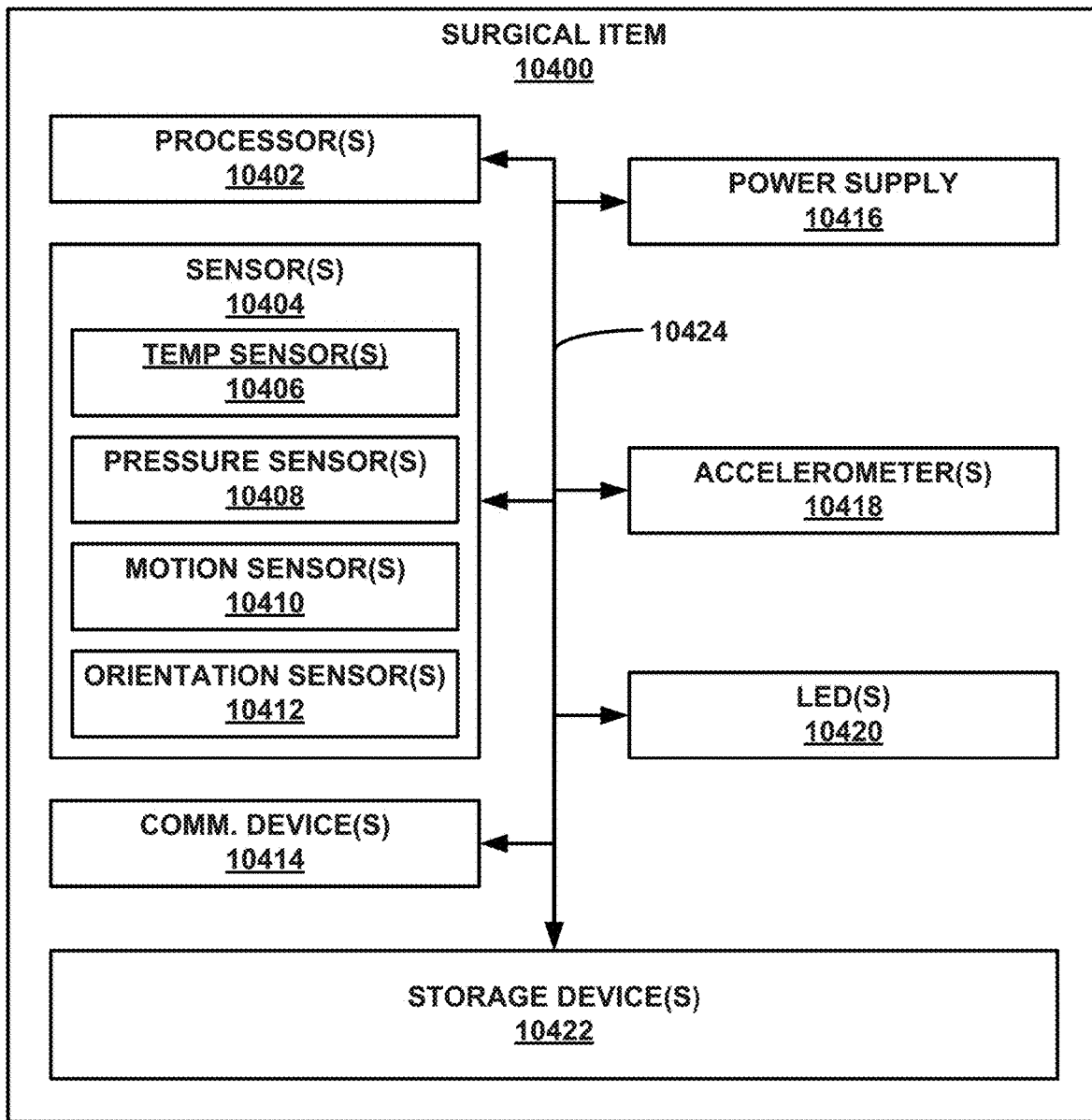
FIG. 104 is a more detailed block diagram of a surgical item, which may correspond to one or more of the surgical items described in this disclosure.

FIG. 104 is a more detailed block diagram of a surgical item 10400, which may correspond to one or more of the surgical items described in this disclosure. Surgical item 10400 may comprise one or more processors 10402 and one or more storage devices 10422 communicative coupled via a communication bus 10424. Surgical item 10400 may further include one or more sensors 10404 such as any of those described herein for surgical item use, surgical item automation, or item tracking. In some examples, surgical item 10400 is illustrated as including one or more temperature sensors 10406, one or more pressure sensor(s) 10408, one or more motion sensor(s) 10410, and one or more orientation sensor(s) 10412. Surgical item 10400 may further include one or more light emitting diode(s) 10420 and one or more accelerometer(s) 10418. Surgical item 10400 may also include a power supply 10416, such as a battery, that powers the components illustrated in surgical item 10400. In addition, surgical item 10400 may also include a communication device 10414, which may comprise a wireless communication device (e.g., with an antenna) for communicating with an external device, such as communication device(s) 616 of visualization device 213. Sensors 10404 may sense various things (e.g., temperature, motion, pressure, orientation, etc.) as indications of surgical item use, and sensed data (and associated timing information, such as time stamps associated with the sensed data) can be stored in storage device(s) 10422 and possibly communicated to visualization device 213, e.g., via wireless communication between communication device(s) 10414 of surgical item 10400 and communication device(s) 616 of visualization device 213.

In general, a device may include a surgical item for use in a surgical procedure, and a light on or within the surgical item, wherein the light is controllable by an external device so as to identify the surgical item for use in the surgical procedure. In some examples, the device may further include an accelerometer and/or one or more sensors. As examples, the surgical item may comprise a sounder, a compactor, a punching tool, a rasping tool, or a surface planing tool. Alternatively, the surgical item comprises a surgical implant, such as a glenoid implant, a humeral implant, a fixation device, or anchoring hardware. The surgical item may be a patient-specific surgical item that includes one or more features designed for an anatomy of a specific patient.

In some examples, the set of surgical items 8302 may define a kit of surgical items that are usable for a surgical procedure. For example, a kit may comprise a plurality of surgical items for use in a surgical procedure, and a light on or within each of the plurality of surgical items, wherein the light is controllable by an external device so as to selectively identify each of the plurality of surgical items for use in the surgical procedure. In some examples, each of the plurality of surgical items may include an accelerometer and/or one or more sensors. As examples, the kit may include a plurality of sounders, a plurality of compactors, a plurality of punching tools, a plurality of rasping tools, or a plurality of surface planing tools. Also, in some cases, at least one of the surgical items may comprise a surgical implant, such as a glenoid implant, a humeral implant, a fixation device, or anchoring hardware. The surgical item may comprise a patient-specific surgical item that includes one or more features designed for an anatomy of a specific patient. Surgical items 8302 may be defined for a given procedure, such as a specific type of shoulder surgery or a specific type of ankle surgery. Accordingly, the items within surgical items 8302 may vary depending on the procedure to be performed.

The term "medical tools" may include any of a wide variety of tools used in an orthopedic surgical procedure, including for example, sounders, compactors, punching tools, rasping tools, surface planing tools, and other tools used in surgical preparation and implantations. In addition, the term "surgical items" may include medical tools as described herein, surgical implants, and other items that may be used in a surgery. In some examples, surgical items may be patient-specific. In other words, the item tracking techniques described herein (e.g., using MR, using advanced features and lighting, or other features) may also apply to surgical items in the form of surgical implants, including such things as glenoid or humeral implants and associated fixation devices, anchoring hardware, or other implants or tools used to implant such devices, e.g., in the example of shoulder joint repair surgery.

As shown in FIG. 83, processing device 8304 is external to the set of surgical items. Processing device 8304 is configured to communicate with the set of surgical items and control the light source in each of the surgical items based on a surgical procedure. For such communication, processing device 8304 and each of the surgical items in the set of surgical items 8302 may include wireless communication capabilities supported by wireless communication hardware components, e.g., such as a transmitter, receiver and modem. Any of a wide variety of communication techniques may be used, although high-speed short-range communication protocols may be especially useful, such as Bluetooth, Zigbee, wireless USB, or another high-speed short-range communication protocol. The wireless communication components within the set of surgical items and processing device 8304 are not shown in FIG. 83 for simplicity and ease of illustration.

Although not required for all examples, each of the surgical items within the set of surgical items 8302 may also include other advanced features, such as accelerometers (shown as A(s)) and other sensors (shown as S(s)). Accelerometers A(s) and other sensors S(s) within the surgical items may facilitate and enhance object tracking in some examples, e.g., by facilitating the ability to identify the location and motion of such surgical items. Other sensors S(s) may include a gyroscope, one or more temperature sensors for tracking ambient room temperature or patient temperature during item use, a pressure sensor for detecting pressure exerted on the surgical item, a fluid sensor for detecting fluid such as blood, additional accelerometers, or any type of sensor that is desired for a surgical item. For example, accelerometers A(s) and other sensors S(s) may allow processing device 8304 to determine when a specific surgical item is being used by the physician based on sensor data and accelerometer data. Sensors S(s) may also provide more advanced information about surgical item use, e.g., based on pressure, temperature or other sensed parameters during a surgical procedure. Such sensed data may be stored in the surgical items or possibly communicated from the surgical items to an external device, such as processing device 8304, visualization device 213 or another external device.

In some examples, light sources L(s) within each of the surgical items within the set of surgical items 8302 can aid a nurse in identifying a sequence of surgical items needed by the physician in a surgical procedure. Processing device 8304 may be configured to the activate or deactivate the light source L(s) in each of the medical surgical item (e.g., Item 1, Item 2, Item 3, . . . Item N) such that different surgical items illuminate at different times. Also, in some cases, processing device 8304 may be configured to the activate or deactivate the light source L(s) in each of the surgical items (e.g., Item 1, Item 2, Item 3, . . . Item N) such that different surgical items illuminate with different colors (and possibly also at different times). A color coordination scheme may be defined so that the nurse is able to use colors to identify which surgical item is being used, which surgical items have already been used, and which surgical item is the next surgical item needed by the physician in the surgical procedure. The sequence of surgical items needed over the course of the surgical procedure may be set forth in a virtual surgical plan for the patient, which also may be patient-specific and include tools, implants and procedure sequences that are specific prescribed for the patient.

In some examples, processing device 8304 is configured to control the set the light sources L(s) in each of the surgical items (Item 1-Item N) so as to identify all of the surgical items in the set of surgical items and to specifically distinguish one of the surgical items. In other words, all of the surgical items (Item 1-Item N) may be illuminated, but a specific one of the surgical items (e.g., item 2) may be distinguished in some way. In this way, the nurse may be able to identify the entire set of items as well as the specific surgical item that is currently needed. The set of surgical item (Item 1-Item N) may be included within a larger collection of surgical items, such that illumination of the set of surgical items (Item 1-Item N) distinguishes the set of surgical items from the larger collection of surgical items, and the distinguished lighting of the specific surgical item (e.g., Item 2) may allow the nurse to more quickly identify the specific surgical item within the set.

In some examples, a different light color may be used to distinguish one of the surgical items from the set of surgical items. In some examples, a lighting effect (e.g., blinking or flashing light, which may define temporal flashing patters or rates on an item-by-item basis) may be used to distinguish one of the surgical items. In some examples, a lighting intensity is used to distinguish one of the surgical items. In other examples, if multiple lights are provided in a surgical item, illumination of a number of lights or a pattern of lights on the surgical item may be used to distinguish the surgical item. These or other examples (as well as any combination of such distinguished lighting) may be used to help the nurse quickly and accurately identify the specific surgical item within the set In some examples, the light source L(s) in each of the surgical items is controlled to distinguish a first subset of the surgical items, a second subset of the surgical items and a third subset of the surgical items. For example, the first subset of the surgical items may correspond to already used surgical items, the second subset of the surgical items may correspond a currently used surgical item, and the third subset of the surgical items may correspond to subsequently needed surgical items.

In some examples, the set of surgical items 8302 (Item 1-Item N) may define similar surgical items of different sizes or shapes, which may be used in succession in the surgical procedure. For example, the set of surgical items 8302 (Item 1-Item N) may correspond to a set of orthopedic sounders (e.g., for sounding the humeral canal) of sequential sizes or shapes for an orthopedic shoulder reconstruction surgery. In some examples, the set of surgical items 8302 (Item 1-Item N) may further comprise one or more punching tools of sequential sizes or shapes for an orthopedic shoulder reconstruction surgery. In some examples, the set of surgical items 8302 (Item 1-Item N) may further comprise one or more compacting tools of sequential sizes or shapes for an orthopedic shoulder reconstruction surgery. In still another example, the set of surgical items 8302 (Item 1-Item N) may further comprise one or more surface planing tools of sequential sizes or shapes for an orthopedic shoulder reconstruction surgery. In these and other examples, the set of surgical items 8302 (Item 1-Item N) of different sizes or shapes may be illuminated, but the illumination may differ depending on whether such surgical items have been previously used, such surgical items are in current use, or such surgical items are planned for subsequent use. The entire set may be illuminated, but the illumination may be conspicuously coded so that the nurse or other user is able to distinguish previously-used surgical items from the current surgical item in use, and to distinguish subsequently needed surgical items from the current surgical item in use and the previously-used surgical items. Different types of light colors, different types of light intensities or different types of lighting effects may be used (possibly in combination) to aid the nurse in surgical item selection. The set of surgical items to be used in the procedure may be defined by a preoperative plan, and the techniques of this disclosure may identify all surgical items of the procedure and may also identify a particular surgical item that is the current surgical item needed in the procedure according to the preoperative plan, e.g., as defined by a virtual patient-specific surgical plan. In some cases, surgical items may range in size from e.g., 1 to 10, and the system may be designed to identify a subset of these sizes for use, e.g., according to a preoperative plan. In some cases, there may be one light for an entire set of surgical items and another light for a specific surgical item to be used from that set.

As mentioned above, in some examples, some or all of the techniques of this disclosure may be implemented with the aid of mixed reality. For example, rather than using lights that are integrated into the surgical items themselves, virtual information may be overlaid on the surgical items by a visualization device, such as a MR headset worn by the nurse during the operating procedure. This may eliminate the need for lighting in surgical items, although lighting may still be desirable even when mixed reality is used. In other words, in some example, the mixed reality implementations may be used in place of physical lighting in the surgical items, although in other examples, mixed reality implementations may be used in combination with physical lighting in the surgical items. Moreover, mixed reality may be used in combination with other advanced features in the surgical items, such as lights, sensors, accelerometers or other item tracking features.

Figure 84:
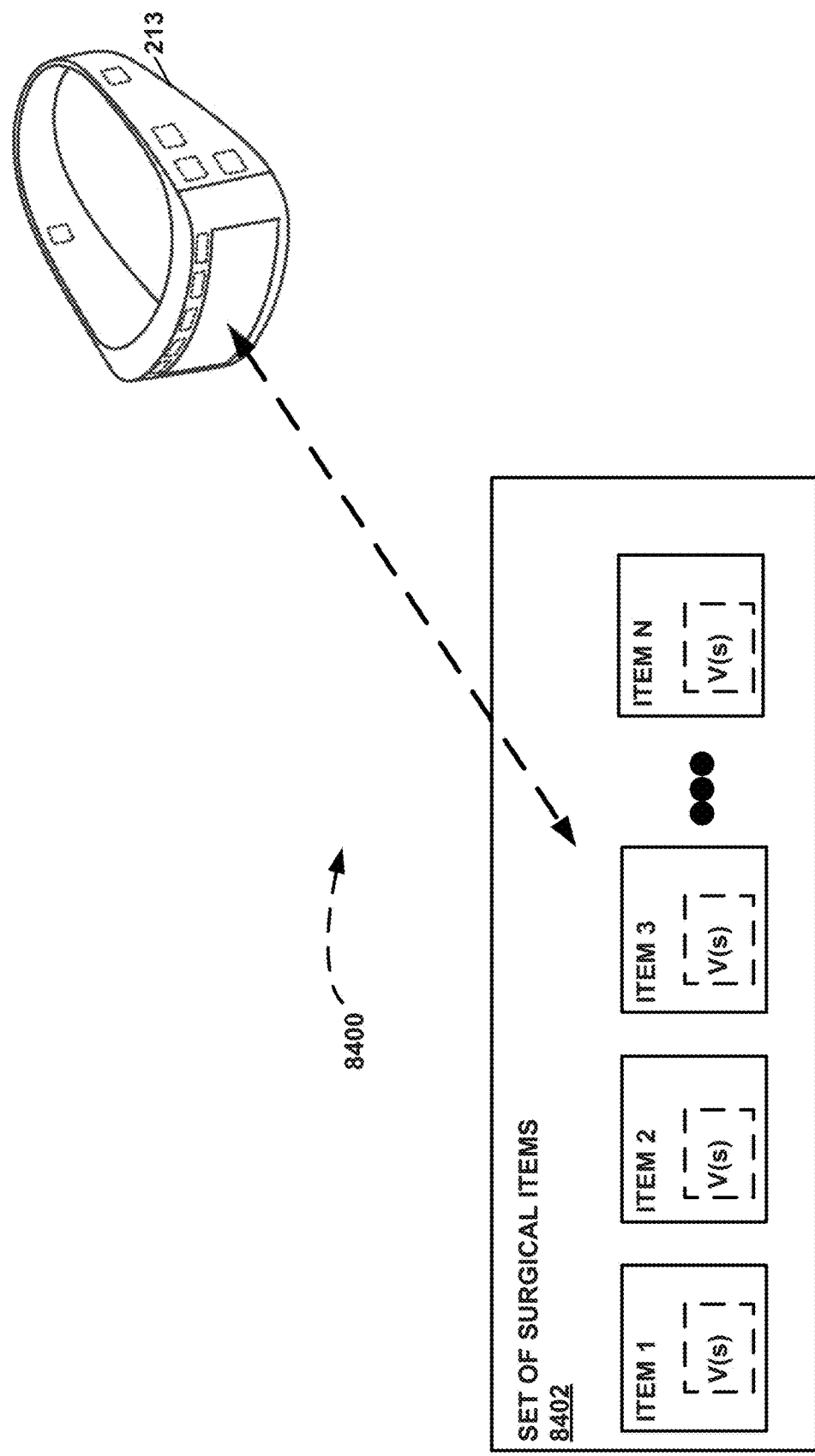
FIG. 84 is a conceptual block diagram illustrating a medical device system comprising a set of surgical items and a processing device in the form of an MR visualization device in accordance with an example of this disclosure.

FIG. 84 is a conceptual block diagram illustrating a medical device system 8400 comprising a set of surgical items 8402 and a processing device in the form of an MR visualization device 213 in accordance with an example of this disclosure. In this example, each of the surgical items in set 8402 is shown with an overlaid virtual element shown as "V(s)." The virtual elements V(s) may be presented to the user of visualization device 213 as virtual elements of a mixed reality presentation. The virtual elements V(s) may function in a similar manner to light sources L(s) shown and described in FIG. 83. However, virtual elements V(s) are not really part of the set of surgical items 8402. Instead, they are elements presented by visualization device 213 so as to appear to be associated with each of the surgical items in the set of surgical items 8402. In this way, rather than using lights that are integrated into the surgical items themselves, mixed reality is used to present virtual information presented or possibly overlaid on the surgical items by visualization device 213. Visualization device 213 may be used for surgical item identification, e.g., for a nurse, while also providing intraoperative guidance and workflow guidance. The views seen on visualization device 213 may be different for a nurse relative to the views of a surgeon. The item identification features or presentation on visualization device 213 may be presented to a nurse, and not presented to the surgeon, although view sharing techniques may also be used, whereby a surgeon is able to select and view images or objects from the nurse's view, as described in greater detail elsewhere in this disclosure.

According to this disclosure, visualization device 213 presents virtual information V(s) on or around each of the surgical items within the set of surgical items 8402 in a way that can aid a nurse in identifying a sequence of surgical items needed by the physician in a surgical procedure. Such virtual information may include virtual halos, outlines, highlighting, marks, text (including lettering and numbers), or other types of virtual elements to distinguish the surgical items. Visualization device 213 may be configured to the activate or deactivate the virtual elements V(s) in each of the surgical item (e.g., Item 1, Item 2, Item 3, . . . Item N) of the set of surgical items 8402 such that different surgical items appear to be illuminated with different colors. For instance, differently colored virtual halos, outlining, or highlighting may be used to illuminate surgical items. A color coordination scheme may be defined so that the nurse is able to use colors to identify which surgical item is being used, which surgical items have already been used, and which of the surgical items is the next surgical item needed by the physician in the surgical procedure. The sequence of surgical items needed over the course of the surgical procedure may be set forth in a preoperative plan.

In some examples, visualization device 213 is configured to control the virtual information V(s) associated with each of the surgical items (Item 1-Item N) within the set of surgical items 8402 so as to identify all of the surgical items in the set of surgical items and to specifically distinguish one of the surgical items. In other words, all of the surgical items (Item 1-Item N) within set 8402 may be identified by virtual information V(s), but a specific one of the items (e.g., item 2 within set 8402) may be distinguished by its associated virtual information V(s). The virtual information V(s) may include any of the types of virtual information described elsewhere in this disclosure for distinguishing surgical items. In this way, mixed reality may be used to help the nurse to identify the entire set of surgical items as well as the specific surgical item that is currently needed. The set 8402 of surgical items (Item 1-Item N) may be included within a larger collection of surgical items, such that virtual identification of the set of surgical items (Item 1-Item N) with virtual information V(s) distinguishes the set of surgical items from the larger collection of surgical items, and the distinguished virtual information of the specific surgical item (e.g., V(s) of Item 2) may allow the nurse to more quickly identify the specific surgical item within the set.

In some examples, virtual elements V(s) that are overlaid on each surgical item in the set of surgical items 8402 may comprise different colors, so as to distinguish one of the surgical items from the set of surgical items. In some examples, a MR lighting effect may be used with virtual elements V(s) (e.g., blinking or flashing light) to distinguish one of the surgical items. In some examples, a lighting intensity applied to virtual elements V(s) to distinguish one of the surgical items. These or other examples (as well as any combination of such distinguished lighting by virtual elements V(s)) may be used to help the nurse quickly and accurately identify the specific surgical item within the set.

In some examples, a medical device system comprises a plurality of surgical items, a visualization device configured to present a MR presentation to a user; and one or more processors configured to select a surgical item of the plurality of surgical items based on a surgical procedure. The one or more processors may be further configured to present, in the MR presentation, virtual information that identifies the selected surgical item among the plurality of surgical items. The virtual information may be presented on or adjacent a position of the selected surgical item visible via the visualization device. The processors may be part of the MR visualization device or the processors may be external to the MR visualization device. As described in greater detail elsewhere in this disclosure, the MR visualization device may comprise one or more see-through holographic lenses and one or more display devices that display an image via the holographic lenses to present the virtual model and the virtual guide to the user.

As further examples of MR content presented to the user, e.g., by visualization device 213, virtual elements V(s) may comprise identification loops or circles circumscribing the surgical item for identification, arrows, X's, reticles, brackets, shapes (circles, rectangles, squares, ovals, numbers, letters, words or symbols, which may flash or have other effects), different background hatching or patterns, combined with colors or intensities. These and a wide variety of other types of MR content could be added as visual elements V(s) to highlight (or distinguish) a given surgical item with the aid of MR.

In some examples, the virtual elements V(s) associated with each of the surgical items are displayed to the user via visualization device 213 in a way to distinguish a first subset of the surgical items, a second subset of the surgical items and a third subset of the surgical items. For example, the first subset of the surgical items may correspond to already used surgical items, the second subset of the surgical items may correspond a currently used surgical item, and the third subset of the surgical items may correspond to subsequently needed surgical items.

In some examples, the set of surgical items (Item 1-Item N) of set 8402 may define similar surgical items of different sizes or shapes, which may be used in succession in the surgical procedure. For example, the set of surgical items 8402 (Item 1-Item N) may correspond to a set of sounders of sequential sizes or shapes for an orthopedic shoulder reconstruction surgery. In addition, the set of surgical items 8402 (Item 1-Item N) may further comprise one or more punching tools of sequential sizes or shapes for an orthopedic shoulder reconstruction surgery. Moreover, the set of surgical items 8402 (Item 1-Item N) may also comprise one or more compacting tools of sequential sizes or shapes for an orthopedic shoulder reconstruction surgery. In addition, the set of surgical items 8402 (Item 1-Item N) may also comprise one or more surface planing tools of sequential sizes or shapes for an orthopedic shoulder reconstruction surgery.

In these and other examples, the set of surgical items 8402 (Item 1-Item N) of different sizes or shapes may be identified with virtual elements V(s). In some examples, each surgical item is identified when it is time for that surgical item to be used. However, in some examples, multiple surgical items may be identified. In some examples, the type of element, color or shape of virtual elements V(s) may differ depending on whether such surgical items have been previously used, such surgical items are in current use, or such surgical items are planned for subsequent use. The entire set may be identified by virtual elements V(s), but the virtual elements V(s) may be conspicuously defined so that the nurse is able to distinguish previously-used surgical items from the current surgical item in use, and to distinguish subsequently needed surgical items from the current surgical item in use and the previously-used surgical items. Different types of colors, different types of intensities or different types of effects may be used with virtual elements V(s) (possibly in combination) to aid the nurse in surgical item selection.

The set of surgical items to be used in the procedure may be defined by a preoperative plan, and the techniques of this disclosure may identify all surgical items of the procedure and may also identify a particular surgical item that is the current surgical item needed in the procedure according to the preoperative plan. Again, visualization device 213 may be used for surgical item identification, e.g., for a nurse, while also providing intraoperative guidance and workflow guidance. The views seen on visualization device 213 may be different for a nurse relative to the views of a surgeon. The item identification features or presentation on visualization device 213 may be presented to a nurse, and not presented to the surgeon, although view sharing techniques may also be used, whereby a surgeon is able to select and view images or objects from the nurse's view, as described in greater detail elsewhere in this disclosure.

Figure 85:
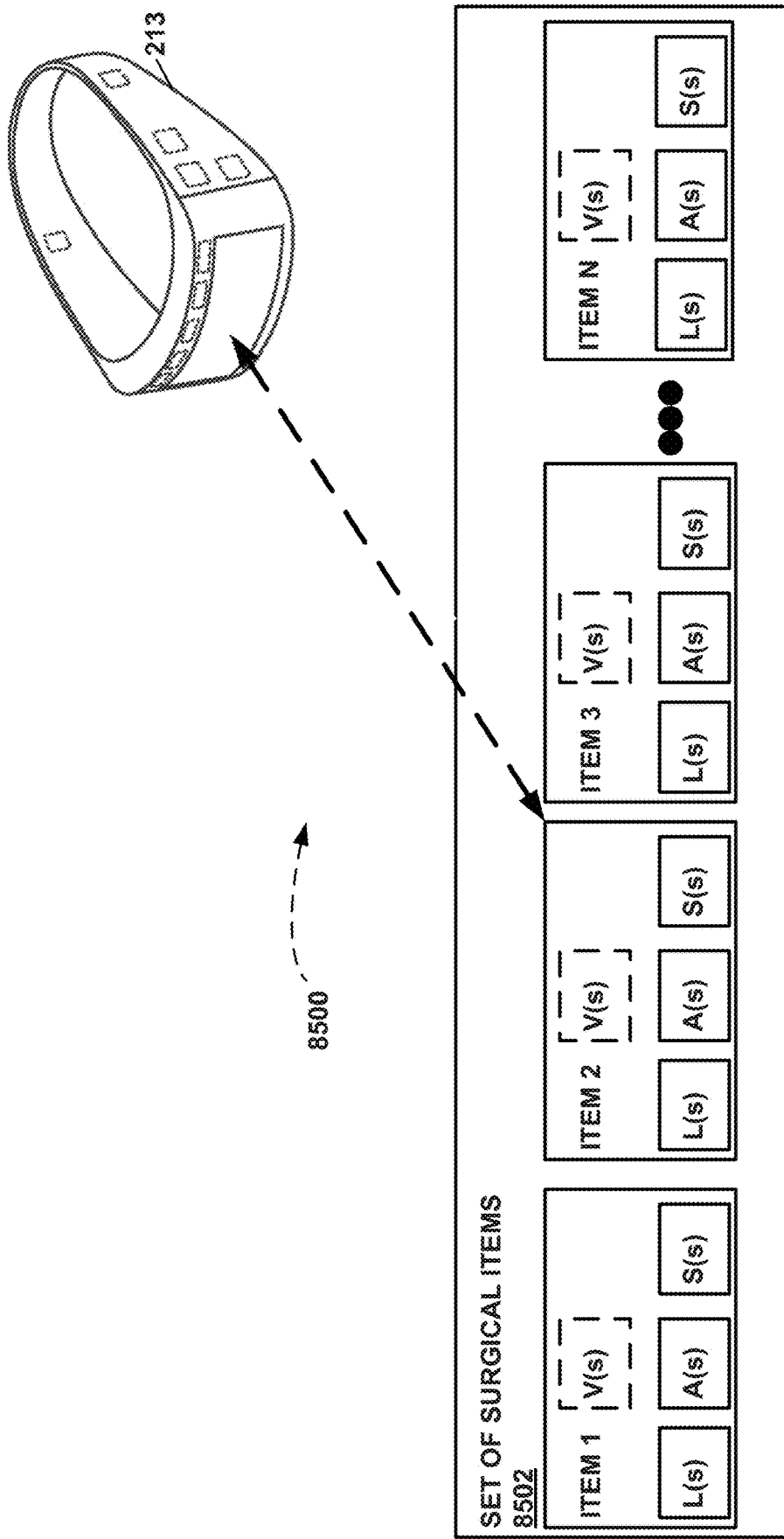
FIG. 85 is another conceptual block diagram illustrating a medical device system comprising a set of surgical items and a processing device in the form of an MR visualization device in accordance with an example of this disclosure.

FIG. 85 is another conceptual block diagram illustrating a medical device system 8500 comprising a set of surgical items 8502 and a processing device in the form of a visualization device 213 in accordance with an example of this disclosure. In this example, medical device system 8500 may include some or all of the features described above with respect to system 8300 of FIG. 83 in combination with some or all of the features described above with respect to system 8500 of FIG. 85. Each of the surgical items in set 8502 may include light sources L(s), accelerometers A(s), other sensors (S(s), as well as one or more virtual elements shown as "V(s)." The virtual elements V(s) may be presented to the user of visualization device 213 as a virtual elements of a mixed reality presentation. In this way, surgical items with advanced features, such as light sources L(s), accelerometers A(s), other sensors (S(s) may be used along with mixed reality and virtual elements V(s) to provide for an advanced set of surgical items with mixed reality controls, item tracking and procedure tracking. The use of virtual elements V(s) in combination with light sources L(s) may allow for item identification by persons wearing or otherwise using a visualization device, as well as persons not using a visualization device. Or light sources L(s) may be used in combination with virtual elements V(s) to improve item identification or different illumination or identification effects.

In some examples, MR system 212 may be configured to allow for item tracking with the aid of mixed reality. Moreover, MR system 212 may also allow for tracking and documentation of the surgical procedure using mixed reality. Item tracking, for example, may be performed by MR system 212 to help document and log the surgical procedure, as well as provide a safety check to ensure that the correct surgical item is being used, e.g., relative to a preoperative plan. MR system 212 may utilize object-based detection of the surgical items.

For example, when a physician is given one of the surgical items in the set of surgical items 8502, MR system 212 may perform visual object detection as a verification to ensure that the correct surgical item is being used. Visual object detection may refer to detection of object shape (or possibly detection of bar code, text, letters, numbers words, or other identifying indicia associated with a surgical item). Such visual object detection may be used in addition to bar code scanning, RFID reading or other item tracking techniques. Moreover, accelerometer data associated with the accelerometer A(s) of a selected surgical item may be used as a further verification and documentation of surgical item use. For example, accelerometer data associated with accelerometers (A(s) may be indicative of surgical item use, surgical item resting, specific type of surgical item positioning. Such data may be useful to identify and document surgical item use (or non-use).

The use of a combination of item tracking techniques may help to improve the accuracy of item tracking and documentation during the procedure. According to this disclosure, two or more of the following techniques may be used to verify surgical item use: accelerometer data, visual object detection of the surgical item with cameras of an MR visualization device, tray tracking by an MR visualization device by tracking and monitoring the absence of the surgical item in the tray during its use so as do identify a likely time of surgical item use, RFID or optical code scanning of the surgical item, or other tracking techniques. Tray tracking may use cameras to identify the absence of a surgical item from a tray and the absence of the surgical item from the tray may be used to infer that the surgical item is likely in use. In some examples, three or more, four or more, or even five or more of these item tracking techniques may be used to help to ensure that item tracking is accurate and well-documented during the procedure.

Item tracking information may be recorded by visualization device 213 during the procedure as a record of the surgical procedure. The recorded item tracking information may include video of how surgical items are used, records of which surgical items were used, records of when individual surgical items were used, and so on. For instance, information about which surgical items were used can be To facilitate such multi-mode tracking of surgical items, in some cases, optical code reading, object detection with the user of cameras, RFID reading or other machine automation may be incorporated into a visualization device, like visualization device 213 in order to allow such automation in an MR environment without the need for additional bar code readers or RFID readers. In this way, surgical procedure documentation may be improved by tracking and verifying that the correct surgical items are used at the proper states of the procedure.

System 8500 may be configured to track item use and recommend the next surgical item to be used for the procedure. For example, system 8500 may be configured to select a surgical item based on a surgical plan, such as a preoperatively-defined surgical plan. In this example, the surgical plan may contain information that specifies which surgical items are to be used in various steps of the surgery defined by the surgical plan. Accordingly, system 8500 may use such information in the surgical plan to select the surgical item based on the surgical plan. Moreover, after using all of the surgical items (Item 1-Item N) in the set of surgical items 8502, system 8500 may be configured to move on to a next stage of the surgical procedure, e.g., possibly identifying an entirely new set of surgical items, e.g., in a different tray or box, for that next step. In some examples, the item tracking and item identification features may be specific to a nurse wearing or otherwise using an MR device such as visualization device 213.

The surgeon may also be wearing or otherwise using a similar MR device, but the surgeon's MR device may not include the item tracking and item identification features performed by MR device of the nurse. In other words, in some examples, the surgeon's MR device be configured to provide all of the functionality of the nurses' MR device, while in other examples, the surgeon's MR device may not be configured present virtual imagery that identifies a particular surgical item and may not include visual detection features or features for processing of accelerometer data for identifying a surgical item or use of a surgical item.

In some examples, view sharing techniques, which are described elsewhere in this disclosure, could be used to enable the surgeon to see the views of the nurse, but typically, the surgeon may be viewing his or her surgeon-specific MR presentation and not the item tracking MR elements seen by the nurse, such that the surgeon may focus attention on the orthopedic surgical procedure and surgical bone or tissue site being addressed. The MR elements seen by the nurse for item identification may be visible to that nurse only when the nurse views the set of surgical items.

A record of the surgical procedure can be very helpful or important for safety tracking, quality control, legal compliance, analysis of the surgical procedure, tracking of how many times an instrument or other surgical item has been used, instrument age, instrument longevity, or other reasons. In addition to tracking surgical item use, visualization device 213 (or possibly another device if MR is not used in the procedure) may be configured to log times associated with surgical item use in the procedure, log a counter for each surgical item use, record time between steps of the procedure, or other timing or tracking. For example, surgical item use and surgical item monitoring may be used to record the amount of time that the surgeon performed sounding, the amount of time that the surgeon performed rasping, the amount of time that the surgeon performed compacting, the amount of time that the surgeon performed surface planing, and so forth. By using surgical item use to track each step of the procedure and by recording the time that each surgical item is used, the system may record a very accurate picture of the entire surgical procedure.

Other things that may be useful to track may include the number of sterilizations performed on a surgical item, the number of times that a surgical item is moved, the number of times or the amount of time that a surgical item is used in a surgical procedure, an indication that a surgical item has been dropped on the floor, or other surgical item-specific types of use or misuse. In order to record steps of a surgical procedure in a surgical procedure log, advanced surgical item features, such as light sources L(s), accelerometers A(s), other sensors S(s), may be used alone or in combination with mixed reality techniques, including MR-based item tracking using visual elements V(s), visual object detection using sensors mounted on a MR visualization device, and the presentation of virtual information V(s) to the nurse.

For example, surgical procedure recordkeeping and surgical item tracking may be divided into stages of a surgical procedure. FIGS. 86-94 shows one example of stages of an anatomic arthroplasty whereby item tracking, item selection and identification and documentation of surgical item use may be performed and recorded for each stage of the procedure. The example set forth in FIGS. 86-94 show humeral preparation and implant in a shoulder arthroplasty for purposes of illustration, but similar techniques to those described herein can be applied to other steps in a shoulder arthroplasty such as glenoid preparation and implant, as well as other orthopedic procedures. Although FIGS. 86-94 as well as FIGS. 95-108 discuss aspects of specific shoulder surgery steps, the techniques of this disclosure may apply to other types of surgery. Moreover, ankle surgery may involves the use of multiple tools and jigs for drilling, cutting, preparing implant sites and installing implants on a patient's talus and tibia, and the tool tracking techniques of this disclosure may be utilized for ankle surgeries, especially when a variety of different tools are used in the procedure.

Figure 89:
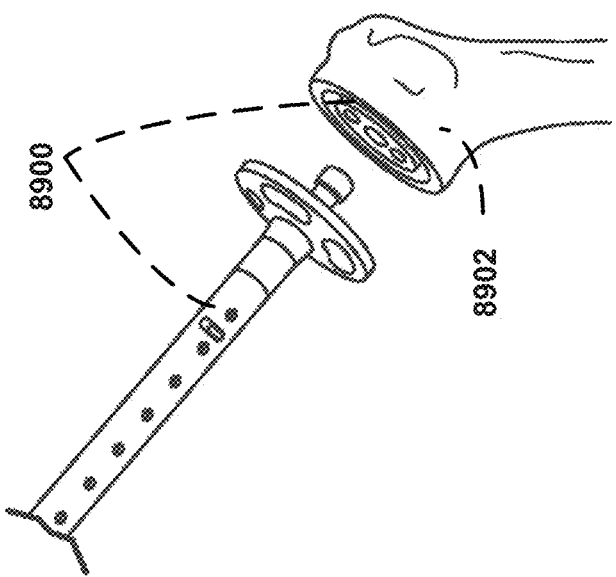
FIG. 89 is a view of an example surface planing procedure in a shoulder arthroplasty procedure.
Figure 88:
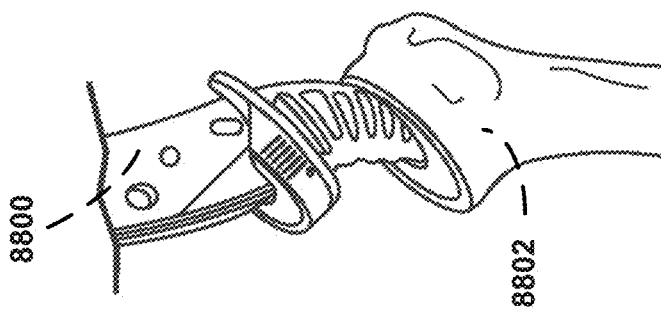
FIG. 88 is a view of an example compacting or rasping procedure in a shoulder arthroplasty procedure.
Figure 87:
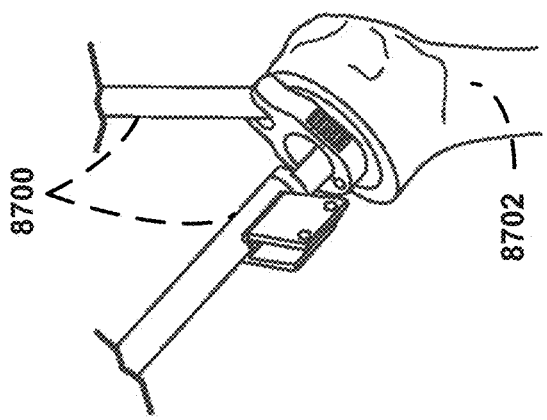
FIG. 87 is a view of an example punching procedure in a shoulder arthroplasty procedure.
Figure 86:
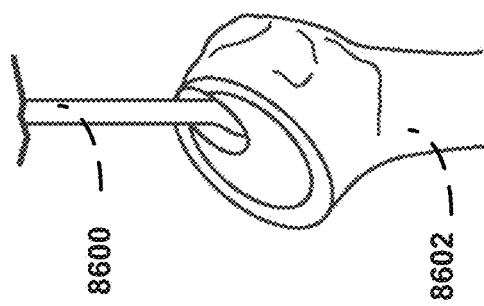
FIG. 86 is a view of an example sounding procedure in a shoulder arthroplasty procedure.

In the example shown in FIG. 86-94, the procedure may be divided into stages, such as a sounding procedure shown in FIG. 86, a punching procedure shown in FIG. 87, a compacting or rasping procedure shown in FIG. 88, a surface planing procedure shown in FIG. 89, a protect procedure shown in FIG. 90, a trial procedure shown in FIGS. 91 and 92, and an implant procedure shown in FIGS. 93 and 94. Each stage may involve the use of multiple surgical items, and the techniques of this disclosure may aid in surgical item selection and surgical item identification of the multiple surgical items used in each stage. In some examples, sets of surgical items are defined for the entire procedure, while in other examples, sets of surgical items are defined for each stage of the overall procedure. In either case, the set of surgical items may be identified while also distinguishing a particular surgical item to be used in a current step of the procedure, e.g., as defined by a preoperative plan. Or the techniques could distinguish a single surgical item in a set of surgical items without identifying other surgical items in the set of surgical items, e.g., identifying one surgical item at a time for each step or stage of the procedure. The sounding procedure shown in FIG. 86 may involve insertion of one or more sounders 8600 into the soft tissue inside a patient's humeral bone 8602. The punching procedure shown in FIG. 87 may involve connection and insertion of punching tools 8700 into the patient's humeral bone 8702 in the area where the sounder was inserted (e.g., shown in FIG. 86). The compacting or rasping procedure shown in FIG. 88 may include the insertion of one or more compacting tools 8800 into the hole created in the patient's humeral bone 8802. Compacting or rasping may be performed with a long stem or a short stem, depending on the circumstances. The surface planing procedure shown in FIG. 89 may include the surface planing via planing tools 8900 on patient's humeral bone 8902. The protect procedure shown in FIG. 90 may include attachment of protection hardware 9000 to the patient's humeral bone 9002. The trial procedure shown in FIGS. 91 and 92 may involve the attachment of additional implantation hardware 9100 or 9200 to the patient's humeral bone 9102 or 9202, and the implant procedure shown in FIGS. 93 and 94 may include attachment of the final implant 9300 or 9400 to the patient's humeral bone 9302 or 9402.

If the procedure is divided into stages, then upon identifying the use of the final surgical item for any given stage, visualization device 213 may be programmed with the stages of the procedure and configured to alert the nurse that the given stage is complete and that its time to prepare for the next stage. In this case, the nurse may be prompted to prepare another set of surgical items as the next set of surgical items to be used in the surgical procedure. For example, after finishing a sounding procedure shown in FIG. 86, which may involve the use of a plurality of differently sized sounders that can be identified and tracked as described herein, the nurse may be prompted by visualization device 213 to prepare the next set of surgical items, i.e., a set of punching tools used for the punching procedure shown in FIG. 87.

Similarly, after finishing the punching procedure shown in FIG. 87, which may involve the use of one or more punching tools that can be identified and tracked as described herein, the nurse may be prompted by visualization device 213 to prepare the next set of surgical item, i.e., a set of compacting tools used for the compacting or rasping procedure shown in FIG. 88. Then, after finishing the compacting or rasping procedure shown in FIG. 88, which may also involve the use of a plurality of different sized compacting tools that can be identified and tracked as described herein, the nurse may be prompted by visualization device 213 to prepare the next set of surgical items, i.e., a set of surface planing tools used for the surface planing procedure shown in FIG. 89. Visualization device 213 may aid in surgical item selection, surgical item preparation, and procedure tracking of each step or sub-step of the surgical procedure. Prompting the nurse for each step may include the presentation of visual cues, virtual elements or other MR content on visualization device 213.

Figure 96:
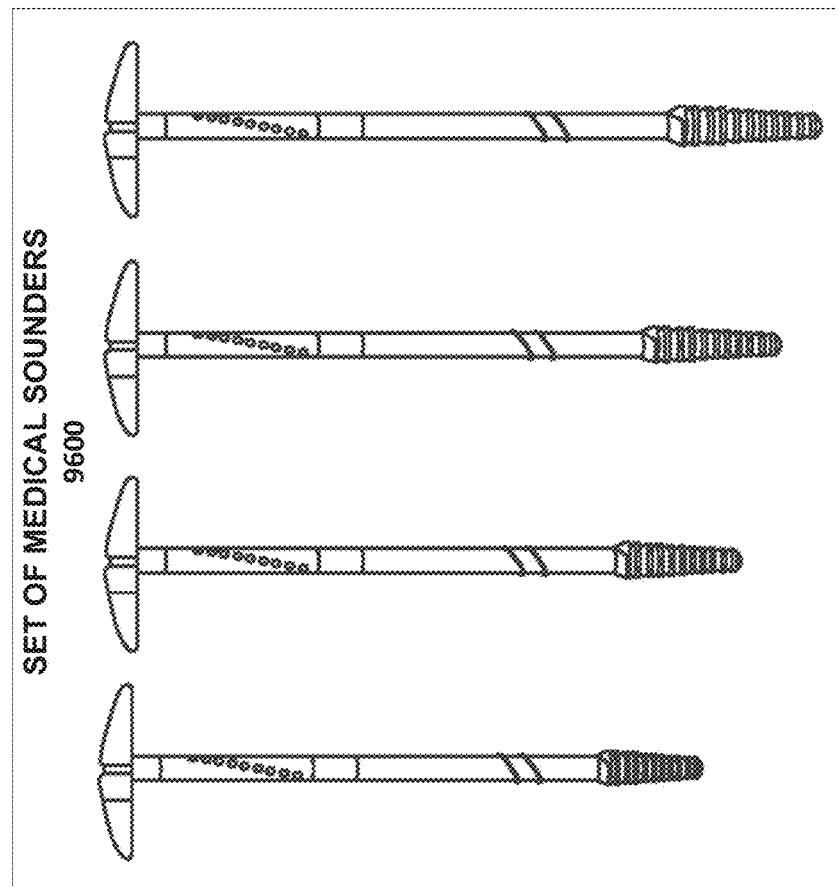
FIG. 96 is an illustration of a set of medical sounders of different sizes for use in the surgical procedure shown in FIG. 95.
Figure 95:
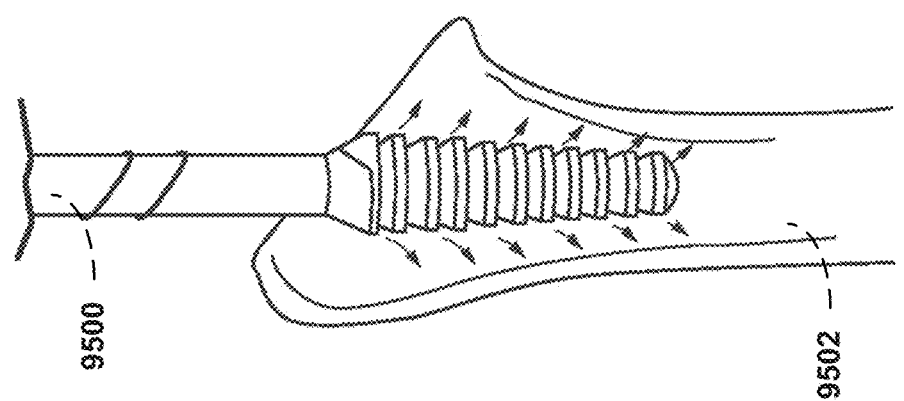
FIG. 95 is a conceptual side view of a sounding procedure being performed on a human humeral bone in which a sounder is inserted into a patient's humeral bone in a shoulder arthroplasty procedure.

FIG. 95 is a conceptual side view of a sounding procedure being performed on a human humeral bone in which a sounder 9500 is inserted into a patient's humeral bone 9502. FIG. 96 is an illustration of a set of medical sounders 9600 of different sizes for use in the surgical procedure shown in FIG. 95. Typically, the sounders are used in succession from a smallest sounder to a largest sounder. Depending on the preoperative plan, some of the sounders may not be used. For example, in some cases the first sounder used may not be the smallest sounder in the set of surgical items, in which case the smallest sounder may not be used in the procedure. Similarly, in some cases, the last sounder used may not be the largest sounder, in which case the largest sounder may not be used in the procedure. The specific sounders to be used may be defined by a preoperative plan, and the surgical item identification techniques may identify surgical items in accordance with the preoperative plan. In some cases, a preoperative surgical plan may identify the surgical items to be used for a given step of a surgical procedure, and visualization device 213 may identify the last surgical item for a given step of a procedure. Then, upon detection of that last surgical item's use, visualization device 213 may automatically identify the next step of the surgical procedure to the user.

According to this disclosure, advanced features (such as accelerometers, light sources or other sensors) may be included in each of the sounders shown in FIG. 96 to enable item identification and item tracking as described herein. Moreover, in some cases, MR system 212 may present virtual elements, e.g., overlaid on or placed on around or adjacent to each of the sounders shown in FIG. 96, to enable item identification and item tracking as described herein. Procedure tracking, timing of use, and documentation of surgical item use may also be recorded by MR system 212 so as to enable automated surgical item identification, procedure tracking and surgical procedure recording.

Figure 97:
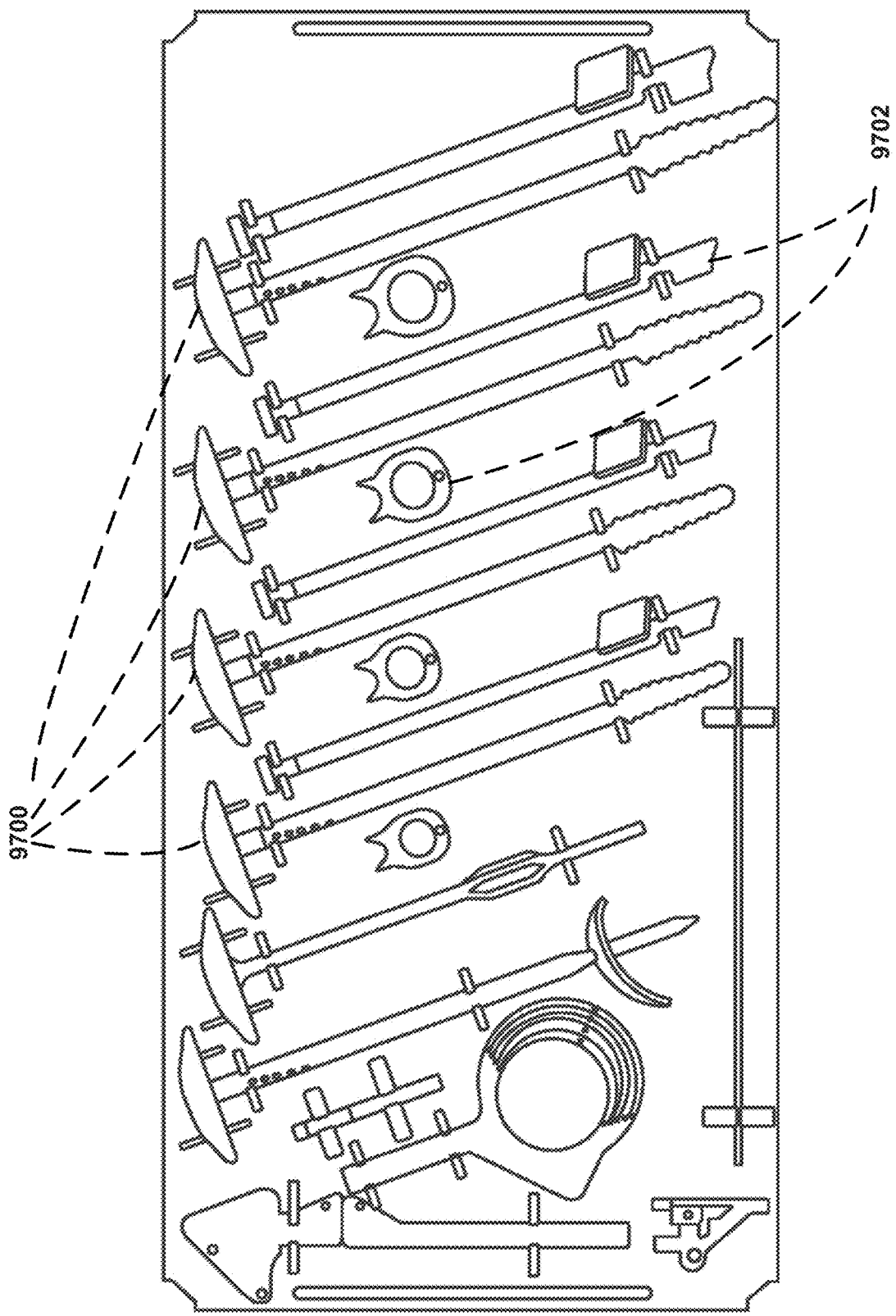
FIG. 97 is an illustration of a set of tools, which include a set of progressively larger sounders.

FIG. 97 is an illustration of a set of surgical items, which include a set of progressively larger sounders 9700. The techniques of this disclosure may take advantage of advanced features (such as accelerometers, light sources or other sensors) in each of the sounders 9700 to enable item identification and item tracking as described herein. Moreover, in some cases, MR system 212 may present virtual elements on each of the sounders 9700 to enable item identification and item tracking as described herein.

Figure 105:
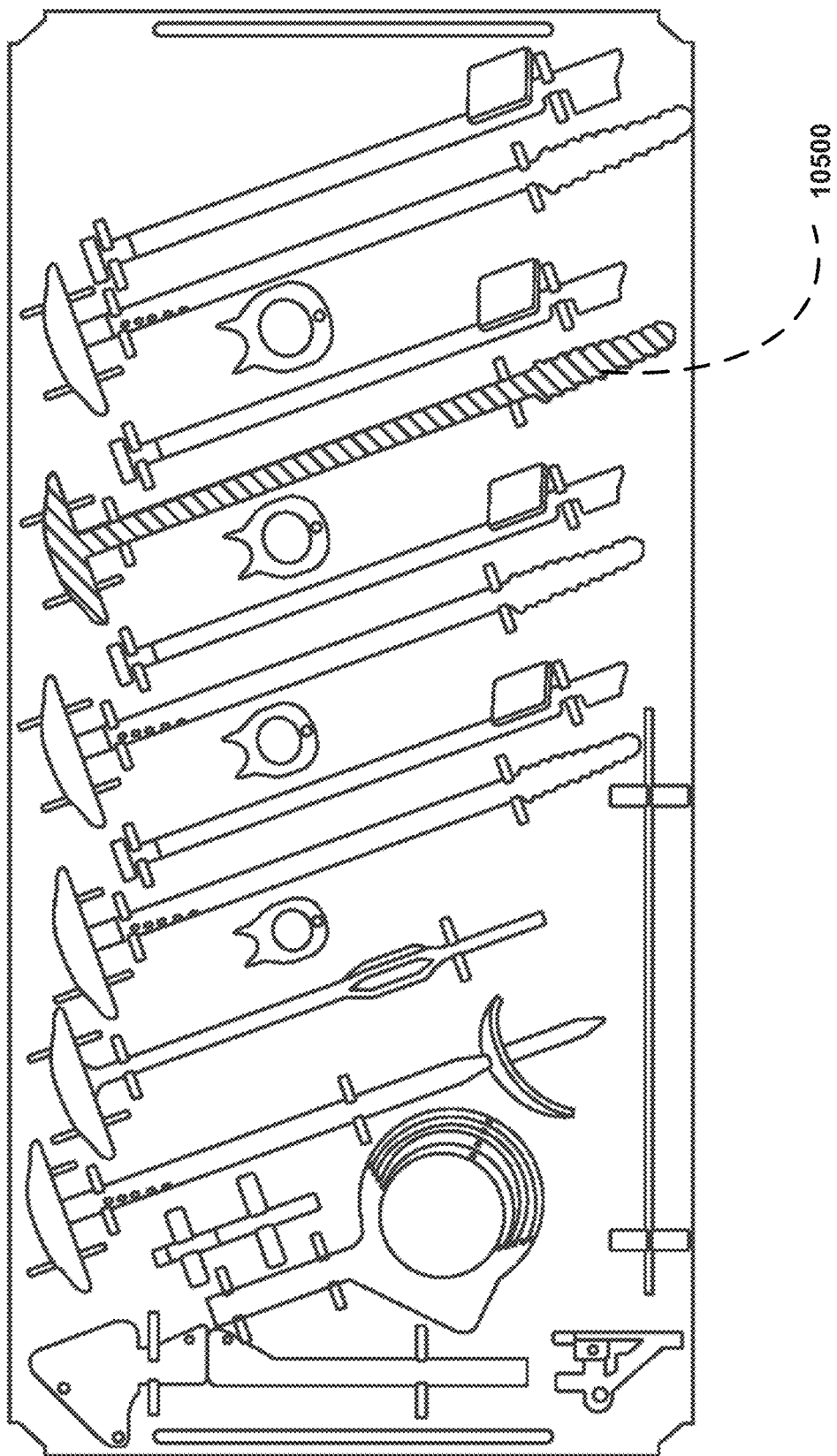
FIG. 105 is an illustration of a set of surgical items similar to those illustrated in FIG. 97 with a virtual element presented to identify a particular surgical item from the set.
Figure 106:
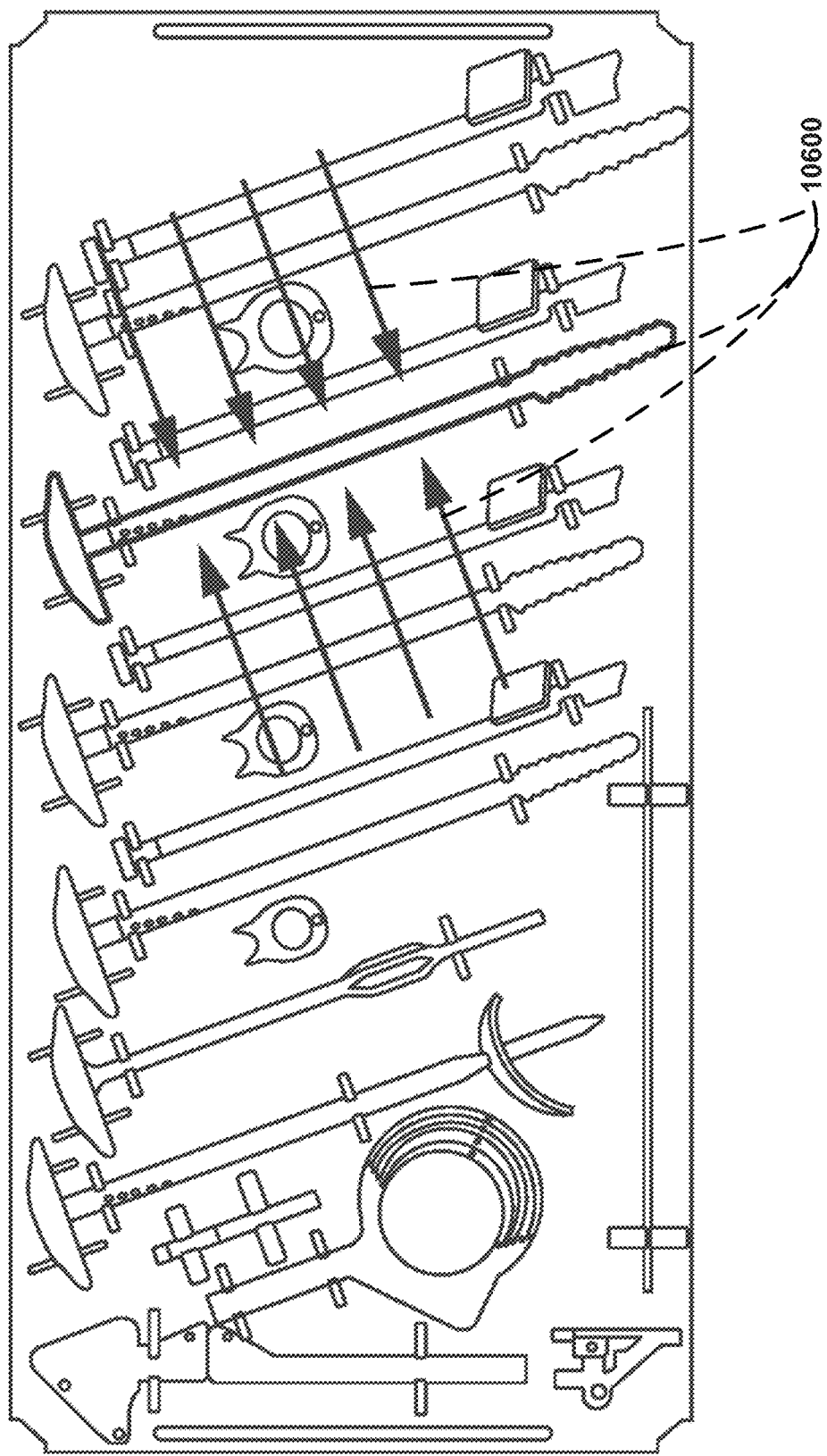
FIG. 106 is another illustration of a set of surgical items similar to those illustrated in FIG. 97 with a virtual element presented to identify a particular surgical item from the set.

The set of surgical items illustrated in FIG. 97 may also include punching tools located next to each size of sounders 9700. According to a surgical procedure, a particular punching tool (e.g., punching tool 9702) may be defined by a preoperative surgical plan as corresponding to a largest sounder size used according to the preoperative plan. In other words, although the set of surgical items shown in FIG. 97 includes progressively sized punching tools, only one of the punching tools may be used in the procedure, e.g., corresponding to the largest sounder used. For this reason, surgical item identification, e.g., by a visualization device 213, to distinguish only that particular punching tool needed for the punching step can be very desirable to help ensure that the correct surgical item is used. Moreover, surgical item tracking and verification described herein may help avoid a scenario where an incorrect sized punching tool is used. FIG. 105 is an illustration of a set of surgical items similar to those illustrated in FIG. 97. FIG. 105 shows one exemplary virtual element 10500, which may be presented by visualization device 213, e.g., as an overlay, to identify or distinguish a particular surgical item needed for a surgical step. FIG. 106 is another exemplary illustration of a set of surgical items similar to those illustrated in FIG. 97. FIG. 106 shows another exemplary virtual element 10600, which may be presented by visualization device 213, e.g., as arrows and/or outlines of a given surgical item, to identify or distinguish that surgical item needed for the next step of the surgical procedure. Although FIGS. 105 and 106 show two examples of virtual elements 10500 and 10600, many other types of virtual elements could be used and presented by vitalization device 213 to identify surgical items.

Figure 99:
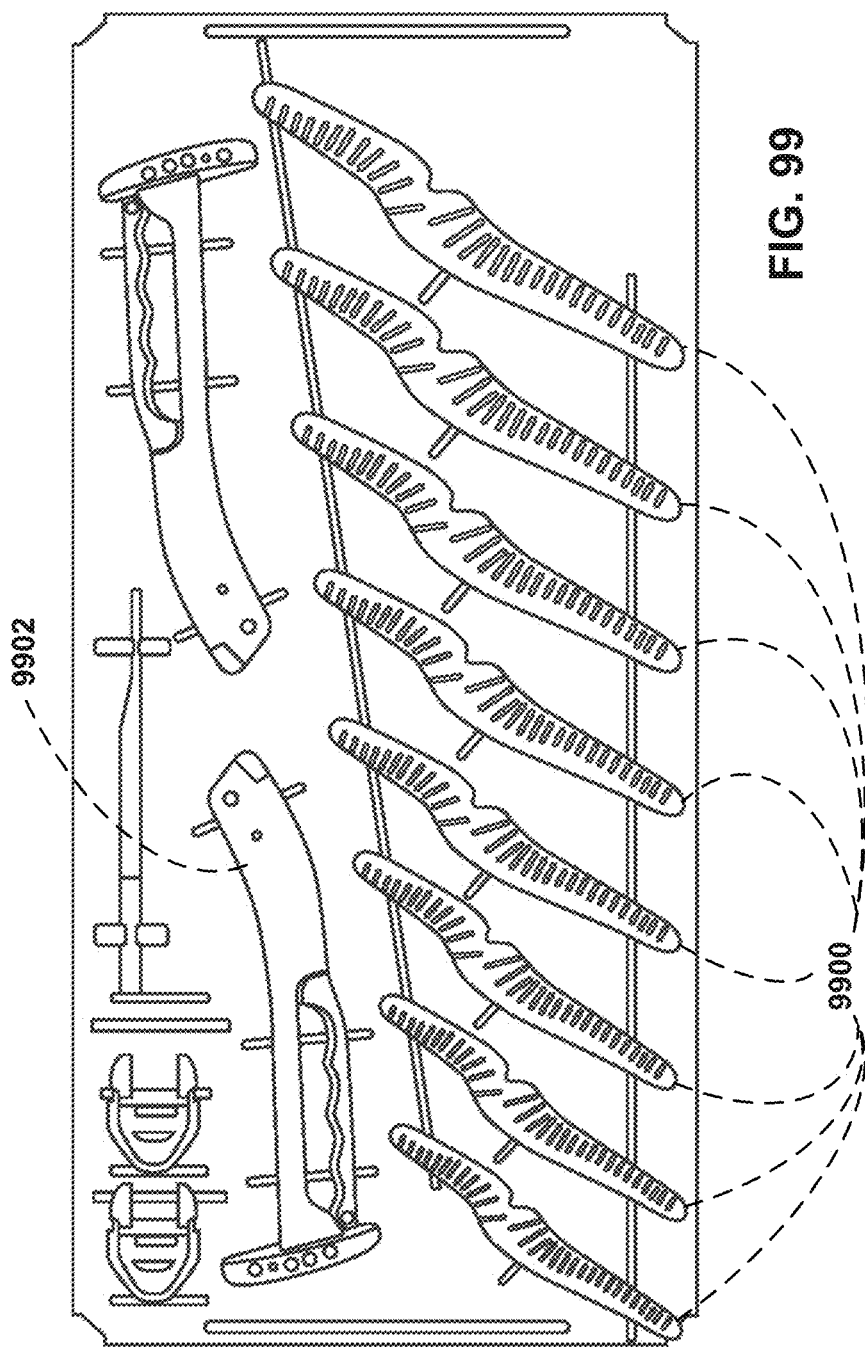
FIG. 99 is an illustration of a set of tools, which include a set of progressively larger compacting tools.
Figure 98:
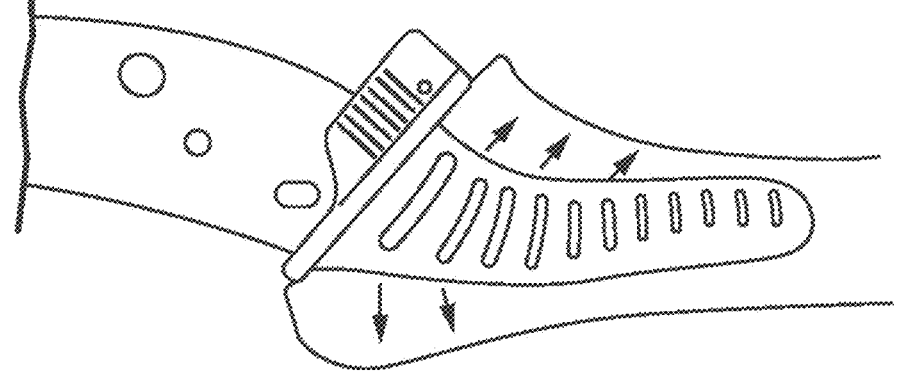
FIG. 98 is a conceptual side view of a compacting or rasping procedure being performed on a human humeral bone.

FIG. 98 is a conceptual side view of a compacting or rasping procedure being performed on a human humeral bone. FIG. 99 is an illustration of a set of surgical items, which include a set of progressively larger compacting tools 9900. The techniques of this disclosure may use advanced features (such as accelerometers, light sources or other sensors) in each of the compacting tools 9900 to enable item identification and item tracking as described herein. Moreover, in some cases, MR system 212 may present virtual elements on each of the compacting tools 9900 to enable item identification and item tracking as described herein.

Items may also require assembly, e.g., requiring attachment of compacting tools 9900 to a handle 9902. Item assembly may be illustrated to the nurse by an instructional diagram, animation or video shown in a visualization device 213 worn by the nurse. The display of the instructional diagram, animation or video may be initiated by a selecting a widget or icon in an MR or AR display so that the nurse can be shown how to properly assemble the items, if such instruction is needed in real time. Instructional diagrams, animations or videos may be presented to illustrate steps of the procedure, and for a nurse, instructional diagrams, animations or videos to illustrate item assembly can be very helpful.

Rasping tools 9900 may comprise two sided tools that have both long stem and short stem rasping elements. Accordingly, item identification (e.g., by lighting or by virtual overlays of virtual elements in mixed reality) may also identify the rasping side that should be used in the procedure (e.g., the long stem or the short stem). This can be very helpful to a nurse in order to ensure that long stem rasping is used when long stem rasping is defined in the preoperative plan, or to ensure that short stem rasping is used with short stem rasping is defined in the preoperative plan. When each rasping tool is two sided and only one side may be used in the procedure, it may be very desirable to identify not only the rasping tool, but also the portion of the rasping tool to be used, e.g., via lighting within the rasping tool or via mixed reality information. Accordingly, the rasping tool may be configured to selectively light one side of the rasping tool to identify that side as being the appropriate side for rasping, or visualization device 213 may be configured to present virtual information that identifies a particular side of the rasping tool as being the appropriate side for rasping. Surgical item assembly may also be shown (e.g., via instructional diagram, animation or video in the nurse's mixed reality presentation) in a way that clearly shows assembly of the rasping tool for short stem rasping or long stem rasping.

Figure 107:
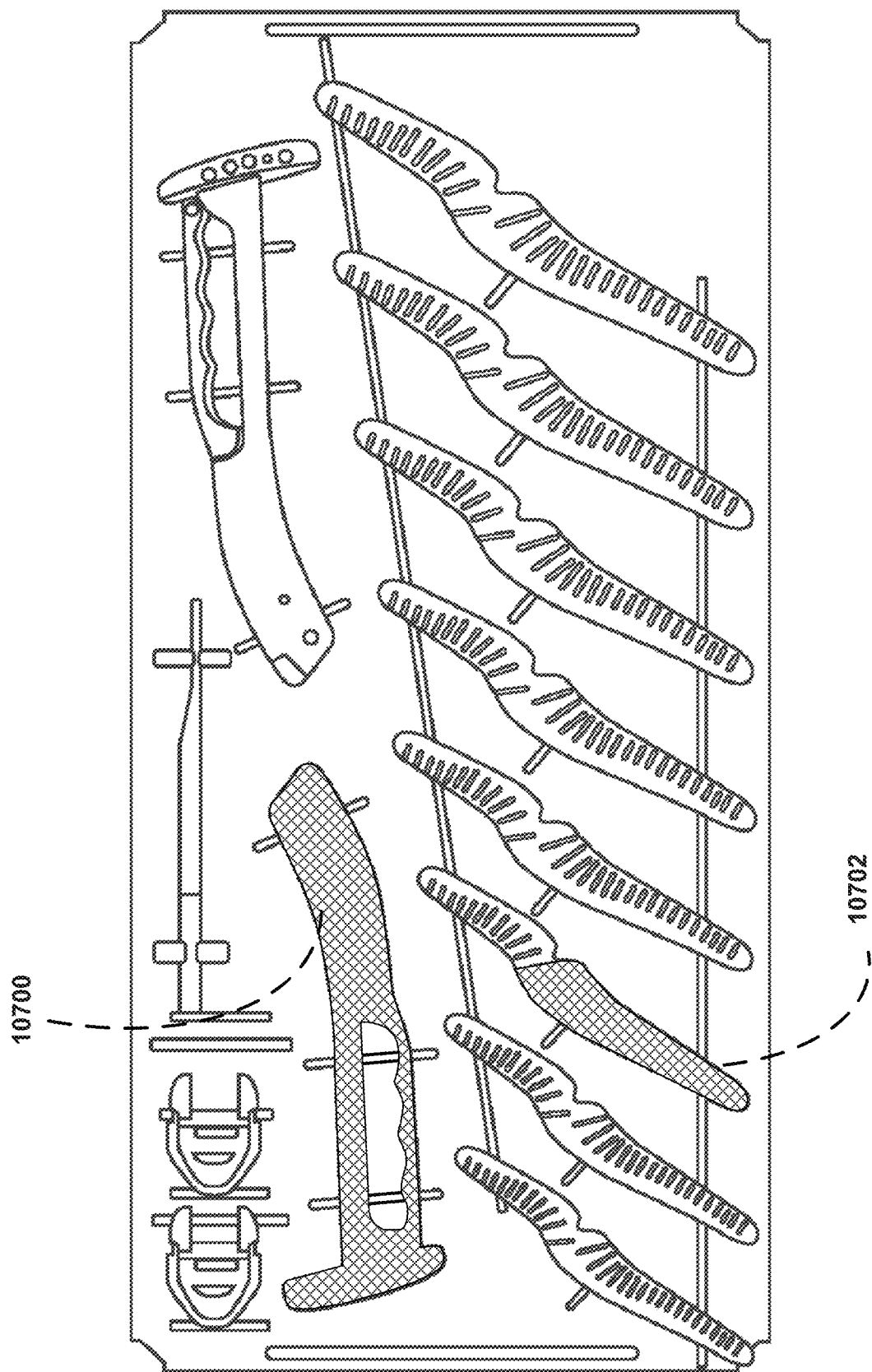
FIG. 107 is an illustration of a set of surgical items similar to those illustrated in FIG. 99 with virtual elements presented to identify items needed in a surgical procedure, to identify items that require assembly and to identify a side to be used on a two-sided item.

In some examples, e.g., according to a preoperative plan, the item identification techniques described herein may identify a particular rasping tool that is three sizes below the final sounder that is used in the sounding process. Rasping may be sequentially performed until satisfactory fixation is achieved. Satisfactory fixation can be assessed by a slight torque motion of the inserter handle. The compactor or rasping tool should not move within the patient's bone. Accordingly, since the final rasping tool size may be undefined by the preoperative surgical plan and defined or selected during the intraoperative process, a sequence of rasping tools may be identified by the techniques of this disclosure with unique coloring, visual effects or even text overlay via an MR device such as visualization device 213. Moreover, the item identification techniques for rasping may explain (with text, animation or videos) or identify to the nurse (via virtual elements) that the final rasping tool size is that which achieves a satisfactory level of fixation, which may be determined by the physician during the procedure. FIG. 107 is an illustration of a set of surgical items similar to those illustrated in FIG. 99. FIG. 107 shows one exemplary set of virtual elements 10700 and 10702, which may be presented by visualization device 213, e.g., as overlays, to identify or distinguish a particular surgical item needed for a surgical step. Virtual elements 10700 and 10702 may require assembly, and in some cases, visualization device 213 may present an instructional video to demonstrate the assembly process (which may be selectable by the nurse and shown only when needed). Furthermore, virtual element 10702 may be configured to not only identify the surgical item, but to identify a side of the surgical item (in this case the long stem of a rasping tool) so as to inform the nurse of the side of a two-sided surgical element that should be used in the surgical procedure.

Figure 101:
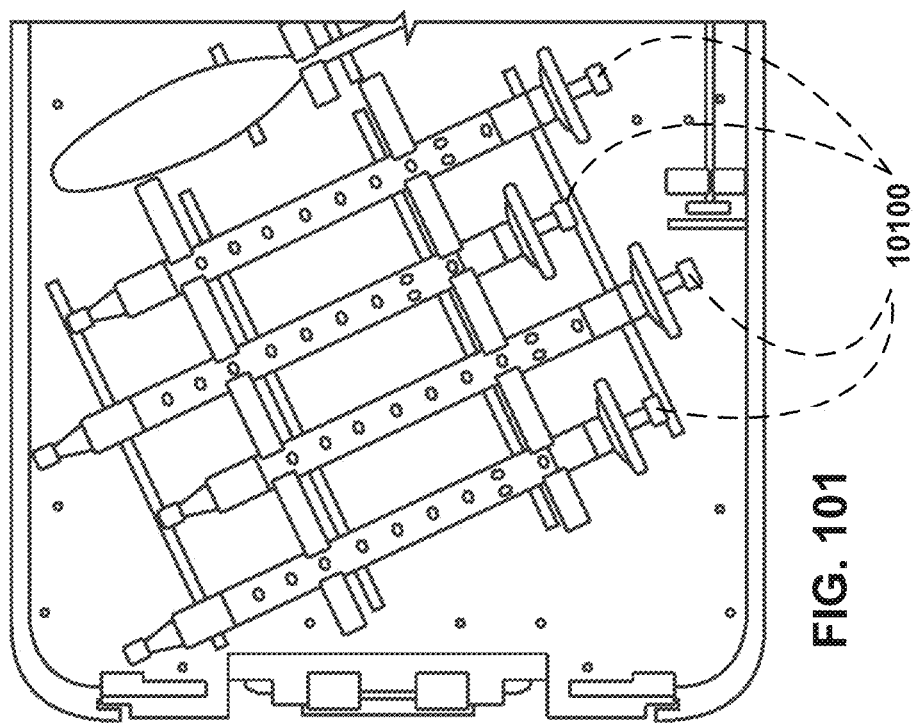
FIG. 101 is an illustration of a set of tools, which include a set of progressively larger surface planing tools.
Figure 100:
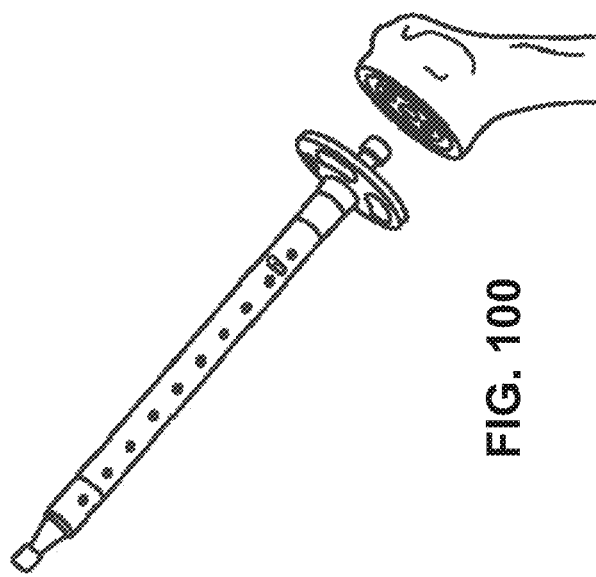
FIG. 100 is a conceptual side view of a surface planing procedure being performed on a human humeral bone.

FIG. 100 is a conceptual side view of a surface planing procedure being performed on a human humeral bone. FIG. 101 is an illustration of a set of surgical items, which include a set of progressively larger surface planing tools 10100. The techniques of this disclosure may take advantage of advanced features (such as accelerometers, light sources or other sensors) in each of the surface planing tools 10100 to enable surgical item identification and surgical item tracking as described herein. Moreover, in some cases, additionally or alternatively, visualization device 213 may present virtual elements on each of the compacting tools 9900 to enable item identification and item tracking as described herein.

Figure 108:
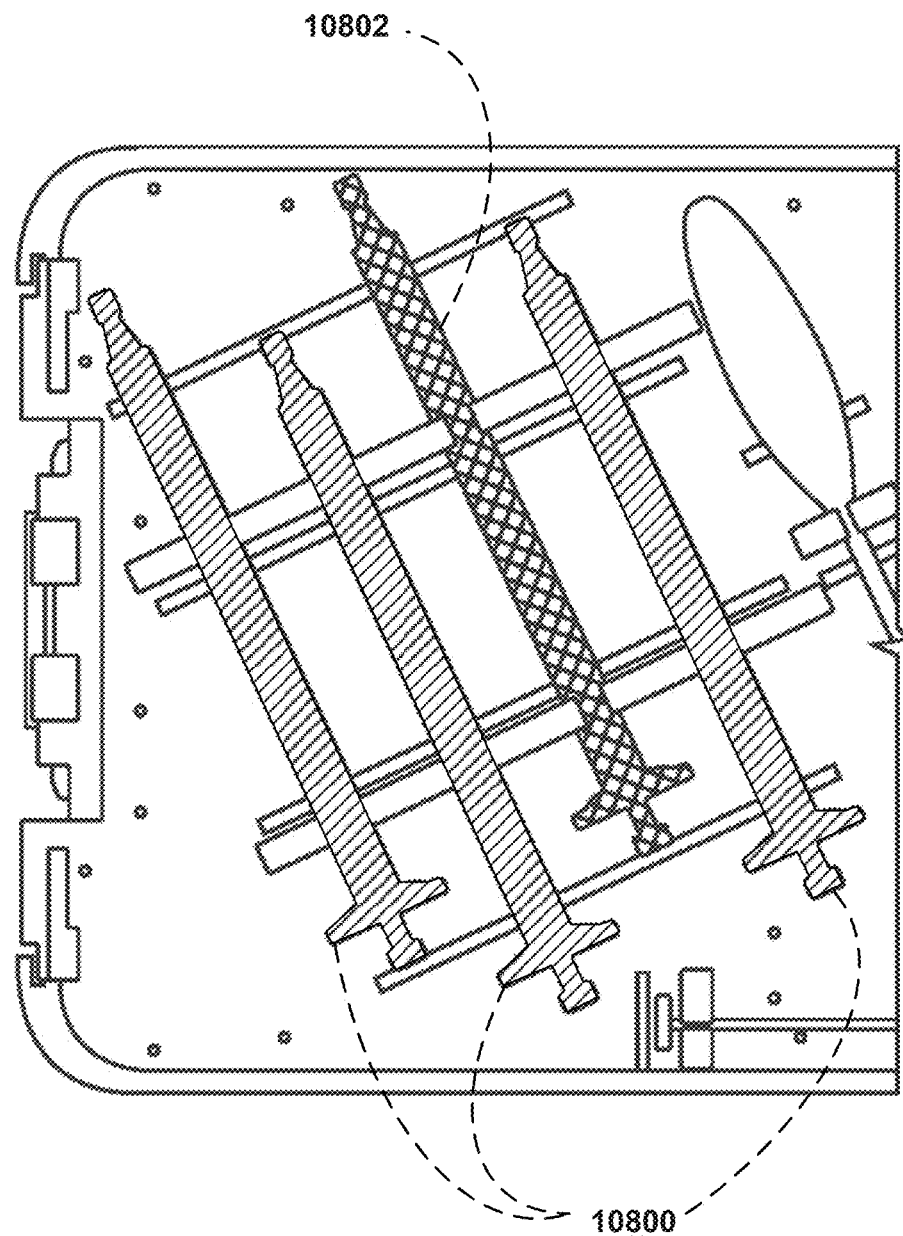
FIG. 108 is an illustration of a set of surgical items similar to those illustrated in FIG. 101 with virtual elements presented to identify a set of surgical items and to distinguish a given surgical item from the other identified surgical items.

Surface planing may involve the use of only one of surface planing tools 10100, e.g., corresponding to a similarly sized largest sounder used as the final sounder and corresponding to the punching tool used. For this reason, surgical item identification to distinguish only that particular surface planing tool needed for the surface planing step can be very desirable to help ensure that the correct surgical item is used. Moreover, item tracking and verification described herein may help avoid a scenario where an incorrect sized punching tool is used. FIG. 108 is an illustration of a set of surgical items similar to those illustrated in FIG. 101. FIG. 108 shows one exemplary set of virtual elements 10800 and 10802, which may be presented by visualization device 213, e.g., as overlays, to identify or distinguish a set of surgical items needed for a surgical procedure. In this example, virtual element 10802 may be configured to distinguish a given surgical item from the other identified surgical items 10800 in order to identify that surgical item as being the one needed in a current surgical step of the surgical procedure.

Figure 102:
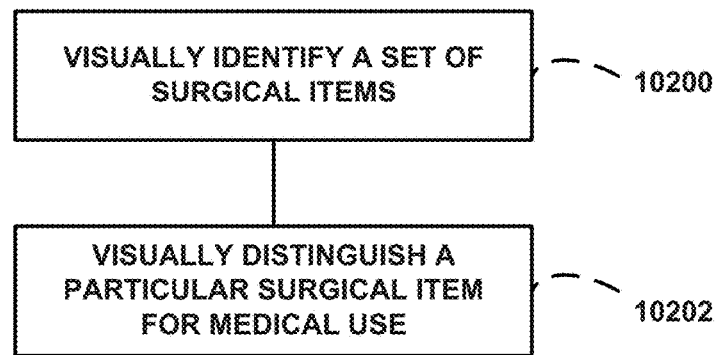
FIG. 102 is a flow diagram illustrating a technique of identifying tools in a surgical procedure.

FIG. 102 is a flow diagram illustrating a technique of identifying surgical items in a surgical procedure. The method of FIG. 102 may be performed, for example, with a visualization device 213 that presents virtual elements or with the use of surgical items that include integrated lighting as described herein. As shown in FIG. 102, a method includes visually identifying a set of surgical items (10200), and visually distinguishing a particular surgical item within the set of surgical items (10202). In some examples, visually identifying the set of surgical items may comprise controlling a light source in each of the surgical items, and visually distinguishing the particular surgical item may comprise controlling a particular light source of the particular surgical item. In this case, visually distinguishing the particular surgical item may comprise one or more of: controlling the particular light source with a unique color; controlling the particular light source with a unique lighting effect; or controlling the particular light source with a unique light intensity.

In other examples, visually identifying the set of surgical items may comprise presenting first mixed reality information in a visualization device, and in this case, visually distinguishing the particular surgical item may comprise presenting second mixed reality information in the visualization device. In this example, visually distinguishing the particular surgical item may comprise one or more of presenting the second mixed reality information with a unique color, presenting the second mixed reality information with a unique effect, or presenting the second mixed reality information with a unique intensity. Other visual effects, as described above, may also be used. More generally, however, identifying a set of surgical items and visually distinguishing the particular surgical item may comprise presenting mixed reality information.

In some examples, the mixed reality information presented on surgical items by visualization device 213 distinguishes a first subset of the surgical items, a second subset of the surgical items and a third subset of the surgical items, wherein the first subset of the surgical items corresponds to already used surgical items, the second subset of the surgical items corresponds a currently used surgical item and the third subset of the surgical items corresponds to subsequently needed surgical items. As described herein, the set of the surgical items may comprise sounders for an orthopedic shoulder repair surgery and the surgical item comprises a current sounder to be used.

In some examples, the set of surgical items comprise sounders for an orthopedic shoulder repair surgery and one or more punching tools for an orthopedic shoulder repair surgery. In some examples, the set of surgical items may comprise sounders for an orthopedic shoulder repair surgery, one or more punching tools for an orthopedic shoulder repair surgery, and one or more compacting tools for an orthopedic shoulder repair surgery. In some examples, the set of the surgical items may comprise sounders for an orthopedic shoulder repair surgery, one or more punching tools for an orthopedic shoulder repair surgery, and one or more compacting tools for an orthopedic shoulder repair surgery, and one or more planing tools for an orthopedic shoulder repair surgery.

In still other examples, visualization device 213 may present virtual elements or surgical items may be identified by integrated lighting as described herein on an item-by-item basis, without necessarily illuminating the entire set. For example, visualization device 213 may present virtual elements sequentially with a surgical process in order to sequentially identify each surgical item (item-by-item) in the procedure. Or integrated lighting may be controlled by an external processing device so as to sequentially illuminate each surgical item according to a surgical process, in order to sequentially identify each surgical item (item-by-item) in the procedure.

Figure 103:
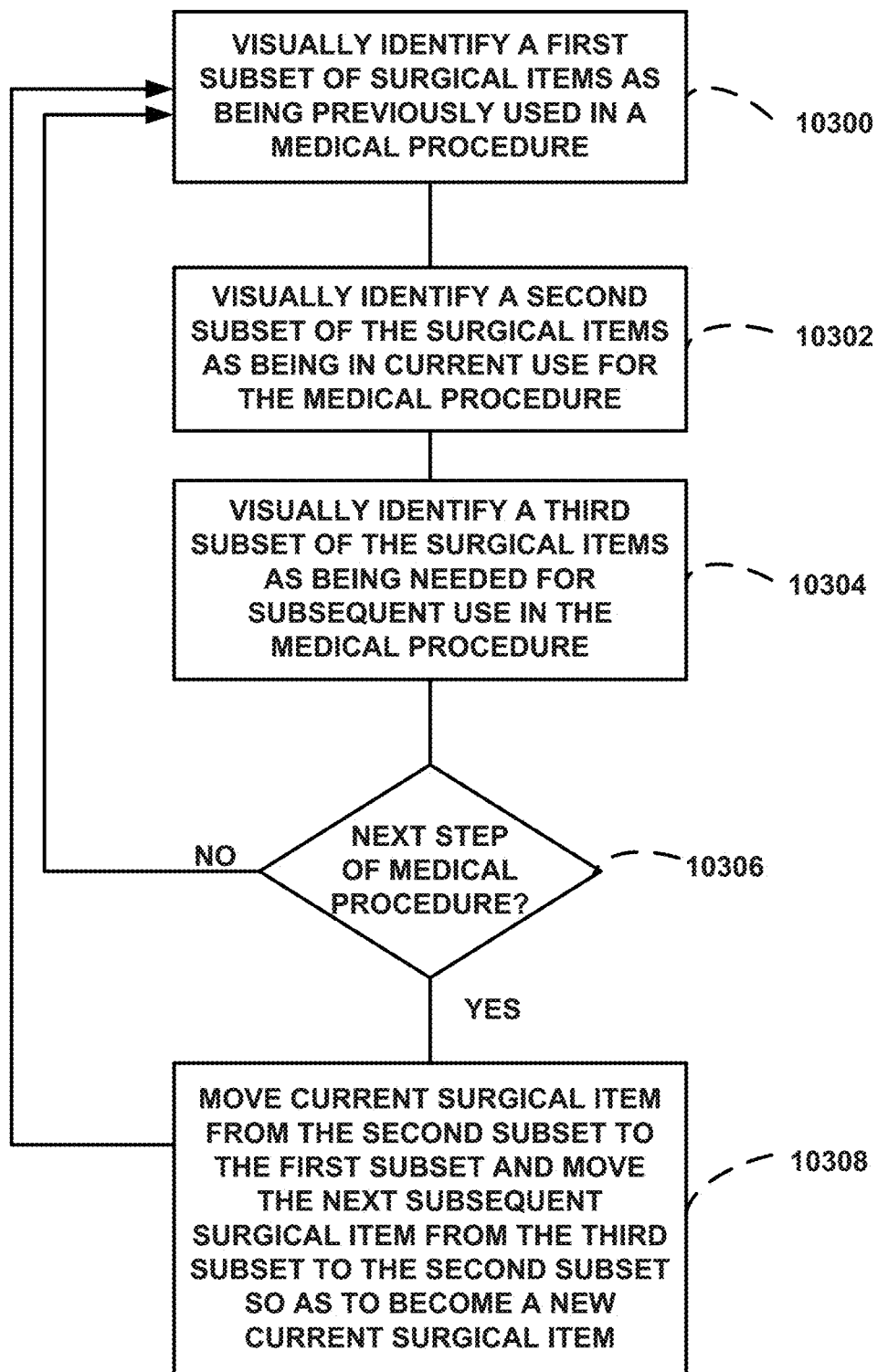
FIG. 103 is a flow diagram illustrating a method for identifying tools in a surgical procedure and changing the identification of such tools based on the stage of the surgical procedure.

FIG. 103 is a flow diagram illustrating a method for identifying surgical items in a surgical procedure and changing the identification of such surgical items based on the stage of the surgical procedure. The method of FIG. 103 may be performed, for example, with a visualization device 213 that presents virtual elements or with the use of surgical items that include integrated lighting as described herein. As shown in FIG. 103, a method includes visually identifying a first subset of surgical items as being previously used in the surgical procedure (10300), and visually identifying a second subset of surgical items as being in current use for the surgical procedure (10302). The method, e.g., as performed by either visualization device 213 with the use of MR or by surgical items with integrated lighting, may further include visually identifying a third subset of surgical items as being needed for subsequent use in the surgical procedure (10304).

According to the example of FIG. 103, at the next step of the medical surgical ("yes" branch of 10306), the "current surgical item" is moved from the second subset to the first subset and the next "subsequent surgical item" is moved from the third subset to the second subset (10308). For example, one or more processors of visualization device 213 may track the procedure based on feedback and/or virtual icon selection by the nurse, and such feedback or icon selection can cause visualization device 213 to move the assignment of surgical items from one set to another. Or an external processor that controls integrated lighting of the surgical items may be configured to track the procedure based on feedback by the nurse, and such feedback can cause the external processor to move the assignment of surgical items from one set to another.

In this way, when the stage of the surgical procedure changes, the item identification (i.e., lighting or the presentation of virtual elements for item identification) can likewise change so as to identify new surgical items (i.e., the next "subsequent surgical item") to the nurse for current use. The manner of visually identifying the surgical items may correspond to any of the examples described herein, including the use of lights within the surgical items, the use of mixed reality information presented by visualization device 213, or both.

Various examples have been described. For example, item identification and tracking techniques have been described for a surgical procedure that leverage surgical items that are designed with advanced features, such as sensors, accelerometers, and light sources. Moreover, mixed reality techniques have also been described for use in item tracking and item identification during a surgical procedure. Techniques for recording and documenting the surgical procedure have also been described, which may use automation.

The item identification techniques of this disclosure have been described by using lights on the surgical items (e.g., tools) themselves, which may be controlled by an external device according to a preoperative plan. Alternatively or additionally, item identification techniques of this disclosure have been described by using mixed reality, e.g., by presenting one or more virtual elements on a visualization device 213 to identify surgical items needed in the surgical procedure, which may be defined according to a preoperative plan. In some situations, however, a surgeon may deviate from the preoperative plan, and in these cases, the techniques of this disclosure may adapt or adjust the item identification process according to the changes made by the surgeon. Moreover, surgical item selection and/or surgical item use may be used to identify such a deviation from the preoperative plan. That is to say, in some examples, a current surgical item in use may be used to identity a next surgical item likely to be used. In other words, processing device 8304 may be configured to select, based on detection of a current surgical item in use, a next surgical item and present virtual information that identifies the next surgical item. For example, if compactor size 3 is being used, this information may be used by the system to recommend compactor size 4 as the next surgical item, or possibly to recommend punching tool size 3 to be used, or possibly to highlight either compactor size 4 or punching tool size 3 to be two alternative surgical items that the surgeon may need next. The current surgical item being used in the surgical procedure may be highly indicative of the next surgical item likely to be used, and processing device 8304 of the example shown in FIG. 83 or visualization device 213 in the example shown in FIG. 84 may be configured to identify a likely next surgical item (or a few possible likely surgical items) based on the current surgical item in use.

Furthermore, when the surgical procedure deviates from a preoperative surgical plan in the operating room, processing device 8304 of the example shown in FIG. 83 or visualization device 213 in the example shown in FIG. 84 may change or adapt the item identification process so as to identify different surgical items that are likely to be needed in the surgical process, given that the surgical process has been changed by the physician in the operating room.

For example, processing device 8304 of the example shown in FIG. 83 or visualization device 213 in the example shown in FIG. 84 may store an information model to track the step being performing (e.g., by visualization or interaction of surgeon with virtual guidance) and predicting which surgical step is next. Then, processing device 8304 of the example shown in FIG. 83 or visualization device 213 in the example shown in FIG. 84 may identify the next surgical item to be used based on this prediction. The information model may include a decision tree that accounts for branches from steps (e.g., step 4 becomes step 4a or step 4b depending on which happened in step 3). The surgical items for the branches may be different, and surgical items may be identified by lighting on the surgical items or by virtual information presented on or around such surgical items according to which branch is predicted. In this way, use of the virtual guidance system or lighting (and associated information model and prediction) can provide an item tracking method that is more adaptive to changes in the operating procedure in real time. Moreover, the item tracking may be synchronized with virtual guidance described herein, e.g., providing item prediction based on virtual guidance steps. Surgical item predictions for different virtual guidance steps can be stored in a memory of visualization device 213 (or in a memory of processing device 8304).

In some examples, the information model that defines item prediction and item identification can be defined based on camera or other sensor input, e.g., possibly using machine learning to learn and predict where a surgeon is within the given surgical procedure (e.g., which step) in order to predict the next step (by identifying the current step of a surgical plan) and to predict the next surgical item that is needed (based on the current step or the current surgical item being used). The information model may comprise a sequence of steps or may include more advanced information, in that it could describe different scenarios based on different events occurring during surgery. In some examples, the information model may define a decision tree-structure that helps to predict the next step of the procedure (by identifying the current step) and/or to help predict the next surgical item that is needed (based on the current step or the current surgical item being used). The decision tree can be stored in a memory of visualization device 213 (or in a memory of processing device 8304), and based on this decision tree, visualization device 213 may present predictions of the next surgical step or visualization device 213 or processing device 8304 may present or identify predictions of the next (or a set of possible next) surgical item(s) needed for the surgical procedure.

In some examples, processing device 8304 may select, based on the detected change in the surgical procedure and based on machine learning, the next surgical item and present second virtual information that identifies the next surgical item. For example, processing device 8304 (or visualization device 213) may apply machine learning over many surgical procedures and may use decisions and changes made in past surgical procedures to drive machine learning and thereby predict the next surgical item. In some cases, the machine learning may be based on past surgical procedures, decisions and changes made by a specific surgeon. In other words, the past surgical procedures, decisions and changes made by a specific surgeon may be stored in memory and used as data for driving a machine learning algorithm that can help to predict the next surgical item. In this way, machine learning can help to predict the next surgical item needed for a given procedure, and the predictions may be based on historical data, such as past surgical procedures, decisions and changes made by a specific surgeon. In some cases, historical data of a variety of surgeons may be used for this machine learning, e.g., whereby past surgical procedures, decisions and changes made by many surgeons can be used to drive machine learning algorithm that can help to predict the next surgical item. For example, if a particular change is made to a surgical plan in the operating room and if a similar change was made to the surgical plan for one or more previous surgeries, the surgical items used in subsequent steps of the previous procedures (following the change made by the surgeon) may be good predictions of surgical items needed in similar subsequent steps of the current surgical procedure. By implementing a machine learning algorithm, processing device 8304 (or visualization device 213) may be configured to predict surgical items needed for a procedure following an interoperative change to that procedure.

As one example, a decision tree may be defined for humerus preparation, providing different branches for virtual guidance and surgical item selection for anatomical preparation relative to reverse anatomical preparation. If the surgeon changes the plan in the operating room, e.g., changing from a preoperative surgical plan for an anatomical repair to a reverse anatomical repair, visualization device 213 may adjust its predictions of the next surgical step or visualization device 213 or processing device 8304 may adjust its predictions of the next (or a set of possible next) surgical item(s) needed for the surgical procedure.

As another example, visualization device 213 and advanced surgical items with sensors may document actual surgical parameters based on what was actually performed by a surgeon, and predictions of virtual guidance and/or surgical item selection may change from that defined in a preoperative surgical plan to that actually being performed in the operating room.

As yet another example, item prediction may be linked to surgical item sizes being used. Thus, if a particular size was used in previous step, the next surgical item may need to be selected to be a different surgical item of the same size or a similar surgical item of a different size. The surgical item prediction may be based on the surgical item currently in use, and possibly the size of the current surgical item in use. Moreover, if surgical items used or surgical item sizes change in the operating room relative to the surgical items and sizes defined in a preoperative plan, visualization device 213 may adjust its predictions of the next surgical step or visualization device 213 or processing device 8304 may adjust its predictions of the next (or a set of possible next) surgical item(s) needed for the surgical procedure. These and other examples of virtual guidance and virtual presentations on visualization device 213 may be implemented via a software system like the BLUEPRINT™ system available from Wright Medical.

Specific sets of surgical items have been described and illustrated for example purposes. However, the techniques may be useful for a wide variety of surgical procedures and a wide variety of surgical items. The techniques may be particularly useful for orthopedic surgical procedures, such as shoulder surgeries, ankle surgeries, knee surgeries, hip surgeries, wrist surgeries, hand or finger surgeries, foot or toe surgeries, or any joint repair surgical procedure or augmentation. Although the techniques may be useful in a wide variety of orthopedic procedures, they may be especially useful in both anatomical and reverse-anatomical shoulder reconstruction surgeries. Indeed, the techniques may be helpful for reversed arthroplasty, augmented reverse arthroplasty, standard total shoulder arthroplasty, augmented total shoulder arthroplasty, hemispherical should surgery, or other types of shoulder surgery. Although FIGS. 86-108 discuss aspects of specific shoulder surgery steps, the techniques of this disclosure may apply to other types of shoulder surgeries. Moreover, ankle surgery may involves the use of multiple tools and jigs for drilling, cutting, preparing implant cites and installing implants on a patients talus and tibia, and the tool tracking techniques of this disclosure may utilized for ankle surgeries, especially when a variety of different tools are used in the procedure. These and other examples are within the scope of this disclosure.

Patients who have damage in a joint frequently have limited range of motion in an appendage associated with the joint. For example, a patient with a damaged left shoulder typically cannot move his or her left arm throughout a range of angles and positions typical of people with undamaged shoulders. In another example, a patient with a damaged ankle may be incapable of elevating or dropping his or her foot beyond a particular angle relative to the patient's lower leg. Such damage may be caused by a variety of conditions and events, such as arthritis, sports injuries, trauma, and so on.

During preoperative phase 302 (FIG. 3), a healthcare professional may evaluate the range of motion of an appendage associated with a joint as part of evaluating the patient's condition. For instance, the healthcare professional may be able to determine the severity of damage or type of damage to a patient's joint based on the range of motion of an appendage associated with the joint. Furthermore, the healthcare professional may ask the patient to identify points in the range of motion of the appendage at which the patient experiences pain in the joint associated with the appendage.

After a patient has undergone a surgery on a joint associated with an appendage (i.e., during postoperative phase 308), a healthcare professional may wish to evaluate the range of motion of the appendage. For instance, the appendage typically has limited mobility immediately after the surgery, but the range of motion of the appendage should increase as the patient heals. The patient's appendage failing to achieve expected ranges of motion within particular time windows may be a sign that additional interventions or physical therapy may be necessary. Accordingly, to check whether additional interventions or physical therapy are necessary, the patient typically visits the healthcare professional who may then perform a physical examination of the appendage's range of motion.

In some instances, to help increase the chances that the appendage achieves a full range of motion, the patient may undergo physical therapy that requires the patient to move the appendage in particular ways. For example, a physical therapist may request the patient to move the appendage through a particular range of motion. In some examples, during the postoperative phase, the patient may be requested to perform physical therapy exercises at home outside of the presence of a physical therapist or other healthcare professional. For instance, in an example where a patient has undergone a shoulder arthroplasty on the patient's left shoulder, the patient may be prescribed a physical therapy exercise that involves the patient attempting to move their left arm to a particular angle relative to a sagittal plane, frontal plane, or transverse plane or the patient.

A variety of challenges confront healthcare professionals and patients in evaluating the range of motion of an appendage associated with a joint. For example, during preoperative phase 302 and postoperative phase 308 (FIG. 3), it may be difficult for a healthcare professional to accurately measure and assess the range of motion of the appendage. Additionally, it may be difficult for the healthcare professional to accurately record positions of the appendage at which the patient experiences pain in the joint associated with the appendage. Similarly, it may be difficult for a patient to know whether he or she is moving their appendages through prescribed ranges of motion. Moreover, it may be inconvenient or costly for a patient to make frequent office visits for physical therapy or physical examination by a healthcare professional. However, avoiding such office visits through interactive telemedicine sessions or remote monitoring may be challenging because it may be difficult for patients to accurately move their appendages to prescribed angles without trained physical assistance, difficult for patients to describe their ranges of motion accurately, and difficult for patients to describe the positions of their appendages at which the patients experience pain. Additionally, it may be challenging for a healthcare professional to interpret and validate the information on range of motion and pain provided by the patient. For instance, it may be difficult for the healthcare professional to know from information provided by the patient whether the information provided by the patient is wrong or whether there is an actual need for intervention.

This disclosure describes techniques that may address one or more of these challenges. For instance, in accordance with an example of this disclosure, a computing system may obtain motion data describing a movement of a motion tracking device connected to an appendage of a patient. In this example, the computing system may determine, based on the motion data, a range of motion of the appendage. Additionally, in this example, the computing system may generate an extended reality visualization of the range of motion of the appendage superimposed on the patient or an avatar of the patient. By viewing the extended reality visualization of the range of motion of the appendage, a user separate from the patient, or in addition to the patient, may be able to visualize and describe the range of motion of the appendage. The extended reality visualization of the range of motion may be a mixed reality (MR) visualization or a virtual reality (VR) visualization.

Figure 109:
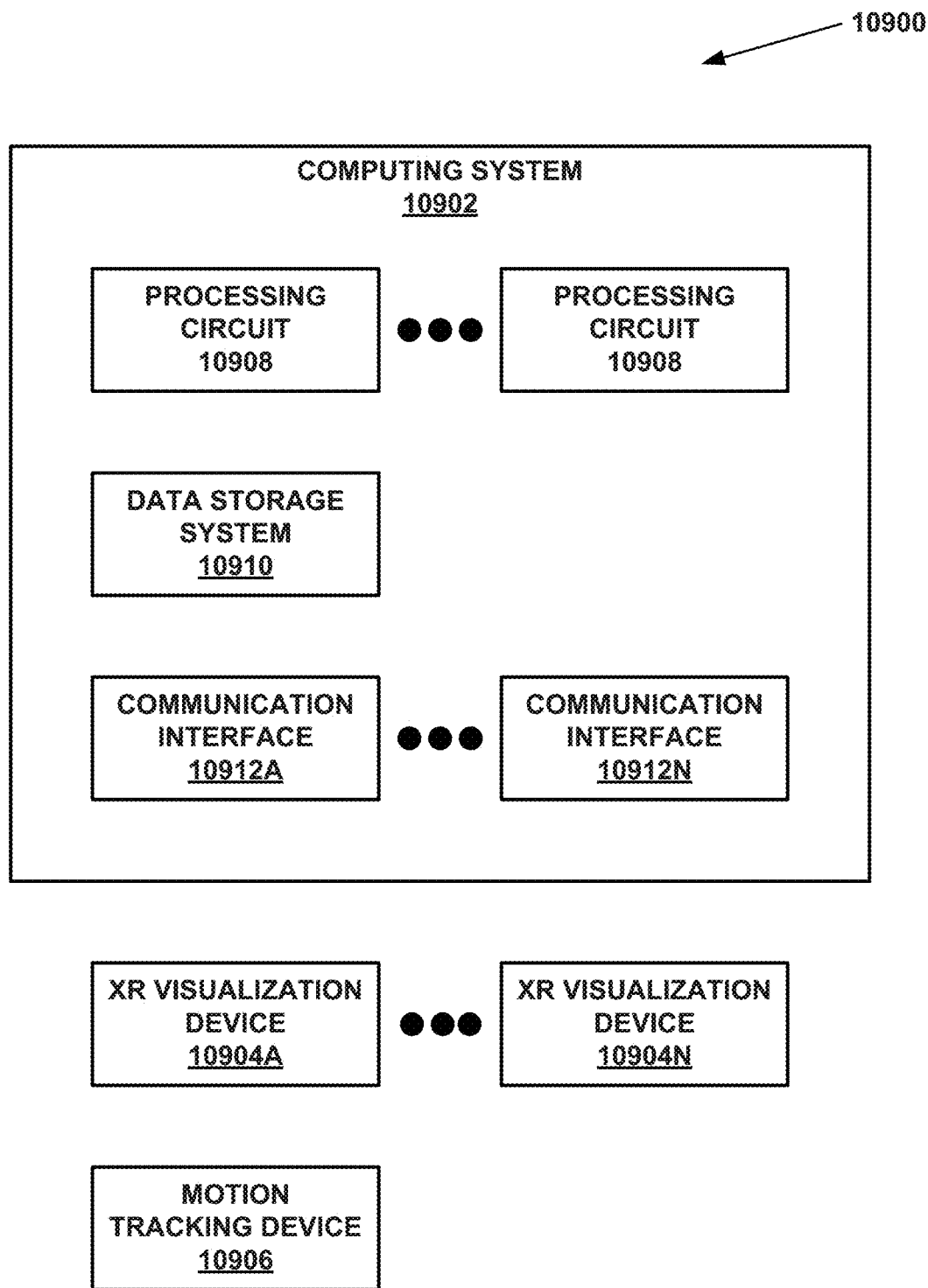
FIG. 109 is block diagram illustrating an example system for generating an extended reality (XR) visualization of a range of motion of an appendage of a patient, in accordance with a technique of this disclosure.

FIG. 109 is block diagram illustrating an example system 10900 for generating an extended reality visualization of a range of motion of an appendage of a patient, in accordance with a technique of this disclosure. As shown in the example of FIG. 109, system 10900 includes a computing system 10902, a set of one or more extended reality (XR) visualization devices 10904A through 10904N (collectively, "XR visualization devices 10904"), and a motion tracking device 10906. In other examples, system 10900 may include more, fewer, or different devices and systems. In some examples, computing system 10902, XR visualization devices 10904, and motion tracking device 10906 may communicate via one or more communication networks, such as the Internet. In some examples, motion tracking device 10906 may communicate with computing system and/or one or more XR visualization devices 10904 via a direct wireless communication link.

Computing system 10902 may include various types of computing devices, such as server computers, personal computers, smartphones, laptop computers, and other types of computing devices. In the example of FIG. 109, computing system 10902 includes one or more processing circuits 10908, a data storage system 10910, and a set of one or more communication interfaces 10912A through 10912N (collectively, "communication interfaces 10912"). Data store 10910 is configured to store data, such as motion data. Communication interfaces 10912 may enable computing system 10902 to communicate (e.g., wirelessly or using wires) to other computing systems and devices, such as XR visualization devices 10904 and motion tracking device 10906. For ease of explanation, this disclosure may describe actions performed by processing circuits 10908, data store 10910, and communication interfaces 10912 as being performed by computing system 10902 as a whole.

Various computing systems of orthopedic surgical system 100 (FIG. 1) may include computing system 10902. For example, virtual planning system 102, pre- and postoperative monitoring system 112, and/or another subsystem of orthopedic surgical system 100 may include computing system 10902. In some examples, one or more of XR visualization devices 10904 includes one or more components of computing system 10902. For instance, one or more of XR visualization devices 10904 may include one or more of processing circuits 10908 of computing system 10902. Thus, in some examples, some or all of the actions described in this disclosure as being performed by computing system 10902 may be performed by processing circuits in one or more of XR visualization devices 10904. In some examples, XR visualization devices 10904 include MR visualization devices, such as MR visualization device 213 (FIG. 2). In some examples, XR visualization devices 10904 include VR visualization devices.

Motion tracking device 10906 is a device configured to detect movement of an appendage of the patient. For instance, in some examples, motion tracking device 10906 may include a device that is connected to the appendage of the patient and detects movement of motion tracking device 10906. Motion tracking device 10906 may, for example, be a device having an inertial measurement unit (IMU) that tracks acceleration of motion tracking device 10906 in multiple dimensions (e.g., 3 dimensions). In some examples, the IMU may also track an orientation of motion tracking device 10906 (e.g., with respect to a gravitational vector or a magnetic pole). Motion tracking device 10906 may be or may include various types of devices. For example, motion tracking device 10906 may be or may include a smartwatch, a smartphone, a ring, a bracelet, an anklet, a head-mounted device, eyewear, a special-purpose motion tracking device, or another type of device configured to detect movement of the device.

In examples where motion tracking device 10906 is or includes a device that is connected to the appendage of the patient and detects movement of motion tracking device 10906, motion tracking device 10906 may be connected to the appendage of the patient in various ways. For instance, motion tracking device 10906 may be connected to a wrist, ankle, thigh, foot, toe, finger, head, knee, calf, upper arm, hand, jaw, or other body part of the patient. Motion tracking device 10906 may be connected to the appendage of the patient in various ways. For example, motion tracking device 10906 may be held by the patient (e.g., as may be the case when the patient holds motion tracking device 10906 in one of the patient's hands); may be strapped to the patient (e.g., as may be the case when motion tracking device 10906 is worn on the patient's wrist or ankle); may be attached with adhesive, may rest on the patient due to gravity and/or compression (e.g., as may be the case when motion tracking device 10906 includes eyewear or headwear); may be held in place by compression (e.g., as may be the case when motion tracking device 10906 is worn as a ring or clamp; or in may connected to the appendage of the patient in other ways such that motion tracking device 10906 moves with the appendage of the patient. In some examples, motion tracking device 10906 may instruct the patient to start a movement at a calibration position (e.g., arm straight down) and track movements relative to the calibration position.

In some examples, motion tracking device 10906 may include one or more cameras or other devices that visually detect the movement of the appendage. For instance, in some examples, one or more cameras may be integrated into an XR visualization device worn by the patient. In some examples where the one or more cameras are integrated into an XR visualization device worn by the patient, the patient may need to be positioned in front of a mirror so that the camera is able to capture images of the movement of the appendage of the patient.

In accordance with an example of this disclosure, computing system 10902 may obtain motion data describing a movement of an appendage of a patient. For example, computing system 10902 may obtain motion data that comprise IMU signals generated by an IMU of motion tracking device 10906 during the movement of the appendage of the patient. In some examples, computing system 10902 may obtain video data that show the movement of the appendage of the patient. In some examples, a storage system (e.g., storage system 206, memory 215, etc.) may store the motion data.

Computing system 10902 may determine, based on the motion data, a range of motion of the appendage. For example, computing system 10902 may determine based on the IMU signals how far motion tracking device 10906 traveled during the motion of the appendage. In this example, based on a previously determined distance of motion tracking device 10906 from the joint associated with the appendage, computing system 10906 may determine the range of motion of the appendage as:

$$\text{range of motion} = \frac{360 * l}{2\pi r}$$

In the equation above, l is the distance motion tracking device 10906 traveled and during the motion of the appendage and r is the distance of motion tracking device 10906 from the joint associated with the appendage. In an example where computing system 10902 obtains video data that show the movement of the appendage of the patient, computing system 10902 may apply image analysis to video data to identify a major axis of the appendage and, in some examples, an applicable axis (e.g., a frontal axis, transverse axis, sagittal axis, etc.) of the patient. For example, computing system 10902 may apply a neural network (e.g., convolutional neural network) trained to recognize areas within images that contain the appendage. In this example, computing system 10902 may then determine a longest dimension of the recognized areas as the major axis of the appendage. In some examples, computing system 10902 may receive an indication of user input indicating the applicable axis. In some examples, computing system 10902 may apply a neural network (e.g., a convolutional neural network) to determine the applicable axis. In such examples, computing system 10902 may compare these axes to determine angles defining the range of motion.

Figure 110:
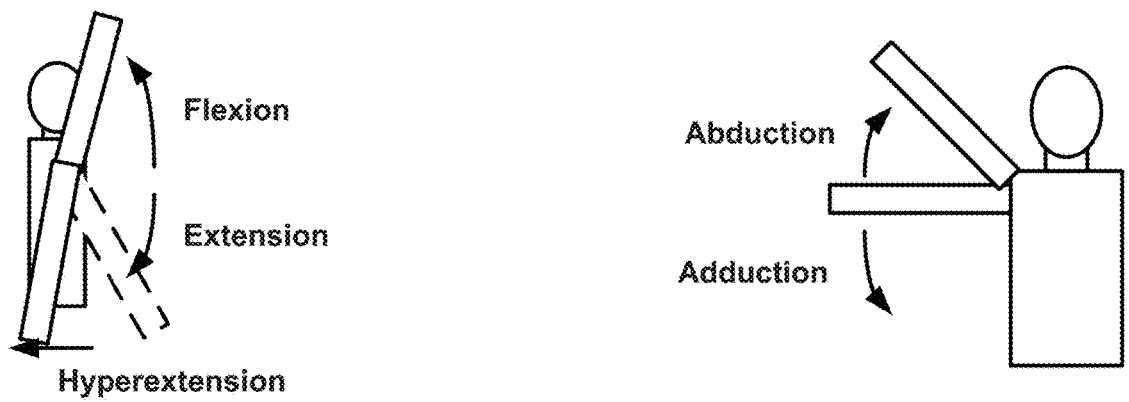
FIG. 110 is a conceptual diagram illustrating example motions of a patient's right arm that occur in the patient's shoulder.
Figure 110:
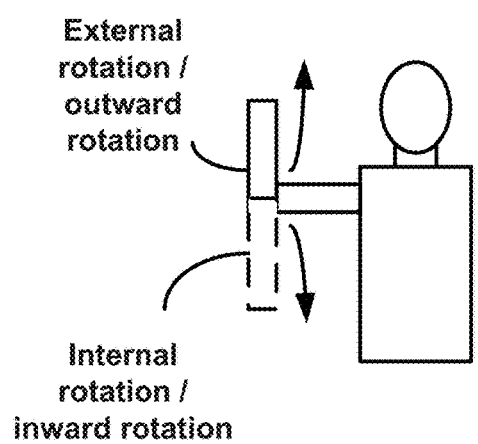

The ranges of different motions of an appendage may be significant. For instance, FIG. 110 is a conceptual diagram illustrating example motions of a patient's right arm that occur in the patient's shoulder. As shown in FIG. 110, flexion occurs when the patient raises the patient's arm upward in a sagittal plane and extension occurs when the patient lowers that patient's arm downward in the sagittal plane. Hyperextension occurs when the patient moves the patient's arm in the sagittal plane past a frontal plane that runs through the patient's shoulder joint. Furthermore, as shown in FIG. 110, abduction is raising the patient's arm in a frontal plane away from the center of the patient's body. Adduction is moving the patient's arm in the frontal plane toward the center of the patient's body. As shown in FIG. 110, internal rotation/inward rotation and external/outward rotation occurs when the patient's arm rotates at the shoulder.

In some examples, the patient may be instructed (e.g., by motion tracking device 10906) to perform a type of movement and the patient may perform a movement in response to being prompted to perform the type of movement. For instance, the type of movement may be a movement of the appendage in a plane that passes through a joint associated with the appendage. As an illustration, for shoulder range of motion, the patient may be instructed (e.g., by motion tracking device 10906), in a first exercise, to move the arm from a point of flexion to a point of extension and, if possible, to a point of hyperextension; in a second exercise, to move the arm from a point of abduction to a point of adduction, and; in a third exercise, to move the arm from a point of external/outward rotation to a point of internal/inward rotation. In another example, for ankle range of motion, the patient may be instructed (e.g., by motion tracking device 10906), in one exercise, to move the patient's foot from a point of plantarflexion to a point of dorsiflexion.

During each exercise, motion tracking device 10906 may track these points to form a representation of the patient's range of motion. For example, upon instructing the patient to undertake movement from abduction to adduction, or vice versa, motion tracking device 10906 may record data indicating for maximum points of abduction and adduction for review by an orthopedic surgeon, physical therapist or other user. In another example, upon instructing the patient to undertake movement from plantarflexion to dorsiflexion, motion tracking device 10906 may record data indicating maximum points of plantarflexion and dorsiflexion for review. For instance, motion tracking device 10906 may record angles for maximum points relative to particular planes, polar coordinates of the maximum points, spherical coordinates of the maximum points, Cartesian coordinates of the maximum points, or other types of data to indicate the maximum points. For instance, in one example, based on the distance that motion tracking device 10906 travels and the distance of motion tracking device 10906 from a joint associated with the appendage, motion tracking device 10906 may determine an angle relative to an applicable plane (e.g., using the equation above) and thereby determine a pair of polar coordinates defined by the distance of motion tracking device 10906 from the joint associated with the appendage and the angle. Motion tracking device 10906, similarly, may record relative or absolute coordinates for maximum points of flexion and extension, and relative or absolute coordinates for maximum points of external/outward rotation and internal/inward rotation during corresponding exercises performed by the patient at the instruction of motion tracking device 10906 for review by an orthopedic surgeon, physical therapist or other user.

The patient may be instructed (e.g., by motion tracking device 10906) to perform a type of movement that requires articulation of a joint associated with an appending in multiple dimensions. For instance, the patient may be instructed to perform movements related to daily activities, such as moving the hand to a contralateral position, moving the arm to comb the patient's hair (or otherwise bring the patient's hand to the patient's head), or place the hand on the patient's back pocket (or buttock) on the side of the patient's body adjacent the pertinent arm undertaking the movement. For each of these common movements, motion tracking device 10906 may record relative or absolute coordinates associated with each of these movements for review by an orthopedic surgeon, physical therapist or other user. Range of motion associated with similar common movements for other joints or appendages or other body parts of the patient may be evaluated.

Additionally, computing system 10902 may generate an XR visualization (e.g., a MR, AR, or VR visualization) of the range of motion of the appendage. XR visualization devices 10904 may output the XR visualization of the range of motion of the appendage for display to a user. XR visualization devices 10904 may output the XR visualization of the range of motion of the appendage such that the XR visualization of the range of motion of the appendage is superimposed on an image of the patient or an avatar of the patient. In some examples, the image of the patient is an image formed by light reflecting, directly or indirectly, off the patient. The image formed by light reflecting indirectly off the patient may be reflected by a mirror after being reflected off the patient and prior to detection by one or more cameras of one or more of XR visualization devices 10904. In some examples, the image of the patient is a previously captured 2-dimensional or 3-dimensional image of the patient. The avatar of the patient may be a virtual human figure representing the patient.

In some examples, the XR visualization of the range of motion is superimposed on the image of the patient or the avatar of the patient such that some visible portion of the XR visualization of the range of motion appears to the user to overlap the image of the patient or the avatar of the patient. In some examples, the XR visualization of the range of motion is superimposed on the image of the patient or the avatar of the patient in the sense that the XR visualization of the range of motion is superimposed on a scene that contains the image of the patient or the avatar of the patient, regardless of whether any visible portion of the XR visualization appears to the user to overlap with the image of the patient or the avatar of the patient.

The extended reality visualization of the range of motion of the appendage may have various forms. For instance, in one example, the XR visualization of the range of motion of the appendage may include a virtual arc spanning an angle between furthest points in the range of motion of the appendage. In some examples, a focal point of the virtual arc may be located at a joint associated with the appendage. In this example, if the appendage is the patient's left arm, the virtual arc may appear superimposed in an area of space around the patient's left shoulder and a focal point of the virtual arc may be located at the patient's left shoulder joint. The ends of the virtual arc may correspond to the limits to which the patient is able to move the patient's left arm in a particular plane of the patient's body, such as a frontal plane (e.g., during abduction and adduction), sagittal plane (e.g., during flexion and extension or during internal and external rotation), or other plane of the patient's body.

In some examples where the XR visualization of the range of motion of the appendage includes such a virtual arc, the virtual arc may be associated with a virtual protractor with labeled angles. In some such examples, the labeled angles of the virtual protractor may be relative to a plane or axis of the patient's body. For instance, if the appendage is the patient's left arm and the range of motion is in the patient's frontal plane (e.g., during abduction and adduction), the angles may be relative to a frontal axis that passes through the patient's left shoulder joint. If the appendage is the patient's left arm and the range of motion is in the patient's sagittal plane (e.g., during flexion and extension), the angles may be relative to a longitudinal axis that passes through the patient's left shoulder joint.

The labeled angles of the virtual protector may include angles at the ends of the virtual arc. In some examples, the labeled angles of the virtual protractor may include intermediate angles between the angles at the ends of the virtual arc. In some examples, the labeled angles may be visible in the XR visualization, but the virtual arc itself is invisible in the XR visualization. In some examples, the virtual protractor is incorporated into the virtual arc or separate from the virtual arc. In some examples where there are multiple virtual arcs, there may be a single virtual protractor for all of the virtual arcs or there may be separate virtual protractors for two or more of the virtual arcs.

Furthermore, in some examples where the XR visualization of the range of motion of the appendage includes a virtual arc, one or more XR visualization devices 10904 may output a current line that is radial from a focal point of the virtual arc and in a plane of the virtual arc. In such examples, computing system 10902 updates the current line so that the current line remains aligned in real time with a major axis of the appendage as the patient moves the appendage in the plane of the virtual arc. In this way, the patient may be able to better visualize the current angle of the appendage relative to the virtual arc. Computing system 10902 may use the motion data, such as IMU signals and/or video data, to determine the current position of the appendage when generating the XR visualization of the current line. In some examples, computing system 10902 may record positions of the current line as the patient moves the appendage.

XR visualization devices 10904 may present XR visualizations of the range of motion to various users. For instance, in some examples, one of XR visualization devices 10904 may present the XR visualization of the range of motion to the patient. For example, the patient may wear or otherwise use an XR visualization device, such as an MR, AR, or VR visualization device. In the case where the XR visualization device used by the patient is an MR visualization device, the MR visualization device may be visualization device 213. In this example, the XR visualization device presents the XR visualization of the range of motion of a joint associated with an appendage when the patient looks at the joint while wearing or otherwise using the XR visualization device. In another example where the patient wears or otherwise uses an XR visualization device, the patient may stand in front of a mirror. In this example, the XR visualization device may present the XR visualization of the range of motion superimposed on the patient's reflection or an avatar of the patient composed based on the patient's reflection. This may be especially useful when it may be difficult for the user to directly see a joint or a range of motion of a joint in a particular direction, as may be the case for the patient's shoulders or neck.

In examples where an XR visualization device presents the XR visualization to the patient, the extended reality visualization may include a first virtual arc spanning an angle between furthest points in the actual range of motion of the appendage achieved by the patient. In this example, the XR visualization may also include a second virtual arc spanning an angle between furthest points in a target range of motion of the appendage. For example, a previously recorded range of motion of the patient's left arm in a frontal plane running through the patient's left shoulder joint may range from −90° to 10°, relative to a frontal axis running through the patient's left shoulder joint.

Accordingly, in this example, the first virtual arc may span from −90° to 10°. In this example, −90° may correspond to the patient's left arm hanging loose at the patient's side and 10° may correspond to the patient's left arm being slightly above horizontal. However, as part of the patient's postoperative rehabilitation or preoperative evaluation, the patient may be prompted to try to move the patient's left arm in the frontal plane through a range of −90° to 20°. Accordingly, in this example, the second arc may span from −90° to 20°. In some examples, the first virtual arc and the second virtual arc are differently colored. In some examples, the first virtual arc is presented in the XR visualization as a segment of the second virtual arc.

In some examples, a target range of motion of an appendage is a typical range of motion of a healthy individual. In some examples, a target range of motion of an appendage is a typical range of motion for a patient at a particular point in a postoperative recovery process. In some examples, a target range of motion of an appendage is a patient-specific range of motion, which may be determined by a healthcare professional or planning software, such as BLUEPRINT™ by Wright Medical. Because the patient is able to perceive the second virtual arc in the XR visualization, the patient may be better able to determine whether the patient is able to achieve the target range of motion than if the patient was merely told in writing or vocally the furthest angles of the target range of motion.

As mentioned above, the target range of motion may be patient specific. Thus, in one example, there may be a first target range of motion that is specific to a first patient. In this example, computing system 10902 may obtain motion data describing a movement of the appendage of a second patient. Furthermore, in this example, computing system 10902 may determine, based on the motion data, a range of motion of the appendage of the second patient. Computing system 10902 may also, in this example, generate, for display by an extended reality visualization device worn by the second patient, a second XR visualization of the range of motion of the appendage of the second patient superimposed on an image of the second patient or an avatar of the second patient. The second XR visualization may include a virtual arc spanning an angle between furthest points in a second target range of motion of the appendage of the second patient. The second target range of motion is different from the first target range of motion.

In some examples, the patient may be prompted to attempt to move the appendage to reach the furthest points in a target range of motion of the appendage, such as the target range of motion represented by the second virtual arc in the example above. The patient may be prompted to attempt to move the appendage to reach the furthest points in the target range in various ways. For example, computing system 10902 may cause one or more speakers of an XR visualization device worn by the patient to output sound prompting the patient to move the appendage in the target range of motion. In some examples, computing system 10902 may cause a written prompt to appear in the XR visualization presented to the patient.

In some examples, the patient may be prompted as part of a preprogrammed diagnostic or physical therapy session that does not actively involve a healthcare professional. In some examples, a smartphone or other device used by the patient may prompt the patient to engage in physical therapy exercises or may specify the target range of motion. A smartphone, smartwatch or other device may also be the motion tracking device 10906 used to record range of motion, hence serving the dual purposes of issuing prompts or instructions for the patient to undertake range or movement exercises and recording data representing the resultant motion. In particular, a smartphone may be held, or a smartwatch or other wearable may be worn, by the patient during movement of an appendage through specified range of motion exercises.

The patient may be prompted to attempt to move the appendage to reach the furthest points in the target range in response to various events. For example, during an interactive session involving the patient and a healthcare professional, computing system 10902 may receive an indication of user input (e.g., voice command, mouse click, tap, etc.) from the healthcare professional to prompt the patient to attempt to move the appendage to reach the furthest points in the target range of the appendage. In this example, computing system 10902 may prompt the patient to attempt to move the appendage to reach the furthest points in the target range in response to the indication of user input from the healthcare professional.

In some examples, during an interactive in-person or telemedicine session involving the patient and a healthcare professional, the healthcare provider may vocally prompt the patient.

The patient may receive the prompt from various devices. For example, motion tracking device 10906 may prompt the patient. For instance, in an example where motion tracking device 10906 is a smartphone or smartwatch, motion tracking device 10906 may display an on-screen message containing the prompt. In some examples, motion tracking device 10906 may output generate audio that prompts the patient to perform the type of movement of the appendage. Furthermore, in some examples, an XR visualization device worn by the patient may prompt the patient. In some such examples, motion tracking device 10906 and/or XR visualization devices may generate such prompts in response to signals generated by computing system 10902.

The prompts received by the patient may include various types of information. For example, a prompt may include text, video, and/or audio describing exercise that the patient is to perform. In examples where an XR visualization device worn by the patient presents the prompt, an MR or AR visualization may contain the prompt.

As noted above, one of the challenges confronting patients and healthcare providers is that it may be difficult for the patient to precisely express the points at which the patient experiences pain as the patient moves an appendage through a range of motion. Knowing the points at which the patient experiences pain may help a healthcare provider (and/or an AI-based diagnostic tool) learn about the patient's condition. To address such challenges, computing system 10902 may, in some examples where the XR visualization is presented to the patient, receive indications of user input indicating one or more pain points within the range of motion. The patient may experience pain when the appendage is at the pain points. Thus, the patient may provide the indication of user input when the appendage is at a point within the range of motion where the patient experiences pain. In response to receiving the indication of the user input, computing system 10902 may generate, based on the motion data, data indicating a pain point, where the pain point is a position or positions of the appendage of the patient at which the patient experiences pain.

For instance, if the appendage is the patient's left arm and computing system 10902 receives an indication of user input at a time when the patient has raised the patient's left arm 10° above a frontal axis running through the patient's left shoulder joint, computing system 10902 may determine that the patient has a pain point when the patient's left arm is 10° above the coronal axis. In this example, the patient does not need to specify that the pain occurs when the patient's left arm is 10° above the frontal axis. Rather, the patient merely needs to provide input when the patient feels pain and computing system 10902 determines that the angle of the patient's left arm was 10° when the patient felt the pain. Without the use of this technique, it may be difficult for the patient to accurately say that the pain point occurs when the patient's left arm is 10° above the frontal axis. Computing system 10902 may store (e.g., in data storage system 10910 of computing system 10902) data indicating the pain points.

Computing system 10902 may receive the indication of user input for a pain point in one or more ways. For example, computing system 10902 may receive (e.g., via a microphone of an XR visualization device worn by the patient, a microphone of motion tracking device 10906, or a microphone of another device) a vocal indication from the patient when the patient moves the appendage to a point where the patient experiences pain. For instance, in this example, the patient may say "pain" when the patient moves the appendage to a point where the patient experiences pain. In another example, computing system 10902 may receive (e.g., via one or more cameras of an XR visualization device worn by the patient) video data showing the user performing a gesture (e.g., a hand gesture, head gesture, etc.) that indicates that the user has experienced pain at the current point in the range of motion. In other examples, computing system 10902 may receive the indication of user input as a tapping gesture, a button push, or another form of user input.

In some examples, one or more of XR visualization devices 10904 may present the extended reality visualization of the range of motion to one or more healthcare professionals, such as doctors, surgeons, or nurses. In other words, an XR visualization device may be worn by a healthcare professional. For example, a healthcare professional and the patient may engage in an interactive session during which the healthcare professional wears or otherwise uses one or more XR visualization devices 10904. In this example, the healthcare professional and the patient may be in separate locations. In other words, an XR visualization device may present the extended reality visualization to the healthcare professional during an interactive session with the patient in which the healthcare professional and the patient are in separate locations, as may be the case during a telemedicine session.

Alternatively, in this example, the healthcare professional and the patient may be in the same location, such as during an office visit, and the healthcare professional and patient may speak directly to one another. In other words, an XR visualization device may present the XR visualization to the healthcare professional during an interactive session with the patient in which the healthcare professional and the patient are in the same location. In either case, the XR visualization device may present the XR visualization of the range of motion to the healthcare professional in real time so that the healthcare professional is able to visualize the range of motion that the patient is able to attain.

In this example, the healthcare professional may communicate with the patient (e.g., via the XR visualization device worn by the healthcare professional and a XR visualization device worn by the patient, via one or more other communication devices, or directly in person) to instruct the patient to attempt to move the patient's appendage through various target ranges of motion. In some examples, the XR visualization presented to the healthcare professional indicates one or more target ranges of motion.

In some examples where one of XR visualization devices 10904 presents the extended reality visualization to a healthcare provider, another one of XR visualization devices 10904 may present another XR visualization to the patient. For example, during a telemedicine session or during an office visit, both the healthcare professional and the patient may wear or otherwise use XR visualization devices. In this example, the XR visualization devices may present XR visualizations to the healthcare professional and the patient showing one or more of an achieved range of motion of an appendage of the patient, a target range of motion, pain points, etc.

In some examples where the XR visualization is presented to a healthcare professional, the healthcare professional views the XR visualization outside the context of an interactive session with the patient. In other words, an XR visualization device may present the XR visualization to a healthcare professional during a session in which the patient is not involved. For example, the patient may perform various exercises that test the ranges of motion of an appendage and computing system 10902 may store (e.g., in data storage system 10910) data indicating the ranges of motion of the appendage.

In this example, computing system 10902 may use the stored data to later generate XR visualizations of the ranges of motion of the appendage. In this example, an XR visualization device worn by the healthcare provider may present the extended reality visualizations to the healthcare provider at any time after the patient performs the exercises. In this way, the healthcare provider may be able to effectively visualize or conceptualize the ranges of motion of the patient's appendage in a way that may be difficult if the healthcare provider were merely looking at written notes indicating angles of the ranges of motion.

In some examples, computing system 10902 may send a notification to the healthcare provider when computing system 10902 receive information indicating that computing system 10902 has received new range of motion data or that the patient is engaging in range of motion exercises. In some examples, computing system 10902 may provide information to a healthcare provider indicating whether the patient has engaged in assigned physical therapy exercises.

Furthermore, in some examples, computing system 10902 may present information to a healthcare provider that shows the evolution of the patient's range of motion over time. For example, computing system 10902 may provide information to an XR visualization device that enables the XR visualization device to display virtual arcs corresponding to that patient's range of motion at various times. In some examples, the XR visualization device may animate the virtual arcs to further help demonstrate the changes in the patient's range of motion. In some examples, an XR visualization device worn by the patient may display similar virtual arcs to help educate the patient with regard to the evolution of the patient's range of motion.

The XR visualizations presented to a healthcare professional may include various virtual objects. In some examples where the XR visualization is presented to a healthcare professional, the XR visualization may include a virtual protractor, as described elsewhere in this disclosure. Furthermore, in some examples, one or more virtual arcs for the range of motion and target range of motion may be presented in the visualization, as described elsewhere in this disclosure. Thus, in one example, the XR visualization presented to the healthcare provider may include a first virtual arc spanning an angle between furthest points of a range of motion of the appendage. In this example, the XR visualization further or alternatively includes a virtual arc spanning an angle between furthest points in a target range of motion of the appendage.

In some examples, the XR visualization presented to a healthcare professional may include indications of the pain points as experienced by the patient. That is, a pain point may be marked in the XR visualization of the range of motion. For instance, in one example, the XR visualization presented to the healthcare professional may include a virtual arc corresponding to an achieved or target range of motion of the patient's appendage and may also include virtual indicators on the virtual arc indicating points at which the patient experiences pain. In other words, the XR visualization of the range of motion of the appendage may include a virtual arc spanning an angle between furthest points in the range of motion of the appendage and a pain point is marked on the virtual arc.

Furthermore, irregularities in the motion of an appendage may provide useful diagnostic information. For example, the patient may be able to lower the appendage in a controlled way through a first part of the range of motion but cannot easily control the motion of the appendage in a second part of the range of motion so that the appendage drops quickly. In this example, this information may be diagnostic of a particular type of health condition, such as tears in particular muscles or slippages in implanted joint replacement surfaces. In another example, sudden or unusual accelerations or decelerations of the motion of an appendage at consistent points within a range of motion may provide valuable diagnostic information. In some instances, these irregularities in the motion of an appendage may be imperceptible to the patient. Such diagnostic information may be useful at various points in the surgical lifecycle, such as during preoperative phase 302 and postoperative phase 308.

Accordingly, computing system 10902 may determine, based on the motion data, whether there are irregularities in the motion of an appendage of a patient. For example, computing system 10902 may compare sets of motion data generated from multiple movements of the appendage through the range of motion to determine whether there is any consistent pattern of motion. For instance, computing system 10902 may apply a dynamic time warping algorithm to generate, based on set of motion signals for different times the patient moved the appendage through the range of motion, a signal representative of the acceleration of the appendage through the range of motion. Computing system 10902 may then compare the resulting signal to a signal representative of acceleration of the appendage through the range of motion in a typical individual.

In some examples, an extended reality visualization of the range of motion may include information regarding irregularities in the motion of the appendage. Thus, computing system 10902 may determine, based on the motion data, a point in the range of motion of the appendage at which an irregular movement of the appendage occurs and may generate the extended reality visualization of the range of motion such that the extended reality visualization indicates the determined point in the range of motion at which the irregular movement of the appendage occurs.

For example, the XR visualization may include virtual points, virtual arcs, or other virtual objects indicating where there are irregularities in the motion of the appendage within the range of motion of the appendage. Information regarding irregularities in the motion of the appendage may be presented to the patient, a healthcare professional, or another user of orthopedic surgical system 100. For instance, in an example where the information regarding the irregularities in the motion of the appendage are presented to the patient, the patient may be prompted (e.g., by a XR visualization device worn by the patient, a smartphone used by the patient, motion tracking device 10906, etc.) to try to move the appendage so that the irregularity does not occur.

In this example, the irregularity may be confirmed if the patient cannot move the appendage in the regular way despite being prompted to do so. In an example where the information regarding the irregularities in the motion of the appendage is presented to a healthcare professional (e.g., by one of XR visualization devices 10904, a monitor, or other visualization device), the XR visualization showing the information regarding the irregularities in the motion of the appendage may help the healthcare professional with diagnosis or physical therapy.

Figure 111:
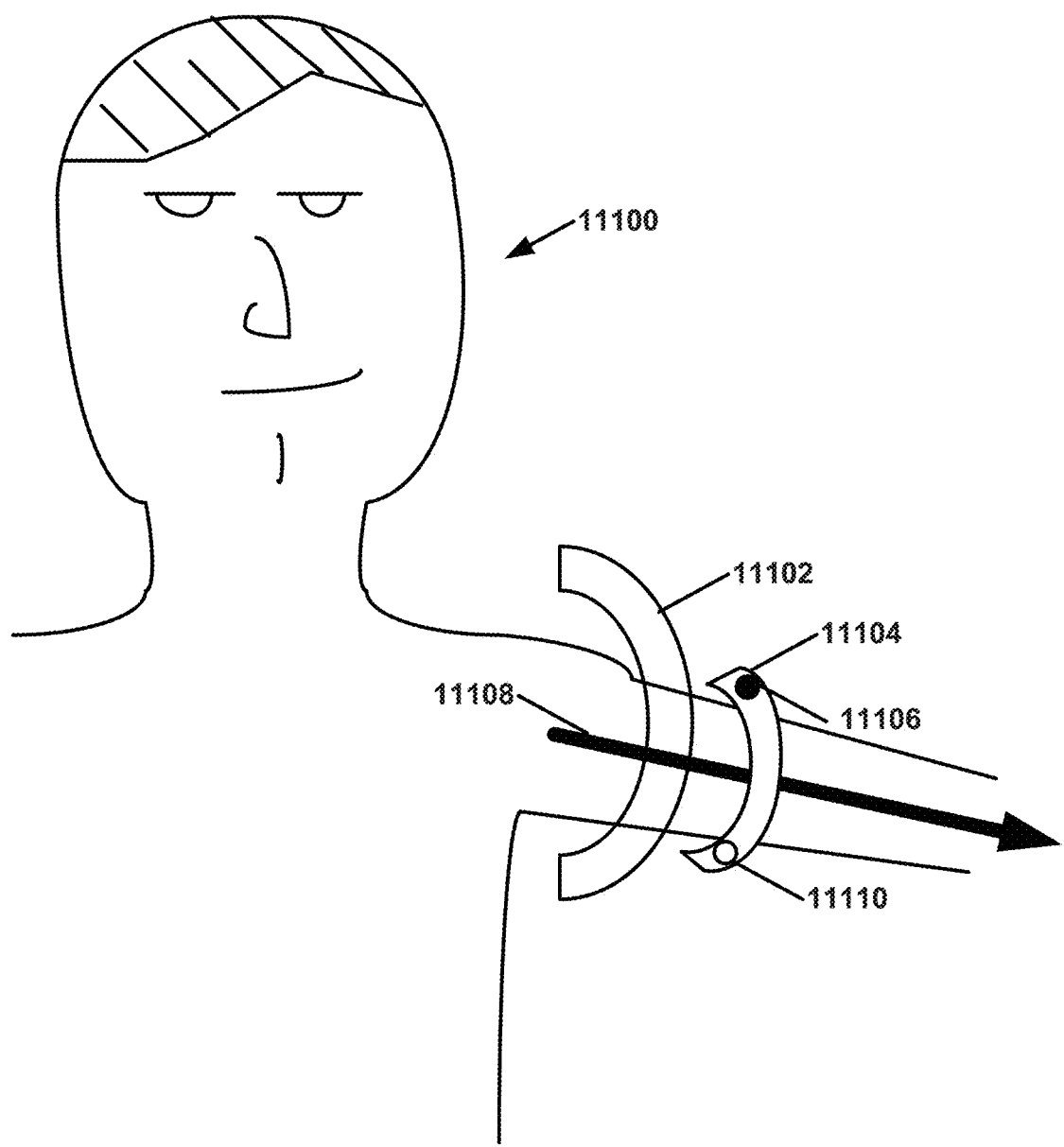
FIG. 111 is a conceptual diagram illustrating an example extended reality visualization of a range of motion, in accordance with a technique of this disclosure.

FIG. 111 is a conceptual diagram illustrating an example extended reality visualization of a range of motion, in accordance with a technique of this disclosure. The XR visualization shown in the example of FIG. 111 may be perceived by a healthcare provider wearing or otherwise using an XR visualization device (e.g., one of XR visualization devices 10904). Alternatively, the XR visualization shown in the example of FIG. 111 may be perceived by a patient wearing or otherwise using an XR visualization device (e.g., one of XR visualization devices 10904) when looking into a mirror.

The XR visualization of FIG. 111 includes an image or avatar 11100 of the patient or part of the patient. Additionally, the extended reality visualization of FIG. 111 includes a virtual arc 11102 that spans an angle corresponding to an actual range of motion of the patient's left arm in a frontal plane passing through the patient's left shoulder joint (e.g., when performing adduction and abduction). Additionally, in the example of FIG. 111, the XR visualization includes a virtual arc 11104 that spans an angle corresponding to a target range of motion of the patient's left arm in the transverse plane.

In other examples, virtual arc 11102 and virtual arc 11104 may be in other planes. Marker 11106 may correspond to a pain point. Marker 11110 may correspond to a point or region of irregular movement of the patient's left arm. Additionally, in the example of FIG. 111, the extended reality visualization includes a current line 11108 that is radial from a focal point of virtual arc 11102 and virtual arc 11104 and in a plane of the virtual arcs. Computing system 10902 may update current line 11108 so that current line 11108 remains aligned with a major axis of the patient's left arm.

Figure 112A:
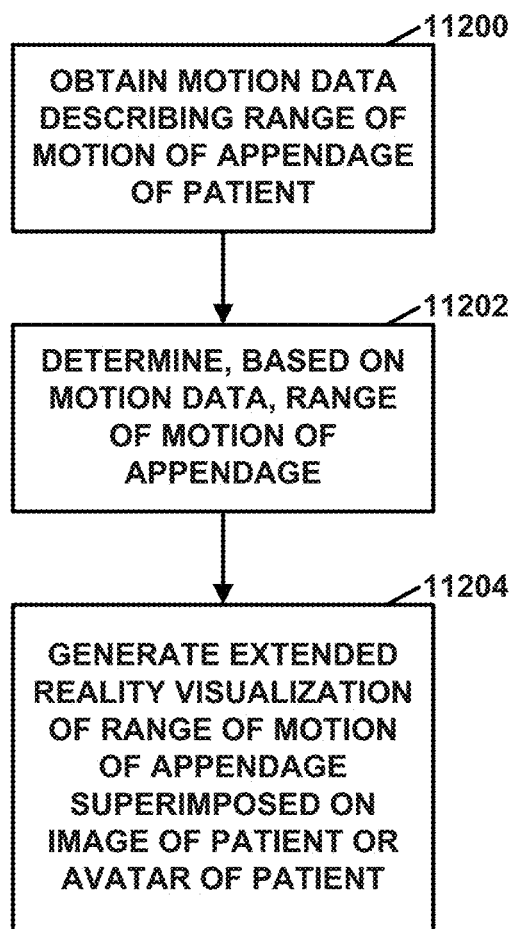
FIG. 112A is a flowchart illustrating an example operation of a system for range of motion analysis and visualization, in accordance with a technique of this disclosure.

FIG. 112A is a flowchart illustrating an example operation of system 10900 for range of motion analysis and visualization, in accordance with a technique of this disclosure. In the example of FIG. 112A, computing system 10902 may obtain motion data describing a movement of an appendage of a patient (11200). For instance, computing device 10902 may obtain the motion data from a motion tracking device, set of cameras, or combination thereof, as described in this disclosure.

Furthermore, in the example of FIG. 112A, computing system 10902 may determine, based on the motion data, a range of motion of the appendage (11202). Computing system 10902 may determine the range of motion of the appendage in accordance with any one or combination of examples provided elsewhere in this disclosure.

Computing system 10902 may generate an XR visualization of the range of motion of the appendage superimposed on the patient or an avatar of the patient (11204). Computing system 10902 may generate the XR visualization in accordance with any one or combination of examples provided elsewhere in this disclosure.

Figure 112B:
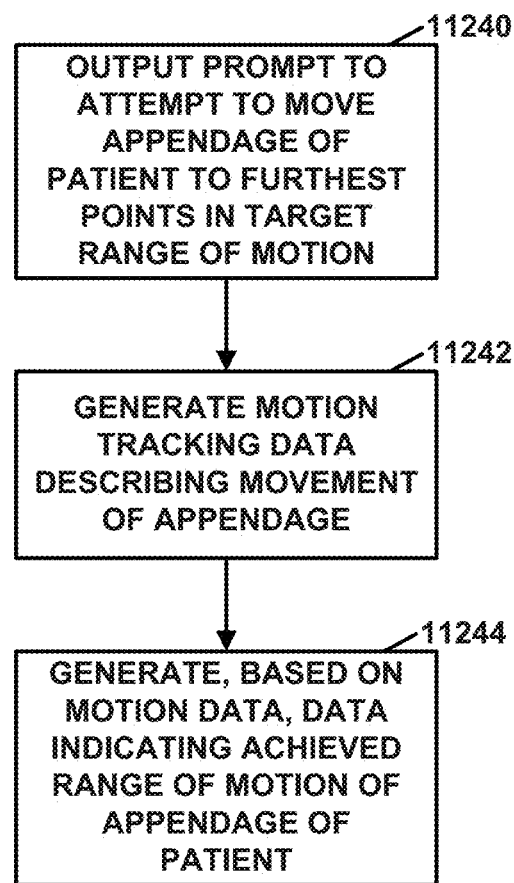
FIG. 112B is a flowchart illustrating an example operation of a system in accordance with a technique of this disclosure.

FIG. 112B is a flowchart illustrating an example operation of system 10900 in accordance with a technique of this disclosure. In the example of FIG. 112B, motion tracking device 10906 of a patient outputs a prompt to attempt to move an appendage of the patient to reach furthest points in a target range of motion of the appendage (11240). For instance, motion tracking device 10906 may output an audio or video description of how to move the appendage. As discussed elsewhere in this disclosure, motion tracking device 10906 may output the prompt in response to various events, such as in response to the indication of user input from the healthcare professional.

Additionally, in the example of FIG. 112B, motion tracking device 10906 may generate motion data describing a movement of the appendage of the patient (11242). For instance, an IMU of motion tracking device 10906 may generate the motion data describing the movement. Motion tracking device 10906 may generate, based on the motion data, data indicating an achieved range of motion of the appendage of the patient (11244). For example, motion tracking device 10906 may generate data indicating coordinates of the starting and stopping points of the achieved range of motion. In some examples, motion tracking device 10906 may send the data indicating the achieved range of motion to a remote database of patient data (e.g., data storage system 10910).

Furthermore, in some examples, motion tracking device 10906 may receive an indication of user input when the appendage of the patient is at a point within the range of motion where the patient experiences pain. In such examples, in response to receiving the indication of the user input, the motion tracking device may generate, based on the motion data, data indicating a pain point. The pain point may be a position of the appendage of the patient at which the patient experiences the pain.

Figure 113:
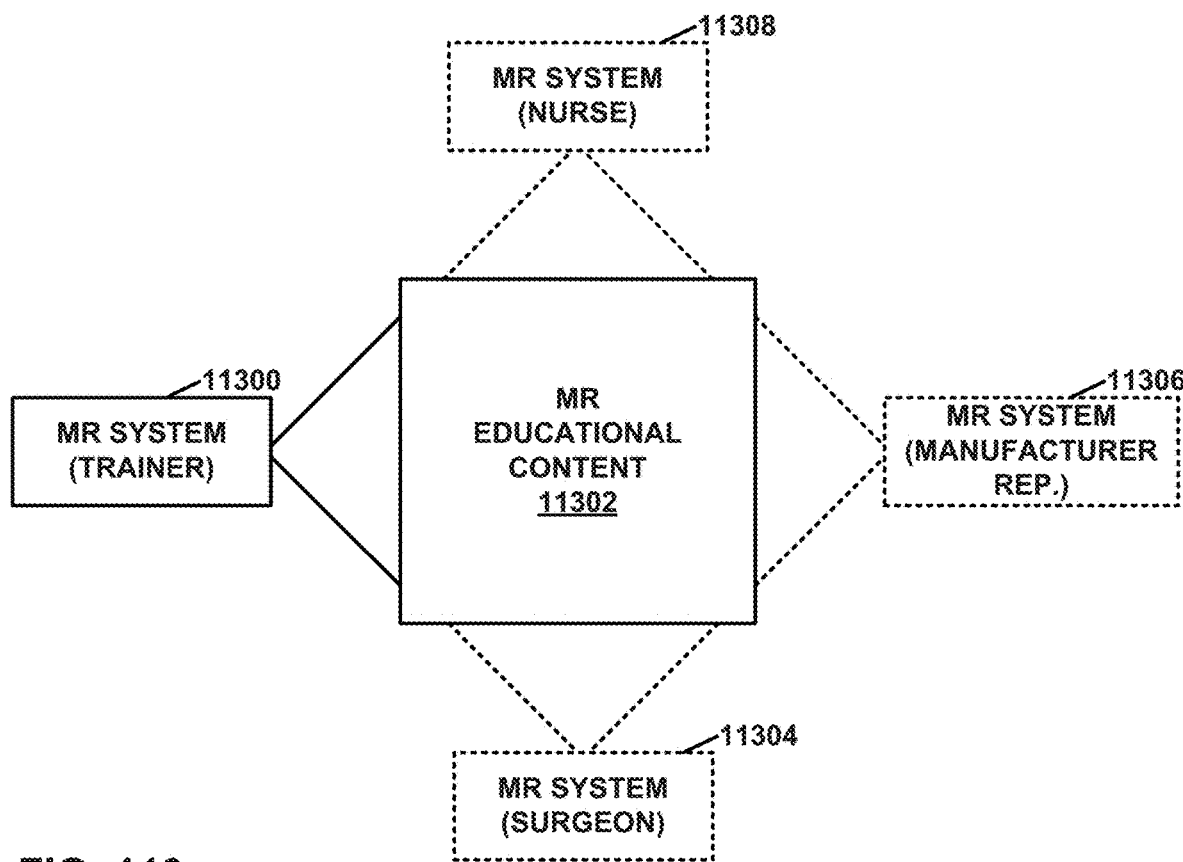
FIG. 113 is a conceptual diagram illustrating an example setting in which a set of users use MR systems for educational purposes.

FIG. 113 is a conceptual diagram illustrating an example setting in which a set of users use MR systems for educational purposes. In the example of FIG. 113, a surgeon may wear or otherwise use a visualization device (e.g., visualization device 213) of a first MR system 11300 (e.g., MR system 212. The visualization device of MR system 11300 may present MR educational content 11302 to a trainer. Furthermore, in the example of FIG. 113, another surgeon may wear or otherwise use a visualization device of a second MR system 11304, a medical device manufacturer representative may wear or otherwise use a visualization device of a third MR system 11306, and/or a nurse may wear or otherwise use a visualization device of a fourth MR system 11308. In one example, a medical device manufacturer representative may wear or otherwise use visualization device of MR system 11306 while the surgeon wears or otherwise uses the visualization device of MR system 11300. In this example, the visualization devices of MR system 11300 and MR system 11306 may present the same MR education content 11302 to the medical device manufacturer representative and the surgeon. In this example, the medical device manufacturer may explain the use of a medical device to the surgeon while the medical device manufacturer and the surgeon view the same MR preoperative content.

This disclosure describes a number of multi-user collaboration techniques for an orthopedic medical procedure that makes use of mixed reality (MR). Although the techniques may be useful in a wide variety of orthopedic procedures, they may be especially useful in both anatomical and reverse-anatomical shoulder reconstruction surgeries. Indeed, the techniques may be helpful for reversed arthroplasty, augmented reverse arthroplasty, standard total shoulder arthroplasty, augmented total shoulder arthroplasty, hemispherical should surgery, or other types of shoulder surgery. More generally, however, the techniques may find useful application with any orthopedic medical procedure that involves multiple participants in the procedure.

Various view sharing techniques and controls are described for mixed reality devices used within the operating room, whereby a user may be able to view the mixed reality presentation (or a portion thereof) of other users in the operating room. Users in the operating room, as well as remote users, may include medical caregivers, such as, for example, one or more surgeons, one or more nurses, one of more medical support personnel (such as technical support representatives of a manufacturer of medical device instruments, implants, equipment or supplies), anesthesiologists, and other operating room personnel.

In some examples, MR content associated with the views of other users (or possibly fixed cameras) may be presented as a window view within the presentation of a user that wants to see a view from another user or perspective. The view of a user may be at least a portion of what the user is able see from the user's own perspective. In some examples, the views of other users may be selectively presented as the main view of the user that wants to see the view seen by another user or perspective. Hence, a user may view a main view and one or more additional views, e.g., in sub-windows, and select any of the views to be presented as the main view. For example, a physician performing an orthopedic surgery may be presented with a mixed reality view from his or her perspective as a main view, but that user may be able to select and see the view of other persons (or fixed cameras) within the operating room, e.g., by selecting one of the sub-windows or other information associated with the views, based on person, view name, or other information. This can allow the physician to view his or her own perspective as a main view but quickly gain other perspectives within the operating room by viewing the sub-windows and/or one of the sub-windows temporarily as the main view. In some examples, the views of others may be presented as windows on a main view of a user, such that the user is able to see his or her main view while simultaneously watching another view of another person in a window presented on the main view. A surgeon, for example, may access the view of a nurse for a different angle or perspective, while performing a surgical step, and the view of the nurse may be shown to the surgeon in a window on the surgeon's main view.

Moreover, this disclosure also describes mixed reality presentations that can vary for different users in the operating room. For example, the mixed reality presentation for a nurse may be different from that of a physician, since the nurse and the physician have different roles in the operating room and mixed reality may be tuned on a user-by-user basis to help each user with their role in the medical procedure. Other participants may have other roles, and their mixed reality presentation may be defined to accommodate such differing roles. As other examples, the mixed reality presentation for medical device representatives, assistants, different nurses, and different physicians may differ from one another. When accessing the view of another person, that person's view may include both real world objects (such as views of the patient's bone or other anatomy), as well as virtual objects (such as virtual elements presented in the MR presentation). Thus, when a physician accesses or observes the view of a nurse, the physician may view both real-world objects viewed by the nurse, as well as virtual objects presented to the nurse in the nurse's MR presentation.

In some examples, some mixed reality information (e.g., virtual elements of the mixed reality presentation) may be common for all participants, while other mixed reality information may be specific and only presented to specific participants based on their role in the medical procedure. This disclosure also contemplates the ability to enable or select mixed reality information from other users on an object-by-object basis, e.g., allowing a physician to enable or disable a virtual element that is part of a nurse's MR presentation so as to show that same element on the physician's MR presentation. Thus, view sharing may include the ability to see the entire view of other users (including real observed objects seen by other users and virtual elements presented to the other users), or the ability to enable or disable virtual objects shown to others on an object-by-object basis. The virtual objects that may be enabled or disabled may comprise mixed reality guidance features, user interfaces, widgets, or any virtual information that is included in an MR presentation.

In still other examples, this disclosure describes techniques that can facilitate participation in a medical procedure by one or more remote participants, possibly with the use of virtual reality. In different examples, the described system and techniques may facilitate active and passive participants, user-specific mixed reality guidance that is defined for different roles in the operating room, view sharing and control of view sharing, and other useful features described in greater detail below. Active participants, for example, may have some level of control over virtual content, view sharing, and the MR presentation of other views, while passive participants may have the ability to view an MR presentation and virtual content without any control over the MR presentation and virtual content.

As mentioned elsewhere in this disclosure, multiple users can simultaneously use MR systems. For example, the MR systems can support a spectator mode in which multiple users each have a visualization device so that the users can view the same information at the same time. In this way, one or more spectators can be active or passive participants in a preoperative, intraoperative, or postoperative procedures.

The ability to include active and passive participants to a procedure may be highly desirable. In some examples, active roles may be assigned or re-assigned during a medical procedure or medical encounter. In other examples, varying levels of active roles may be defined. Indeed, different MR experiences and features may be provided to different persons using MR systems. For example, a physician may be presented with a first MR interface and a nurse may be presented with a second MR interface that is different from the first MR interface. For example, selectable widgets 524 (FIG. 5) of a user interface 522 shown in an MR screen 520 of visualization device 213 may be defined for a physician, and different selectable widgets 524 may be defined for a nurse (or other user) that uses a different processing device(s) 210 (FIG. 2) than that used by the physician. Other variations between the MR experience for a first user and the MR experience of a second user may also be defined based on the user. For example, a passive participant user may be presented with viewable MR elements without any selectable control widgets, which may be desirable for students or other passive observers to the procedure. Such passive MR participants may benefit from viewing MR elements of the procedure but may be prevented from being able to select or modify anything in the MR world.

Figure 114:
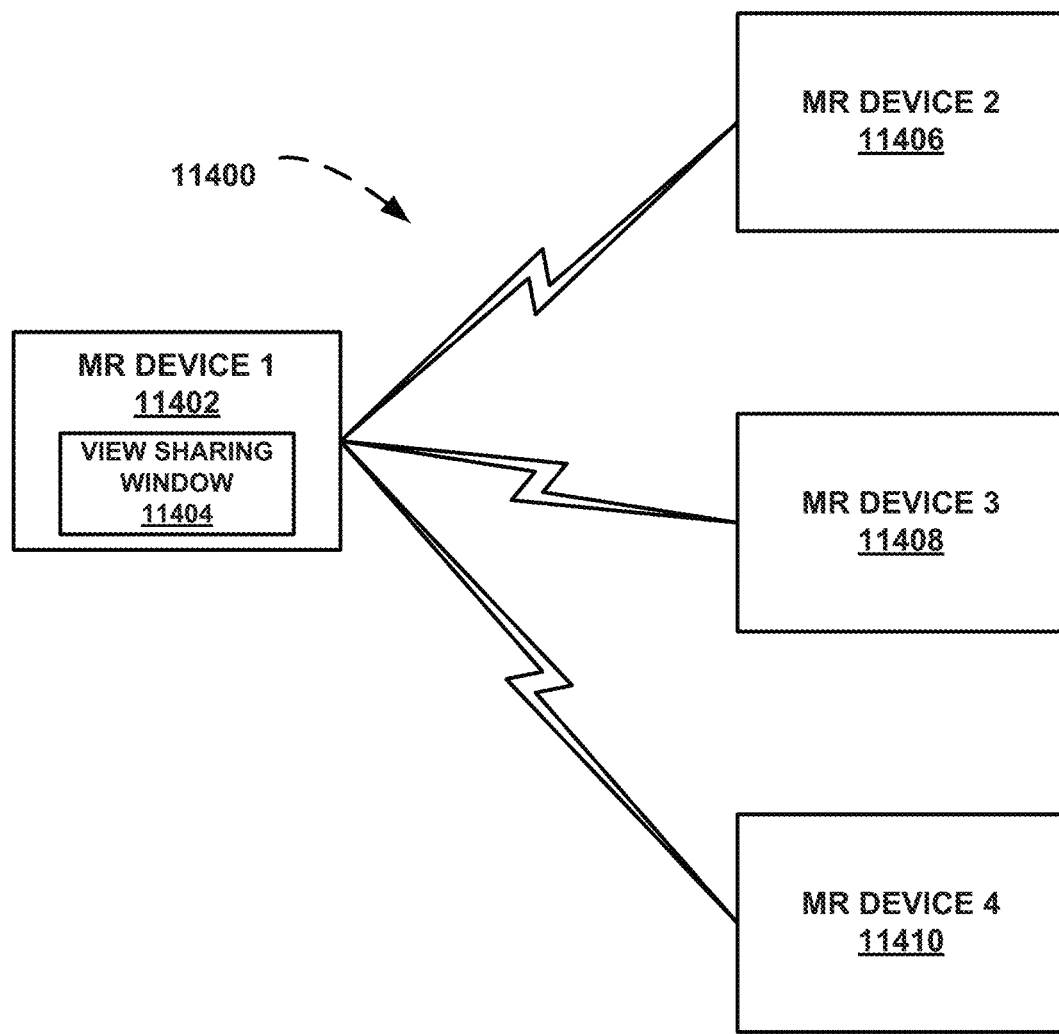
FIG. 114 is a block diagram of a system that includes multiple MR devices that communicate with one another.

FIG. 114 is a block diagram of a system 11400 that includes multiple MR devices that communicate with one another. Each of the illustrated MR devices may comprise visualization devices similar to visualization device 213 (FIG. 2, FIG. 5) described herein. FIG. 114 shows four MR devices (11402, 11406, 11408 and 11410) although more or fewer devices could be used. Visualization devices of the MR devices (11402, 11406, 11408 and 11410) may be worn by users in an operating room during an orthopedic medical procedure, e.g., surgery. As shown, MR device 1 (11402) includes a view sharing window 11404. According to this disclosure, MR device 1 (11402) is configured to present one or more of the views of other MR devices on MR device 1 (11402). Although shown as a view sharing window (11404), the view sharing may be presented in other ways.

MR device 1 (11402) may be configured for a particular user, whereas MR device 2 (11406), MR device 3 (11408) and MR device 4 (11410) may be configured for other users. In this way user specific rolls may be defined in the operating room, and mixed reality presentations may be defined for each participant. Since the participants may have different roles in the operating room, the MR presentations may be different for different users. For this reason, view sharing may be desirable, e.g., to allow the physician to see a nurse's view or a technician's view, so as to allow for more collaboration in the operating room. View sharing may also be desirable to enable different angles of view in the operating room or different perspectives. View sharing may occur between different MR devices, and possibly from one or more additional fixed cameras (not shown in FIG. 114). In some cases, one or more of MR devices (11402, 11406, 11408, 11410) may be located remotely relative to the surgical procedure. In this case, the remote participant may be able to view the same virtual elements as other participants, but the real-world views may differ due to the MR devices being used in different locations. View sharing may be especially useful in this type of setting so as to allow the remote participant to see the views of local participants.

Different levels of active participation and passive participation may also be defined for different active participants to an orthopedic surgical procedure, such as an ankle surgery procedure or a shoulder surgery procedure. For example, a physician may be given particular levels of control of the displayed elements of an MR presentation during a medical procedure, and nurses or assistants may be given different levels of control. Also, the MR interface may vary for different users. Accordingly, physicians may be presented with an MR interface for the physician that is designed to provide virtual guidance to aid the physician with the procedure (such as virtual guidance features to aid the physician with the procedure), and nurses may be presented with a different MR interface designed to aid the nurse with particular tasks of the nurse (such as tool selection and tracking and documentation of the procedure). Other types of users may also be defined, such as medical device personnel, additional physicians, anesthesiologists, physician assistants, nurse assistants, medical technicians, or other users. In some examples, a master role may be defined to provide overall control over the process, and in some cases, the master role may be delegated among users. For example, referring again to FIG. 114, MR device 1 (11402) may be assigned as the master device, and other users associated with MR devices 2-4 (11406, 11408 and 11410) may have less control than MR device 1 (11402). In some cases, however, the master role may be assigned or changed amongst the users.

In some examples, this disclosure describes a MR system (e.g., MR system 11400) comprising a first MR device (e.g., MR device 1 11402) configured to provide first medical information to a first user via a first MR presentation, and a second MR device (e.g., MR device 11406) configured to provide second medical information to a second user via a second MR presentation. The first and second MR devices may comprise visualization devices as described elsewhere in this disclosure. In some examples, the first medical information is the same as the second medical information. In some examples, the first medical information and the second medical information are different. The first MR device may be controllable to present the second MR presentation to the first user. For example, the first MR device may be configured to present the second MR presentation to the first user as a viewable window within the first MR presentation. In another example, the first MR device may be configured to allow the first user to select and view either the first MR presentation or the second MR presentation. Each of the MR presentations may include views of real-world objects and one or more virtual elements.

In some examples, a MR system (e.g., MR system 11400) may comprise a first MR device (e.g., visualization device 213) configured to provide first medical information regarding an orthopedic medical procedure to a physician via a first MR presentation wherein the first MR presentation includes physician-specific information associated with the orthopedic medical procedure. The MR system may further include a second MR device (e.g., another visualization device 213) configured to provide second medical information to a second user via a second MR presentation wherein the second MR presentation includes information that differs from the first MR presentation. In some examples, the first medical information is the same as the second medical information. In some examples, the first medical information and the second medical information are different. The first MR device may be controllable to present the second MR presentation to the physician. For example, the first MR device may be configured to present the second MR presentation to the first user as a viewable window within the first MR presentation. In some examples, the first MR device is configured to allow the first user to select the first MR presentation or the second MR presentation. The physician-specific information may include surgical guidance information. Moreover, in some examples, the second MR presentation may include nurse-specific information associated with the orthopedic medical procedure. For example, the nurse-specific information may include surgical item information. In other examples, the second MR presentation may include technician-specific information associated with the orthopedic medical procedure. For example, the technician-specific information may include registration guidance for registering one or more virtual elements in the second MR presentation. For instance, the registration guidance may include guidance for how to register a virtual element (e.g., a virtual 3D model of a bone) with a real-world object, such as a bone.

In some examples, a method according to this disclosure may comprise presenting first medical information to a first user via a first MR presentation on a first visualization device and presenting second medical information to a second user via a second MR presentation on a second visualization device. In this example, the first visualization device may be controllable to present the second MR presentation to the first user. The second MR presentation may include views of real-world objects and one or more virtual elements.

In some examples, a method according to this disclosure may comprise presenting first medical information to a first user via a first MR presentation on a first visualization device, receiving second medical information comprising a second MR presentation from a second visualization device, and controlling the first visualization device to selectively present the second MR presentation on the first visualization device. In some examples, the first medical information is the same as the second medical information. In some examples, the first medical information and the second medical information are different. These and other methods described in this disclosure may be executed by one or more processors, in which case the techniques may be embodied in processor-executable instructions stored in a computer readable medium. The one or more processors may comprise one or more processors of visualization device 213 and the computer-readable storage medium may comprise a memory of the visualization device 213.

Workflow management tools and checklists may also be used to provide additional checks and controls on the surgical process. When multiple MR participants are involved with a surgery, for example, different persons may be assigned for approval of different steps. One person may need to approve a first medical procedure step before the system allows the surgery to proceed to the next step, and in some cases, a different person may need to approve a second medical procedure step before the system allows the surgery to proceed to yet another step. In this way, checks and approvals of surgical steps may be distributed amongst different participants (or observers) to the surgery. Workflow management tools and checklists may be especially helpful for complex multi-step surgical procedures, such as a shoulder arthroplasty, an ankle arthroplasty, or any other type of orthopedic surgery that requires many different steps.

In some examples, physician may be presented with a first MR interface and a nurse may be presented with a second MR interface that is different from the first MR interface. For example, referring again to FIG. 114, MR device 1 (11402) may present the first MR interface for a physician, and MR device 2 (11406) may present the second MR interface for a nurse. Moreover, other users, such as assistants or medical device technicians may be presented with still other types of MR interfaces. In this way, the MR interface presented to each user may be specifically defined or tuned to aid that participant with their specific role in the procedure. For example, MR-based intraoperative guidance features (cutting axes, drilling axes, reaming axes, virtual jigs, implant positioning targets, or other intraoperative aids) for use in guiding operative steps in a surgical procedure may be presented to the surgeon responsible for such steps, but some of these intraoperative guidance features may not be presented to other users, such as nurses, assistants or medical device technicians. Moreover, menus or controls for such intraoperative guidance features may be presented to a physician on the MR device for that physician, but such menus or controls may be eliminated from the views of other users on their MR device(s). Similarly, tool selection prompts, medical device inventory tracking, and medical procedure documentation features may be presented to the nurse (as well as menus and controls), but some or all of these features may be eliminated from the views of the surgeon. Also, other features or controls may be presented to a medical device technician, such as features for registering virtual elements into the MR presentation, but such technician-specific MR for that technician may be eliminated from the views of surgeons and nurses. In some cases, users may be allowed to selecting enable or disable virtual elements shown to other users. For example, nurse-specific virtual elements may be selectively enabled or disabled by the surgeon, if the surgeon finds a need or desire to view virtual elements that are typically shown to the nurse and not to the physician.

Some virtual elements may be viewable by all participants, while other virtual elements or controls may be viewable by only select participants. In this way, the MR systems can help to guide each participant with tools and features that are tuned to the role of that participant in the medical procedure. Moreover, eliminating features or controls that are not pertinent to the role of a given participant can improve the MR experience and help to eliminate visual clutter in the MR experience. For example, tool selection prompts may be highly desirable to aid a nurse in identifying tools and a succession or sequence of the planned use of such tools in the procedure. But a surgeon may find tool selection prompts to be distracting, particularly while the surgeon is focused on a patient operative tissue or bone site, and the physician may simply rely on the nurse to provide the tools in their proper order for the procedure, e.g., as requested by the surgeon and/or as indicated by virtual guidance provided to the nurse regarding tool selection and sequence and overall surgical procedure workflow. For these and other reasons, selectable widgets 524 of a user interface 522 shown in an MR screen 520 of visualization device 213 may be defined for a physician, and different selectable widgets 524 may be defined for a nurse (or other user) so that each MR experience can be better suited to the roll of that participant in the procedure.

The users of MR devices, including active participants and spectators, may be physically present during the procedure, using MR visualization devices. Alternatively, one or more users or spectators may be physically remote relative to the location of the procedure. When one or more users or spectators are located remotely, they may participate in the procedure or view the procedure via remote display screens such as on laptop computers, desktop computers, smart phones, or other types of display screens. In other examples, remote participants may view the procedure via a mixed reality (MR) visualization device, or with virtual reality (VR) rather than MR. If MR is used for remote participants, the remote participant may be able to view the same virtual elements as other participants, but the real-world views may differ due to the MR devices being used in different locations. View sharing may be especially useful in this type of setting so as to allow the remote participant to see the views of local participants.

In some examples, a system may comprise both VR devices and MR devices. In this case, the VR environment presented to the remote user may comprise images and objects captured and presented by MR systems that are used by local participants. In this way, the MR environment, which includes real-world objects, may be captured and presented to remote users as a VR environment. A VR visualization may comprise imagery of a VR environment. In the VR environment, the real-world objects seen by an MR participant may be represented by VR images of said real-world objects. In some examples, a VR presentation presented to the VR user may comprise one of the MR views of one of the MR participants. However, in other examples, the VR presentation presented to the VR user may comprise information from two or more MR views of two or more of the MR participants. With multiple MR views, the creation of an accurate VR representation of the procedure may be enhanced relative to the use of a single MR view to render the VR presentation. For example, MR participants may provide input for room mapping so that the room can be mapped and presented as a virtual environment to a VR participant.

Figure 115:
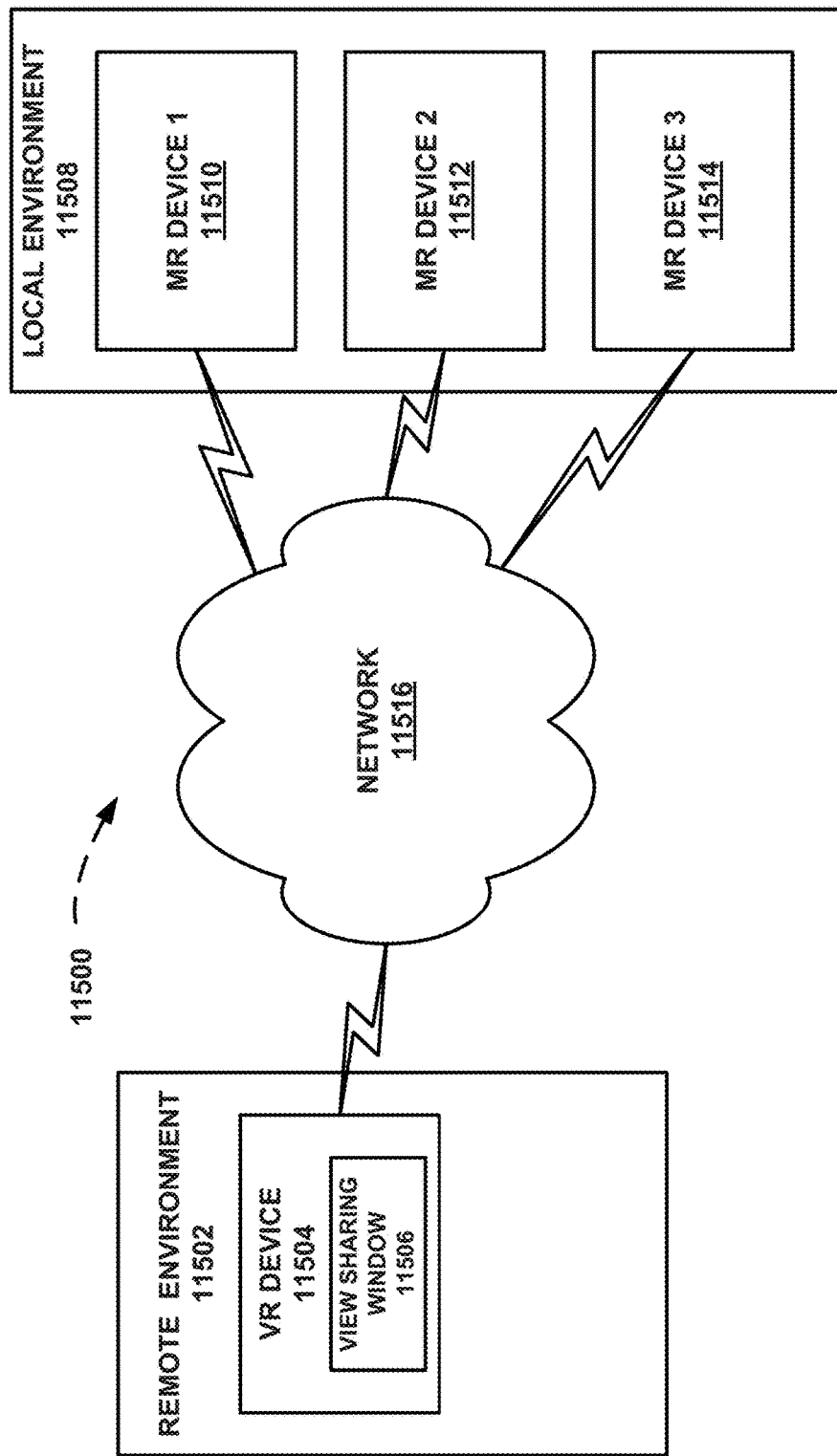
FIG. 115 is a block diagram illustrating a distributed MR system that includes one or more users at a local environment that are in communication with one or more users in a remote environment.

FIG. 115 is a block diagram illustrating a distributed MR system 11500 that includes one or more users at local environment 11508 that are in communication with one or more users in a remote environment 11502. The communication may occur over any type of network (e.g., shown as network 11516). In some example, local environment 11508 may comprise an operating room. MR devices 1-3 (11510, 11512 and 11514) may correspond to users in the operating room, such as a physician, nurse, medical technician, anesthesiologist, or other users.

In general, local environment 11508 may be an environment where users are in viewable proximity to a patient, whereas remote environment 11502 may correspond to a location where users are not in viewable proximity to a patient. Since remote environment 11502 is not at the same location as local environment 11508, any user of system 11500 at remote environment 11502 may operate in a purely virtual reality. VR device 11504 may facilitate this virtual reality environment, which may be a virtual reality world that is generated based on views and data from one or more of the MR devices in local environment 11508 (e.g., room mapping).

As shown in FIG. 115, VR device 1 (11504) includes a view sharing window 11506. According to this disclosure, VR device 1 (11504) is configured to present one or more of the views of MR devices in the local environment 11508 in view sharing window 11506. Although shown as a view sharing window (11404), the view sharing may be presented in other ways, such as via a remotely located MR device with a view sharing window or by VR device 11504 assuming the view of a selected one of the MR devices in local environment 11508.

In some examples, a surgeon may perform one or more procedures on a patient in an operating room, with the aid of MR. During the procedure, the MR environment may be captured and presented to remote users via display screens or as a VR environment. The surgeon may be able to view the patient directly in the operating room via an MR device, such as with a visualization device 213. The MR users may utilize visualization devices that deliver mixed or augmented reality to the user, whereas remote VR users may utilize a visualization device that is pure virtual reality.

Alternatively, rather than using VR, remote users may use MR device that are located remotely or may simply view display screens (such as desktop computers, laptop computers, or smartphones) that include camera feeds from cameras or the MR devices used by local participants. In some examples, the remote display screens used by one or more remote users may show the same virtual elements that are shown to local MR participants. The remote participant may be able to select between MR views and switch them at will, and the views selected by the remote participant may include the virtual elements that are shown to the local MR participants that have that same corresponding local views that are selected by the remote participant.

In some examples, the MR systems can capture the images viewed by the surgeon and then use those captured images to render VR images that can be displayed to a remote spectator via VR. In this way, the remote spectator may be presented with a VR environment that is similar or identical to the MR environment viewed by the local surgeon. Of course, the view of the VR participant may not be available to MR participants, since the VR participant is typically not present in the operating room.

When one or more MR participants and one or more VR participants are using the system, the MR and VR participants may also be presented to one another in the MR and VR environments. For example, a surgeon working in the operating room with the aid of MR may be presented with an MR environment that includes one or more VR participants, which may be shown as MR objects (e.g., avatars) in the MR environment. Similarly, the VR participants may be presented with a VR environment that includes the same objects and images shown in the MR environment. Thus, real objects shown in the MR environment to MR users may be presented as VR objects in the VR environment to VR users. In this way, the MR and VR worlds can be intertwined such that MR participants can see the VR participants as VR objects in the MR world. Similarly, VR participants can view the MR objects and MR participants (e.g., avatars), as well as real-world objects as VR objects in the VR world. When objects move in the MR world, the object movements are captured by one or more of the MR participants. The VR world is then adjusted to reflect the changes in the MR world that is captured by the MR participants. In this way, the VR participants are able to view a VR world, in real-time, that is based on the MR world. Again, in some examples, the VR presentation to the VR user may comprise one of the MR views of one of the MR participants. However, in other examples, the VR presentation to the VR user may comprise information from two or more MR views of two or more of the MR participants. With multiple MR views, the creation of an accurate VR representation of the procedure may be enhanced relative to the use of a single MR view to render the VR. For example, multiple MR participants may provide input for room mapping so that the room can be mapped and presented as a virtual environment to a VR participant.

As mentioned, one or more of the VR participants can be located remotely relative to the MR setting, such as an operating room or a remote location for patient interaction. This allows the VR participant to be a remote participant relative to the location of the patient encounter, procedure, or surgery. The ability to accommodate a VR participant can be highly desirable for many situations and settings. For example, surgical experts may be consulted as VR participants in an otherwise MR procedure in the operating room, thereby providing more expertise to the procedure by virtue of the remotely-located VR participant. For instance, in this example, a user of an MR visualization device in the operating room may request a remote surgical expert for a consultation during the surgery. In this example, the remote surgical expert may use a VR visualization device to obtain a VR visualization of a scene in the operating room. A local physician using MR could then ask questions or receive guidance from a remote VR participant so as to help improve the medical process. A remote VR participant may be able to see what the local MR surgeon is seeing, e.g., by selecting the surgeon's MR view as the VR view for the remote VR participant. In some examples, the remote VR participant may be a surgical expert that is summoned during a medical procedure in order to gain insight or advice on the procedure.

In some examples, a MR system comprises a first MR device (e.g., a visualization device 213) configured to provide first medical information about an orthopedic medical procedure to a first user via a first MR presentation, and a second MR device (e.g., another visualization device 213) configured to provide second medical information about the orthopedic medical procedure to a second user via a second MR presentation. The first and second medical information, for example, may comprise surgical guidance information in the form of one or more virtual elements presented in the first or second MR presentations. In some examples, the first medical information is the same as the second medical information. In some examples, the first medical information and the second medical information are different. The virtual elements, for example, may comprise any of the virtual information described in this disclosure, such as virtual planes, virtual axes, virtual menus or widgets, or any virtual information that may be useful in the surgical procedure. The MR system may further include a VR device configured to present a VR presentation that provides at least some of the first or second medical information about the orthopedic medical procedure to a third user. The VR presentation may be based at least in part on the first MR presentation or the second MR presentation. In some examples, the VR presentation comprises one of the first MR presentation and the second MR presentation, and in some examples, the VR presentation is selectable on the VR device between the first MR presentation and the second MR presentation. The first user and the second user may be located in viewable proximity to a patent and the third user may be located remotely relative to the patient. The VR device may be configured to present the VR presentation to the third user in substantially real-time relative to MR presentation. The first MR device may be configured to present the third user an avatar in the first MR presentation and the second MR device is configured to present the third user an avatar in the second MR presentation. In addition, the VR device may be configured to present the first and second users as avatars in the VR presentation.

In some examples, this disclosure describes a VR device for use by a remote medical professional, the VR device comprising a display configured to present a VR presentation that provides medical information associated with a patient to the remote medical professional, wherein the VR presentation is based at least in part on a MR presentation, and one or more processors that control the display, wherein the MR presentation is captured locally by a local user of an MR device located within viewable proximity to the patient.

In some examples, an MR system comprises a first MR device configured to present first medical information and first real-world information to a first user via a first MR presentation, a second MR device configured to provide second medical information and second real-world information to a second user via a second MR presentation; and a third device configured to provide third information to a third user, wherein the third information is based at least in part on the first MR presentation or the second MR presentation. In some examples, the first medical information is the same as the second medical information. In some examples, the first medical information and the second medical information are different. The third device may be configured to allow for selection between the first MR presentation and the second MR presentation on the third device. The first user and the second user may be located in viewable proximity to a patient and the third user may be located remotely relative to the patient. In some examples, the third device presents the third information to the third user in real-time relative to the first MR presentation on the first MR device and the second MR presentation on the second device. The third device may comprise a display screen that presents the third information, or alternatively, the third device may comprise a VR device that presents the third information.

In some examples, a method according to this disclosure may comprise presenting first medical information about an orthopedic medical procedure to a first user via a first mixed reality presentation on a first visualization device, presenting second medical information about the orthopedic medical procedure to a second user via a second MR presentation on a second visualization device, and presenting a VR presentation that provides at least some of the first or second medical information about the orthopedic medical procedure to a third user of a VR device, wherein the VR presentation is based at least in part on the first MR presentation or the second MR presentation. In some examples, the first medical information is the same as the second medical information. In some examples, the first medical information and the second medical information are different.

These and other methods described in this disclosure may be executed by one or more processors, in which case the techniques may be embodied in processor-executable instructions stored in a computer readable medium. The one or more processors may comprise one or more processors of visualization device 213 and the computer-readable storage medium may comprise a memory of visualization device 213.

Many of the examples of view sharing and the participation of remote participants to a procedure have described in this disclosure have been described in the context of a surgical process. However, view sharing and the use of remote participants may also be used in other settings, such as in a pre-operative encounter with the patient, a post-operative encounter, or other settings. For example, in a pre-operative or post-operative encounter, a remote participant may be consulted (e.g., with the aid of MR, VR or other techniques described herein) in order to leverage the expertise of that remote participant, who may be a medical expert, a medical device technician, a surgical expert, a nurse, or any other person that may need to be consulted. In general, view sharing and the participation of remote participants to a medical procedure may be desirable in a wide variety of settings, including operating room settings, educational settings, pre-operative meetings or settings, post-operative meetings or settings, physical therapy settings, or other settings.

As another example, MR may be used locally in the field for patient encounters, checkups, or field emergencies, such as for a remote checkup with a patient at a patient's residence or for emergency care. Referring again to FIG. 115, for example, local environment 11508 may comprise any location where patient care is needed. In these types of examples, a remote participant may be consulted in real time during this remote checkup or emergency care with the use of VR device 11504. In such examples, the MR participant(s) may comprise a physician, nurse, or other person that interacts locally with the patient, e.g., at the patient's home. The objects and images viewed by the MR participant may be actual objects mixed with virtual objects. These same objects and images may also be presented to a remote participant with the use of VR by presenting objects as virtual objects to the remote participant. This can allow medical personal (working with AR) to leverage the opinions and expertise of a remote VR participant in real time. In this way, a VR participant need not be present at the location of the patient in order to view, diagnose, and help with patient care. In other examples, the remote participant may simply view one or more display screens, which may include information that is captured by MR participants or other cameras.

In some examples, the views and images captured by one or more MR participants may be viewed by a remote VR participant. For example, a physician using VR may be able to access the views and images seen locally by an MR participant to the procedure. Using VR, the physician may be presented with the views and images seen locally by the MR participant. In this way, the physician may be located remotely relative to the patient but may view real-time objects and images of the patient and the patient's environment so as to aid and facilitate remote diagnosis and treatment by the physician using VR.

In some examples, the view of one or more MR users may be a selectable choice for one or more remote users. In this way, multiple different view options associated with multiple different MR perspectives may be accessed by remote users. For example, a remote physician using VR may be able to select and see the view of a first MR participant or a second MR participant. In this way, the VR world viewed by the remote user may comprise the same MR view shown by a local MR participant to the procedure. In addition, the remote VR user may be able to change views to present a different MR view associated with a different MR participant to the procedure. Selectable views for the VR participant may be desirable for operating room environments as well as remote patient checkups and remote emergencies in the field.

In order to select the view of other users, users may select avatars, sub-windows, gaze lines, icons, or selections from drop down menus. These or other types of control mechanisms may be implemented as virtual objects presented on a visualization device in a user's MR or VR presentation. Then, when a first user selects the view of a second user, that second user's view may be presented to the first user. In this way, view sharing and the selectability of the view of other users may provide more information to MR users.

Relative to a local process or procedure, the VR participant may be presented as an MR object (e.g., an avatar) in the MR world, which is shown to the MR participants. In this way, the VR participant may be presented as being "in the room" relative to the MR participants. Thus, the VR participant can appear to be more integrated into the process with the MR participant, giving the impression to MR participants that the VR participant is present, e.g., in the operating room or at the location of care. MR and VR participants may interact and even view at one another, as though they are interacting in the same room. The MR participant, however, is merely seeing an object (e.g., an avatar) of the VR participant and vice versa.

In some examples, a VR participant is able to interact or select from views associated with a plurality of MR participants. The VR participant may be able to view a first VR world defined by the views of a first MR participant, and the VR participant may then be able to change views to that captured by a second MR participant. In this way, for example, a VR participant may be given more control over the views seen in real time. Also, in yet additional examples, the room may be mapped and presented to the VR participant in the VR world based on multiple MR views from multiple local users. In this way, the VR world can be a more accurate reflection of the MR world and the real world seen by the multiple MR users. Object rendition in the VR world may be determined by a voting scheme or another prioritization scheme such that objects seen by multiple MR users are more likely to be shown in the VR world than objects seen by only one MR user.

In some examples, the VR participant may comprise a check on the work performed by a local MR physician. In this example, the VR participant may view and monitor a medical process performed by the local MR physician. The VR participant may communicate and provide verbal feedback to the local MR physician, while observing the views of the local MR physician in real time. This types of collaboration and safety checks by VR participants relative to the work of local MR physicians can be helpful for a positive patient outcome. Audio input may be provided by MR or VR users and all users may hear the audio input as though all users reside in the same room. This can provide more a more intimate experience for the patient and MR users relative to the presence of the VR user.

The level of control that is given to the remote VR participant may vary in different scenarios and settings. In some examples, the VR participant may be given a check on one or more steps of a procedure, such as a surgery. In this example, completion of a step of the procedure may be conditioned on the VR participant providing approval of completion of that step of the procedure. In this way, a local surgeon using MR may be guided and aided by the expertise of a remote physician using VR. In some examples, the MR system may require input from the remote physician using VR such that that the remote physician needs to approve the procedure or step performed locally by the local physician using MR. The remote physician using VR can watch the process in real time, provide feedback, and decide whether the process or step has been performed properly by the local surgeon.

In still other examples, an MR system may comprise local MR users at the location of the patient, and a remote observer may be able to view the MR environment via one or more remote display screens. In this case, the remote observer may be able to select the views of the local MR users, or possibly select views associated with stationary cameras in the location of the patient. In this way, a remote participant may be able to select different views and thereby gain an appreciation or understanding of the procedure. For example, the remote participant may comprise a physician, who may be consulted during the procedure. As another example, the remote participant may comprise a medical technician, such as a medical device technician, who may be consulted regarding information about the device or the implantation procedure. In general, "local" MR users may be users that are in viewable proximity to a patient or procedure, whereas "remote" users may be users that are not in viewable proximity to a patient or procedure. In some examples, the system can reduce the need for assistance from a medical device technician, and possibly make the attendance of the medical device technician unnecessary in some surgeries.

Figure 116:
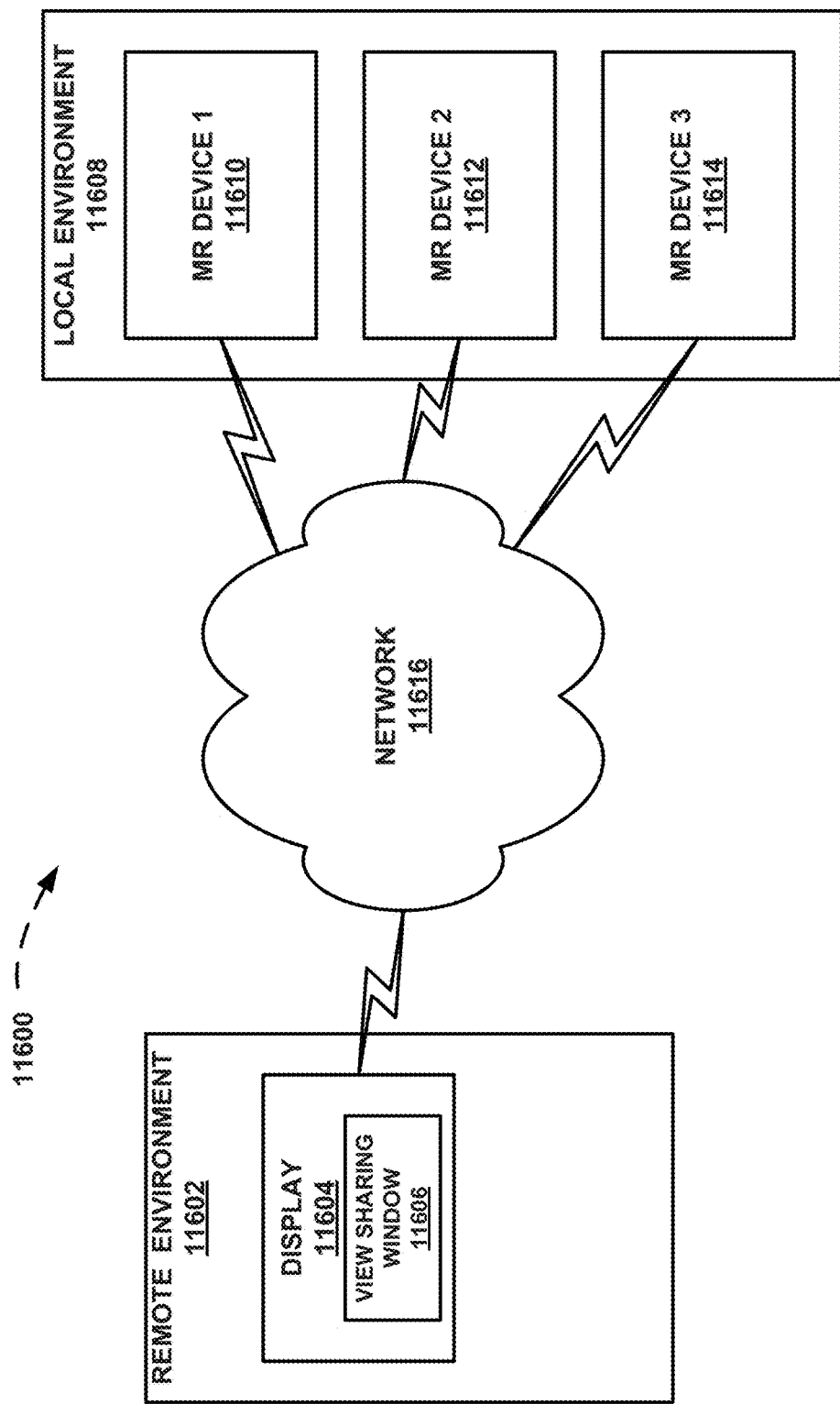
FIG. 116 is another block diagram illustrating an MR system that includes one or more users at a local environment that are in communication with one or more users in a remote environment.

FIG. 116 is another block diagram illustrating an MR system 11600 that includes one or more users at local environment 11608 that are in communication with one or more users in a remote environment 11602. The communication may occur over any type of network (e.g., shown as network 11616). In some examples, local environment 11508 may comprise an operating room. MR devices 1-3 (11610, 11612 and 11614) may correspond to users in the operating room, such as a physician, nurse, medical technician, anesthesiologist, or other users. In some examples, FIG. 116 may be considered an instance of the scenario of FIG. 18, in which multiple users may view the same MR intraoperative guidance content 1802.

As with the example of FIG. 115, in FIG. 116, local environment 11608 may be an environment where users are in viewable proximity to a patient, whereas remote environment 11602 may correspond to a location where users are not in viewable proximity to a patient. Since remote environment 11602 is not at the same location as local environment 11608, any user of system 11600 at remote environment 11502 may need access to views or data from the MR devices in local environment 11608.

As shown in FIG. 116, a user at remote environment 11602 may utilize a display 11604 configured to include a view sharing window 11606. Display 11604 and view sharing window 11606 may be controlled or driven by one or more processors (not shown). In any case, display 11604 is configured to present one or more of the views of MR devices in the local environment 11608 in view sharing window 11606. Although shown as a view sharing window (11404), the view sharing may be presented in other ways, such as display 11604 assuming the view of a selected one of the MR devices in local environment 11608. FIG. 116 generally shows how a remote participant could use view sharing without the need for virtual reality. Instead, remote environment 11602, in this example, may simply use one or more display screens to convey information from local environment 11608 to one or more users at remote environment 11602.

In another example, an MR system that includes both MR users and remote users (e.g., VR users or remote users that view one or more display screens) may be used to facilitate remote patient checkups. In this case, a remote user may be leveraged to assist an MR user with a local patient encounter via an MR system. For example, a nurse using MR may involve a remote physician using VR or remote display screens, to aid in a patient encounter. The MR environment may include a nurse and patient using MR, and a remotely located physician using VR (such as shown in FIG. 116) or display screens that display the MR views that are captured locally (such as shown in FIG. 116). In the case of the remote physician using VR (such as shown in FIG. 116), the patient may interact with the remote physician as though the physician was in the room with the nurse and patient. In such cases, the physician may leverage the MR views of the nurse in order to deliver medical advice to the patient.

In another yet example, an MR system that includes both MR and remote users (such as VR users or users that have display screens that display the MR views of others) may be used to facilitate emergency care. In this case, a remote user may be leveraged to assist an MR user with emergency care via an MR system. For example, an emergency medical technician (EMT) using MR may involve a remote physician (using VR or display screens that show local MR views) to aid in an emergency patient encounter. The physician may leverage the MR views of the EMT in order to deliver immediate medical diagnosis for the patient. The MR environment may include the EMT using MR and a remotely located physician using VR in order to give the perception that the remote physician is "in the field" for the emergency care.

As mentioned elsewhere in this disclosure, an MR system can include multiple visualization devices so that multiple users can simultaneously see the same images and share the same 3D scene, such as MR intraoperative guidance content 1802 (FIG. 18). In such examples, one of the visualization devices can be designated as the master device and the other visualization devices can be designated as observers. Any observer device can be re-designated as the master device at any time, as may be desired by the users of the MR system.

With any of the examples described herein, it may also be desirable to have one master device and many observer devices. Moreover, since assignment of the master device may change, the master role may be reassigned to different observers, essentially passing the master role among persons in the room. In one example of an orthopedic shoulder reconstruction surgery, one person may perform a drilling operation to pinpoint a location on a patient's glenoid bone, a different person may perform a reaming operation on the patient's glenoid bone, and then a third person may place an implant at the identified and reamed location of the patient's glenoid bone. In this example or other surgical examples with multiple participants, each person may be assigned as a master with regard to one or more steps of the medical procedure that they perform, and each person may be assigned as an observer with regard to the other steps, which are performed by others. In one example, the master may be allowed to voluntarily accept from or relinquish the master control over to the MR system. In another example, master control may be assigned or re-assigned automatically based on a specific master assignment procedure, such as a procedure that requires approval of two or more (or possibly a majority) of MR participants in order to change a specific user to be the master.

In yet another example, a local surgeon could perform surgical cuts, and another local or remote person (using VR) could perform one or more registration steps of the procedure, such as "SET," "ADJUST," and "MATCH" as described in this disclosure, e.g., for placement of MR objects in a field of view for registration with physical anatomical objects. In other words, registration of a 3D model may be performed locally by an expert as an MR participant or possibly even remotely by an expert as a VR participant. In these examples, the expert may be a medical device representative and the expert may be an MR or VR participant assigned to perform an initialization stage of a 3D model with real bone or tissue of the patient.

If the expert is a VR participant, the expert may view images from one or more of the MR participants in order to view real time images of the patient's bone structure relative to a 3D model that is superimposed on the patient's bone structure. The expert participant may use commands, hand gestures, gaze or other control mechanisms to orient the 3D model relative to the patient's bone structure shown to the remote physician as VR elements. The use of VR to accommodate a remote participant may allow for a more qualified physician to perform the initialization stage. Alternatively, the expert may be a local MR participant, in which case it may still be advantageous to assign an initialization process of a registration process to that expert. Then, after initialization, one of the MR or VR users may initiate an optimization algorithm, such as a minimization algorithm to more precisely match the 3D model with real bone of the patient. The ability to involve a remote expert to a surgical procedure may be especially helpful for complex multi-step surgical procedures, such as a shoulder arthroplasty, an ankle arthroplasty, or any other type of orthopedic surgery that requires one or more complex steps.

Computer-aided steps, in particular, may be well-suited for a remote physician, whereas physical steps (such as cutting, reaming, drilling or other steps) may need a physical presence by the physician. Initialization steps, for example, may be well-suited for remote execution by a VR participant or a local expert such as a medical device technician. In some examples, one or all of the virtual object registration steps, e.g., of "SET," "ADJUST," and "MATCH" as described in this disclosure, may be well-suited for remote execution by a VR participant or by a local participant that is an expert with the MR system or medical devices used in the procedure, such as a medical device technician.

Furthermore, as mentioned elsewhere in this disclosure, the images displayed on a UI of an MR system (e.g., UI 522 of FIG. 5) can be viewed outside or within the operating environment and, in spectator mode, can be viewed by multiple users outside and within the operating environment at the same time.

In some examples, an MR system, such as MR system 212, may support the ability to view share amongst MR devices worn by different participants within the operating room. Moreover, view sharing may also be implemented with one or more fixed cameras in the operating room, e.g., allowing a physician to have immediate and re-occurring access to a specific view of fixed cameras or other users. In this way, for example, a physician may be able to gain visual information very quickly, without needing to move around or change his or her view.

For example, the physician (or other user) involved in an orthopedic surgery may be presented with a mixed reality view from his or her perspective, but that user may be able to select and view the views of other persons (or fixed cameras) within the operating room. This can allow the physician to quickly gain other perspectives within the operating room. The views of other persons may comprise mixed reality views that include real objects and superimposed virtual objects as part of that user's mixed reality presentation. When the physician (or other user) selects the view of another person in the physician's mixed reality presentation, e.g., on visualization device 213, that view of the other person may be presented to the physician on the physician's MR device, e.g., as a display window or an entire view on the MR device.

A shared view may include one or more real objects and one or more virtual objects. The virtual objects shown in each user's MR visualization device 213 may differ since different users have different roles in the medical procedure, but when view sharing is implemented, the virtual objects of one user's view may be shared with other users. In this way, view sharing may allow for users to share unique MR presentations that include virtual elements that might otherwise not be viewable to a user if view sharing was not available.

For example, a nurse and a physician may be presented with different MR presentations, but when the physician selects the view of the nurse, the nurse's view may be presented to the physician and may include nurse-specific virtual elements that might otherwise not be presented in the physician's MR presentation. Accordingly, by presenting the views of other users, the physician may be able to gain different visual perspectives, different angles of view, and different virtual elements presented in the view.

When different users are presented with different MR presentations, the virtual elements presented to such users may differ. This allows the virtual elements seen by one user to be specific to that user, and allows the virtual elements seen by another user to be specific for that other user. Again, for example, physicians and nurses may be presented with different MR presentations that include virtual elements defined for the doctor and for the nurse. In some examples, view sharing may allow the physician to see the MR presentation of the nurse. Or in some examples, view sharing may be implemented on an element-by-element basis. That is to say, one or more virtual elements presented to the nurse may be enabled or disabled by the physician so that the physician is able to view selectively share with the nurse with respect to specific virtual elements.

For example, tool identification elements may be presented to the nurse in the nurse's MR presentation to aid the nurse with tool selection and tool tracking. Such tool identification elements (or other nurse specific elements) may be initially hidden from the physician. With object-specific view sharing, however, the physician may be able to enable or disable the virtual elements of the nurse on the physician's MR presentation. Accordingly, the physician (or other user) can be able to enable and disable virtual elements seen by other users so as to customize the MR presentation of that physician (or another MR user).

In some examples, an MR system may be used for preoperative, intraoperative or postoperative education purposes. The educational benefits may be provided to the patient, or in some cases, the educational benefits may be provided to third-party observers, such as medical students or other physicians. For example, an MR system may be used to provide education to a remote observer to the process. In this example, the remote observer may implement a VR device, such as described herein. Alternatively, the remote observer may merely have the ability to view MR feeds of local MR participants.

MR visualization devices may allow surgeons to view 3D content and visualize exactly what will happen, step-by-step, during a procedure. The step-by-step explanation may be virtual content provided to the MR visualization device used by the physician. Information provided to the physician may comprise general patient information based on information from the general patient population or may be patient-specific information associated with the specific patient on which a given procedure will be performed.

In some examples, an MR visualization device such as visualization device 213 can be configured to present a virtual person to the MR visualization device used by the physician, the patient, or another user, and the virtual person may explain one or more details about the surgery or other medical procedure to be performed. The virtual person may be an automated recording, or may comprise an actual physician, located remotely and operating with a remote VR device that interacts with MR visualization devices in the operating room. Videos or instructional queues may be selectable widgets to the user of MR visualization device, and such videos or instructional queues may be defined for different steps or stages of a medical procedure. This type of interactive and selectable real-time intraoperative instruction may be especially useful to aid surgeons that do not perform the procedure regularly, frequently, or on a higher volume basis.

In some examples, an MR visualization device (e.g., visualization device 213) may allow the physician to place virtual bone, virtual implants or other virtual elements on the patient for educational or planning purposes. For example, actual patient images or segmentations of the patient's bones or other physical features may be presented in AR, and virtual implants, jigs or other elements may be placed on the patient virtually by the physician. The virtual placement of implants or jigs relative to the patient may improve the sizing and selection of the implants or jigs or may facilitate or improve patient-specific implants or jigs that accommodate unique anatomical features of the patient.

The physician may view virtual 3D images of implants, jigs or other elements from different perspectives, and may manipulate the 3D images relative to images or segmentations of the patient using hand gestures, voice commands, gaze direction and/or other control inputs. For example, the physician may place a virtual representation of an implant or jig into an implantation location of the patient, e.g., in the patient's shoulder. Placement may involve setting and adjusting the virtual implant via "SET" and "ADJUST" techniques, e.g., as described elsewhere in this disclosure in relation to the example of MR-based intraoperative guidance for glenoid bone procedures. Once placed in an initialization process, a matching algorithm may be implemented to "MATCH" the implantation to the patient's anatomy via a computer algorithm, e.g., as described elsewhere in this disclosure in relation to the example of MR-based intraoperative guidance for glenoid bone procedures.

Moreover, as described elsewhere in this disclosure, virtual three-dimensional representations may be defined in the MR presentation to aid the physician with the procedure. The virtual 3D representations may illustrate a cutting axis relative to an anatomical element, such as a cutting axis on a humoral bone for shoulder reconstruction surgery. As another example, the virtual 3D representations may illustrate a reaming access relative to an anatomical element, such as a reaming axis relative to a patient's glenoid bone for shoulder reconstruction surgery. As yet another example, the three-dimensional representations may illustrate a drilling axis relative to an anatomical element. Of course, the virtual 3D representations may be defined by the surgical procedure being performed. In ankle surgery, for example, virtual 3D representations may include virtual elements presented relative to a virtual ankle model or a model of the talus and/or tibia.

As still another example, the three-dimensional representations may illustrate placement of a virtual jig relative to the anatomical element, and in this case, the three-dimensional representations may also illustrate an axis (e.g., a reaming axis) relative to the virtual jig. In these examples, the anatomical element may be a real bone of the patient, or it may comprise a 3D virtual representation of an anatomical feature of a patient that is generated based on one or more real images of the anatomical feature of the patient. The 3D virtual representation of an anatomical feature may be registered to the actual anatomical element of the patient, i.e., the real anatomy of the patient, so that it is shown as an overlay in an MR view of the actual, physical anatomical element. In this way, preoperative planning associated with the 3D virtual representation (e.g., cutting axes, reaming axes, drilling locations, virtual jigs, or other features) may be defined with regard to the 3D virtual representation so that when the 3D virtual representation is registered to the real anatomical feature of the patient, the preoperative planning features (e.g., cutting axes, reaming axes, drilling locations, virtual jigs, or other features) are also aligned properly with regard to the real anatomical feature of the patient.

In some examples, an MR system may allow for educational collaboration with a patient or with other medical professionals. The MR-based collaboration may occur during a preoperative meeting with the patient in order to explain the procedure to the patient with the aid of MR. The MR-based collaboration may use real patient imagery in combination with virtual representations of implants, jigs or other medical devices, in order to illustrate the details of the procedure to the patient.

In other examples, MR system may allow for postoperative case analysis. In this case, actual images of surgical results may be compared with images of other surgical results of other patients. As another example, actual images of surgical results may be compared with virtual images in order to provide for postoperative assessment. Postoperative collaboration, like the preoperative collaboration may be performed with the patient or with other medical professionals all participating in mixed reality with MR visualization devices or VR visualization devices like those described herein.

In still other examples, MR systems may allow for educational training during a medical procedure or surgery. That is to say, one or more passive viewers to the procedure may have passive MR visualization devices that provide the user with a view of the MR environment without any control over the MR environment. Such passive viewers may be located in the operating room, or in a viewing room adjacent the operating room, or remotely from the operating room. Alternatively, in some cases, a passive viewer may be located remotely, essentially viewing one or more of the MR presentations seen by persons in the operating room. Such passive viewing from a remote location without any presence or collaboration with members in the operating room may be used for training and educational purposes. Such an MR viewing tool may be very useful for use in either real time or delayed viewing of the procedure.

In some examples, an MR system may maintain a database of information associated with prior patients or prior surgeries, e.g., stored in a storage system of visualization device 213 or stored in a database (e.g., storage system 206 of FIG. 2) communicatively coupled to visualization device 213. In this case, the database of information may be used to identify situations or circumstances of a prior surgery or procedure that may impart knowledge or information germane to a current surgery or procedure. Particular parameters, such as patient measurements, anatomical feature sizes, shapes or anomalies, sizes of implants or jigs, or other parameters may be used for identifying similarities or matches between prior surgeries or procedures stored in the database and the current procedure.

In this way, an MR system can be used to help a physician identify case similarities between a current procedure associated with a current patient and past procedures performed on past patients. In some cases, an MR system may be configured to present surgical recommendations to the user physician (such as sizes and shapes of implants, types of implants, recommendations for anatomical or reverse anatomical procedures, or other types of recommendations). The recommendations, for example, may be defined by machine learning techniques that leverage the data stored in the database.

During intraoperative phase 306 (FIG. 3), a surgeon may perform an orthopedic surgery that follows a complex series of workflow steps, some or all of which may proceed according to prescribed sequence. Although surgeons are typically well trained to perform the steps of an orthopedic surgery, incidents may occur where one or more steps of the orthopedic surgery are accidentally omitted or performed in an incorrect manner. Moreover, incidents may occur where the surgeon remembers to perform a step of an orthopedic surgery, but misremembers how to perform one or more aspects the step, or would otherwise benefit from a reminder of how to perform the step or guidance about one or more aspects of the step, some of which may vary according to a specific surgical plan generated for a particular patient.

Such incidents could impact surgical procedure efficiency, surgical procedure efficacy or patient outcomes. Paper checklists may be used to remind surgeons and operating room (OR) staff to perform the steps of the surgery. However, there are numerous drawbacks to the use of paper checklists. For example, it might not be easy for a surgeon to see a paper checklist, especially when the surgeon is holding surgical tools. Moreover, because the surgeon must preserve sterility, it may be impossible for the surgeon to use her or his hands to mark off items in the paper checklist. Additionally, a paper checklist includes visual clutter regarding completed and upcoming steps and it may take the surgeon valuable time to process the paper checklist. Moreover, the visual clutter in the paper checklist may allow the surgeon to visually skip over a step of the surgery. Having a nurse maintain and read back the checklist to the surgeon may increase expenses because this approach may require a dedicated nurse to be present for this purpose. Furthermore, a paper checklist does not allow the surgeon to access any more information than the information that is provided on the paper itself.

Presenting a computerized version of a paper checklist on a computer screen in the OR may have many of the same problems as a conventional paper checklist. For example, presenting all steps of the surgery on the computer screen may result in visual clutter that may delay or confuse the surgeon, and may require the surgeon to look away from a surgical site. Moreover, a dedicated nurse may be required to control the checklist presented on the computer screen. Furthermore, although a computerized version of a paper checklist may, in principle, allow the surgeon to access more information during the surgery, the surgeon would have difficulty requesting the display of such information. For instance, because of the need to preserve sterility, the surgeon may be unable to use a mouse or keyboard to control the computer. The surgeon may be able to provide voice instructions to the computer or a nurse, but voice commands may be misinterpreted by computers and nurses, which may result in lost time, or may again require a dedicated nurse be available to control the computer just in case the surgeon wants the computer to display additional information.

An additional problem with checklists presented on computer screens is that the computer screens are frequently somewhat distant from the orthopedic surgeon during a surgery in order to ensure that the orthopedic surgeon and other healthcare professionals have adequate room to work around the patient. For instance, the computer monitors may be mounted to the walls of the operating room. However, this alone may cause certain problems for orthopedic surgeons. For instance, in one example, some orthopedic surgeons may wear magnifying loupe eyewear or standard corrective eyewear to help the surgeon better see the surgical site on the patient. However, since the surgical site on the patient is typically much closer to the orthopedic surgeon than the location where the computer monitor is located, the surgeon's eyewear may make it difficult to see the computer monitor that is at a further distance. In other words, the difference in focal distance between the surgical site and the computer monitor may be so great that the orthopedic surgeon cannot clearly see both the surgical site and the computer monitor when wearing (or without wearing) particular eyewear. Thus, the surgeon may need to remove or change the eyewear in order to see the computer monitor. Removing or changing eyewear may consume time and may introduce another potential vector for the spread of germs and other types of contamination.

This disclosure describes techniques that use extended reality (XR) to assist users (e.g., surgeons or other types of persons) through the workflow steps of orthopedic surgeries in a way that may address challenges such as those mentioned above. As described elsewhere in this disclosure, XR may include VR, MR, and AR. In examples where XR is used to assist a user through the workflow steps of an orthopedic surgery and XR takes the form of VR, the user may be performing a simulation of the orthopedic surgery or may be performing the orthopedic surgery remotely. In examples where XR is used to assist a user through workflow steps of an orthopedic surgery and XR takes the form of MR or AR, the surgeon may concurrently perceive real-world objects and virtual objects during the orthopedic surgery.

Figure 117:
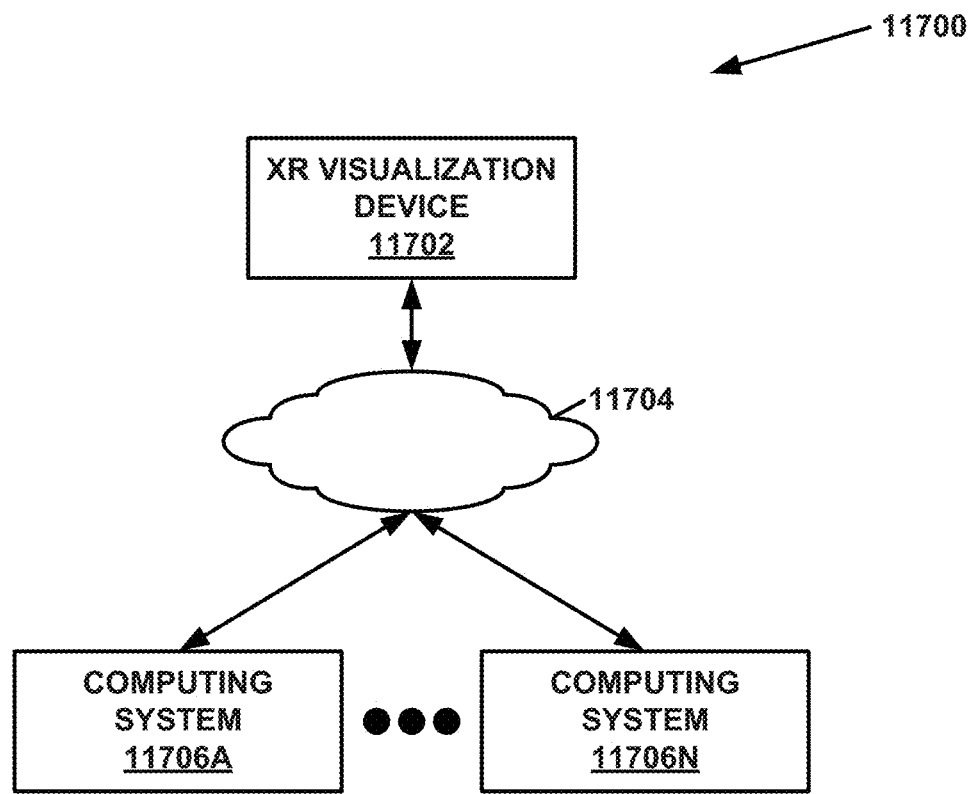
FIG. 117 is a block diagram illustrating an example system that may assist a user, such as a surgeon, nurse, or other medical technicians, through steps in the workflow steps of orthopedic surgeries, in accordance with a technique of this disclosure.

For instance, FIG. 117 is a block diagram illustrating an example system 11700 that may assist a user, such as a surgeon, nurse or other medical technician, through steps in the workflow steps of orthopedic surgeries, in accordance with a technique of this disclosure. In the example of FIG. 117, system 11700 includes an XR visualization device 11702, a communication network 11704, and one or more computing systems 11706A through 11706N (collectively, "computing systems 11706"). In other examples, system 11700 may include more, fewer, or different devices and systems.

Computing systems 11706 may include various types of computing devices, such as server computers, personal computers, smartphones, laptop computers, and other types of computing devices. For ease of explanation, this disclosure may describe actions performed by processing circuits, data storage systems, and communication interfaces of XR visualization device 11702 and computing systems 11706 as being performed by XR visualization device 11702 and computing systems 11706 as a whole. Communication network 11704 may include various types of networks, such as a local area network, the Internet, and/or other types of communication networks. Various computing systems of orthopedic surgical system 100 (FIG. 1) may include system 11700. For example, intraoperative guidance system 108 may include system 11700. In some examples, XR visualization device 11702 may be implemented as shown in the example of FIG. 5.

In the example of FIG. 117, XR visualization device 11702 may be worn by an orthopedic surgeon and may output an XR visualization for display. In some examples, XR visualization device 11702 is worn by another type of user (e.g., a nurse, medical technician, or other type of user) and may output the XR visualization for display. XR visualization device 11702 may access information about workflow steps of an orthopedic surgery from one or more of computing systems 11706. XR visualization devices substantially similar or identical to XR visualization device 11702 may be worn by other persons in a surgical operating room, such as one or more nurses, one or more medical technicians, or one or more additional surgeons, such that one or multiple persons may observe AR, MR and/or VR imagery providing guidance regarding workflow steps of an orthopedic surgery.

In an example, the XR visualization includes a set of one or more virtual checklist items. Each of the one or more virtual checklist items corresponds to an item in a checklist of steps of an orthopedic surgery (e.g., a shoulder arthroplasty, an ankle arthroplasty, or any other type of orthopedic surgery). The steps may be arranged in sequence according to an order in which the steps are to be performed or may be arranged topically into step topics according to physical or functional characteristics of the procedural steps. Furthermore, in this example, a camera or other sensor of XR visualization device 11702 may detect a command of the orthopedic surgeon or other user to select a virtual checklist item in the set of virtual checklist items. In some examples, one or more devices separate from XR visualization device 11702 may detect the command. For instance, one or more cameras, microphones, or other types of devices positioned in an operating room may detect the command. Nevertheless, for ease of explanation, this disclosure describes XR visualization device 11702 as detecting the command. However, discussion of XR visualization device 11702 detecting the command may apply to one or more other types of devices detecting the command. In response to detecting the contactless command, XR visualization device 11702 may update the XR visualization to include additional information regarding a step of the orthopedic surgery corresponding to the selected virtual checklist item.

In some examples, the command is a contactless command. The contactless command is performed without the orthopedic surgeon or other user touching any solid object. For example, the contactless command may be a hand gesture performed in the air. For instance, the contactless command may be a pinching gesture directed to a virtual element of the XR visualization. In some examples, the contactless command is a voice command.

In other examples, XR visualization device 11702 may detect a command that involves contact. For example, XR visualization device 11702 may detect a first command in the form of a hand gesture in which a user (e.g., the orthopedic surgeon or other type of user) taps one or more fingers of the user's left hand onto the back of the user's right hand. In this example, XR visualization device 11702 may detect a second commend in the form of a hand gesture in which the user taps one or more fingers of the user's right hand onto the back of the user's left hand. In another example, the user may tap on a surface (e.g., a sterilized surface), such as a corner of the operating table or a surgical item.

In examples where the command is a contactless command, because the orthopedic surgeon or other user is able to view the additional information without touching any solid object, there is no additional risk of contamination from the orthopedic surgeon or other user touching a physical computer user interface device, such as a mouse, keyboard or touchscreen. Similar considerations regarding reduction of risk of contamination may apply with contact-based commands on surfaces that are already sterilized, such as the surgeon's own hands or a sterilized surgical item. Additionally, in examples where the command (e.g., a contactless command) is a hand gesture, the use of the hand gesture to access the information may avoid the problems with voice commands discussed above, although voice commands also may be used in some examples. In this way, a computing system (e.g., XR visualization device 11702, one of computing system 11706, etc.) that handles the workflow checklist for the orthopedic surgery may be improved by decreasing the computing system's risk of acting as a vector for spreading contamination. Furthermore, because the virtual checklist items may be presented in an XR visualization in a focal plane that is relatively close to a focal plane of the surgical site, the orthopedic surgeon may not need to change or remove eyewear in order to see the virtual checklist items. Thus, in various examples, the techniques of this disclosure may improve the accessibility of the computing system, especially for orthopedic surgeons or other users with vision impairments and may enable the orthopedic surgeon or other users to skip steps otherwise needed to access the virtual checklist items, thereby improving efficiency of use of the computing system.

XR visualization device 11702 may present various virtual checklist items in the XR visualization. For example, the XR visualization may include virtual checklist items corresponding to a current step of the orthopedic surgery that the orthopedic surgeon is performing. In this example, the XR visualization may exclude virtual checklist items corresponding to completed steps of the orthopedic surgery. Furthermore, in some examples, the XR visualization may exclude virtual checklist items corresponding to one or more steps of the orthopedic surgery occurring after the current step of the orthopedic surgery. For instance, in one example, XR visualization device 11702 may exclude virtual checklist items corresponding to all steps of the orthopedic surgery occurring after the current step. In another example, the XR visualization may exclude checklist items corresponding to all steps of the orthopedic surgery except a next step of the orthopedic surgery. In some examples, the displayed set of virtual checklist items in the XR visualization is user configurable.

There are different steps for different orthopedic surgeries. For instance, the series of steps to perform a knee arthroplasty is different from the series of steps required to perform a reverse shoulder arthroplasty. In one example, the series of steps for a shoulder arthroplasty may include: an incision step, a step of severing the humeral head, a step of drilling a hole for a reaming guide pin, a step for performing a glenoid reaming process, a step for installing a glenoid implant, a step for preparing the humerus, a step for installing a humeral implant, and a step for closing the incision. In some examples, the steps may include nested sub-steps. In some examples, the series of steps may include the graft, humerus cut, install guide, glenoid reaming, and glenoid implant steps of FIG. 10. In some such examples, the next step of the orthopedic surgery may be a sub-step. Steps such as those described above may be presented as checklist items, e.g., using AR, MR, or VR visualization. Of course, the steps for ankle arthroplasty would also differ from those of other types of orthopedic surgeries, and virtual workflow guidance and virtual checklists may defined to guide and track the specific steps defined for a given type of ankle arthroplasty or other orthopedic surgical procedure.

Moreover, an orthopedic surgery may be customized to a particular patient. For example, an additional step of removing osteophytes may be required in a shoulder arthroplasty surgery for one patient but might not be required in the shoulder arthroplasty surgery of another patient. That fact that there may be variations within the same surgery for different patients may increase the mental load on surgeons and operating room personnel. Accordingly, the XR visualization may include virtual checklist items corresponding to patient-specific steps or sub-steps of the orthopedic surgery customized for the particular patient. Including virtual checklist items corresponding to patient-specific steps or sub-steps may be helpful in reminding surgical personnel of how the orthopedic surgery is to be performed for the individual patient.

The XR visualization may present various types of information in the virtual checklist items. For instance, in one example, a virtual checklist item in the XR visualization may include text identifying a corresponding step of the orthopedic surgery. In some examples, a virtual checklist item in the XR visualization may include an icon or other non-text graphic representing the corresponding step of the orthopedic surgery. In some examples, a virtual checklist item may specify which surgical items (e.g., tools, implants, etc.) to use in the corresponding step of the orthopedic surgery. The XR visualization may present the virtual checklist items according to various formats. For example, the XR visualization may present the virtual checklist items as a row or a column of items, each of which may contain text, icons, or other information. In some examples, the XR visualization may present the virtual checklist items in a 3-dimensional stack-of-cards format, where virtual checklist items are in different virtual cards that may be removed or added to the stack.

In some examples, the virtual checklist items may correspond to steps of the orthopedic surgery that are specific to an individual patient. In other words, a virtual checklist item may correspond to a step included in a version of an orthopedic surgery specific to a patient that is not included in a version of the orthopedic surgery of other patients. For example, in the example of the shoulder arthroplasty surgery provided above, the XR visualization may include a virtual checklist item that corresponds to a step of removing osteophytes during the surgery for a first patient but does not include this virtual checklist item in the surgery for a second patient who does not have osteophytes that need to be removed.

XR visualization device 11702 may present various types of additional information in the XR visualization. In one example, the additional information may include additional text describing a step of the orthopedic surgery. For instance, the additional information may include previously prepared notes by the orthopedic surgeon or other person. In some examples, the previously prepared notes may be specific to the patient on which the orthopedic surgeon is operating. For instance, the previously prepared notes specific to the patient may tell the orthopedic surgeon to install screws in a particular way so as to avoid cysts present at particular positions in a bone of a first patient. In this example, other patients may not have cysts at the same positions as the first patient. In some examples, the previously prepared notes may be common across patients but specific to an individual surgeon, hospital, care network, or other grouping. For instance, a surgeon may always want to have access to his or her personal notes regarding a particular step of the surgery.

In some examples, the additional information may include one or more virtual 3-dimensional objects associated with the step of the orthopedic surgery. In other words, XR visualization device 11702 may update the XR visualization to include one or more virtual 3-dimensional objects associated with the step of the orthopedic surgery. The 3-dimensional objects may include one or more virtual 3-dimensional models of bones involved with the step of the orthopedic surgery. For instance, in the context of a shoulder arthroplasty surgery described elsewhere in this disclosure, the 3-dimensional objects may include a 3-dimensional model of a patient's scapula. In this example, the XR visualization may include one or more virtual 3-dimensional objects that do not correspond to real-world objects. For instance, the virtual 3-dimensional objects may include a virtual reaming axis. The virtual 3-dimensional models shown in the XR visualization during the surgery may be the same as virtual 3-dimensional models shown during preoperative phase 302. Thus, an orthopedic surgeon or other user may already be familiar with the virtual 3-dimensional models because the orthopedic surgeon may have used the virtual 3-dimensional models during the preoperative planning phase. Thus, in some examples, the XR visualization may include virtual 3-dimensional models such as those shown in FIG. 15A, FIG. 15B, FIG. 15C, FIG. 15D, FIG. 16, FIG. 17, FIG. 27, FIG. 28, FIG. 29, FIG. 30, and so on. In some examples, one or more of the 3-dimensional models is specific to an individual patient undergoing surgery. In some examples, one or more of the 3-dimensional models is generic across patients.

In some examples, the XR visualization may also include virtual controls for controlling the virtual 3-dimensional objects. The orthopedic surgeon or other user may use contactless commands (e.g., hand gestures or voice commands) or contact-based commands to select the virtual controls. The virtual controls may allow the orthopedic surgeon or other user to hide or display individual virtual 3-dimensional objects, rotate the virtual 3-dimensional objects, scale the virtual 3-dimensional objects or otherwise control the virtual 3-dimensional objects. FIG. 13, described in detail elsewhere in this disclosure, is an example of an interface in a XR visualization that includes virtual controls for controlling the virtual 3-dimensional objects associated with a step of an orthopedic surgery. Particularly, FIG. 13 is an example of an interface in a XR visualization that includes virtual controls for controlling the virtual 3-dimensional objects associated with a glenoid reaming step of a shoulder arthroplasty surgery. In some examples, XR visualization device 11702 may update the XR visualization to rotate or scale the one or more virtual 3-dimensional objects in response to a command from the orthopedic surgeon or other user. In some such examples, the command may be a contactless command, such as a hand gesture or a voice command.

Furthermore, in some examples, XR visualization device 11702 may update the XR visualization to show to the orthopedic surgeon or other user an animation of the step of the orthopedic surgery as applied to the one or more virtual 3-dimensional objects. The animation may show progressive movement of one or more virtual 3D objects, such as tools or implants, from initial positions, to intermediate positions, and to final positions to represent the operations needed to complete the step in the procedure. For example, in the context of a shoulder arthroplasty, the XR visualization may show an animation of how to perform a step of cutting a humeral head. This may help the orthopedic surgeon or other user remember how to perform a step of the orthopedic surgery, or how to perform the step in a particular way in accordance with a patient-specific surgical plan. In some examples, the animation is specific to an individual patient. In some examples, the animation is generic across a set of patients.

In some examples, XR visualization device 11702 may detect a command (e.g., a contactless command or contact-based command) from the orthopedic surgeon or other user to mark the step of the orthopedic surgery complete. In examples where the command is a contactless command, the contactless command may be a hand gesture or a voice command. Marking a step as complete may comprise storing data (e.g., by one of computing systems 11706) indicating that the step is complete. Furthermore, based on the command, XR visualization device 11702 may update the XR visualization to include a virtual checklist item corresponding to a next step in the checklist of steps of the orthopedic surgery. For instance, XR visualization device 11702 may update the XR visualization to mark the current step of the orthopedic surgery complete in response to detecting the command from the orthopedic surgeon.

In some examples, one or more of computing systems 11706 may display virtual checklist items to one or more persons other than the orthopedic surgeon. For instance, an XR visualization device or computer may display the same virtual checklist items that XR visualization device 11702 displays to the orthopedic surgeon. This may allow the other person to track the progress of the surgery. Such other persons may include nurses, product representatives, students, other surgeons, and so on. Techniques for intraoperative collaboration and education are described elsewhere in this disclosure.

In some examples, a person other than the surgeon may be involved in marking a step of the orthopedic surgery complete. For example, in response to detecting a command from the orthopedic surgeon to mark a step of the orthopedic surgery complete, a computing device (e.g., one of computing systems 11706) associated with a second person may prompt the second person to confirm that the step of the orthopedic surgery is complete. In this example, the computing device associated with the second person is communicatively coupled to the XR visualization device (e.g., an MR or VR visualization device). Thus, operating room staff (e.g., surgeons, nurses, etc.) may communicate with and/or consult with remote users who may be able to view virtual checklist items.

For instance, the computing device associated with the second person may be a XR visualization device worn by the second person, a smartphone of the second person, a computer used by the second person and so on. The computing device associated with the second person may be communicatively coupled to the XR visualization device via communication network 11704. In some examples, one or more other computing devices (e.g., other ones of computing systems 11706) may process information from XR visualization device 11702 or other devices to generate information sent to the computing device associated with the second person. Receiving such information may cause the computing device associated with the second person to generate the prompt.

In this example, as part of updating the XR visualization to include the virtual checklist item corresponding to the next step in the checklist of steps of the orthopedic surgery, XR visualization device 11702 may update the XR visualization to include the virtual checklist item corresponding to the next step in the checklist of steps of the orthopedic surgery in response to the second person confirming that the step of the orthopedic surgery is actually complete. In this way, the second person has the opportunity to verify that the step of the orthopedic surgery is actually complete. This may help prevent the accidental skipping of steps of the surgical procedure and/or ensure that steps are performed according to general standards of care or patient-specific requirements. In other examples, a person other than the orthopedic surgeon may make the initial command to mark a step of the orthopedic surgery complete and the surgeon or other person may confirm that the step is actually complete.

In some examples, to enable the second person to verify that a step is complete, the computing device associated with the second person may display a video feed from a camera that is positioned to see the surgical site. For instance, in one example, the camera is integrated into XR visualization device 11702 worn by the orthopedic surgeon. In another example, the camera is mounted to a frame or wall of the operating room.

In some examples, one of computing systems 11706 may control various surgical tools based on which step of the surgical procedure is the current step of the surgical procedure. For example, the computing system may disable a particular tool if the tool is not supposed to be used during the current step. For instance, in the context of a shoulder arthroplasty surgery, the computing system may disable a reaming drill during a step of cutting the patient's humeral head if the reaming drill should not be used during the step of cutting the patient's humeral head. This may help prevent the surgeon from skipping a step of the orthopedic surgery. To control which surgical tools may be used with a particular step, computing system 11706 may access a predefined list of surgical tools that may be used in particular steps of the surgical procedure.

In some examples, the workflow management process described herein may guide a process for helping a nurse provide the correct tools to the surgeon, as described elsewhere in this disclosure. For instance, a virtual object in an XR visualization presented to the nurse may indicate to the nurse which tools to provide to the surgeon for the next step of the orthopedic surgery. In another example, lights built into the surgical tools or trays may indicate to the nurse which tools are to be used in the next step of the orthopedic surgery. Such examples are described in greater detail elsewhere in this disclosure.

In some examples, a computing system (e.g., one of computing systems 11706) outputs checklist items for display to a nurse or other individual. In some such examples, rather than XR visualization device 11702 detecting a command to mark a step of the orthopedic surgery complete, the computing system may mark the step of the orthopedic surgery complete when the nurse uses a device of the computing system to optically scan a code (e.g., a bar code) of a surgical item (e.g., surgical tool, implant, box of surgical items, etc.) used in the next step of the orthopedic surgery. This may have the combined effect of advancing the checklist and updating an inventory of available surgical items. In this example, the computing system may warn the nurse if the nurse did not scan the expected surgical item for a next step of the orthopedic surgery.

In some examples, a computing system in system 11700 may record surgical notes and automatically associate the surgical notes with steps of the orthopedic surgery. For instance, the surgeon may dictate notes during the course of the orthopedic surgery. In this example, a microphone of XR visualization device 11702 or one of the computing systems 11706 may detect and record the surgeon's voice. One of computing systems 11706 may store (and in some examples transcribe) the spoken notes. In some examples, a nurse may transcribe the notes dictated by the surgeon. Additionally, the computing system may associate the notes dictated while a particular step of the orthopedic surgery is the current step with the particular step. In other words, notes dictated during the surgery may be associated with the steps of the surgery in which the notes were dictated. Thus, the notes for particular steps of the orthopedic surgery may be retrieved based on the steps of the orthopedic surgery.

Similarly, in some examples, one or more computing systems 11706 may automatically associate portions of a video of the surgery with the corresponding step of the surgery. This may allow users to quickly jump to portions of the video corresponding to steps of the surgery that are of interest to the users.

Figure 118:
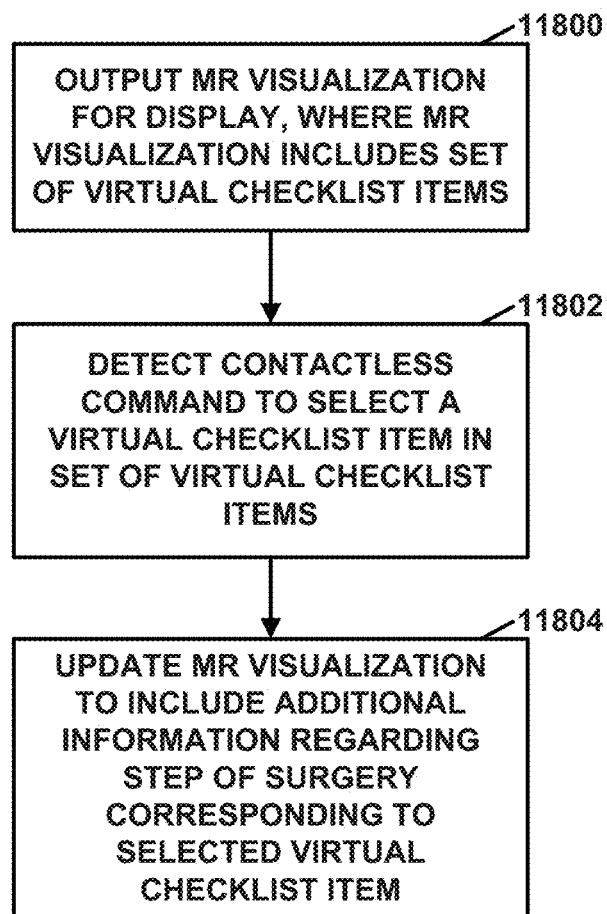
FIG. 118 is a flowchart illustrating an example operation to assist users, such as surgeons, nurses, or other medical technicians, through steps in the workflows of orthopedic surgeries, in accordance with a technique of this disclosure.

FIG. 118 is a flowchart illustrating an example operation to assist users, such as surgeons, nurses, or other medical technicians, through steps in the workflows of orthopedic surgeries, in accordance with a technique of this disclosure. In the example of FIG. 118, a XR visualization device 11702 worn by an orthopedic surgeon may output a XR visualization for display (11800). The XR visualization includes a set of one or more virtual checklist items. Each of the one or more virtual checklist items corresponds to an item in a checklist of steps of an orthopedic surgery, such as ankle arthroplasty or shoulder arthroplasty.

Furthermore, XR visualization device 11702 may detect a contactless command (e.g., a hand gesture or voice command) of the orthopedic surgeon to select a virtual checklist item in the set of virtual checklist items (11802). The contactless command is performed without the orthopedic surgeon touching any solid object and may be detected by a camera, microphone, or other sensor associated with XR visualization device 11702 worn by the surgeon, an XR visualization device worn by other person in the operating room, or another sensor not carried by an XR visualization device. Furthermore, in response to detecting the contactless command, XR visualization device 11702 may update the XR visualization to include additional information regarding a step of the orthopedic surgery corresponding to the selected virtual checklist item (11804).

In some examples, XR visualization device 11702 is a MR visualization device or AR visualization device that the orthopedic surgeon wears or otherwise uses during surgery. In some examples, XR visualization device 11702 is a VR visualization device. In such examples, the orthopedic surgeon may use the VR visualization device to perform a simulation of the orthopedic surgery. During such a simulation, it may be helpful to the orthopedic surgeon to see the virtual checklist items in the same way that the orthopedic surgeon would see the virtual checklist items in a MR visualization device or an AR visualization device.

Figure 119:
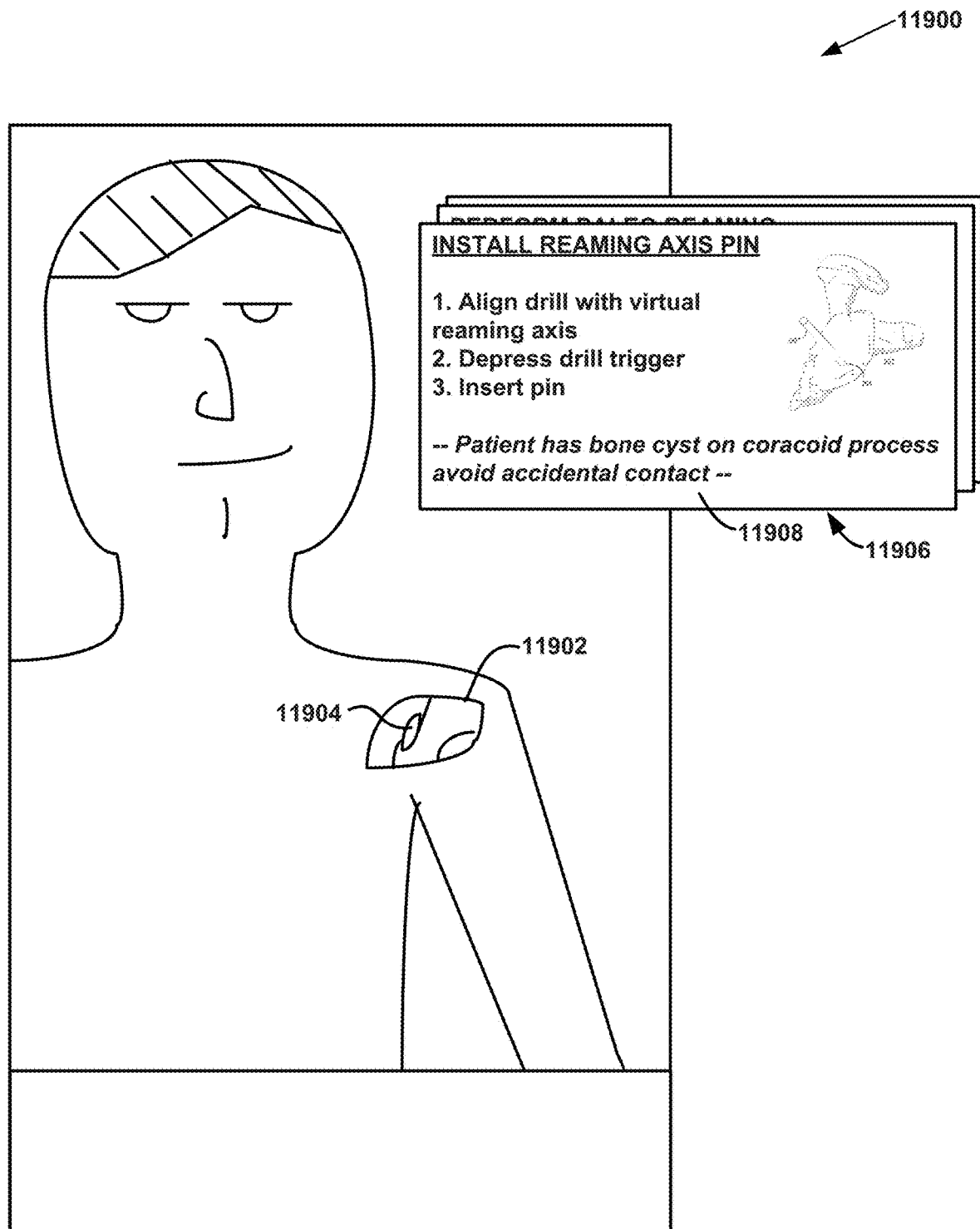
FIG. 119 is a conceptual diagram illustrating an example XR visualization that includes a set of one or more virtual checklist items, as viewed by a user, such as an orthopedic surgeon, nurse, or other medical technician, while performing an orthopedic surgery on a shoulder of a patient.

FIG. 119 is a conceptual diagram illustrating an example XR visualization 11900 that includes a set of one or more virtual checklist items, as viewed by a user, such as an orthopedic surgeon, nurse, or other medical technician, while performing an orthopedic surgery on a shoulder of a patient. In the example of FIG. 119, the patient is lying on an operating table and the orthopedic surgeon is viewing the patient from above. The orthopedic surgeon has already made an incision 11902 in the patient's shoulder and exposed a glenoid surface 11904.

In accordance with a technique of this disclosure, XR visualization 11900 includes a set of virtual checklist items 11906. Virtual checklist items 11906 correspond to items in a checklist of steps of the orthopedic surgery that the orthopedic surgeon is performing on the patient. In the example of FIG. 119, virtual checklist items 11906 are presented in the form of a stack of virtual cards, each corresponding to a step (or sub-step) of the orthopedic surgery. In other examples, one or more virtual checklist items 11906 may be presented in an XR visualization in a column form. In some examples, one or more virtual checklist items 11906 are in a row form, similar to the arrangement of selectable buttons 1002 in FIG. 10.

A virtual checklist item 11908 includes text describing a step of the orthopedic surgery and a graphic corresponding to the step. In particular, virtual checklist item 11908 includes text describing a step for installing a reaming guide pin. Furthermore, as shown in the example of FIG. 119, virtual checklist item 11908 includes patient-specific content, namely that the patient has a bone cyst on a coracoid process and to avoid accidental contact. Such patient-specific content would not be present for all patients. In some examples, virtual checklist item 11908 may include one or more warnings associated with the current step. For instance, a virtual checklist item associated with a step of installing fixation screws 16102A and 16102B of FIG. 161 may include a textual or graphical warning against over torquing fixation screws 16102A and 16102B.

As described elsewhere in this disclosure, a surgical plan may be developed for an orthopedic surgery during preoperative phase 302 (FIG. 3). For instance, the surgical plan may be developed using the BLUEPRINT™ system. However, a surgeon may deviate from the surgical plan when performing the orthopedic surgery. In other words, the surgeon's actions during intraoperative phase 306 (FIG. 3) may be different from the actions set forth in the surgical plan defined during preoperative phase 302 (FIG. 3).

There are many reasons why a surgeon may deviate from the surgical plan. For example, the surgical plan developed during preoperative phase 302 may be based on incorrect estimations or assumptions regarding the anatomy of the patient. For instance, in one example, the surgical plan developed during preoperative phase 302 may be based on incorrect estimates of the positions or sizes of osteophytes.

In another example of why a surgeon may deviate from the surgical plan developed during preoperative phase 302, the surgical plan may be based on incorrect estimates of the patient's pathology. For instance, the surgeon may discover upon opening the patient's shoulder joint that a level of glenoid erosion in the patient's shoulder joint is consistent with a different category in the Walch glenohumeral osteoarthritis classification system than was understood from previous imaging of the patient's shoulder joint. In the case of a shoulder repair surgery, an incorrect estimate of the patient's pathology may require the surgeon to perform a reverse shoulder arthroplasty instead of a standard anatomic shoulder arthroplasty, or vice versa.

In another example of why a surgeon may deviate from the surgical plan developed during preoperative phase 302, the surgical plan may be based on incorrect estimates of bone density. For instance, in this example, if bone density is too low in a particular area of a bone, such as the humerus or scapula, the bone may not be able to adequately support an implant, such as the implant type planned during preoperative phase 302. The bone may fracture if the bone is not able to adequately support the implant or it may be impossible to securely mount the implant onto the bone. As a result, the surgeon may be compelled to cut, drill, or ream the bone in a manner that differs from the surgical plan to improve the seating of the implant, or use a different implant type. For instance, in one example, the initial surgical plan may call for the use of a stemless humeral implant, but if the bone density of the humerus is too low in certain areas, the surgeon may want to switch to a stemmed humeral implant.

In other examples of why a surgeon may deviate from the surgical plan developed during the preoperative phase 302, the surgeon may simply realize that there were errors in the surgical plan. The surgeon may also deviate from the surgical plan inadvertently. For example, the surgeon may cut a bone at an angle that differs somewhat from the angle indicated by the surgical plan. For instance, the surgeon may cut away too much of the humeral head. In some instances, different angles of a cut may result in different potential ranges of motion if not compensated for by using different implants.

In accordance with a technique of this disclosure, a computing system may obtain an information model specifying a first surgical plan, which may be a preoperatively-defined surgical plan. The computing system may modify the first surgical plan during intraoperative phase 306 of an orthopedic surgery to generate a second surgical plan (FIG. 3). Furthermore, in accordance with a technique of this disclosure, an XR system may present an XR visualization for display that is based on the second surgical plan. This may allow the surgeon to start using XR visualizations to help the surgeon execute the second surgical plan.

Figure 120:
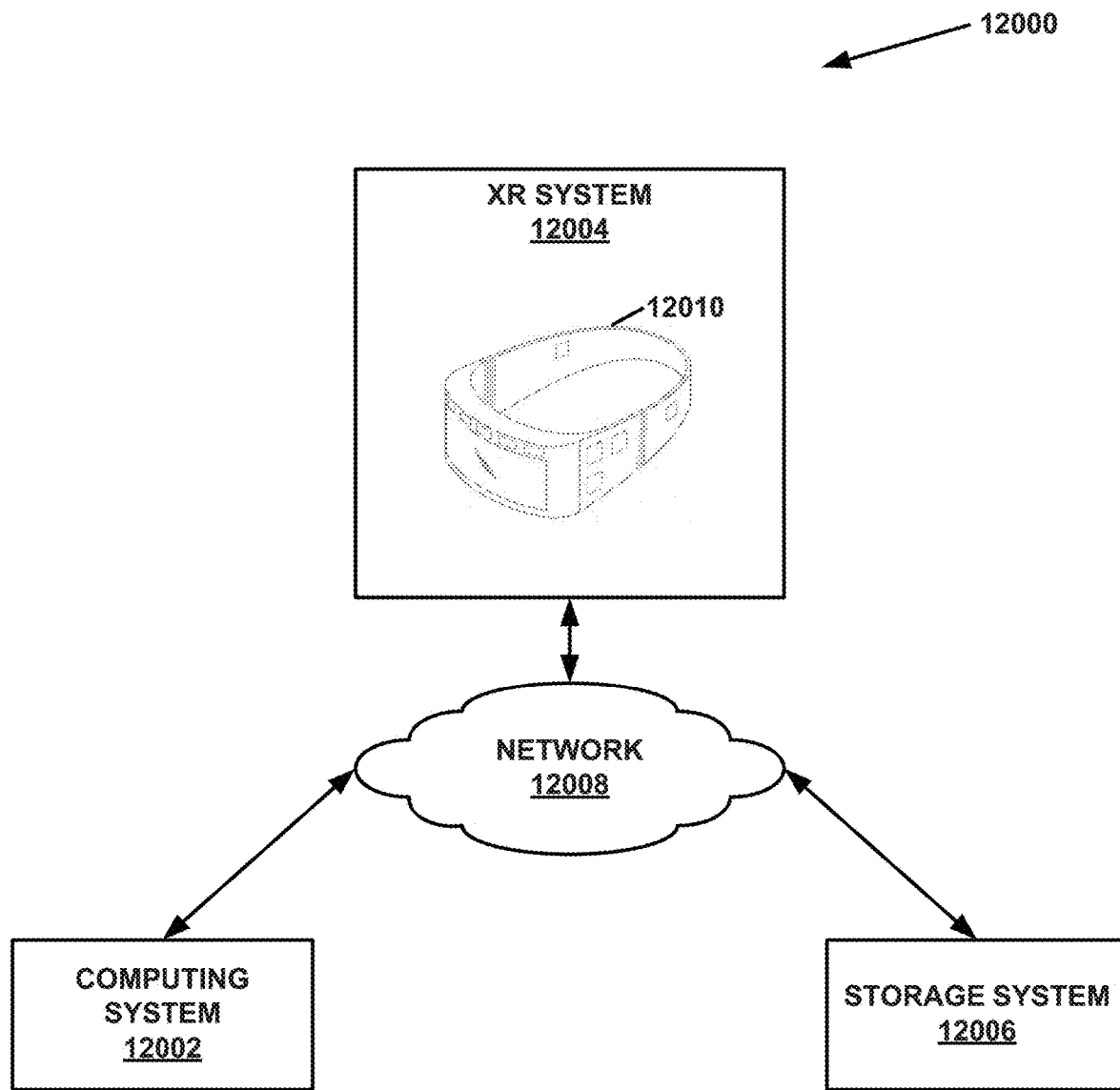
FIG. 120 is a conceptual diagram illustrating an example system in which a first surgical plan is modified during an intraoperative phase to generate a second surgical plan, in accordance with a technique of this disclosure.

FIG. 120 is a conceptual diagram illustrating an example system 12000 in which a first surgical plan is modified during intraoperative phase 306 to generate a second surgical plan, in accordance with a technique of this disclosure. System 12000 includes a computing system 12002, an XR system 12004, a storage system 12006, and a network 12008. In the example of FIG. 120, XR system 12004 includes a visualization device 12010. Similar to MR system 212 of FIG. 2, XR system 12004 may also include other components, such as one or more processors and storage devices separate from visualization device 12010. As shown in the example of FIG. 120, visualization device 12010 may be a head-mounted visualization device. In other examples, visualization device 12010 may be a holographic projector or other type of device that enables a user to visualize an MR visualization. In some examples, the functions of computing system 12002 are performed by one or more processors included in visualization device 12010 or XR system 12004. In other examples, some or all functions of computing system 12002 are performed by processors external to visualization device 12010.

As discussed elsewhere in this disclosure, computing system 12002 may comprise one or more computing devices operating as a system. In some examples, computing system 12002 is part of virtual planning system 102 (FIG. 1) or intraoperative guidance system 108 (FIG. 1). Computing system 12002 may obtain an information model that describes a surgical plan. For example, computing system 12002 may generate the information model e.g., using surgical planning software, such as BLUEPRINT™. In some examples, computing system 12002 may obtain the information model from a computer readable medium, such as a communication medium or non-transitory computer-readable medium. Storage system 12006 may store the information model.

Figure 121:
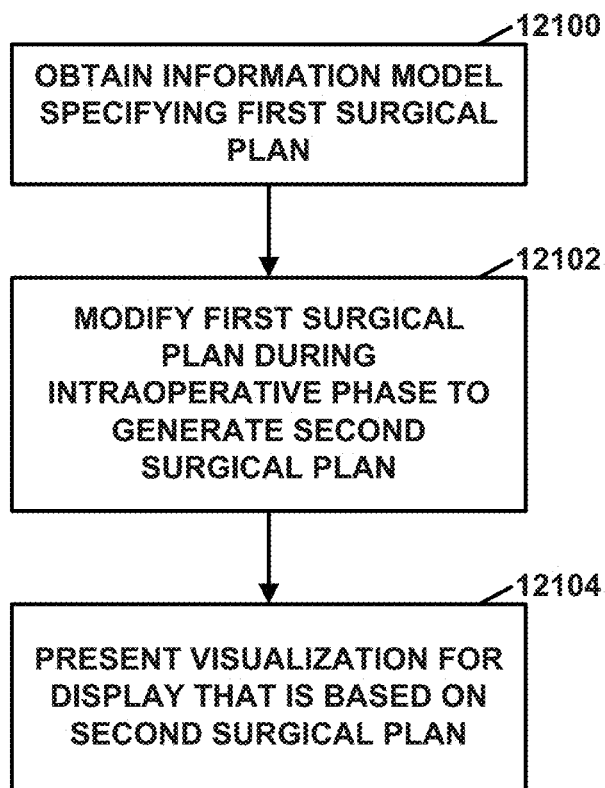
FIG. 121 is a flowchart of an example operation in which a first surgical plan is modified during an intraoperative phase to generate a second surgical plan, in accordance with a technique of this disclosure.

FIG. 121 is a flowchart of an example operation in which a first surgical plan is modified during intraoperative phase 306 to generate a second surgical plan, in accordance with a technique of this disclosure. In the example of FIG. 121, computing system 12002 may obtain an information model specifying a first surgical plan for an orthopedic surgery to be performed on a patient (12100). For instance, computing system 12002 may generate or receive the first surgical plan as described elsewhere in this disclosure. Furthermore, in the example of FIG. 121, computing system 12002 may modify the first surgical plan during intraoperative phase 306 (FIG. 3) of the orthopedic surgery to generate a second surgical plan (12102). Visualization device 12010 may present, during intraoperative phase 306 of the orthopedic surgery, a visualization for display that is based on the second surgical plan (12104). The visualization may be an XR visualization, such as an MR visualization or a VR visualization.

In some examples, the first surgical plan is a preoperatively-defined surgical plan for the orthopedic surgery to be performed on the patient. In other words, the first surgical plan may be defined during preoperative phase 302 (FIG. 3). In some examples, the first surgical plan is an intraoperatively-defined surgical plan for the orthopedic surgery to be performed on the patient. For instance, in one example, a preoperatively-defined surgical plan may have been modified during the course of the orthopedic surgery to generate the first surgical plan, which may be further modified to generate the second surgical plan.

The first surgical plan may differ from the second surgical plan in various ways. For example, the first surgical plan may specify use of a first surgical item, such as a surgical tool or implant. In this example, computing system 12002 may modify the first surgical plan such that the second surgical plan specifies use of a second surgical item instead of the first surgical item. In this example, the second surgical item is different from the first surgical item. For instance, the first surgical item and the second surgical item may be different sizes of the same type of item or may be different types of items altogether. For instance, the first surgical item may be a stemless humeral implant and the second surgical item may be a stemmed humeral implant, or vice versa. In some examples, the first surgical plan may differ from the second surgical plan with respect to a cutting angle or position (e.g., a cutting angle or position of a resection of the humeral head).

In some examples, the first surgical plan may specify performance of a first type of surgery. In this example, computing system 12002 may modify the first surgical plan such that the second surgical plan specifies a second type of surgery that is different from the first type of surgery. For instance, the first type of surgery and the second type of surgery may be different ones of: a stemless standard total shoulder arthroplasty, a stemmed standard total shoulder arthroplasty, a stemless reverse shoulder arthroplasty, a stemmed reverse shoulder arthroplasty, an augmented glenoid standard total shoulder arthroplasty, or an augmented glenoid reverse shoulder arthroplasty. In other examples, the first type of surgery and the second type of surgery may be different types of ankle surgery or other types of joint surgery. Although techniques are described with reference to shoulder surgical procedures, similar interoperative changes to the surgical plan may also occur with regard to other types of orthopedic surgical procedures, such as for an ankle arthroplasty procedure.

In some examples where the orthopedic surgery is a shoulder repair surgery, the first surgical plan may specify a first reaming axis on a glenoid of the patient. In this example, the second surgical plan may specify a second reaming axis on the glenoid of the patient different from the first reaming axis. For instance, the first reaming axis and the second reaming axis may have different parameters, such as angles, entry points, and so on. In some examples where the orthopedic surgery is a shoulder repair surgery, the first surgical plan may specify a first reaming depth on a glenoid of the patient. In this example, the second surgical plan may specify a second reaming depth on the glenoid of the patient different from the first reaming depth.

Furthermore, in some examples where the orthopedic surgery is a shoulder repair surgery, the first surgical plan may specify a first humerus cut depth and the second surgical plan may specify a second humerus cut depth different from the first humerus cut depth. In some examples where the orthopedic surgery is a shoulder repair surgery, the first surgical plan specifies a first humerus cut angle and the second surgical plan specifies a second humerus cut angle different from the first humerus cut angle.

In some examples, the first surgical plan may specify a first implant position and the second surgical plan specifies a second implant position different from the first implant position. For instance, in one example, the first implant position and the second implant position may be different positions at which to mount an implant to a bone. In another example, the first implant position and the second implant position may be different depths of a stem of the implant, such as a humeral implant.

Computing system 12002 may perform various actions to determine whether and how to modify the first surgical plan to generate the second surgical plan. For example, computing system 12002 may generate, based on the first surgical plan, a planned depth map that represents a 3-dimensional shape that a surface of a bone of the patient will have after performance of a step of the orthopedic surgery if the step of the orthopedic surgery is performed according to the first surgical plan. Furthermore, computing system 12002 may generate a realized depth map that represents a 3-dimensional shape of the surface of the bone of the patient after a surgeon has actually performed the step of the orthopedic surgery. In this example, computing system 12002 may use information provided by one or more depth cameras (e.g., depth camera(s) 532 (FIG. 5)) of visualization device 12010 to generate the depth maps (e.g., the realized depth maps). Computing system 12002 may determine differences between the realized depth map and the planned depth map. For instance, computing system 12002 may determine differences in angles or depths between the realized depth map and the planned depth map. Computing system 12002 may generate the second surgical plan based on the determined differences between the realized depth map and the planned depth map. For instance, computing system 12002 may determine that different type of surgery or different surgical item may be preferable given the differences between the realized depth map and the planned depth map. In some examples, computing system 12002 uses markers (e.g., marker 3010 of FIG. 30) to determine depths and orientations of objects, such as bones and surgical tools.

In some examples, the orthopedic surgery is a shoulder repair surgery that includes a step of severing a humeral head (e.g., resecting a humeral head) with an oscillating saw tool. In such examples, a planned cut plane is a plane along which the oscillating saw tool will cut the humeral head if the step of the step of severing the humeral head is performed according to the first surgical plan. Furthermore, in this example, a realized cut plane is a plane along which the oscillating saw tool actually cut the humeral head during performance of the step of severing the humeral head. In this example, computing system 12002 may determine differences between the planned cut plane and the realized cut plane. In addition, computing system 12002 may generate the second surgical plan based on the determined differences between the realized cut plane and the planned cut plane.

In some examples where the orthopedic surgery is a shoulder repair surgery that includes a step of severing a humeral head with an oscillating saw tool, computing system 12002 may generate a depth map that represents 3-dimensional shapes within a scene that includes the humeral head and the oscillating saw tool. In such examples, computing system 12002 may determine the realized cut plane based on the depth map. In some examples, a marker is fixed to the oscillating saw tool and computing system 12002 determines the realized cut plane based on video images (e.g., RGB images) of the marker captured during performance of the step of severing the humeral head.

Furthermore, in one example where the orthopedic surgery is a shoulder repair surgery that includes a step of severing a humeral head with an oscillating saw tool, the first surgical plan specifies use of a first humeral implant. In this example, computing system 12002 may determine, based on the realized cut plane, a first range of motion that would result from using the first humeral implant. Additionally, computing system 12002 may determine that use of a second humeral implant would result in a second range of motion instead of the first range of motion given the realized cut plane, where the second humeral implant is different from the first humeral implant. In this example, computing system 12002 may determine the first range of motion using a database of case studies that maps realized cut planes to ranges of motion, using a mathematical model, or based on other algorithms. Furthermore, in this example, computing system 12002 may generate the second surgical plan such that the second surgical plan specifies use of the second humeral implant instead of the first humeral implant.

In some examples where the orthopedic surgery is a shoulder repair surgery that includes a step of reaming a glenoid of the patient with a reaming tool, a planned reaming depth is a depth to which the reaming tool will ream the glenoid if the step of reaming the glenoid is performed according to the first surgical plan. In such examples, a realized reaming depth is a depth to which the reaming tool actually reamed the glenoid during performance of the step of reaming the glenoid. In one such example, computing system 12002 may determine differences between the planned reaming depth and the realized reaming depth. Furthermore, in this example, computing system 12002 may generate the second surgical plan based on the determined differences between the realized reaming depth and the planned reaming depth.

Furthermore, in one example where the orthopedic surgery is a shoulder repair surgery that includes a step of reaming the glenoid of the patient, computing system 12002 may generate a depth map that represents 3-dimensional shapes within a scene that includes the glenoid and the reaming tool. In this example, computing system 12002 may determine the realized reaming depth based on the depth map. For instance, computing system 12002 may use the depth values in the depth map that correspond to the glenoid after reaming to determine how deeply the glenoid was reamed. In some examples, a first marker is fixed to the reaming tool and a second marker is fixed to a scapula that has the glenoid. In such examples, computing system 12002 may determine the realized reaming depth based on video images of the first marker and the second marker captured during performance of the step of reaming the glenoid.

Furthermore, in one example where the orthopedic surgery is a shoulder repair surgery that includes a step of reaming the glenoid, the first surgical plan may specify use of a first glenoid implant. In this example, computing system 12002 may determine, based on the realized reaming depth, a first range of motion that would result from using the first glenoid implant. Additionally, in this example, computing system 12002 may determine that use of a second glenoid implant would result in a second range of motion instead of the first range of motion given the realized reaming depth, where the second glenoid implant is different from the first glenoid implant. Computing system 12002 may determine the ranges of motion in accordance with any of the examples provided elsewhere in this disclosure for determining ranges of motion. Furthermore, computing system 12002 may generate the second surgical plan such that the second surgical plan specifies use of the second glenoid implant instead of the first glenoid implant. In some examples, the second range of motion is greater than the first range of motion.

As mentioned above, visualization device 12010 may present an XR visualization based on the second surgical plan. The XR visualization based on the second surgical plan may include various types of content, such as any of the intraoperative MR content described elsewhere in this disclosure. For instance, the XR visualization may comprise one or more virtual checklist items corresponding to items in a checklist of steps of the orthopedic surgery that conforms to the second surgical plan. In examples where the visualization is an MR visualization, the MR visualization may include virtual checklist items and also include images of real-world objects. In such examples, the images of the real-worlds objects may be the images of the patient and operating room as seen by the surgeon through a see-through holographic lens of visualization device 12010 or as seen by the surgeon on a screen of visualization device 12010.

In some examples, system 12000 may enable a surgeon to assess the consequences of deviating from a surgical plan before the surgeon deviates from the surgical plan. For example, the surgeon may want to assess what the consequences would be of using a different cutting angle or depth, different reaming depth, or different surgical item than specified in the surgical plan e.g., because the surgeon has discovered certain osteophytes, different bone density than expected, or other factors. In some examples where system 12000 enables the surgeon to assess the consequences of deviating from the surgical plan, computing system 12002 may generate, during intraoperative phase 306 (FIG. 3), a modified surgical plan based on a proposed deviation from the surgical plan. The surgeon may then have the opportunity to review the modified surgical plan intraoperatively. For instance, visualization device 12010 may present an XR visualization based on the modified surgical plan. In some examples, system 12000 may determine one or more ranges of motion that may result from deviating from the surgical plan. The ranges of motion may be determined based on data in a database of historical cases, based on a mathematical model, based on a neural network model, or using another type of algorithm. An XR visualization may present the ranges of motion. For instance, system 12000 may present the ranges of motion resulting from the modified surgical plan in the manner described with respect to FIG. 11A and FIG. 11B.

The surgeon may specify a proposed deviation from the surgical plan in various ways. For instance, in an example where the surgeon is using an oscillating saw tool, the surgeon may hold the oscillating saw tool at a particular angle with respect to a cutting plane specified by a surgical plan for a bone. In this example, the surgeon may then provide input that asks system 12000 to determine the consequences of cutting the bone at the particular angle. For instance, the surgeon may provide a voice command saying, "what happens if I use this cutting plane instead?" In an example where the surgeon is using drilling tool, the surgeon may issue a voice command indicating how the surgeon proposes changing a position or depth of a drilling hole. Similarly, where the surgeon is using a reaming tool, the surgeon may issue a voice command indicating a proposed alternative reaming depth.

When computing system 12002 modifies a surgical plan, computing system 12002 may attempt to optimize one or more surgical parameters of the orthopedic surgery given the constraints imposed by the deviation from the surgical plan. For example, computing system 12002 may attempt to optimize the anticipated range of motion, optimize contact with cortical bone, optimize contact points of implants with high quality (e.g., dense) portions of the bone, or other factors. These factors may drive positions of implants, stem sizes of implants, surface sizes of implants, and other surgical parameters. Furthermore, in some examples, when computing system 12002 modifies a surgical plan, processing device 8304 (FIG. 83), which may be part of computing system 12002 or another computing system, may identify a next surgical item based on the modified surgical plan and present virtual information in a MR presentation that identifies the next surgical item.

This disclosure describes to the orthopedic classification and surgery planning using artificial intelligence (AI) techniques such as neural networks. In some examples, such AI techniques may be employed during preoperative phase 302 (FIG. 3) or another phase of a surgical lifecycle. Artificial neural networks (ANNs), including deep neural networks (DNNs), have shown great promise as classification tools. A DNN includes an input layer, an output layer, and one or more hidden layers between the input layer and the output layer. ANNs and DNNs may also include one or more other types of layers, such as pooling layers.

Each layer may include a set of artificial neurons, which are frequently referred to simply as "neurons." Each neuron in the input layer receives an input value from an input vector. Outputs of the neurons in the input layer are provided as inputs to a next layer in the ANN. Each neuron of a layer after the input layer may apply a propagation function to the output of one or more neurons of the previous layer to generate an input value to the neuron. The neuron may then apply an activation function to the input to compute an activation value. The neuron may then apply an output function to the activation value to generate an output value for the neuron. An output vector of the ANN includes the output values of the output layer of the ANN.

There have been several challenges associated with application of ANNs to planning orthopedic surgery, particularly with respect to shoulder pathology. For example, some challenges relate to how to structure and train an ANN so that the ANN is able to provide meaningful output regarding shoulder pathology. In another example of a challenge associated with application of ANNs to planning orthopedic surgery, patients and healthcare professionals are understandably reluctant to trust decisions made by a computer, especially when it is unclear how the computer made those decisions. There are therefore problems about how to generate output in a way that helps ensure that patients and healthcare professionals are comfortable in trusting the output of an ANN.

This disclosure describes techniques that may resolve these challenges and provide an ANN structure that provides meaningful output regarding shoulder pathology. For example, an artificial neural network (ANN), such as a DNN, has an input layer, an output layer, and one or more hidden layers between the input layer and the output layer. The input layer includes a plurality of input layer neurons. Each input layer neuron in the plurality of input layer neurons corresponds to a different input element in a plurality of input elements. The output layer includes a plurality of output layer neurons.

Each output layer neuron in the plurality of output layer neurons corresponds to a different output element in a plurality of output elements. Each output element in the plurality of output elements corresponds to a different classification in one or more shoulder pathology classification systems. In this example, a computing system may generate a plurality of training datasets from past shoulder surgery cases. Each respective training dataset corresponds to a different training data patient in a plurality of training data patients and comprises a respective training input vector and a respective target output vector.

For each respective training dataset, the training input vector of the respective training dataset comprises a value for each element of the plurality of input elements. For each respective training dataset, the target output vector of the respective training dataset comprises a value for each element of the plurality of output elements. In this example, the computing system may use the plurality of training datasets to train the neural network. Additionally, in this example, the computing system may obtain a current input vector that corresponds to a current patient. The computing system may apply the DNN to the current input vector to generate a current output vector. The computing system may then determine, based on the current output vector, a classification of a shoulder condition of the current patient, which also may be referred to as a shoulder classification. In some instances, the classification is a diagnosis.

In this example, by having different output elements in the plurality of output elements correspond to different classes in one or more shoulder pathology classification systems, the DNN may be able to provide meaningful output information that can be used in the classification of shoulder conditions of patients. For instance, this may be more efficient computationally and in terms of training time than a system in which different values of a neuron in the output layer correspond to different classes. Furthermore, in some examples, the output values of neurons in the output layer indicate measures of confidence that the classified shoulder condition of a patient belongs in the corresponding class in one of the shoulder pathology classification systems. Such confidence values may help users consider the likelihood that the patient may have a different class of shoulder condition than that determined by the computing system using the DNN. Furthermore, it may be computationally efficient for the output of the same output layer neurons to both express confidence levels and be used as the basis for determining a classification (e.g., diagnosis) of a shoulder condition of a patient.

Figure 122:
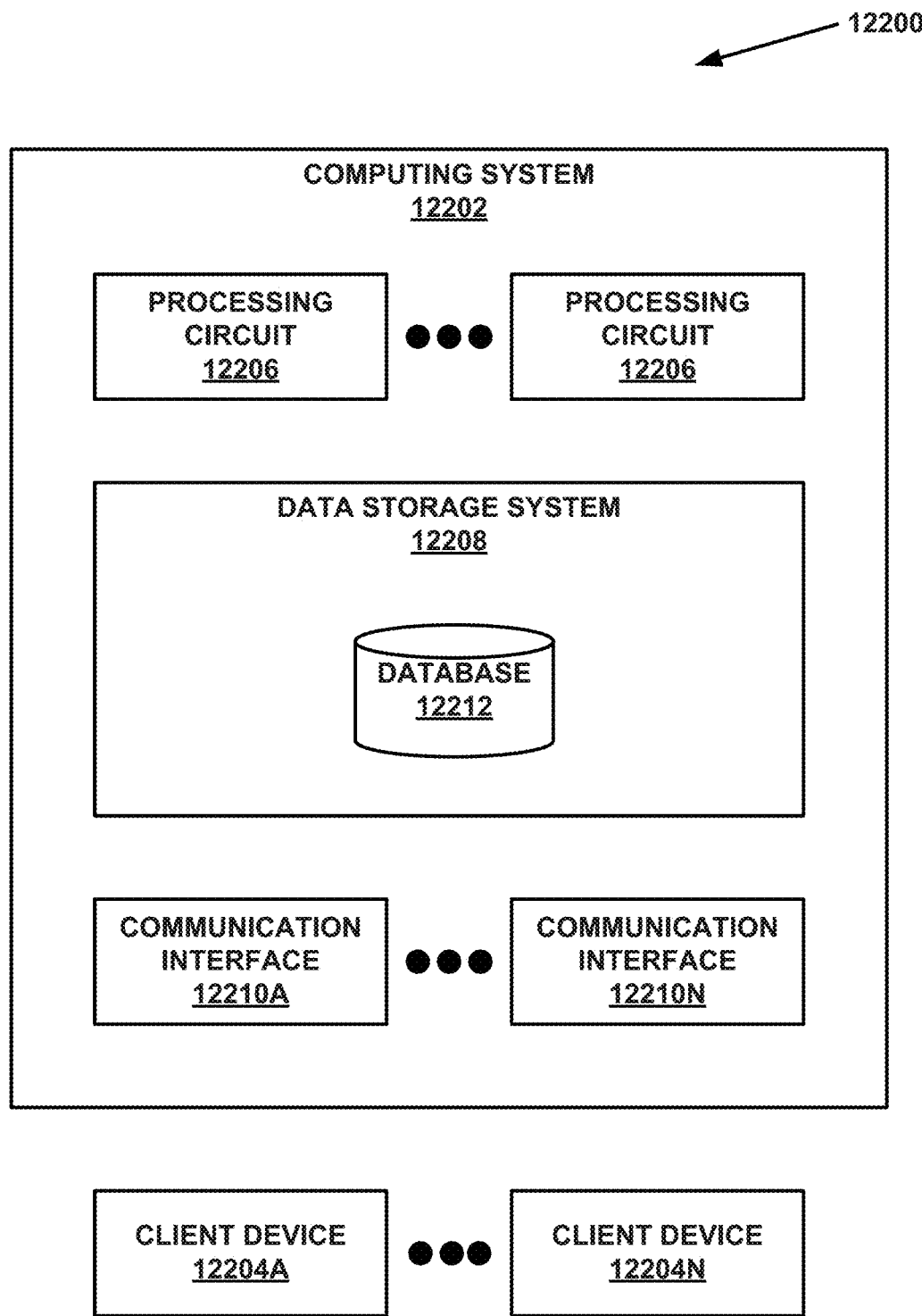
FIG. 122 is a block diagram illustrating an example computing system that implements a DNN usable for determining a classification of a shoulder condition of the patient, in accordance with a technique of this disclosure.

FIG. 122 is a block diagram illustrating an example computing system 12202 that implements a DNN usable for determining a classification of a shoulder condition of the patient, in accordance with a technique of this disclosure. Computing system 12202 may be part of orthopedic surgical system 100 (FIG. 1). Computing system 12202 may use the DNN to classify the shoulder condition of the patient as part of classifying a pathology in step 802 of FIG. 8. In some examples, computing system 12202 includes a XR visualization device (e.g., an MR visualization device or a VR visualization device) that includes one or more processors that perform operations of computing system 12202.

As shown in the example of FIG. 122, system 10900 includes a computing system 12202, a set of one or more client devices (collectively, "client devices 12204"). In other examples, system 12200 may include more, fewer, or different devices and systems. In some examples, computing system 12202 and client devices 12204 may communicate via one or more communication networks, such as the Internet.

Computing system 12202 may include one or more computing devices. Computing system 12202 and client devices 12204 may include various types of computing devices, such as server computers, personal computers, smartphones, laptop computers, and other types of computing devices. In the example of FIG. 122, computing system 12202 includes one or more processing circuits 12206, a data storage system 12208, and a set of one or more communication interfaces 12210A through 12210N (collectively, "communication interfaces 12210"). Data store 12208 is configured to store data. Communication interfaces 12210 may enable computing system 12202 to communicate (e.g., wirelessly or using wires) to other computing systems and devices, such as client devices 12204. For ease of explanation, this disclosure may describe actions performed by processing circuits 12206, data store 12208, and communication interfaces 12210 as being performed by computing system 10902 as a whole. One or more sub-systems of orthopedic surgical system 100 (FIG. 1) may include computing system 12202 and client devices 12204. For example, virtual planning system 102 may include computing system 12202 and client devices 12204.

Users may use client devices 12204 to access information generated by computing system 12202. For example, computing system 12202 may determine a classification of a shoulder condition of a current patient. The classification may be represented by a shoulder class among a plurality of shoulder classes in a shoulder pathology classification system. In this example, users may use client devices 12204 to access information regarding the classification. Because computing system 12202 may be remote from client devices 12204, users of client devices 12204 may consider computing system 12202 to be in a cloud-based computing system. In other examples, some or all the functionality of computing system 12202 may be performed by one or more of client devices 12204.

Computing system 12202 may implement a neural network (NN), such as a DNN. Storage system 12208 may comprise one or more computer-readable data storage media. Storage system 12208 may store parameters of the NN. For instance, storage system 12208 may store weights of neurons of the NN, bias values of neurons of the NN, and so on.

Computing system 12202 may determine a classification of a shoulder condition of a patient based on output of the NN. In accordance with a technique of this disclosure, output elements of the NN include output elements corresponding to different classes in one or more shoulder pathology classification systems. The shoulder pathology classification systems may include a primary glenohumeral osteoarthritis classification system, a rotator cuff classification system, and classification systems for other shoulder pathologies. For instance, the Walch classification system and the Favard classification system are two different primary glenohumeral osteoarthritis classification systems. The Warner classification system and the Goutalier classification system are two different rotator cuff classification systems. In some examples, a shoulder pathology classification system may include classes for more general categories of shoulder pathology, such as one or more of: primary glenoid humeral osteoarthritis (PGHOA), rotator cuff tear arthropathy (RCTA) instability, massive rotator cuff tear (MRCT), rheumatoid arthritis, post-traumatic arthritis, and osteoarthritis.

The Walch classification system, for example, specifies five classes: 1A, 1B, 2A, 2B, and 3. The Favard classification system, as another example, specifies five classes: E0, E1, E2, E3, and E4. The Warner classification system, as a further example, specifies four classes of rotator cuff atrophy: none, mild, moderate, and severe. The Goutalier classification system, as a further example, specifies five classes: 0 (completely normal muscle), I (some fatty streaks), II (amount of muscle is greater than fatty infiltration), III (amount of muscle is equal to fatty infiltration), IV (amount of fatty infiltration is greater than muscle).

In some examples, computing system 12202 may determine the classification of the shoulder condition of the patient based on a comparison of the values of the output elements generated by the NN. For example, the values of the output elements may correspond to confidence values that indicate levels of confidence that the patient's shoulder condition belongs in the classes that correspond to the output layer neurons that generated the values. For instance, the values of the output elements may be the confidence values or computing system 12202 may calculate the confidence values based on the values of the output elements.

In some examples, the output function of the output layer neurons generates the confidence values. Furthermore, computing system 12202 may identify which of the confidence values is highest. In this example, computing system 12202 may determine that the shoulder pathology class corresponding to the highest confidence value is the classification of the shoulder condition of the current patient. In some examples, if none of the confidence values is above a threshold, computing system 12202 may generate output indicating that computing system 12202 is unable to make a definitive classification.

As mentioned above, in some examples, the output elements of the NN include confidence values. In one such example, a confidence value function outputs confidence values. The confidence value function may be the output function of the output layer neurons of the NN. In this example, all possible confidence values output by the confidence value function are within a predefined range. Furthermore, in this example, computing system 12202 may apply the NN to an input vector to generate an output vector. As part of applying the NN, computing system 12202 may, for each respective output layer neuron in the plurality of output layer neurons, calculate an output value of the respective output layer neuron.

Computing system 12202 may then apply the confidence value function with the output value of the respective output layer neuron as input to the confidence value function. The confidence value function outputs a confidence value for the respective output layer neuron. In this example, for each respective output layer neuron in the plurality of output layer neurons, the output element corresponding to the respective output layer neuron specifies the confidence value for the respective output layer neuron. Furthermore, for each respective output layer neuron in the plurality of output layer neurons, the confidence value for the respective output layer neuron is a measure of confidence that the shoulder condition of the current patient belongs to a class in the one or more shoulder pathology classification systems that corresponds to the output element corresponding to the respective output layer neuron.

Computing system 12202 may use various confidence value functions. For example, computing system 12202 may apply a hyperbolic tangent function, a sigmoid function, or another type of function that output values that are within a predefined range. The hyperbolic tangent function (tan h) has the form $\gamma(c)=\tan h(c)=(e^c-e^{-c})/(e^c+e^{-c})$. The hyperbolic tangent function takes real-valued arguments, such as output values of output layer neurons, and transforms them to the range $(-1, 1)$. The sigmoid function has the form $\gamma(c)=1/(1+e^{-c})$. The sigmoid function takes real-valued arguments, such as output values of output layer neurons, and transforms them to the range $(0, 1)$.

Computing system 12202 may use a plurality of training datasets to train the NN. Each respective training dataset may correspond to a different training data patient in a plurality of previously classified training data patients. For instance, a first training dataset may correspond to a first training data patient, a second training dataset may correspond to a second training data patient, and so on. A training dataset may correspond to a training data patient in the sense that the training dataset may include information regarding the patient. The training data patients may be real patients who have classified shoulder conditions. In some examples, the training data patients may include simulated patients.

Each respective training dataset may include a respective training input vector and a respective target output vector. For each respective training dataset, the training input vector of the respective training dataset comprises a value for each element of the plurality of input elements. In other words, the training input vector may include a value for each input layer neuron of the NN. For each respective training dataset, the target output vector of the respective training dataset may comprise a value for each element of the plurality of output elements. In other words, the target output vector may include a value for each output layer neuron of the NN.

In some examples, the values in the target output vector are based on confidence values. Such confidence values may, in turn, be based on levels of confidence expressed by one or more trained healthcare professionals, such as orthopedic surgeons. For instance, a trained healthcare professional may be given the information in the training input vector of a training dataset (or information from which the training input vector of the training dataset is derived) and may be asked to provide a confidence level that the training data patient has a shoulder condition belonging to each class in each of the shoulder pathology classification systems.

For instance, in an example where the shoulder pathology classification systems include the Walch classification system, the healthcare professional may indicate that her level of confidence that the training data patient's shoulder condition belongs to class A1 is 0 (meaning she does not at all believe that the training data patient's shoulder condition belongs to class A1), indicate that her level of confidence that the training data patient's shoulder condition belongs to class A2 is 0; indicate that her level of confidence that the training data patient's shoulder condition belongs to class B1 is 0.75 (meaning she is fairly confident that the training data patient's shoulder condition belongs to class B1); indicate that her level of confidence that the training data patient's shoulder condition belongs to class A2 is 0.25 (meaning she believes that there is a smaller chance that the training data patient's shoulder condition belongs to class A2); and may indicate that her level of confidence that the training data patient's shoulder condition belongs to class C is 0. In some examples, computing system 12202 may apply the inverse of the confidence value function to the confidence values provided by the healthcare professional to generate values to include in the target output vector. In some examples, the confidence values provided by the healthcare professional are the values included in the target output vector.

Different healthcare professionals may have different levels of confidence that the same training data patient has a shoulder condition belonging to each class in each of the shoulder pathology classification systems. Hence, in some examples, the confidence values upon which the values in the target output vector are based may be averages or otherwise determined from the confidence levels provided by multiple healthcare professionals.

In some such examples, the confidence levels of some healthcare professionals may be given greater weight in a weighted average of confidence levels than the confidence levels of other healthcare professionals. For instance, the confidence levels of a preeminent orthopedic surgeon may be given greater weight than the confidence levels of other orthopedic surgeons. In another example, the confidence levels of healthcare professionals or training data patients in particular regions or hospitals may be given greater weight than healthcare professionals or training data patients from other regions or hospitals. Advantageously, such weighted averaging may allow the NN to be tuned according to various criteria and preferences.

For instance, a healthcare professional may prefer to use a NN that has been trained such that confidence levels are weighted in particular ways. In some examples where training datasets include training datasets based on a healthcare professional's own cases, the healthcare professional (e.g., an orthopedic surgeon) may prefer to use a NN trained using training datasets where the healthcare professional's own cases are weighted more heavily or exclusively using the healthcare professional's own cases. In this way, the NN may generate output tailored to the healthcare professional's own style of practice. Moreover, as mentioned above, healthcare professionals and patients may have difficulty trusting the output of a computing system. Accordingly, in some examples, computing system 12202 may provide information indicating that the NN was trained to emulate the decisions of the healthcare professionals themselves and/or particularly trusted orthopedic surgeons.

In some examples, the confidence levels of different healthcare professionals for the same training data patient may be used in generating different training datasets. For instance, the confidence levels of a first healthcare professional with respect to a particular training data patient may be used to generate a first training dataset and the confidence levels of a second healthcare professional with respect to the same training data patient may be used to generate a second training dataset.

Furthermore, in some examples, computing system 12202 may provide confidence values for output to one or more users. For instance, computing system 12202 may provide the confidence values to client devices 12204 for display to one or more users. In this way, the one or more users may be better able to understand how computing system 12202 may have arrived at the classification of the shoulder condition of a patient.

In some examples, to expand the universe of training datasets, computing system 12202 may automatically generate confidence values from electronic medical records. For instance, in one example, an electronic medical record for a patient may include data from which computing system 12202 may form an input vector and may include data indicating a surgeon's classification of a patient's shoulder condition. In this example, computing system 12202 may infer a default level of confidence from the classification. The default level of confidence may have various values (e.g., 0.75, 0.8, etc.). While such a default level of confidence may not reflect the surgeon's actual level of confidence, imputing a level of confidence may be help increase the number of available training datasets, which may improve the accuracy of the NN.

In some examples, the training datasets are weighted based on health outcomes of the training data patients. For example, a training dataset may be given higher weight if the training data patient associated with the training dataset had all positive health outcomes. However, a training dataset may be given a lower weight if the associated training data patient had less positive health outcomes. During training, computing system 12202 may use a loss function that weights the training datasets based on the weights given to the training datasets.

In some examples, as part of generating the training datasets, computing system 12202 may select the plurality of training datasets from a database of training datasets based on one or more training dataset selection criteria. In other words, computing system 12202 may exclude certain training datasets from the training process of the NN if the training datasets do not satisfy the training dataset selection criteria. In the example of FIG. 122, data storage system 12208 stores a database 12212 that contains training datasets from past shoulder surgery cases.

There may be a wide variety of training dataset selection criteria. For instance, in one example, the one or more training data set selection criteria may include which surgeon operated on the plurality of training data patients. In some examples, the one or more training dataset selection criteria include a region in which the training data patients live. In some examples, the one or more training dataset selection criteria include a region associated with one or more surgeons (e.g., a region in which the one or more surgeons practice, live, were licensed, were trained, etc.).

In some examples, the one or more training dataset selection criteria include postoperative health outcomes of the training data patients. In such examples, the postoperative health outcomes of the training data patients may include one or more of: postoperative range of motion, presence of postoperative infection, or postoperative pain. Thus, in such examples, the training datasets upon which the NN is trained may exclude training datasets where adverse health outcomes occurred.

Additional training datasets may be added to the database over time and computing system 12202 may use the additional training datasets to train the NN. Thus, the NN may continue to improve over time as more training datasets are added to the database.

Computing system 12202 may apply one of various techniques to use the training datasets to train the NN. For example, computing system 12202 may use one of the various standard backpropagation algorithms known in the art. For instance, as part of training the NN, computing system 12202 may apply a cost function to determine cost values based on differences between the output vector generated by the NN and the target output vector. Computing system 12202 may then use the cost values in a back-propagation algorithm to update the weights of neurons in the NN.

Figure 123:
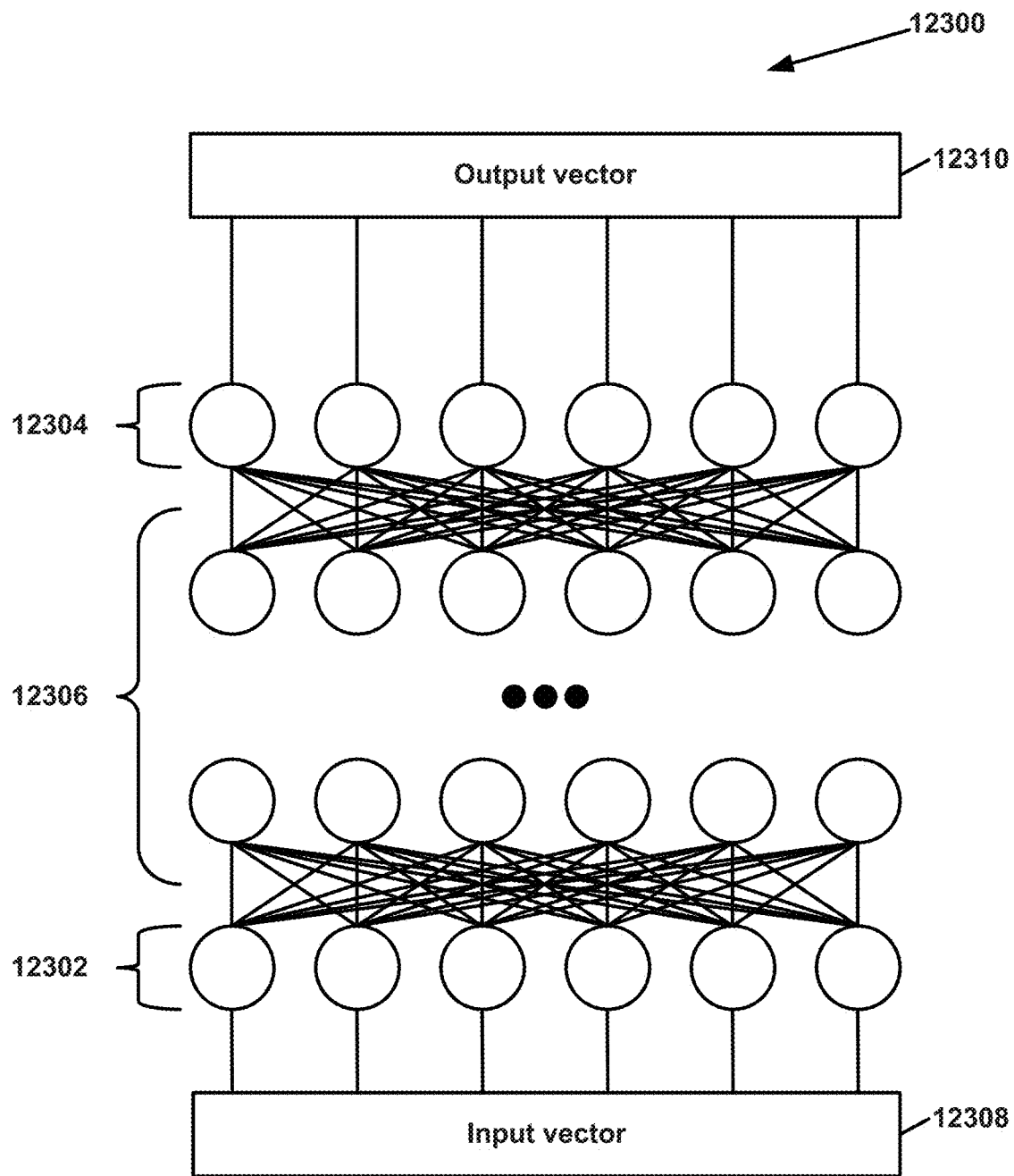
FIG. 123 illustrates an example deep neural network (DNN) that may be implemented by a computing system with the system of FIG. 122.

FIG. 123 illustrates an example NN 12300 that may be implemented by computing system 12202 with the system of FIG. 122. In the example of FIG. 123, NN 12300 includes an input layer 12302, an output layer 12304, and one or more hidden layers 12306 between input layer 12302 and output layer 12304. In the example of FIG. 123, neurons are represented as circles. Although in the example of FIG. 123, each layer is shown as including six neurons, layers in NN 12300 may include more or fewer neurons. Furthermore, although NN 12300 is shown in FIG. 123 as being a fully connected network, NN 12300 may have a different architecture. For instance, NN 12300 may not be a fully connected network, may have one or more convolutional layers, or may otherwise have a different architecture from that shown in FIG. 123.

In some implementations, NN 12300 can be or include one or more artificial neural networks (also referred to simply as neural networks). A neural network can include a group of connected nodes, which also can be referred to as neurons or perceptrons. A neural network can be organized into one or more layers. Neural networks that include multiple layers can be referred to as "deep" networks. A deep network can include an input layer, an output layer, and one or more hidden layers positioned between the input layer and the output layer. The nodes of the neural network can be connected or non-fully connected.

NN 12300 can be or include one or more feed forward neural networks. In feed forward networks, the connections between nodes do not form a cycle. For example, each connection can connect a node from an earlier layer to a node from a later layer.

In some instances, NN 12300 can be or include one or more recurrent neural networks. In some instances, at least some of the nodes of a recurrent neural network can form a cycle. Recurrent neural networks can be especially useful for processing input data that is sequential in nature. In particular, in some instances, a recurrent neural network can pass or retain information from a previous portion of the input data sequence to a subsequent portion of the input data sequence through the use of recurrent or directed cyclical node connections.

In some examples, sequential input data can include time-series data (e.g., sensor data versus time or imagery captured at different times). For example, a recurrent neural network can analyze sensor data versus time to detect or predict a swipe direction, to perform handwriting recognition, etc. Sequential input data may include words in a sentence (e.g., for natural language processing, speech detection or processing, etc.); notes in a musical composition; sequential actions taken by a user (e.g., to detect or predict sequential application usage); sequential object states; etc. Example recurrent neural networks include long short-term (LSTM) recurrent neural networks; gated recurrent units; bi-direction recurrent neural networks; continuous time recurrent neural networks; neural history compressors; echo state networks; Elman networks; Jordan networks; recursive neural networks; Hopfield networks; fully recurrent networks; sequence-to-sequence configurations; etc.

In some implementations, NN 12300 can be or include one or more convolutional neural networks. In some instances, a convolutional neural network can include one or more convolutional layers that perform convolutions over input data using learned filters. Filters can also be referred to as kernels. Convolutional neural networks can be especially useful for vision problems such as when the input data includes imagery such as still images or video. However, convolutional neural networks can also be applied for natural language processing.

NN 12300 may be or include one or more other forms of artificial neural networks such as, for example, deep Boltzmann machines; deep belief networks; stacked autoencoders; etc. Any of the neural networks described herein can be combined (e.g., stacked) to form more complex networks.

In the example of FIG. 123, an input vector 12308 includes a plurality of input elements. Each of the input elements may be a numerical value. Input layer 12302 includes a plurality of input layer neurons. Each input layer neuron in the plurality of input layer neurons included in input layer 12302 may correspond to a different input element in a plurality of input elements. In other words, input layer 12302 may include a different neuron for each input element in input vector 12308.

Furthermore, in the example of FIG. 123, an output vector 12310 includes a plurality of output elements. Each of the output elements may be a numerical value. Output layer 12304 includes a plurality of output layer neurons. Each output layer neuron in the plurality of output layer neurons corresponds to a different output element in the plurality of output elements. In other words, each output layer neuron in output layer 12304 corresponds to a different output element in output vector 12310.

Input vector 12308 may include a wide variety of information. For example, input vector 12308 may include morphological measurements of the patient. In some examples where input vector 12308 includes measurements of the patient's morphology, input vector 12308 may determine the measurements based on medical images of the patient, such as CT images, MRI images, or other types of images. For instance, computing system 12202 may obtain the medical images of a current patient. For instance, computing system 12202 may obtain the medical images from an imaging machine (e.g., a CT machine, MRI machine, or other type of imaging machine), an electronic medical record of the patient, or another data source. In this example, computing system 12202 may segment the medical images to identify internal structures of the current patient, such as soft tissue and bone. For instance, in one example, computing system 12202 may apply an artificial neural network trained to identify portions of medical images that correspond to bones or soft tissue. Furthermore, in this example, computing system 12202 may determine the plurality of measurements based on relative positions of the identified internal structures of the current patient. In this example, the plurality of input elements may include an input element for each measurement in the plurality of measurements.

As mentioned elsewhere in this disclosure, computing system 12202 may include one or more computing devices. Hence, various functions of computing system 12202 may be performed by various combinations of the computing devices of computing system 12202. For instance, in some examples, a first computing device of computing system 12202 may segment the images, a second computing device of computing system 12202 may train the DNN, a third computing device of computing system 12202 may apply the DNN, and so on. In other examples, a single computing device of computing system 12202 may segment the images, train the DNN, and apply the DNN.

As mentioned above, computing system 12202 may determine a plurality of measurements of morphological characteristics of the patient. Such measurements may include distance measurements, angle measurements, and other types of numerical characterizations of measurable relationships of and/or between structures of a patient. For example, the measurements may include any combination of values relating to one or more of:

a glenoid version: an angular orientation of an axis of the glenoid articular surface relative to a transverse axis of the scapula.

a glenoid inclination: the superior/inferior tile of the glenoid relative to the scapula.

a glenoid orientation/direction: the 3-dimensional orientation of the glenoid in a 3-dimensional space.

a glenoid best fit sphere radius: a radius of a best-fit sphere for the patient's glenoid. The best-fit sphere is a conceptual sphere that is sized such that a sector of the sphere would sit flush as possible with the patient's glenoid.

a glenoid best fit sphere root mean square error: the mean square error of the difference between the patient's glenoid and the sector of the best-fit sphere.

a reverse shoulder angle: the tilt of the inferior part of the glenoid.

a critical shoulder angle: the angle between the plane of the glenoid fossa and the connecting line to the most inferolateral point of the acromion.

acromion humeral space: the space between the acromion and the top of the humerus.

glenoid humeral space: the space between the glenoid and the humerus.

humeral version: the angle between the humeral orientation and the epicondylar axis.

humeral neck shaft angle: the angle between the humeral anatomic neck normal vector and the intramedullary axis.

humeral head best fit sphere radius and root mean square error: a radius of a best-fit sphere for the head of the patient's humerus. The best-fit sphere is a conceptual sphere that is sized such that a sector of the sphere matches the surface of the humeral head as much as possible. The root mean square error indicates the error between the best-fit sphere and the patient's actual humeral head.

humeral subluxation: a measure of the subluxation of the humerus relative to the glenoid.

humeral orientation/direction: the orientation of the humeral head in a 3-dimensional space.

a measurement of an epiphysis of the patient's humerus,
a measurement of a metaphysis of the patient's humerus,
a measurement of a diaphysis of the patient's humerus,
retroversion of a bone In some examples, input vector 12308 may include information (e.g., in combination with zero or more other example types of input data described herein) based on a rotator cuff assessment of the patient. For instance, input vector 12308 may include information, alone or in combination with morphological inputs described above, regarding fatty infiltration of the rotator cuff, atrophy of the rotator cuff, and/or other information about the patient's rotator cuff. In some examples, fatty infiltration measures and atrophy measures for soft tissue used as inputs to the neural network may be derived, for example, by any of the soft tissue modeling techniques as described in this application.

In some examples, the information regarding the patient's rotator cuff may be expressed in terms of a class in a shoulder pathology classification system, such as a Warner classification system or a Goutalier classification system.

In some examples, input vector 12308 may include (e.g., in combination with zero or more other example types of input data described herein) patient range of motion information. In some examples, the patient range of motion information may be generated using a motion tracking device, as described elsewhere in this disclosure.

Furthermore, in some examples, input vector 12308 may include information (e.g., in combination with zero or more other example types of input data described herein) that specifies a class in one or more shoulder pathology classification systems. In such examples, the output vector may include output elements corresponding to classes in one or more different shoulder pathology classification systems. For example, input vector 12308 may include information that specifies a class in a rotator cuff classification system and output vector 12310 may include output elements corresponding to classes in a glenohumeral osteoarthritis classification system.

In some examples, input vector 12308 may include information (e.g., in combination with zero or more other example types of input data described herein, including morphological inputs and/or rotator cuff inputs) that specifies bone density scores for humerus and/or glenoid. Other information included in input vector 12308 may include demographic information, such as patient age, patient activities, patient gender, patient body mass index (BMI), and so on. In some examples, input vector 12308 may include information regarding the speed of onset of the symptoms (e.g., gradual or sudden). The plurality of input elements in input vector 12308 also may include patient objectives for participation in activities such as particular exercises/sport types, ranges of motion, etc.

Figure 124:
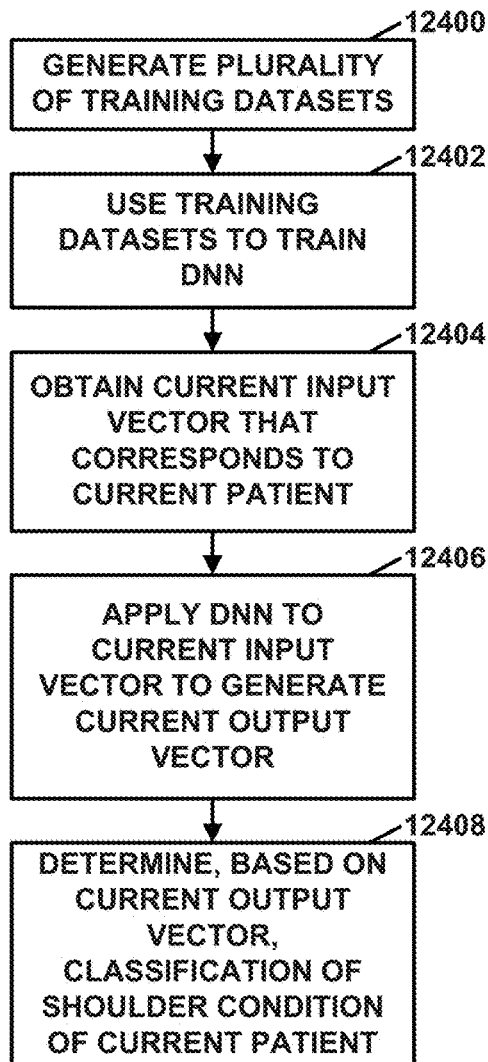
FIG. 124 is a flowchart illustrating an example operation of a computing system in using a DNN to determine a classification of a shoulder condition, in accordance with a technique of this disclosure.

FIG. 124 is a flowchart illustrating an example operation of computing system 12202 in using a DNN to determine a classification of a shoulder condition, in accordance with a technique of this disclosure. In the example of FIG. 124, computing system 12202 generates a plurality of training datasets from past shoulder surgery cases (12400). In some examples, generating the plurality of training datasets comprises retrieving selected training datasets from a database of historical shoulder cases. In the example of FIG. 124, a NN, such as NN 12300 (FIG. 123) has an input layer, an output layer, and one or more hidden layers between the input layer and the output layer. The input layer includes a plurality of input layer neurons. Each input layer neuron in the plurality of input layer neurons corresponds to a different input element in a plurality of input elements. The output layer includes a plurality of output layer neurons. Each output layer neuron in the plurality of output layer neurons corresponds to a different output element in a plurality of output elements. Each output element in the plurality of output elements corresponds to a different class in one or more shoulder pathology classification systems.

Each respective training dataset corresponds to a different training data patient in a plurality of training data patients from past shoulder surgery cases and comprises a respective training input vector and a respective target output vector. For each respective training dataset, the training input vector of the respective training dataset comprises a value for each element of the plurality of input elements. For each respective training dataset, the target output vector of the respective training dataset comprises a value for each element of the plurality of output elements.

Furthermore, in the example of FIG. 124, computing system 12202 uses the plurality of training datasets to train the NN (12402). Additionally, computing system 12202 may obtain a current input vector that corresponds to a current patient (12404), e.g., including a combination of various patient inputs as described above. Computing system 12202 may apply the NN to the current input vector to generate a current output vector (12406). For instance, computing system 12202 may provide the current input vector to the input layer of the NN and may perform forward propagation through the NN to generate the current output vector.

Furthermore, computing system 12202 may determine, based on the current output vector, a classification of a shoulder condition of the current patient (12408). In some examples, the classification of the shoulder condition of the current patient may be a diagnosis. As discussed above, the shoulder condition may be expressed by a classification from a selected shoulder classification system. In addition, shoulder condition may be accompanied by a confidence measure, value or other indication. Computing system 12202 may perform these actions in accordance with any of the examples or combination of examples provided elsewhere in this disclosure.

Healthcare professionals may use the classification of the shoulder condition in various ways. For example, a surgeon may use the classification to select a type of surgery to perform on the patient. In some examples, the surgeon may use the classification to select surgical items (e.g., implants, tools, etc.) to use to perform a surgery on the patient. In some examples, a physical therapist or other healthcare professional may use the classification to determine a rehabilitation plan for the patient.

In an example, the disclosure relates to the orthopedic surgery planning, including surgical procedure type selection, using artificial intelligence techniques such as neural networks. Prior research has not resolved questions regarding how to structure and train a NN so that the NN is able to provide meaningful output regarding shoulder pathology, prior research has not resolved questions regarding how to structure and train a NN so that the NN is able to provide meaningful output regarding which type of shoulder surgery to perform on a patient. Example types of shoulder surgeries may include a standard total shoulder arthroplasty and a reverse shoulder arthroplasty. In another example of a challenge associated with application of NNs to planning orthopedic surgery, patients and healthcare professionals are understandably reluctant to trust decisions made by a computer, especially when it is unclear how the computer made those decisions. There are therefore problems about how to generate output in a way that helps ensure that patients and healthcare professionals are comfortable in trusting the output of a NN.

This disclosure describes techniques that may resolve these challenges and may provide a NN structure that provides meaningful output regarding a recommended type of shoulder surgery for a patient. In accordance with a technique of this disclosure, a NN (e.g., a DNN) may have an input layer, an output layer, and one or more hidden layers between the input layer and the output layer. The input layer includes a plurality of input layer neurons. Each input layer neuron in the plurality of input layer neurons corresponds to a different input element in a plurality of input elements. The output layer includes a plurality of output layer neurons. Each output layer neuron in the plurality of output layer neurons corresponds to a different output element in a plurality of output elements. The plurality of output elements includes a plurality of surgery type output elements.

In accordance with a technique of this disclosure, each surgery type output element in the plurality of surgery type output elements corresponds to a different type of shoulder surgery in a plurality of types of shoulder surgery. Furthermore, in accordance with this technique, a computing system may generate a plurality of training datasets. Each respective training dataset corresponds to a different training data patient in a plurality of training data patients and comprises a respective training input vector and a respective target output vector. For each respective training dataset, the training input vector of the respective training dataset comprises a value for each element of the plurality of input elements. For each respective training dataset, the target output vector of the respective training dataset comprises a value for each element of the plurality of output elements. The computing system may use the plurality of training datasets to train the NN.

Additionally, the computing system may obtain a current input vector that corresponds to a current patient. The computing system may apply the NN to the current input vector to generate a current output vector. Additionally, the computing system may determine, based on the current output vector, a recommended type of shoulder surgery for the current patient. The computing system may use the NN to determine the recommended type of shoulder surgery for the current patient as part of selecting a surgical plan for the patient in step 804 of FIG. 8.

In this example, by having different output elements in the plurality of output elements correspond to different shoulder types of shoulder surgeries, the NN may be able to provide meaningful output information that can be used in the selection of shoulder surgery procedure types to be used to treat shoulder conditions of patients. Furthermore, in some examples, the output values of neurons in the output layer indicate measures of confidence that the patient should undergo a particular type of shoulder surgery. Such confidence values may help users consider the likelihood that the patient should instead undergo a different type of shoulder surgery. Furthermore, it may be computationally efficient for the output of the same output layer neurons to both express confidence levels and be used as the basis for recommending a particular type of shoulder surgery for a patient.

Figure 125:
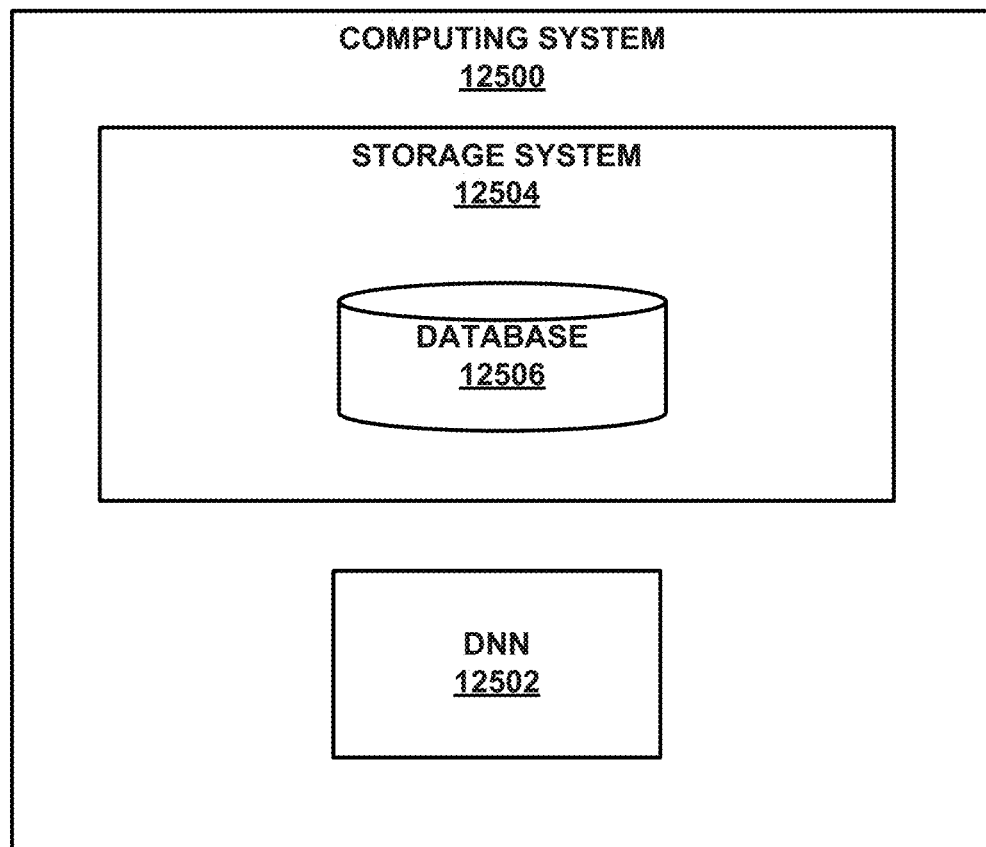
FIG. 125 is a block diagram illustrating example functional components of a computing system for using a DNN to determine a recommended surgery for a shoulder condition, in accordance with a technique of this disclosure.

FIG. 125 is a block diagram illustrating example functional components of a computing system 12500 for using a NN to determine a recommended surgery for a shoulder condition, in accordance with a technique of this disclosure. Computing system 12500 may be implemented in the same way as computing system 12202 (FIG. 122) and may form part of orthopedic surgical system 100 (FIG. 1). In some examples, the same computing system performs the roles of both computing system 12202 and computing system 12500. In some examples, computing system 12500 includes an XR visualization device (e.g., an MR visualization device or a VR visualization device) that includes one or more processors that perform operations of computing system 12500.

In the example of FIG. 125, computing system 12500 includes a NN 12502 and storage system 12504. Storage system 12504 may store a database 12506. NN 12502 may be implemented in a manner similar to NN 12300 of FIG. 123. That is, NN 12502 may include an input layer, an output layer, and one or more hidden layers between the input layer and the output layer. Moreover, each input layer neuron in the plurality of input layer neurons of the input layer of NN 12502 may correspond to a different input element in a plurality of input elements in an input vector. Each output layer neuron in the plurality of output layer neurons in the output layer of NN 12502 may correspond to a different output element in a plurality of output elements in an output vector. However, NN 12502 may have different parameters, such as different numbers of hidden layers, different numbers of neurons in the input layer, different numbers of neurons in the output layer, and so on.

Storage system 12504 may comprise one or more computer-readable data storage media. Storage system 12504 may store parameters of NN 12502. For instance, storage system 12504 may store weights of neurons of NN 12502, bias values of neurons of NN 12502, and so on. Like database 12212, database 12506 may contain training datasets from past shoulder surgery cases Computing system 12500 may apply NN 12502 to an input vector to generate an output vector. For example, the output layer of NN 12502 may include (and in some examples be limited to) a plurality of output layer neurons. Each of the output layer neurons may correspond to a different output element in a plurality of surgery type output elements. The output vector may include the plurality of surgery type output elements. Each of the surgery type output elements may correspond to a different type of shoulder surgery. Example types of shoulder surgery types, which may be presented as outputs, may include a stemless standard total shoulder arthroplasty, a stemmed standard total shoulder arthroplasty, a stemless reverse shoulder arthroplasty, a stemmed reverse shoulder arthroplasty, an augmented glenoid standard total shoulder arthroplasty, an augmented glenoid reverse shoulder arthroplasty, and other types of orthopedic shoulder surgery. A shoulder surgery may be "standard" in the sense that, after surgery, the patient's shoulder joint has the standard anatomical configuration where the scapula side of the shoulder joint has a concave surface and the humerus side of the shoulder surgery has a convex surface. A "reverse" shoulder surgery on the other hand results in the opposite configuration where a convex surface is attached to the scapula and a concave surface is attached to the humerus. In some examples, the types of shoulder surgery types include a plurality of revision surgeries on a patient's shoulder. Examples of revision surgeries on the patient's shoulder include . . . .

Additionally, computing system 12500 may determine a recommended type of shoulder surgery for a patient based on the current output vector. For example, computing system 12500 may determine which output element in the output vector corresponds to the type of shoulder surgery with the greatest confidence value.

The input vector for NN 12502 may include some, a combination of, or all of the input elements described above with respect to computing system 12202 and NN 12300. For example, the input elements may include one or more of measurements of morphological characteristics of a patient (including soft tissue modeling and bone modeling), demographic information regarding the patient, range of motion information regarding the patient, and so on. Furthermore, the training datasets used in training NN 12502 may be selected and generated in accordance with the examples provided above with respect to the NN for classifying a patient's shoulder condition. For instance, the training datasets may be selected based on one or more training dataset selection criteria. As described elsewhere in this disclosure, such training dataset selection criteria may include which surgeon operated on the plurality of training data patients, a region in which the training data patients live, a region associated with one or more surgeons, postoperative health outcomes of the training data patients, and so on. NN 12502 may be trained in a manner similar to the examples provided above with respect to the NN for classifying a patient's shoulder condition. For instance, the target output vectors of training datasets NN 12502 may include output elements indicating confidence levels that a particular type of shoulder surgery should be performed on a patient.

Figure 126:
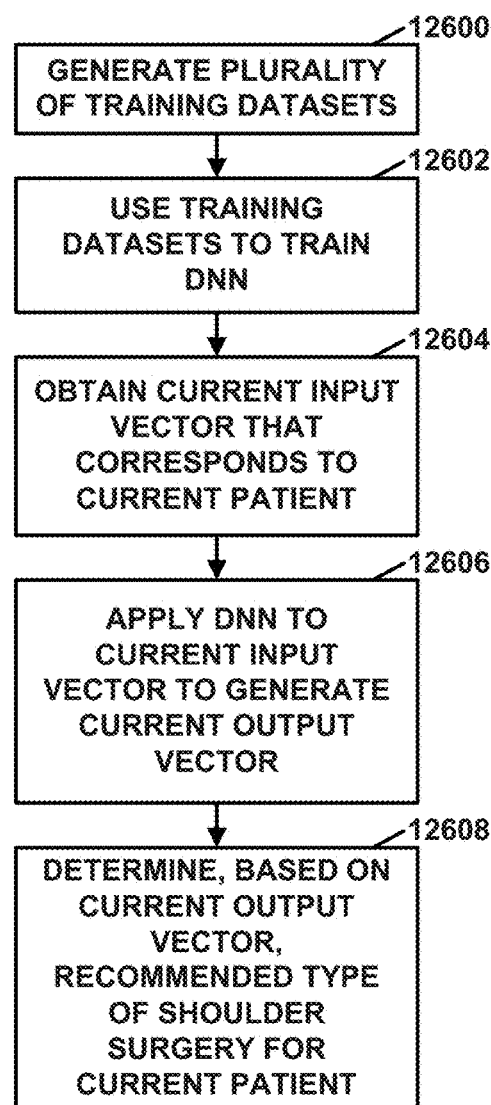
FIG. 126 is a flowchart illustrating an example operation of a computing system that uses a DNN to determine a recommended type of shoulder surgery for a patient, in accordance with a technique of this disclosure.

FIG. 126 is a flowchart illustrating an example operation of a computing system that uses a NN to determine a recommended type of shoulder surgery for a patient, in accordance with a technique of this disclosure. In the example of FIG. 126, computing system 12500 generates a plurality of training datasets (12600). In this example, a NN has an input layer, an output layer, and one or more hidden layers between the input layer and the output layer. The input layer includes a plurality of input layer neurons. Each input layer neuron in the plurality of input layer neurons corresponding to a different input element in a plurality of input elements. The output layer includes a plurality of output layer neurons.

Each output layer neuron in the plurality of output layer neurons corresponding to a different output element in a plurality of output elements. The plurality of output elements includes a plurality of surgery type output elements. Each surgery type output element in the plurality of surgery type output elements corresponds to a different type of shoulder surgery in a plurality of types of shoulder surgery. Each respective training dataset corresponds to a different training data patient in a plurality of training data patients and comprises a respective training input vector and a respective target output vector. For each respective training dataset, the training input vector of the respective training dataset comprises a value for each element of the plurality of input elements. For each respective training dataset, the target output vector of the respective training dataset comprises a value for each element of the plurality of output elements.

Furthermore, in the example of FIG. 126, computing system 12500 uses the plurality of training datasets to train the NN (12602). Additionally, computing system 12500 may obtain a current input vector that corresponds to a current patient (12604). Computing system 12500 may apply the NN to the current input vector to generate a current output vector (12606). Computing system 12500 may determine, based on the current output vector, a recommended type of shoulder surgery for the current patient (12608). Computing system 12500 may perform these activities in accordance with the examples provided elsewhere in this disclosure.

Although MR system 212 has been described above in the context of a system for use in planning and implementing surgical repair procedures for the shoulder, applications of MR system 212 are not so limited. For example, MR system 212 and Augmented Surgery Mode can be used to facilitate replacement of other joints or repair or reconstruction of other bones. Thus, any of the features described above can be used to assist with any orthopedic surgical procedures, including but not limited to procedures involving the elbow, ankle, knee, hip, or foot. It should also be understood that MR system 212 and its features can be used in surgical procedures in which external fixation devices are used to fixate or repair bone, such as a Charcot procedure involving the foot. Furthermore, MR system 212 and its features are not limited to applications involving only bone structures. As an example, because certain types of image data, such as CT images and MRI images, can provide information about soft tissue structures, including the skin, MR system 212 can be used to visualize and locate an optimal incision location and thus can further enhance minimally invasive surgeries.

The use of MR system 212 and its augmented surgery features are not limited to use by surgeons or other care providers. As an example, the information generated by MR system 212, including registration and tracking, can be used to control robotic arms that may be present in an operating environment.

MR system 212 can be one component of an advanced surgical system for enhancing surgical outcomes. In addition to the virtual preplanning and the use of mixed reality to perform the surgery, the implant can include various sensors to provide information after the surgery, as well as transceivers (e.g., RF transceivers) that facilitate collection of the data gathered by the sensors. Such data can be used to, for example, monitor the patient's recovery and assist with the patient's recovery (e.g., by prompting the patient to move the joint, such as via an application installed on a mobile device used by the patient, as one example). The data gathered by the sensors also can be input into a database where it can be used by surgeons or artificial intelligence systems to assist with planning future surgical cases.

Although many of examples of this disclosure have been provided with respect to shoulder joint repair surgery, many techniques of this disclosure are applicable to other types of orthopedic surgery. For example, many techniques of this disclosure may be applicable to ankle surgery (e.g., total ankle arthroplasty). In the example of a total ankle arthroplasty, a surgeon may perform a distal tibial cut, a proximal calcaneus cut, and two other medial/lateral cuts. To do so, the surgeon may need to place a cutting guide on the ankle joint. The cutting guide is placed so that the cuts will be perpendicular to the mechanical axis of the tibia. The placement of the cutting guide is then refined by adjusting three angles relative to the three anatomical planes (axial, sagittal and coronal). The surgeon can perform these cuts using a cut jig or can perform these cuts directly using an oscillating saw. Next, the surgeon performs the posterior and anterior talar chamfer cut.

Many of the examples provided above with regards to cutting and drilling are applicable to the cutting and drilling operations performed during a total ankle arthroplasty. For example, during preoperative phase 302 (FIG. 3) and intraoperative phase 306 (FIG. 3), orthopedic surgical system 100 (FIG. 1) may provide XR visualizations (e.g., MR visualizations or VR visualizations) that include patient-specific virtual 3D models of a patient's ankle anatomy. This may help surgeons plan and perform total ankle arthroplasties.

Furthermore, during the intraoperative phase 306 (FIG. 3) of a total ankle arthroplasty, visualization device 213 of MR system 212 may present an MR visualization that includes virtual guidance, such as virtual cutting planes, virtual drilling axes, and virtual entry points that help the surgeon perform precise cuts, drill holes, and position or place prosthetic components. For instance, the MR visualization may include cutting planes for the distal tibial cut, the proximal calcaneus cut, and so on. Prosthetic implant components for ankle arthroplasty may include, in one example, a talar dome, a tibial tray, and associated pegs or other anchor components. Moreover, a registration process similar to that described elsewhere in this disclosure with respect to shoulder repair surgery may be used in the context of total ankle arthroplasty. For instance, instead of using a center of a glenoid as a landmark for aligning a virtual 3D model with the patient's real anatomy, another landmark (e.g., the bottom of the tibia) on the patient's ankle may be used.

FIG. 150 is a flowchart illustrating example stages of an ankle joint repair surgery. The surgeon may wear or otherwise use a visualization device, such as visualization device 213, during some or all of the steps of the surgical process of FIG. 150. In other examples, an ankle surgery may include more, fewer, or different steps. For example, an ankle surgery may include steps for adding cement, and/or other steps. In some examples, visualization device 213 may present virtual guidance to guide the surgeon, nurse, or other users through the steps in the surgical workflow.

In the example of FIG. 150, a surgeon performs an incision process (15002). During the incision process, the surgeon makes a series of incisions to expose a patient's ankle joint (e.g., to expose at least a portion of the patient's tibia and at least a portion of the patient's talus). In some examples, an MR system (e.g., MR system 212, MR system 1800A, etc.) may help the surgeon perform the incision process, e.g., by displaying virtual guidance imagery illustrating how and/or where to make the incision. As discussed above, MR system 212 may display a virtual checklist, with each item on the checklist items corresponding to an item in a checklist of steps of an orthopedic surgery. For instance, MR system 212 may display a virtual checklist having a checklist item specifying a current step of performing an incision process.

The surgeon may perform a registration process that registers a virtual tibia object with the patient's actual tibia bone (15004) in the field of view presented to the surgeon by visualization device 213. For instance, MR system 212 may obtain the virtual tibia object from storage system 206 of FIG. 2. Similar to the virtual glenoid object discussed above, the virtual tibia object may be generated based on pre-operative imaging (e.g., CT imaging) of the patient's tibia. MR system 212 may perform the registration using any suitable process. For instance, MR system 212 may perform the registration of the virtual tibia object with the patient's actual tibia bone using any of the registration techniques discussed above with reference to FIGS. 20A-31. As discussed above, the registration may produce a transformation matrix between the virtual tibia object with the patient's actual tibia bone. As discussed above, MR system 212 may display an animation, video, or text to describe how a particular step or steps are to be performed. For instance, MR system 212 may cause visualization device 213 to display a diagram or animation showing how the registration process is to be performed. As also discussed above, MR system 212 may display a virtual checklist, with each item on the checklist items corresponding to an item in a checklist of steps of an orthopedic surgery. For instance, MR system 212 may display a virtual checklist having a checklist item specifying a current step of registering a virtual tibia object with the patient's actual tibia bone.

The surgeon may perform various work steps to prepare the tibia bone (15006). Example work steps to prepare the tibia bone include, but are not limited to, installing one or more guide pins into the tibia bone, drilling one or more holes in the tibia bone, and/or attaching one or more guides to the tibia bone. MR system 212 may provide virtual guidance to assist the surgeon with the various work steps to prepare the tibia bone. As discussed above, MR system 212 may display an animation, video, or text to describe how a particular step or steps are to be performed. For instance, MR system 212 may cause visualization device 213 to display a diagram or animation showing how the tibia is to be prepared. As also discussed above, MR system 212 may display a virtual checklist, with each item on the checklist items corresponding to an item in a checklist of steps of an orthopedic surgery. For instance, MR system 212 may display a virtual checklist having a checklist item specifying a current step, or sequence of steps, of preparing the tibia bone.

FIGS. 151A and 151B are conceptual diagrams illustrating example attachment of guide pins to a tibia. The incision process may expose at least a portion of tibia 15102, fibula 15110, and talus 15108 of ankle 15100. After performing the incision process, the surgeon may install guide pins 15104A, 15104B, 15106A, and 15106B into tibia 15102.

In some examples, such as the example of FIG. 151B, the surgeon may install guide pins 15104A, 15104B, 15106A, and 15106B using a physical guide. For instance, the surgeon may place tibial guide 15112 on tibia 15102 and utilize one or more holes in tibial guide 15112 to guide installation of guide pins 15104A, 15104B, 15106A, and 15106B. In some examples, tibial guide 15112 may be a patient-specific guide that is manufactured with a surface designed to conform with the contours of tibia 15102. One example of such a patient specific guide is the Prophecy Tibial Alignment Guide of the Prophecy® Infinity® Total Ankle system produced by Wright Medical Group N.V.

In addition to, or in place of tibial guide 15112, MR system 212 may provide virtual guidance to assist the surgeon with the installation of guide pins 15104A, 15104B, 15106A, and 15106B. For instance, visualization device 213 may display a virtual marker that guides a surgeon in installing a guide pin. Visualization device 213 may display the marker with an appearance that it is overlaid on tibia 15102 (e.g., to indicate the position and/or orientation at which the guide pin is to be installed). The virtual marker may be a virtual axis (e.g., similar to axis 3400 of FIG. 34) at a point on tibia 15102 that guides a surgeon in installing a guide pin. For instance, as shown in FIG. 151A, visualization device 213 may display virtual axes 15114A, 15114B, 15116A, and 15116B to respectively guide installation of guide pins 15104A, 15104B, 15106A, and 15106B, e.g., along the axes. While virtual axes 15114A, 15114B, 15116A, and 15116B are illustrated in FIG. 151A as being displayed with an appearance similar to guide pins 15104A, 15104B, 15106A, and 15106B of FIG. 151B, the display of virtual markers that guide installation of guide pins (e.g., guide pins 15104A, 15104B, 15106A, and 15106B) is not so limited. Other examples of virtual markers that MR system 212 may display include, but are not limited to axes, arrows, points, circles, rings, polygons, X shapes, crosses, targets, or any other shape or combination of shapes. MR system 212 may display the virtual markers as static features or with various animations or other effects.

MR system 212 may utilize different types of virtual markers depending on whether or not a physical guide is also used. As one example, in the example of FIG. 151B where tibial guide 15112 is used, MR system 212 may utilize an arrow to guide installation of a guide pin is to be installed. As shown in FIG. 151B, visualization device 213 may display an arrow to guide installation of guide pin 15106A via a particular hole of tibial guide 15112. As another example, in the example of FIG. 151A where tibial guide 15112 is not used, MR system 212 may utilize a virtual axis to guide installation of a guide pin. As shown in FIG. 151A, visualization device 213 may display virtual axis 15116A to guide installation of guide pin 15106A.

In examples where multiple guide pins are to be installed, visualization device 213 may display a respective virtual marker for each guide pin. In the example of FIG. 151, visualization device 213 may display multiple virtual markers to guide installation of guide pins 15104A, 15104B, 15106A, and 15106B. In some examples, visualization device 213 may display the virtual markers concurrently. For instance, visualization device 213 may display virtual axes 15114A, 15114B, 15116A, and 15116B, e.g., for alignment of guide pins, at the same time. In other examples, visualization device 213 may display fewer than all of the virtual markers at a particular time. For instance, visualization device 213 may display the virtual markers sequentially. As one example, at a first time, visualization device 213 may display a first virtual marker that guides installation of a first guide pin (e.g., guide pin 15104A). At a second time that is after the first time (e.g., after guide pin 15104A has been installed), visualization device 213 may display a second virtual marker that guides installation of a second guide pin (e.g., guide pin 15104B). In other words, responsive to determining that guide pin 15404A has been installed, visualization device 213 may cease to display the virtual marker that guided installation of guide pin 15404A and display a virtual marker to a next guide pin to be installed. Visualization device 213 may continue to sequentially display virtual markers until all necessary guide pins are installed (e.g., until guide pins 15104A, 15104B, 15106A, and 15106B are installed). In this way, MR system 212 may display a plurality of a virtual axes each having parameters obtained from the virtual surgical plan, each of the virtual axes configured to guide installation of a respective guide pin of a plurality of pins in the tibia.

MR system 212 may display the virtual markers with particular colors. For instance, in some examples, MR system 212 may preferably display the virtual markers in a color other than red, such as green, blue, yellow, etc. Displaying the virtual markers in a color or colors other than red may provide one or more benefits. For instance, as blood appears red and blood may be present on or around the anatomy of interest, a red colored virtual marker may not be visible.

In some examples, such as where visualization system 213 displays multiple virtual markers at the same time, visualization system 213 may alter or otherwise modify the display of a virtual marker after the surgeon has completed a corresponding work step. Alterations of the display of virtual markers may include, but are not limited to, changing a color, changing a marker type, animating (e.g., blinking or flashing), displaying an additional element (e.g., an X or a checkmark on or near the virtual marker) or any other visually perceptible alteration. For instance, visualization system 213 may initially display a first virtual marker to guide installation of guide pin 15104A as a virtual axis and a second virtual marker to guide installation of guide pin 15104B as a virtual axis. After the surgeon installs guide pin 15104A, visualization system 213 may modify the first virtual marker displayed to guide installation of guide pin 15104A (e.g., changing from a virtual axis to a reticle) while maintaining the display of the second virtual marker as a virtual axis.

MR system 212 may provide other virtual guidance in addition to, or in place of, the virtual markers. For instance, MR system 212 may display depth guidance to enable the surgeon to install the guide pins to a target depth (e.g., depth guidance similar to the depth guidance discussed above with reference to FIGS. 66-68). As another example, MR system 212 may provide targeting guidance. For instance, MR system 212 may display one or both of a virtual marker that identifies a center point or prescribed axis of the pin installation (e.g., as discussed above with reference to FIGS. 36A-36D) and/or an indication of whether the guide pin is aligned with the prescribed axis. As discussed above, MR system 212 may determine whether the guide pin is aligned with the prescribed axis by monitoring a position/orientation of the guide pin and/or a drill driving the guide pin, and comparing the monitored position/orientation with the prescribed axis.

The surgeon may install guide pins 15104A, 15104B, 15106A, and 15106B using the virtual guidance. In examples where tibial guide 15112 was used, the surgeon may remove tibial guide 15112 after installation of guide pins 15104A, 15104B, 15106A, and 15106B.

FIG. 152 is a conceptual diagram illustrating example drilling of holes in a tibia. As shown in FIG. 152, the surgeon may install drilling guide 15202 onto tibia 15102 using guide pins 15104A, 15104B, 15106A, and 15106B. Drilling guide 15202 includes one or more channels that guide drilling of holes into tibia 15102. For instance, as shown in FIG. 152, drilling guide 15202 include first channel 15204A and second channel 15204B. The surgeon may utilize a drill (e.g., a surgical motor with tibial corner drill bit) to drill a hole using each of first channel 15204A and second channel 15204B. In this way, the surgeon may bi-cortically drill both proximal corners of tibia 15102.

In addition to, or in place of drilling guide 15202, MR system 212 may provide virtual guidance to assist the surgeon with the drilling of the proximal corners of tibia 15102. For instance, visualization device 213 may display a virtual marker that guides a surgeon in drilling a hole in tibia 15102. Visualization device 213 may display the virtual marker overlaid on tibia 15102 (e.g., to indicate the position and/or orientation at which the hole is to be drilled). The virtual marker may be a virtual drilling axis (e.g., similar to axis 3400 of FIG. 34) at a point on tibia 15102 that guides a surgeon in performing the drilling. Similar to the virtual markers discussed above that guide installation of guide pins, visualization device 213 device may display the virtual markers that guide the drilling of the proximal corners of tibia 15102 concurrently or sequentially, and the virtual markers that guide the drilling may each respective proximal corner of the tibia.

MR system 212 may provide other virtual guidance in addition to, or in place of, the virtual markers. For instance, MR system 212 may display depth guidance to enable the surgeon to drill the holes to a target depth (e.g., depth guidance similar to the depth guidance discussed above with reference to FIGS. 66-68). As another example, MR system 212 may provide targeting guidance. For instance, MR system 212 may display one or both of a virtual marker that identifies a center point or prescribed axis of the drilling (e.g., as discussed above with reference to FIGS. 36A-36D), e.g., into the tibia or talus, and/or an indication of whether the drill bit is aligned with the prescribed axis. As discussed above, MR system 212 may determine whether the drill bit is aligned with the prescribed axis by monitoring a position/orientation of the drill bit and/or a drill driving the drill bit, and comparing the monitored position/orientation with the prescribed axis.

In some examples, MR system 212 may utilize the surgical item tracking techniques described in this disclosure (e.g., with reference to FIGS. 83-108) to assist with the ankle arthroplasty. For instance, MR system 212 may select a surgical item of a plurality of surgical items. The plurality of surgical items may be included in one or more trays for performing the ankle arthroplasty procedure. Example surgical items include, but are not limited to, tools, instruments, implants, associated hardware. MR system 212 may cause a second visualization device (e.g., worn by a nurse or someone other than the surgeon) to display virtual information that identifies the selected surgical item among the plurality of surgical items, wherein the virtual information is presented on or adjacent a position of the selected surgical item visible via the second visualization device. MR system 212 may select the surgical item as a surgical item associated with a current step of the ankle arthroplasty procedure. For instance, in the example of FIG. 152 where the surgeon may use drilling guide 15202 to drill the tibial corners, MR system 212 may select drilling guide 15202 as the selected surgical item. The second visualization device may display virtual information that identifies drilling guide 15202 (e.g., highlight or otherwise identify drilling guide 15202 in a manner similar to FIGS. 105-108)

With continued reference to the stages of an ankle joint repair surgery of FIG. 150, the surgeon may perform a tibia resection process (15008). For instance, the surgeon may remove a portion of tibia 15102 to make room for subsequent installation of a tibial implant. In some examples, the surgeon may perform the tibial resection by making three cuts (e.g., a proximal cut, a medial cut, and a lateral cut) in tibia 15102 to remove a portion of tibia 15102 and create a space for subsequent installation of a tibial implant. As discussed above, MR system 212 may display an animation, video, or text to describe how a particular step or steps are to be performed. For instance, MR system 212 may cause visualization device 213 to display a diagram or animation showing how the tibia resection is to be performed. As also discussed above, MR system 212 may display a virtual checklist, with each item on the checklist items corresponding to an item in a checklist of steps of an orthopedic surgery. For instance, MR system 212 may display a virtual checklist having a checklist item specifying a current step, or sequence of steps, of performing the tibial resection.

FIG. 153 is a conceptual diagram illustrating example resection of a tibia. As shown in FIG. 153, the surgeon may install resection guide 15302 onto tibia 15102 using guide pins 15104A, 15104B, 15106A, and 15106B. Resection guide 15302 includes one or more channels that guide performing cuts into tibia 15102. For instance, as shown in FIG. 153, resection guide 15202 include first channel 15306A that guides performance of a medial cut, second channel 15306B that guides performance of a proximal cut, and third channel 15306C that guides performance of a lateral cut. In some examples, resection guide 15302 may include a fourth channel that guides performance of a resection of talus 15108. For instance, as shown in FIG. 153, resection guide 15302 may include fourth channel 15304. The surgeon may utilize a saw blade (e.g., an oscillating bone saw) to perform the medial, lateral, and proximal cuts using channels 15306A-15306C. In this way, the surgeon may perform a resection of tibia 15102.

In addition to, or in place of resection guide 15302, MR system 212 may provide virtual guidance to assist the surgeon with performing the resection of tibia 15102. For instance, visualization device 213 may display a virtual marker that guides a surgeon in performing a cut in tibia 15102. Visualization device 213 may display the marker overlaid on tibia 15102 (e.g., to indicate the position and/or orientation at which the cut is to be made). The virtual marker may be a virtual cutting line, a virtual cutting surface or a virtual cutting plane (e.g., similar to virtual cutting plane 4200 of FIGS. 42A and 42B) at a point on tibia 15102 that guides a surgeon in performing the cut. Similar to the virtual markers discussed above that guide installation of guide pins, visualization device 213 device may display the virtual markers that guide the performance of the proximal, medial, and lateral cuts concurrently or sequentially. In this way, MR system 212 may display a plurality of virtual cutting surfaces each having parameters obtained from the virtual surgical plan, the plurality of virtual cutting surfaces configured to guide resection of the tibia.

MR system 212 may provide other virtual guidance in addition to, or in place of, the virtual markers. For instance, MR system 212 may display depth guidance to enable the surgeon to perform the cuts to a target depth (e.g., depth guidance similar to the depth guidance discussed above with reference to FIGS. 66-68). As another example, MR system 212 may provide targeting guidance. For instance, MR system 212 may display one or both of a virtual marker that identifies a prescribed plane of the cutting (e.g., as discussed above with reference to FIGS. 36A-36D) and/or an indication of whether the saw blade is aligned with the prescribed plane. As discussed above, MR system 212 may determine whether the saw blade is aligned with the prescribed plane by monitoring a position/orientation of the saw blade and/or a motor driving the saw blade the guide pin, and comparing the monitored position/orientation with the prescribed plane.

The surgeon may remove the resection (i.e., the portion of tibia 15102 separated via the cuts). Guide pins 15104A and 15104B may be attached to the resection and removed as a consequence of the resection removal.

As discussed above, MR system 212 may cause the second visualization device to display virtual information that identifies surgical item selected for a current step of the ankle arthroplasty procedure. For instance, in the example of FIG. 153 where the surgeon may use resection guide 15302 to perform the tibial resection, MR system 212 may select resection guide 15302 as the selected surgical item.

Furthermore, with reference to the stages of the ankle joint repair surgery of FIG. 150, the surgeon may perform a registration process that registers a virtual talus object with the patient's actual talus bone (15010) in the field of view presented to the surgeon by visualization device 213. For instance, MR system 212 may obtain the virtual talus object from storage system 206 of FIG. 2. Similar to the virtual tibia object discussed above, the virtual talus object may be generated based on pre-operative imaging (e.g., CT imaging) of the patient's talus. MR system 212 may perform the registration using any suitable process. For instance, MR system 212 may perform the registration of the virtual talus object with the patient's actual talus bone using any of the registration techniques discussed above with reference to FIGS. 20A-31. As discussed above, the registration may produce a transformation matrix between the virtual talus object with the patient's actual talus bone. As also discussed above, MR system 212 may display a virtual checklist, with each item on the checklist items corresponding to an item in a checklist of steps of an orthopedic surgery. For instance, MR system 212 may display a virtual checklist having a checklist item specifying a current step, or sequence of steps, of registering a virtual talus object with the patient's actual talus bone.

Additionally, in the example of FIG. 150, the surgeon may perform various work steps to prepare the talus bone (15012). Example work steps to prepare the talus bone include, but are not necessarily limited to, installing one or more guide pins into the talus bone, drilling one or more holes in the talus bone, and/or attaching one or more guides (e.g., cutting guides, drilling guides, reaming guides, etc.) to the talus bone. MR system 212 may provide virtual guidance to assist the surgeon with the various work steps to prepare the talus bone. As discussed above, MR system 212 may display an animation, video, or text to describe how a particular step or steps are to be performed. For instance, MR system 212 may cause visualization device 213 to display a diagram or animation showing how the talus is to be prepared. As also discussed above, MR system 212 may display a virtual checklist, with each item on the checklist items corresponding to an item in a checklist of steps of an orthopedic surgery. For instance, MR system 212 may display a virtual checklist having a checklist item specifying a current step, or sequence of steps, of preparing the talus bone.

FIGS. 154A and 154B are conceptual diagrams illustrating example guide pins installed in a talus during the talus preparation process. As shown in FIGS. 154A and 154B, the surgeon may install guide pins 15402A and 15402B into talus 15108.

In some examples, such as the example of FIG. 154B, the surgeon may install guide pins 15402A and 15402B using a physical guide. For instance, the surgeon may place talar guide 15404 on talus 15108 and utilize one or more holes in talar guide 15404 to guide installation of guide pins 15402A and 15402B. In some examples, talar guide 1540 may be a patient-specific guide that is manufactured with a surface designed to conform with the contours of talus 15108. One example of such a patient-specific guide is the Prophecy Talus Alignment Guide of the Prophecy® Infinity® Total Ankle system produced by Wright Medical Group N.V.

In addition to, or in place of talar guide 15404, MR system 212 may provide virtual guidance to assist the surgeon with the installation of guide pins 15402A and 15402B. For instance, visualization device 213 may display one or more virtual markers that guide a surgeon in installing a guide pin of guide pins 15402A and 15402B. For instance, as shown in FIG. 154A, visualization device 213 may display virtual axes 15406A and 15406B to respectively guide installation of guide pins 15402A and 15402B. Visualization device 213 may display the virtual markers in a manner similar to that described above with reference to FIGS. 151A and 151B. MR system 212 may provide other virtual guidance to assist with the installation of guide pins 15402A and 15402B in addition to, or in place of, the virtual markers. For instance, MR system 212 may provide any of the additional virtual guidance (e.g., depth guidance, targeting guidance, etc.) discussed above. In this way, MR system 212 may display a plurality of a virtual axes each having parameters obtained from the virtual surgical plan, and each of the virtual axes configured to guide installation of a respective guide pin in the talus. A virtual axis may guide installation of a corresponding guide pin by providing a visual reference with which a surgeon may align the physical guide pin during installation of the guide pin. As discussed herein, in some examples, MR system 212 may provide feedback as to whether the physical guide pin is actually aligned with the virtual axis.

The surgeon may install guide pins 15402A and 15402B using the virtual guidance. For example, the surgeon may align guide longitudinal axes of pins 15402A and 15402B with respective virtual axes to place the pins in bone. In examples where talar guide 15404 was used, the surgeon may remove talar guide 15404 after installation of guide pins 15402A and 15402B.

As discussed above, MR system 212 may cause the second visualization device to display virtual information that identifies a surgical item selected for a current step of the ankle arthroplasty procedure. For instance, in the example of FIG. 154B where the surgeon may use talar guide 15404 to install guide pins 15402A and 15402B, MR system 212 may select talar guide 15404 as the selected surgical item.

With continued reference to FIG. 150, after performing the talus preparation process, the surgeon may perform various perform a talus resection process (15014). For instance, the surgeon may remove a portion of talus 15108 to make room for subsequent installation of a talus implant. In some examples, the surgeon may perform the talus resection by making a single cut in talus 15108 to remove a portion of talus 15108 and create a space for subsequent installation of a talus implant. As discussed above, MR system 212 may display an animation, video, or text to describe how a particular step or steps are to be performed. For instance, MR system 212 may cause visualization device 213 to display a diagram or animation showing how the talus resection is to be performed. As also discussed above, MR system 212 may display a virtual checklist, with each item on the checklist items corresponding to an item in a checklist of steps of an orthopedic surgery. For instance, MR system 212 may display a virtual checklist having a checklist item specifying a current step, or sequence of steps, of performing the talar resection.

FIG. 155 is a conceptual diagram illustrating example resection of a talus. As shown in FIG. 155, the surgeon may install resection guide 15302 onto talus 15108 using guide pins 15402A and 15402B. In the example of FIG. 155, the surgeon may utilize the same resection guide (i.e., resection guide 15302) as was used to perform the tibial resection. In other examples, a talus specific resection guide may be used. The surgeon may perform the talus resection using resection guide 15302. For instance, the surgeon may utilize a saw blade (e.g., an oscillating bone saw) to perform a cut using channel 15304. In this way, the surgeon may perform a resection of talus 15108.

In addition to, or in place of resection guide 15302, MR system 212 may provide virtual guidance to assist the surgeon with performing the resection of talus 15308. For instance, visualization device 213 may display a virtual marker that guides a surgeon in performing a cut in talus 15108. Visualization device 213 may display the marker overlaid on talus 15108 (e.g., to indicate the position and/or orientation at which the cut is to be made). The virtual marker may be a virtual cutting line, virtual cutting surface or virtual cutting plane (e.g., similar to virtual cutting plane 4200 of FIGS. 42A and 42B) at a point on talus 15108 that guides a surgeon in performing the cut. In this way, MR system 212 may display a virtual cutting surface having parameters obtained from the virtual surgical plan, the virtual cutting surface configured to guide primary resection of the talus.

MR system 212 may provide other virtual guidance in addition to, or in place of, the virtual markers. For instance, MR system 212 may display depth guidance to enable the surgeon to perform the cut to a target depth (e.g., depth guidance similar to the depth guidance discussed above with reference to FIGS. 66-68). As another example, MR system 212 may provide targeting guidance. For instance, MR system 212 may display one or both of a virtual marker that identifies a prescribed plane of the cutting (e.g., as discussed above with reference to FIGS. 36A-36D) and/or an indication of whether the saw blade is aligned with the prescribed plane. As discussed above, in some examples, MR system 212 may determine whether the saw blade is aligned with the prescribed plane by registering the saw blade or something connected thereto (e.g., a saw motor body, a saw handle, a physical registration marker, etc.) with a corresponding virtual model, and comparing the position of the corresponding virtual model with the prescribed plane.

The surgeon may remove the resection (i.e., the portion of talus 15108 separated via the cuts). In some examples, the surgeon may use various tools (e.g., a reciprocating saw or bone rasp) to remove any excess bone left after the resection has been removed. FIG. 156 is a conceptual diagram of an example ankle after performance of a tibial resection and a talar resection.

The surgeon may perform one or more additional work steps on one or both of tibia 15102 and/or talus 15108 to prepare tibia 15102 and/or talus 15108 to receive implants. Example additional work steps include, but are not necessarily limited to, tibial tray trialing, tibial peg broaching, talar chamfer resections, and talar peg drilling.

FIGS. 157A-157C are conceptual diagrams illustrating an example of tibial tray trialing. In some examples, it may be desirable to ensure that, when installed, a posterior edge of the tibial implant will at least reach the posterior portion of tibia 15102. Additionally, in some examples, there may be multiple size tibial implants available. As such, it may be desirable for the surgeon to determine which size tibial implant to utilize. To ensure that the posterior edge of the tibial implant will at least reach the posterior portion of tibia 15102 and/or to determine which size tibial implant to utilize, the surgeon may perform tibial tray trialing.

To perform tibial tray trialing, the surgeon may attach tibial tray trial 15702 to tibia 15102. As shown in FIG. 157A, tibial tray trial 15702 may include posterior edge 15704, indicator 15710, guide pin holes 15712A and 15712B, broaching holes 15714A and 15714B (an additional anterior broaching hole 15714C is not shown), and anterior surface 15716. The surgeon may attach tibial tray trial 15702 to tibia 15102 by sliding guide pins 15106A and 15106B into corresponding guide pin holes 15712A and 15712B. In some examples, after attaching tibial tray trial 15702, the surgeon may trim guide pins 15106A and 15106B to be flush with anterior surface 15716 of tibial tray trial 15702 (e.g., as shown in FIG. 158).

In some examples, the surgeon may utilize fluoroscopy to perform the tibial tray trialing. For instance, the surgeon may utilize fluoroscopy to determine the relative positions of tibial tray trial 15702 and tibia 15102.

MR system 212 may provide virtual guidance to assist with tibial tray trialing. As one example, visualization device 213 may display a synthesized view showing the relative positions of tibial tray trial 15702 and tibia 15102. Visualization device 213 may display the synthesized view in a manner similar to that discussed above with reference to FIGS. 66-68. For instance, MR system 212 may register tibial tray trial 15702 to a corresponding virtual model of tibial tray trial and utilize the registered virtual models of tibial tray trial 15702 and tibia 15102 to synthesize a view showing the relative positions of the virtual models of tibial tray trial 15702 and tibia 15102. As the virtual models of tibial tray trial 15702 and tibia 15102 are respectively registered to tibial tray trial 15702 and tibia 15102, the relative positions of the virtual models of tibial tray trial 15702 and tibia 15102 corresponds to the relative positions of tibial tray trial 15702 and tibia 15102. The synthesized views may appear similar to the conceptual diagrams of FIGS. 157B and 157C.

The surgeon may utilize the synthesized view to perform one or more adjustments on tibial tray trial 15702. For instance, if the synthesized view indicates that posterior edge 15704 of tibial tray trial 15702 extends past posterior edge 15706 of tibia 15102, the surgeon may adjust tibial tray trial 15702 to anteriorly advance posterior edge 15704 of tibial tray trial 15702. For instance, the surgeon may utilize tool 15708 to anteriorly translate tibial tray trial 15702.

The surgeon may utilize the synthesized view to determine which size tibial implant is to be utilized. For instance, if the synthesized view indicates that indicator 15710 (illustrated in FIG. 157C as a notch) of tibial tray trial 15702 extends past posterior edge 15706 of tibia 15102, the surgeon may determine that a first size tibial implant (e.g., a standard size) is to be utilized. If the synthesized view indicates that indicator 15710 of tibial tray trial 15702 does not extend past posterior edge 15706 of tibia 15102, the surgeon may determine that a second size tibial implant (e.g., a long size) is to be utilized.

As described above, MR system 212 may enable the surgeon to perform tibial tray trialing using virtual guidance. In some examples, MR system 212 may enable the surgeon to perform tibial tray trialing without using fluoroscopy.

As discussed above, MR system 212 may cause the second visualization device to display virtual information that identifies surgical item selected for a current step of the ankle arthroplasty procedure. For instance, in the example of FIGS. 157A-157C where the surgeon may use tibial tray trial 15702, MR system 212 may select tibial tray trial 15702 as the selected surgical item.

The surgeon may create anchorage points for the tibial implant. For instance, the surgeon may utilize tibial tray trial to perform tibial peg broaching. FIG. 158 is a conceptual diagram illustrating an example creation of tibial implant anchorage. As shown in FIG. 158, the surgeon may utilize anterior tibial peg broach 15802A to broach a first anterior hole in tibia 15102 using broaching hole 15714A, utilize anterior tibial peg broach 15802A to broach a second anterior hole in tibia 15102 using broaching hole 15714C, and utilize posterior tibial peg broach 15802B to broach a hole in tibia 15102 using broaching hole 15714B. The holes broached in tibia 15102 may constitute anchorage points for the tibial implant.

As discussed above, MR system 212 may cause the second visualization device to display virtual information that identifies surgical item selected for a current step of the ankle arthroplasty procedure. For instance, in the example of FIG. 158 where the surgeon may use anterior tibial peg broach 15802A and posterior tibial peg broach 15802B, MR system 212 may select anterior tibial peg broach 15802A and posterior tibial peg broach 15802B as the selected surgical item (or items). As discussed above, MR system 212 may cause the second visualization device, and/or visualization device 213, to visually distinguish the selected surgical items (i.e., anterior tibial peg broach 15802A and posterior tibial peg broach 15802B).

The surgeon may perform one or more talar chamfer resections to further prepare talus 15108 to receive the talar implant. In some examples, the surgeon may perform an anterior talar chamfer resection and a posterior talar chamfer resection. To perform the one or more talar resections, the surgeon may attach one or more guide pins to talus 15108.

FIGS. 159A and 159B are conceptual diagrams illustrating an example attachment of guide pins to talus 15108. MR system 212 may provide virtual guidance to guide the surgeon in attaching guide pins 15904A and 15904B to talus 15108. For instance, as shown in FIG. 159A, visualization device 213 may display virtual axes 15902A and 15902B overlaid on talus 15108 to guide installation of guide pins 15904A and 15904B to talus 15108. While illustrated in FIG. 159A as virtual axes, visualization device 213 may display any of the virtual markers described herein to guide installation of guide pins 15904A and 15904B to talus 15108.

In some examples, the surgeon may utilize a physical guide to assist with the installation of guide pins 15904A and 15904B to talus 15108. For instance, the surgeon may utilize fluoroscopy to position a talar dome trial component. When the talar dome trial component is positioned, the surgeon may utilize holes in the talar dome trial component to guide the installation of guide pins 15904A and 15904B.

The surgeon may perform the talar chamfer resections using guide pins 15904A and 15904B. For instance, as shown in FIG. 160, the surgeon may position talar resection guide base 16002 on talus 15108 using guide pins 15904A and 15904B. The surgeon may utilize one or more components to secure talar resection guide base 16002 to talus 15108. For instance, as shown in FIG. 161, the surgeon may install fixation screws 16102A and 16102B through resection guide base 16002 into talus 15108.

MR system 212 may provide virtual guidance to assist the surgeon with the installation of fixation screws 16102A and 16102B. As one example, visualization device 213 may display virtual markers that indicate the location and axis at which fixation screws 16102A and 16102B are to be installed. As another example, visualization device 213 may provide depth guidance to enable the surgeon to install fixation screws 16102A and 16102B to a target depth (e.g., depth guidance similar to the depth guidance discussed above with reference to FIGS. 66-68). In some examples, MR system 212 may utilize closed-loop tool control to positively control a drill used to attach fixation screws 16102A and 16102B. For instance, MR system 212 may utilize the closed-loop tool control techniques discussed above, e.g., with reference to FIG. 72, to reduce a speed of and/or stop the drill used to attach fixation screws 16102A and 16102B when a desired depth and/or torque is reached.

The surgeon may utilize talar resection guide base 16002 to perform the posterior talar chamfer resection. For instance, as shown in FIG. 161, the surgeon may insert saw blade 16104 into slot 16004 of talar resection guide base 16002 to perform the posterior talar chamfer resection.

As discussed above, MR system 212 may cause the second visualization device to display virtual information that identifies surgical item selected for a current step of the ankle arthroplasty procedure. For instance, in the example of FIG. 161 where the surgeon may use talar resection guide base 16002, MR system 212 may select talar resection guide base 16002 as the selected surgical item.

In addition to, or in place of talar resection guide base 16002, MR system 212 may provide virtual guidance to assist the surgeon with performing the posterior talar chamfer resection. For instance, visualization device 213 may display a virtual marker that guides a surgeon in performing the posterior talar chamfer resection. Visualization device 213 may display the marker overlaid on talus 15108 (e.g., to indicate the position and/or orientation at which the cut is to be made). The virtual marker may be a virtual surface or virtual cutting plane (e.g., similar to virtual cutting plane 4200 of FIGS. 42A and 42B) at a point on talus 15108 that guides a surgeon in performing the cut.

The surgeon may utilize talar resection guide base 16002 to perform the anterior talar chamfer resection. For instance, as shown in FIG. 162, the surgeon may attach anterior talar guide 16202 to talar resection guide base 16002. The surgeon may utilize a drill with talar reamer 16204 to ream the anterior surface of talus 15108. For instance, the surgeon may slide talar reamer 16204 horizontally through anterior talar guide 16202 to prepare the surface of talus 15108 for an anterior flat of the talar implant. As shown in FIG. 162, talar reamer 16204 may include depth stop 16206 that engages surface 16208 of anterior talar guide 16202 to control the reaming depth. The surgeon may rotate talar guide 16202 180 degrees and again slide talar reamer 16204 horizontally through (the now rotated) anterior talar guide 16202 to prepare the surface of talus 15108 for an anterior chamfer of the talar implant. As discussed above, talar reamer 16204 may include depth stop 16206 that engages surface 16208 of anterior talar guide 16202 to control the reaming depth.

In some examples, for one or both of the anterior flat and anterior chamfer preparation, the surgeon may perform plunge cuts (e.g., using talar reamer 16204) to prepare talus 15108 for reaming. For instance, the surgeon may attach a pilot guide with holes that guide performance of the plunge cuts. Depth stop 16206 of talar reamer 16204 may engage with a surface of the pilot guide the control the plunge depth.

In addition to, or in place of talar resection guide base 16002, MR system 212 may provide virtual guidance to assist the surgeon with performing the anterior talar chamfer resection. For instance, visualization device 213 may display one or more virtual markers that guide a surgeon in performing the plunge cuts and/or horizontal reaming. As one example, visualization device 213 may display a respective virtual axis for each of the plunge cuts. MR system 212 may provide other virtual guidance to assist with performing the plunge cuts and/or horizontal reaming in addition to, or in place of, the virtual markers. For instance, MR system 212 may provide any of the additional virtual guidance (e.g., depth guidance, targeting guidance, etc.) discussed above.

The surgeon may perform talar peg drilling to create anchorage points in talus 15108 for the talar implant. MR system 212 may provide virtual guidance to assist the surgeon with performing the anterior talar chamfer resection. For instance, visualization device 213 may display one or more virtual markers that guide a surgeon in drilling holes in talus 15108. As shown in FIG. 164, visualization device 213 may display virtual axes 16402A and 16402B that guide drilling of peg holes 16502A and 16502B of FIG. 165. MR system 212 may provide other virtual guidance to assist with creating the anchorage in addition to, or in place of, the virtual markers. For instance, MR system 212 may provide any of the additional virtual guidance (e.g., depth guidance, targeting guidance, etc.) discussed above. In this way, MR system 212 may display a plurality of virtual drilling axes each having parameters obtained from the virtual surgical plan, each of the virtual drilling axes configured to guide drilling of an anchorage point in the talus.

With continued reference to FIG. 150, the surgeon may perform a tibia implant installation process (15016). FIG. 166 is a conceptual diagram illustrating an example tibial implant. As shown in FIG. 166, tibial implant 16602 includes posterior peg 16604A, and anterior pegs 16604B and 16604C. FIG. 167 is a conceptual diagram illustrating an example tibia as prepared using the steps described above. As shown in FIG. 167, tibia 15102 includes peg holes 16702A-16702C that were created during the broaching process described above with reference to FIG. 158.

The surgeon may install tibial implant 16602 such that posterior peg 16604A, and anterior pegs 16604B and 16604C of tibial implant 16602 engage with peg holes 16702A-16702C of tibia 15102. For instance, the surgeon may position tibial implant 16602 such that posterior peg 16604A lines up with peg hole 16702A, anterior peg 16604B lines up with peg hole 16702B, and anterior peg 16604C lines up with peg hole 16702C. Once the pegs are lined up with their corresponding peg holes, the surgeon may impact tibial implant 16602 into tibia 15102. As discussed above, MR system 212 may display an animation, video, or text to describe how a particular step or steps are to be performed. For instance, MR system 212 may cause visualization device 213 to display a diagram or animation showing how tibial implant 16602 is to be installed. As also discussed above, MR system 212 may display a virtual checklist, with each item on the checklist items corresponding to an item in a checklist of steps of an orthopedic surgery. For instance, MR system 212 may display a virtual checklist having a checklist item specifying a current step, or sequence of steps, of installing the tibial implant.

FIG. 168 is a conceptual diagram illustrating example impaction of a tibial implant into a tibia. As shown in FIG. 168, the surgeon may utilize tray impactor 16802 to impact tibial implant 16602 into tibia 15102. For instance, the surgeon may place tip 16806 of tray impactor 16802 on tibial implant 16602 and strike one or both of impaction points 16804A and/or 16804B with an impactor (e.g., a hammer).

With continued reference to FIG. 150, the surgeon may perform a talus implant installation process (15018). FIG. 169 is a conceptual diagram illustrating an example talar implant. As shown in FIG. 169, talar implant 16902 includes first peg 16904A and second peg 16904B.

The surgeon may install talar implant 16902 such that first peg 16904A and second peg 16904B of talar implant 16902 engage with peg holes 16502A and 16502B of talus 15108. For instance, the surgeon may position talar implant 16902 such that first peg 16904A lines up with peg hole 16502A, and second peg 16904B of talar implant 16902 lines up with peg hole 16502B. Once the pegs are lined up with their corresponding peg holes, the surgeon may impact talar implant 16902 into talus 15108.

As discussed above, MR system 212 may cause the second visualization device to display virtual information that identifies a surgical item selected for a current step of the ankle arthroplasty procedure. For instance, in the example of FIG. 168 where the surgeon may use tray impactor 16802, MR system 212 may select tray impactor 16802 as the selected surgical item.

FIG. 170 is a conceptual diagram illustrating example impaction of a talar implant into a talus. As shown in FIG. 170, the surgeon may utilize talar impactor 17002 to impact talar implant 16902 into talus 15108. For instance, the surgeon may place tip 17004 of talar impactor 17002 on talar implant 16902 and strike an impaction point of talar impactor 17002 with an impactor (e.g., a hammer).

As discussed above, MR system 212 may cause the second visualization device to display virtual information that identifies surgical item selected for a current step of the ankle arthroplasty procedure. For instance, in the example of FIG. 168 where the surgeon may use talar impactor 17002, MR system 212 may select talar impactor 17002 as the selected surgical item. As discussed above, MR system 212 may display an animation, video, or text to describe how a particular step or steps are to be performed. For instance, MR system 212 may cause visualization device 213 to display a diagram or animation showing how talar implant 16902 is to be installed. As also discussed above, MR system 212 may display a virtual checklist, with each item on the checklist items corresponding to an item in a checklist of steps of an orthopedic surgery. For instance, MR system 212 may display a virtual checklist having a checklist item specifying a current step, or sequence of steps, of installing the talar implant.

With continued reference to FIG. 150, the surgeon may perform a bearing installation process (15020). The surgeon may install a bearing between tibial implant 16602 and talar implant 16902. For instance, as shown in FIG. 171, the surgeon may install bearing 17102 between tibial implant 16602 and talar implant 16902. As discussed above, MR system 212 may display an animation, video, or text to describe how a particular step or steps are to be performed. For instance, MR system 212 may cause visualization device 213 to display a diagram or animation showing how bearing 17102 is to be installed. As also discussed above, MR system 212 may display a virtual checklist, with each item on the checklist items corresponding to an item in a checklist of steps of an orthopedic surgery. For instance, MR system 212 may display a virtual checklist having a checklist item specifying a current step, or sequence of steps, of installing the bearing.

Subsequently, in the example of FIG. 150, the surgeon may perform a wound closure process (15022). During the wound closure process, the surgeon may reconnect tissues severed during the incision process in order to close the wound in the patient's ankle. As discussed above, MR system 212 may display an animation, video, or text to describe how a particular step or steps are to be performed. For instance, MR system 212 may cause visualization device 213 to display a diagram or animation showing how the wound is to be closed. As also discussed above, MR system 212 may display a virtual checklist, with each item on the checklist items corresponding to an item in a checklist of steps of an orthopedic surgery. For instance, MR system 212 may display a virtual checklist having a checklist item specifying a current step, or sequence of steps, of closing the wound.

FIG. 172 is a flow diagram illustrating an example technique for MR aided surgery, in accordance with one or more techniques of this disclosure. As discussed above, a surgeon may wear a visualization device of an MR system, such as visualization device 213 of MR system 212.

MR system 212 may register, via a visualization device, a virtual model of a portion of an anatomy of a patient to a corresponding portion of the anatomy viewable via the visualization device (17202). For instance, MR system 212 may perform the registration of a virtual tibia object with the patient's actual tibia bone viewable via visualization device 213 using any of the registration techniques discussed above with reference to FIGS. 20A-31. As discussed above, MR system 212 may obtain the virtual model from a virtual surgical plan for a surgical procedure to attach a prosthetic to the anatomy.

As discussed above, visualization device 213 may display at least a portion of the virtual model during the registration of the virtual model of the portion of the anatomy to the corresponding portion of the anatomy. For instance, as shown in FIG. 24, visualization device 213 may display a virtual model (e.g., a virtual bone model) and the user (i.e., the wearer of visualization device 213) may shift their gaze to align the virtual model with the corresponding portion of the anatomy. In some examples, visualization device 213 may cease display of the virtual model after the registration process. In some examples, visualization device 213 may maintain the display of the virtual model after the registration process and/or re-display the virtual model at a later time during the surgical procedure.

MR system 212 may display, via the visualization device and overlaid on the portion of the anatomy, a virtual guide that guides at least one of preparation of the anatomy for attachment of the prosthetic or attachment of the prosthetic to the anatomy (17204). For instance, MR system 212 may cause visualization device 213 to display any of the virtual guidance/guides discussed above. As discussed above, example virtual guides include, but are not limited to, virtual axes, virtual cutting surfaces, and the like. As also discussed above, visualization device 213 may display the virtual guide overlaid on the portion of the anatomy such that the virtual guide appears to be part of the real-world scene, e.g., with the virtual guide appearing to the user to be in overlay or otherwise integrated within the actual, real-world scene.

As discussed above, in some examples, visualization device 213 may cease display of the virtual model after the registration process. As such, in some examples, visualization device 213 may display the virtual guide at a different time (e.g., not contemporaneously) with the display of the virtual model. As also discussed above, in some examples, visualization device 213 may maintain the display of the virtual model after the registration process and/or re-display the virtual model at a later time during the surgical procedure. As such, in some examples, visualization device 213 may display the virtual guide at the same time (e.g., contemporaneously) with the display of the virtual model.

The closed-loop tool control techniques described elsewhere in this disclosure may also be used in the context of total ankle arthroplasty. For instance, in one example, the closed-loop control may be applied to the saw used in making the distal tibial cut, proximal calcaneus cut, the medial cut and the lateral cut, during the total ankle arthroplasty. In another example, the depth control techniques described elsewhere in this disclosure may be applied in the context of a total ankle arthroplasty to help ensure that the surgeon does not drill too deeply. For instance, as discussed above, the depth control techniques described elsewhere in this disclosure may be applied to assist the surgeon when performing the tibial resection.

The surgical item tracking techniques described elsewhere in this disclosure with respect to shoulder joint repair surgery may also apply to total ankle arthroplasty to help healthcare professionals select surgical items and track use of the surgical items. Additionally, the workflow management process described elsewhere in this disclosure may be adapted for use in total ankle arthroplasty. For example, an XR visualization device (e.g., XR visualization device 11702) may output an XR visualization (e.g., an MR visualization or VR visualization) that includes a set of virtual checklist items that correspond to items in a checklist of steps of a total ankle arthroplasty. For instance, instead of virtual checklist items corresponding to the steps of FIG. 19, the XR visualization may include virtual checklist items corresponding to steps of FIG. 150 or any other steps of an ankle arthroplasty.

The collaboration and education techniques described elsewhere in this disclosure may also be used in the context of ankle surgery, such as total ankle arthroplasty. For instance, in one example, a surgeon may use MR and/or VR to consult with a remote surgeon during a total ankle arthroplasty or other type of ankle surgery. In another example, visualization device 213 may present an MR visualization to a surgeon that includes a secondary view window that contains another person's view of the patient's ankle, e.g., including both actual anatomical objects, i.e., the real patient anatomy, captured by a camera of the other person's visualization device and virtual objects generated as an MR visualization by the other person's visualization device. The range of motion tracking techniques described elsewhere in this disclosure may also be applied in the context of a patient's ankle instead of the patient's shoulder.

In some examples, any of the techniques, devices, or methods described herein may be used for medical and surgical educational purposes. For example, visualization devices that present mixed reality objects or information may be used to educate students about an orthopedic surgical procedure or one or more steps or stages of that procedure. The students being educated about the orthopedic surgical procedure may comprise physicians being trained on the procedure or medical students being trained generally or specifically on the procedure. Alternatively, in some cases, a student being educated about the orthopedic medical procedure may be a patient on which the procedure will be performed, or a caretaker, guardian or family member of a patient. In this case, the teacher may comprise the surgeon or another medical professional that trains the patient student. Also, medical technicians, nurses, physician assistants, medical researchers, or any other person may be a student according to the techniques and methods described herein. In some examples, one or more teachers may provide illustrative instruction (and possibly demonstrations) to one or more students though the use of mixed reality. Moreover, in still other examples, the student or students may use visualization devices to perform practice techniques or training techniques of the orthopedic medical procedure with the aid of mixed reality. In still other cases, students and teachers may comprise a panel of experts working in a collaborative environment, in which case, student and teacher roles may change during a teaching session. In general, anyone being taught with the aid of mixed reality (or virtual reality) may be a student according to this disclosure, and similarly, anyone that teaches with the aid of mixed reality (or virtual reality) may be a teacher according to this disclosure.

Figure 127:
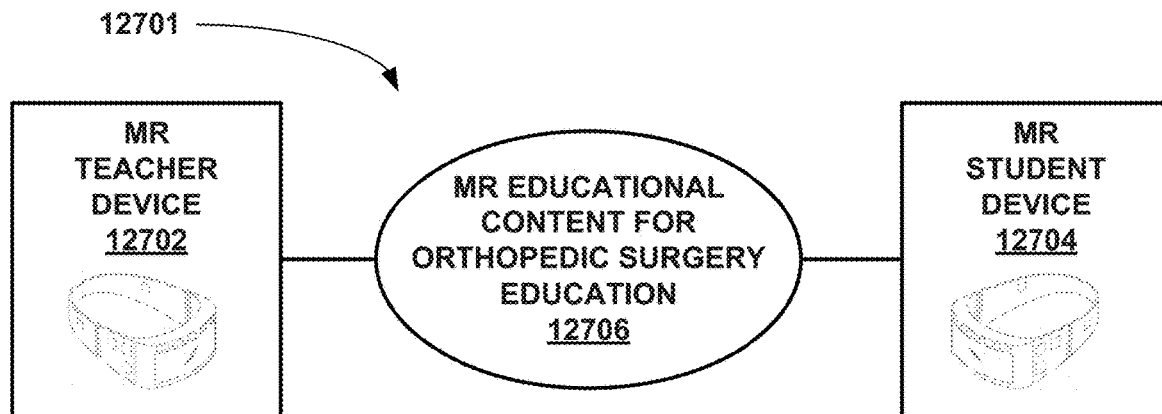
FIG. 127 is a conceptual block diagram of an educational system comprising an MR teacher device and an MR student device for orthopedic surgical education.

FIG. 127 is a conceptual block diagram of an educational system 12701 comprising an MR teacher device 12702 and an MR student device 12704. MR teacher device 12702 and MR student device 12704 may each comprise a visualization device 213, which is described in detail throughout this disclosure. MR teacher device 12702 may present the teacher with MR educational content for orthopedic surgery education 12706. Similarly, MR student device 12704 may present the student with similar MR educational content for orthopedic surgery education 12706. The MR educational content 12706, along with the tutelage of the teacher wearing MR teacher device 12702, may help to educate the student wearing MR student device 12704. In most cases, MR teacher device and MR student device operate in the same physical location, although the techniques of this discloser are not limited in this respect. For example, it is also possible for MR teacher device 12702 and MR student device 12704 to operate at remote physical locations relative to one another, in which case users may share MR educational content 12706 while viewing different real-world backgrounds.

MR educational content 12706 may comprise one or more virtual elements including a 3D virtual representation of one or more anatomical features associated with the orthopedic surgical procedure. For example, the 3D virtual representation of the one or more anatomical features within educational content 12706 may comprises a 3D virtual model of a human shoulder, such as shown for example as 3D virtual models 1008, 1010 in FIG. 10. In some examples, the virtual representation of the one or more anatomical features within educational content 12706 may comprise a 3D virtual illustration of a humeral head, a virtual illustration of a scapula, a 3D virtual illustration of a humeral bone or a 3D virtual illustration of a glenoid. In still other examples, the virtual representation of the one or more anatomical features within educational content 12706 may comprise a 3D virtual illustration of an ankle, a virtual illustration of a talus, or a 3D virtual illustration tibia or a tibia head. Many educational details below are described in the context of 3D virtual representations of shoulder anatomy, but the techniques are also very useful for other anatomy, especially complex anatomical elements, such as ankle anatomy.

Moreover, in addition to the 3D virtual representation of the one or more anatomical features, educational content 12706 may further comprise additional virtual elements demonstrate at least one aspect of the orthopedic surgical procedure. These additional elements, for example may comprise virtual pre-operative plan elements relative to the 3D virtual representation, one or more virtual surgical guidance features relative to the 3D virtual representation, or one or more surgical results virtually illustrated on the 3D virtual representation so as to demonstrate at least one aspect of the orthopedic surgical procedure.

The users of educational system 12701 (e.g., a teacher and a student wearing MR student device 12704 and MR teacher device 12702) may view and manipulate virtual 3D elements through virtual controls, such as via gestures, gaze-based controls, voice inputs, or any control technique useful in mixed reality or virtual reality. For example, the student or teacher may control virtual motion of a 3D virtual shoulder model and enable or disable virtual elements to demonstrate one or more aspect (pre-operative, inter-operative, and/or post-operative) of the orthopedic surgical procedure. Also, manual keypad input, touch screen entry, pointer controls, combinations of any virtual control mechanisms, or other types of controls may be used by teacher to manipulate virtual 3D elements within educational content 12706.

In some cases, MR student device 12704 and/or MR teacher device 12702 may include a haptic device that provides touch-based information to a user to help the users learn physical properties about virtual elements and to manipulate virtual elements. The haptic device, for example, may comprise one or more haptic gloves, one or more haptic wrist bands, a haptic pen-type device, or another haptic device. The haptic device may operate with a visualization device to provide haptic feedback to a user and the haptic feedback may be associated with one or more victual elements presented to the user by the visualization device. Such haptic feedback may be especially useful for surgical simulations performed by MR student device 12704. In this case, MR student device 12704 may comprise a visualization device that presents one or more virtual elements and a haptic device that provide haptic feedback. In some cases, the haptic feedback may be synchronized or coordinated with manipulations performed by the user on the one or more virtual elements presented by the visualization device.

Using an MR device such as MR student device 12704 or MR teacher device 12702, teachers or students may rotate, re-size, reposition, or otherwise move virtual 3D elements in space for educational reasons. MR student device 12704 or MR teacher device 12702 may enable or disable viewing of different segments of a virtual shoulder model, enable or disable virtual elements showing virtual implants on a 3D virtual model, virtual surgical planning on the 3D virtual model, virtual surgical guidance on the 3D virtual model, and/or virtual post-operative results on the 3D model.

Moreover, teachers or students may show anatomical movement of bones within a shoulder socket or within a human ankle. The example teacher model 1008 shown in FIG. 11 for example shows a 3D model of a shoulder, along with virtual elements showing a virtual 3D representation of shoulder implant components 1010 and virtual elements showing a likely impingement point 1106 that may be caused by shoulder implantation components 1010. Using an MR device such as MR student device 12704 or MR teacher device 12702, teachers or students may be able to rotate the virtual humeral bone relative to the glenoid to show shoulder motion. In addition, teachers or students may also enable or disable viewing of different illustrated elements, which may be segmented. Portions of humeral bone may be segmented and selectively enabled or disabled, e.g., to show a humeral cutting plane and a location for one or more shoulder implant components on the humeral bone. Also, portions of a scapula or glenoid may be segmented and selectively enabled or disabled, e.g., to show a location for one or more shoulder implant components on the scapula or glenoid.

The 3D virtual representations of one or more anatomical features may be based on actual patient images or may be based on images of one or more patients. The 3D virtual representations may be segmented into different sub-components, which may be enabled or disabled by users. In some cases, the 3D virtual representations may be computer-generated. In some cases, the 3D virtual representations may be selected from a catalog of 3D virtual representations (e.g., stored in memory of MR student device 12704 or MR teacher device 12702 or stored remotely). The different 3D virtual representations in the catalog may demonstrate a wide variety of different shoulder conditions that may require orthopedic surgical repair. A teacher using MR teacher device 12702, for example, may select one or more 3D virtual representations from the catalog of 3D images in order to make educational demonstrations to a student wearing MR student device 12704.

The 3D virtual representations may be selected for specific lesions by the teacher to the student. MR teacher device 12702, for example may present a 3D shoulder model within MR educational content 12706 to illustrate a shoulder with a particular type of classification (e.g. a type of Walch classification), which may call for a particular type of surgical procedure or selection of particular implant components with particular sizes, angles, and implant positions. For other lessons, MR teacher device 12702 may present different shoulder models having different classifications, thereby calling for a different type of surgical procedure or different implant components, sizes, angles and/or implant positions.

In addition to 3D virtual representation of one or more anatomical elements, such as a virtual of one or more anatomical elements, MR educational content 12706 may comprise any of a wide variety of MR content described herein, such as MR surgical guidance information, MR registrational content, MR-based axes, planes or markers, MR-based jigs or guides, MR-based bone models or soft tissue models, MR-based guidance on surgical tools, virtual implants, MR-based workflow checklists, range of motion information, pre-operative animations, or other MR-based information. The particular MR content used in any given educational setting, however, may depend on the student that is being educated. For example, educational system 12701 may be used to educate or train a physician, a medical student, a technician, a nurse, a physician assistant, or any other person that may be involved in an orthopedic medical procedure. Alternatively, educational system 12701 may be used to educate a patient (or caretaker, guardian, patient family member, and/or patient friends) about a procedure to be performed. In still other cases, educational system 12701 may be used to educate researchers or any other person that may have interests or reasons to learn one or more details about an orthopedic surgical procedure. The MR educational content for orthopedic surgery education 12706 may be selected or defined for different educational settings.

MR educational content 12706 may comprise one or more virtual elements that include a 3D virtual representation of one or more anatomical features associated with the orthopedic surgical procedure. The 3D virtual representation of one or more anatomical features, for example, may comprise a 3D virtual model of a human shoulder, or possibly a segment of a human shoulder, such as a 3D virtual illustration of a humeral head or a 3D virtual illustration of a glenoid. The virtual elements may be controllable by MR teacher device 12702 and/or MR student device 12704. MR teacher device 12702 may typically control the virtual elements, but in some cases virtual control may be given to a student wearing one of MR student devices 12704. Control of the virtual elements may be performed by the user of MR teacher device 12702 (or MR student devices 12704) with gestures, gazes, voice inputs, combinations or gestures gazes or voice inputs, or other techniques used for MR or VR control and manipulations of virtual content.

In some examples, MR educational content 12706 may comprise surgical guidance information and this surgical guidance information may allow the user of MR teacher device 12702 to train the user of MR student device 12704 on the surgical procedure. In such cases, MR educational content 12706 may comprise one or more virtual elements that include a 3D virtual representation of one or more anatomical features, as well as virtual guidance elements or information to guide a user on surgical steps shown or illustrated relative to the 3D virtual representation of one or more anatomical features. In other examples, the MR educational content 12706 may comprise one or more virtual elements positioned relative to a physical (e.g., synthetic) anatomical model or anatomy of a cadaver. Example physical anatomical models are commercially available from Sawbones USA, Vashon Island, Wash., USA. Cadaver anatomy may include an entire cadaver or cadaveric specimens.

As one example, MR educational content 12706 may comprise a virtual reaming axis positioned relative to a virtual 3D representation of a glenoid or relative to a physical model or a glenoid bone of a cadaver. In some cases, a virtual reaming contour may also be included in MR educational content 12706. As another example, MR educational content 12706 may comprise a virtual cutting plane, such as a virtual humeral cutting plane shown relative to a 3D virtual representation of a humeral head or a virtual cutting plane relative to a physical model of a humeral bone or the humeral bone of a cadaver. In other examples, MR educational content 12706 may comprise a virtual jig or guide and may illustrate placement of the virtual jig or guide relative to a 3D virtual representation of one or more anatomical features (such as a virtual glenoid) or positioned relative to a physical model or anatomy of a cadaver. In other examples, MR educational content 12706 may illustrate a virtual drilling point or virtual drilling axis for insertion of a guide post into a 3D virtual representation of a glenoid (or other virtual anatomical model) or for insertion of a guide post into a physical anatomical model or the cadaver. In such examples, MR educational content 12706 may also illustrate a virtual axis relative to the virtual jig or guide. In still other examples, MR educational content 12706 may comprise virtual markers relative to a 3D virtual representation of one or more anatomical features (e.g., a virtual model) or relative to a physical model or cadaver anatomy. The virtual markers may specify locations, points or axes for drilling, reaming, grinding, preparation for an implant, attachment of an implant, or anything that might be shown for intra-operative surgical guidance with respect to anatomy of a patient. Indeed, any of the surgical guidance features described elsewhere in this disclosure could also be presented virtually by MR teacher device 12702 and MR student device 12704 relative to a virtual anatomical model (or a physical model or cadaver) to facilitate training on the surgical procedure.

The physical model may comprise a physical bone model, such as a physical bone model commercially available from Sawbones USA or another source. With the aid of mixed reality, students may practice reaming or other surgical steps on the physical bone model. In other examples, virtual tissue models can be presented to students, allowing students to perform simulated surgical cuts or other manipulations on the virtual tissue models via MR student device 12704. Gestures by a user's figures may simulate cutting on virtual tissue models via MR student device 12704 such that students can cut tissue, expose anatomical features (such as the glenoid) and place virtual implants or other components relative to the virtual tissue model. Using gestures, such as finger-based cutting gestures, students may manipulate virtual tissue models to expose layers of skin, fat, muscle, bone, or other anatomy. The virtual tissue model may be segmented, which may allow for different layers (skin, fat, muscle and bone) of the virtual tissue model to be shown, exposed and manipulated by students wearing MR student device 12704 or by a teacher wearing MR teacher device 12702. MR student device 12704 may perform finger tracking and hand tracking to illustrate virtual cuts or other manipulations on a virtual tissue model. Physical models or virtual tissue models of human shoulders may be used for shoulder surgery education, and similarly, physical models or virtual tissue models of human ankles may be used for ankle surgery education. Other types of physical models or virtual tissue models (fingers, elbows, knees, back, neck, etc.) may also be used to promote orthopedic surgical education with respect to other parts of the body.

When virtual elements are presented relative to physical models, cadavers, or virtual tissue models, it may be desirable to ensure that the virtual elements match the elements of the physical models, cadavers, or virtual models. Thus, it may be desirable to know the actual physical dimensions of the physical models, cadavers, or virtual tissue models, which may be obtained by scans or imaging. Accordingly, it may be desirable to have virtual elements that are generated or defined based on scans or images of the physical models. This can ensure that the virtual elements can be matched and properly registered to the physical models, cadavers, or virtual models. Also, in a teaching environment, it may be useful to have many identical physical models that have corresponding virtual elements that match the physical model. In this case, different students may perform actual manipulations on different identical physical models, with the aid of virtual elements and virtual guidance that is precisely defined based on the anatomy of the identical physical models.

In some examples, a system comprises a plurality of physical models of an anatomical element, wherein the plurality of physical models are substantially identical, and a computer-readable medium comprising instructions that upon execution by a visualization device, cause the visualization device to present virtual elements associated with an anatomical orthopedic surgical procedure relative to one of the physical models, wherein the virtual elements include a virtual representation of the anatomical element that is substantially identical in size and shape to the physical models.

In some examples, a system may include multiple physical models that are physically used by different students or teachers with the aid of mixed reality. For example, a system may comprise a plurality of physical models of an anatomical element wherein the plurality of physical models are substantially identical. The system may include a first visualization device configured to display a first mixed reality presentation to a first user, wherein the first mixed reality presentation includes one or more first virtual elements that are controllable by the first user while the first user is wearing the first device and wherein the one or more first virtual elements comprise a first 3D virtual representation of one or more anatomical features associated with the orthopedic surgical procedure and wherein the first 3D virtual representation is positioned relative to a first physical model of the plurality of physical models. In addition, the system may include a second visualization device configured to display a second mixed reality presentation to a second user wherein the second mixed reality presentation includes one or more second virtual elements that are controllable by the second user while the second user is wearing the second device and wherein the one or more second virtual elements comprise a second 3D virtual representation of one or more anatomical features associated with the orthopedic surgical procedure and wherein the second 3D virtual representation is positioned relative to a second physical model of the plurality of physical models. In this example, the first and second visualization devices may be used by students or teachers, and each user (the students and/or teachers) may have their own physical model and their own mixed reality presentation shown with respect to their own physical model. In some examples, physical models may be created based on images or segmentations of actual patient or cadaver anatomical elements. In this case, the physical models may be 3D printed to generate a plurality of identical 3D models, and virtual elements can be defined based on the same images or segmentations of the actual patient or cadaver anatomical elements. Students and teachers can perform trial surgical steps on their own physical model (that is a 3D representation of actual patient or cadaver anatomy) and mixed-reality virtual elements or virtual models can be presented relative to the different physical models by visualization devices worn by the students and teachers.

In these and other examples, MR educational content 12706 may be useful for training a physician on how to perform steps of an orthopedic joint repair procedure, such as any of a variety shoulder surgery procedures (e.g., such as an anatomical or reverse shoulder arthroplasty procedure) or any of a variety of ankle surgery procedures (e.g., such as an ankle arthroplasty procedures). Accordingly, in these examples, the student wearing MR student device 12704 would typically be a surgeon, although other students could also benefit from the MR-based education.

In other examples, MR educational content 12706 may comprise virtual content illustrative of a registration process for registering a virtual model to an actual anatomical feature of a patient, a physical bone or soft tissue model, or a cadaver feature. For example, MR teacher device 12702 and MR student device 12704 may be configured to perform a registration process for registering a virtual model to an actual anatomical feature, e.g., registering a virtual model of a glenoid to an actual glenoid or a physical model, such as from a cadaver or a synthetic bone model, respectively. In this case, a teacher wearing MR teacher device 12702 may comprise a medical device technician. To register a virtual model on an actual glenoid mode or a physical model, the teacher may instruct a student (e.g., a surgeon) wearing MR student device 12704 on the registration steps of "SET," "MATCH," and "RESET," described in greater detail elsewhere in this disclosure for registering a virtual model to an actual anatomical feature of a patient.

In still other examples, MR educational content 12706 may comprise virtual trialing information, e.g., to compare a virtual model of reamed bone to a virtual model of an implant to see whether the virtual model of the reamed bone has been shaped properly to receive an implant. In other words, MR educational content 12706 may include virtual elements in the form of a virtual model of implant components that can be positioned relative to a 3D virtual model (e.g., a virtual glenoid) or relative to a physical model of the glenoid or a cadaver to see whether the virtual implant fits on the virtual reamed glenoid bone, physical model, or cadaver bone. In this case, a teacher wearing MR teacher device 12702 may instruct a student wearing MR student device 12704 on the reaming process. In some cases, the student can view a virtual implant relative to a virtual model of reamed bone. In other cases, the student may actually perform the reaming process on a cadaver glenoid bone or a model glenoid bone, e.g., using virtual intra-operative guidance provided via MR student device 12704, and then MR student device 12704 and MR teacher device 12702 can present a virtual model of the implant. The student or teacher can then manipulate the position of the virtual model of the implant relative to the reamed bone or reamed model to see whether the implant fits properly. This process can provide useful training to the student on the reaming process of a shoulder surgery, as one example of an orthopedic surgical procedure task, and in this example, student may comprise a medical student, a surgeon, or any person being trained on the surgical procedure. Similar training may also be used for ankle procedures or other relatively complex orthopedic procedures, allowing students to practice an MR-guided procedure or procedure step on the talus and/or tibia of a cadaver.

In other examples, MR educational content 12706 may comprise information to aid in a registration process of a depth aid element, such as described in greater detail elsewhere in this disclosure. For example, as described in detail elsewhere in this disclosure, a depth aid element may be used to aid in depth calculations of a tooling bit, such as a reaming element, a drilling element or other another tooling bit. The registration process shown and described, for example, with reference to FIGS. 80-82 may be implemented by MR student device 12704 and MR teacher device 12702 in order to train a student (e.g., a surgeon) on how to perform the registration process. In some cases, the teacher wearing the MR teacher device 12702 may comprise a medical device technician that may train surgeons on how to perform the registration process on the depth aid element.

In other examples, MR educational content 12706 may comprise virtual information on surgical tool or implant component selection or virtual aids, such as virtual elements that identify tools or implant components for use in an orthopedic surgical procedure. Indeed, this disclosure describes many examples of virtual elements that can be presented by a visualization device in order to aid nurses or other surgical participants with tool selection. Such techniques and tools may also be useful in educational system 12701. In such cases, MR student device 12704 may be worn by a nurse or medical assistant, and MR teacher device 12702 may be worn by a person training the nurse on the surgical procedure and tool selection. MR student device 12704 and MR teacher device 12702 may present MR visualizations for nurse training that are similar to those described elsewhere in this disclosure for use by the nurse in the actual surgical procedure. Educational training on the surgical procedure, including tool selection training for the nurse, may help to improve the surgical procedure.

In some examples, MR educational content 12706 may relate to planning of the surgical procedure and may include implant components, size, positions, angles, reaming axis, reaming contour, cutting plane, or other features so that a student can visualize reaming of the glenoid and placement of a particular implant with cutting of the humeral bone and placement of a humeral implant, with selected sizes, positions, angles, (e.g., for different procedures such as anatomical or reverse shoulder arthroplasty). The student wearing MR student device 12704 may practice planning a surgical procedure for a particular virtual shoulder model having a particular type of problem, and the teacher wearing MR teacher device 12702 may train the student on multiple different shoulder models representing different shoulder problems, different shoulder classifications, and/or different types of surgery to be planned.

In other examples, MR educational content 12706 may comprise virtual training information or virtual visual aids on the use of automated tools that includes closed loop control. For example, automated tools have been described herein for use in an orthopedic surgical procedure whereby the tools can be automatically enabled or disabled based on the use of the tool. As one example, closed loop-controlled tools have been described that may automatically disable once the tool has performed its function (such as a reamer that is disabled once a desired reaming depth is achieved). Educational training on the usage of such tools can be helpful to a surgeon. Accordingly, in some examples, MR student device 12704 and MR teacher device 12702 may present virtual elements that illustrate or demonstrate tool usage, as well as tool disabling once the tool has performed its function.

In still other examples, MR educational content 12706 may comprise MR surgical workflow guidance information, such as a step-by-step workflow or a checklist that is presented by MR student device 12704 and MR teacher device 12702. A student wearing MR student device 12704 may watch a virtual workflow that is presented as a surgeon wearing MR teacher device 12702 performs the procedure. For instance, MR student device 12702 may generate an MR visualization that contains virtual checklist items. In some cases, the virtual workflow presented to the student wearing MR student device 12704 may be different (possibly more conspicuous) than that presented to the surgeon wearing MR teacher device 12702. This can allow the student to be well informed and educated about the surgical procedure, as the procedure occurs. In this example, the student may be a medical student or possibly a surgeon (i.e., a student surgeon) that is being trained by another surgent (i.e., a teacher surgeon).

In other examples, MR educational content 12706 may comprise virtual information about range of motion. In this case, a physician or surgeon wearing MR teacher device 12702 may educate a patient wearing MR student device 12704 by showing virtual demonstrations of range of motion information associated with an orthopedic surgical procedure, such as a shoulder surgery. Also, MR educational content 12706 comprising range of motion information may also be useful for training surgeons, medical students, or others on the range of motion affects associated with a surgical step. For example, MR educational content 12706 may comprise range of motion information indicative or range of motion (or loss of range of motion) associated with the implantation of a particular implant. If, for example, an incorrectly sized or positioned implant is implanted in a patient, this may have negative consequences on range of motion. MR teacher device 12702 and MR student device 12704 may present range of motion visualizations showing the likely range of motion consequences associated with a particular implant. In this case, for example, MR educational content 12706 may comprise range of motion information or range of motion demonstrations that virtually illustrate possible impingement points over a desired range of motion, where the impingements may be caused by an incorrectly sized or positioned implant. In some cases, MR educational content 12706 may include virtual markers of likely impingement points due to placement of an implant in a patient.

In yet other examples, MR educational content 12706 may comprise virtual pre-operative animations, e.g., which may show desirable results or problems associated with any given implantation or implantation procedure. For example, MR teacher device 12702 and MR student device 12704 may present virtual animations showing possible impingements associated with the implantation of an incorrectly sized implant. Similarly, MR teacher device 12702 and MR student device 12704 may present virtual animations showing a desirable outcome associated with the implantation of a correctly sized implant. In some cases, MR teacher device 12702 and MR student device 12704 may present instant virtual feedback to the teacher and the student, which demonstrates or illustrates ramifications (e.g., desirable outcomes, or undesirable impingements or loss of range of motion) associated with a particular implant or a particular implantation procedure.

Educational system 12701 of FIG. 127 is one example of a system that can demonstrate at least one aspect of an orthopedic surgical procedure. A first device (e.g., MR teacher device 12702) can be configured to display a presentation to a first user (i.e., a teacher), wherein the presentation includes one or more virtual elements that are controllable by the first user while the first user is wearing the first device, wherein the one or more virtual elements comprise a 3D virtual representation of one or more anatomical features associated with the orthopedic surgical procedure. A second device (e.g., MR student device 12704) may also be configured to display the presentation to a second user, wherein the one or more virtual elements further include one or more virtual pre-operative plan elements relative to the 3D virtual representation, one or more virtual surgical guidance features relative to the 3D virtual representation, one or more surgical results virtually illustrated on the 3D virtual representation so as to demonstrate at least one aspect of the orthopedic surgical procedure. Demonstrating at least one aspect of the orthopedic surgical procedure, for example, may comprise presenting virtual pre-operative plan elements relative to the 3D virtual representation, presenting one or more virtual surgical guidance features relative to the 3D virtual representation, and/or presenting one or more surgical results virtually illustrated on the 3D virtual representation so as to demonstrate at least one aspect of the orthopedic surgical procedure.

The one or more virtual elements that are controllable by the first user while the first user is wearing the first device and viewable by the second user while the second user is wearing the second device may facilitate education on an orthopedic surgical procedure. MR educational content 12706 may comprise the one or more virtual elements that are controllable by the first user while the first user is wearing the first device (e.g., MR teacher device 12702) and viewable by the second user while the second user is wearing the second device (e.g., MR student device 12704).

The one or more virtual elements may include a 3D virtual representation of one or more anatomical features associated with the orthopedic surgical procedure. In some examples, the one or more virtual elements may illustrate a virtual cutting axis relative to the 3D virtual representation. In some examples, the one or more virtual elements may illustrate a virtual reaming axis relative to the 3D virtual representation. In some examples, the one or more virtual elements may illustrate a virtual drilling axis relative to the 3D virtual representation. In some examples, the one or more virtual elements may illustrate placement of a virtual jig or guide relative to 3D virtual representation. In some examples, the one or more virtual elements may illustrate a virtual axis relative to a virtual jig or guide. In some examples, the one or more virtual elements may comprise surgical guidance information presented relative to the 3D virtual representation. In some examples, the one or more virtual elements may illustrate a registration process for registering the 3D virtual representation to a physical model or a corresponding feature of a cadaver. In some examples, the one or more virtual elements may include trialing information associated with a prepared implantation location for implant component. In some examples, the one or more virtual elements may illustrate a registration process for registering a depth aid element. In some examples, the one or more virtual elements may comprise virtual training information or virtual visual aids on the use of automated tools that include closed loop control. In some examples, the one or more virtual elements may comprise virtual information about range of motion. In some examples, the one or more virtual elements may comprise a virtual pre-operative animation. In some examples, the one or more virtual elements may illustrate one or more virtual implant components relative to the 3D virtual representation.

Figure 128:
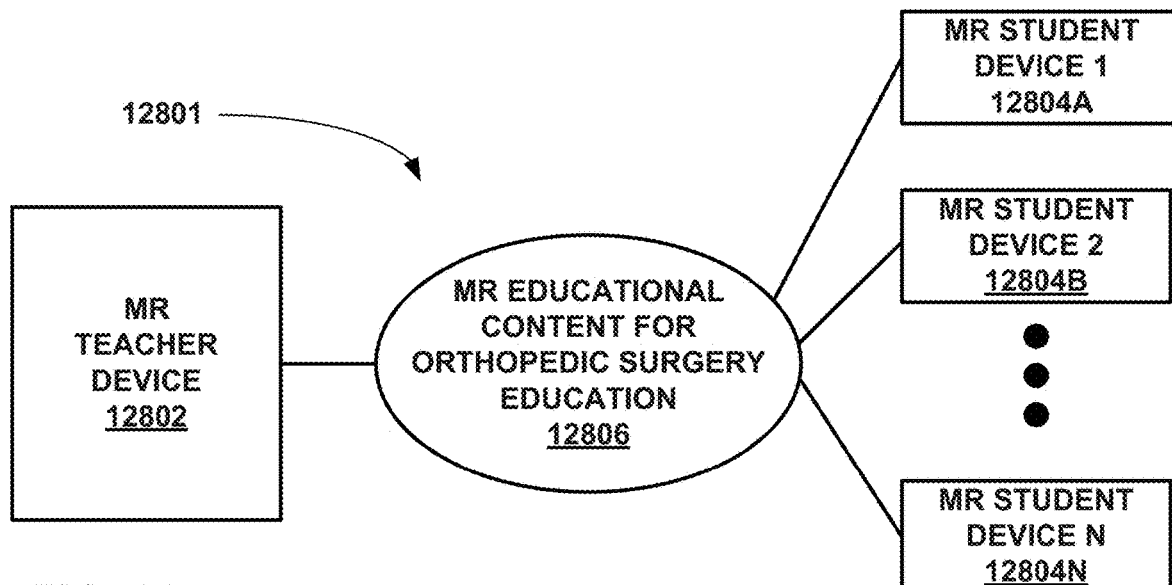
FIG. 128 is a conceptual block diagram of an educational system comprising an MR teacher device and a plurality of MR student devices for orthopedic surgical education.

FIG. 128 is a conceptual block diagram of an educational system 12801 comprising an MR teacher device 12802 and a plurality of MR student devices 12804A and 12804B through 12804N (collectively student devices 12804). MR teacher device 12802 and MR student devices 12804 may each comprise a visualization device 213, which is described in detail throughout this disclosure. MR teacher device 12802 may present the teacher with MR educational content for orthopedic surgery education 12806. Similarly, MR student devices 12804 may present the student with similar MR educational content for orthopedic surgery education 12806. The MR educational content 12806, along with the tutelage of the teacher wearing MR teacher device 12802, may help to educate the student wearing MR student device 12804.

MR educational content 12806 may comprise content that is similar or identical to MR educational content 12706 shown and described in FIG. 127. Moreover, MR educational content 12806 may comprise any of the MR content disclosed elsewhere in this disclosure, which may also be used for surgical guidance, surgical planning, post-operative analysis or other reasons. Indeed, MR educational content 12806 may comprise any of a wide variety of MR content described herein. In some cases, MR student devices 12804 and/or MR teacher device 12802 may comprise both a visualization device that presents virtual elements to a user and a haptic device that provides touch-based information to a user.

As with other examples, the actual MR content used in any given educational setting, however, may depend on the student that is being educated. For example, educational system 12801 may be used to educate or train physicians, medical students, technicians, nurses, physician assistants, or any other persons (such as patients, caregivers, guardians, family or others) that may be involved in an orthopedic medical procedure. Alternatively, educational system 12801 may be used to educate a patients, family and friends about a procedure to be performed on a patient. In still other cases, educational system 12801 may be used to educate researchers or any other person that may have interests or reasons to learn one or more details about an orthopedic surgical procedure. According to FIG. 128, multiple students associated with MR student devices 12804 may benefit from the teaching of a teacher using MR teacher device 12802.

Educational system 12801 of FIG. 128 is another example of a system that can demonstrate at least one aspect of an orthopedic surgical procedure. A first device (e.g., MR teacher device 12802) can be configured to display a presentation to a first user (i.e., a teacher), wherein the presentation includes one or more virtual elements that are controllable by the first user while the first user is wearing the first device and wherein the one or more virtual elements comprise a 3D virtual representation of one or more anatomical features associated with the orthopedic surgical procedure. A second device (e.g., one of MR student devices 12804) may also be configured to display the presentation to a second user. The one or more virtual elements may further include one or more virtual pre-operative plan elements relative to the 3D virtual representation, one or more virtual surgical guidance features relative to the 3D virtual representation, or one or more surgical results virtually illustrated on the 3D virtual representation so as to demonstrate at least one aspect of the orthopedic surgical procedure.

For shoulder surgery educational examples, the virtual representation of the one or more anatomical features that forms part of MR educational content 12806 may comprise a 3D virtual model of a human shoulder. As another example, the virtual representation of the one or more anatomical features that forms part of MR educational content 12806 may comprise a 3D virtual illustration of a humeral head or a 3D virtual illustration of a glenoid. However, for other types of orthopedic surgery educational examples, different types of virtual 3D models of anatomical features may be presented in MR educational content 12806. For example, ankle surgery education may involve the presentation of a 3D virtual illustration of a human ankle or 3D virtual illustrations of the talus and/or the tibia.

One or more virtual elements that are controllable by the first user while the first user wearing the first device and viewable by the second user while the second user is wearing the second device may facilitate education on an orthopedic surgical procedure. MR educational content 12806 may comprise the one or more virtual elements that are controllable by the first user while the first user is wearing the first device (e.g., MR teacher device 12802) and viewable by the second user while the second user is wearing the second device (e.g., one of MR student devices 12804). The one or more virtual elements may include any of those described above (or combinations of those described above) with regard to MR educational content 12706 of FIG. 127.

Figure 129:
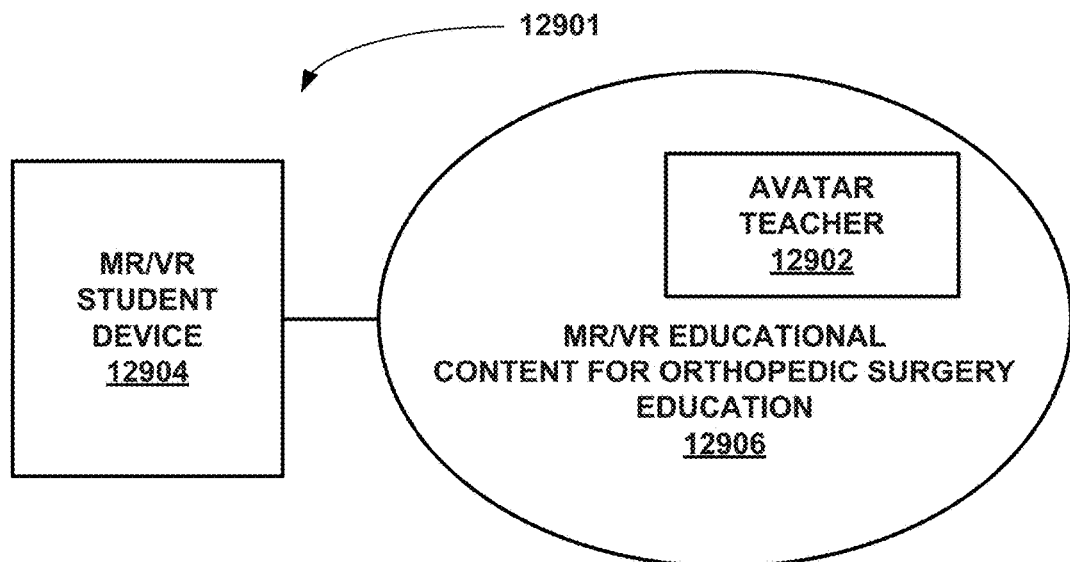
FIG. 129 is a conceptual block diagram of an educational system for orthopedic surgical education to be used by a student without a live teacher.

FIG. 129 is a conceptual block diagram of an educational system 12901. Educational system 12901 comprises an MR/VR student device 12904, which may each comprise a mixed reality device, such as visualization device 213 described in detail throughout this disclosure, or a virtual reality device that presents only virtual information and no real-world views. MR/VR student device 12904 may present the student with MR/VR (mixed reality or virtual reality) educational content for orthopedic surgery education 12906.

In this example, however, the MR/VR educational content 12906 includes an avatar teacher 12902.

In the example of FIG. 129, MR/VR educational content may comprise pre-recorded content presented by a pre-recorded avatar teacher 12902. The user of MR student device 12904 may select content from a menu or list and may view the content via MR student device 12904. In some cases, MR student device 12904 may include a visualization device that presents virtual elements to a user and a haptic device that provides touch-based information to the user.

Similar to MR educational content 12706 of FIG. 127 and MR educational content 12806 of FIG. 128, MR/VR educational content 12906 shown in FIG. 129 may comprise any of the virtual content disclosed elsewhere in this disclosure. For example, MR/VR educational content 12906 may comprise any of a wide variety of content described herein, such as one or more virtual elements including a 3D virtual representation of one or more anatomical features associated with the orthopedic surgical procedure. In addition to the 3D virtual representation (e.g., a virtual model of a human shoulder, a virtual model of a glenoid or glenoid surface, or a virtual model of a humeral bone or humeral head), MR/VR educational content 12906 may comprise additional virtual content. This additional virtual content may include any of the content virtual content or virtual elements (or combinations of such virtual elements) described above with regard to MR educational content 12706 of FIG. 127.

As with other examples, the actual content used in any given educational setting, however, may depend on the student that is being educated. For example, educational system 12901 may be used to educate or train physicians, medical students, technicians, nurses, physician assistants, or any other persons (such as patients, caregivers, guardians, family or others) that may be involved in an orthopedic medical procedure. In many cases, however, educational system 12901 may be useful to educate a patients, family and friends about a procedure to be performed on a patient. For example, MR/VR educational content 12906 may comprise virtual information stored on a server that is accessible to users wearing MR/VR student device 12904. Pre-recorded orthopedic surgery content may be especially useful for educating non-expert users, such as patients, family and friends of a patient.

Figure 130:
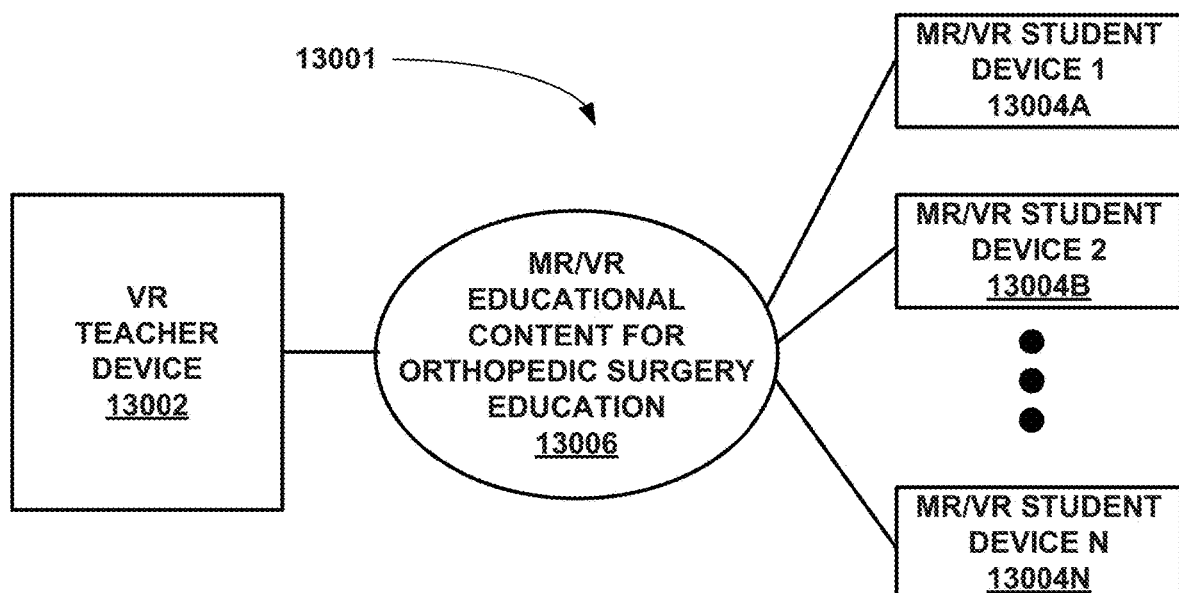
FIG. 130 is a conceptual block diagram of an educational system for orthopedic surgical education to be used by a teacher that is located remotely relative to students.

FIG. 130 is a conceptual block diagram of an educational system 13001, which may be useful for a remote teaching environment. In the example shown in FIG. 130, the teacher may be located remotely relative to the students, and the teacher may wear VR teacher device 13002, which may comprise a virtual reality device. Students may interact with the teacher via MR/VR student devices 13004A and 13004B through 13004N (collectively MR/VR student devices 13004).

MR/VR student devices 13004 may each comprise a mixed reality device, such as visualization device 213 described in detail throughout this disclosure, or a virtual reality device that presents only virtual information and no real-world views. MR/VR student devices 13004 may present each student with MR/VR (mixed reality or virtual reality) educational content for orthopedic surgery education 13006. Similar to MR educational content 12706 of FIG. 127 and MR educational content 12806 of FIG. 128, and MR/VR educational content 12906 of FIG. 128, MR/VR educational content 13006 of FIG. 130 may comprise any of the virtual content disclosed elsewhere in this disclosure. In some cases, MR/VR student devices 13004 and/or VR teacher device 13002 may comprise both a visualization device that presents virtual elements to a user and a haptic device that provides touch-based information to that same user.

MR/VR educational content for orthopedic surgery education 13006 may comprise a 3D virtual representation of one or more anatomical features associated with the orthopedic surgical procedure. In addition to the 3D virtual representation (e.g., a virtual model of a human shoulder, a virtual model of a glenoid or glenoid surface, or a virtual model of a humeral bone or humeral head), MR/VR educational content 13006 may comprise additional virtual content. This additional virtual content may include one or more additional virtual elements such as any of those described above (or combinations of those described above) with regard to MR educational content 12706 of FIG. 127.

As with other examples, the actual content used in any given educational setting, however, may depend on the student that is being educated. For example, educational system 13001 may be used to educate or train physicians, medical students, technicians, nurses, physician assistants, or any other persons (such as patients, caregivers, guardians, family or others) that may be involved in an orthopedic medical procedure. Moreover, the use of virtual reality (e.g., VR teacher device 13002) can allow the teacher to located remotely relative to the students. In this example, the students may use either mixed reality or virtual reality (e.g., MR/VR student devices 13004) to interact with the teacher wearing VR teacher device 13002 and to view MR/VR educational content 13006, which may be selected, presented or otherwise assigned to the students by the teacher.

Educational system 13001 of FIG. 130 is another example of a system that can demonstrate at least one aspect of an orthopedic surgical procedure. A first device (e.g., VR teacher device 13002) can be configured to display a presentation to a first user (i.e., a teacher), wherein the presentation includes one or more virtual elements that are controllable by the first user wearing the first device and wherein the one or more virtual elements comprise a 3D virtual representation of one or more anatomical features associated with the orthopedic surgical procedure. A second device (e.g., one of MR/VR student devices 13004) may also be configured to display the presentation to a second user. The one or more virtual elements may further include one or more virtual pre-operative plan elements shown relative to the 3D virtual representation, one or more virtual surgical guidance features shown relative to the 3D virtual representation, or one or more surgical results virtually illustrated on the 3D virtual representation so as to demonstrate at least one aspect of the orthopedic surgical procedure.

The one or more virtual elements that are controllable by the first user wearing the first device and viewable by the second user wearing the second device may facilitate education on an orthopedic surgical procedure. For example, MR/VR educational content 13006 may comprise any of a wide variety of content described herein and may include a 3D virtual representation of one or more anatomical features associated with the orthopedic surgical procedure. In addition to the 3D virtual representation (e.g., a virtual model of a human shoulder, a virtual model of a glenoid or glenoid surface, or a virtual model of a humeral bone or humeral head), MR/VR educational content 13006 may comprise additional virtual content. This additional virtual content may include any of the virtual elements (or combinations) described with regard to MR educational content 12706 of FIG. 127.

Figure 131:
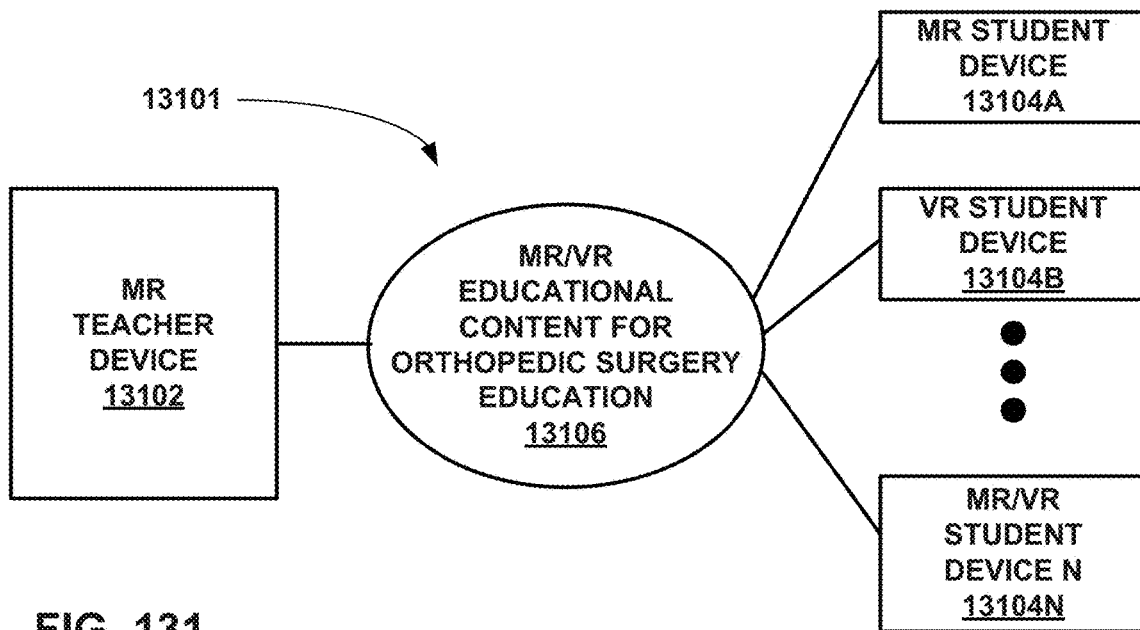

FIG. 131 is another conceptual block diagram of an educational system, e.g., educational system 13101, which may be useful for a remote teaching environment. In this example, a teacher may wear MR teacher device 13102 to present MR/VR educational content 13106 to various students. A first student may wear MR student device 13104A, such as visualization device 213 described in detail throughout this disclosure. The first student and the teacher may be physically located in the same room to facilitate a shared MR experience. A second student, however, may be located remotely relative to the teacher and may wear VR student device 13104B to participate in the teaching exercise. VR student device 13104B may present only virtual information and no real-world views. In some cases, the teacher and the other students (e.g., the teacher wearing MR teacher device 13102 and the first student wearing MR student device 13104A) may be presented as avatars in the VR presentation of VR student device 13104B, giving the perception that the students and teacher are all located in the same room even though the student associated with VR student device 13104B is located remotely. Similarly, the second student may also be presented as an avatar to the teacher wearing MR teacher device 13102 and the first student wearing MR student device 13104A. FIG. 131 also illustrates MR/VR student device N 13104N, which generally means that any number of MR or VR participants may be present in the educational session. In some cases, MR devices may be used by participants that are located remotely relative to one another, in which case, users may share views of virtual elements without sharing the same real-world views.

Like the examples shown in FIGS. 127, 128, 129 and 130, in the example of FIG. 131, MR/VR educational content 13106 may comprise any of the virtual content disclosed elsewhere in this disclosure such as one or more virtual elements including a 3D virtual representation of one or more anatomical features associated with the orthopedic surgical procedure. In addition to the 3D virtual representation (e.g., a virtual model of a human shoulder, a virtual model of a glenoid or glenoid surface, or a virtual model of a humeral bone or humeral head), MR/VR educational content 13006 may comprise additional virtual content. This additional virtual content may include one or more virtual elements presented relative to the 3D virtual representation and may include any of those described above (or combinations of those described above) with regard to MR educational content 12706 of FIG. 127. Also, in some cases, student devices 13104 and/or MR teacher device 13102 may comprise both a visualization device that presents virtual elements to a user and a haptic device that provides touch-based information to the user.

As with other examples, the actual content used in any given educational setting, however, may depend on the student that is being educated. For example, educational system 13101 may be used to educate or train physicians, medical students, technicians, nurses, physician assistants, or any other persons (such as patients, caregivers, guardians, family or others) that may be involved in an orthopedic medical procedure. Moreover, the use of virtual reality (e.g., VR student device 13104B) can allow one or more of the students to be located remotely relative to the teacher, who in this example, wears MR teacher device MR teacher device 13102. At the same time, however, the teacher may be able to view and interact with any local students, such as a student wearing MR student device 13104B.

Educational system 13101 of FIG. 131 is another example of a system that can demonstrate at least one aspect of an orthopedic surgical procedure. A first device (e.g., MR teacher device 13102) can be configured to display a presentation to a first user (i.e., a teacher), wherein the presentation includes one or more virtual elements that are controllable by the first user wearing the first device and wherein the one or more virtual elements comprise a 3D virtual representation of one or more anatomical features associated with the orthopedic surgical procedure. A second device (e.g., MR student device 13104A or VR student device 13104B) may also be configured to display the presentation to a second user. The one or more virtual elements may further include one or more virtual pre-operative plan elements shown relative to the 3D virtual representation, one or more virtual surgical guidance features shown relative to the 3D virtual representation, or one or more surgical results virtually illustrated on the 3D virtual representation so as to demonstrate at least one aspect of the orthopedic surgical procedure.

The one or more virtual elements that are controllable by the first user wearing the first device and viewable by the second user wearing the second device may facilitate education on an orthopedic surgical procedure. MR educational content 13106 may comprise the one or more virtual elements that are controllable by the first user wearing the first device (e.g., MR teacher device 13102) and viewable by the second user wearing the second device (e.g., MR student device 13104A or MR student device 13104B).

Figure 132:
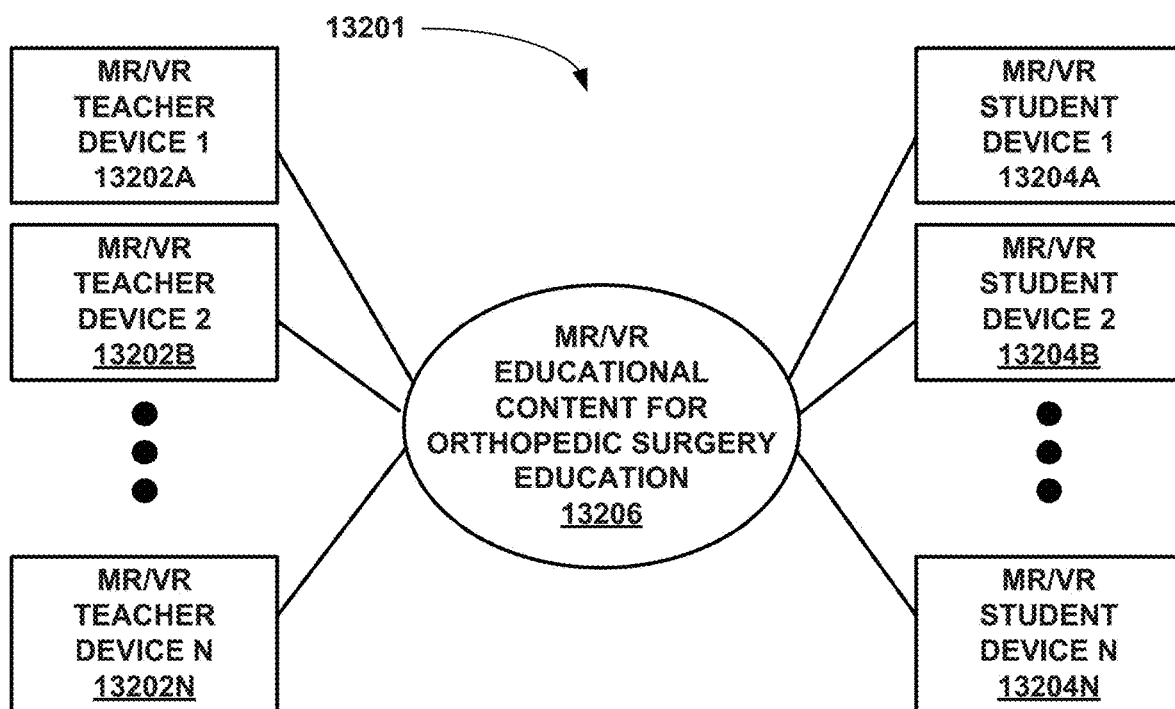
Figure 133:
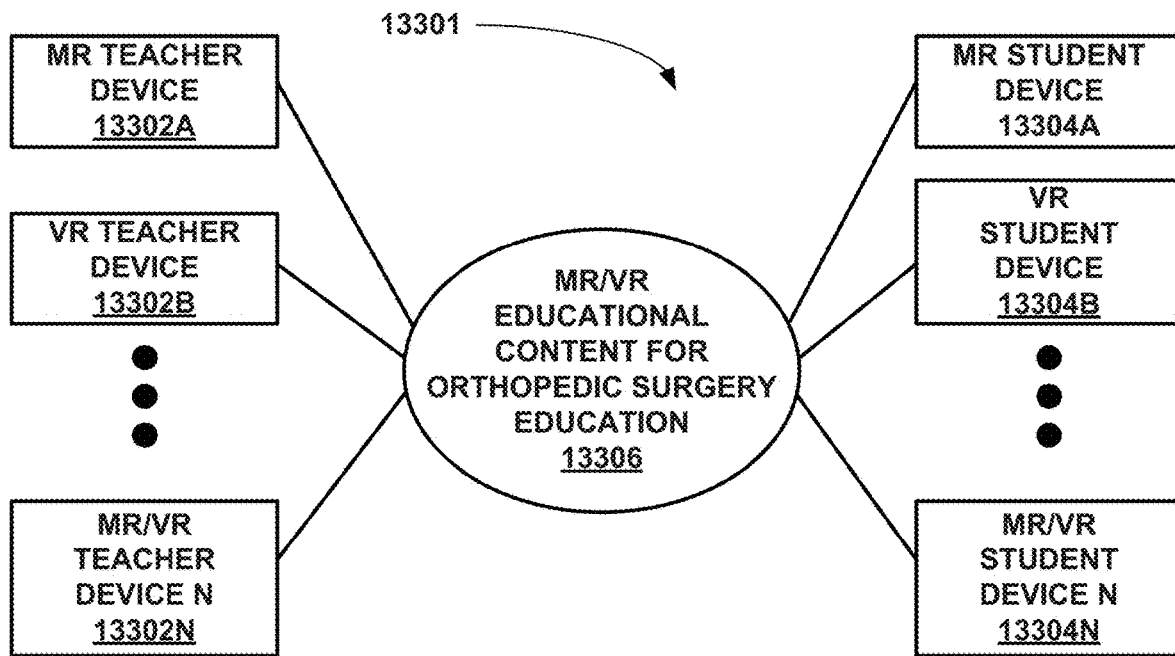

FIGS. 132 and 133 are conceptual block diagrams of other educational systems 13201 and 13301 that use mixed reality and virtual reality for orthopedic surgical education. In the example of FIG. 132, multiple teachers wear MR/VR teacher devices 13202A and 13202B through 13202N (collectively MR/VR teacher devices 13202). Moreover, in the example of FIG. 132, multiple students wear MR/VR student devices 13204A and 13204B through 13204N (collectively MR/VR student devices 13204). In this example, any of the participants (teachers or students) may participate in the teaching session using mixed reality or virtual reality. That is to say, any of MR/VR teacher devices 13202 and MR/VR student devices 13204 may comprise mixed reality devices such as visualization device 213, or alternatively, MR/VR teacher devices 13202 and MR/VR student devices 13204 may comprise virtual reality devices the present only virtual information, in which case real-world information presented to users wearing mixed reality devices may be presented as virtual information to users wearing virtual reality devices. Moreover, MR users wearing mixed reality devices may be presented as avatars to VR users wearing virtual reality devices, and VR users wearing virtual reality devices may be presented as avatars to MR users wearing mixed reality devices.

The example of FIG. 133 is somewhat similar to that of FIG. 132. In the example of FIG. 133, a first teacher wears MR teacher device 13302A and a second teacher wears VR teaching device 13302B. Moreover, in the example of FIG. 133, a first student wears MR student device 13304A and a second student wears VR student device 13304B. Additional teachers or students may also be present using mixed reality or virtual reality, as generally illustrated by MR/VR teacher device N 13302N and MR/VR student device N 13304N. In general, any MR device (e.g., MR teacher device 13302A and MR student device 13304B) uses mixed reality whereas any VR device (e.g., VR teacher device 13302B or VR student device 13304 uses virtual reality).

According to the example shown in FIG. 133, real-world information or objects viewed by users wearing mixed reality devices (such as MR teacher device 13302A and MR student device 13304A) may be presented as virtual information to users wearing virtual reality devices (such as VR teacher device 13302B and VR student device 13304B). For example, a user of MR teacher device 13302A may view a real-world object (such as a cadaver) and that real-world object may be presented to VR devices (such as VR teacher device 13302B and VR student device 13304B) as a virtual object. Moreover, MR users wearing mixed reality devices may be presented as avatars to VR users wearing virtual reality devices, and VR users wearing virtual reality devices may be presented as avatars to MR users wearing mixed reality devices.

Similar to the other examples shown in FIGS. 127, 128, 129, 130, and 131, in the examples of FIGS. 132 and 133, MR/VR educational content 13206 or 13306 may comprise any of the virtual content disclosed elsewhere in this disclosure. For example, MR/VR educational content 13206 may comprise any of a wide variety of content described herein, such as one or more virtual elements including a 3D virtual representation of one or more anatomical features associated with the orthopedic surgical procedure. In addition to the 3D virtual representation (e.g., a virtual model of a human shoulder, a virtual model of a glenoid or glenoid surface, or a virtual model of a humeral bone or humeral head), MR/VR educational content 13206 may comprise additional virtual content. This additional virtual content may include any of the virtual elements described above (or combinations of those described above) with regard to MR educational content 12706 of FIG. 127. Also, in some cases, student devices 13304, 13404 and/or teacher devices 13302, 13402 may each comprise both a visualization device that presents virtual elements to a user and a haptic device that provides touch-based information to the user.

Again, the actual content used in any given educational setting, however, may depend on the student that is being educated. For example, educational system 13201 or 13301 may be used to educate or train physicians, medical students, technicians, nurses, physician assistants, or any other persons (such as patients, caregivers, guardians, family or others) that may be involved in an orthopedic medical procedure. Moreover, the use of virtual reality (e.g., VR teacher device 13302B or VR student device 13304B) can allow one or more of the students and teachers to be located remotely relative to one another. At the same time, any users of mixed reality (e.g., MR teacher device 13302A or MR student device 13304A) may be able to view and interact with other local participants using mixed reality.

Educational system 13201 of FIG. 132 is another example of a system that can demonstrate at least one aspect of an orthopedic surgical procedure. A first device (e.g., one of MR/VR teacher devices 13202) can be configured to display a presentation to a first user (i.e., a teacher), wherein the presentation includes one or more virtual elements that are controllable by the first user wearing the first device and wherein the one or more virtual elements comprise a 3D virtual representation of one or more anatomical features associated with the orthopedic surgical procedure. A second device (e.g., one of MR/VR student devices 13204) may also be configured to display the presentation to a second user. The one or more virtual elements may further include one or more virtual pre-operative plan elements shown relative to the 3D virtual representation, one or more virtual surgical guidance features shown relative to the 3D virtual representation, or one or more surgical results virtually illustrated on the 3D virtual representation so as to demonstrate at least one aspect of the orthopedic surgical procedure.

The one or more virtual elements that are controllable by the first user wearing the first device and viewable by the second user wearing the second device may facilitate education on an orthopedic surgical procedure. MR educational content 13206 may comprise the one or more virtual elements that are controllable by the first user wearing the first device (e.g., one of MR/VR teacher devices 13202) and viewable by the second user wearing the second device (e.g., one of MR/VR student devices 13204).

Educational system 13301 of FIG. 133 is another example of a system that can demonstrate at least one aspect of an orthopedic surgical procedure. A first device (e.g., MR teacher device 13302A or VR teacher device 13302B) can be configured to display a presentation to a first user (i.e., a teacher), wherein the presentation includes one or more virtual elements that are controllable by the first user wearing the first device and wherein the one or more virtual elements comprise a 3D virtual representation of one or more anatomical features associated with the orthopedic surgical procedure. A second device (e.g., MR student device 13304A or VR student device 13304B) may also be configured to display the presentation to a second user. The one or more virtual elements may further include one or more virtual pre-operative plan elements shown or illustrated relative to the 3D virtual representation, one or more virtual surgical guidance features shown or illustrated relative to the 3D virtual representation, or one or more surgical results virtually illustrated on the 3D virtual representation so as to demonstrate at least one aspect of the orthopedic surgical procedure.

The one or more virtual elements that are controllable by the first user wearing the first device and viewable by the second user wearing the second device may facilitate education on an orthopedic surgical procedure. MR educational content 13306 may comprise the one or more virtual elements that are controllable by the first user wearing the first device (e.g., MR teacher device 13302A or VR teacher device 13302B) and viewable by the second user wearing the second device (e.g., MR student device 13304A or VR student device 13304). In various examples, the one or more virtual elements may include any of the virtual elements any of those described above (or combinations of those described above) with regard to MR educational content 12706 of FIG. 127.

Figure 134:
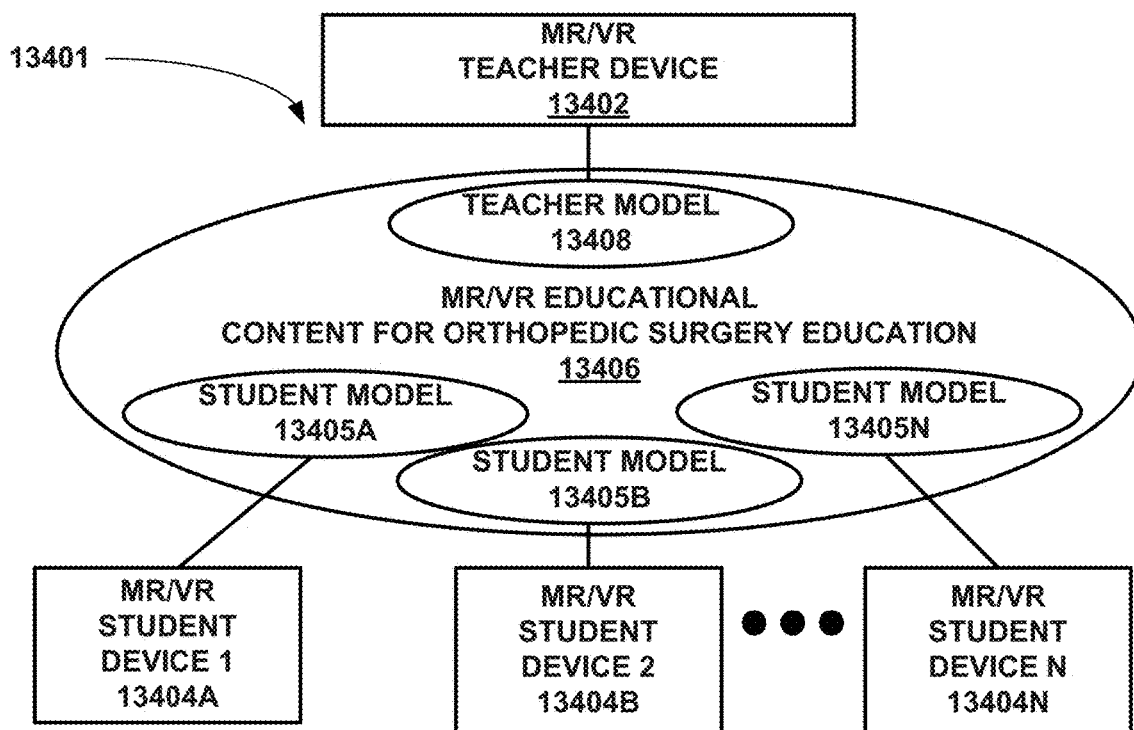

FIG. 134 is another conceptual block diagram of an educational system, e.g., educational system 13401 that uses mixed reality and/or virtual reality for orthopedic surgical education. In the example of FIG. 134, a teacher wears MR/VR teacher device 13402 and multiple students wear MR/VR student devices 13404A and 13404B through 13404N (collectively MR/VR student devices 13404). In this example, any of the participants (teacher or students) may participate in the teaching session using mixed reality or virtual reality. That is to say, any of MR/VR teacher device 13402 and MR/VR student devices 13404 may comprise mixed reality devices such as visualization device 213, or alternatively, MR/VR teacher device 13402 and MR/VR student devices 13404 may comprise virtual reality devices that present only virtual information, in which case real-world information presented to users wearing mixed reality devices may be presented as virtual information to users wearing virtual reality devices and the virtual information may be based on real world objects viewed by users of MR devices. MR/VR educational content 13406 may comprise any of the virtual content disclosed elsewhere in this disclosure, such as any of the educational content described with respect to FIGS. 127-133 or elsewhere in this disclosure. In addition, with the example shown in FIG. 134, MR/VR educational content 13406 may include multiple different virtual models to be used and manipulated by the students and the teacher, which are shown in FIG. 13408 as teacher model 13408 and student model 13405A and 13405B through 13405N (collectively referred to as student models 13405). The separate virtual models for students and teachers may comprise virtual content, such as student and teacher copies of virtual models (e.g., student and teacher copies of 3D virtual models of a human shoulder, student and teacher copies of 3D virtual models of a segment of a human shoulder, student and teacher copies of a 3D virtual illustration of a humeral head, or student and teacher copies of a 3D virtual illustration of a glenoid). In addition, virtual student and teacher content may include additional virtual elements presented relative to such virtual models 13408 and 13405.

Educational system 13401 may be useful in demonstrating at least one aspect of an orthopedic surgical procedure. System 13401 may comprise a first device (e.g., MR/VR teacher device 13402) configured to display a presentation to a first user wherein the presentation includes teacher model 13408 in the form of a 3D virtual illustration of an anatomical element, wherein teacher model 13408 is controllable by the first user (i.e., the teacher) wearing the first device. System 13401 may further comprise a second device (e.g., one of MR/VR student devices 13404) configured to display the presentation to a second user (e.g., one of the students) wherein the presentation also one of student models 13405 in the form of an additional 3D virtual illustrations of the anatomical element, wherein the student model (one of models 13405) is controllable by the second user (i.e., one of the students) wearing the first device.

In addition to the 3D virtual illustrations of an anatomical element, teacher model 13408 may include additional virtual elements (such as one more of those described above with regard to FIGS. 127-133) to demonstrate at least one aspect of the orthopedic surgical procedure. Moreover, student models 13405A, 13405B or 13405N) may likewise include such additional virtual elements (like one or more of those described above with regard to FIGS. 127-133). In other words, additional virtual elements may be presented relative to student models 13405A, 13405B or 13405N and teacher model 13408 and such virtual elements may comprise any of the virtual elements disclosed and described elsewhere in this disclosure, such as any of those described above (or combinations of those described above) with regard to MR educational content 12706 of FIG. 127, or virtual elements described elsewhere in this disclosure. Also, in some examples, MR/VR student devices 13404 and/or MR/VR teacher device 13402 may comprise both a visualization device that presents virtual elements to a user and a haptic device that provides touch-based information to the user.

The use of separate virtual models for different students may be highly useful for orthopedic surgical education. In some examples, teacher model 13408 may comprise a virtual model of an anatomical feature, which may be registered to an actual bone or soft tissue model (such as an artificial model of bone or actual bone of a cadaver). Similarly, in some examples, student models 13405 may comprise virtual models of an anatomical feature, which may be registered to corresponding physical models or cadaver bones. In other examples, however, teacher model 13408 and student models 13405 may be used for education without the need for any physical models or cadavers. If virtual models are being registered to an actual physical model or a cadaver, then typically MR would be used to combine virtual elements (such as a virtual model) with real world views that include the actual physical model or cadaver.

A teacher wearing MR/VR teacher device 13402 may manipulate teacher model 134-09 to provide guidance and instruction to the students. Students may then attempt to properly manipulate student models 13405 based on the example and tutelage of the teacher. The teacher wearing MR/VR teacher device 13402 is able to view each of student models 13405 via MR teacher device 13402. Students wearing MR student devices 13404 may be able to view their corresponding student models (e.g., student device 1 13404A may be able to view student model 13405A, and student device 2 13404B may be able to view student model 13405B). In some cases, student devices 13404 may be able to view student models associated with other students, and in other cases, student devices 13404 may be unable to view the student models of other students. In any case, the use of different copies of virtual models for the teacher and the students can be very useful for orthopedic surgical education by allowing each student to perform their own manipulations on their corresponding virtual content. The manipulations may include any of the controls described herein, such as rotations, re-sizing, repositioning, or other movements of virtual 3D elements. In addition, manipulations may include surgical plan selections, such as selections of implants, implant sizes, surgical types, shoulder types, shoulder classifications, or other selections. Also, manipulations may include enabling or disabling of pre-operative, interoperative or post-operative animations. Any type of virtual control, movement, or virtual selection may be considered a manipulation of the virtual content. In some cases, the students and/or teacher may compare teacher model 13408 to one or more of student models 13405 to access whether the student is performing the correct steps and correct manipulations of the student content 13405.

MR/VR student devices 13404 may allow students to manipulate and control their respective student models 13405 through virtual controls, such as via gestures, gaze-based controls, voice inputs, combinations of such virtual controls, or any control technique useful in mixed reality. Also, manual keypad input, touch screen entry, pointer controls, or other types of controls may be used by students to manipulate respective student models 13405. Similarly, MR/VR teacher device 13402 may allow students to manipulate and control teacher model 13408

As noted, teacher model 13408 and student model 13405 may comprise virtual models of an anatomical feature, such as a virtual model of an example glenoid bone or an example humeral bone. In addition, teacher model 13408 and student content 13405 may include additional virtual content designed to aid in surgical steps that may be performed on the anatomical feature. For example, each of the content may include surgical guidance information, registrational content, virtual axes, planes or markers, virtual jigs, virtual guidance on surgical tools, virtual implants, virtual workflow information, virtual range of motion information, virtual operative animations, or other virtual information. Using MR/VR student devices 13404, each respective student may be allowed to manipulate their respective student model, e.g., performing surgical steps, surgical preparation, registration, setting axes for drilling or reaming, setting a cutting plane, placing a virtual gig, selecting tools, placing virtual implants, choosing virtual workflow, viewing the affects any selection may have on range of motion, and so forth. A teacher wearing MR/VR teaching device 13402 may provide an instructional example with respect to teacher model 13408 and the students wearing MR/VR/student devices 13404 may attempt to mimic the steps performed by the teacher using their own respective student content (13405A, 13405B or 13405N). Such "hands on" training can be very helpful to effectively organize, schedule, and train students. The models (as well as outcomes such as shown by virtual range of motion information) can be compared to assess the efficacy and effectiveness of student manipulations on the respective student models 13405 relative to the efficacy and effectiveness of teacher manipulations on the teacher model 13408.

Student and teacher models shown in FIG. 134 may also be very useful in an educational setting that focuses on surgical planning and surgical decisions or selections. Different students may select surgery type (e.g., anatomical vs reverse shoulder arthroplasty) or may select among different sized surgical tools or different sized surgical implants. The teacher may provide instructional guidance and tutelage using teacher model 13402 and student chooses and outcomes can be assessed by the teacher by observing and critiquing student models 13405.

FIG. 148 is a conceptual diagram showing a virtual teacher model and multiple student models, which in some examples may correspond to the teacher and student models illustrated in FIG. 134. Again, although FIG. 148 shows an example of shoulder models, similar educational techniques may be used for other joints, such as an ankle, in which case the models used by teachers and students would be 3D virtual models of ankles or portions thereof. As shown in FIG. 148, using an MR or VR device, a teacher is able to view and manipulate teacher model 14801 through virtual controls, such as via gestures, gaze-based controls, voice inputs, or any control technique useful in mixed reality or virtual reality. Also, manual keypad input, touch screen entry, pointer controls, combinations of any virtual control mechanisms, or other types of controls may be used by teacher to manipulate teacher model 14801. Using an MR or VR device, for example, a teacher may rotate, re-size, reposition, or otherwise move teacher model 14801 in space. Moreover, a teacher may show anatomical movement of bones within a shoulder socket. The example teacher model 14801 comprises a 3D model of a shoulder, along with virtual elements showing a virtual 3D representation of shoulder implant components 14803 and virtual elements showing a likely impingement point 14805 that may be caused by shoulder implantation components 14803. The teacher may be able to rotate the virtual humeral bone relative to the glenoid to show shoulder motion. The teacher may also be able to enable or disable viewing of different illustrated elements, which may be segmented. Although FIG. 148 shows models in the form of shoulder illustrations with an implant, any type of anatomical elements, virtual surgical plans, or virtual results may be presented as teacher and student models according to this disclosure in order to achieve education no orthopedic surgery.

Like the teacher's ability to manipulate and control teacher model 14801, using an MR or VR device, students can manipulate student models 14802A, 14802B and 14802N (collectively student models 14802) via virtual controls, gestures, gaze-based controls, voice inputs, manual keypad input, touch screen entry, pointer controls, combination of such virtual controls, or any control technique useful in mixed reality or virtual reality. Like the teacher, for example, students may rotate, re-size, reposition, or otherwise move student models 14802 in space. Moreover, students may enable or disable viewing of different components or segmentations of student models 14802, cause shoulder movement, enable or disable viewing of implants 14804A, 14204B and 14204N, present other implants, enable or disable viewing of impingements 14806A, 14806B, and 14806N or otherwise manipulate student models 14802. Again, the models illustrated in FIG. 148 are exemplary of some specific virtual elements that form teacher model 14801 and student models 14802. This disclosure contemplates a wide variety of 3D models that could be useful for orthopedic surgical education, including but not limited to any of the 3D models described throughout this disclosure. According to FIGS. 134 and 148, the presentation and use of different models for the teacher and the students can be very useful for educating students on orthopedic surgery, orthopedic surgery planning, and expected results.

Figure 135:
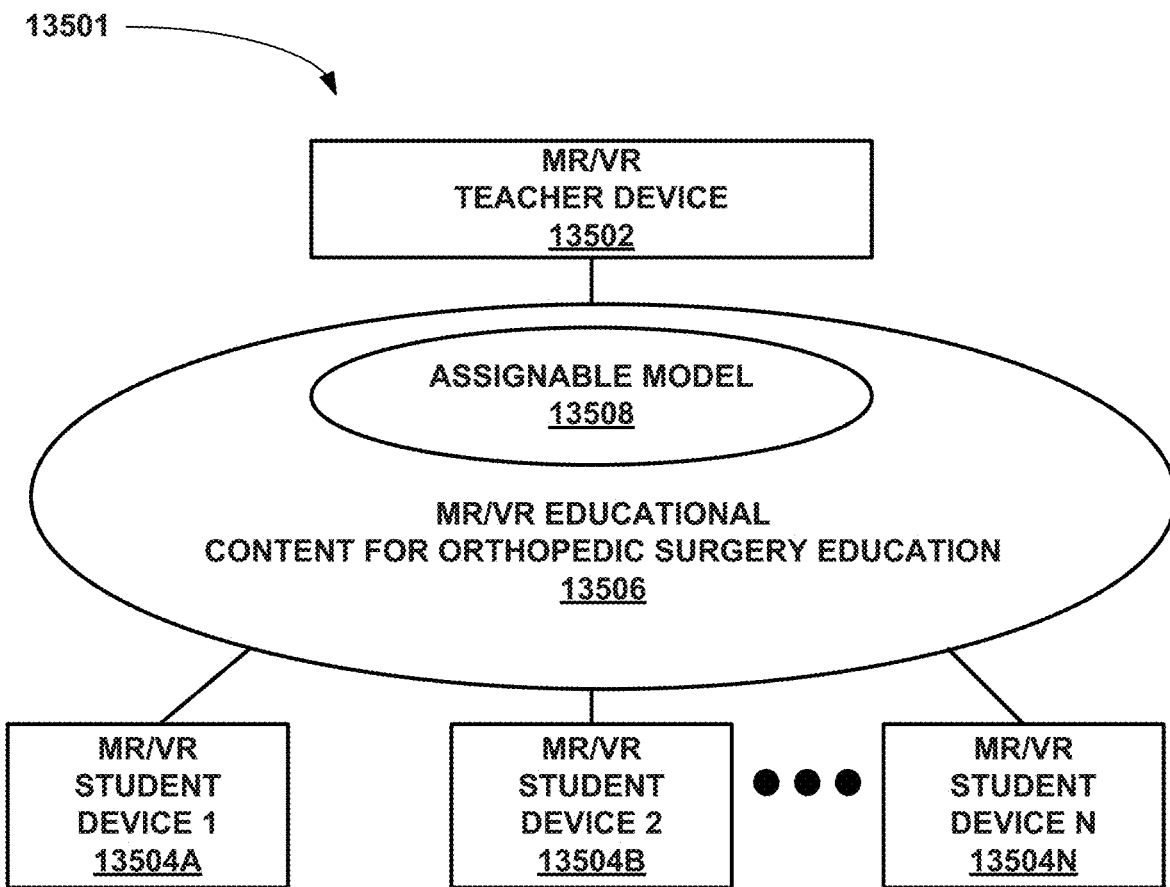

FIG. 135 is another conceptual block diagram of an educational system, e.g., educational system 13501 that uses mixed reality and/or virtual reality for orthopedic surgical education. In the example of FIG. 135, a teacher wears MR/VR teacher device 13502 and multiple students wear MR/VR student devices 13504A and 13405B through 13405N (collectively MR/VR student devices 13504). In this example, any of the participants (teacher or students) may participate in the teaching session using mixed reality or virtual reality. That is to say, any of MR/VR teacher device 13502 and MR/VR student devices 13504 may comprise mixed reality devices such as visualization device 213, or alternatively, MR/VR teacher device 13502 and MR/VR student devices 13504 may comprise virtual reality devices the present only virtual information, in which case real-world information presented to users wearing mixed reality devices may be presented as virtual information to users wearing virtual reality devices. MR/VR educational content 13506 may comprise any of the virtual content disclosed elsewhere in this disclosure, such as any of the educational content described with respect to FIGS. 127-133 or elsewhere in this disclosure. Also, in some cases, MR/VR student devices 13504 and/or MR/VR teacher device 13502 may comprise both a visualization device that presents virtual elements to a user and a haptic device that provides touch-based information to the user.

With the example shown in FIG. 135, MR educational content 13406 may comprise assignable model 13508. For example, a teacher wearing MR/VR teaching device 13502 may have control over assignable model 13508 and may be allowed to assign general or specific manipulation rights to one or more students, so that the one or more students are able to control and manipulate assignable model 13508 when manipulation rights are assigned to them. Thus, in this example, rather than using separate teacher and student models, one assignable model 13508 is presented in the mixed reality or virtual reality presentation. Using MR/VR teacher device 13502, the teacher can manipulate assignable model 13508, and when desired, the teacher may assign control of assignable model 13508 to a student associated with one of MR/VR student devices 13504. In some cases, a teacher may provide total control rights of assignable model 13508, and in other cases, only limited manipulation rights may be assigned to students. For example, in some cases, a teacher may assign rights for a student to select an implant or make some other pre-operative, interoperative or post-operative selection, but the ability to move, re-align, or resize the virtual model may be retained by the teacher and not assigned to the student. Such limited assignment of manipulation rights may be useful especially for an educational setting that has multiple students viewing the same 3D virtual model.

Educational system 13501 may be useful in demonstrating at least one aspect of an orthopedic surgical procedure. System 13501 may comprise a first device (e.g., MR/VR teacher device 13502) configured to display a presentation to a first user (i.e. the teacher) wherein the presentation includes one or more assignable virtual elements (e.g., assignable model 13508). System 13501 may further comprise a second device (e.g., one of MR/VR student devices 13504) configured to display the presentation to a second user (i.e., one of the students). According to this example, the one or more assignable virtual elements (e.g., assignable model 13508) demonstrate at least one aspect of the orthopedic surgical procedure, and control of the one or more virtual elements are assignable from the first device (e.g., MR/VR teacher device 13502) to the second device (e.g., one of MR/VR student devices 13504). Assignable model 13508, for example may comprise a 3D virtual representation of one or more anatomical features, such as a shoulder or a portion of a shoulder or any of the other 3D virtual representations or virtual models described herein.

Assignable model 13508 may be useful for an educational setting. A teacher wearing MR/VR teacher device 13502 may manipulate assignable model 13508 to provide guidance and instruction to the students. Using MR/VR teacher device 13502, the teacher may then assign manipulation rights for the assignable virtual model 13508 to one or more students wearing MR/VR student devices 13504, such as by selecting an assign icon, or using gaze and/or hand gestures to identify the assignee student. Once manipulation rights are assigned to one or more students, the student or students may be able to manipulate assignable model 13508. The teacher wearing MR/VR teacher device 13502 and each of the students wearing MR/VR student devices 13504 may be able to view assignable model 13508, but only those students that are granted manipulation rights (or those granted limited manipulation rights or a subset of manipulation rights) by the teacher are able to control and manipulate assignable model 13508. Upon assigning manipulation rights to a student, the manipulations and controls by the student may be viewable to the entire class, or possibly viewable only by the teacher device and the student device of the student that is given manipulation rights.

Assignable control over assignable model 13508 can be very useful for orthopedic surgical education by allowing students to perform manipulations on the assignable model under the guidance of the teacher and the other students. This may amount to a group teaching exercise where different students are given a chance to manipulate assignable virtual model 13508 while being watched by the class.

Similar to other examples described herein, assignable model 13508 may comprise a virtual model of an anatomical feature, such as a virtual model of an example glenoid bone or an example humeral bone, or an entire shoulder. In addition, assignable model 13504 may include additional virtual content designed to aid in surgical planning, surgical steps, or post operative analysis that may be performed on the anatomical feature. For example, assignable model 13508 may include any of the virtual elements described above (or combinations of those described above) with regard to MR educational content 12706 of FIG. 127.

Using MR/VR student devices 13504, once MR/VR teacher device 13502 grants control, a student or students may be allowed to manipulate assignable virtual model 13508 in front of the class, e.g., performing surgical steps, surgical preparation, registration, setting axes for drilling or reaming, setting a cutting plane, placing a virtual gig, selecting tools, placing virtual implants, choosing virtual workflows, viewing the affects any selection may have on range of motion, and so forth. A teacher wearing MR/VR teaching device 13402 may provide instructional guidance to effectively train students. The assignable virtual model 13508 may be reset by MR/VR teacher device 13502 after the manipulation is completed and analyzed for each given student. Outcomes (such as shown by virtual range of motion information) can be compared amongst the students to assess the efficacy and effectiveness of student manipulations on the assignable virtual model 13508 relative to the efficacy and effectiveness of manipulations by other students on assignable virtual model 13508.

In some cases, the act of assigning the assignable model 13508 may be akin to calling on a student in class. The teacher wearing MR/VR teaching device 13502 may grant user controls or editing rights to a given student, such as by selecting an "assign" widget from a user interface of MR/VR teacher device 13502, or by using hand gestures, gaze-based selections, or combinations of these selection techniques. In some cases, a teacher wearing MR/VR teaching device maintains control over assignable virtual model 13508 and the ability to manipulate assignable virtual model 13508. At the same time, however, a teacher wearing MR/VR teaching device may grant access to one or more students, so that they can perform steps or procedures on assignable virtual model 13508 in front of the virtual class.

In some examples, a visualization device 213 configured to assist a teacher in education about an orthopedic surgical procedure ma comprise one or more processors 514 configured to generate one or more virtual elements generate one or more virtual elements wherein the one or more virtual elements comprise a 3D virtual representation of one or more anatomical features associated with the orthopedic surgical procedure, and a screen 520, which may comprise a transparent mixed reality display screen (such as a see-through holographic lens) configured to present the one or more virtual elements as part of a mixed reality presentation by the teacher for one or more students. The mixed reality presentation is configured to promote instruction of the one or more students wearing other visualization devices about the orthopedic surgical procedure, wherein processor 514 is configured to control the one or more virtual elements and wherein processor 514 is further configured to assign control of the one or more virtual elements to one of the other users of the other visualization devices. In some cases, processor 514 may assign control to a student in response to input from the teacher. In other examples, processor 514 may be configured to assign control based on input from the one or more students to one of the other visualization devices (worn by a student) wherein the other visualization device (worn by the student) communicates the input to visualization device 213 worn by the teacher.

In various examples, the one or more virtual elements generated by processor 514 may include any of those described above (or combinations of those described above) with regard to MR educational content 12706 of FIG. 127.

Figure 136:
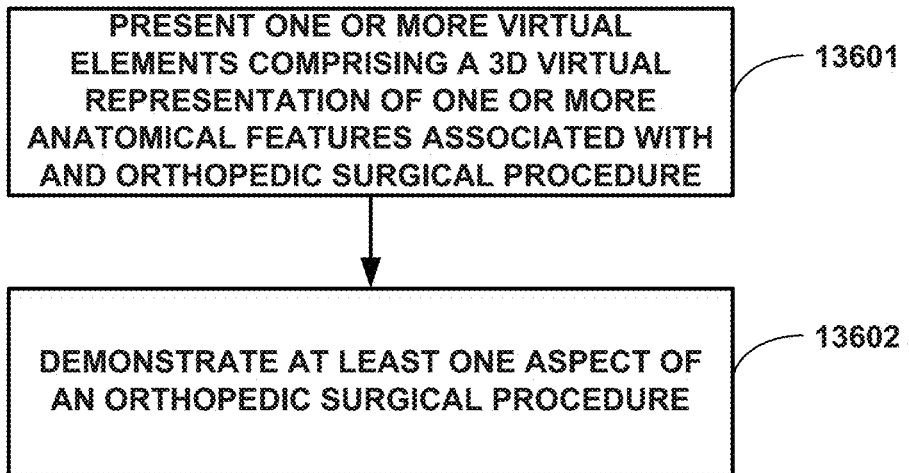

In some examples, visualization device 213 may generate one or more virtual elements comprising a 3D virtual representation of one or more anatomical features associated with the orthopedic surgical procedure, receive user input to control the one or more virtual elements for education about an orthopedic surgical procedure, and receive user input to assign control of at least some of the virtual elements to another device. As examples, the virtual representation of the one or more anatomical features may comprise a 3D virtual model of a human shoulder, or a 3D virtual illustration of a humeral head or a 3D virtual illustration of a glenoid, receiving user input to control the one or more virtual elements may comprise visualization device 213 being controlled by the teacher and presenting one or more steps of a surgical plan relative to the 3D virtual representation, and then, after receiving the user input, visualization device 213 may assign control of at least some of the virtual elements to the other device, and receive additional input from the other device (e.g. a student device) to adjust one or more steps of the surgical plan relative to the 3D virtual representation FIG. 136 is a flow diagram illustrating a general educational technique that may be performed by a visualization device according to this disclosure. The visualization device may comprise visualization device 213 described in detail in this disclosure, and may be worn by any type of student, such as a patient, a surgeon, a physician, a medical student, a technician, a nurse, a physician assistant, relatives of a patient, a researcher, or any other person that may desire education about an orthopedic medical procedure.

As shown in FIG. 136, visualization device 213 presents one or more virtual elements comprising a 3D virtual representation of one or more anatomical features associated with the orthopedic surgical procedure (13601). For example, a person wearing visualization device 213 may view a virtual model of an anatomical feature of a patient, such as a virtual shoulder model, a glenoid model, humeral bone model, or another anatomical 3D model. Visualization device 213 may then demonstrate at least one aspect of an orthopedic surgical procedure to the person wearing visualization device 213 (13602). In some cases, the act of presenting the one or more virtual elements on visualization device 213 (13601) may be educational to the user so as to demonstrate at least one aspect of the orthopedic surgical procedure (13602). In other cases, the step of demonstrating at least one aspect of the orthopedic surgical procedure on visualization device 213 (13602) may involve some type of change or manipulation of the one or more virtual elements on visualization device 213. In such cases, these changes or manipulations of the one or more virtual elements on visualization device 213 may comprise animations, visualizations, or possibly demonstrations by a teacher wearing a different visualization device or a virtual reality device. The student wearing visualization device 213 may view such animations, visualizations, or demonstrations performed by a teacher, and with the aid of the one or more virtual elements presented on visualization device 213, the student can be educated on one or more aspects of the surgical procedure.

In addition to presenting the 3D virtual representation, as examples, the act of presenting one or more virtual elements (13601) may further comprise presenting virtual pre-operative planning information, presenting virtual interoperative surgical guidance information, or presenting post-operative analysis. Visualization device 213 may be configured to present one or more virtual elements including any of those described above (or combinations of those described above) with regard to MR educational content 12706 of FIG. 127. This virtual information presented by visualization device 213 may help to demonstrate at least one aspect of an orthopedic surgical procedure (13602), such as by demonstrating a preoperative plan or portion thereof, demonstrating an interoperative surgical step, or providing pre-operative, inter-operative or post-operative analysis.

In one example, visualization device 213 may present one or more virtual elements (13601) in the form of guidance information that is presented relative to an anatomical model or an anatomical feature of a cadaver. In this case, the surgical guidance information may allow the user of another visualization device to train the student wearing visualization device 213 on the surgical procedure using a demonstration that is viewed by the student wearing visualization device 213. Example virtual elements that may be useful to present for demonstrating at least one aspect of a surgical procedure (13601) may comprise a reaming axis positioned relative to a synthetic model glenoid or the glenoid of a cadaver.

In yet other examples, visualization device 213 may present one or more virtual elements (13601) that comprise pre-operative animations, e.g., which may show desirable results or problems associated with any given implantation or implantation procedure. For example, visualization device 213 may present animations showing possible impingements associated with the implantation of an incorrectly sized implant or animations showing a desirable outcome associated with the implantation of a correctly sized implant. In some cases, visualization device 213 may present instant feedback to user, which demonstrates or illustrates ramifications (e.g., desirable outcomes, or undesirable impingements or loss of range of motion) associated with a particular implant or a particular implantation procedure.

Figure 137:
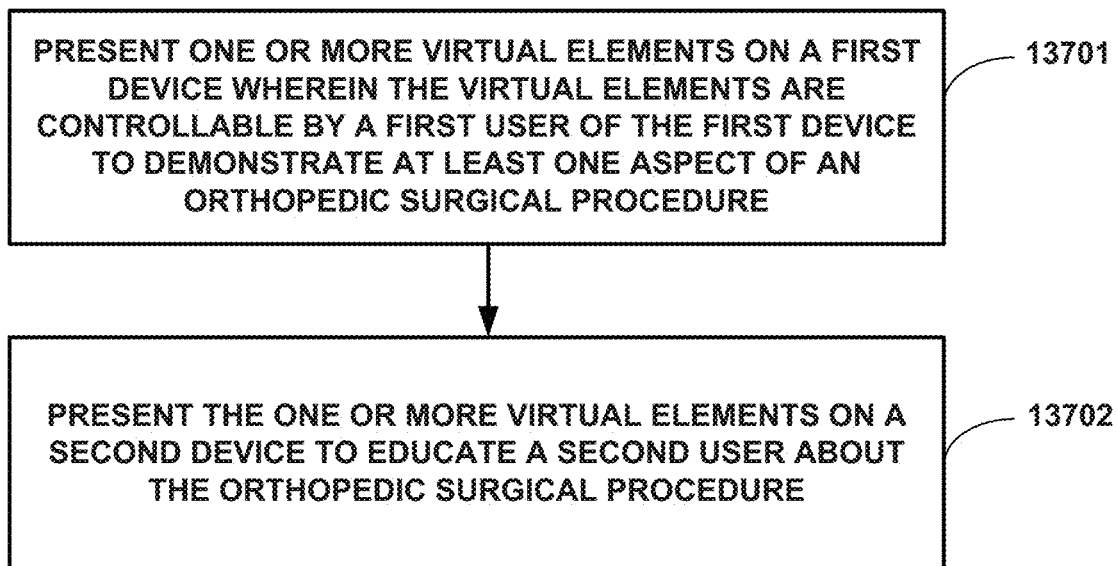

FIG. 137 is a flow diagram illustrating a general educational technique that may be performed by two different devices (e.g., a teacher device and a student device) according to this disclosure. The first and second devices may each comprise a visualization device 213 described in detail in this disclosure. Alternatively, one or both of the first and second devices may comprise virtual reality (VR) devices. As shown in FIG. 137, one or more virtual elements are presented on a first device, wherein the one or more virtual elements are controllable by a first user (e.g., a teacher) to demonstrate at least one aspect of an orthopedic surgical procedure (13701). The one or more virtual elements are also presented on a second device to educate a second user (e.g., a student) about the orthopedic surgical procedure (13702). In general, anyone being taught with the aid of mixed reality (or virtual reality) may be a student according to this disclosure, and similarly, anyone that teaches with the aid of mixed reality (or virtual reality) may be a teacher according to this disclosure.

As with other examples, in the example process of FIG. 137, the one or more virtual elements that are controllable by the first user wearing the first device and viewable by the second user wearing the second device may facilitate education on an orthopedic surgical procedure. A wide variety of such virtual elements are described above, including for example, a 3D virtual representation of one or more anatomical features, and additional virtual elements to show pre-operative steps, interoperative guidance steps, or surgical results.

In some examples where mixed reality is used, any of the MR student devices described herein may comprise a visualization device (such as visualization device 213) configured to educate a user about an orthopedic surgical procedure. The visualization device 213 may comprise one or more processors 514 configured to generate one or more virtual elements, and a screen 520, which may comprise a transparent mixed reality display screen (such as a see-through holographic lens) configured to present a presentation to a user, wherein the mixed reality presentation includes the one or more virtual elements, wherein the one or more virtual elements comprise a 3D virtual representation of one or more anatomical features associated with the orthopedic surgical procedure, and wherein the one or more virtual elements further include one or more virtual pre-operative plan elements shown or illustrated relative to the 3D virtual representation, one or more virtual surgical guidance features shown or illustrated relative to the 3D virtual representation, or one or more surgical results virtually illustrated on the 3D virtual representation such that the mixed reality presentation is configured to educate the user about the orthopedic surgical procedure.

Again, as non-limiting examples, the virtual representation of the one or more anatomical features may comprise a 3D virtual model of a human shoulder, a 3D virtual illustration of a humeral head, or a 3D virtual illustration of a glenoid. In addition, the one or more virtual elements may include any of those described above (or combinations of those described above) with regard to MR educational content 12706 of FIG. 127.

In still other examples, visualization device 213 may be configured to demonstrate a registration process to register the 3D virtual representation with the physical model of the anatomical element or the corresponding anatomical feature of the cadaver. In some examples, the one or more virtual elements comprise surgical guidance information, include trialing information associated with a prepared implantation location for an implant component, illustrate a registration process for registering a depth aid element, comprise virtual training information or virtual visual aids on the use of automated tools that include closed loop control, comprise virtual information about range of motion, include a virtual pre-operative animation, include one or more virtual implant components positioned relative to the 3D virtual representation, or provide other features that can be educational about the orthopedic surgical procedure.

Figure 138:
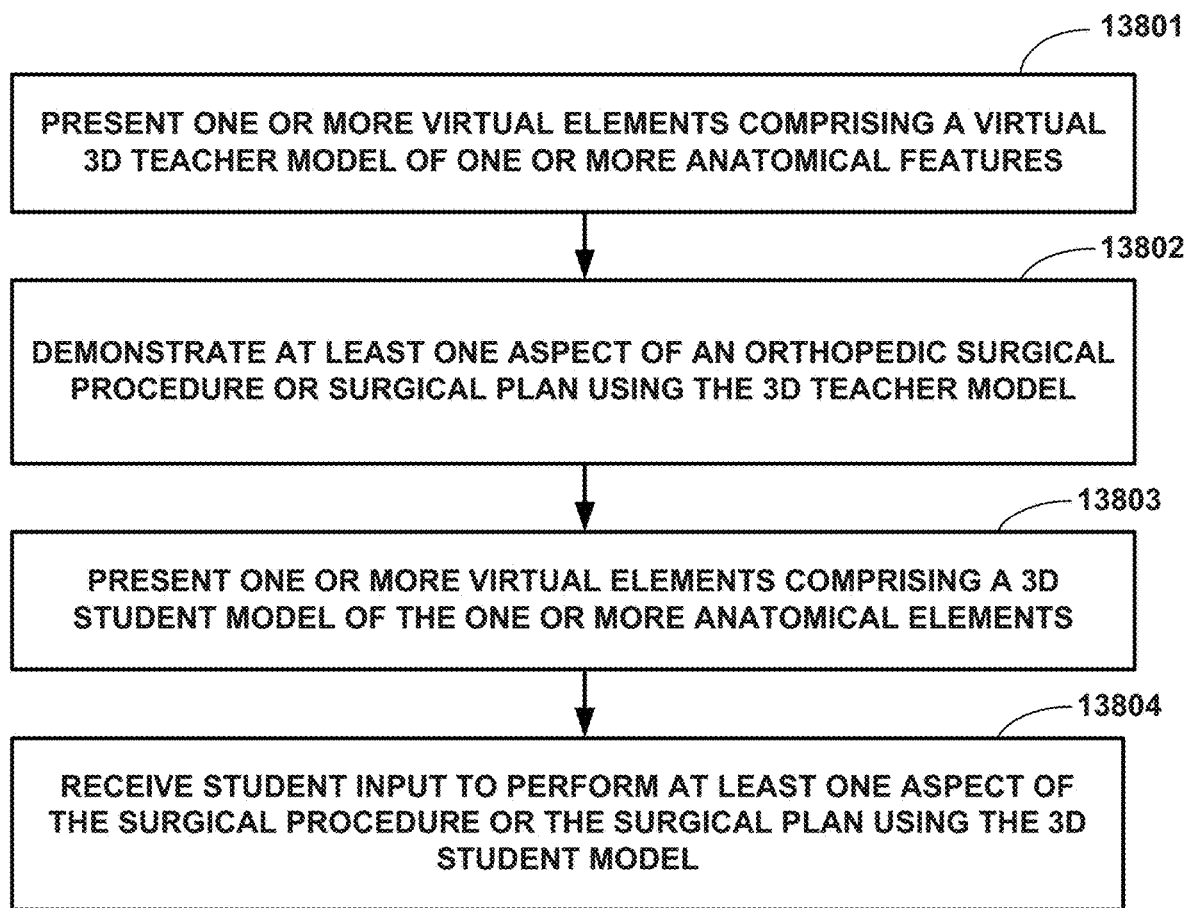

FIG. 138 is another flow diagram illustrating an educational technique that can be performed with the aid of mixed reality and/or virtual reality. FIG. 138 will be described by referring again to educational system 13401 of FIG. 34, which may be useful in demonstrating at least one aspect of an orthopedic surgical procedure. However, other educational systems may also implement techniques similar to that shown in FIG. 138. As shown in FIG. 138, a first device (e.g., MR/VR teacher device 13402) may display one or more virtual elements comprising a teacher model 13408 (13801). The teacher wearing MR/VR teacher device 13402 demonstrates one or more aspects of an orthopedic surgical procedure or a surgical plan using the teacher model 13408 (13802). Similarly, a second device (e.g., one of MR/VR student devices 13404) may present one or more virtual elements comprising a student model 13405 (13803). The second device may receive input from a student to perform at least one aspect of the surgical procedure or the surgical plan using the student model 13405 (13804). In this way, a first set of virtual elements comprising teacher model 13408 may be manipulated by a teacher to demonstrate at least one aspect of the orthopedic surgical procedure or surgical plan, and additional sets of virtual elements comprising student models 13405A, 13405B or 13405N, which may be similar to teacher model 13408 may be manipulated by different students. In some cases, the student may attempt to mimic surgical steps performed by the teacher, and the use of student-specific virtual elements for each student (similar to the teacher-specific virtual elements used by the teacher) may provide for a very useful teaching system for orthopedic surgical education. In other cases, students may attempt to select or define a surgical plan, select implant size, select surgical type, or make other surgical plan decisions based on student models 13405, and the plan and selections made by each student can be compared to that of the teacher, or possibly to a plan defined by a computer algorithm.

In some examples, teacher model 13408 may be positioned by teacher device 13402 relative to a physical model or an anatomical feature of a cadaver, and the student models 13405A, 13405B or 13405N may be positioned by one of student devices 13404 relative to a second anatomical model or an anatomical feature of a second cadaver. That is to say, the teacher and the student may manipulate virtual elements that are positioned relative to different models or different cadavers. Moreover, additional guidance-based virtual elements may be presented relative to the student and teacher models to aid in a trial surgical process on the cadavers.

Figure 139:
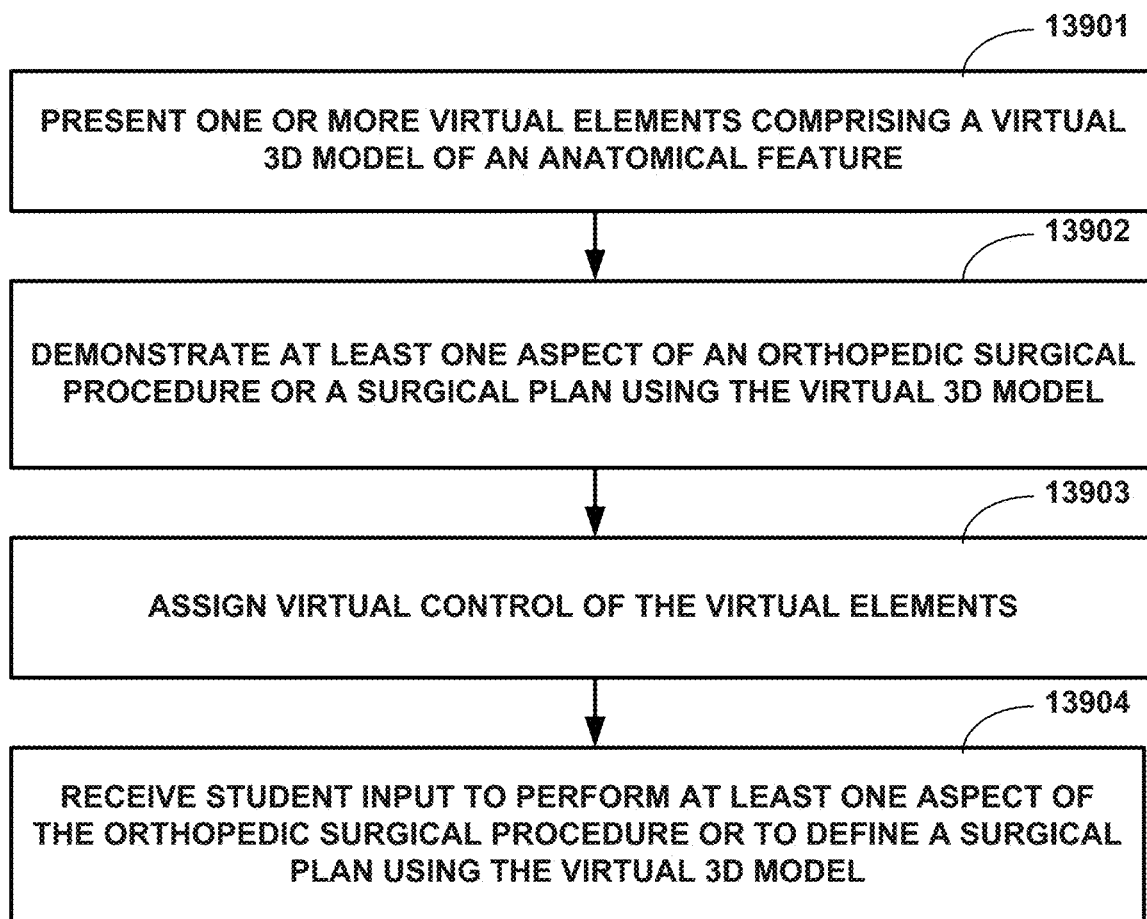

FIG. 139 is another flow diagram illustrating an educational technique, e.g., which may be performed by a visualization device 213, which may also be shown as MR/VR teacher device 13502 of FIG. 135. As shown in FIG. 139, visualization device 213 presents one or more virtual elements to the user (e.g., the teacher), wherein the virtual elements comprise a virtual 3D model of an anatomical feature (13901). Using visualization device 213, the teacher demonstrates at least one aspect of an orthopedic surgical procedure or an orthopedic surgical plan (13902), e.g., by using and manipulating the virtual 3D model and selecting or presenting other virtual features relative to the virtual 3D model. The teacher may then assign virtual control of the virtual elements (or a subset of such virtual controls) to one of the students (13903) who used a different visualization device 213 than that worn by the teacher. Once virtual control of the assignable virtual elements is granted to the student, the visualization device 213 worn by the student may then receive student input to perform at least one aspect of the orthopedic surgical procedure or to define one or more aspects of a surgical plan using the virtual 3D model (13904). In this way, a teacher may use visualization device 213 to generate and control virtual elements and then assign control to a student (wherein the student uses another visualization device 213). The teacher may observe and assess the student's ability to mimic the orthopedic surgical steps performed by the teacher, or to assess the student's ability to make good pre-operative decisions and selections for a surgical plan.

Figure 140:
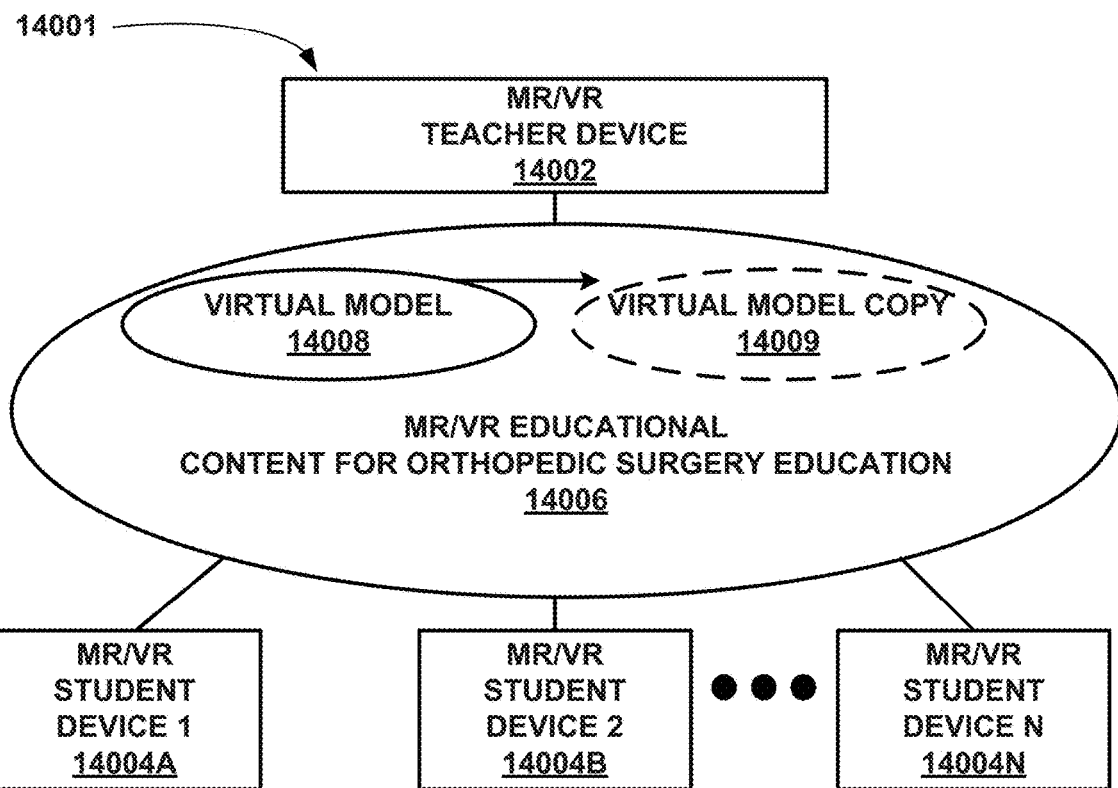

FIG. 140 is a conceptual block diagram of an educational system, e.g., educational system 14001 that use mixed reality and/or virtual reality for orthopedic surgical education, where a user is able to launch a manipulatable copy of virtual content that includes virtual elements. In the example of FIG. 140, a teacher wears MR/VR teacher device 14002 and multiple students wear MR/VR student devices 14004A and 14004B through 14004N (collectively MR/VR student devices 14004). In this example, any of the participants (teacher or students) may participate in the teaching session using mixed reality or virtual reality. That is to say, any of MR/VR teacher device 14002 and MR/VR student devices 14004 may comprise mixed reality devices such as visualization device 213, or alternatively, MR/VR teacher device 14002 and MR/VR student devices 14004 may comprise virtual reality devices the present only virtual information, in which case real-world information presented to users wearing mixed reality devices may be presented as virtual information to users wearing virtual reality devices.

MR/VR educational content 14006 may comprise any of the virtual content disclosed elsewhere in this disclosure, such as any of the educational content described with respect to FIGS. 127-133 or elsewhere in this disclosure. In addition, with the example shown in FIG. 140, MR educational content 14006 may include a virtual model 14008, as well as a copy 14009 of the virtual model, which may be launched by one of MR/VR student device 14004 (or MR/VR teacher device 14002) during an educational session. Virtual model 14008 and the copy 14009 of the virtual model may each comprise a 3D virtual representation of one or more anatomical features associated with the orthopedic surgical procedure, such as a 3D virtual model of a human shoulder, a 3D virtual illustration of a humeral head, a 3D virtual illustration of a glenoid, or another 3D model of anatomical features associated with any orthopedic surgical procedure. In some cases, MR/VR student devices 14004 and/or MR/VR teacher device 14002 may comprise both a visualization device that presents virtual elements to a user and a haptic device that provides touch-based information to the user.

The ability for students (or the teacher) to launch a copy of a virtual model, e.g., virtual model copy 14009, during an educational session may be very useful for orthopedic surgical procedure education. Virtual model copy 14009, for example, may be launched in the middle of an educational session, after MR/VR teacher device 14002 has been used to manipulate virtual model 14008. In some cases, virtual model copy 14009 may comprise virtual content indicative of an interoperative surgical step, where the teacher has already performed some prior surgical-related manipulations on virtual model 14008. In other cases, virtual model copy 14009 may be launched to allow the student to perform surgical planning steps, selections of implants, selections of surgical types (e.g., reverse vs. anatomic) placement of implants, selections of implant sizes, selection of surgical tools, or other surgical planning steps or decisions.

Educational system 14001 may be useful in demonstrating at least one aspect of an orthopedic surgical procedure, such as surgical steps or a surgical plan. A teacher wearing MR/VR teacher device 14002 may demonstrate one or more aspects of a surgical steps or the surgical planning. During the demonstration or at any time, one of MR/VR student device 14004 (or MR/VR teacher device 14002) may launch virtual model copy 14009, which is a copy of virtual model 14008, possibly after the teacher has performed one or more surgical-related manipulations on virtual model 14008 or some prior surgical planning steps on virtual model. This way, a student may be able to focus on a particular planning stage or a particular interoperative surgical step of the procedure. In some cases, virtual model copy 14009 may be discarded after student manipulations and teacher review, but in other cases, virtual model copy 14009 may be adopted by the teacher so as to replace virtual model 14008. In this later example, student manipulations of virtual model copy 14009 may be accepted by the teacher and adopted as virtual model 14008 as the teacher continues to educate the students on the next step of the orthopedic surgical procedure or the next step in the surgical planning.

In some examples, system 14001 may comprise a first device (e.g., MR/VR teacher device 14002) configured to display a presentation to a first user (i.e., a teacher) wherein the presentation includes virtual model 14008 comprising one or more virtual elements that are controllable by the first user wearing the first device and wherein the one or more virtual elements comprise a 3D virtual representation of one or more anatomical features associated with the orthopedic surgical procedure. Moreover, system 14001 may comprise a second device (e.g., one of MR/VR student devices 14004) configured to display the presentation to a second user (i.e., one of the students). Virtual model 14008 comprising one or more virtual element may demonstrate at least one aspect of the orthopedic surgical procedure, such as a surgical step of the procedure or a surgical planning step for the procedure. The second device (e.g., one of MR/VR student devices 14004) or the first device (e.g., MR/VR teacher device 14002) may be configured to generate a copy 14009 of the virtual model in response to input from the second user (i.e., one of the students) or the first user (i.e., the teacher). And the copy 14009 of the virtual model may be controllable by the second user wearing the second device. In some cases, the first device may be further configured to replace virtual model 14008 with the copy 14009 of the virtual model in the presentation, after the copy 14009 of the virtual model is manipulated by the second user wearing the second device. In other words, for example, if the student performs the correct steps or manipulations on the student's copy of the virtual content, the teacher may adopt the student's copied version of the virtual model after such student manipulations as the new teacher content for all students, and the teacher may then continue the educational session to demonstrate later surgical steps or surgical planning steps of the orthopedic surgical procedure.

As examples, virtual model 14008 (as well as virtual model copy 14009) may comprise additional virtual elements that illustrate pre-operative plan elements relative to the 3D virtual representation, one or more virtual surgical guidance features illustrated relative to the 3D virtual representation, or one or more surgical results virtually illustrated on the 3D virtual representation. A wide variety of such additional virtual elements are described throughout this disclosure.

In some examples, a visualization device 213 configured to educate a user about an orthopedic surgical procedure may comprise a screen 520, which may comprise a transparent mixed reality display screen (such as a see-through holographic lens) configured to present a mixed reality presentation to a user, wherein the mixed reality presentation includes the one or more virtual elements comprising a 3D virtual representation of one or more anatomical features associated with the orthopedic surgical procedure. In other words, a visualization device 213 worn by a student may view a mixed reality presentation on orthopedic surgical procedures (e.g. surgical steps or surgical planning) that is generated and controlled by a different visualization device worn by a teacher. The visualization device 213 worn by the student (or that worn by the teacher) may comprise a processor 514 configured to generate a copy of a virtual model shown by the teacher, wherein the copy is controllable by visualization device 213 worn by the student. In this way, a student (or the teacher) may be able to launch and manipulate a copy of virtual content presented by the teacher during a presentation by the teacher. The copy of virtual content that is launched and manipulated by the student may include surgical planning (or surgical steps) that the teacher may have already performed with regard to the virtual content before such content is launched and manipulated by the student. In this way, student copies of virtual models may be designed for teaching specific surgical planning steps or specific surgical operation steps.

As examples, the virtual model that may be launched and manipulated by a student as a copy of teacher model may comprise any of the additional virtual information described herein in order to facilitate education on surgical planning steps or surgical operating steps. Such additional virtual information, for example, may comprise such things as a virtual cutting axis shown or illustrated relative to the 3D virtual representation, a virtual reaming axis shown or illustrated relative to the 3D virtual representation, a virtual drilling axis shown or illustrated relative to the 3D virtual representation, placement or selection of a virtual jig or guide relative to 3D virtual representation, a virtual axis shown or illustrated relative to a virtual jig or guide, surgical guidance information presented relative to the 3D virtual representation, an illustration of a registration process for registering the 3D virtual representation to a physical model or a corresponding feature of a cadaver, trialing information associated with a prepared implantation location for implant component, information showing a registration process for registering a depth aid element, virtual training information or virtual visual aids on the use of automated tools that include closed loop control, virtual information about range of motion, a virtual pre-operative animation, an illustration of one or more virtual implant components relative to the 3D virtual representation, selections of decisions of surgical plan, selections of implants or implant sizes, selection of surgical tools or tool sizes, selections or decisions of surgical type, or other elements related to surgical planning or surgical guidance.

In some examples, a method may comprise displaying a mixed reality presentation of an orthopedic surgical procedure on a student device and a teacher device, wherein the mixed reality presentation includes a teacher copy of virtual elements controlled by a teacher device and wherein the virtual elements comprise a 3D virtual representation of one or more anatomical features associated with the orthopedic surgical procedure; and In some cases, MR/VR teacher device 14002 may always include a master model of virtual model 14008. One or more copies (e.g., virtual model copy 14009) may be generated for student use by one of MR/VR student devices 14004, and in some cases, such copies (e.g., virtual model copy 14009) may be presented as a comparison to a master model (e.g., virtual model 14008) controlled by MR/VR teacher device 14002. In some cases, virtual model copy 14009 may be superimposed on virtual model 14008, possibly after student manipulation, to allow for precise comparison between virtual model 14008 and virtual model copy 14009. In some cases, each student may have corresponding virtual model copy 14009. In some cases, the virtual model copy 14009 for each student may be viewable only by that corresponding MR/VR student devices 14004, and in other cases each of MR/VR student devices may be able to view virtual model copy 14009 associated with other ones of MR/VR student devices 14004.

Figure 141:
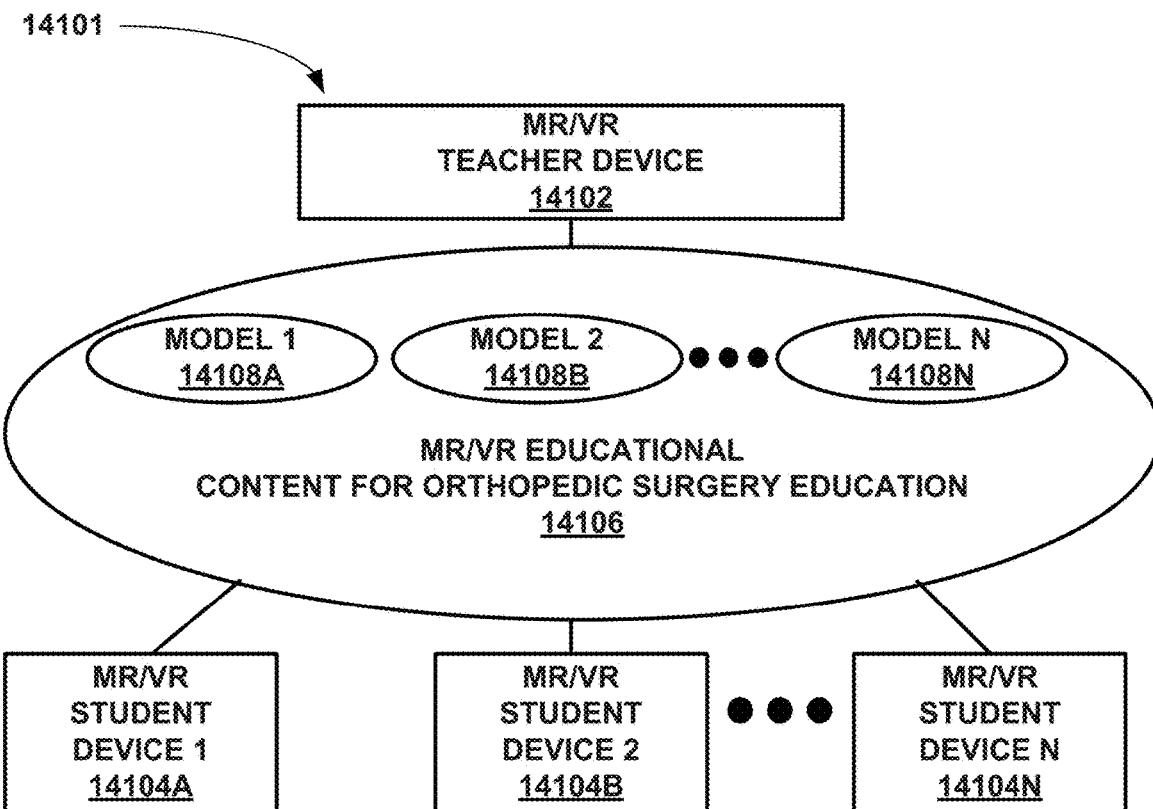

FIG. 141 is a conceptual block diagram of an educational system, e.g., educational system 14101 that use mixed reality and/or virtual reality for orthopedic surgical education where students and teachers are able to view and compare several different 3D virtual models, which may include additional virtual elements as described here. In the example of FIG. 141, a teacher wears MR/VR teacher device 14102 and multiple students wear MR/VR student devices 14104A and 14104B through 14104N (collectively MR/VR student devices 14104). In this example, any of the participants (teacher or students) may participate in the teaching session using mixed reality or virtual reality. That is to say, any of MR/VR teacher device 14102 and MR/VR student devices 14104 may comprise mixed reality devices such as visualization device 213, or alternatively, MR/VR teacher device 14102 and MR/VR student devices 14104 may comprise virtual reality devices the present only virtual information, in which case real-world information presented to users wearing mixed reality devices may be presented as virtual information to users wearing virtual reality devices. MR/VR educational content 14106 may comprise any of the virtual content disclosed elsewhere in this disclosure, such as any of the educational content described with respect to FIGS. 127-133 or elsewhere in this disclosure. Also, in some cases, MR/VR student devices 14104 and/or MR/VR teacher device 14102 may comprise both a visualization device that presents virtual elements to a user and a haptic device that provides touch-based information to the user.

As shown in the example of FIG. 141, MR/VR educational content 14106 includes a plurality of models (e.g., model 1 14108A and model 2 14108B through model N 14108N). In some cases, the plurality of models (collectively models 14108) may show different surgical plans on the same anatomy. Presenting a plurality of models 14108 as part of a collective presentation may be very useful to promote education of an orthopedic surgical procedure or surgical planning. This may present a side-by side comparison of a current surgical plan relative to other examples. For example, model 1 14108A may comprise a current patient model planned for surgery, and the other models (model 2 14108B through model N 14108N) may comprise models planned by others based on the same anatomy, models associated with achieved case studies, models of theoretical cases, models generated by a computer algorithm, or any case study that may be useful to compare with model 1 14108B. In other examples, the plurality of models 14108 may comprise student models relative to a teacher model, e.g., which may be presented and compared at different stages of an educational orthopedic surgical process, or presented to show different surgical plans different aspects of the surgical plan. In some cases, MR/VR student devices 14104 may be worn by surgeons that collaborate and share experiences with one another by presenting different models in a side-by-side comparison, within an MR or VR presentation. In some cases, MR/VR student devices 14104 may participate in a "crowd sourcing" session in which the different students collaborate on a similar problem or issue with the use of MR or VR to showcase presentation of a case study of a specific patient, or a specific issue in a particular case study.

In some cases, the plurality of models 14108 may be selected from a catalog of 3D virtual representations (e.g., stored in memory of MR/VR student device 14104 or MR teacher device 14102 or stored remotely). The different models in the catalog may demonstrate a wide variety of different shoulder conditions that may require orthopedic surgical repair. A teacher using MR/VR teacher device 14102, for example, may select one or more 3D virtual representations from the catalog of 3D images in order to make educational demonstrations to a student wearing one of MR/VR student devices 14104. In some cases, 3D virtual models of patient anatomy may be compared to 3D virtual models in the catalog for side-by-side comparisons, which can help users identify similarities between the patient anatomy and other example antinomy from the catalog that illustrates one or more shoulder problems.

In still other cases, the plurality of models 14108 may be selected to illustrate shoulders with different types of classification (e.g. different types of Walch classifications). The different classifications may call for different types of surgical procedures or selection of different implant components with particular sizes, angles, and implant positions. Preoperative, interoperative or post-operative steps may be demonstrated side-by-side in the plurality of models 14108 in order to illustrate differences in procedures desirable for different types of shoulder classifications. In still other cases, the plurality of models 14108 may comprise ankle models used for demonstrating one or more aspects of an orthopedic ankle procedure.

In some cases, different ones of models 14108 may illustrate different surgical procedures or different surgical plans associated with a common patient, e.g., to help the users of MR teacher device 14102 and MR student devices 14104 identify a most desirable surgical procedure or plan for a given shoulder classification. For example, model 1 14108A may present a model of an anatomical surgical implant and model 2 14108B may present a model of a reverse surgical implant. In this way, MR teacher device 14102 and MR student devices 14104 may compare implants, possibly for pre-operative determinations to identify the best type of surgical procedure for a given shoulder classification. In some examples, MR teacher device 14102 and MR student devices 14104 may be worn by a panel of experts or a panel of instructors that exchange or share the teaching roll. In some cases, each user may have the ability to take control or be granted control to become MR teacher device 14102.

Figure 142:
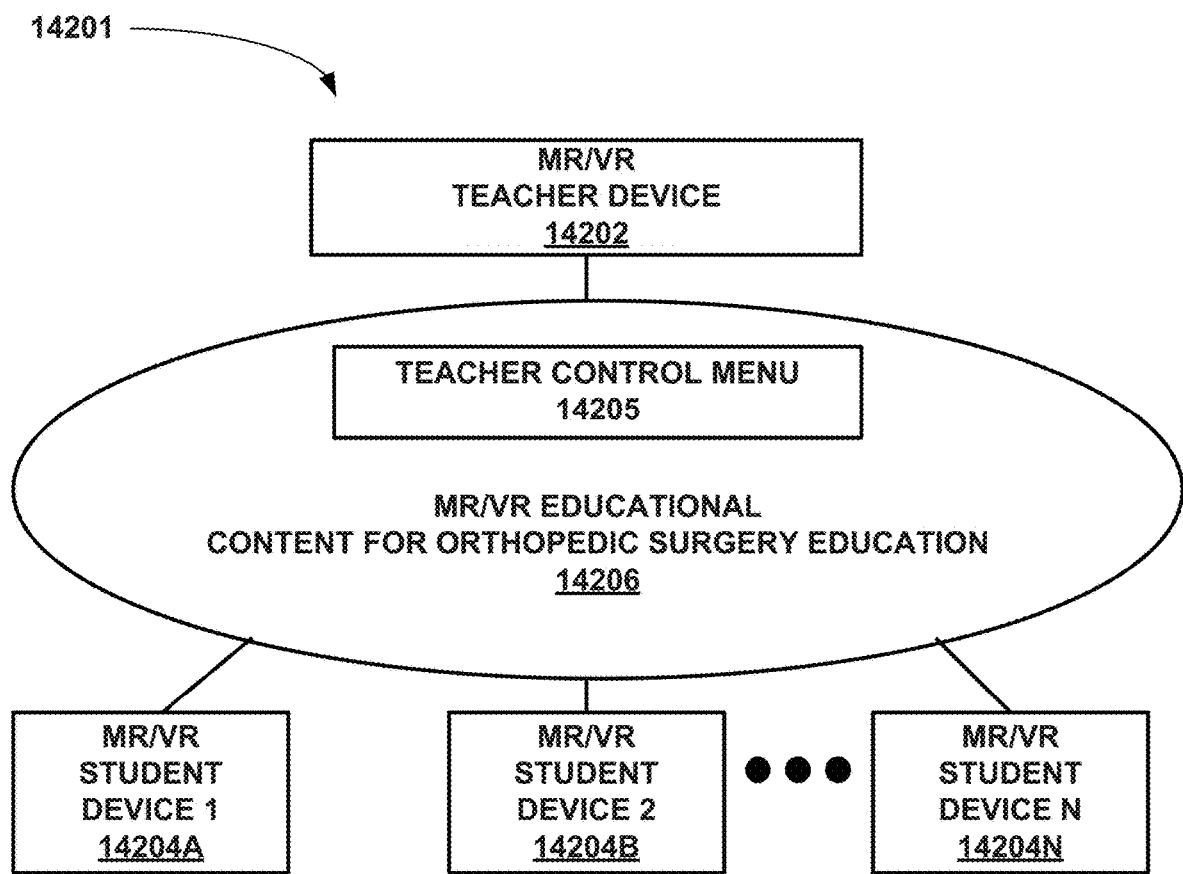

FIG. 142 is a conceptual block diagram of an educational system, e.g., educational system 14201 that use mixed reality and/or virtual reality for orthopedic surgical education where a teacher has a teacher control menu that comprises virtual control elements to allow the teacher to control MR/VR educational content. Like other examples, in the example of FIG. 142, a teacher wears MR/VR teacher device 14202 and multiple students wear MR/VR student devices 14204A and 14204B through 14204N (collectively MR/VR student devices 14204). In this example, any of the participants (teacher or students) may participate in the teaching session using mixed reality or virtual reality. That is to say, any of MR/VR teacher device 14202 and MR/VR student devices 14204 may comprise mixed reality devices such as visualization device 213, or alternatively, MR/VR teacher device 14202 and MR/VR student devices 14204 may comprise virtual reality devices the present only virtual information, in which case real-world information presented to users wearing mixed reality devices may be presented as virtual information to users wearing virtual reality devices. MR/VR educational content 14206 may comprise any of the virtual content disclosed elsewhere in this disclosure, such as any of the educational content described with respect to FIGS. 127-133 or elsewhere in this disclosure. Also, in some cases, MR/VR student devices 14204 and/or MR/VR teacher device 14202 may comprise both a visualization device that presents virtual elements to a user and a haptic device that provides touch-based information to the user.

As shown in the example of FIG. 142, MR/VR educational content 14206 comprises a teacher control menu 14205, which may comprise virtual control elements for controlling an MR or VR presentation on an orthopedic surgical procedure. In some cases, teacher control menu 14205 may be visible only to the teacher wearing MR/VR teacher device 14202 and may be hidden from the MR/VR educational content that is shown on MR/VR student devices 14204.

Teacher control menu 14205 may comprise selectable elements, such as virtual control widgets, that can be selected by a teacher wearing MR/VR teacher device 14202 in order to control an MR or VR presentation using gazes, gestures towards the widgets, voice commands or other ways of selection. In particular, teacher control menu 14205 may present elements for controlling or launching MR or VR features or elements described in this disclosure, and users may select such elements using gazes, gestures, voice controls or other selections used in mixed reality or virtual reality. For example, teacher control menu 14205 may comprise one or more elements for presenting and/or manipulating MR/VR educational content 14206, which may comprise any of the virtual content described herein for use in orthopedic surgical procedures or orthopedic surgical procedure education. Teacher control menu 14205 may comprise educational tools such as icons for launching videos, images, presentations (such as power point presentations), spreadsheets, or anything that may be useful in a mixed reality or virtual reality teaching environment.

As one example, teacher control menu 14205 may comprise a virtual element or icon for assigning virtual control of MR/VR educational content 14204 to one of MR/VR student devices 14204. In another example, teacher control menu 14205 may comprise a virtual element or icon for launching a student copy of virtual content for a specific MR/VR student device, or for launching multiple copies of virtual content for all of the MR/VR student devices 14204. More generally, teacher control menu 14205 may include one or more virtual elements or icons for presenting teacher content that is manipulatable by the teacher wearing MR/VR teacher device 14202 or for presenting student content that is manipulatable by students wearing MR/VR student devices 14204. The virtual elements or icons may be selected via gazes, gestures, voice controls or other selections used in mixed reality or virtual reality In other examples, teacher control menu 14205 may comprise one or more virtual elements or icons for presenting multiple models for collaborative and comparative viewing. In other examples, teacher control menu 14205 may comprise one or more virtual elements or icons for presenting video, for presenting CT scans, images or segmentations, for presenting pre-operative images or videos, for selecting or launching presentations or presentation tools (such as a power point presentation). In other examples, teacher control menu 14205 may include a notepad for notetaking, a record icon for recording an educational session or recording a portion of an educational session. In other examples, teacher control menu 14205 may comprise virtual elements or icons for archiving content of a given educational session, for accessing recorded videos of other cases, or for loading prior examples or prior models for class demonstrations or discussion.

In still other examples, teacher control menu 14205 may comprise one or more virtual elements or icons for sharing the ability to view virtual content or for sharing the ability to control such virtual content. The sharing elements or icons may allow for sharing with specific ones of MR/VR student devices 14204 or for sharing with all MR/VR student devices 14204.

In other examples, teacher control menu 14205 may comprise a file queue, e.g., for organizing a class session. Also, teacher control menu 14205 may include content related to educational credit (such as continuing medical education credit), such as for presenting the availability of such credit or for soliciting student responses to verify student attendance.

In some examples, teacher control menu 14205 may include selectable elements or icons for assigning editing rights to some or all virtual elements. In some examples, teacher control menu 14205 may comprise a drop-down menu of participants, facilitating the ability of MR/VR teacher device 14002 to select or call on other participants wearing MR/VR student devices 14204. In other examples, teacher control menu 14205 may comprise selectable icons or avatars that can be selected by the user of MR/VR teacher device 14202 to call on students or assign virtual control to students, e.g., using hand gesture or gaze-based user controls.

Teacher control menu 14205 may include elements or icons for filters that identify similar cases by procedure similarity, e.g., locating one or more procedures or procedure steps that may be similar to a procedure or step of interest. Upon selection of a specific filter icon by the teacher, MR/VR teacher device 14202 may access a database (located locally or remotely) and identify one or more example case studies or prior surgeries that are close matches to a current case study. MR/VR teacher device 14202 may then load archived models or examples into MR/VR educational content 14206 for presentation to the students. The ability to identify archived case studies or example procedures that have similarities with a current case study may be very helpful for educating and may have particular use in a collaborative educational session where students work together (e.g., in a crowd sourcing session) to brainstorm on how best to address a current case study.

The elements or icons presented on teacher control menu 14205 may be selectable by the teacher wearing MR/VR teacher device 14202 via hand gestures, gaze-based controls, facial expressions, or possibly with the use of a selection tool (such as a wand or laser pointer). The teacher may select icons or elements from teacher control menu 14205 to control the MR/VR presentation and to control and manipulate virtual content, which may include any of the virtual content described herein for use in orthopedic surgery or orthopedic surgical education, including but not limited to a 3D virtual representation (e.g., a virtual model of a human shoulder, a virtual model of a glenoid or glenoid surface, or a virtual model of a humeral bone or humeral head), and/or additional virtual content such as any of the virtual elements (or combinations) described with regard to MR educational content 12706 of FIG. 127.

In still other examples, teacher control menu 14205 may comprise a set of saved surgical plans or illustrations for selecting and demonstrating different procedures such as a reverse shoulder arthroplasty vs an anatomical shoulder arthroplasty.

Figure 143:
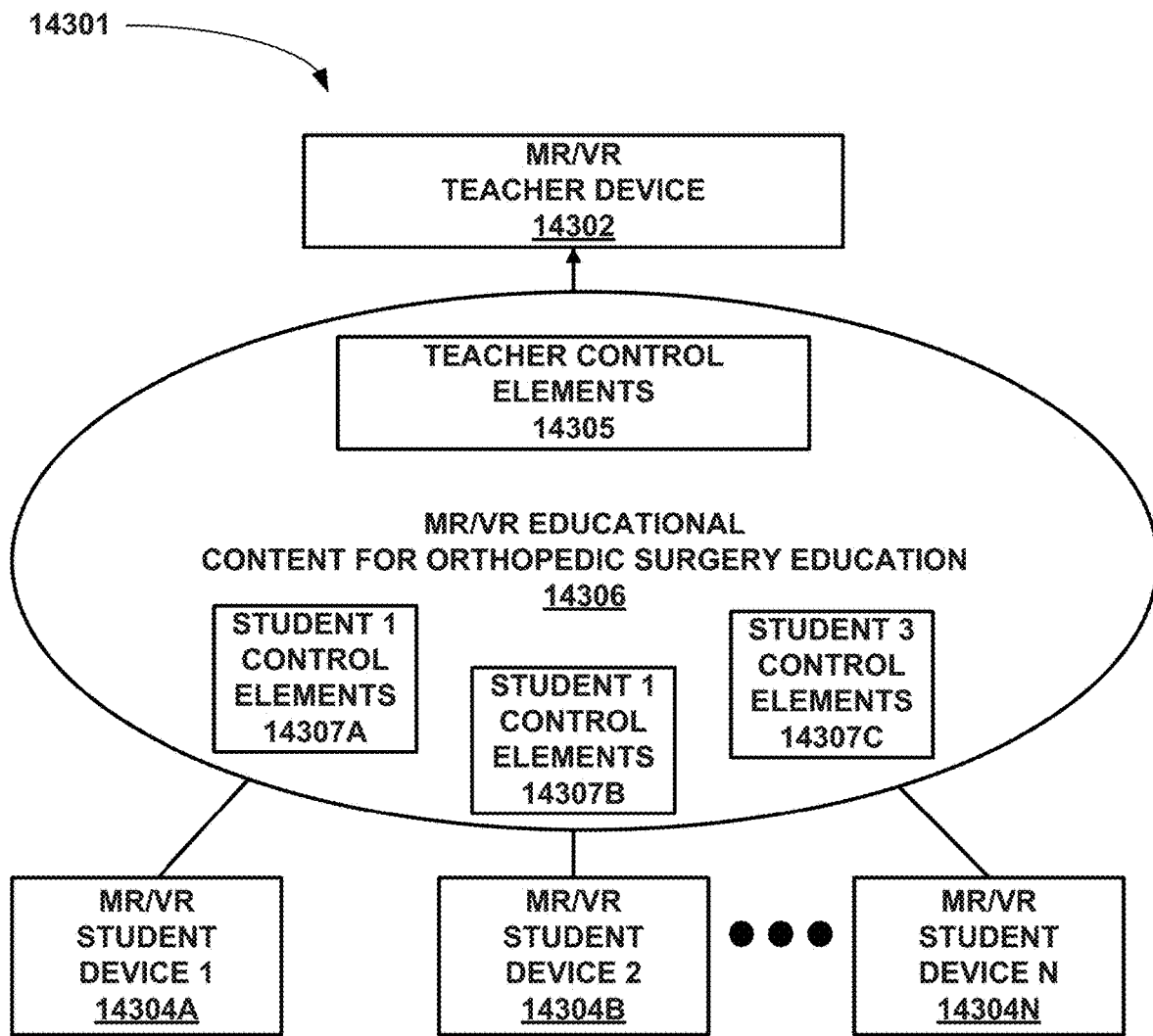

FIG. 143 is another conceptual block diagram of an educational system, e.g., educational system 14301 that use mixed reality and/or virtual reality for orthopedic surgical education where both a teacher and the students have virtual control elements for controlling MR/VR educational content. Like other examples, in the example of FIG. 143, a teacher wears MR/VR teacher device 14302 and multiple students wear MR/VR student devices 14304A and 14304B through 14304N (collectively MR/VR student devices 14304). In this example, any of the participants (teacher or students) may participate in the teaching session using mixed reality or virtual reality. That is to say, any of MR/VR teacher device 14302 and MR/VR student devices 14304 may comprise mixed reality devices such as visualization device 213, or alternatively, MR/VR teacher device 14302 and MR/VR student devices 14304 may comprise virtual reality devices the present only virtual information, in which case real-world information presented to users wearing mixed reality devices may be presented as virtual information to users wearing virtual reality devices. MR/VR educational content 14306 may comprise any of the virtual content disclosed elsewhere in this disclosure, such as any of the educational content described with respect to FIGS. 127-133 or elsewhere in this disclosure. Also, in some cases, MR/VR student devices 14304 and/or MR/VR teacher device 14302 may comprise both a visualization device that presents virtual elements to a user and a haptic device that provides touch-based information to the user.

Teacher control elements 14305 may comprise any of the features, elements, icons, or controls described above with regard to teacher control elements 14205 of system 14202 shown in FIG. 143. In the example of FIG. 143, however, MR/VR student devices 14304 are also presented with virtual controls as part of MR/VR educational content 14206. For example, MR/VR student device 1 14304A may be configured to present corresponding student 1 control elements 14307 and MR/VR student device 2 14304B may be configured to present corresponding student 2 control elements 14307B. Each of a plurality of student devices have corresponding virtual controls, and the virtual controls of each device may only view viewable by the user of that device. That is to say, student 1 control elements 14307A may be viewable by MR/VR student device 1 14304A, but student 1 control elements 14307A may be unviewable by MR/VR student device 2 14304B. Similarly, student 2 control elements 14307B may be viewable by MR/VR student device 2 14304B, but student 2 control elements 14307B may be unviewable by MR/VR student device 1 14304A. In some cases, MR/VR teacher device 14302 may be able to view only teacher control elements 14305 and may be unable to view student control elements 14307, but in other cases, MR/VR teacher device 14302 may be able to view all of the control elements including student control elements 14307 associated with the student devices 14304. In some cases, teacher control elements 14305 may include icons or elements for enabling or disabling the viewability of student control elements 14307 by MR/VR teacher device 14302, which may be useful when a teacher needs to explain to a student how to use such controls.

In general, each of student control elements 14307 may comprise any of the features, elements, icons, or controls that are included within teacher control elements 14305. Moreover, each of student control elements 14307 may comprise any of the features, elements, icons, or controls that are described above with regard to teacher control elements 14205 of system 14202 shown in FIG. 143. In most cases, however, student control elements 14307 may comprise a more limited number of control elements relative to teacher control elements 14305. In most cases, for example, teacher control elements 14305 may provide universal control over MR/VR educational content 14206, whereas student control elements 14307 may have a more limited control over MR/VR educational content 14206. In still other cases, different ones of MR/VR student devices 14304 may be afforded different levels of control over MR/VR educational content, and in some cases, MR/VR teacher device 14302 may be configured to assign or unassign such different levels of control to MR/VR student devices 14304.

In some examples, teacher control elements 14305 and/or student control elements 14307 may include note taking features for recording notes of the different users. Also, recordings of the training session and any virtual manipulations that are performed by the students or the teacher may be recorded and documented as part of MR/VR educational content 14306.

Figure 144:
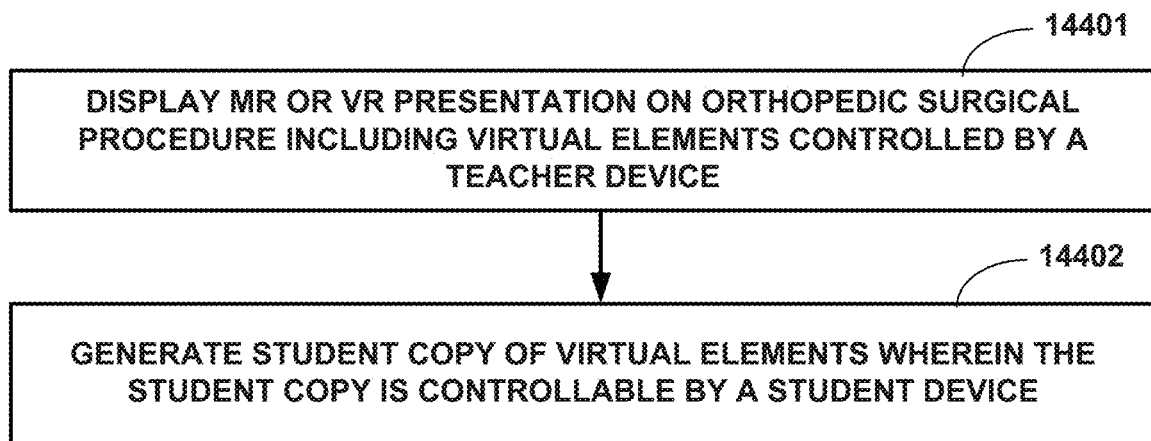

FIG. 144 is a flow diagram illustrating another educational technique that can be performed with the aid of mixed reality and/or virtual reality. FIG. 144 will be described from the perspective of system 14001 of FIG. 140, although other systems could use a similar technique. As shown in FIG. 144, an MR/VR device (such as MR/VR teacher device 14002 or one of MR/VR student devices 14004) displays an MR or VR presentation on an orthopedic surgical procedure including virtual elements (e.g., virtual model 14008) that are controlled by MR/VR teacher device 14002 (14401). The MR/VR device (such as MR/VR teacher device 14002 or one of MR/VR student devices 14004) then generates a student copy of the virtual elements (e.g., virtual model copy 14009) wherein the student copy is controllable by a student device (e.g., one of MR/VR student devices 14004) (14402).

In some cases, MR/VR teacher device 14002 generates the student copy for each student, and in some cases, the MR/VR student devices 14004 are able to generate respective student copies of the virtual elements. In some cases, the copy is not an original version of the virtual elements, but rather the copy may comprise a version of the virtual elements after some initial manipulation by the teacher. For example, the teacher or students may be able to generate copies of the virtual content during an ongoing virtual presentation, allowing student copies to be generated at different stages of an orthopedic surgical procedure or different stages of a surgical planning session so that the student can mimic or practice specific surgical steps or make surgical planning decisions associated with specific surgical planning steps. Moreover, in some cases, MR/VR teacher device 14002 may replace virtual model 14008 with the copy of virtual model 14009, after the student has manipulated the copy 14009.

In some examples, system 14001 demonstrates at least one aspect of an orthopedic surgical procedure and comprises a first device (e.g., MR/VR teacher device 14002) configured to display a presentation to a first user wherein the presentation includes one or more virtual elements that are controllable by the first user wearing the first device wherein the one or more virtual elements comprise a 3D virtual representation of one or more anatomical features associated with the orthopedic surgical procedure. In addition, system 14001 comprises a second device (e.g., one of MR/VR student devices 14004) configured to display the presentation to a second user. The one or more virtual elements demonstrate at least one aspect of the orthopedic surgical procedure. In some cases, the second device (e.g., one of MR/VR student devices 14004) or the first device (e.g., MR/VR teacher device 14002) may be configured to generate a copy of the one or more virtual elements in response to input from the first user or the second user and wherein the copy of the one or more virtual elements are controllable by the second user wearing the second device. In other cases, however, MR/VR teacher device 14002 may generate and assign copies to the MR/VR student devices 14004A. In some examples, the first device may be further configured to replace the copy of the one or more virtual elements with the copy of the one or more virtual elements in the presentation after the copy of the one or more virtual elements is manipulated by the second user wearing the second device.

As examples, the one or more virtual elements represented as virtual model 14008 (as well as the student copy or copies of the virtual elements represented as virtual model copy 14009) may comprise 3D virtual representation of one or more anatomical features as well as additional surgical guidance information or surgical planning information for the 3D virtual representation.

In some examples, a visualization device 213 may be configured to educate a user about an orthopedic surgical procedure and visualization device 213 may comprise a screen 520, which may comprise a transparent mixed reality display screen (such as a see-through holographic lens) configured to present a mixed reality presentation to a user, wherein the mixed reality presentation includes the one or more virtual elements comprising a 3D virtual representation of one or more anatomical features associated with the orthopedic surgical procedure. In addition, visualization device 213 may further comprise one or more processors 514 configured to generate a copy of the one or more virtual elements, wherein the copy is controllable with the visualization device. In some cases, the original mixed reality presentation is generated and controlled by another user of another visualization device (e.g., a teacher device) and the copy is generated and controlled by visualization device 213 worn by a student. In other cases, however, copies may be generated by MR/VR teacher device 14002 and assigned to one of MR/VR student devices 14004. In some examples, a method may comprise displaying a mixed reality presentation of an orthopedic surgical procedure on a student device and a teacher device, wherein the mixed reality presentation includes a teacher copy of virtual elements controlled by a teacher device and wherein the virtual elements comprise a 3D virtual representation of one or more anatomical features associated with the orthopedic surgical procedure, and generating a student copy of the virtual elements, wherein the student copy is controllable by the student device.

Figure 145:
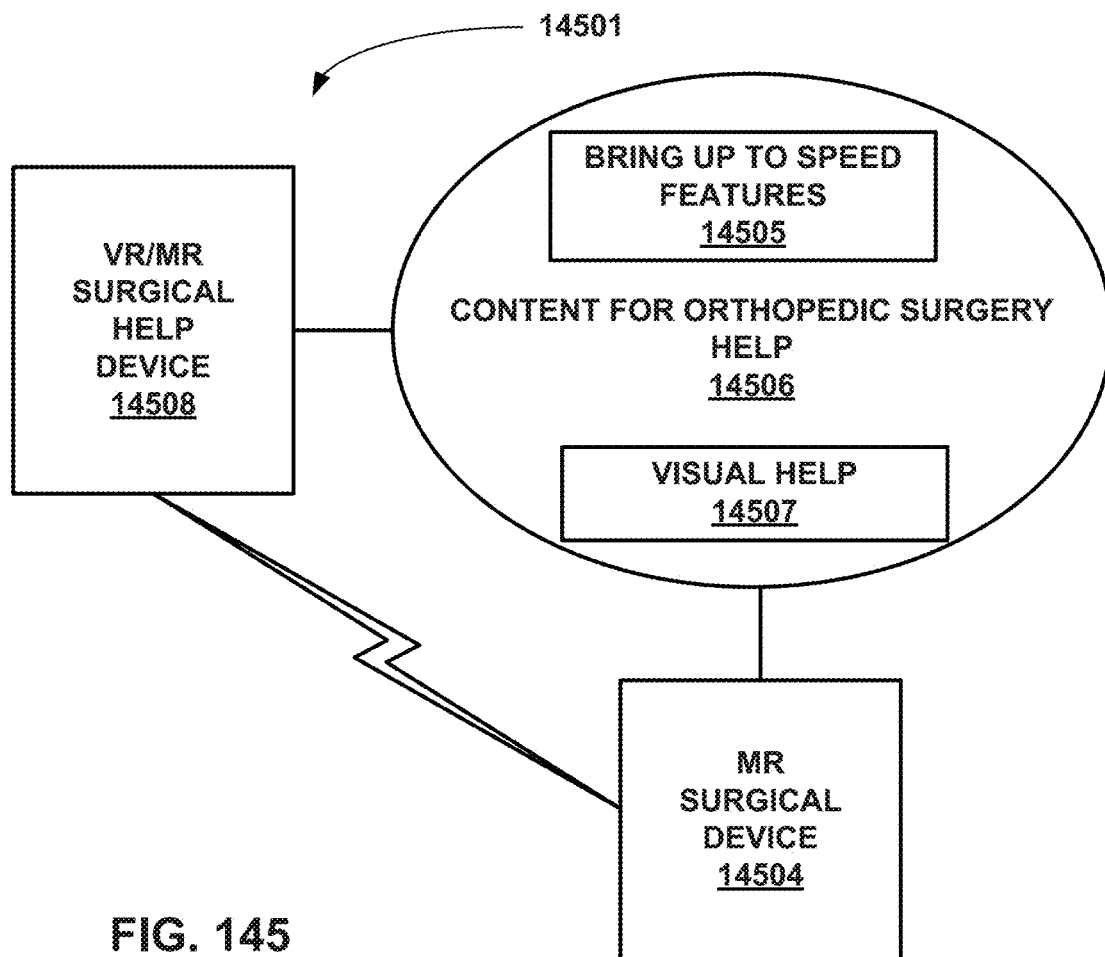

FIG. 145 is a conceptual block diagram of an educational system that includes features to help educate a remote user on specific details of an ongoing surgical procedure. Educational system 14501 sets forth a specific educational scenario of orthopedic surgical education specially related to an interoperative setting. Other sections of this disclosure describe a variety of scenarios and settings where interoperative interaction is performed between or amongst different users, and in many collaborative situations, one or more surgical participants may be remote participants that interact with the operating room participants thought the use of MR or possibly VR. In some cases, surgical help may be located in the operating room and in other cases, surgical help may be located remotely. Regardless, FIG. 145 illustrates an educational scenario where a surgical participant (such as a surgeon) wearing MR surgical device 14504 elicits surgical help from another person (such as s surgical expert) wearing or otherwise using MR/VR surgical help device 14508.

MR surgical device 14504 may comprise a mixed reality device such as visualization device 213 described in detail throughout this disclosure. For example, MR surgical device 14504 may comprise a visualization device worn by a surgeon to provide virtual interoperative assistance to the surgeon. MR surgical device 14504 may implement any of the features described in this disclosure to assist a user (e.g., a surgeon or possibly another surgical participant) with orthopedic surgical steps.

VR/MR surgical help device 14508 may comprise a mixed reality device such as visualization device 213, or alternatively, VR/MR surgical help device 14508 may comprise a virtual reality device. In any case, the user of MR surgical help device 14504 may elicit expert help during a procedure, and to do so, MR surgical device 14504 may be configured to initiate a communication session with VR/MR surgical help device 14508. Or in other examples, expert help may be contacted in another way such as via a telephone call, e-mail, text message, or any other type of message, and in response to being contacted, the surgical expert may join the procedure occurring in the operating room (either physically or remotely) via VR/MR surgical help device 14508. In some cases, MR surgical device 14504 and VR/MR surgical help device 14508 may communicate with one another directly or via a network.

A surgeon wearing MR surgical device 14504 may benefit from expert help on a surgical procedure for a wide variety of situations. Anytime the surgeon encounters difficulties, complications, or unexpected situations, surgeon wearing MR surgical device 14504 may benefit from expert help. For example, upon opening a shoulder or ankle and attempting to install an implant, a surgeon wearing MR surgical device 14504 may discover that the patient's bone quality is too poor for the implant. In this case, the surgeon wearing MR surgical device 14504 may determine that its difficult or impossible to implement a planned fixation, and in this case, it may be beneficial to contact an expert to show the expert the patient's CT-images and a 3D reconstruction of the patient's anatomy, along with the real scene images (e.g., obtained via MR surgical device 14504). In these and other cases, it may be very beneficial for a surgical expert wearing VR/MR surgical help device 14508 to join the surgical procedure.

Upon joining the surgical procedure, however, the surgical expert wearing VR/MR surgical help device 14508 may benefit from educational features illustrated as "bring up to speed" features 14505 which may inform the user of VR/MR surgical help device 14508 on one or more previously-executed steps of the orthopedic surgical procedure. For example, in order to provide useful help to the user of MR surgical device 14504 at the time a user of VR/MR surgical help device 14508 is engaged, the user of VR/MR surgical help device 14508 may need to be educated and essentially "brought up to speed" with regard to previous steps that already occurred in the procedure. Indeed, in order to classify problems or issues in the ongoing surgical procedure, the user of VR/MR surgical help device may require some knowledge about steps of the procedure that were previously performed. Accordingly, content for orthopedic surgical help 14506 may comprise "bring up to speed" features 14505 to provide specific interoperative education in a quick and efficient manner. Moreover, in some cases, visual help 14507 may also be provided, e.g., as visual aids to the user of VR/MR surgical help device 14508.

In one example, a surgical system 14501 is configured to provide for interoperative education to VR/MR surgical help device 14508 during an ongoing surgical procedure. System 14501 comprises first device (e.g., MR surgical device 14504) configured to display a first presentation to a first user (e.g., a surgeon or other surgical participant). The first presentation includes one or more virtual elements configured to assist the first user in an orthopedic surgical procedure. System 14501 may further comprise a second device (e.g., VR/MR surgical help device 14508) configured to display a second presentation to a second user (e.g., an expert surgeon or other expert associated with one or more steps of the orthopedic surgical process). The second user may be contacted during the procedure in order to provide surgical assistance on the orthopedic surgical procedure. According to this disclosure, in order to adequately educate the user of the second device, the second device is further configured to display content that informs or educates the second user on one or more previously-executed steps of the orthopedic surgical procedure.

In some cases, the first device (e.g., MR surgical device 14504) is configured to elicit the surgical assistance from the second user of the second device (e.g., VR/MR surgical help device 14508). However, the surgical assistance could also be elicited in other ways, such as via a telephone call, e-mail, text, or any other type of message. As examples, "bring up to speed" features 14505 may comprise one or more of: scans of a patient or segmentations of image data of the patient, information associated with one or more previously-executed steps of the orthopedic surgical procedure, information associated with previously-used surgical tools, information associated with an implanted device, information associated with a jig or guide used in the orthopedic surgical procedure, information associated with a pre-operative plan, information associated with timing of one or more of the previously-executed steps of the orthopedic surgical procedure, or patient data associated with one or more of the previously-executed steps of the orthopedic surgical procedure. In some cases, "bring up to speed" features 14505 may include patient data that was acquired before the surgery, such as CT-Scans, 3D reconstructions of the patient anatomy, surgery plans or planning information, patient age, patient weight, patient vital information, or any other patient data. In some cases, MR surgical device 14504 may automatically track steps of the surgery and in this case, "bring up to speed" features may include information that identifies the current step and previously executed steps of the surgical procedure.

Moreover, as noted, visual help 14507 may also help with interoperative education and may be especially useful to accelerate the educational process, which may be important during an ongoing surgical procedure. Accordingly, educational content for orthopedic surgery help 14506 may comprise visual help 14507, such as one or more images associated with one or more of the previously-executed surgical steps, one or more videos of one or more of the previously-executed surgical steps, one or more images or videos of a prepared anatomical surface of a patient that was prepared for an implant, animations or illustrations of planned surgical steps, one or more images or videos of a surgical plan, and one or more images or videos of the orthopedic surgical procedure.

In some examples, "bring up to speed" features 14505 and/or visual help 147 may comprise one or more images or videos of the orthopedic surgical procedure, which may be captured by MR surgical device during the orthopedic surgical procedure or captured by another camera or another MR device located in the operating room during the orthopedic surgical procedure. In order to facilitate quick and efficient review by the user of VR/MR surgical help device 14508, the images or videos may be time-indexed. Or in some cases, the images or videos may be indexed based on surgical steps or stages so that VR/MR surgical help device 14508 can select particular surgical steps or stages and view images or videos recorded at those steps or stages. The steps or stages many include pre-operative planning steps, which are typically shown with images, and inter-operative steps, which may be shown with video or images.

In some examples, content 14506 may be acquired by cameras located in the operating room or via one or more cameras on MR surgical device 14504 so that the VR/MR surgical help device 14508 can see the perspective of the surgeon (or some other person in the room such as a nurse or technician) or from a camera in the room. Such content may also include any virtual imagery that was presented to the surgeon during the procedure, and in some examples, VR/MR surgical help device 14508 could enable or disable the virtual imagery to view patient shoulder anatomy or patient shoulder anatomy plus virtual imagery. Also, a virtual anatomical model could be presented to show the virtual surgical plan, and VR/MR surgical help device 14508 may be able to selectively see the virtual surgical plan, bone model only, bone model plus virtual guidance (e.g., virtual elements to aid in reaming, cutting, drilling, screwing, or other positioning makers). In still other cases, VR/MR surgical help device 14508 may be able to selectively view a virtual surgical plan, plus a bone model, plus virtual guidance features. Such content may be recorded during the procedure or planning stages and may be stored as images are video could be time indexed or task indexed (e.g., indexed to a point in the workflow such as glenoid reaming, glenoid implant placement). Such content may also identify such things as a plate for an anatomical procedure or hemi for reverse anatomical procedure, humeral cutting, humeral implant placement (e.g., hemi with stem or stemless for anatomical or plate with stem or stemless for reverse), and/or other things.

The "bring up to speed" features 14505 and/or visual help 147 may comprise features for informing or educating a remote surgeon or another interoperative surgical participant wearing VR/MR surgical help device 14508. Moreover, in some cases, educational content 14506 may also include features that can aid the wearer of MR/VR surgical help device 14508 for educating the person wearing MR surgical device 14504. In other words, after being "brought up to speed" and sufficiently educated on the previous steps of the surgical procedure, VR/MR surgical help device 14508 may present features that can aid in providing the expert help to the user of MR surgical device 14504. For example, educational content 14506 may include an archive of video clips (such as video clips of the surgery or video clips of similar surgeries) that can be accessed and presented by MR/VR surgical help device 14508 to MR surgical device 14504. Moreover, visual help 14507 may include such video clips or possibly an archive of problem-solving videos. In some cases, VR/MR surgical help device 14508 may be granted control over a virtual model or other virtual elements so that the wearer of MR/MR surgical help device 14508 can present demonstrations to aid the user of MR surgical device 14504. If, for example, MR surgical device 14504 presents a virtual model of an anatomical element registered to a patient's actual anatomy (e.g., a virtual model of a patient's glenoid bone registered to an actual patient's glenoid bone), VR/MR surgical help device 14508 may be given control over a virtual model so that VR/MR surgical help device 14508 can manipulate the virtual model (e.g., demonstrating a location of a drill hole or a location of a reaming axis). In some cases, any manipulations performed by VR/MR surgical help device 14508 on the model may be shown to MR surgical device 14504 as manipulations on a corresponding registered model that is registered to patient anatomy. Thus, VR/MR surgical help device may manipulate a virtual model presented to VR/MR surgical help device 14508 in space, and the manipulations may be presented to MR surgical device 14504 on another virtual model that is viewable by MR surgical device 14504 and also registered to patient anatomy in the operating room and viewable by MR surgical device 14504. In this way, for example, VR/MR surgical help device 14508 could present virtual elements relative to a virtual model, and such virtual elements may be viewable by MR surgical device 14504 so as to appear relative actual patient anatomy in the operating room. In some examples, the virtual elements presented within content 14508 may include any of the virtual elements described above (or combinations of those described above) with regard to MR educational content 12706 of FIG. 127.

In some cases, VR/MR surgical help device 14508 may be configured with a menu of selectable elements to assist in the interoperative education of the user of/MR surgical help device 14508. For example, VR/MR surgical help device 14508 may be configured to present a plurality of selectable virtual elements corresponding to a plurality of educational content elements associated with the ongoing surgical procedure, wherein upon selection of one of the virtual elements, the second device is configured to educate the second user on one or more of the previously-executed steps associated with the surgical procedure.

Moreover, in some cases, manipulations by VR/MR surgical help device 14508 on a virtual model of patient anatomy in space may appear to MR surgical device 14504 as virtual manipulations on a registered virtual model that is registered to the patient anatomy in the operating room. For example, the user of VR/MR surgical help device 14508 may demonstrate a desired location of a virtual reaming axis relative to a virtual model in space, and this demonstration may appear to MR surgical device 14504 as a virtual reaming axis that is properly positioned relative to patient anatomy since the virtual model is registered to the patient anatomy when viewed by MR surgical device 14504. This type of demonstration may be very useful for the user of VR/MR surgical help device 14508 to provide expert assistance to the user of MR surgical help device 14504.

In some examples, a visualization device 213 may be configured to educate a user about previously-executed steps of an orthopedic surgical procedure. In this example, the visualization device may correspond to VR/MR surgical help device 14508, and may comprise one or more processors 514 configured to generate one or more virtual elements, and a screen 520, which may comprise a transparent mixed reality display screen (such as a see-through holographic lens) configured to present the one or more virtual elements to a user as part of a mixed reality presentation, wherein the one or more virtual elements define educational content that educates the user on one or more previously-executed steps of the orthopedic surgical procedure. In some cases, visualization device 213 may be configured to educate the user about the previously-executed steps of the orthopedic surgical procedure in response to a request for assistance.

As non-limiting examples, educational content that may be useful for interoperative surgical education to educate an expert surgical helper (such as an expert surgent that is located remotely and contacted to provide help) during a surgical procedure may include such things as: scans of a patient or segmentations image data of the patient, information associated with previously-executed surgical steps, information associated with previously-used surgical tools, information associated with an implanted device, information associated with a jig or guide used in the orthopedic surgical procedure, one or more images or videos of a prepared anatomical surface of a patient that was prepared for an implant, information associated with a pre-operative plan, one or more images associated with previously-executed surgical steps, one or more videos of previously-executed surgical steps, information associated with timing of previously-executed surgical steps, patient data associated with previously-executed surgical steps animations or illustrations of planned surgical steps, one or more images or videos of a surgical plan, and one or more images or videos of the orthopedic surgical procedure.

In some cases, a screen 520 of visualization device 213 may be s configured to present a plurality of selectable virtual elements corresponding to a plurality of educational content elements, wherein upon selection of one of the virtual elements, visualization device 213 is configured to inform the user on one or more of the previously-executed steps associated with the surgical procedure. Screen 520, for example, may comprise a transparent mixed reality display screen, such as a see-through holographic lens.

In some examples, a method may comprise presenting a first mixed reality presentation on a first device to aid a first user in steps of an orthopedic surgical procedure, eliciting surgical help on the orthopedic surgical procedure, and in response to eliciting the surgical help, presenting educational content via a second mixed reality device or a virtual reality device, wherein the educational content comprises information on one or more previously-executed steps of the orthopedic surgical procedure.

From the perspective of a VR/MR surgical help device 14508, a method may comprise receiving a request for assistance in an orthopedic surgical procedure, and in response to the request, presenting educational content via a mixed reality device or a virtual reality device, wherein the educational content comprises information on one or more previously-executed steps of the orthopedic surgical procedure. Upon receiving and studying the educational content, the user of the VR/MR surgical help device 14508 may be better equipped to delivering educated expert assistance on the orthopedic surgical procedure.

In some cases, remote users of VR/MR surgical help device 14508 may be contacted by MR surgical device 14504 or another device located in the surgical room as part of a surgical workflow, and possibly contacted automatically at defined steps of the surgical workflow. Local MR devices may detect the current stage of the surgical workflow and request surgical assistance from a user of VR/MR surgical help device 14508 for particular steps of the procedure. In this case, VR/MR surgical help device 14508 could be contacted automatically based on the current stage of the surgical workflow. In this way, high volume surgical experts using VR/MR surgical help device 14508 can be consulted at defined stages of the surgical procedure so that they can be involved only when expert surgical help is desired.

In some cases, the user of VR/MR surgical help device 14508 may be connected to MR surgical device 14504 during the surgical session at a particular step of the procedure. Local surgical participants can manually call the user of VR/MR surgical help device 14508 for help on a particular step, or the call or other manner of contact to VR/MR surgical help device 14508 could be automatic by MR surgical device 14504 based on the current stage or step of the surgical workflow.

Also, if the surgical workflow process is used by MR surgical device 14504 to solicit help from VR/MR surgical help device 14508, in some cases, VR/MR surgical help device 14508 may be given advance notice by MR surgical device 14504 of the need for help in the near future. For example, based on the current workflow of the surgical procedure, one or more local MR devices (such as by MR surgical device 14504) may contact VR/MR surgical help device 14508 to indicate that future help is needed. As part of this request for help by MR surgical device 14504, VR/MR surgical help device 14508 may be given advance warning or notice by MR surgical device 14504 of when help will be needed, such as a countdown that provides notice of when help will be needed. Artificial intelligence may be used to provide predictions of when help is needed (for defined steps or stages of a procedure) based on the current step or stages of the surgical procedure that are currently in progress (and based on information about previously conducted surgical procedures). Image detection and sound detection may be used by MR surgical device 14504 to define or confirm the current step or stage of the surgical procedure so as to provide a better estimate of when the future step or stage will occur (thereby requiring, desiring, or planning for future surgical help by the user of VR/MR surgical help device 14508). Artificial intelligence may help guide and predict the timing for calling the user of VR/MR surgical help device 14508 by MR surgical device 14504, e.g., by MR surgical device 14504 learning the process and predicting the timing of future steps or stages or the surgical procedure based on the current step or stages of the surgical procedure currently in progress. Recording the procedure, and identifying sounds, images, work steps, or other aspects of the procedure may allow artificial intelligence implemented by MR surgical device 14504 to predict the time when help from VR/MR surgical help device 14508 is needed or desired. Inputs (such as sounds, images, work steps) may be correlated with current surgical workflow steps, and this may then be used by MR surgical device 14504 to predict the timing of future workflow steps. This can help to provide notice or scheduling for the user of VR/MR surgical help device 14508 and avoid down-time in the surgical procedure when help is needed from a remote participant.

Figure 146:
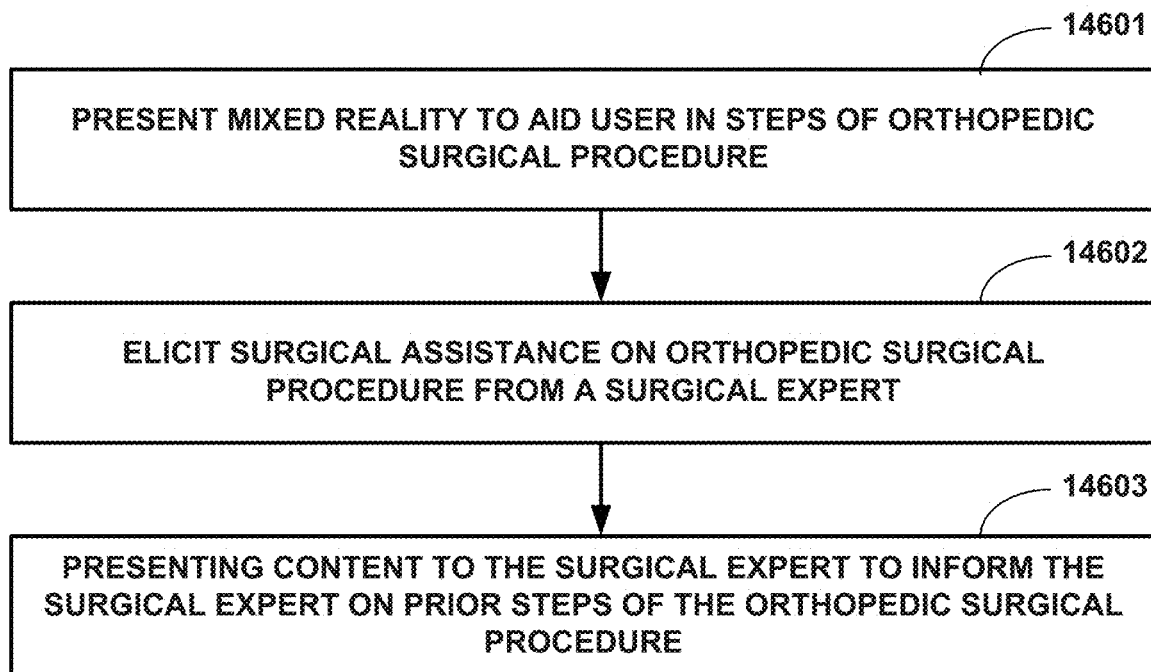
Figure 147:
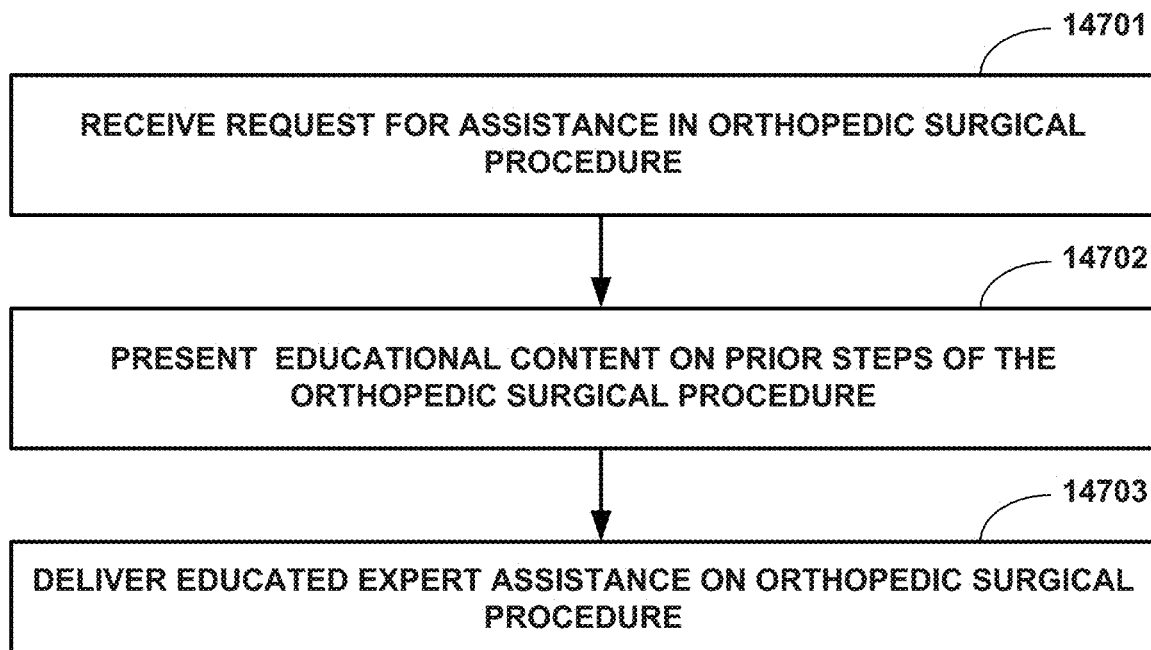

FIGS. 146 and 147 are flow diagrams illustrating interoperative educational techniques that to help educate a remote user on specific details of an ongoing surgical procedure. As shown in FIG. 146, a visualization device 213 worn by a surgeon or another surgical participant may present mixed reality to aid the user in steps of an orthopedic surgical procedure (14601). The visualization device 213 (or another means) may elicit surgical help on the orthopedic surgical procedure (14602). Interoperative educational content may then be provided to the surgical assistance via an MR device or a VR device to educate the surgical expert on prior steps of the orthopedic surgical procedure (14603). In this way, the surgical expert (e.g., an expert surgeon that is consulted intraoperatively through the use of MR or VR) can be educationally brought up to speed with regard to the procedure to ensure that the surgical assistance is useful and accurate.

FIG. 147 illustrates an example method from the perspective on an exemplary VR/MR surgical help device 14508 of a surgical system 14501 shown in FIG. 145. As shown in FIG. 147, VR/MR surgical help device 14508 (or the user of VR/MR surgical help device 14508) receives a request for assistance in an orthopedic surgical procedure (14701). In some examples, VR/MR surgical help device 14508 receives the request for assistance from MR surgical device 14504. In other examples, the request for assistance may comprise a request to the user of VR/MR surgical help device 14508, such as a telephone call, e-mail, text message, or any other type of message from MR surgical device 14504 to the user of VR/MR surgical help device 14508. Also, in some examples, it may be desirable for MR surgical device 14504 to use voice-to-text technology to send a text-based request to the user of VR/MR surgical help device 14508 in response to a voice utterance by a user of MR surgical device 14504 (e.g., a local surgeon). Voice-to-text technology may be useful especially when the local surgeon is unable to use his or her hands to communicate with the user of VR/MR surgical help device 14508. In some cases, voice-to-text technology may be used by MR surgical device 14504 to deliver a written summary or the current state or the procedure, one or more events of the procedure, surgical progress, and/or problems that have been encountered in the surgical procedure.

In some examples, MR surgical device 14504 may be configured to automatically send a request for help to VR/MR surgical help device 14508 in response to receiving an indication of user input from the user of MR surgical device 14504. For example, the user of MR surgical device 14504 may select a virtual icon or widget to cause MR surgical device 14504 to send a request for help to VR/MR surgical help device 14508. In some examples, MR surgical device 14504 may send a request for help to VR/MR surgical help device 14508 in response to detecting a voice utterance of the user of MR surgical device 14504 that says "I want to contact an expert" or some other trigger phrase. In examples where MR surgical device 14504 automatically sends the request for help, some or all of the "bring up to speed" features described herein may be likewise communicated automatically to VR/MR surgical help device 14508.

For example, in response to the request for assistance, VR/MR surgical help device 14508 is configured to present interoperative educational content on prior steps of the orthopedic surgical procedure (14702). The prior steps, for example, may include any of the operative or pre-operative steps that were already performed in relation to the orthopedic surgical procedure. Using VR/MR surgical help device 14508, an expert may then deliver educated expert assistance on the orthopedic surgical procedure (14703).

Again, some non-limiting and non-exhaustive examples of content that may be useful for interoperative surgical education to inform an expert surgical helper (such as an expert surgent that is located remotely and contacted to provide help) during a surgical procedure may include such things as: scans of the patient or segmentations image data of the patient, information associated with previously-executed steps of the ongoing orthopedic surgical procedure, information associated with previously-used surgical tools, information associated with an implanted device, information associated with a jig or guide used in the orthopedic surgical procedure, one or more images or videos of a prepared anatomical surface of a patient that was prepared for an implant, information associated with a pre-operative plan, one or more images associated with previously-executed steps of the ongoing orthopedic surgical procedure, one or more videos of previously-executed steps of the ongoing orthopedic surgical procedure, information associated with timing of previously-executed steps of the ongoing orthopedic surgical procedure, patient data associated with previously-executed surgical steps animations or illustrations of planned surgical steps, one or more images or videos of a surgical plan, and one or more images or videos of the orthopedic surgical procedure.

Also, in some examples, content 14506 may comprise one or more images or videos of the orthopedic surgical procedure, which may be captured by MR surgical device 14504 during the orthopedic surgical procedure or captured by another camera or another MR device located in the operating room during the orthopedic surgical procedure. The images or videos may be time-indexed. Or in some cases, the images or videos may be indexed based on surgical steps or stages so that VR/MR surgical help device 14508 an select particular surgical steps or stages and view images or videos recorded at those steps or stages. The steps or stages many include pre-operative planning steps, which are typically shown with images, and inter-operative steps, which may be shown with video or images. In some examples, VR/MR surgical help device 14508 may present virtual elements or views seen by MR surgical device 14504. In such examples, VR/MR surgical help device 14508 may also present a MR pre-operative planning model (e.g., above or in a side view on the presentation seen by VR/MR surgical help device 14508).

Although VR/MR surgical help device 14508 is shown as one device, it is also possible to have multiple VR/MR surgical help devices 14508, each of which may be associated with different surgical experts needed at different stages of the surgical procedure. Multiple VR/MR surgical help devices 14508 may allow for a team or community of experts to provide help. Multiple experts may help collectively on a particular issue, or an issue may be assigned to a specific member of the team or the issue may be assigned to a community of experts. For example, a local surgeon may elicit help from a team of remote surgical, and a member of the team may accept the request to provide the help via one of VR/MR surgical help devices 14508. In some examples, the request for help could be assigned by MR surgical device 14504 to remote participants on a first-come-first-serve basis. In some examples, the request for help could be assigned by MR surgical device 14504 to specific members of a help team based on the expertise of specific members of the help team.

In some examples, delivering educated expert assistance on the orthopedic surgical procedure (14703) includes presenting virtual information. Moreover, in some examples, the virtual information is viewable and manipulatable by a first device (VR/MR surgical help device 14508) associated with a person providing the assistance and the virtual information is viewable relative to patient anatomy by a second device (e.g., MR surgical device 14504) associated with a person requesting the assistance. For example, VR/MR surgical help device 14508 present a virtual model in free space, which is manipulated by the user that is providing assistance, and this virtual model may be viewable to MR surgical device 14504 and registered by patient anatomy from the perspective of MR surgical device 14504. More generally, any virtual content, virtual models or virtual elements described above with regard to MR educational content 12706 of FIG. 127 could be included within content for orthopedic surgical help 14506, e.g., for informing the user of VR/MR surgical help device 14508 or for providing virtual-assisted help from the user of VR/MR surgical help device 14508 to the user of MR surgical device 14504.

While the techniques been disclosed with respect to a limited number of examples, those skilled in the art, having the benefit of this disclosure, will appreciate numerous modifications and variations there from. For instance, it is contemplated that any reasonable combination of the described examples may be performed. It is intended that the appended claims cover such modifications and variations as fall within the true spirit and scope of the invention.

It is to be recognized that depending on the example, certain acts or events of any of the techniques described herein can be performed in a different sequence, may be added, merged, or left out altogether (e.g., not all described acts or events are necessary for the practice of the techniques). Moreover, in certain examples, acts or events may be performed concurrently, e.g., through multi-threaded processing, interrupt processing, or multiple processors, rather than sequentially.

In one or more examples, the functions described may be implemented in hardware, software, firmware, or any combination thereof. If implemented in software, the functions may be stored on or transmitted over as one or more instructions or code on a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transitory media, but are instead directed to non-transitory, tangible storage media. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Operations described in this disclosure may be performed by one or more processors, which may be implemented as fixed-function processing circuits, programmable circuits, or combinations thereof, such as one or more digital signal processors (DSPs), general purpose microprocessors, application specific integrated circuits (ASICs), field programmable gate arrays (FPGAs), or other equivalent integrated or discrete logic circuitry. Fixed-function circuits refer to circuits that provide particular functionality and are preset on the operations that can be performed. Programmable circuits refer to circuits that can programmed to perform various tasks and provide flexible functionality in the operations that can be performed. For instance, programmable circuits may execute instructions specified by software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. Accordingly, the terms "processor" and "processing circuitry," as used herein may refer to any of the foregoing structures or any other structure suitable for implementation of the techniques described herein.

Various examples have been described. These and other examples are within the scope of the following claims.

What is claimed is:

1. A method comprising:
   obtaining, a virtual model of a portion of an anatomy of a patient obtained from a virtual surgical plan for an orthopedic joint repair surgical procedure to attach a prosthetic to the anatomy;
   identifying, by one or more processors of a head-mounted visualization device and based on data obtained by one or more optical sensors of the head-mounted visualization device, positions of one or more optical three-dimensional physical markers attached to the anatomy of the patient;
   identifying, by the one or more processors, positions of one or more virtual markers on the anatomy of the patient, wherein identifying a position of a particular virtual marker the one or more virtual markers comprises:
      receiving user input to virtually position the particular virtual marker on a surface of the virtual model of an observed portion of the anatomy within a corresponding region of interest on a surface of a portion of the anatomy in direct line of sight of a wearer of the head-mounted visualization device; and
      determining the position of the particular virtual marker based on the received user input;
   registering, by the one or more processors and based on the identified positions of the one or more physical markers and the identified positions of the one or more virtual markers, the virtual model of the portion of the anatomy with a corresponding observed portion of the anatomy; and
   displaying, via the visualization device and overlaid on the portion of the anatomy, a virtual guide that guides at least one of preparation of the anatomy for attachment of the prosthetic or attachment of the prosthetic to the anatomy, wherein a position of the virtual guide is determined based on the registration.

2. The method of claim 1, wherein registering the virtual model comprises initially registering the virtual model.

3. The method of claim 2, wherein registering the virtual model comprises re-registering the virtual model.

4. The method of claim 3, wherein re-registering the virtual model comprises:
   responsive to determining that registration of the virtual model has been lost, re-registering the virtual model based on the identified positions.

5. The method of claim 1, wherein registering the virtual model of the portion of the anatomy with the corresponding observed portion of the anatomy comprises:
   generating, based on an alignment between the virtual model of the portion of the anatomy with a corresponding observed portion of the anatomy, a transformation matrix between the virtual model of the portion of the anatomy and the corresponding observed portion of the anatomy, wherein the transformation matrix provides a coordinate system for translating virtual guides indicated by the virtual surgical plan to the observed portion of the anatomy.

6. The method of claim 5, further comprising determining the alignment by at least:
   adjusting an orientation of the virtual model so that a virtual surface normal vector associated with the virtual marker is aligned with a real surface normal vector associated with the corresponding region of interest.

7. The method of claim 6, wherein registering the virtual model comprises:
   performing an initialization procedure; and
   performing an optimization procedure.

8. The method of claim 7, wherein performing the initialization procedure comprises determining the alignment, and wherein performing the optimization procedure comprises generating the transformation matrix.

9. The method of claim 6, wherein the region of interest is an anatomical landmark of the portion of the anatomy, wherein the anatomical landmark is a center region of a glenoid or a center region of a humeral head.

10. The method of claim 6, wherein receiving the user input comprises one or more of:
    receiving motion data from one or more sensors of the visualization device;
    receiving audio data indicating one or more voice commands; and
    receiving data indicating performance of one or more hand gestures.

11. The method of claim 1, further comprising:
displaying, via a visualization device and overlaid on the portion of the anatomy viewable via the visualization device, the virtual model of the portion of the anatomy.

12. The method of claim 1, further comprising:
outputting an indication that the physical markers may be removed.

13. The method of claim 12, wherein outputting the indication that the physical markers may be removed comprises:
outputting the indication in response to determining that registration can be maintained without the physical markers remaining present.

14. The method of claim 12, wherein outputting the indication that the physical markers may be removed comprises:
outputting the indication in response to determining that registration is no longer needed.

15. The method of claim 1, wherein the physical markers comprise one or more passive physical markers.

16. The method of claim 15, wherein at least one of the passive physical markers comprises a sticker.

17. The method of claim 1, further comprising:
obtaining, a virtual model of an instrument;
identifying, based on data obtained by the one or more optical sensors, positions of one or more second optical physical markers attached to the instrument; and
registering, based on the identified positions of the one or more second optical physical markers, the virtual model of the instrument with a corresponding observed portion of the instrument.

18. The method of claim 1, further comprising:
determining a confidence of the registration of the virtual model.

19. The method of claim 18, wherein determining the confidence of the registration comprises:
determining a confidence distance that represents a maximum distance between a point on the virtual model and a corresponding point on the observed portion of the anatomy.

20. The method of claim 19, further comprising:
determining that registration of the virtual model has been lost in response to determining that the confidence distance is greater than a threshold confidence distance; and
responsive to determining that registration of the virtual model has been lost, registering the virtual model.

21. The method of claim 20, wherein the threshold confidence distance is the same for all work steps of the orthopedic joint repair surgical procedure.

22. The method of claim 20, further comprising:
selecting a first threshold confidence distance for a first work step of the orthopedic joint repair surgical procedure; and
selecting a second threshold confidence distance for a second work step of the orthopedic joint repair surgical procedure.

23. The method of claim 21, further comprising:
outputting a representation of the confidence of the registration.

24. The method of claim 23, wherein outputting the representation of the confidence comprises one or more of:
displaying a numerical value of the confidence distance; and
displaying a graphical representation of the confidence distance.

25. The method of claim 1, wherein the anatomy is bone.

26. A mixed reality system comprising:
a memory that stores at least a portion of a virtual surgical plan for an orthopedic joint repair surgical procedure to attach a prosthetic to an anatomy of a patient;
one or more optical three-dimensional physical markers;
a head-mounted visualization device comprising:
one or more optical sensors; and
one or more processors implemented configured to:
obtain, a virtual model of a portion of an anatomy of a patient obtained from a virtual surgical plan for an orthopedic joint repair surgical procedure to attach a prosthetic to the anatomy;
identify, based on data obtained by one or more optical sensors, positions of one or more physical markers attached to the anatomy of the patient;
identify positions of one or more virtual markers on the anatomy of the patient, wherein, to identify a position of a particular virtual marker the one or more virtual markers, the one or more processors are configured to:
receive user input to virtually position the particular virtual marker on a surface of the virtual model of an observed portion of the anatomy within a corresponding region of interest on a surface of a portion of the anatomy in direct line of sight of a wearer of the head-mounted visualization device; and
determine the position of the particular virtual marker based on the received user input;
register, based on the identified positions of the one or more physical markers and the identified positions of the one or more virtual markers, the virtual model of the portion of the anatomy with a corresponding observed portion of the anatomy; and
display, overlaid on the portion of the anatomy, a virtual guide that guides at least one of preparation of the anatomy for attachment of the prosthetic or attachment of the prosthetic to the anatomy, wherein a position of the virtual guide is determined based on the registration.

27. The mixed reality system of claim 26, wherein, to register the virtual model, the one or more processors are configured to:
initially registering the virtual model at a first time; and
re-register the virtual model at a second time that is after the first time.

28. The mixed reality system of claim 26, wherein the one or more processors are further configured to:
output an indication that the physical markers may be removed.

29. The mixed reality system of claim 28, wherein, to output the indication that the physical markers may be removed, the one or more processors are configured to:
output the indication in response to determining that registration can be maintained without the physical markers remaining present.

30. The mixed reality system of claim 28, wherein, to output the indication that the physical markers may be removed, the one or more processors are configured to:
output the indication in response to determining that registration is no longer needed.

31. The mixed reality system of claim 26, wherein the physical markers comprise one or more passive physical markers.

32. The mixed reality system of claim 26, wherein the physical markers comprise one or more active physical markers.

33. The mixed reality system of claim 32, wherein at least one of the active physical markers comprises an electromagnetic marker.

34. The mixed reality system of claim 26, wherein the one or more processors are further configured to:
    obtain, a virtual model of an instrument;
    identify, based on data obtained by the one or more sensors, positions of one or more second optical physical markers attached to the instrument; and
    register, based on the identified positions of the one or more second optical physical markers, the virtual model of the instrument with a corresponding observed portion of the instrument.

35. The mixed reality system of claim 26, wherein the one or more processors are further configured to:
    determine a confidence of the registration of the virtual model.

36. The mixed reality system of claim 35, wherein, to determine the confidence of the registration, the one or more processors are configured to:
    determine a confidence distance that represents a maximum distance between a point on the virtual model and a corresponding point on the observed portion of the anatomy.

37. The mixed reality system of claim 36, wherein the one or more processors are further configured to:
    determine that registration of the virtual model has been lost in response to determining that the confidence distance is greater than a threshold confidence distance; and
    responsive to determining that registration of the virtual model has been lost, register the virtual model.

38. A computer-readable storage medium storing instructions that, when executed, cause one or more processors of a head-mounted visualization device of a mixed reality system to:
    obtain, a virtual model of a portion of an anatomy of a patient obtained from a virtual surgical plan for an orthopedic joint repair surgical procedure to attach a prosthetic to the anatomy;
    identify, based on data obtained by one or more sensors, positions of one or more physical markers attached to the anatomy of the patient;
    identify positions of one or more virtual markers on the anatomy of the patient, wherein the instructions that cause the one or more processors to identify a position of a particular virtual marker the one or more virtual markers comprise instructions that cause the one or more processors to:
        receive user input to virtually position the particular virtual marker on a surface of the virtual model of an observed portion of the anatomy within a corresponding region of interest on a surface of a portion of the anatomy in direct line of sight of a wearer of the head-mounted visualization device; and
        determine the position of the particular virtual marker based on the received user input;
    register, based on the identified positions of the one or more physical markers and the identified positions of the one or more virtual markers, the virtual model of the portion of the anatomy with a corresponding observed portion of the anatomy; and
    display, via the visualization device and overlaid on the portion of the anatomy, a virtual guide that guides at least one of preparation of the anatomy for attachment of the prosthetic or attachment of the prosthetic to the anatomy, wherein a position of the virtual guide is determined based on the registration.

* * * * *